(12) United States Patent
Chafeev et al.

(10) Patent No.: US 8,106,087 B2
(45) Date of Patent: *Jan. 31, 2012

(54) SPIRO-OXINDOLE COMPOUNDS AND THEIR USES AS THERAPEUTIC AGENTS

(75) Inventors: Mikhail Chafeev, Burnaby (CA); Nagasree Chakka, Waltham, MA (US); Sultan Chowdhury, Surrey (CA); Robert Fraser, North Vancouver (CA); Jianmin Fu, Coquitlam (CA); Duanjie Hou, Burnaby (CA); Tom Hsieh, Toronto (CA); Rajender Kamboj, Burnaby (CA); Shifeng Liu, Coquitlam (CA); Vandna Raina, Haryana (IN); Mehran Seid Bagherzadeh, Vancouver (CA); Jianyu Sun, San Mateo, CA (US); Shaoyi Sun, Coquitlam (CA); Serguei Sviridov, Burnaby (CA)

(73) Assignee: Xenon Pharmaceuticals Inc., Burnaby, B.C. (CA)

( * ) Notice: Subject to any disclaimer, the term of this patent is extended or adjusted under 35 U.S.C. 154(b) by 0 days.

This patent is subject to a terminal disclaimer.

(21) Appl. No.: 12/650,196

(22) Filed: Dec. 30, 2009

(65) Prior Publication Data

US 2010/0125072 A1    May 20, 2010

Related U.S. Application Data

(63) Continuation of application No. 11/402,310, filed on Apr. 11, 2006, now Pat. No. 7,700,641.

(60) Provisional application No. 60/670,896, filed on Apr. 11, 2005.

(51) Int. Cl.
*A61K 31/407* (2006.01)
*A61K 31/5377* (2006.01)

(52) U.S. Cl. .............. 514/409; 514/232.8; 514/256; 514/321; 514/338

(58) Field of Classification Search .............. 514/409, 514/232.8, 256, 321, 338
See application file for complete search history.

(56) References Cited

U.S. PATENT DOCUMENTS

| | | | |
|---|---|---|---|
| 3,189,617 A | 6/1965 | Archer et al. | 260/319 |
| 3,723,459 A | 3/1973 | Paragamian | 260/325 |
| 3,845,770 A | 11/1974 | Theeuwes et al. | 128/260 |
| 4,045,576 A | 8/1977 | Welstead, Jr. et al. | 424/309 |
| 4,326,525 A | 4/1982 | Swanson et al. | 128/260 |
| 4,438,130 A | 3/1984 | Kaplan | 424/274 |
| 4,440,785 A | 4/1984 | Walsh | 424/317 |
| 4,670,566 A | 6/1987 | Walsh | 548/485 |
| 4,886,788 A | 12/1989 | Skuballa et al. | 514/58 |
| 4,935,446 A | 6/1990 | Imaki et al. | 514/530 |
| 5,023,265 A | 6/1991 | Scherlock et al. | 514/300 |
| 5,116,854 A | 5/1992 | Marfat | 514/365 |
| 5,182,289 A | 1/1993 | Ting et al. | 514/278 |
| 5,278,162 A | 1/1994 | Wilkerson | 514/252 |
| 5,296,478 A | 3/1994 | Teleha | 514/235.2 |
| 5,453,516 A | 9/1995 | Fischer et al. | 548/543 |
| 5,663,431 A | 9/1997 | Di Malta et al. | 562/828 |
| 5,686,624 A | 11/1997 | Di Malta et al. | 548/410 |
| 5,696,145 A | 12/1997 | Foulon et al. | 514/409 |
| 5,723,625 A | 3/1998 | Keplinger et al. | 548/408 |
| 5,726,322 A | 3/1998 | Di Malta et al. | 548/410 |
| 5,728,723 A | 3/1998 | Di Malta et al. | 514/418 |
| 5,763,471 A | 6/1998 | Fourtillan et al. | 514/409 |
| 5,767,128 A | 6/1998 | Guillaumet et al. | 514/300 |
| 5,776,936 A | 7/1998 | Lee et al. | 514/250 |
| 5,849,780 A | 12/1998 | Di Malta et al. | 514/409 |
| 5,994,350 A | 11/1999 | Foulon et al. | 514/232.8 |
| 6,046,341 A | 4/2000 | Foulon et al. | 548/411 |
| 6,090,818 A | 7/2000 | Foulon et al. | 514/278 |
| 6,110,969 A | 8/2000 | Tani et al. | 514/530 |
| 6,225,347 B1 | 5/2001 | Buchmann et al. | 514/530 |

(Continued)

FOREIGN PATENT DOCUMENTS

CA    2095718 A1    5/1992

(Continued)

OTHER PUBLICATIONS

Adams et al., "Bicyclic N-Hydroxyurea Inhibitors of 5-Lipoxygenase: Pharmacodynamic, Pharmacokinetic, and in Vitro Metabolic Studies Characterizing N-Hydroxy-N-(2,3-dihydro-6-(phenylmethoxy)-3-benzofuranyl)urea," *J. Med. Chem.* 39(26): 5035-5046, 1996.
Akai, "Development of Novel Asymmetric Reactions Oriented to Next-Generation Enzymatic Organic Syntheses," *Yakugaku Zasshi* 123(11): 919-931, 2003.
Alabaster et al., "The Synthesis of 5-Substituted 2,3-Dihydrobenzofurans," *Synthesis* 12: 950-952, Dec. 1988.
Alcaide et al., "Efficient Entry to Diversely Functionalized Spirocyclic Oxindoles from Isatins through Carbonyl-Addition/Cyclization Reaction Sequences," *J. Org. Chem.* 71(6): 2346-2351, 2006.

(Continued)

*Primary Examiner* — Charanjit Aulakh
(74) *Attorney, Agent, or Firm* — Seed IP Law Group PLLC

(57) ABSTRACT

This invention is directed to spiro-oxindole compounds of formula (I):

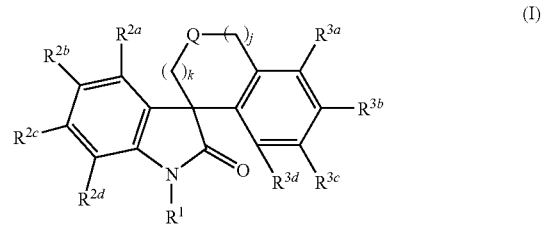

wherein k, j, Q, $R^1$, $R^{2a}$, $R^{2b}$, $R^{2c}$, $R^{2d}$, $R^{3a}$, $R^{3b}$, $R^{3c}$, and $R^{3d}$ are as defined herein, as a stereoisomer, enantiomer, tautomer thereof or mixtures thereof; or a pharmaceutically acceptable salt, solvate or prodrug thereof, which are useful for the treatment and/or prevention of sodium channel-mediated diseases or conditions, such as pain. Pharmaceutical compositions comprising the compounds and methods of preparing and using the compounds are also disclosed.

6 Claims, No Drawings

U.S. PATENT DOCUMENTS

| | | | |
|---|---|---|---|
| 6,235,780 B1 | 5/2001 | Ohuchida et al. | 514/530 |
| 6,262,293 B1 | 7/2001 | Tani et al. | 560/18 |
| 6,288,119 B1 | 9/2001 | Ohuchida et al. | 514/573 |
| 6,355,627 B1 | 3/2002 | Ishida et al. | 514/58 |
| 6,414,153 B1 | 7/2002 | Kelly et al. | 546/113 |
| 6,670,357 B2 | 12/2003 | Leftheris et al. | 514/218 |
| 6,964,973 B2 | 11/2005 | Zhi et al. | 514/312 |
| 7,368,470 B2 | 5/2008 | Sundermann et al. | 514/415 |
| 7,700,641 B2 * | 4/2010 | Chafeev et al. | 514/409 |
| 7,935,721 B2 | 5/2011 | Sun et al. | 514/409 |
| 2002/0039790 A1 | 4/2002 | Keplinger et al. | 435/371 |
| 2004/0038970 A1 | 2/2004 | Thurieau et al. | 514/234.2 |
| 2004/0167224 A1 | 8/2004 | Ozaki et al. | 514/616 |
| 2005/0004137 A1 | 1/2005 | Romano | 514/253.07 |
| 2005/0004138 A1 | 1/2005 | Romano | 514/253.07 |
| 2005/0014764 A1 | 1/2005 | Romano et al. | 514/253.06 |
| 2005/0020617 A1 | 1/2005 | Bastian et al. | 514/300 |
| 2005/0038036 A1 | 2/2005 | Romano et al. | 514/253.06 |
| 2005/0075351 A1 | 4/2005 | Berg et al. | 514/266.2 |
| 2005/0153998 A1 | 7/2005 | Ito et al. | 514/278 |
| 2005/0159473 A1 | 7/2005 | Sall et al. | 514/414 |
| 2005/0171186 A1 | 8/2005 | Fensome et al. | 514/418 |
| 2005/0256110 A1 | 11/2005 | Collins et al. | 514/224.2 |
| 2005/0256144 A1 | 11/2005 | Kath et al. | 514/275 |
| 2006/0247441 A1 | 11/2006 | Wilk | 548/408 |
| 2006/0252758 A1 | 11/2006 | Chafeev et al. | 514/249 |
| 2007/0049609 A1 | 3/2007 | Broka et al. | 514/269 |
| 2007/0072831 A1 | 3/2007 | Cai et al. | 514/80 |
| 2007/0105820 A1 | 5/2007 | Chafeev et al. | 514/80 |
| 2007/0299102 A1 | 12/2007 | Felding et al. | 514/299 |
| 2008/0103151 A9 | 5/2008 | Chafeev et al. | 514/248 |
| 2010/0099728 A1 | 4/2010 | Chafeev et al. | 514/409 |
| 2010/0137299 A1 | 6/2010 | Chafeev et al. | 514/232.8 |
| 2010/0160291 A1 | 6/2010 | Chafeev et al. | 514/211.09 |
| 2010/0160362 A1 | 6/2010 | Cadieux et al. | 514/278 |
| 2010/0173967 A1 | 7/2010 | Chafeev et al. | 514/409 |
| 2010/0331386 A1 | 12/2010 | Chafeev et al. | 514/409 |
| 2011/0034500 A1 | 2/2011 | Chafeev et al. | 514/278 |
| 2011/0086899 A1 | 4/2011 | Winters et al. | 514/409 |
| 2011/0087027 A1 | 4/2011 | Cadieux et al. | 546/15 |

FOREIGN PATENT DOCUMENTS

| | | |
|---|---|---|
| CA | 2107348 A1 | 7/1993 |
| CA | 2129215 A1 | 1/1995 |
| CA | 2 274 898 A1 | 6/1998 |
| CA | 2 450 550 A1 | 1/2003 |
| CA | 2 466 915 A1 | 8/2003 |
| CA | 2 487 494 A1 | 12/2003 |
| CA | 2 235 686 C | 6/2007 |
| DE | 1 956 237 A | 5/1971 |
| DE | 2113343 A1 | 9/1972 |
| EP | 0 147 805 A2 | 7/1985 |
| EP | 0 164 860 A1 | 12/1985 |
| EP | 0 175 551 A1 | 3/1986 |
| EP | 0 608 058 A1 | 7/1994 |
| EP | 1 422 217 A2 | 5/2004 |
| EP | 1 557 166 A1 | 7/2005 |
| FR | 2 722 195 A1 | 1/1996 |
| JP | 10-95766 A | 4/1998 |
| WO | WO 86/03749 A1 | 7/1986 |
| WO | WO 91/01306 A1 | 2/1991 |
| WO | WO 91/04974 A1 | 4/1991 |
| WO | WO 91/06545 A1 | 5/1991 |
| WO | WO 92/09577 A1 | 6/1992 |
| WO | WO 93/12786 A1 | 7/1993 |
| WO | WO 93/15051 A1 | 8/1993 |
| WO | WO 94/03427 A1 | 2/1994 |
| WO | WO 95/06688 A1 | 3/1995 |
| WO | WO 95/14667 A1 | 6/1995 |
| WO | WO 97/15556 A1 | 5/1997 |
| WO | WO 97/36895 A1 | 10/1997 |
| WO | WO 98/25901 A1 | 6/1998 |
| WO | WO 98/50016 A2 | 11/1998 |
| WO | WO 00/06556 A1 | 2/2000 |
| WO | WO 00/71129 A1 | 11/2000 |
| WO | WO 01/38564 A2 | 5/2001 |
| WO | WO 01/38564 A3 | 5/2001 |
| WO | WO 01/74775 A1 | 10/2001 |
| WO | WO 02/30868 A1 | 4/2002 |
| WO | WO 02/38544 A2 | 5/2002 |
| WO | WO 03/000677 A1 | 1/2003 |
| WO | WO 03/037274 A2 | 5/2003 |
| WO | WO 03/037890 A2 | 5/2003 |
| WO | WO 03/064425 A1 | 8/2003 |
| WO | WO 03/078394 A1 | 9/2003 |
| WO | WO 03/106457 A1 | 12/2003 |
| WO | WO 04/000225 A2 | 12/2003 |
| WO | WO 04/000227 A2 | 12/2003 |
| WO | WO 2004/048320 A1 | 6/2004 |
| WO | WO 2005/011657 A2 | 2/2005 |
| WO | WO 2005/016913 A1 | 2/2005 |
| WO | WO 2005/019208 A1 | 3/2005 |
| WO | WO 2005/035498 A1 | 4/2005 |
| WO | WO 2005/092304 A2 | 10/2005 |
| WO | WO 2005/092895 A2 | 10/2005 |
| WO | WO 2005/097107 A2 | 10/2005 |
| WO | WO 2005/097122 A2 | 10/2005 |
| WO | WO 2005/099689 A1 | 10/2005 |
| WO | WO 2005/104711 A2 | 11/2005 |
| WO | WO 2005/105753 A2 | 11/2005 |
| WO | WO 2005/110992 A1 | 11/2005 |
| WO | WO 2005/111024 A1 | 11/2005 |
| WO | WO 2006/012173 A1 | 2/2006 |
| WO | WO 2006/017075 A1 | 2/2006 |
| WO | WO 2006/023107 A1 | 3/2006 |
| WO | WO 2006/023109 A1 | 3/2006 |
| WO | WO 2006/049290 A1 | 5/2006 |
| WO | WO 2006/055752 A2 | 5/2006 |
| WO | WO 2006/087019 A1 | 8/2006 |
| WO | WO 2006/091646 A2 | 8/2006 |
| WO | WO 2006/110654 A1 | 10/2006 |
| WO | WO 2006/110917 A2 | 10/2006 |
| WO | WO 2006/113864 A2 | 10/2006 |
| WO | WO 2006/113875 A2 | 10/2006 |
| WO | WO 2008/046046 A1 | 4/2008 |
| WO | WO 2008/046049 A1 | 4/2008 |
| WO | WO 2008/046065 A1 | 4/2008 |
| WO | WO 2008/046082 A2 | 4/2008 |
| WO | WO 2008/046083 A2 | 4/2008 |
| WO | WO 2008/046084 A2 | 4/2008 |
| WO | WO 2008/046087 A2 | 4/2008 |
| WO | WO 2008/060789 A2 | 5/2008 |
| WO | WO 2008/117050 A1 | 10/2008 |
| WO | WO 2010/045197 A1 | 4/2010 |
| WO | WO 2010/045251 A2 | 4/2010 |
| WO | WO 2010/053998 A1 | 5/2010 |
| WO | WO 2010/078307 A1 | 7/2010 |
| WO | WO 2010/132352 A2 | 11/2010 |
| WO | WO 2011/002708 A1 | 1/2011 |
| WO | WO 2011/047173 A2 | 4/2011 |
| WO | WO 2011/047174 A1 | 4/2011 |
| WO | WO 2011/106729 A2 | 9/2011 |

OTHER PUBLICATIONS

Alper et al., "Eine neuartige Methode zur Synthese von Spiro[pyrrolidin-3,3'-oxindolen]: katalysierte Ringerweiterung von Cyclopropanen mit Aldiminen," *Angew. Chem.* 111(21): 3379-3381, 1999.

Alper et al., "Facile, Novel Methodology for the Synthesis of Spiro[pyrrolidin-3,3'-oxindoles]: Catalyzed Ring Expansion Reactions of Cyclopropanes by Aldimines," *Angew. Chem. Int. Ed.* 38(21): 3186-3189, 1999.

Anger et al., "Medicinal Chemistry of Neuronal Voltage-Gated Sodium Channel Blockers," *Journal of Medicinal Chemistry* 44(2): 115-137, Jan. 18, 2001.

Autrey and Tahk, "The Synthesis and Stereochemistry of Some Isatylideneacetic Acid Derivatives," *Tetrahedron* 23: 901-917, 1967.

Bacher et al., "Oxindole alkaloids from *Uncaria tomentosa* induce apoptosis in proliferating, G0/G1-arrested and bcl-2-expressing acute lymphoblastic leukaemia cells," *British Journal of Haematology* 132: 615-622, 2005.

Basavaiah et al., "$TiCl_4$ catalyzed tandem construction of C—C and C—O bonds: a simple and one-pot atom-economical stereoselective synthesis of spiro-oxindoles," *Chem. Commun.* 2621-2623, 2005.

Bean et al., "Lidocaine Block of Cardiac Sodium Channels," *J. Gen. Physiol.* 81: 613-642, May 1983.

Bennett and Xie, "A peripheral mononeuropathy in rat that produces disorders of pain sensation like those seen in man," *Pain* 33: 87-107, 1988.

Beyersbergen Van Henegouwen et al., "First Total Synthesis of *ent*-Gelsedine via a Novel Iodide-Promoted Allene *N*-Acyliminium Ion Cyclization," *J. Org. Chem.* 65(24): 8317-8325, 2000.

Beyersbergen Van Henegouwen et al., "Total Synthesis of (+)-Gelsedine," *Angw. Chem. Int. Ed.* 38(15): 2214-2217, 1999.

Billert and Beckert, "Beiträge zur Chemie der Pyrido[1,2-α]pyrazine—Reaktivität gegenüber Heterocumulenen der Kohlensäurereihe and Ketenen," *J. Prakt. Chem.* 341(4): 332-341, 1999.

Braude and Lindwall, "Condensations of Isatin with Acetone by the Knoevenagel Method," *Journal of the American Chemical Society* 55: 325-327, Jan. 1933.

Canas-Rodriguez and Leeming, "N-Phenyl-2-indolinones and N-Phenylindolines. A New Class of Antidepressant Agents," *Journal of Medicinal Chemistry* 15(7): 762-770, 1972.

Cestèele and Catterall, "Molecular mechanisms of neurotoxin action on voltage-gated sodium channels," *Biochimie* 82: 883-892, 2000.

Chande et al., "Facile synthesis of active antitubercular, cytotoxic and antibacterial agents: a Michael addition approach," *European Journal of Medicinal Chemistry* 40: 1143-1148, 2005.

Clare et al., "Voltage-gated sodium channels as therapeutic targets," *Drug Discovery Today* 5(11): 506-520, Nov. 2000.

Cossy et al., "A Convenient Route to Spiropyrrolidinyl-Oxindole Alkaloids via C-3 Substituted Ene-Pyrrolidine Carbamate Radical Cyclization," *Tetrahedron Letters* 39: 2331-2332, 1998.

Cravotto et al., "Azomethine Ylide Cycloaddition/Reductive Heterocyclization Approach to Oxindole Alkaloids: Asymmetric Synthesis of (−)-Horsfiline," *J. Org. Chem.* 66(25): 8447-8453, 2001.

Creveling and Daly, "Batrachotoxinin A [$^3$H]Benzoate Binding to Sodium Channels," *Methods in Neurosciences* 8: 25-37, 1992.

Dallacker and Sanders, "Darstellung und Reaktionen von 5-(3'-Hydroxy-oxindol-3'-yl)-1,3-benzdioxole," *Chemiker-Zeitung* 110(11): 405-411, 1986.

Devers and Galer, "Topical Lidocaine Patch Relieves a Variety of Neuropathic Pain Conditions: An Open-Label Study," *Clinical Journal* 16(3): 205-208, Sep. 2000, obtained from URL=http://ovidsp.tx.ovid.com/spb/ovidweb.cgi, download date Apr. 18, 2008, 5 pages.

Ding et al., "Structure-Based Design of Spiro-oxindoles as Potent, Specific Small-Molecule Inhibitors of the MDM2-p53 Interaction," *J. Med. Chem* 49(12): 3432-3435, 2006.

Diss et al., "A potential novel marker for human prostate cancer: voltage-gated sodium channel expression in vivo," *Prostate Cancer and Prostatic Diseases* 8: 266-273, 2005.

Domingo et al., "Studies on the Biosynthesis of Paraherquamide A and VM99955. A Theoretical Study of Intramolecular Diels—Alder Cycloaddition," *J. Org. Chem.* 68(7): 2895-2902, 2003.

Doyle et al., "Rhodium (II) Acetate and Nafion-H Catalyzed Decomposition of *N*-Aryldiazoamides. An Efficient Synthesis of 2(3*H*)-Indolinones," *J. Org. Chem* 53(5): 1017-1022, 1988.

Dutton et al., "A Total Synthesis of Gelsemine: Oxindole Spiroannelation," *J. Chem. Soc., Chem. Commun.* 765-766, 1994.

Dutton et al., "Synthesis of Hindered Spiro-Oxindoles by Photolysis of 1-(1-Alkenyl)benzotriazoles," *Tetrahedron* 55: 11927-11942, 1999.

El-Ahl, "Three-Component 1,3-Dipolar Cycloaddition Reactions in Synthesis of Spiro[pyrrolidine-2,3'-oxindoline] Derivatives," *Heteroatom Chemistry* 13(4): 324-329, 2002.

El-Gendy and Ahmedy, "Synthesis and Antimicrobial Activity of some New 2-Indolinone Derived Oximes and Spiro-Isoxazolines," *Arch. Pharm. Res.* 23(4): 310-314, 2000.

Feldman and Karatjas, "Extending Pummerer Reaction Chemistry. Asymmetric Synthesis of Spirocyclic Oxindoles via Chiral Indole-2-sulfoxides," *Org. Lett.* 8(18): 4137-4140, 2006.

Feldman et al., "Extending Pummerer Reaction Chemistry. Development of a Strategy for the Regio- and Stereoselective Oxidative Cyclization of 3-(ω-Nucleophile)-Tethered Indoles," *J. Org. Chem.* 70(16): 6429-6440, 2005.

Feldman and Vidulova, "Extending Pummerer Reaction Chemistry. Application to the Oxidative Cyclization of Indole Derivatives," *Organic Letters* 6(11): 1869-1871, 2004.

Fokas et al., "Solution Phase Synthesis of a Spiro[pyrrolidine-2,3'-oxindole] Library via a Three Component 1,3-Dipolar Cycloaddition Reaction," *Tetrahedron Letters* 39: 2235-2238, 1998.

Foster et al., "457. Furano-compounds. Part VII. A Synthesis of 2 : 3-Dihydropsoralene," *J. Chem. Soc.* 2254-2260, 1948.

Fraser et al., "Voltage-Gated Sodium Channel Expression and Potentiation of Human Breast Cancer Metastasis," *Clin. Cancer Res.* 11(15): 5381-5389, Aug. 1, 2005.

Fuchs and Funk, "Indol-2-one Intermediates: Mechanistic Evidence and Synthetic Utility. Total Syntheses of (±)-Flustramines A and C," *Org. Lett.* 7(4): 677-680, 2005.

Gálvez and García, "Synthesis of Isomeric β-Haloethylthienopyrroles," *J. Heterocyclic Chem.* 21: 393-395, Mar.-Apr. 1984.

Ganguly et al., "Solution- and solid-phase synthesis of enantiomerically pure spiro oxindoles," *Tetrahedron Letters* 43: 8981-8983, 2002.

Ganguly et al., "Synthesis of heterocyclic compounds using radical reactions and evidence for the formation of spiro radical intermediates, *Tetrahedron Letters* 45: 883-886, 2004. See also Ganguly et al., "Corrigendum to 'Synthesis of heterocyclic compounds using radical reactions and evidence for the formation of spiro radical intermediates,'" [*Tetrahedron Letters* 45: 883-886, 2004]," *Tetrahedron Letters* 45: 3835, 2004.

Garden et al., "Investigation of the selective reduction of isatin derivatives. Synthesis of α-hydroxyacetophenone derivatives and ethyl *spiro*-3,3-(ethylenedioxy)-2-hydroxyindoline carboxylates," *Tetrahedron Letters* 44: 7617-7621, 2003.

Garden et al., "A versatile synthetic methodology for the synthesis of tryptophols," *Tetrahedron* 58: 8399-8412, 2002.

González-López De Turiso and Curran, "Radical Cyclization Approach to Spirocyclohexadienones," *Organic Letters* 7(1): 151-154, 2005.

Grigg et al., "Palladium Catalysed Ter- and Tetra-molecular Queuing Processes. One-pot Routes to 3-Spiro-2-Oxindoles and 3-Spiro-2(3H)-Benzofuranones," *Tetrahedron Letters* 37(5): 695-698, 1996.

Grigg et al., "Spiro-oxindoles via bimetallic [Pd(0)/Ag(I)] catalytic intramolecular Heck-1,3-dipolar cycloaddition cascade reactions," *Tetrahedron Letters* 43: 2605-2608, 2002.

Ikoma et al., "The neurobiology of itch," *Nature Reviews Neuroscience* 7: 535-547, Jul. 2006.

Islip and White, "236. Some Reactions of 2-(3-Oxindolyl)ethylamines," *Journal of the Chemical Society* 1201-1204, 1964.

Julian et al., "Studies in the Indole Series. VI. On the Synthesis of Oxytryptophan and Further Studies of 3-Alkylation of Oxindoles," *Journal of the American Chemical Society* 57: 2026-2029, Nov. 1935.

Julian et al., "Studies in the Indole Series. VIII. Yohimbine (Part 1). The Mechanism of Dehydrogenation of Yohimbine and Related Compounds," *Journal of the American Chemical Society* 70: 174-179, Jan. 1948.

Kang et al., "Pteropodine and isopteropodine positively modulate the function of rat muscarinic $M_1$ and $5-HT_2$ receptors expressed in *Xenopus* oocyte," *European Journal of Pharmacology* 444: 39-45, 2002.

Karp et al., "Preparation of 4-Hydroxy-2-trifluoromethylthiophene: A Novel Bioisostere of α,α,α-Trifluoro-*m*-cresol," *Synthesis* 8: 1078-1080, 2000.

Kende et al., "Intramolecular Radical Cyclization of Phenolic Enolates," *J. Am. Chem. Soc.* 110: 2210-2218, 1988.

Klugbauer et al., "Structure and functional expression of a new member of the tetrodotoxin-sensitive voltage-activated sodium channel family from human neuroendocrine cells," *EMBO J.* 14(6): 1084-1090, 1995.

Kobayashi and Furukawa, "Studies on Indole Derivatives. I. Synthesis of 3-Phenyl-9*H*-pyridazino-[3,4-*b*]indole Derivatives," *Chemical & Pharmaceutical Bulletin* 12(10): 1129-1135, Oct. 1964.

Kollmar et al., "2-Amino-3-Fluorobenzoic Acid [Benzoic acid, 2-amino-3-fluoro-]," *Organic Syntheses, Coll.* 79: 196, 2002, 5 pages.

Kornet and Thio, "Oxindole-3-spiropyrrolidines and -piperidines. Synthesis and Local Anesthetic Activity," *Journal of Medicinal Chemistry* 19(7): 892-898, 1976.

Kotha et al., "Recent applications of the Suzuki-Miyaura cross-coupling reaction in organic synthesis," *Tetrahedron* 58: 9633-9695, 2002.

Kumar et al., "A New Route to Spiropyrrolidinyl-oxindole Alkaloids via Iodide Ion Induced Rearrangement of [(N-Aziridinomethylthio)methylene]-2-oxindoles," *Organic Letters* 3(26): 4193-4196, 2001.

Kuzma et al., "Progress in the Development of Ultra-Long-Acting Local Anesthetics," *Regional Anesthesia* 22(6): 543-551, Nov.-Dec. 1997.

Laus, "Kinetics of isomerization of tetracyclic spiro oxindole alkaloids," *J. Chem. Soc., Perkin Trans.* 2: 315-317, 1998.

Laus et al., "Analysis of the kinetics of isomerization of spiro oxindole alkaloids," *J. Chem. Soc., Perkin Trans.* 2: 1931-1936, 1996.

Lee-Son et al., "Stereoselective Inhibition of Neuronal Sodium Channels by Local Anesthetics," *Anesthesiology* 77: 324-335, 1992.

Lerchner and Carreira, "Synthesis of (±)-Strychnofoline via a Highly Convergent Selective Annulation Reaction," *Chem. Eur. J.* 12: 8208-8219, 2006.

Leuwer et al., "An improved model for the binding of lidocaine and structurally related local anaesthetics to fast-inactivated voltage-operated sodium channels, showing evidence of cooperativity," *British Journal of Pharmacology* 141(1): 47-54, 2004.

Lindwall and Maclennan, "A Condensation of Acetophenone with Isatin by the Knoevenagel Method," *Journal of the American Chemical Society* 54: 4739-4744, Dec. 1932.

Lossin et al., "Molecular Basis of an Inherited Epilepsy," *Neuron* 34: 877-884, Jun. 13, 2002.

Lutz and Clark, "Acid-Catalyzed Rearrangements of the γ-(Methylanilino)lactone of cis-β-(p-Bromobenzoyl)-β-methylacrylic Acid, and of trans-β-(p-Bromobenzoyl)acrylic Methylanilide, to Oxindoles," *J. Org. Chem.* 25: 193-196, Feb. 1960.

Ma and Cai, "N,N-Dimethyl Glycine-Promoted Ullmann Coupling Reaction of Phenols and Aryl Halides," *Organic Letters* 5(21): 3799-3802, 2003.

Maercker and Theysohn, "Versuche zur Umlagerung von 2-Cyclopropyl-äthyl-Anionen," *Liebigs Ann. Chem.* 759: 132-157, 1972.

Maginnity and Gaulin, "Derivatives of o-, m- and p-Aminobenzotrifluoride," *J. Am. Chem. Soc.* 73: 3579-3580, Aug. 1951.

Majumdar et al., "1-Alkylisatins via Aldol-Retro-aldol Condensation," *J. Chem. Research (S)*, 460-461, 1996.

Mann et al., "The Synthesis of Lignans and Related Structures using Quinodimethanes and Isobenzofurans: Approaches to the Podophyllins," *J. Chem. Soc. Perkin Trans. I*: 2081-2088, 1984.

Mannaioni et al., "Tryptophan Metabolism and Hepatic Encephalopathy. Studies on the Sedative Properties of Oxindole," *Advances in experimental medicine and biology* 467: 155-167, 1999.

Mao and Baldwin, "New Spirocyclic Oxindole Synthesis Based on a Hetero Claisen Rearrangement," *Organic Letters* 6(14): 2425-2428, 2004.

Mao and Chen, "Systemic lidocaine for neuropathic pain relief," *Pain* 87: 7-17, 2000.

Marcantonio et al., "An Investigation into Causes and Effects of High Cyanide Levels in the Palladium-Catalyzed Cyanation Reaction," *Organic Letters* 6(21): 3723-3725, 2004.

Marti and Carreira, "Construction of Spiro[pyrrolidine-3,3'-oxindoles]—Recent Applications to the Synthesis of Oxindole Alkaloids," *Eur. J. Org. Chem.* 2209-2219, 2003.

Marti and Carreira, "Total Synthesis of (−)-Spirotryprostatin B: Synthesis and Related Studies," *J. Am. Chem. Soc.* 127(32): 11505-11515, 2005.

McNeal et al., "[³H]Batrachotoxinin A 20α-Benzoate Binding to Voltage-Sensitive Sodium Channels: A Rapid and Quantitative Assay for Local Anesthetic Activity in a Variety of Drugs," *J. Med. Chem.* 28(3): 381-388, 1985.

Miyake et al., "Preparation and Synthetic Applications of 2-Halotryptamines: Synthesis of Elacomin and Isoelacomine," *Organic Letters* 6(5): 711-713, 2004.

Miyamoto et al., "Highly Diastereoselective One-Pot Synthesis of Spirocyclic Oxindoles through Intramolecular Ullmann Coupling and Claisen Rearrangement," *Angew. Chem. Int. Ed.* 45: 2274-2277, 2006.

Miyaura and Suzuki, "Palladium-Catalyzed Cross-Coupling Reactions of Organoboron Compounds," *Chem. Rev.* 95: 2457-2483, 1995.

Muci and Buchwald, "Practical Palladium Catalysts for C—N and C—O Bond Formation," *Topics in Current Chemistry* 219: 131-209, 2002.

Muhammad et al., "Two stereoisomeric pentacyclic oxindole alkaloids from *Uncaria tomentosa*; uncarine C and uncarine E," *Acta Cyst.* C57: 480-482, 2001.

Nair et al., "Formal dipolar cycloaddition of allylsilanes to o-quinonoid compounds: a convenient route to benzofused and spirofused heterocycles," *Tetrahedron Letters* 43: 5349-5351, 2002.

Nair et al., "N-Heterocyclic Carbene Catalyzed Reaction of Enals and 1,2-Dicarbonyl Compounds: Stereoselective Synthesis of Spiro γ-Butyrolactones," *Org. Lett.* 8(3): 507-509, 2006.

Nagakura et al., "Allodynia and Hyperalgesia in Adjuvant-Induced Arthritic Rats: Time Course of Progression and Efficacy of Analgesics," *The Journal of Pharmacology and Experimental Therapeutics* 306(2): 490-497, 2003, obtained from URL=http://jpet.aspetjournals.org, download date Aug. 14, 2009.

Okita and Isobe, "Synthesis of the Pentacyclic Intermediate for Dynemicin A and Unusual Formation of Spiro-oxindole Ring," *Tetrahedron* 50(38): 11143-11152, 1994.

Onishi et al., "Concise, Asymmetric Total Synthesis of Spirotryprostatin A," *Organic Letters* 5(17): 3135-3137, 2003.

Onishi et al., "Concise, asymmetric total synthesis of spirotryprostatin A," *Tetrahedron* 60: 9503-9515, 2004.

Overman and Watson, "Diasteroselection in the Formation of Spirocyclic Oxindoles by the Intramolecular Heck Reaction," *J. Org. Chem* 71: 2587-2599, 2006.

Popp and Pajouhesh, "Potential Anticonvulsants IV: Condensation of Isatin with Benzoylacetone and Isopropyl Methyl Ketone," *Journal of Pharmaceutical Sciences* 71(9): 1052-1054, Sep. 1982.

Popp et al., "Synthesis of Potential Anticonvulsants: Consensation of Isatins with Acetone and Related Ketones," Journal of Pharmaceutical Sciences 69(10): 1235-1237, Oct. 1980.

Popp, "Potential Anticonvulsants. V. The Condensation of Isatins with C-Acetyl Heterocyclic Compounds," *J. Heterocyclic Chem.* 19: 589-592, May-Jun. 1982.

Raj and Raghunathan, "A Novel Entry into a New Class of Spiro Heterocyclic Framework: A Facile Synthesis of Dispiro[oxindole-1,2,3,4-tetrahydro-naphthalen-1-one]pyrrolidines and Spiro[1,2,3,4-tetrahydro-naphthalen-1-one]pyrrolidines," *Synthetic Communications* 33(7): 1131-1139, 2003.

Raj and Raghunathan, "A novel entry into a new class of spiroheterocyclic framework: regioselective synthesis of dispiro[oxindole-cyclohexanone]-pyrrolidines and dispiro[oxindole-hexahydroindazole]pyrrolidines," *Tetrahedron* 57: 10293-10298, 2001.

Raj et al., "Synthesis, Antimicrobial and Antifungal Activity of a New Class of Spiro Pyrrolidines," *Bioorganic & Medicinal Chemistry* 11: 407-419, 2003.

Reddy et al., "Synthesis and Pharmacological Evaluation of N,N-Diarylguanidines as Potent Sodium Channel Blockers and Anticonvulsant Agents," *J. Med. Chem.* 41(17): 3298-3302, 1998.

Ren and Dubner, "Enhanced Descending Modulation of Nociception in Rats With Persistent Hindpaw Inflamation," *Journal of Neurophysiology* 76(5): 3025-3037, Nov. 1996.

Rivalle and Bisagni, "Ethyl (4-N-Acylaminopyridin-3-yl)glyoxylate and 5-Azaisatin as New Synthons for a Route to Various New Polyheterocycles," *J. Heterocyclic Chem.* 34: 441-444, Mar.-Apr. 1997.

Rossiter, "A convenient synthesis of 3-methyleneoxindoles: cytotoxic metabolites of indole-3-acetic acids," *Tetrahedron Letters* 43: 4671-4673, 2002.

Sawyer, "Recent Advances in Diaryl Ether Synthesis," *Tetrahedron* 56: 5045-5065, 2000.

Schnyder et al., "Synthesis of Primary Aromatic Amides by Aminocarbonylation of Aryl Halides Using Formamide as an Ammonia Synthon," *J. Org. Chem.* 66: 4311-4315, 2001.

Schulenburg and Archer, "An Unusual Base-catalyzed Cyclization," *Journal of the American Chemical Society* 83(14): 3091-3096, Jul. 20, 1961.

Sebahar et al., "Asymmetric, stereocontrolled total synthesis of (+) and (−)- spirotryprostatin B via a diastereoselective azomethine ylide [1,3]-dipolar cycloaddition reaction," *Tetrahedron* 58: 6311-6322, 2002.

Shoop et al., "Anthelmintic Activity of Paraherquamide in Sheep," *J. Parasitol.* 76(3): 349-351, Jun. 1990.

Simas et al., "Regioselective Lithiation of Resorcinol Derivatives: Synthesis of Mono O-MOM- and O-Benzylresorcinols Prenylated at C-2 or C-4 Positions," *Synthesis* 6: 1017-1021, 1999.

Singh et al., "Novel cAMP PDE III Inhibitors: Imidazo[4,5-*b*]pyridine-2(3*H*)-ones and Thiazolo[4,5-*b*]pyridin-2(3*H*)-ones and Their Analogs," *J. Med. Chem.* 37: 248-254, 1994.

Smith et al., "Sodium channel protein expression enhances the invasiveness of rat and human prostate cancer cells," *FEBS Letters* 423: 19-24, 1998.

Sridhar and Raghunathan, "Rapid Access for the Synthesis of 1-N-Methyl-spiro[2.3' ]oxindole-spiro[3.7"] (3"-Aryl)-5"-methyl-3",3a",4",5",6",7"-hexahydro-2H-pyrazolo[4,3-c]pyridine-4-aryl-pyrrolidines Through Sequential 1,3-Dipolar Cycloaddition and Annulation," *Synthetic Communications* 36: 21-29, 2006.

Subramaniyan et al., "A facile entry into a new class of spiroheterocycles: synthesis of dispiro[oxindolechromanone/flavanone/tetralone]pyrroloisoquinoline ring systems," *Tetrahedron* 58: 9075-9079, 2002.

Suchý et al., "Synthesis, Absolute Configuration, and Enantiomeric Enrichment of a Cruciferous Oxindole Phytoalexin, (*S*)-(−)-Spirobrassinin, and Its Oxazoline Analog," *J. Org. Chem.* 66: 3940-3947, 2001.

Tacconi et al., "Heterodiene Syntheses—V 1,2- versus 1,4-cycloaddition reactions of enamines to n-substituted 3-oxindolideneacetophenones," *Tetrahedron* 27: 561-579, 1971.

Takahashi et al., "Palladium(0)-Catalyzed Carbonylation on the Multipin™ System," *Tetrahedron Letters* 40: 7843-7846, 1999.

Tanelian and Brose, "Neuropathic Pain Can Be Relieved by Drugs That Are Use-dependent Sodium Channel Blockers: Lidocaine, Carbamazepine, and Mexiletine," *Anesthesiology* 74(5): 949-951, May 1991.

Ting et al., "Substituted 1,3-Dihydro-2*H*-pyrrolo[2,3-b]pyridin-2-ones as Potential Antiinflammatory Agents," *J. Med. Chem.* 33(10): 2697-2706, 1990.

Tokunaga et al., "Oxindole Derivatives as Orally Active Potent Growth Hormone Secretagogues," *J. Med. Chem.* 44(26): 4641-4649, 2001.

Trost and Brennan, "Palladium Asymmetric Allylic Alkylation of Prochiral Nucleophiles: Horsfiline," *Org. Lett.* 8(10): 2027-2030, 2006.

Trost and Frederiksen, "Palladium-Catalyzed Asymmetric Allylation of Prochiral Nucleophiles: Synthesis of 3-Allyl-3-Aryl Oxindoles," *Angew. Chem. Int. Ed.* 44: 308-310, 2005.

Venkatesan et al., "Total Synthesis of SR 121463 A, a Highly Potent and Selective Vasopressin $V_2$ Receptor Antagonist," *Journal of Organic Chemistry* 66(11): 3653-3661, Jun. 1, 2001.

Viaud et al., "Pyrrolo[2,3-*b*]pyridin-2(2*H*)-one Derivatives as Potential Non-opioid Analgesic Agents," *Pharmaceutical Sciences* 3: 283-287, 1997.

Viaud et al., "Acylation of Oxazolo[4,5-*b*]pyridin-2(3*H*)-ones, 2-Phenyloxazolo[4,5-*b*]pyridines and Pyrrolo[2,3-*b*]pyridin-2(2*H*)-ones," *Tetrahedron* 53(14): 5159-5168, 1997.

Villamil et al., "Efficacy of lidocaine in the treatment of pruritus in patients with chronic cholestatic liver diseases," *The American Journal of Medicine* 118: 1160-1163, 2005.

Vippagunta et al., "Crystalline solids," *Advanced Drug Delivery Reviews* 48: 3-26, 2001.

Walker et al., "Limitations in Ring Rearrangement of Fused γ-Lactams Imposed by a Quaternary Carbon Atom. Cyclization of Acid Lactams to Spiro Keto Lactams," *J. Org. Chem.* 30(9): 2973-2983, Sep. 1965.

Wang and Ganesan, "A Biomimetic Total Synthesis of (−)-Spirotryprostatin B and Related Studies," *J. Org. Chem.* 65(15): 4685-4693, 2000.

Wolff (ed.), *Burger's Medicinal Chemistry and Drug Discovery, Fifth Edition, vol. I: Principles and Practice*, John Wiley & Sons, Inc., New York, New York, 1994, pp. 975-977.

Wrona et al., "Hydroxyl Radical-Mediated Oxidation of Serotonin: Potential Insights into the Neurotoxicity of Methamphetamine," *J. Neurochem.* 64(3): 1390-1400, 1995.

Yang and Williams, "Palladium-Catalyzed Cyanation of Aryl Bromides Promoted by Low-Level Organotin Compounds," *Organic Letters* 6(17): 2837-2840, 2004.

Zinser et al., "Anthelmintic paraherquamides are cholinergic antagonists in gastrointestinal nematodes and mammals," *J. vet. Pharmacol. Therap.* 25: 241-250, 2002.

Database CAPLUS online, Accession No. 1960:50362, 1 page.

Office Action dated Jun. 20, 2008 from U.S. Appl. No. 11/407,859, filed Apr. 20, 2006.

Office Action dated Dec. 15, 2008 from U.S. Appl. No. 11/408,269, filed Apr. 20, 2006.

Office Action dated Jan. 15, 2009 from U.S. Appl. No. 11/407,859, filed Apr. 20, 2006.

Office Action dated Apr. 24, 2009 from U.S. Appl. No. 11/402,200, filed Apr. 11, 2006.

Office Action dated Nov. 17, 2009 from U.S. Appl. No. 11/402,200, filed Apr. 11, 2006.

International Search Report and Written Opinion for PCT/US2006/014352 filed Apr. 11, 2006, 11 pages.

International Preliminary Report on Patentability for PCT/US2006/014352 filed Apr. 11, 2006, 6 pages.

Al-Thebeiti and El-Zohry, "A Facile Route For the Synthesis of Some New Spiro[indoline-3,3'-indan]-2,1'-dione Derivatives," *Heterocycles* 41(11): 2475-2480, 1995.

Banfi et al., "High Diastereoface Selection in an Ester Enolate Addition to α-Alkoxy Aldehydes: Stereoselective Synthesis of α-Methylene-β-hydroxy-γ-alkoxy Esters," *J. Org. Chem.* 49: 3784-3790, 1984.

Binder et al., "Disease mechanisms in neuropathic itch," *Nature Clinical Practice/Neurology* 4(6): 329-337, Jun. 2008.

Blair and Bean, "Roles of Tetrodotoxin (TTX)-Sensitive $Na^+$ Current, TTX-Resistant $Na^+$ Current, and $Ca^{2+}$ Current in the Action Potentials of Nociceptive Sensory Neurons," *Journal of Neuroscience* 22(23): 10277-10290, Dec. 1, 2002.

Bond et al., "Cyclopiamines A and B, Novel Oxindole Metabolites of *Penicillium cyclopium* Westling," *Journal of the Chemical Society, Perkin Transaction 1: Organic and Bio-Organic Chemistry* 7: 1751-1761, 1979.

Brackenbury and Djamgoz, "Activity-dependent regulation of voltage-gated $Na^+$ channel expression in Mat-LyLu rat prostate cancer cell line," *J. Physiol.* 573.2: 343-356, 2006.

Bramson et al., "Oxindole-Based Inhibitors of Cyclin-Dependent Kinase 2 (CDK2): Design, Synthesis, Enzymatic Activities, and X-ray Crystallographic Analysis," *J. Med. Chem.* 44: 4339-4358, 2001.

Caldwell et al., "Sodium channel $Na_v1.6$ is localized at nodes of Ranvier, dendrites, and synapses," *PNAS* 97(10): 5616-5620, May 9, 2000.

Capilla et al., "Synthesis of isoquinolines and tetrahydroisoquinolines as potential antitumour agents," *Tetrahedron* 57: 8297-8303, 2001.

Carlson et al., "Potential hypolipidemic agents: VI. Syntheses of some new halo-substituted pyridine compounds. Effects on noradrenaline-stimulated free fatty acid mobilization," *Acta Pharm. Suecica* 9: 411-418, 1972.

Cassebaum and Liedel, "Beziehungen zwischen Konstitution und α-Aminosäure-dehydrogenasewirkung von Isatinen," *Journal für praktische Chemie* 4(12):91-95, 1960.

Chaplan et al., "Quantitative assessment of tactile allodynia in the rat paw," *Journal of Neuroscience Methods* 53: 55-63, 1994.

Chioni et al., "A novel adhesion molecule in human breast cancer cells: Voltage-gated $Na^+$ channel β1 subunit," *The International Journal of Biochemistry & Cell Biology* 41: 1216-1227, 2009.

Chung and Chung, "Sodium channels and neuropathic pain," *Novartis Found Symposium* 261: 19-31, 2004.
Claudi et al., "Synthesis and Dopamine Receptor Affinities of 2-(4-Fluoro-3-hydroxyphenyl)ethylamine and N-Substituted Derivatives," *J. Med. Chem.* 33: 2408-2412, 1990.
Coppola, "N-Arylation of Isatins. A Direct Route to N-Arylisatoic Anhydrides," *J. Heterocyclic Chem.* 24: 1249-1251, Sep./Oct. 1987.
Cox et al., "An SCN9A channelopathy causes congenital inability to experience pain," *Nature* 444: 894-898, Dec. 14, 2006.
Craner et al., "Molecular changes in neurons in multiple sclerosis: Altered axonal expression of $Na_v1.2$ and $Na_v1.6$ sodium channels and $Na^+ / Ca^{2+}$ exchanger," *PNAS* 101(21): 8168-8173, May 25, 2004.
Cube et al., "3-(2-Ethoxy-4-{4-[3-hydroxy-2-methyl-4-(3-methylbutanoyl)-phenoxy]butoxy}phenyl)propanoic acid: a brain penetrant allosteric potentiator at the metabotropic glutamate receptor 2 (mGluR2)," *Bioorganic & Medicinal Chemistry Letters* 15: 2389-2393, 2005.
Dib-Hajj et al., "Genetics and Molecular Pathophysiology of $Na_v1.7$-Related Pain Syndromes," *Advances in Genetics* 63: 85-110, 2008.
Dib-Hajj et al., "NaN, a novel voltage-gated Na channel, is expressed preferentially in peripheral sensory neurons and down-regulated after axotomy," *Proc. Natl. Acad. Sci. USA* 95: 8963-8968, Jul. 1998.
Do and Bean, "Subthreshold Sodium Currents and Pacemaking of Subthalamic Neurons: Modulation by Slow Inactivation," *Neuron* 39: 109-120, Jul. 3, 2003.
Dubuisson and Dennis, "The Formalin Test: A Quantitative Study of the Analgesic Effects of Morphine, Meperidine, and Brain Stem Stimulation in Rats and Cats," *Pain* 4: 161-174, 1977.
Ettinger and Argoff, "Use of Antiepileptic Drugs for Nonepileptic Conditions: Psychiatric Disorders and Chronic Pain," *Neurotherapeutics: The Journal of the American Society for Experimental Neuro Therapeutics* 4:75-83, Jan. 2007.
Fishman et al., "Intravenous Lidocaine for Treatment-resistant Pruritus," *American Journal of Medicine* 102: 584-585, Jun. 1997.
Flanagan et al., "Radical cyclisation reactions with indoles," *Tetrahedron Letters* 44: 1795-1798, 2003.
Fuchs and See, "Basolateral amygdala inactivation abolishes conditioned stimulus- and heroin-induced reinstatement of extinguished heroin-seeking behavior in rats," *Psychopharmacology* 160: 425-433, 2002.
Fuji et al., "Direct Asymmetric Synthesis of Quaternary Carbon Centers via Addition-Elimination Process: Nitroolefination of α-Substituted δ-Lactones," *J. Am. Chem. Soc.* 111: 7921-7925, 1989.
Fujita et al., "The Beckmann Rearrangement by Means of Phosphoryl Chloride/N,N-Dimethylacetamide; A Novel and Convenient Method for Preparing Benzoxazoles," *Synthesis* 68-69, Jan. 1982.
Goldberg et al., "Loss-of-function mutations in the $Na_v1.7$ gene underlie congenital indifference to pain in multiple human populations," *Clin. Genet.* 71: 311-319, 2007.
Goldberg, "The Significance of Molecular Type, Shape and Complementarity in Clathrate Inclusion," *Topics in Current Chemistry* 149: 1-44, 1988.
Grigoryan et al., "Synthesis and antispasmodic activity of spiro[β-carbolineindolones] and spiro[indoleindolo[2,3-c]azepinones]," *Hayastani Kimiakan Handes* 58(3): 100-104, 2005, CAPLUS Database Accession No. 2005:876436, 4 pages.
Guillaumet et al., "Synthèse d'un analogue dioxinique du psoralene," *Tetrahedron Letters* 29(22): 2665-2666, 1988.
Hains et al., "Upregulation of Sodium Channel $Na_v1.3$ and Functional Involvement in Neuronal Hyperexcitability Associated with Central Neuropathic Pain after Spinal Cord Injury," *Journal of Neuroscience* 23(26): 8881-8892, Oct. 1, 2003.
Hamann et al., "Motor disturbances in mice with deficiency of the sodium channel gene Scn8a show features of human dystonia," *Experimental Neurology* 184: 830-838, 2003.
Haufe et al., "The promiscuous nature of the cardiac sodium current," *Journal of Molecular and Cellular Cardiology* 42: 469-477, 2007.
Hiemstra et al., "Models of Folate Coenzymes—VIII: An Approach to Yohimbane Alkaloids Via Carbon-Fragment Transfer From $N^5$, $N^{10}$-Methylenetetrahydrofolate Models," *Tetrahedron* 39(23): 1981-1986, 1983.

Inan et al., "Inhibitory effect of lidocaine on pain and itch using formalin-induced nociception and 5'-guanidinonaltrindole-induced scratching models in mice: Behavioral and neuroanatomical evidence," *European Journal of Pharmacology* 616: 141-146, 2009.
Iranpoor et al., "A novel method for the highly efficient synthesis of 1,2-benzisoxazoles under neutral conditions using the $Ph_3P/DDQ$ system," *Tetrahedron Letters* 47: 8247-8250, 2006.
Ishiyama et al., "Synthesis of Arylboronates via the Palladium(0)-Catalyzed Cross-Coupling Reaction of Tetra(alkoxo)diborons with Aryl Triflates," *Tetrahedron Letters* 38(19): 3447-3450, 1997.
Itoh et al., "Introduction of a Hydroxy Group at the Para Position and N-Iodophenylation of N-Arylamides Using Phenyliodine(III) Bis(Trifluoracetate)," *J. Org. Chem.* 67: 7424-7428, 2002.
Jarvis et al., "A-803467, a potent and selective $Na_v1.8$ sodium channel blocker, attenuates neuropathic and inflammatory pain in the rat," *PNAS* 104(20): 8520-8525, May 15, 2007.
Jorgensen and Berteau, "Thyroxine Analogs. 21. o- and m-L-Thyroxine and Related Compounds," *Journal of Medicinal Chemistry* 14(12): 1199-1202, 1971.
Kaila et al., "Synthesis and Biological Evaluation of Quinoline Salicylic Acids as P-Selectin Antagonists," *J. Med. Chem.* 50: 21-39, 2007.
Kamara et al., "The First Direct Transformation of 2,2'-Dihydroxychalcones into Coumestans," *Tetrahedron* 55: 861-868, 1999.
Kamiya et al., "A Nonsense Mutation of the Sodium Channel Gene SCN2A in a Patient with Intractable Epilepsy and Mental Decline," *Journal of Neuroscience* 24(11): 2690-2698, Mar. 17, 2004.
Kim et al., "BACE1 regulates voltage-gated sodium channels and neuronal activity," *Nature Cell Biology* 9(7): 755-764, Jul. 2007.
Kim et al., "Design, synthesis, and evaluation of dioxane-based antiviral agents targeted against the Sindbis virus capsid protein," *Bioorganic & Medicinal Chemistry Letters* 15: 3207-3211, 2005.
King et al., "Hydroxy-quinoxalines and -phenazines, and Experiments on the Preparation of Hydroxyquinoxaline Di-N-oxides," *J. Chem. Soc.* 3012-3016, 1949.
Kirmse et al., "Intramolecular Reactivity of Arylcarbenes: Derivatives of o-Tolylcarbene," *J. Org. Chem.* 59: 3821-3829, 1994.
Kubo et al., "Michael Additions of Indoles to 2-oxoindolin-3-ylidene Ketones," *Heterocycles* 4(10), 1675-1680, 1976.
Lackey and Sternbach, "Synthesis of Substituted Quinoline-4-carboxylic Acids," *Synthesis*: 993-997, Oct. 1993.
Lai et al., "The role of voltage-gated sodium channels in neuropathic pain," *Current Opinion in Neurobiology* 13:291-297, 2003.
Lindemann et al., "Zur Kenntnis der Indoxazene," *Justus Liebigs Annalen der Chemie* 456: 284-311, 1927.
Liu et al., "Mutations in Cardiac Sodium Channels: Clinical Implications," *Am. J. Pharmacogenomics* 3(3): 173-179, 2003.
Loudon and Ogg, "2:3-Dihydro-3-oxobenz-1:4-oxazines," *J. Chem. Soc.*: 739-744, 1955.
Lyalin et al., [title unavailable], *Zhurnal Organicheskoi Khimii* 20(4): 846-849, 1984.
MacNicol, "Clathrates and Molecular Inclusion Phenomena," *Chemical Society Reviews* 7(1): 65-87, 1978.
McMurtrey and Daves, Jr., "König's Adducts of N-Alkyl(aryl)aminoethanols and Quinones. 3,4-Dihydro-4-alkyl(aryl)-8a-hydroxy-2H-1,4,benzoxazin-6(8aH)-ones," *J. Org. Chem.* 35(12): 4252-4253, 1970.
Meisler et al., "Sodium channel gene family: epilepsy mutations, gene interactions and modifier effects," *J. Physiol.* 588.11: 1841-1848, 2010.
Morie et al., "Asymmetric Synthesis of the Enantiomers of 2-Aminomethyl-4-(4-Fluorobenzyl)morpholine, an Intermediate of Mosapride, a Gastroprokinetic Agent," *Heterocycles* 38(5): 1033-1040, 1994.
Morinville et al., "Distribution of the Voltage-Gated Sodium Channel $Na_v1.7$ in the Rat: Expression in the Autonomic and Endocrine Systems," *Journal of Comparative Neurology* 504: 680-689, 2007.
Morton et al., "Novel solid-phase synthesis of 1,5-benzothiazepine-4-one derivatives," *Tetrahedron Letters* 41: 3029-3033, 2000.
Nagamura and Saito, "Antitumor Antibiotics: Duocarmycins," *Chemistry of Heterocyclic Compounds* 34(12): 1386-1405, 1998.

Nagamura et al., "Wagner-Meerwein Rearrangement of Duocarmycins," *Chem. Pharm. Bull.* 44(5): 933-939, May 1996.

Nakamura et al., "Cancer preventive agents, Part 2: Synthesis and evaluation of 2-phenyl-4-quinolone and 9-oxo-9,10-dihydroacridine derivatives as novel antitumor promoters," *Bioorganic & Medicinal Chemistry* 13: 4396-4401, 2005.

Newkome et al., "α-Methyl Functionalization of Electron-Poor Heterocycles: Free Radical Chlorination," *Synthesis* 676-679, Aug. 1984.

Nicolaus, *Decision Making in Drug Research*, Raven Press, New York, 1983, Franz Gross (ed.), "Symbiotic Approach to Drug Design," pp. 173-186.

Niemann et al., "The Synthesis of 3'-Fluoro-*dl*-thyronine and Some of its Iodinated Derivatives," *J. Am. Chem. Soc.* 63: 609-611, Feb. 1941.

Oguri et al., "Amino Acids and Peptides. XXVIII. A New Synthesis of α-Amino Acid Derivatives by Alkylation of Schiff Bases derived from Glycine and Alanine," *Chem. Pharm. Bull.* 25(9): 2287-2291, 1977.

Orlova et al., "Synthesis of 2,3,4,5-Tetrahydro-1,5-Benzox(and Thi)azepines and Their Utilization for the Preparation of Condensed Indoles," Translated from *Khimiya Geterotsiklicheskikh Soedinenii* 9: 1262-1266, Sep. 1975, 5 pag.

Papale et al., "Heterozygous mutations of the voltage-gated sodium channel SCN8A are associated with spike-wave discharges and absence epilepsy in mice," *Human Molecular Genetics* 18(9): 1633-1641, 2009.

Pereira et al., "Severe epilepsy, retardation, and dysmorphic features with a 2q deletion including SCN1A and SCN2A," *Neurology* 63: 191-192, 2004.

Pouton, "Lipid formulations for oral administration of drugs: non-emulsifying, self-emulsifying and 'self-microemulsifying' drug delivery systems," *European Journal of Pharmaceutical Sciences* 11(Suppl 2): S93-S98, 2000.

Priest, "Future potential and status of selective sodium channel blockers for the treatment of pain," *Current Opinion in Drug Discovery & Development* 12(5): 682-692, 2009.

Puopolo et al., "Roles of Subthreshold Calcium Current and Sodium Current in Spontaneous Firing of Mouse Midbrain Dopamine Neurons," *Journal of Neuroscience* 27(3): 645-656, Jan. 17, 2007.

Raymond et al., "Expression of Alternatively Spliced Sodium Channel α-Subunit Genes," *Journal of Biological Chemistry* 279(44): 46234-46241, Oct. 29, 2004.

Rehn et al., "The Three-Component Reaction between Isatin, α-Amino Acids, and Dipolarophiles," *Eur. J. Org. Chem.* 413-418, 2004.

Reimann et al., "Pain perception is altered by a nucleotide polymorphism in SCN9A," *PNAS* 107(11): 5148-5153, Mar. 16, 2010.

Rhodes et al., "Noninactivating voltage-gated sodium channels in severe myoclonic epilepsy of infancy," *PNAS* 101(30): 11147-11152, Jul. 27, 2004.

Rosevear and Wilshire, "Cyclization Reactions in Azole Chemistry: The Reaction of Some Azoles with *o*-Fluoro-acetophenone, *o*-Fluorobenzaldehyde and *o*-Fluorobenzophenone," *Aust. J. Chem.* 44: 1097-1114, 1991.

Ross et al., "Loss of Inhibitory Interneurons in the Dorsal Spinal Cord and Elevated Itch in *Bhlhb5* Mutant Mice," *Neuron* 65: 886-898, Mar. 25, 2010.

Ruan et al., "Sodium channel mutations and arrhythmias," *Nature Reviews Cardiology* 6: 337-348, May 2009.

Sadler, "Separation of Isomeric Isatins," *J. Org. Chem.* 21(2): 169-170, 1956.

Saenger, "Cyclodextrin Inclusion Compounds in Research and Industry," *Angew. Chem. Int. Ed. Engl* 19: 344-362, 1980.

Sakaki et al., "Discovery of IRL 3461: A Novel and Potent Endothelin Antagonist With Balanced $ET_A/ET_B$ Affinity," *Biooganic & Medicinal Chemistry Letters* 8: 2241-2246, 1998.

Sauviat et al., "Blockade of sodium channels by Bistramide A in voltage-clamped frog skeletal muscle fibres," *Biochimica et Biophysica Acta* 1103: 109-114, 1992.

Sircar et al., "Synthesis and SAR of *N*-Benzoyl-L-Biphenylalanine Dervatives: Discovery of TR-14035, A Dual $\alpha_4\beta_7/\alpha_4\beta_1$ Integrin Antagonist," *Bioorganic & Medicinal Chemistry Letters* 10: 2051-2066, 2002.

Steinhoff et al., "Proteinase-Activated Receptor-2 Mediates Itch: A Novel Pathway for Pruritus in Human Skin," *Journal of Neuroscience* 23(15): 6176-6180, Jul. 16, 2003.

Tamaoka, "Paramyotonia Congenita and Skeletal Sodium Channelopathy," *Internal Medicine* 42(9): 769-770, Sep. 2003.

Twycross et al., "Itch: scratching more than the surface," *Q. J. Med.* 96: 7-26, 2003.

Usman et al., "1-Acetyl-3-(2-chloro-2,3-dihydrobenzofuran-3-yl)-1,2-dihydro-3-hydroxy-2-oxo-3*H*-indole," *Acta Cryst. E58*: o37-o39, 2002.

Watanabe et al., "$Na_v2$/NaG Channel Is Involved in Control of Salt-Intake Behavior in the CNS," *Journal of Neuroscience* 20(20): 7743-7751, Oct. 15, 2000.

Weber and Czugler, "Functional Group Assisted Clathrate Formation—Scissor-Like and Roof-Shaped Host Molecules," *Topics in Current Chemistry* 149: 45-135, 1988.

Weidmann et al., "2-[(2-Pyridylmethyl)sulfinyl]-1*H*-thieno[3,4-*d*]imidazoles. A Novel Class of Gastric $H^+/K^+$-ATPase Inhibitors," *J. Med. Chem.* 35: 438-450, 1992.

Wood et al., "Voltage-Gated Sodium Channels and Pain Pathways," *J. Neurobiol.* 61: 55-71, 2004.

Wu et al., "The Effect of Hypercholesterolemia on the Sodium Inward Currents in Cardiac Myocyte," *J. Mol. Cell. Cardiol.* 27: 1263-1269, 1995.

Yang et al., "Nucleophilic-Type Radical Cyclizations of Indoles: Conversion of 2-Cyano 3-Substituted Indoles to Spiro-Annelated Indolines and Tetrahydrocarbazolones," *J. Org. Chem.* 58: 3100-3105, 1993.

Zhang et al., "Crystal structure of *syn*-1-acetyl-9'aH-8'-methoxyspiro[indole-3,2'-oxeto[3',2':4,5]furo [3,2-*g*][1] benzopyran]2,6'-dione," *Journal of Chemical Crystallography* 33(3): 165-168, Mar. 2003.

Zhang et al., "Photoinduced [2+2] cycloadditions (the Paterno-Büchi reaction) of 1-acetylisatin with enol ethers—regioselectivity, diastereo-selectivity and acid catalysed transformations of the spirooxetane products," *J. Chem. Soc., Perkin Trans.* 1: 345-353, 2002.

Invitation to Pay Additional Fees, mailed Aug. 23, 2006, for PCTAN PCT/US2006/014845, 11 pages.

International Search Report and Written Opinion, mailed Oct. 31, 2006, for PCTAN PCT/US2006/014865, 26 pages.

International Preliminary Report on Patentability, mailed Nov. 1, 2007, for PCTAN PCT/US2006/014865, 13 pages.

Chafeev et al., entitled Oxindole Compounds and Their Uses As Therapeutic Agents, Preliminary Amendment dated Jul. 14, 2006, for U.S. Appl. No. 11/408,269, 6 pages.

Chafeev et al., entitled Oxindole Compounds and Their Uses As Therapeutic Agents, Restriction Requirement mailed Sep. 9, 2008, for U.S. Appl. No. 11/408,269, 10 pages.

Chafeev et al., entitled Oxindole Compounds and Their Uses As Therapeutic Agents, Response to Restriction Requirement dated Oct. 9, 2008, for U.S. Appl. No. 11/408,269, 3 pages.

Sun et al., entitled Spiro-Oxindole Compounds and Their Uses As Therapeutic Agents, Office Action dated Jul. 12, 2010, for U.S. Appl. No. 12/650,218, 26 pages.

Sun et al., entitled Spiro-Oxindole Compounds and Their Uses As Therapeutic Agents, Amendment dated Nov. 10, 2010, for U.S. Appl. No. 12/650,218, 28 pages.

Sun et al., entitled Spiro-Oxindole Compounds and Their Uses As Therapeutic Agents, Notice of Allowance mailed Dec. 13, 2010, for U.S. Appl. No. 12/650,218, 19 pages.

Sun et al., entitled Spiro-Oxindole Compounds and Their Uses As Therapeutic Agents, Supplemental Amendment dated Mar. 2, 2011, for U.S. Appl. No. 12/650,218, 3 pages.

Invitation to Pay Additional Fees, mailed Jan. 2, 2007, for PCTAN PCT/US2006/014887, 9 pages.

International Search Report and Written Opinion, mailed Mar. 15, 2007, for PCTAN PCT/US2006/014887, 22 pages.

International Preliminary Report on Patentability, mailed Nov. 1, 2007, for PCTAN PCT/US2006/014887, 12 pages.
Chafeev et al., entitled Heterocyclic Compounds and Their Uses As Therapeutic Agents, Preliminary Amendment dated Jul. 14, 2006, for U.S. Appl. No. 11/407,859, 6 pages.
Chafeev et al., entitled Heterocyclic Compounds and Their Uses As Therapeutic Agents, Restriction Requirement mailed Mar. 31, 2008, for U.S. Appl. No. 11/407,859, 9 pages.
Chafeev et al., entitled Heterocyclic Compounds and Their Uses As Therapeutic Agents, Response to Restriction Requirement dated Apr. 30, 2008, for U.S. Appl. No. 11/407,859, 39 pages.
Chafeev et al., entitled Heterocyclic Compounds and Their Uses As Therapeutic Agents, Amendment dated Oct. 17, 2008, for U.S. Appl. No. 11/407,859, 41 pages.
International Search Report and Written Opinion, mailed Aug. 11, 2006, for PCTAN PCT/US2006/013318, 15 pages.
International Preliminary Report on Patentability, mailed Oct. 16, 2007, for PCTAN PCT/US2006/013318, 9 pages.
Chafeev et al., entitled Spiroheterocyclic Compounds and Their Uses As Therapeutic Agents, Preliminary Amendment dated Jul. 7, 2006, for U.S. Appl. No. 11/402,200, 6 pages.
Chafeev et al., entitled Spiroheterocyclic Compounds and Their Uses As Therapeutic Agents, Restriction Requirement mailed Feb. 10, 2009, for U.S. Appl. No. 11/402,200, 6 pages.
Chafeev et al., entitled Spiroheterocyclic Compounds and Their Uses As Therapeutic Agents, Response to Restriction Requirement dated Feb. 27, 2009, for U.S. Appl. No. 11/402,200, 31 pages.
Chafeev et al., entitled Spiroheterocyclic Compounds and Their Uses As Therapeutic Agents, Amendment dated Aug. 24, 2009, for U.S. Appl. No. 11/402,200, 36 pages.
Chafeev et al., entitled Spiroheterocyclic Compounds and Their Uses As Therapeutic Agents, Amendment dated Mar. 17, 2010, for U.S. Appl. No. 11/402,200, 17 pages.
Chafeev et al., entitled Spiroheterocyclic Compounds and Their Uses As Therapeutic Agents, Notice of Allowance dated May 13, 2010, for U.S. Appl. No. 11/402,200, 16 pages.
Chafeev et al., entitled Spiroheterocyclic Compounds and Their Uses As Therapeutic Agents, Preliminary Amendment dated Oct. 25, 2010, for U.S. Appl. No. 12/855,514, 32 pages.
International Search Report and Written Opinion, mailed Mar. 3, 2008, for PCTAN PCT/US2007/081240, 16 pages.
International Preliminary Report on Patentability mailed Apr. 23, 2009, for PCTAN PCT/US2007/081240, 9 pages.
International Search Report and Written Opinion, mailed Oct. 13, 2008, for PCTAN PCT/US2007/081323, 21 pages.
International Preliminary Report on Patentability, mailed Apr. 15, 2009, for PCTAN PCT/US2007/081323, 12 pages.
International Search Report and Written Opinion, mailed Mar. 3, 2008, for PCTAN PCT/US2007/081244, 21 pages.
International Preliminary Report on Patentability, mailed Apr. 23, 2009, for PCTAN PCT/US2007/081244, 12 pages.
International Search Report and Written Opinion, mailed Apr. 1, 2011, for PCTAN PCT/US2010/052704, 12 pages.
Invitation to Pay Additional Fees, mailed Jul. 16, 2008, for PCTAN PCT/US2007/081319, 10 pages.
International Search Report and Written Opinion, mailed Dec. 29, 2008, for PCTAN PCT/US2007/081319, 18 pages.
International Preliminary Report on Patentability, mailed Apr. 15, 2009, for PCTAN PCT/US2007/081319, 8 pages.
International Search Report and Written Opinion, mailed May 19, 2008, for PCTAN PCT/US2007/081247, 18 pages.
International Preliminary Report on Patentability, mailed Apr. 15, 2009, for PCTAN PCT/US2007/081247, 10 pages.
Chafeev et al., entitled Use of Spiro-Oxindole Compounds As Therapeutic Agents, Preliminary Amendment dated Mar. 4, 2010, for U.S. Appl. No. 12/445,264, 18 pages.
International Search Report and Written Opinion, mailed May 13, 2008, for PCTAN PCT/US2007/081318, 12 pages.
International Preliminary Report on Patentability, mailed Apr. 15, 2009, for PCTAN PCT/US2007/081318, 5 pages.
International Search Report and Written Opinion, mailed Mar. 6, 2008, for PCTAN PCT/US2007/081297, 18 pages.
International Preliminary Report on Patentability, mailed Apr. 15, 2009, for PCTAN PCT/US2007/081297, 10 pages.
Invitation to Pay Additional Fees, mailed Jan. 27, 2009, for PCTAN PCT/US2007/081320, 7 pages.
Written Opinion of the International Searching Authority, mailed Jan. 5, 2009, for PCTAN PCT/US2007/081320, 11 pages.
International Preliminary Report on Patentability, mailed May 5, 2009, for PCTAN PCT/US2007/081320, 12 pages.
Winters et al., entitled Pharmaceutical Compositions for Oral Administration, Preliminary Amendment dated Dec. 27, 2010, for U.S. Appl. No. 12/905,048, 9 pages.
International Search Report and Written Opinion, mailed Feb. 9, 2010, for PCTAN PCT/US2009/063290, 13 pages.
International Search Report and Written Opinion, mailed Oct. 1, 2010, for PCTAN PCT/US2010/040187, 13 pages.
Invitation to Pay Additional Fees, mailed Feb. 9, 2010, for PCTAN PCT/US2009/060537, 8 pages.
International Search Report and Written Opinion, mailed Oct. 6, 2010, for PCTAN PCT/US2009/060537, 18 pages.
International Preliminary Report on Patentability, mailed Apr. 19, 2011, for PCTAN PCT/US2009/060537, 11 pages.
Chafeev et al., entitled Spiro-Oxindole Compounds and Their Use As Therapeutic Agents, Preliminary Amendment dated Jan. 12, 2010, for U.S. Appl. No. 12/578,148, 57 pages.
International Search Report and Written Opinion, mailed Jan. 22, 2010, for PCTAN PCT/US2009/060455, 14 pages.
International Preliminary Report on Patentability, mailed Apr. 19, 2011, for PCTAN PCT/US2009/060455, 7 pages.
Chafeev et al., entitled Spiro-Oxindole Compounds and Their Use As Therapeutic Agents, Office Action dated Apr. 1, 2011, for U.S. Appl. No. 12/577,799, 49 pages.
International Search Report and Written Opinion, mailed Apr. 8, 2010, for PCTAN PCT/US2009/069663, 13 pages.
Invitation to Pay Additional Fees, mailed Aug. 18, 2010 for PCTAN PCT/US2010/034223, 7 pages.
Official Action from Intellectual Property India, mailed Mar. 28, 2011, for India Patent Application No. 4596/CHENP/2007, 4 pages.
Official Action from Intellectual Property Australia, dated Jan. 12, 2011, for Patent Application No. 2006235593, 5 pages.
Official Action from State Intellectual Property Office of China, dated Dec. 25, 2009, for Patent Application No. 200680011733.9, 4 pages.
Official Action from State Intellectual Property Office of China, dated Oct. 9, 2010, for Patent Application No. 200680011733.9, 4 pages.
Official Action from European Patent Office, dated Apr. 9, 2010, for Patent Application No. 06 750 402.7, 4 pages.
Response to Official Action from European Patent Office, dated Aug. 19, 2010, for Patent Application No. 06 750 402.7, 105 pages.
Official Action from European Patent Office, dated Sep. 14, 2010, for Patent Application No. 06 750 402.7, 3 pages.
Response to Official Action from European Patent Office, dated Jul. 6, 2011, for Patent Application No. 06 750 402.7, 175 pages.
Official Action from Israel Patent Office, dated Jan. 17, 2011, for Patent Application No. 186616, 3 pages.
Response to Official Action from Israel Patent Office, mailed Jul. 14, 2011, for Patent Application No. 186616, 5 pages.
Official Action from Intellectual Property India, mailed Apr. 29, 2011, for India Patent Application No. 4597/CHENP/2007, 2 pages.
Official Action from Intellectual Property Office of New Zealand, dated Sep. 1, 2009, for Patent Application No. 561210, 2 pages.
Response to Official Action from Intellectual Property Office of New Zealand, dated Nov. 22, 2010, for Patent Application No. 561210, 2 pages.
Official Action from Intellectual Property Office of New Zealand, dated Nov. 30, 2010, for Patent Application No. 561210, 1 page.
Response to Official Action from Intellectual Property Office of New Zealand, dated Feb. 21, 2011, for Patent Application No. 561210, 2 pages.
Official Action from Intellectual Property Office of New Zealand, dated Feb. 25, 2011, for Patent Application No. 591268, 2 pages.

Official Action from Intellectual Property Office of Republic of the Philippines, dated Sep. 22, 2010, for Patent Application No. 1-2007-502050, 2 pages.
Response to Official Action from Intellectual Property Office of the Philippines, dated Jan. 20, 2011, for Patent Application No. 1-2007-502050, 85 pages.
Translation of Official Action from Intellectual Property Office of Russia, dated Mar. 16, 2010, for Patent Application No. 2007141632/04(045572), 7 pages.
Translation of Official Action from Intellectual Property Office of Russia, dated Sep. 22, 2010, for Patent Application No. 2007141632/04(045572), 7 pages.
Sun et al., entitled Spiro-Oxindole Compounds and Their Uses As Therapeutic Agents, Preliminary Amendment dated Jun. 24, 2011, for U.S. Appl. No. 13/078,678, 32 pages.
Official Action from European Patent Office, dated Aug. 5, 2008, for Patent Application No. 06 758 436.7, 5 pages.
Official Action from European Patent Office, dated Nov. 27, 2008, for Patent Application No. 06 740 804.7, 3 pages.
Response to Official Action from European Patent Office, dated Feb. 11, 2009, for Patent Application No. 06 740 804.7, 3 pages.
Official Action from Israel Patent Office, dated Jan. 16, 2011, for Patent Application No. 186615, 3 pages.
Response to Official Action from Israel Patent Office, dated Jul. 13, 2011, for Patent Application No. 186615, 3 pages.
Official Action from Intellectual Property of India, dated May 18, 2009, for Patent Application No. 4598/CHENP/2007, 2 pages.
Response to Official Action from Intellectual Property of India, dated Mar. 15, 2010, for Patent Application No. 4598/CHENP/2007, 27 pages.
Official Action from Intellectual Property Corporation of Malaysia, dated May 31, 2011, for Patent Application No. PI 20061651, 3 pages.
Official Action from Intellectual Property Office of New Zealand, dated Aug. 27, 2009, for Patent Application No. 561204, 2 pages.
Response to Official Action from Intellectual Property Office of New Zealand, dated Nov. 22, 2010, for Patent Application No. 561204, 2 pages.
Official Action from Intellectual Property Office of New Zealand, dated Dec. 6, 2010, for Patent Application No. 561204, 1 page.
Response to Official Action from Intellectual Property Office of New Zealand, dated Feb. 16, 2011, for Patent Application No. 561204, 2 pages.
Translation of Official Action from Intellectual Property Office of Russia, dated Feb. 27, 2010, for Patent Application No. 2007141633/04(045573), 4 pages.
Official Action from State Intellectual Property Office of China, dated May 5, 2011, for Patent Application No. 200780038272.9, 9 pages.
Official Action from European Patent Office, dated Nov. 27, 2008, for Patent Application No. 06 740 804.7, 3 pages.

Response to Official Action from European Patent Office, dated Feb. 11, 2009, for Patent Application No. 06 740 804.7, 3 pages.
Official Action from State Intellectual Property Office of China, dated Oct. 28, 2010, for Patent Application No. 200780038111.X, 5 pages.
Official Action from State Intellectual Property Office of China, dated Jul. 14, 2011, for Patent Application No. 200780038111.X, 5 pages.
Official Action from European Patent Office, dated Jul. 7, 2009, for Patent Application No. 07 868 434.7, 3 pages.
Official Action from European Patent Office, dated Jul. 23, 2010, for Patent Application No. 07 868 434.7, 6 pages.
Response to Official Action from European Patent Office, dated May 23, 2011, for Patent Application No. 07 868 434.7, 3 pages.
International Preliminary Report on Patentability, mailed May 10, 2011, for PCTAN PCT/US2009/063290, 7 pages.
Chafeev et al., entitled Enantiomers of Spiro-Oxindole Compounds and Their Uses As Therapeutic Agents, Restriction Requirement mailed Jun. 20, 2011, for U.S. Appl. No. 12/825,168, 8 pages.
Chafeev et al., entitled Enantiomers of Spiro-Oxindole Compounds and Their Uses As Therapeutic Agents, Response to Restriction Requirement and Preliminary Amendment, filed Jul. 20, 2011, for U.S. Appl. No. 12/825,168, 5 pages.
Chafeev et al., entitled Spiro-Oxindole Compounds and Their Use As Therapeutic Agents, Amendment dated Jul. 1, 2011, for U.S. Appl. No. 12/577,799, 21 pages.
International Preliminary Report on Patentability, mailed Jun. 29, 2011, for PCTAN PCT/US2009/069663, 6 pages.
International Search Report and Written Opinion, mailed Jul. 11, 2011, for PCTAN PCT/US2010/034223, 18 pages.
International Search Report and Written Opinion, mailed Jun. 9, 2011, for PCTAN PCT/US2011/026359, 14 pages.
Hoffman, *Organic Chemistry: An Intermediate Text*—Second Edition, John Wiley & Sons, Inc., Hoboken, New Jersey, 2004, 124, 138-144.
Patani and LaVoie, "Bioisosterism: A Rational Approach in Drug Design," *Chem. Rev.* 96(8): 3147-3176, 1996.
Stella and Nti-Addae, "Prodrug strategies to overcome poor water solubility," *Advanced Drug Delivery Reviews* 59: 677-694, 2007.
Response to Official Action from Intellectual Property Corporation of Malaysia, filed Aug. 11, 2011, for Patent Application No. PI 20061651, 30 pages.
Chafeev et al., entitled Spiroheterocyclic Compounds and Their Uses As Therapeutic Agents, Office Action mailed Aug. 25, 2011, for U.S. Appl. No. 12/855,514, 43 pages.
Chafeev et al., entitled Enantiomers of Spiro-Oxindole Compounds and Their Uses As Therapeutic Agents, Office Action, mailed Aug. 29, 2011, for U.S. Appl. No. 12/825,168, 43 pages.
Chafeev et al., entitled Spiro-Oxindole Compounds and Their Use As Therapeutic Agents, Restriction Requirement mailed Aug. 15, 2011, for U.S. Appl. No. 12/578,148, 10 pages.

* cited by examiner

SPIRO-OXINDOLE COMPOUNDS AND THEIR USES AS THERAPEUTIC AGENTS

CROSS-REFERENCES TO RELATED APPLICATIONS

This application is a continuation of U.S. patent application Ser. No. 11/402,310, filed Apr. 11, 2006 (now U.S. Pat. No. 7,700,641); which claims the benefit under 37 U.S.C. §119(e) of U.S. Provisional Patent Application No. 60/670,896, filed Apr. 11, 2005. These applications are incorporated herein by reference in their entireties.

FIELD OF THE INVENTION

The present invention is directed to spiro-oxindole compounds. In particular, this invention is directed to spiro-oxindole compounds that are sodium channel blockers and are therefore useful in treating sodium channel-mediated diseases or conditions, such as pain, as well as other diseases and conditions associated with the mediation of sodium channels.

BACKGROUND OF THE INVENTION

Voltage-gated sodium channels, transmembrane proteins that initiate action potentials in nerve, muscle and other electrically excitable cells, are a necessary component of normal sensation, emotions, thoughts and movements (Catterall, W. A., *Nature* (2001), Vol. 409, pp. 988-990). These channels consist of a highly processed alpha subunit that is associated with auxiliary beta subunits. The pore-forming alpha subunit is sufficient for channel function, but the kinetics and voltage dependence of channel gating are in part modified by the beta subunits (Goldin et al., *Neuron* (2000), Vol. 28, pp. 365-368). Each alpha-subunit contains four homologous domains, I to IV, each with six predicted transmembrane segments. The alpha-subunit of the sodium channel, forming the ion-conducting pore and containing the voltage sensors regulating sodium ion conduction has a relative molecular mass of 260,000. Electrophysiological recording, biochemical purification, and molecular cloning have identified ten different sodium channel alpha subunits and four beta subunits (Yu, F. H., et al., *Sci. STKE* (2004), 253; and Yu, F. H., et al., *Neurosci.* (2003), 20:7577-85).

The hallmarks of sodium channels include rapid activation and inactivation when the voltage across the plasma membrane of an excitable cell is depolarized (voltage-dependent gating), and efficient and selective conduction of sodium ions through conducting pores intrinsic to the structure of the protein (Sato, C., et al., *Nature* (2001), 409:1047-1051). At negative or hyperpolarized membrane potentials, sodium channels are closed. Following membrane depolarization, sodium channels open rapidly and then inactivate. Channels only conduct currents in the open state and, once inactivated, have to return to the resting state, favoured by membrane hyperpolarization, before they can reopen. Different sodium channel subtypes vary in the voltage range over which they activate and inactivate as well as their activation and inactivation kinetics.

The sodium channel family of proteins has been extensively studied and shown to be involved in a number of vital body functions. Research in this area has identified variants of the alpha subunits that result in major changes in channel function and activities, which can ultimately lead to major pathophysiological conditions. Implicit with function, this family of proteins are considered prime points of therapeutic intervention. $Na_v1.1$ and $Na_v1.2$ are highly expressed in the brain (Raymond, C. K., et al., *J. Biol. Chem.* (2004), 279(44):46234-41) and are vital to normal brain function. In humans, mutations in $Na_v1.1$ and $Na_v1.2$ result in severe epileptic states and in some cases mental decline (Rhodes, T. H., et al., *Proc. Natl. Acad. Sci.* USA (2004), 101(30):11147-52; Kamiya, K., et al., *J. Biol. Chem.* (2004), 24(11):2690-8; Pereira, S., et al., *Neurology* (2004), 63(1):191-2). As such both channels have been considered as validated targets for the treatment of epilepsy (see PCT Published Patent Publication No. WO 01/38564).

$Na_v1.3$ is broadly expressed throughout the body (Raymond, C. K., et al., op. cit.). It has been demonstrated to have its expression upregulated in the dorsal horn sensory neurons of rats after nervous system injury (Hains, B. D., et al., *J. Neurosci.* (2003), 23(26):8881-92). Many experts in the field have considered $Na_v1.3$ as a suitable target for pain therapeutics (Lai, J., et al., *Curr. Opin. Neurobiol.* (2003), (3):291-72003; Wood, J. N., et al., *J. Neurobiol.* (2004), 61(1):55-71; Chung, J. M., et al., *Novartis Found Symp.* (2004), 261:19-27; discussion 27-31, 47-54).

$Na_v1.4$ expression is essentially limited to muscle (Raymond, C. K., et al., op. cit.). Mutations in this gene have been shown to have profound effects on muscle function including paralysis, (Tamaoka A., *Intern. Med.* (2003), (9):769-70). Thus, this channel can be considered a target for the treatment of abnormal muscle contractility, spasm or paralysis.

The cardiac sodium channel, $Na_v1.5$, is expressed mainly in the heart ventricles and atria (Raymond, C. K., et al., op. cit.), and can be found in the sinovial node, ventricular node and possibly Purkinje cells. The rapid upstroke of the cardiac action potential and the rapid impulse conduction through cardiac tissue is due to the opening of $Na_v1.5$. As such, $Na_v1.5$ is central to the genesis of cardiac arrhythmias. Mutations in human $Na_v1.5$ result in multiple arrhythmic syndromes, including, for example, long QT3 (LQT3), Brugada syndrome (BS), an inherited cardiac conduction defect, sudden unexpected nocturnal death syndrome (SUNDS) and sudden infant death syndrome (SIDS) (Liu, H. et al., *Am. J. Pharmacogenomics* (2003), 3(3):173-9). Sodium channel blocker therapy has been used extensively in treating cardiac arrhythmias. The first antiarrhythmic drug, quinidine, discovered in 1914, is classified as a sodium channel blocker.

$Na_v1.6$ encodes an abundant, widely distributed voltage-gated sodium channel found throughout the central and peripheral nervous systems, clustered in the nodes of Ranvier of neural axons (Caldwell, J. H., et al., *Proc. Natl. Acad. Sci.* USA (2000), 97(10): 5616-20). Although no mutations in humans have been detected, $Na_v1.6$ is thought to play a role in the manifestation of the symptoms associated with multiple sclerosis and has been considered as a target for the treatment of this disease (Craner, M. J., et al., *Proc. Natl. Acad. Sci.* USA (2004), 101(21):8168-73).

$Na_v1.7$ was first cloned from the pheochromocytoma PC12 cell line (Toledo-Aral, J. J., et al., *Proc. Natl. Acad. Sci.* USA (1997), 94:1527-1532). Its presence at high levels in the growth cones of small-diameter neurons suggested that it could play a role in the transmission of nociceptive information. Although this has been challenged by experts in the field as $Na_v1.7$ is also expressed in neuroendocrine cells associated with the autonomic system (Klugbauer, N., et al., *EMBO J.* (1995), 14(6):1084-90) and as such has been implicated in autonomic processes. The implicit role in autonomic functions was demonstrated with the generation of $Na_v1.7$ null mutants; deleting $Na_v1.7$ in all sensory and sympathetic neurons resulted in a lethal perinatal phenotype. (Nassar, et al., *Proc. Natl. Acad. Sci.* USA (2004), 101(34):12706-11.). In contrast, by deleting the $Na_v1.7$ expression in a subset of sensory neurons that are predominantly nociceptive, a role in pain mechanisms, was demonstrated (Nassar, et al., op. cit.). Further support for $Na_v1.7$ blockers active in a subset of neurons is supported by the finding that two human heritable pain conditions, primary erythromelalgia and familial rectal pain, have been shown to map to $Na_v1.7$ (Yang, Y., et al., *J. Med. Genet.* (2004), 41(3):171-4).

The expression of $Na_v1.8$ is essentially restricted to the DRG (Raymond, C. K., et al., op. cit.). There are no identified human mutations for $Na_v1.8$. However, $Na_v1.8$-null mutant mice were viable, fertile and normal in appearance. A pronounced analgesia to noxious mechanical stimuli, small deficits in noxious thermoreception and delayed development of inflammatory hyperalgesia suggested to the researchers that $Na_v1.8$ plays a major role in pain signalling (Akopian, A. N., et al., *Nat. Neurosci.* (1999), 2(6): 541-8). Blocking of this channel is widely accepted as a potential treatment for pain (Lai, J, et al., op. cit.; Wood, J. N., et al., op. cit.; Chung, J. M., et al., op. cit.). PCT Published Patent Application No. WO03/037274A2 describes pyrazole-amides and sulfonamides for the treatment of central or peripheral nervous system conditions, particularly pain and chronic pain by blocking sodium channels associated with the onset or recurrance of the indicated conditions. PCT Published Patent Application No. WO03/037890A2 describes piperidines for the treatment of central or peripheral nervous system conditions, particularly pain and chronic pain by blocking sodium channels associated with the onset or recurrence of the indicated conditions. The compounds, compositions and methods of these inventions are of particular use for treating neuropathic or inflammatory pain by the inhibition of ion flux through a channel that includes a PN3 ($Na_v1.8$) subunit.

The tetrodotoxin insensitive, peripheral sodium channel $Na_v1.9$, disclosed by Dib-Hajj, S. D., et al. (see Dib-Hajj, S. D., et al., *Proc. Natl. Acad. Sci.* USA (1998), 95(15):8963-8) was shown to reside solely in the dorsal root ganglia. It has been demonstrated that $Na_v1.9$ underlies neurotrophin (BDNF)-evoked depolarization and excitation, and is the only member of the voltage gated sodium channel superfamily to be shown to be ligand mediated (Blum, R., Kafitz, K. W., Konnerth, A., *Nature* (2002), 419 (6908):687-93). The limited pattern of expression of this channel has made it a candidate target for the treatment of pain (Lai, J, et al., op. cit.; Wood, J. N., et al., op. cit.; Chung, J. M. et al., op. cit.).

NaX is a putative sodium channel, which has not been shown to be voltage gated. In addition to expression in the lung, heart, dorsal root ganglia, and Schwann cells of the peripheral nervous system, NaX is found in neurons and ependymal cells in restricted areas of the CNS, particularly in the circumventricular organs, which are involved in body-fluid homeostasis (Watanabe, E., et al., *J. Neurosci.* (2000), 20(20):7743-51). NaX-null mice showed abnormal intakes of hypertonic saline under both water- and salt-depleted conditions. These findings suggest that the NaX plays an important role in the central sensing of body-fluid sodium level and regulation of salt intake behaviour. Its pattern of expression and function suggest it as a target for the treatment of cystic fibrosis and other related salt regulating maladies.

Studies with the sodium channel blocker tetrodotoxin (TTX) used to lower neuron activity in certain regions of the brain, indicate its potential use in the treatment of addiction. Drug-paired stimuli elicit drug craving and relapse in addicts and drug-seeking behavior in rats. The functional integrity of the basolateral amygdala (BLA) is necessary for reinstatement of cocaine-seeking behaviour elicited by cocaine-conditioned stimuli, but not by cocaine itself. BLA plays a similar role in reinstatement of heroin-seeking behavior. TTX-induced inactivation of the BLA on conditioned and heroin-primed reinstatement of extinguished heroin-seeking behaviour in a rat model (Fuchs, R. A. and See, R. E., *Psychopharmacology* (2002) 160(4):425-33).

This closely related family of proteins has long been recognised as targets for therapeutic intervention. Sodium channels are targeted by a diverse array of pharmacological agents. These include neurotoxins, antiarrhythmics, anticonvulsants and local anesthetics (Clare, J. J., et al., *Drug Discovery Today* (2000) 5:506-520). All of the current pharmacological agents that act on sodium channels have receptor sites on the alpha subunits. At least six distinct receptor sites for neurotoxins and one receptor site for local anesthetics and related drugs have been identified (Cestèle, S. et al., *Biochimie* (2000), Vol. 82, pp. 883-892).

The small molecule sodium channel blockers or the local anesthetics and related antiepileptic and antiarrhythmic drugs, interact with overlapping receptor sites located in the inner cavity of the pore of the sodium channel (Catterall, W. A., *Neuron* (2000), 26:13-25). Amino acid residues in the S6 segments from at least three of the four domains contribute to this complex drug receptor site, with the IVS6 segment playing the dominant role. These regions are highly conserved and as such most sodium channel blockers known to date interact with similar potency with all channel subtypes. Nevertheless, it has been possible to produce sodium channel blockers with therapeutic selectivity and a sufficient therapeutic window for the treatment of epilepsy (e.g. lamotrignine, phenytoin and carbamazepine) and certain cardiac arrhythmias (e.g. lignocaine, tocainide and mexiletine). However, the potency and therapeutic index of these blockers is not optimal and have limited the usefulness of these compounds in a variety of therapeutic areas where a sodium channel blocker would be ideally suited.

Management of Acute and Chronic Pain

Drug therapy is the mainstay of management for acute and chronic pain in all age groups, including neonates, infants and children. The pain drugs are classified by the American Pain Society into three main categories: 1) non-opioid analgesics—acetaminophen, and non-steroidal anti-inflammatory drugs (NSAIDs), including salicylates (e.g. aspirin), 2) opioid analgesics and 3) co-analgesics.

Non-opioid analgesics such as acetaminophen and NSAIDs are useful for acute and chronic pain due to a variety of causes including surgery, trauma, arthritis and cancer. NSAIDs are indicated for pain involving inflammation because acetaminophen lacks anti-inflammatory activity. Opioids also lack anti-inflammatory activity. All NSAIDs inhibit the enzyme cyclooxygenase (COX), thereby inhibiting prostaglandin synthesis and reducing the inflammatory pain response. There are at least two COX isoforms, COX-1 and COX-2. Common non-selective COX inhibitors include, ibuprofen and naproxen. Inhibition of COX-1, which is found in platelets, GI tract, kidneys and most other human tissues, is thought to be associated with adverse effects such as gastrointestinal bleeding. The development of selective COX-2 NSAIDs, such as Celecoxib, Valdecoxib and Rofecoxib, have the benefits of non-selective NSAIDs with reduced adverse effect profiles in the gut and kidney. However, evidence now suggests that chronic use of certain selective COX-2 inhibitors can result in an increased risk of stroke occurrence.

The use of opioid analgesics is recommended by the American Pain Society to be initiated based on a pain-directed history and physical that includes repeated pain assessment. Due to the broad adverse effect profiles associated with opiate use, therapy should include a diagnosis, integrated interdisciplinary treatment plan and appropriate ongoing patient monitoring. It is further recommended that opioids be added to non-opioids to manage acute pain and cancer related pain that does not respond to non-opioids alone. Opioid analgesics act as agonists to specific receptors of the mu and kappa types in the central and peripheral nervous system. Depending on the opioid and its formulation or mode of administration it can be of shorter or longer duration. All opioid analgesics have a risk of causing respiratory depression, liver failure, addiction and dependency, and as such are not ideal for long-term or chronic pain management.

A number of other classes of drugs may enhance the effects of opioids or NSAIDSs, have independent analgesic activity in certain situations, or counteract the side effects of analgesics. Regardless of which of these actions the drug has, they are collectively termed "coanalgesics". Tricyclic antidepressants, antiepileptic drugs, local anaesthetics, glucocorticoids, skeletal muscle relaxants, anti-spasmodil agents, antihistamines, benzodiazepines, caffeine, topical agents (e.g. capsaicin), dextroamphetamine and phenothizines are all used in the clinic as adjuvant therapies or individually in the treatment of pain. The antiepileptic drugs in particular have enjoyed some success in treating pain conditions. For instance, Gabapentin, which has an unconfirmed therapeutic target, is indicated for neuropathic pain. Other clinical trials are attempting to establish that central neuropathic pain may respond to ion channel blockers such as blockers of calcium, sodium and/or NMDA (N-methyl-D-aspartate) channels. Currently in development are low affinity NMDA channel blocking agents for the treatment of neuropathic pain. The literature provides substantial pre-clinical electrophysiological evidence in support of the use of NMDA antagonists in the treatment of neuropathic pain. Such agents also may find use in the control of pain after tolerance to opioid analgesia occurs, particularly in cancer patients.

Systemic analgesics such as NSAIDs and opioids are to be distinguished from therapeutic agents which are useful only as local analgesics/anaesthetics. Well known local analgesics such as lidocaine and xylocaine are non-selective ion channel blockers which can be fatal when administered systemically. A good description of non-selective sodium channel blockers is found in Madge, D. et al., *J. Med. Chem.* (2001), 44(2): 115-37.

Several sodium channel modulators are known for use as anticonvulsants or antidepressants, such as carbamazepine, amitriptyline, lamotrigine and riluzole, all of which target brain tetradotoxin-sensitive (TTX-S) sodium channels. Such TTX-S agents suffer from dose-limiting side effects, including dizziness, ataxia and somnolence, primarily due to action at TTX-S channels in the brain.

Sodium Channels Role in Pain

Sodium channels play a diverse set of roles in maintaining normal and pathological states, including the long recognized role that voltage gated sodium channels play in the generation of abnormal neuronal activity and neuropathic or pathological pain (Chung, J. M. et al.). Damage to peripheral nerves following trauma or disease can result in changes to sodium channel activity and the development of abnormal afferent activity including ectopic discharges from axotomised afferents and spontaneous activity of sensitized intact nociceptors. These changes can produce long-lasting abnormal hypersensitivity to normally innocuous stimuli, or allodynia. Examples of neuropathic pain include, but are not limited to, post-herpetic neuralgia, trigeminal neuralgia, diabetic neuropathy, chronic lower back pain, phantom limb pain, and pain resulting from cancer and chemotherapy, chronic pelvic pain, complex regional pain syndrome and related neuralgias.

There has been some degree of success in treating neuropathic pain symptoms by using medications, such as gabapentin, and more recently pregabalin, as short-term, first-line treatments. However, pharmacotherapy for neuropathic pain has generally had limited success with little response to commonly used pain reducing drugs, such as NSAIDS and opiates. Consequently, there is still a considerable need to explore novel treatment modalities.

There remains a limited number of potent effective sodium channel blockers with a minimum of adverse events in the clinic. There is also an unmet medical need to treat neuropathic pain and other sodium channel associated pathological states effectively and without adverse side effects. The present invention provides compounds, methods of use and compositions that include these compounds to meet these critical needs.

SUMMARY OF THE INVENTION

The present invention is directed to spiro-oxindole compounds that are useful for the treatment and/or prevention of sodium channel-mediated diseases or conditions, such as pain. The compounds of the present invention are also useful for the treatment of other sodium channel-mediated diseases or conditions, including, but not limited to central nervous conditions such as epilepsy, anxiety, depression and bipolar disease; cardiovascular conditions such as arrhythmias, atrial fibrillation and ventricular fibrillation; neuromuscular conditions such as restless leg syndrome, essential tremour and muscle paralysis or tetanus; neuroprotection against stroke, glaucoma, neural trauma and multiple sclerosis; and channelopathies such as erythromyalgia and familial rectal pain syndrome.

Accordingly, in one aspect, the invention provides compounds of formula (I):

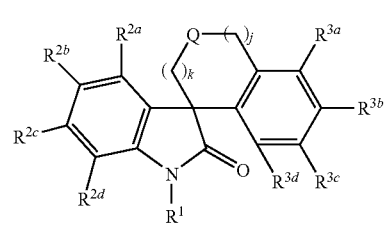

wherein:
j and k are each independently 0, 1, 2 or 3;
Q is —C(R$^{1a}$)H—, —C(O)—, —O—, —S(O)$_m$— (where m is 0, 1 or 2), —CF$_2$—, —C(O)O—, —C(O)N(R$^5$)— or —N(R$^5$)C(O)—;
R$^{1a}$ is hydrogen or —OR$^5$;
R$^1$ is hydrogen, alkyl, alkenyl, alkynyl, haloalkyl, aryl, cycloalkyl, cycloalkylalkyl, heteroaryl, heterocyclyl, —R$^8$—C(O)R$^5$, —R$^8$—C(O)OR$^5$, —R$^8$—C(O)N(R$^4$)R$^5$, —S(O)$_2$—R$^5$, —R$^9$—S(O)$_m$—R$^5$ (where m is 0, 1 or 2), —R$^8$—OR$^5$, —R$^8$—CN, —R$^9$—P(O)(OR$^5$)$_2$, or —R$^9$—O—R$^9$—OR$^5$;
or R$^1$ is aralkyl substituted by —C(O)N(R$^6$)R$^7$ where:
R$^6$ is hydrogen, alkyl, aryl or aralkyl; and
R$^7$ is hydrogen, alkyl, haloalkyl, —R$^9$—CN, —R$^9$—OR$^5$, —R$^9$—N(R$^4$)R$^5$, aryl, aralkyl, cycloalkyl, cycloalkylalkyl, heterocyclyl, heterocyclylalkyl, heteroaryl or heteroarylalkyl;
or R$^6$ and R$^7$, together with the nitrogen to which they are attached, form a heterocyclyl or heteroaryl;

and wherein each aryl, aralkyl, cycloalkyl, cycloalkylalkyl, heterocyclyl, heterocyclylalkyl, heteroaryl and heteroarylalkyl group for $R^6$ and $R^7$ may be optionally substituted by one or more substituents selected from the group consisting of alkyl, cycloalkyl, aryl, aralkyl, halo, haloalkyl, $-R^8-CN$, $-R^8-OR^5$, heterocyclyl and heteroaryl;

or $R^1$ is aralkyl optionally substituted by one or more substituents selected from the group consisting of $-R^8-OR^5$, $-C(O)OR^5$, halo, haloalkyl, alkyl, nitro, cyano, aryl, aralkyl, heterocyclyl and heteroaryl;

or $R^1$ is $-R^9-N(R^{10})R^{11}$, $-R^9-N(R^{12})C(O)R^{11}$ or $-R^9-N(R^{10})C(O)N(R^{10})R^{11}$ where:

each $R^{10}$ is hydrogen, alkyl, aryl, aralkyl or heteroaryl;

each $R^{11}$ is hydrogen, alkyl, haloalkyl, cycloalkyl, cycloalkylalkyl, aryl, aralkyl, heterocyclyl, heterocyclylalkyl, heteroaryl, heteroarylalkyl, $-R^9-OC(O)R^5$, $-R^9-C(O)OR^5$, $-R^9-C(O)N(R^4)R^5$, $-R^9-C(O)R^5$, $-R^9-N(R^4)R^5$, $-R^9-OR^5$, or $-R^9-CN$; and $R^{12}$ is hydrogen, alkyl, aryl, aralkyl or $-C(O)R^5$;

and wherein each aryl, aralkyl, cycloalkyl, cycloalkylalkyl, heterocyclyl, heterocyclylalkyl, heteroaryl and heteroarylalkyl group for $R^{10}$ and $R^{11}$ may be optionally substituted by one or more substituents selected from the group consisting of alkyl, cycloalkyl, aryl, aralkyl, halo, haloalkyl, nitro, $-R^8-CN$, $-R^8-OR^5$, $-R^8-C(O)R^5$, heterocyclyl and heteroaryl;

or $R^1$ is heterocyclylalkyl or heteroarylalkyl where the heterocyclylalkyl or the heteroarylalkyl group is optionally substituted by one or more substituents selected from the group consisting of oxo, alkyl, halo, haloalkyl, cycloalkyl, cycloalkylalkyl, aryl, aralkyl, heterocyclyl, heterocyclylalkyl, heteroaryl, heteroarylalkyl, $-R^8-OR^5$, $-R^8-C(O)OR^5$, $-R^8-N(R^4)R^5$, $-R^8-C(O)N(R^4)R^5$, $-R^8-N(R^5)C(O)R^4$, $-R^8-S(O)_mR^4$ (where m is 0, 1 or 2), $-R^8-CN$, or $-R^8-NO_2$;

$R^{2a}$, $R^{2b}$, $R^{2c}$ and $R^{2d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, $-R^8-CN$, $-R^8-NO_2$, $-R^8-OR^5$, $-R^8-N(R^4)R^5$, $-N=C(R^4)R^5$, $-S(O)_mR^4$, $-OS(O)_2CF_3$, $-R^8-C(O)R^4$, $-C(S)R^4$, $-C(R^4)_2C(O)R^5$, $-R^8-C(O)OR^4$, $-C(S)OR^4$, $-R^8-C(O)N(R^4)R^5$, $-C(S)N(R^4)R^5$, $-N(R^5)C(O)R^4$, $-N(R^5)C(S)R^4$, $-N(R^5)C(O)OR^4$, $-N(R^5)C(S)OR^4$, $-N(R^5)C(O)N(R^4)R^5$, $-N(R^5)C(S)N(R^4)R^5$, $-N(R^5)S(O)_nR^4$, $-N(R^5)S(O)_nN(R^4)R^5$, $-R^8-S(O)_nN(R^4)R^5$, $-N(R^5)C(=NR^5)N(R^4)R^5$, and $-N(R^5)C(=N-CN)N(R^4)R^5$, wherein each m is independently 0, 1, or 2 and each n is independently 1 or 2;

and wherein each of the cycloalkyl, cycloalkylalkyl, aryl, aralkyl, aralkenyl, heterocyclyl, heterocyclylalkyl, heteroaryl and heteroarylalkyl groups for $R^{2a}$, $R^{2b}$, $R^{2c}$ and $R^{2d}$ may be optionally substituted by one or more substituents selected from the group consisting of alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, $-R^8-CN$, $-R^8-NO_2$, $-R^8-OR^5$, $-R^8-N(R^4)R^5$, $-S(O)_mR^4$, $-R^8-S(O)_nN(R^4)R^5$, $-R^8-C(O)R^4$, $-R^8-C(O)OR^4$, $-R^8-C(O)N(R^4)R^5$, $-N(R^5)C(O)R^4$, and $-N(R^5)S(O)_nR^4$, wherein each m is independently 0, 1, or 2 and each n is independently 1 or 2;

or $R^{2a}$ and $R^{2b}$, together with the carbon ring atoms to which they are directly attached, may form a fused ring selected from cycloalkyl, aryl, heterocyclyl and heteroaryl, and $R^{2c}$ and $R^{2d}$ are as defined above;

or $R^{2b}$ and $R^{2c}$, together with the carbon ring atoms to which they are directly attached, may form a fused ring selected from cycloalkyl, aryl, heterocyclyl and heteroaryl, and $R^{2a}$ and $R^{2d}$ are as defined above;

or $R^{2c}$ and $R^{2d}$, together with the carbon ring atoms to which they are directly attached, may form a fused ring selected from cycloalkyl, aryl, heterocyclyl and heteroaryl, and $R^{2a}$ and $R^{2b}$ are as defined above;

$R^{3a}$, $R^{3b}$, $R^{3c}$ and $R^{3d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, $-R^8-CN$, $-R^8-NO_2$, $-R^8-OR^5$, $-R^8-N(R^4)R^5$, $-N=C(R^4)R^5$, $-S(O)_mR^4$, $-OS(O)_2CF_3$, $-R^8-C(O)R^4$, $-C(S)R^4$, $-C(R^4)_2C(O)R^5$, $-R^8-C(O)OR^4$, $-C(S)OR^4$, $-R^8-C(O)N(R^4)R^5$, $-C(S)N(R^4)R^5$, $-N(R^5)C(O)R^4$, $-N(R^5)C(S)R^4$, $-N(R^5)C(O)OR^4$, $-N(R^5)C(S)OR^4$, $-N(R^5)C(O)N(R^4)R^5$, $-N(R^5)C(S)N(R^4)R^5$, $-N(R^5)S(O)_nR^4$, $-N(R^5)S(O)_nN(R^4)R^5$, $-R^9-S(O)_nN(R^4)R^5$, $-N(R^5)C(=NR^5)N(R^4)R^5$, and $-N(R^5)C(=C(R^4)R^5)N(R^4)R^5$, wherein each m is independently 0, 1, or 2 and each n is independently 1 or 2;

or $R^{3a}$ and $R^{3b}$, together with the carbon ring atoms to which they are directly attached, form a fused ring selected from cycloalkyl, heterocyclyl, aryl or heteroaryl, and $R^{3c}$ and $R^{3d}$ are as defined above;

or $R^{3b}$ and $R^{3c}$, together with the carbon ring atoms to which they are directly attached, may form a fused ring selected from cycloalkyl, heterocyclyl, aryl or heteroaryl, and $R^{3a}$ and $R^{3d}$ are as defined above;

or $R^{3c}$ and $R^{3d}$, together with the carbon ring atoms to which they are directly attached, may form a fused ring selected from cycloalkyl, heterocyclyl, aryl or heteroaryl, and $R^{3a}$ and $R^{3b}$ are as defined above;

each $R^4$ and $R^5$ is independently selected from the group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when $R^4$ and $R^5$ are each attached to the same nitrogen atom, then $R^4$ and $R^5$, together with the nitrogen atom to which they are attached, may form a heterocyclyl or heteroaryl;

each $R^8$ is a direct bond or a straight or branched alkylene chain, a straight or branched alkenylene chain or a straight or branched alkynylene chain; and each $R^9$ is a straight or branched alkylene chain, a straight or branched alkenylene chain or a straight or branched alkynylene chain;

as a stereoisomer, enantiomer, tautomer thereof or mixtures thereof;

or a pharmaceutically acceptable salt, solvate or prodrug thereof.

In another aspect, the invention provides methods for the treatment of pain in a mammal, preferably a human, wherein the methods comprise administering to the mammal in need thereof a therapeutically effective amount of a compound of the invention as set forth above.

In another aspect, the present invention provides a method for treating or lessening the severity of a disease, condition, or disorder where activation or hyperactivity of one or more of $Na_v1.1$, $Na_v1.2$, $Na_v1.3$, $Na_v1.4$, $Na_v1.5$, $Na_v1.6$, $Na_v1.7$, $Na_v1.8$, or $Na_v1.9$ is implicated in the disease state. In another aspect, the invention provides methods of treating a range of sodium channel-mediated diseases or conditions, for example, pain associated with HIV, HIV treatment induced neuropathy, trigeminal neuralgia, post-herpetic neuralgia, eudynia, heat sensitivity, tosarcoidosis, irritable bowel syndrome, Crohns disease, pain associated with multiple sclerosis (MS), amyotrophic lateral sclerosis (ALS), diabetic neuropathy, peripheral neuropathy, arthritic, rheumatoid arthritis, osteoarthritis, atherosclerosis, paroxysmal dystonia, myasthenia syndromes, myotonia, malignant hyperthermia, cystic fibrosis, pseudoaldosteronism, rhabdomyolysis, hypothyroidism, bipolar depression, anxiety, schizophrenia, sodium channel toxin related illnesses, familial erythromelalgia, primary erythromelagia, familial rectal pain, cancer, epilepsy, partial and general tonic seizures, restless leg syndrome, arrhythmias, fibromyalgia, neuroprotection under ischaemic conditions caused by stroke, glaucoma or neural trauma, tachy-arrhythmias, atrial fibrillation and ventricular fibrillation.

In another aspect, the invention provides methods of treating a range of sodium channel-mediated disease or condition through inhibition of ion flux through a voltage-dependent sodium channel in a mammal, preferably a human, wherein the methods comprise administering to the mammal in need thereof a therapeutically effective amount of a compound of the invention as set forth above.

In another aspect, the invention provides pharmaceutical compositions comprising the compounds of the invention, as set forth above, and pharmaceutically acceptable excipients. In one embodiment, the present invention relates to a pharmaceutical composition comprising a compound of the invention in a pharmaceutically acceptable carrier and in an amount effective to treat diseases or conditions related to pain when administered to an animal, preferably a mammal, most preferably a human.

In another aspect, the invention provides pharmaceutical therapy in combination with one or more other compounds of the invention or one or more other accepted therapies or as any combination thereof to increase the potency of an existing or future drug therapy or to decrease the adverse events associated with the accepted therapy. In one embodiment, the present invention relates to a pharmaceutical composition combining compounds of the present invention with established or future therapies for the indications listed in the invention.

DETAILED DESCRIPTION OF THE INVENTION

Definitions

Certain chemical groups named herein are preceded by a shorthand notation indicating the total number of carbon atoms that are to be found in the indicated chemical group. For example; $C_7$-$C_{12}$alkyl describes an alkyl group, as defined below, having a total of 7 to 12 carbon atoms, and $C_4$-$C_{12}$cycloalkylalkyl describes a cycloalkylalkyl group, as defined below, having a total of 4 to 12 carbon atoms. The total number of carbons in the shorthand notation does not include carbons that may exist in substituents of the group described. For example, the following terms have the meaning indicated:

"$C_1$-$C_{10}$alkyl" refers to an alkyl radical as defined below containing one to ten carbon atoms. The $C_1$-$C_{10}$alkyl radical may be optionally substituted as defined below for an alkyl group.

"$C_2$-$C_{12}$alkynyl" refers to an alkenyl radical as defined below containing two to twelve carbon atoms. The $C_2$-$C_{12}$alkenyl radical may be optionally substituted as defined below for an alkenyl group.

"$C_1$-$C_{12}$alkoxy" refers to an alkoxy radical as defined below containing one to twelve carbon atoms. The alkyl part of the $C_1$-$C_{12}$alkoxy radical may be optionally substituted as defined below for an alkyl group.

"$C_2$-$C_{12}$alkoxyalkyl" refers to an alkoxyalkyl radical as defined below containing two to twelve carbon atoms. Each alkyl part of the $C_2$-$C_{12}$alkoxyalkyl radical may be optionally substituted as defined below for an alkyl group.

"$C_7$-$C_{12}$aralkyl" refers to an aralkyl group as defined below containing seven to twelve carbon atoms. The aryl part of the $C_7$-$C_{12}$aralkyl radical may be optionally substituted as described below for an aryl group. The alkyl part of the $C_7$-$C_{12}$aralkyl radical may be optionally substituted as defined below for an alkyl group.

"$C_7$-$C_{12}$aralkenyl" refers to an aralkenyl group as defined below containing seven to twelve carbon atoms. The aryl part of the $C_7$-$C_{12}$aralkenyl radical may be optionally substituted as described below for an aryl group. The alkenyl part of the $C_7$-$C_{12}$aralkenyl radical may be optionally substituted as defined below for an alkenyl group.

"$C_3$-$C_{12}$cycloalkyl" refers to a cycloalkyl radical as defined below having three to twelve carbon atoms. The $C_3$-$C_{12}$cycloalkyl radical may be optionally substituted as defined below for a cycloalkyl group.

"$C_4$-$C_{12}$cycloalkylalkyl" refers to a cycloalkylalkyl radical as defined below having four to twelve carbon atoms. The $C_4$-$C_{12}$cycloalkylalkyl radical may be optionally substituted as defined below for a cycloalkylalkyl group.

In addition to the foregoing, as used in the specification and appended claims, unless specified to the contrary, the following terms have the meaning indicated:

"Amino" refers to the —$NH_2$ radical.
"Cyano" refers to the —CN radical.
"Hydroxyl" refers to the —OH radical.
"Imino" refers to the =NH substituent.
"Nitro" refers to the —$NO_2$ radical.
"Oxo" refers to the =O substituent.
"Thioxo" refers to the =S substituent.
"Trifluoromethyl" refers to the —$CF_3$ radical.

"Alkyl" refers to a straight or branched hydrocarbon chain radical consisting solely of carbon and hydrogen atoms, containing no unsaturation, having from one to twelve carbon atoms, preferably one to eight carbon atoms or one to six carbon atoms, and which is attached to the rest of the molecule by a single bond, e.g., methyl, ethyl, n-propyl, 1-methylethyl(iso-propyl), n-butyl, n-pentyl, 1,1-dimethylethyl(t-butyl), 3-methylhexyl, 2-methylhexyl, and the like. Unless stated otherwise specifically in the specification, an alkyl group may be optionally substituted by one of the following groups: alkyl, alkenyl, halo, haloalkenyl, cyano, nitro, aryl, cycloalkyl, heterocyclyl, heteroaryl, oxo, trimethylsilanyl, —$OR^{14}$, —OC(O)—$R^{14}$, —$N(R^{14})_2$, —C(O)$R^{14}$, —C(O)$OR^{14}$, —C(O)N$(R^{14})_2$, —N$(R^{14})$C(O)$OR^{16}$, —N$(R^{14})$C(O)$R^{16}$, —N$(R^{14})$S(O)$_tR^{16}$ (where t is 1 to 2), —S(O)$_tOR^{16}$ (where t is 1 to 2), —S(O)$_tR^{16}$ (where t is 0 to 2), and —S(O)$_tN(R^{14})_2$ (where t is 1 to 2) where each $R^{14}$ is independently hydrogen, alkyl, haloalkyl, cycloalkyl, cycloalkylalkyl, aryl (optionally substituted with one or more halo groups), aralkyl, heterocyclyl, heterocyclylalkyl, heteroaryl or heteroarylalkyl; and each $R^{16}$ is alkyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted unless otherwise indicated.

"Alkenyl" refers to a straight or branched hydrocarbon chain radical group consisting solely of carbon and hydrogen atoms, containing at least one double bond, having from two to twelve carbon atoms, preferably one to eight carbon atoms and which is attached to the rest of the molecule by a single bond, e.g., ethenyl, prop-1-enyl, but-1-enyl, pent-1-enyl, penta-1,4-dienyl, and the like. Unless stated otherwise specifically in the specification, an alkenyl group may be optionally substituted by one of the following groups: alkyl, alkenyl, halo, haloalkenyl, cyano, nitro, aryl, cycloalkyl, heterocyclyl, heteroaryl, oxo, trimethylsilanyl, —OR$_{14}$, —OC(O)—R$^{14}$, —N(R$^{14}$)$_2$, —C(O)R$^{14}$, —C(O)OR$^{14}$, —C(O)N(R$^{14}$)$_2$, —N(R$^{14}$)C(O)OR$^{16}$, —N(R$^{14}$)C(O)R$^{16}$, —N(R$^{14}$)S(O)$_t$R$^{16}$ (where t is 1 to 2), —S(O)$_t$OR$^{16}$ (where t is 1 to 2), —S(O)$_t$R$^{16}$ (where t is 0 to 2), and —S(O)$_t$N(R$^{14}$)$_2$ (where t is 1 to 2) where each R$^{14}$ is independently hydrogen, alkyl, haloalkyl, cycloalkyl, cycloalkylalkyl, aryl (optionally substituted with one or more halo groups), aralkyl, heterocyclyl, heterocyclylalkyl, heteroaryl or heteroarylalkyl; and each R$^{16}$ is alkyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted unless otherwise indicated.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, e.g., methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon or any two carbons within the chain. Unless stated otherwise specifically in the specification, an alkylene chain may be optionally substituted by one of the following groups: alkyl, alkenyl, halo, haloalkenyl, cyano, nitro, aryl, cycloalkyl, heterocyclyl, heteroaryl, oxo, trimethylsilanyl, —OR$^{14}$, —OC(O)—R$^{14}$, —N(R$^{14}$)$_2$, —C(O)R$^{14}$, —C(O)OR$^{14}$, —C(O)N(R$^{14}$)$_2$, —N(R$^{14}$)C(O)OR$^{16}$, —N(R$^{14}$)C(O)R$^{16}$, —N(R$^{14}$)S(O)$_t$R$^{16}$ (where t is 1 to 2), —S(O)$_t$OR$^{16}$ (where t is 1 to 2), —S(O)$_t$R$^{16}$ (where t is 0 to 2), and —S(O)$_t$N(R$^{14}$)$_2$ (where t is 1 to 2) where each R$^{14}$ is independently hydrogen, alkyl, haloalkyl, cycloalkyl, cycloalkylalkyl, aryl (optionally substituted with one or more halo groups), aralkyl, heterocyclyl, heterocyclylalkyl, heteroaryl or heteroarylalkyl; and each R$^{16}$ is alkyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted unless otherwise indicated.

"Alkenylene" or "alkenylene chain" refers to a straight or branched divalent hydrocarbon chain linking the rest of the molecule to a radical group, consisting solely of carbon and hydrogen, containing at least one double bond and having from two to twelve carbon atoms, e.g., ethenylene, propenylene, n-butenylene, and the like. The alkenylene chain is attached to the rest of the molecule through a single bond and to the radical group through a double bond or a single bond. The points of attachment of the alkenylene chain to the rest of the molecule and to the radical group can be through one carbon or any two carbons within the chain. Unless stated otherwise specifically in the specification, an alkenylene chain may be optionally substituted by one of the following groups: alkyl, alkenyl, halo, haloalkenyl, cyano, nitro, aryl, cycloalkyl, heterocyclyl, heteroaryl, oxo, trimethylsilanyl, —OR$^{14}$, —OC(O)—R$^{14}$, —N(R$^{14}$)$_2$, —C(O)R$^{14}$, —C(O)OR$^{14}$, —C(O)N(R$^{14}$)$_2$, —N(R$^{14}$)C(O)OR$^{16}$, —N(R$^{14}$)C(O) R$^{16}$, —N(R$^{14}$)S(O)$_t$R$^{16}$ (where t is 1 to 2), —S(O)$_t$OR$^{16}$ (where t is 1 to 2), —S(O)$_t$R$^{16}$ (where t is 0 to 2), and —S(O)$_t$ (R$^{14}$)$_2$ (where t is 1 to 2) where each R$^{14}$ is independently hydrogen, alkyl, haloalkyl, cycloalkyl, cycloalkylalkyl, aryl (optionally substituted with one or more halo groups), aralkyl, heterocyclyl, heterocyclylalkyl, heteroaryl or heteroarylalkyl; and each R$^{16}$ is alkyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted unless otherwise indicated.

"Alkynylene" or "alkynylene chain" refers to a straight or branched divalent hydrocarbon chain linking the rest of the molecule to a radical group, consisting solely of carbon and hydrogen, containing at least one triple bond and having from two to twelve carbon atoms, e.g., propynylene, n-butynylene, and the like. The alkynylene chain is attached to the rest of the molecule through a single bond and to the radical group through a double bond or a single bond. The points of attachment of the alkynylene chain to the rest of the molecule and to the radical group can be through one carbon or any two carbons within the chain. Unless stated otherwise specifically in the specification, an alkynylene chain may be optionally substituted by one of the following groups: alkyl, alkenyl, halo, haloalkenyl, cyano, nitro, aryl, cycloalkyl, heterocyclyl, heteroaryl, oxo, trimethylsilanyl, —OR$^{14}$, —OC(O)—R$^{14}$, —N(R$^{14}$)$_2$, —C(O)R$^{14}$, —C(O)OR$^{14}$, —C(O)N(R$^{14}$)$_2$, —N(R$^{14}$)C(O)OR$^{16}$, —N(R$^{14}$)C(O)R$^{16}$, —N(R$^{14}$)S(O)$_t$R$^{16}$ (where t is 1 to 2), —S(O)$_t$OR$^{16}$ (where t is 1 to 2), —S(O)$_t$R$^{16}$ (where t is 0 to 2), and —S(O)$_t$N(R$^{14}$)$_2$ (where t is 1 to 2) where each R$^{14}$ is independently hydrogen, alkyl, haloalkyl, cycloalkyl, cycloalkylalkyl, aryl (optionally substituted with one or more halo groups), aralkyl, heterocyclyl, heterocyclylalkyl, heteroaryl or heteroarylalkyl; and each R$^{16}$ is alkyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted unless otherwise indicated.

"Alkynyl" refers to a straight or branched hydrocarbon chain radical group consisting solely of carbon and hydrogen atoms, containing at least one triple bond, having from two to twelve carbon atoms, preferably one to eight carbon atoms and which is attached to the rest of the molecule by a single bond, e.g., ethynyl, propynyl, butynyl, pentynyl, hexynyl, and the like. Unless stated otherwise specifically in the specification, an alkynyl group may be optionally substituted by one of the following groups: alkyl, alkenyl, halo, haloalkyl, haloalkenyl, cyano, nitro, aryl, aralkyl, cycloalkyl, cycloalkylalkyl, heterocyclyl, heterocyclylalkyl, heteroaryl, heteroarylalkyl, —OR$^{14}$, —OC(O)—R$^{14}$, —N(R$^{14}$)$_2$, —C(O)R$^{14}$, —C(O)OR$^{14}$, —C(O)N(R$^{14}$)$_2$, —N(R$^{14}$)C(O)OR$^{16}$, —N(R$^{14}$)C(O)R$^{16}$, —N(R$^{14}$)S(O)$_t$R$^{16}$ (where t is 1 to 2), —S(O)$_t$OR$^{16}$ (where t is 1 to 2), —S(O)$_t$R$^{16}$ (where t is 0 to 2), and —S(O)$_t$N(R$^{14}$)$_2$ (where t is 1 to 2) where each R$^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; and each R$^{16}$ is alkyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted.

"Alkoxy" refers to a radical of the formula —OR$_a$ where R$_a$ is an alkyl radical as defined above containing one to twelve carbon atoms. The alkyl part of the alkoxy radical may be optionally substituted as defined above for an alkyl radical.

"Alkoxyalkyl" refers to a radical of the formula —R$_a$—O—R$_a$ where each R$_a$ is independently an alkyl radical as defined above. The oxygen atom may be bonded to any carbon in either alkyl radical. Each alkyl part of the alkoxyalkyl radical may be optionally substituted as defined above for an alkyl group.

"Aryl" refers to aromatic monocyclic or multi cyclic hydrocarbon ring system consisting only of hydrogen and carbon and containing from 6 to 18 carbon atoms, where the ring system may be partially saturated. Aryl groups include, but are not limited to groups such as fluorenyl, phenyl and naphthyl. Unless stated otherwise specifically in the specification, the term "aryl" or the prefix "ar-" (such as in "aralkyl") is meant to include aryl radicals optionally substituted by one or more substituents independently selected from the group consisting of alkyl, alkenyl, halo, haloalkyl, haloalkenyl, cyano, nitro, aryl, heteroaryl, heteroarylalkyl, $-R^{15}-OR^{14}$, $-R^{15}-OC(O)-R^{14}$, $-R^{15}-N(R^{14})_2$, $-R^{15}-C(O)R^{14}$, $-R^{15}-C(O)OR^{14}$, $-R^{15}-C(O)N(R^{14})_2$, $-R^{15}-N(R^{14})C(O)OR^{16}$, $-R^{15}-N(R^{14})C(O)R^{16}$, $-R^{15}-N(R^{14})S(O)_tR^{16}$ (where t is 1 to 2), $-R^{15}-S(O)_tOR^{16}$ (where t is 1 to 2), $-R^{15}-S(O)_tR^{16}$ (where t is 0 to 2), and $-R^{15}-S(O)_tN(R^{14})_2$ (where t is 1 to 2) where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted.

"Aralkyl" refers to a radical of the formula $-R_aR_b$ where $R_a$ is an alkyl radical as defined above and $R_b$ is one or more aryl radicals as defined above, e.g., benzyl, diphenylmethyl and the like. The aryl radical(s) may be optionally substituted as described above.

"Aryloxy" refers to a radical of the formula $-OR_b$ where $R_b$ is an aryl group as defined above. The aryl part of the aryloxy radical may be optionally substituted as defined above.

"Aralkenyl" refers to a radical of the formula $-R_cR_b$ where $R_c$ is an alkenyl radical as defined above and $R_b$ is one or more aryl radicals as defined above, which may be optionally substituted as described above. The aryl part of the aralkenyl radical may be optionally substituted as described above for an aryl group. The alkenyl part of the aralkenyl radical may be optionally substituted as defined above for an alkenyl group.

"Aralkyloxy" refers to a radical of the formula $-OR_b$ where $R_b$ is an aralkyl group as defined above. The aralkyl part of the aralkyloxy radical may be optionally substituted as defined above.

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like. Unless otherwise stated specifically in the specification, the term "cycloalkyl" is meant to include cycloalkyl radicals which are optionally substituted by one or more substituents independently selected from the group consisting of alkyl, alkenyl, halo, haloalkyl, haloalkenyl, cyano, nitro, oxo, aryl, aralkyl, cycloalkyl, cycloalkylalkyl, heterocyclyl, heterocyclylalkyl, heteroaryl, heteroarylalkyl, $-R^{15}-OR^{14}$, $-R^{15}-OC(O)-R^{14}$, $-R^{15}-N(R^{14})_2$, $-R^{15}-C(O)R^{14}$, $-R^{15}-C(O)OR^{14}$, $-R^{15}-C(O)N(R^{14})_2$, $-R^{15}-N(R^{14})C(O)OR^{16}$, $-R^{15}-N(R^{14})C(O)R^{16}$, $-R^{15}-N(R^{14})S(O)_tR^{16}$ (where t is 1 to 2), $-R^{15}-S(O)_tOR^{16}$ (where t is 1 to 2), $-R^{15}-S(O)_tR^{16}$ (where t is 0 to 2), and $-R^{15}-S(O)_tN(R^{14})_2$ (where t is 1 to 2) where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted.

"Cycloalkylalkyl" refers to a radical of the formula $-R_aR_d$ where $R_a$ is an alkyl radical as defined above and $R_d$ is a cycloalkyl radical as defined above. The alkyl radical and the cycloalkyl radical may be optionally substituted as defined above.

"Halo" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. The alkyl part of the haloalkyl radical may be optionally substituted as defined above for an alkyl group.

"Heterocyclyl" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above which are optionally substituted by one or more substituents selected from the group consisting of alkyl, alkenyl, halo, haloalkyl, haloalkenyl, cyano, oxo, thioxo, nitro, aryl, aralkyl, cycloalkyl, cycloalkylalkyl, heterocyclyl, heterocyclylalkyl, heteroaryl, heteroarylalkyl, $-R^{15}-OR^{14}$, $-R^{15}-OC(O)-R^{14}$, $-R^{15}-N(R^{14})_2$, $-R^{15}-C(O)R^{14}$, $-R^{15}-C(O)OR^{14}$, $-R^{15}-C(O)N(R^{14})_2$, $-R^{15}-N(R^{14})C(O)OR^{16}$, $-R^{15}-N(R^{14})C(O)R^{16}$, $-R^{15}-N(R^{14})S(O)_tR^{16}$ (where t is 1 to 2), $-R^{15}-S(O)_tOR^{16}$ (where t is 1 to 2), $-R^{15}-S(O)_tR^{16}$ (where t is 0 to 2), and $-R^{15}-S(O)_tN(R^{14})_2$ (where t is 1 to 2) where each $R^{14}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, alkenyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted.

"Heterocyclylalkyl" refers to a radical of the formula —R$_a$R$_e$ where R$_a$ is an alkyl radical as defined above and R$_e$ is a heterocyclyl radical as defined above, and if the heterocyclyl is a nitrogen-containing heterocyclyl, the heterocyclyl may be attached to the alkyl radical at the nitrogen atom. The alkyl part of the heterocyclylalkyl radical may be optionally substituted as defined above for an alkyl group. The heterocyclyl part of the heterocyclylalkyl radical may be optionally substituted as defined above for a heterocyclyl group.

"Heteroaryl" refers to a 5- to 18-membered aromatic ring radical which consists of one to seventeen carbon atoms and from one to ten heteroatoms selected from the group consisting of nitrogen, oxygen and sulfur. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyl, naphthyridinyl, oxadiazolyl, 2-oxoazepinyl, oxazolyl, oxiranyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, pyrrolyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, the term "heteroaryl" is meant to include heteroaryl radicals as defined above which are optionally substituted by one or more substituents selected from the group consisting of alkyl, alkenyl, alkoxy, halo, haloalkyl, haloalkenyl, cyano, oxo, thioxo, nitro, oxo, aryl, aralkyl, cycloalkyl, cycloalkylalkyl, heterocyclyl, heterocyclylalkyl, heteroaryl, heteroarylalkyl, —R$^{15}$—OR$^{14}$, —R$^{15}$—OC(O)—R$^{14}$, —R$^{15}$—N(R$^{14}$)$_2$, —R$^{15}$—C(O)R$^{14}$, —R$^{15}$—C(O)OR$^{14}$, —R$^{15}$—C(O)N(R$^{14}$)$_2$, —R$^{15}$—N(R$^{14}$)C(O)OR$^{16}$, —R$^{15}$—N(R$^{14}$)C(O)R$^{16}$, —R$^{15}$—N(R$^{14}$)S(O)$_t$R$^{16}$ (where t is 1 to 2), —R$^{15}$—S(O)$_t$OR$^{16}$ (where t is 1 to 2), —R$^{15}$—S(O)$_t$R$^{16}$ (where t is 0 to 2), and —R$^{15}$—S(O)$_t$N(R$^{14}$)$_2$ (where t is 1 to 2) where each R$^{14}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each R$^{15}$ is independently a direct bond or a straight or branched alkylene or alkenylene chain; and each R$^{16}$ is alkyl, alkenyl, haloalkyl, cycloalkyl, cycloalkylalkyl, aryl, aralkyl, heterocyclyl, heterocyclylalkyl, heteroaryl or heteroarylalkyl, and where each of the above substituents is unsubstituted.

"Heteroarylalkyl" refers to a radical of the formula —R$_a$R$_f$ where R$_a$ is an alkyl radical as defined above and R$_f$ is a heteroaryl radical as defined above. The heteroaryl part of the heteroarylalkyl radical may be optionally substituted as defined above for a heteroaryl group. The alkyl part of the heteroarylalkyl radical may be optionally substituted as defined above for an alkyl group.

"Heteroarylalkenyl" refers to a radical of the formula —R$_b$R$_f$ where R$_b$ is an alkenyl radical as defined above and R$_f$ is a heteroaryl radical as defined above. The heteroaryl part of the heteroarylalkenyl radical may be optionally substituted as defined above for a heteroaryl group. The alkenyl part of the heteroarylalkenyl radical may be optionally substituted as defined above for an alkenyl group.

"Trihaloalkyl" refers to an alkyl radical, as defined above, that is substituted by three halo radicals, as defined above, e.g., trifluoromethyl. The alkyl part of the trihaloalkyl radical may be optionally substituted as defined above for an alkyl group.

"Trihaloalkoxy" refers to a radical of the formula —OR$_g$ where R$_g$ is a trihaloalkyl group as defined above. The trihaloalkyl part of the trihaloalkoxy group may be optionally substituted as defined above for a trihaloalkyl group.

"Analgesia" refers to an absence of pain in response to a stimulus that would normally be painful.

"Allodynia" refers to a condition in which a normally innocuous sensation, such as pressure or light touch, is perceived as being extremely painful.

"Prodrugs" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)). A discussion of prodrugs is provided in Higuchi, T., et al., "Pro-drugs as Novel Delivery Systems," A.C.S. Symposium Series, Vol. 14, and in Bioreversible Carriers in Drug Design, Ed. Edward B. Roche, American Pharmaceutical Association and Pergamon Press, 1987, both of which are incorporated in full by reference herein.

The term "prodrug" is also meant to include any covalently bonded carriers, which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds of the invention and the like.

The invention disclosed herein is also meant to encompass all pharmaceutically acceptable compounds of formula (I) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$Cl, $^{123}$I, and $^{125}$I, respectively. These radiolabelled compounds could be useful to help determine or measure the effectiveness of the compounds, by characterizing, for example, the site or mode of action on the sodium channels, or binding affinity to pharmacologically important site of action on the sodium channels. Certain isotopically-labelled compounds of formula (I), for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of formula (I) can generally be prepared by conventional techniques known to those skilled in the art or by processes analogous to those described in the Examples and Preparations as set out below using an appropriate isotopically-labeled reagent in place of the non-labeled reagent previously employed.

The invention disclosed herein is also meant to encompass the in vivo metabolic products of the disclosed compounds. Such products may result from, for example, the oxidation, reducation, hydrolysis, amidation, esterification, and the like of the administered compound, primarily due to enzymatic processes. Accordingly, the invention includes compounds produced by a process comprising contacting a compound of this invention with a mammal for a period of time sufficient to yield a metabolic product thereof. Such products are typically are identified by administering a radiolabelled compound of the invention in a detectable dose to an animal, such as rat, mouse, guinea pig, monkey, or to human, allowing sufficient time for metabolism to occur, and isolating its coversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

"Mammal" includes humans and both domestic animals such as laboratory animals and household pets, (e.g. cats, dogs, swine, cattle, sheep, goats, horses, rabbits), and non-domestic animals such as wildlife and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Therapeutically effective amount" refers to that amount of a compound of the invention which, when administered to a mammal, preferably a human, is sufficient to effect treatment, as defined below, of a sodium channel-mediated disease or condition in the mammal, preferably a human. The amount of a compound of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) relieving the symptoms resulting from the disease or condition, i.e., relieving pain without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts may contain one or more asymmetric centres and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallisation. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

Also within the scope of the invention are intermediate compounds of formula (I) and all polymorphs of the aforementioned species and crystal habits thereof.

The chemical naming protocol and structure diagrams used herein are a modified form of the I.U.P.A.C. nomenclature system, using the ACD/Name Version 9.07 software program, wherein the compounds of the invention are named herein as derivatives of the central core structure, i.e., the 2-oxindole structure. For complex chemical names employed herein, a substituent group is named before the group to which it attaches. For example, cyclopropylethyl comprises an ethyl backbone with cyclopropyl substituent. In chemical structure diagrams, all bonds are identified, except for some carbon atoms, which are assumed to be bonded to sufficient hydrogen atoms to complete the valency.

Thus, for example, a compound of formula (I) wherein j is 0, k is 1, Q is —O—, $R^1$ is pentyl, $R^{2a}$ is 3,5-dichlorophenyl, $R^{2b}$, $R^{2c}$ and $R^{2d}$ are each hydrogen, $R^{3a}$ and $R^{3d}$ are each hydrogen, and $R^{3b}$ and $R^{3c}$, together with the carbon ring atoms to which they are attached, form a fused dioxolyl ring; i.e., a compound of the following formula:

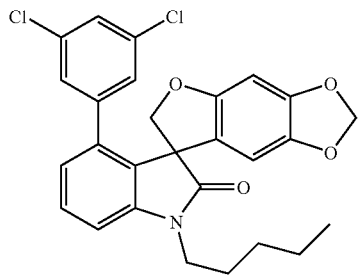

is named herein as 4'-(3,5-dichlorophenyl)-1-pentylspiro[furo[2,3-f][1,3]benzodioxole-7,3'-indol]-2'(1'H)-one.

Embodiments of the Invention

Of the various aspects of the invention set forth above in the Summary of the Invention, certain embodiments are preferred.

One embodiment of the invention are the compounds of formula (I) as set forth above in the Summary of the invention wherein:

at least one of j and k is 1 and the other is 0 or 1;
Q is —O—;
$R^1$ is hydrogen, alkyl, alkenyl, alkynyl, haloalkyl, aryl, cycloalkyl, cycloalkylalkyl, heteroaryl, heterocyclyl, —$R^8$—C(O)$R^5$, —$R^8$—C(O)O$R^5$, —C(O)N($R^4$)$R^5$, —S(O)$_2$—$R^5$, —$R^9$—S(O)$_m$—$R^5$ (where m is 0, 1 or 2), —$R^8$—O$R^5$, —$R^8$—CN, —$R^9$—P(O)(O$R^5$)$_2$, or —$R^9$—O—$R^9$—O$R^5$;
$R^{2a}$, $R^{2b}$, $R^{2c}$ and $R^{2d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—NO$_2$, —$R^8$—O$R^5$, —$R^8$—N($R^4$)$R^5$, —N=C($R^4$)$R^5$, —S(O)$_m$$R^4$, —OS(O)$_2$CF$_3$, —$R^8$—C(O)$R^4$, —C(S)$R^4$, —C($R^4$)$_2$C(O)$R^5$, —$R^8$—C(O)O$R^4$, —C(S)O$R^4$, —$R^8$—C(O)N($R^4$)$R^5$, —C(S)N($R^4$)$R^5$, —N($R^5$)C(O)$R^4$, —N($R^5$)C(S)$R^4$, —N($R^5$)C(O)O$R^4$, —N($R^5$)C(S)O$R^4$, —N($R^5$)C(O)N($R^4$)$R^5$, —N($R^5$)C(S)N($R^4$)$R^5$, —N($R^5$)S(O)$_n$$R^4$, —N($R^5$)S(O)$_n$N($R^4$)$R^5$, —$R^8$—S(O)$_n$N($R^4$)$R^5$, —N($R^5$)C(=N$R^5$)N($R^4$)$R^5$, and —N($R^5$)C(=N—CN)N($R^4$)$R^5$, wherein each m is independently 0, 1, or 2 and each n is independently 1 or 2;

and wherein each of the cycloalkyl, cycloalkylalkyl, aryl, aralkyl, aralkenyl, heterocyclyl, heterocyclylalkyl, heteroaryl and heteroarylalkyl groups for $R^{2a}$, $R^{2b}$, $R^{2c}$ and $R^{2d}$ may be optionally substituted by one or more substituents selected from the group consisting of alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—$NO_2$, —$R^8$—$OR^5$, —$R^8$—$N(R^4)R^5$, —$S(O)_mR^4$, —$R^8$—$S(O)_nN(R^4)R^5$, —$R^8$—$C(O)R^4$, —$R^8$—$C(O)OR^4$, —$R^8$—$C(O)N(R^4)R^5$, —$N(R^5)C(O)R^4$, and —$N(R^5)S(O)_nR^4$, wherein each m is independently 0, 1, or 2 and each n is independently 1 or 2;

or $R^{2a}$ and $R^{2b}$, together with the carbon ring atoms to which they are directly attached, may form a fused ring selected from cycloalkyl, aryl, heterocyclyl and heteroaryl, and $R^{2c}$ and $R^{2d}$ are as defined above;

or $R^{2b}$ and $R^{2c}$, together with the carbon ring atoms to which they are directly attached, may form a fused ring selected from cycloalkyl, aryl, heterocyclyl and heteroaryl, and $R^{2a}$ and $R^{2d}$ are as defined above;

or $R^{2c}$ and $R^{2d}$, together with the carbon ring atoms to which they are directly attached, may form a fused ring selected from cycloalkyl, aryl, heterocyclyl and heteroaryl, and $R^{2a}$ and $R^{2b}$ are as defined above;

$R^{3a}$, $R^{3b}$, $R^{3c}$ and $R^{3d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—$NO_2$, —$R^8$—$OR^5$, —$R^8$—$N(R^4)R^5$, —N=$C(R^4)R^5$, —$S(O)_mR^4$, —$OS(O)_2CF_3$, —$R^8$—$C(O)R^4$, —$C(S)R^4$, —$C(R^4)_2C(O)R^5$, —$R^8$—$C(O)OR^4$, —$C(S)OR^4$, —$R^8$—$C(O)N(R^4)R^5$, —$C(S)N(R^4)R^5$, —$N(R^5)C(O)R^4$, —$N(R^5)C(S)R^4$, —$N(R^5)C(O)OR^4$, —$N(R^5)C(S)OR^4$, —$N(R^5)C(O)N(R^4)R^5$, —$N(R^5)C(S)N(R^4)R^5$, —$N(R^5)S(O)_nR^4$, —$N(R^5)S(O)_nN(R^4)R^5$, —$R^8$—$S(O)_nN(R^4)R^5$, —$N(R^5)C(=NR^5)N(R^4)R^5$, and —$N(R^5)C(N=C(R^4)R^5)N(R^4)R^5$, wherein each m is independently 0, 1, or 2 and each n is independently 1 or 2;

or $R^{3a}$ and $R^{3b}$, together with the carbon ring atoms to which they are directly attached, form a fused ring selected from cycloalkyl, heterocyclyl, aryl or heteroaryl, and $R^{3c}$ and $R^{3d}$ are as defined above;

or $R^{3b}$ and $R^{3c}$, together with the carbon ring atoms to which they are directly attached, may form a fused ring selected from cycloalkyl, heterocyclyl, aryl or heteroaryl, and $R^{3a}$ and $R^{3d}$ are as defined above;

or $R^{3c}$ and $R^{3d}$, together with the carbon ring atoms to which they are directly attached, may form a fused ring selected from cycloalkyl, heterocyclyl, aryl or heteroaryl, and $R^{3a}$ and $R^{3b}$ are as defined above;

each $R^4$ and $R^5$ is independently selected from the group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when $R^4$ and $R^5$ are each attached to the same nitrogen atom, then $R^4$ and $R^5$, together with the nitrogen atom to which they are attached, may form a heterocyclyl or heteroaryl;

each $R^8$ is a direct bond or a straight or branched alkylene chain, a straight or branched alkenylene chain or a straight or branched alkynylene chain; and each $R^9$ is a straight or branched alkylene chain, a straight or branched alkenylene chain or a straight or branched alkynylene chain.

Another embodiment of the invention are the compounds of formula (I) as set forth above in the Summary of the invention wherein:

j is 0 and k is 1;

Q is —O—;

$R^1$ is hydrogen, alkyl, alkenyl, alkynyl, haloalkyl, aryl, cycloalkyl, cycloalkylalkyl, heteroaryl, heterocyclyl, —$R^8$—$C(O)R^5$, —$R^8$—$C(O)OR^5$, —$R^8$—$C(O)N(R^4)R^5$, —$S(O)_2$—$R^5$, —$R^9$—$S(O)_m$—$R^5$ (where m is 0, 1 or 2), —$R^8$—$OR^5$, —$R^8$—CN, —$R^9$—$P(O)(OR^5)_2$, or —$R^9$—O—$R^9$—$OR^5$;

$R^{2a}$, $R^{2b}$, $R^{2c}$ and $R^{2d}$ are each independently selected from hydrogen, halo or alkyl;

$R^{3a}$, $R^{3b}$, $R^{3c}$ and $R^{3d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—$NO_2$, —$R^8$—$OR^5$, —$R^8$—$N(R^4)R^5$, —N=$C(R^4)R^5$, —$S(O)_mR^4$, —$OS(O)_2CF_3$, —$R^8$—$C(O)R^4$, —$C(S)R^4$, —$C(R^4)_2C(O)R^5$, —$R^8$—$C(O)OR^4$, —$C(S)OR^4$, —$R^8$—$C(O)N(R^4)R^5$, —$C(S)N(R^4)R^5$, —$N(R^5)C(O)R^4$, —$N(R^5)C(S)R^4$, —$N(R^5)C(O)OR^4$, —$N(R^5)C(S)OR^4$, —$N(R^5)C(O)N(R^4)R^5$, —$N(R^5)C(S)N(R^4)R^5$, —$N(R^5)S(O)_nR^4$, —$N(R^5)S(O)_nN(R^4)R^5$, —$R^8$—$S(O)_nN(R^4)R^5$, —$N(R^5)C(=NR^5)N(R^4)R^5$, and —$N(R^5)C(N=C(R^4)R^5)N(R^4)R^5$, wherein each m is independently 0, 1, or 2 and each n is independently 1 or 2;

or $R^{3b}$ and $R^{3c}$, together with the carbon ring atoms to which they are directly attached, form a fused ring selected from cycloalkyl, heterocyclyl, aryl or heteroaryl, and $R^{3a}$ and $R^{3c}$ are as defined above;

each $R^4$ and $R^5$ is independently selected from the group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when $R^4$ and $R^5$ are each attached to the same nitrogen atom, then $R^4$ and $R^5$, together with the nitrogen atom to which they are attached, may form a heterocyclyl or heteroaryl;

each $R^8$ is a direct bond or a straight or branched alkylene chain, a straight or branched alkenylene chain or a straight or branched alkynylene chain; and each $R^9$ is a straight or branched alkylene chain, a straight or branched alkenylene chain or a straight or branched alkynylene chain.

Another embodiment of the invention are the compounds of formula (I) as set forth above in the Summary of the invention wherein:

$R^1$ is hydrogen, alkyl, alkenyl, alkynyl, haloalkyl, cycloalkyl, cycloalkylalkyl, —$R^8$—$OR^5$, —$R^8$—$C(O)R^5$, —$R^8$—$C(O)OR^5$, —$R^8$—$C(O)N(R^4)R^5$, —$S(O)_2$—$R^5$, —$R^8$—CN, —$R^9$—$P(O)(OR^5)_2$, or —$R^9$—O—$R^9$—$OR^5$;

$R^{2a}$, $R^{2b}$, $R^{2c}$ and $R^{2d}$ are each independently selected from hydrogen, halo or alkyl;

$R^{3a}$ and $R^{3d}$ are both hydrogen;

$R^{3b}$ and $R^{3c}$, together with the carbon ring atoms to which they are directly attached, form a fused dioxolyl ring;

each $R^4$ and $R^5$ is independently selected from the group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when $R^4$ and $R^5$ are each attached to the same nitrogen atom, then $R^4$ and $R^5$, together with the nitrogen atom to which they are attached, may form a heterocyclyl or heteroaryl;

each $R^8$ is a direct bond or a straight or branched alkylene chain, a straight or branched alkenylene chain or a straight or branched alkynylene chain; and each $R^9$ is a straight or branched alkylene chain, a straight or branched alkenylene chain or a straight or branched alkynylene chain.

Another embodiment of the invention are the compounds of formula (I) as set forth above in the Summary of the Invention wherein:

$R^1$ is hydrogen, alkyl, alkenyl, alkynyl, haloalkyl, cycloalkyl, cycloalkylalkyl, —$R^8$—$OR^5$, —$R^8$—$C(O)R^5$, —$R^8$—C(O)$OR^5$, —$R^8$—C(O)N($R^4$)$R^5$, —S(O)$_2$—$R^5$, —$R^8$—CN, —$R^9$—P(O)(O$R^5$)$_2$, or —$R^9$—O—$R^9$—O$R^5$;

$R^{2a}$, $R^{2b}$, $R^{2c}$ and $R^{2d}$ are each independently selected from hydrogen, halo or alkyl;

$R^{3a}$, $R^{3b}$, $R^{3c}$ and $R^{3d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—NO$_2$, —$R^8$—O$R^5$, —$R^8$—N($R^4$)$R^5$, —N=C($R^4$)$R^5$, —S(O)$_m$$R^4$, —OS(O)$_2$CF$_3$, —$R^8$—C(O)$R^4$, —C(S)$R^4$, —C($R^4$)$_2$C(O)$R^5$, —$R^8$—C(O)O$R^4$, —C(S)O$R^4$, —$R^8$—C(O)N($R^4$)$R^5$, —C(S)N($R^4$)$R^5$, —N($R^5$)C(O)$R^4$, —N($R^5$)C(S)$R^4$, —N($R^5$)C(O)O$R^4$, —N($R^5$)C(S)O$R^4$, —N($R^5$)C(O)N($R^4$)$R^5$, —N($R^5$)C(S)N($R^4$)$R^5$, —N($R^5$)S(O)$_n$$R^4$, —N($R^5$)S(O)$_n$N($R^4$)$R^5$, —$R^8$—S(O)$_n$N($R^4$)$R^5$, —N($R^5$)C(=N$R^5$)N($R^4$)$R^5$, and —N($R^5$)C(N=C($R^4$)$R^5$)N($R^4$)$R^5$, wherein each m is independently 0, 1, or 2 and each n is independently 1 or 2;

each $R^4$ and $R^5$ is independently selected from the group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when $R^4$ and $R^5$ are each attached to the same nitrogen atom, then $R^4$ and $R^5$, together with the nitrogen atom to which they are attached, may form a heterocyclyl or heteroaryl;

each $R^8$ is a direct bond or a straight or branched alkylene chain, a straight or branched alkenylene chain or a straight or branched alkynylene chain; and each $R^9$ is a straight or branched alkylene chain, a straight or branched alkenylene chain or a straight or branched alkynylene chain.

Another embodiment of the invention are the compounds of formula (I) as set forth above in the Summary of the Invention wherein:

$R^1$ is hydrogen, alkyl, alkenyl, alkynyl, haloalkyl, cycloalkyl, cycloalkylalkyl, —$R^8$—O$R^5$, —$R^8$—C(O)$R^5$, —$R^8$—C(O)O$R^5$, —$R^8$—C(O)N($R^4$)$R^5$, —S(O)$_2$—$R^5$, —$R^8$—CN, —$R^9$—P(O)(O$R^5$)$_2$, or —$R^9$—O—$R^9$—O$R^5$;

$R^{2a}$, $R^{2b}$, $R^{2c}$ and $R^{2d}$ are each independently selected from hydrogen, halo or alkyl;

$R^{3a}$ and $R^{3d}$ are both hydrogen;

$R^{3b}$ and $R^{3c}$, together with the carbon ring atoms to which they are directly attached, form a fused optionally substituted heterocyclyl ring or a fused optionally substituted cycloalkyl ring;

each $R^4$ and $R^5$ is independently selected from the group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when $R^4$ and $R^5$ are each attached to the same nitrogen atom, then $R^4$ and $R^5$, together with the nitrogen atom to which they are attached, may form a heterocyclyl or heteroaryl;

each $R^8$ is a direct bond or a straight or branched alkylene chain, a straight or branched alkenylene chain or a straight or branched alkynylene chain; and each $R^9$ is a straight or branched alkylene chain, a straight or branched alkenylene chain or a straight or branched alkynylene chain.

Another embodiment of the invention are the compounds of formula (I) as set forth above in the Summary of the Invention wherein:

$R^1$ is aryl, heteroaryl or heterocyclyl;

$R^{2a}$, $R^{2b}$, $R^{2c}$ and $R^{2d}$ are each hydrogen; and $R^{3b}$ and $R^{3c}$, together with the carbon ring atoms to which they are directly attached, form a fused dioxolyl ring.

Another embodiment of the invention are the compounds of formula (I) as set forth above in the Summary of the invention wherein:

at least one of j and k is 1 and the other is 0 or 1;

Q is —O—;

$R^1$ is hydrogen, alkyl, —$R^8$—C(O)O$R^5$ or —$R^8$—C(O)N($R^4$)$R^5$;

$R^{2a}$ is selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—NO$_2$, —$R^8$—O$R^5$, —$R^8$—N($R^4$)$R^5$, —N=C($R^4$)$R^5$, —S(O)$_m$$R^4$, —OS(O)$_2$CF$_3$, —$R^8$—C(O)$R^4$, —C(S)$R^4$, —C($R^4$)$_2$C(O)$R^5$, —$R^8$—C(O)O$R^4$, —C(S)O$R^4$, —$R^8$—C(O)N($R^4$)$R^5$, —C(S)N($R^4$)$R^5$, —N($R^5$)C(O)$R^4$, —N($R^5$)C(S)$R^4$, —N($R^5$)C(O)O$R^4$, —N($R^5$)C(S)O$R^4$, —N($R^5$)C(O)N($R^4$)$R^5$, —N($R^5$)C(S)N($R^4$)$R^5$, —N($R^5$)S(O)$_n$$R^4$, —N($R^5$)S(O)$_n$N($R^4$)$R^5$, —$R^8$—S(O)$_n$N($R^4$)$R^5$, —N($R^5$)C(=N$R^5$)N($R^4$)$R^5$, and —N($R^5$)C(=N—CN)N($R^4$)$R^5$, wherein each m is independently 0, 1, or 2 and each n is independently 1 or 2;

and wherein each of the cycloalkyl, cycloalkylalkyl, aryl, aralkyl, aralkenyl, heterocyclyl, heterocyclylalkyl, heteroaryl and heteroarylalkyl groups for $R^{2a}$ is optionally substituted by one or more substituents selected from the group consisting of alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—NO$_2$, —$R^8$—O$R^5$, —$R^8$—N($R^4$)$R^5$, —S(O)$_m$$R^4$, —$R^8$—S(O)$_n$N($R^4$)$R^5$, —$R^8$—C(O)$R^4$, —$R^8$—C(O)O$R^4$, —$R^8$—C(O)N($R^4$)$R^5$, —N($R^5$)C(O)$R^4$, and —N($R^5$)S(O)$_n$$R^4$, wherein each m is independently 0, 1, or 2 and each n is independently 1 or 2;

$R^{2b}$, $R^{2c}$ and $R^{2d}$ are each hydrogen;

$R^{3a}$, $R^{3b}$, $R^{3c}$ and $R^{3d}$ are each independently selected from hydrogen or halo;

or $R^{3b}$ and $R^{3c}$, together with the carbon ring atoms to which they are directly attached, form a fused ring selected from cycloalkyl, heterocyclyl, aryl or heteroaryl and $R^{3a}$ and $R^{3d}$ are as defined above;

each $R^4$ and $R^5$ is independently selected from the group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when $R^4$ and $R^5$ are each attached to the same nitrogen atom, then $R^4$ and $R^5$, together with the nitrogen atom to which they are attached, may form a heterocyclyl or heteroaryl;

each $R^8$ is a direct bond or a straight or branched alkylene chain, a straight or branched alkenylene chain or a straight or branched alkynylene chain; and each $R^9$ is a straight or branched alkylene chain, a straight or branched alkenylene chain or a straight or branched alkynylene chain.

Another embodiment of the invention are the compounds of formula (I) as set forth above in the Summary of the invention wherein:

j is 0 and k is 1 or j is 1 and k is 0;

Q is —O—;

$R^1$ is hydrogen or alkyl;

$R^{2a}$ is selected from the group consisting of alkyl, haloalkenyl, aryl, aralkyl, aralkenyl, heterocyclyl, heteroaryl, —$R^8$—C(O)N($R^4$)$R^5$, and —$R^8$—N($R^4$)$R^5$;

wherein each of the aryl, aralkyl, aralkenyl, heterocyclyl and heteroaryl groups for $R^{2a}$ is optionally substituted by one or more substituents selected from the group consisting of alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—NO$_2$, —$R^8$—OR$^5$, —$R^8$—N($R^4$)$R^5$, —S(O)$_m$R$^4$, —$R^8$—S(O)$_n$N($R^4$)$R^5$, —$R^8$—C(O)R$^4$, —$R^8$—C(O)OR$^4$, —$R^8$—C(O)N($R^4$)$R^5$, —N($R^5$)C(O)R$^4$, and —N($R^5$)S(O)$_n$R$^4$, wherein each m is independently 0, 1, or 2 and each n is independently 1 or 2;

$R^{2b}$, $R^{2c}$ and $R^{2d}$ are each hydrogen;

$R^{3a}$, $R^{3b}$, $R^{3c}$ and $R^{3d}$ are each independently selected from hydrogen or halo;

or $R^{3b}$ and $R^{3c}$, together with the carbon ring atoms to which they are directly attached, form a fused dioxolyl ring or a fused optionally substituted tetrahydrofuranyl ring, and $R^{3a}$ and $R^{3d}$ are as defined above;

each $R^4$ and $R^5$ is independently selected from the group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when $R^4$ and $R^5$ are each attached to the same nitrogen atom, then $R^4$ and $R^5$, together with the nitrogen atom to which they are attached, may form a heterocyclyl or heteroaryl; and each $R^8$ is a direct bond or a straight or branched alkylene chain, a straight or branched alkenylene chain or a straight or branched alkynylene chain.

Another embodiment of the invention are the compounds of formula (I) as set forth above in the Summary of the invention wherein:

at least one of j and k is 1 and the other is 0 or 1;

Q is —O—;

$R^1$ is aralkyl substituted by —C(O)N($R^6$)$R^7$ where:

$R^6$ is hydrogen, alkyl, aryl or aralkyl; and $R^7$ is hydrogen, alkyl, haloalkyl, —$R^9$—CN, —$R^9$—OR$^5$, —$R^9$—N($R^4$)$R^5$, aryl, aralkyl, cycloalkyl, cycloalkylalkyl, heterocyclyl, heterocyclylalkyl, heteroaryl or heteroarylalkyl;

or $R^6$ and $R^7$, together with the nitrogen to which they are attached, form a heterocyclyl or heteroaryl;

and wherein each aryl, aralkyl, cycloalkyl, cycloalkylalkyl, heterocyclyl, heterocyclylalkyl, heteroaryl and heteroarylalkyl group for $R^6$ and $R^7$ may be optionally substituted by one or more substituents selected from the group consisting of alkyl, cycloalkyl, aryl, aralkyl, halo, haloalkyl, —$R^8$—CN, —$R^8$—OR$^5$, heterocyclyl and heteroaryl;

$R^{2a}$, $R^{2b}$, $R^{2c}$ and $R^{2d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—NO$_2$, —$R^8$—OR$^5$, —$R^8$—N($R^4$)$R^5$, —N=C($R^4$)$R^5$, —S(O)$_m$R$^4$, —OS(O)$_2$CF$_3$, —$R^8$—C(O)R$^4$, —C(S)R$^4$, —C($R^4$)$_2$C(O)R$^5$, —$R^8$—C(O)OR$^4$, —C(S)OR$^4$, —$R^8$—C(O)N($R^4$)$R^5$, —C(S)N($R^4$)$R^5$, —N($R^5$)C(O)R$^4$, —N($R^5$)C(S)R$^4$, —N($R^5$)C(O)OR$^4$, —N($R^5$)C(S)OR$^4$, —N($R^5$)C(O)N($R^4$)$R^5$, —N($R^5$)C(S)N($R^4$)$R^5$, —N($R^5$)S(O)$_n$R$^4$, —N($R^5$)S(O)$_n$N($R^4$)$R^5$, —$R^8$—S(O)$_n$N($R^4$)$R^5$, —N($R^5$)C(=NR$^5$)N($R^4$)$R^5$, and —N($R^5$)C(=N—CN)N($R^4$)$R^5$, wherein each m is independently 0, 1, or 2 and each n is independently 1 or 2;

and wherein each of the cycloalkyl, cycloalkylalkyl, aryl, aralkyl, aralkenyl, heterocyclyl, heterocyclylalkyl, heteroaryl and heteroarylalkyl groups for $R^{2a}$, $R^{2b}$, $R^{2c}$ and $R^{2d}$ may be optionally substituted by one or more substituents selected from the group consisting of alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—NO$_2$, —$R^8$—OR$^5$, —$R^8$—N($R^4$)$R^5$, —S(O)$_m$R$^4$, —$R^8$—S(O)$_n$N($R^4$)$R^5$, —$R^8$—C(O)R$^4$, —$R^8$—C(O)OR$^4$, —$R^8$—C(O)N($R^4$)$R^5$, —N($R^5$)C(O)R$^4$, and —N($R^5$)S(O)$_n$R$^4$, wherein each m is independently 0, 1, or 2 and each n is independently 1 or 2;

or $R^{2a}$ and $R^{2b}$, together with the carbon ring atoms to which they are directly attached, may form a fused ring selected from cycloalkyl, aryl, heterocyclyl and heteroaryl, and $R^{2a}$ and $R^{2d}$ are as defined above;

or $R^{2b}$ and $R^{2c}$, together with the carbon ring atoms to which they are directly attached, may form a fused ring selected from cycloalkyl, aryl, heterocyclyl and heteroaryl, and $R^{2a}$ and $R^{2d}$ are as defined above;

or $R^{2c}$ and $R^{2d}$, together with the carbon ring atoms to which they are directly attached, may form a fused ring selected from cycloalkyl, aryl, heterocyclyl and heteroaryl, and $R^{2a}$ and $R^{2b}$ are as defined above;

$R^{3a}$, $R^{3b}$, $R^{3c}$ and $R^{3d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—NO$_2$, —$R^8$—OR$^5$, —$R^8$—N($R^4$)$R^5$, —N=C($R^4$)$R^5$, —S(O)$_m$R$^4$, —OS(O)$_2$CF$_3$, —$R^8$—C(O)R$^4$, —C(S)R$^4$, —C($R^4$)$_2$C(O)R$^5$, —$R^8$—C(O)OR$^4$, —C(S)OR$^4$, —$R^8$—C(O)N($R^4$)$R^5$, —C(S)N($R^4$)$R^5$, —N($R^5$)C(O)R$^4$, —N($R^5$)C(S)R$^4$, —N($R^5$)C(O)OR$^4$, —N(R5)C(S)OR$^4$, —N($R^5$)C(O)N($R^4$)$R^5$, —N($R^5$)C(S)N($R^4$)$R^5$, —N($R^5$)S(O)$_n$R$^4$, —N($R^5$)S(O)$_n$N($R^4$)$R^5$, —$R^8$—S(O)$_n$N($R^4$)$R^5$, —N($R^5$)C(=NR$^5$)N($R^4$)$R^5$, and —N($R^5$)C(N=C($R^4$)$R^5$)N($R^4$)$R^5$, wherein each m is independently 0, 1, or 2 and each n is independently 1 or 2;

or $R^{3a}$ and $R^{3b}$, together with the carbon ring atoms to which they are directly attached, form a fused ring selected from cycloalkyl, heterocyclyl, aryl or heteroaryl, and $R^{3c}$ and $R^{3d}$ are as defined above;

or $R^{3b}$ and $R^{3c}$, together with the carbon ring atoms to which they are directly attached, may form a fused ring selected from cycloalkyl, heterocyclyl, aryl or heteroaryl, and $R^{3a}$ and $R^{3d}$ are as defined above;

or $R^{3c}$ and $R^{3d}$, together with the carbon ring atoms to which they are directly attached, may form a fused ring selected from cycloalkyl, heterocyclyl, aryl or heteroaryl, and $R^{3a}$ and $R^{3b}$ are as defined above;

each $R^4$ and $R^5$ is independently selected from the group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when $R^4$ and $R^5$ are each attached to the same nitrogen atom, then $R^4$ and $R^5$, together with the nitrogen atom to which they are attached, may form a heterocyclyl or heteroaryl;

each $R^8$ is a direct bond or a straight or branched alkylene chain, a straight or branched alkenylene chain or a straight or branched alkynylene chain; and each $R^9$ is a straight or branched alkylene chain, a straight or branched alkenylene chain or a straight or branched alkynylene chain.

Another embodiment of the invention are the compounds of formula (I) as set forth above in the Summary of the invention wherein:

j is 0 and k is 1;

Q is —O—;

$R^1$ is aralkyl substituted by —C(O)N($R^6$)$R^7$ where:
  $R^6$ is hydrogen, alkyl, aryl or aralkyl; and
  $R^7$ is hydrogen, alkyl, haloalkyl, —$R^9$—CN, —$R^9$—$OR^5$, —$R^9$—N($R^4$)$R^5$, aryl, aralkyl, cycloalkyl, cycloalkylalkyl, heterocyclyl, heterocyclylalkyl, heteroaryl or heteroarylalkyl;
  or $R^6$ and $R^7$, together with the nitrogen to which they are attached, form a heterocyclyl or heteroaryl;
  and wherein each aryl, aralkyl, cycloalkyl, cycloalkylalkyl, heterocyclyl, heterocyclylalkyl, heteroaryl and heteroarylalkyl group for $R^6$ and $R^7$ may be optionally substituted by one or more substituents selected from the group consisting of alkyl, cycloalkyl, aryl, aralkyl, halo, haloalkyl, —$R^8$—CN, —$R^8$—$OR^5$, heterocyclyl and heteroaryl;

$R^{2a}$, $R^{2b}$, $R^{2c}$ and $R^{2d}$ are each hydrogen;

$R^{3a}$ and $R^{3d}$ are each hydrogen;

$R^{3b}$ and $R^{3c}$, together with the carbon ring atoms to which they are directly attached, form a fused ring selected from cycloalkyl, heterocyclyl, aryl or heteroaryl;

each $R^4$ and $R^5$ is independently selected from the group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when $R^4$ and $R^5$ are each attached to the same nitrogen atom, then $R^4$ and $R^5$, together with the nitrogen atom to which they are attached, may form a heterocyclyl or heteroaryl;

each $R^8$ is a direct bond or a straight or branched alkylene chain, a straight or branched alkenylene chain or a straight or branched alkynylene chain; and each $R^9$ is a straight or branched alkylene chain, a straight or branched alkenylene chain or a straight or branched alkynylene chain.

Another embodiment of the invention are the compounds of formula (I) as set forth above in the Summary of the invention wherein:

j is 0 and k is 1;

Q is —O—;

$R^1$ is aralkyl substituted by —C(O)N($R^6$)$R^7$ where:
  $R^6$ is hydrogen, alkyl, aryl or aralkyl; and
  $R^7$ is hydrogen, alkyl, haloalkyl, —$R^9$—CN, —$R^9$—$OR^5$ or —$R^9$—N($R^4$)$R^5$;
  or $R^6$ and $R^7$, together with the nitrogen to which they are attached, form a heterocyclyl or heteroaryl;
  wherein each aryl, aralkyl, heterocyclyl and heteroaryl groups for $R^6$ and $R^7$ is optionally substituted by one or more substituents selected from the group consisting of alkyl, cycloalkyl, aryl, aralkyl, halo, haloalkyl, —$R^8$—CN, —$R^8$—$OR^5$, heterocyclyl and heteroaryl;

$R^{2a}$, $R^{2b}$, $R^{2c}$ and $R^{2d}$ are each hydrogen;

$R^{3a}$ and $R^{3d}$ are each hydrogen;

$R^{3b}$ and $R^{3c}$, together with the carbon ring atoms to which they are directly attached, form a fused dioxolyl ring;

each $R^4$ and $R^5$ is independently selected from the group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when $R^4$ and $R^5$ are each attached to the same nitrogen atom, then $R^4$ and $R^5$, together with the nitrogen atom to which they are attached, may form a heterocyclyl or heteroaryl;

each $R^8$ is a direct bond or a straight or branched alkylene chain, a straight or branched alkenylene chain or a straight or branched alkynylene chain; and each $R^9$ is a straight or branched alkylene chain, a straight or branched alkenylene chain or a straight or branched alkynylene chain.

Another embodiment of the invention are the compounds of formula (I) as set forth above in the Summary of the invention wherein:

j is 0 and k is 1;

Q is —O—;

$R^1$ is aralkyl substituted by —C(O)N($R^6$)$R^7$ where:
  $R^6$ is hydrogen, alkyl, aryl or aralkyl; and
  $R^7$ is aryl, aralkyl, cycloalkyl, cycloalkylalkyl, heterocyclyl, heterocyclylalkyl, heteroaryl or heteroarylalkyl;
  and wherein each aryl, aralkyl, cycloalkyl, cycloalkylalkyl, heterocyclyl, heterocyclylalkyl, heteroaryl and heteroarylalkyl group for $R^6$ and $R^7$ may be optionally substituted by one or more substituents selected from the group consisting of alkyl, cycloalkyl, aryl, aralkyl, halo, haloalkyl, —$R^8$—CN, —$R^8$—$OR^5$, heterocyclyl and heteroaryl;

$R^{2a}$, $R^{2b}$, $R^{2c}$ and $R^{2d}$ are each hydrogen;

$R^{3a}$ and $R^{3d}$ are each hydrogen;

$R^{3b}$ and $R^{3c}$, together with the carbon ring atoms to which they are directly attached, form a fused dioxolyl ring;

each $R^4$ and $R^5$ is independently selected from the group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when $R^4$ and $R^5$ are each attached to the same nitrogen atom, then $R^4$ and $R^5$, together with the nitrogen atom to which they are attached, may form a heterocyclyl or heteroaryl;

each $R^8$ is a direct bond or a straight or branched alkylene chain, a straight or branched alkenylene chain or a straight or branched alkynylene chain; and each $R^9$ is a straight or branched alkylene chain, a straight or branched alkenylene chain or a straight or branched alkynylene chain.

Another embodiment of the invention are the compounds of formula (I) as set forth above in the Summary of the invention wherein:

at least one of j and k is 1 and the other is 0 or 1;

Q is —O—;

$R^1$ is aralkyl optionally substituted by one or more substituents selected from the group consisting of —$R^8$—$OR^5$, —$C(O)OR^5$, halo, haloalkyl, alkyl, nitro, cyano, aryl, aralkyl, heterocyclyl and heteroaryl;

$R^{2a}$, $R^{2b}$, $R^{2c}$ and $R^{2d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—$NO_2$, —$R^8$—$OR^5$, —$R^8$—$N(R^4)R^5$, —N=$C(R^4)R^5$, —$S(O)_m R^4$, —$OS(O)_2 CF_3$, —$R^8$—C(O)$R^4$, —$C(S)R^4$, —$C(R^4)_2 C(O)R^5$, —$R^8$—$C(O)OR^4$, —$C(S)OR^4$, —$R^8$—$C(O)N(R^4)R^5$, —$C(S)N(R^4)R^5$, —$N(R^5)C(O)R^4$, —$N(R^5)C(S)R^4$, —$N(R^5)C(O)OR^4$, —$N(R^5)C(S)OR^4$, —$N(R^5)C(O)N(R^4)R^5$, —$N(R^5)C(S)N(R^4)R^5$, —$N(R^5)S(O)_n R^4$, —$N(R^5)S(O)_n N(R^4)R^5$, —$R^8$—$S(O)_n N(R^4)R^5$, —$N(R^5)C(=NR^5)N(R^4)R^5$, and —$N(R^5)C(=N-CN)N(R^4)R^5$, wherein each m is independently 0, 1, or 2 and each n is independently 1 or 2;

and wherein each of the cycloalkyl, cycloalkylalkyl, aryl, aralkyl, aralkenyl, heterocyclyl, heterocyclylalkyl, heteroaryl and heteroarylalkyl groups for $R^{2a}$, $R^{2b}$, $R^{2c}$ and $R^{2d}$ may be optionally substituted by one or more substituents selected from the group consisting of alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—$NO_2$, —$R^8$—$OR^5$, —$R^8$—$N(R^4)R^5$, —$S(O)_m R^4$, —$R^8$—$S(O)_n N(R^4)R^5$, —$R^8$—$C(O)R^4$, —$R^8$—$C(O)OR^4$, —$R^8$—$C(O)N(R^4)R^5$, —$N(R^5)C(O)R^4$, and —$N(R^5)S(O)_n R^4$, wherein each m is independently 0, 1, or 2 and each n is independently 1 or 2;

or $R^{2a}$ and $R^{2b}$, together with the carbon ring atoms to which they are directly attached, may form a fused ring selected from cycloalkyl, aryl, heterocyclyl and heteroaryl, and $R^{2c}$ and $R^{2d}$ are as defined above;

or $R^{2b}$ and $R^{2c}$, together with the carbon ring atoms to which they are directly attached, may form a fused ring selected from cycloalkyl, aryl, heterocyclyl and heteroaryl, and $R^{2a}$ and $R^{2d}$ are as defined above;

or $R^{2c}$ and $R^{2d}$, together with the carbon ring atoms to which they are directly attached, may form a fused ring selected from cycloalkyl, aryl, heterocyclyl and heteroaryl, and $R^{2a}$ and $R^{2b}$ are as defined above;

$R^{3a}$, $R^{3b}$, $R^{3c}$ and $R^{3d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—$NO_2$, —$R^8 OR^5$, —$R^8$—$N(R^4)R^5$, —N=$C(R^4)R^5$, —$S(O)_m R^4$, —$OS(O)_2 CF_3$, —$R^8$—C(O)$R^4$, —$C(S)R^4$, —$C(R^4)_2 C(O)R^5$, —$R^8$—$C(O)OR^4$, —$C(S)OR^4$, —$R^8$—$C(O)N(R^4)R^5$, —$C(S)N(R^4)R^5$, —$N(R^5)C(O)R^4$, —$N(R^5)C(S)R^4$, —$N(R^5)C(O)OR^4$, —$N(R^5)C(S)OR^4$, —$N(R^5)C(O)N(R^4)R^5$, —$N(R^5)C(S)N(R^4)R^5$, —$N(R^5)S(O)_n R^4$, —$N(R^5)S(O)_n N(R^4)R^5$, —$R^8$—$S(O)_n N(R^4)R^5$, —$N(R^5)C(=NR^5)N(R^4)R^5$, and —$N(R^5)C(N=C(R^4)R^5)N(R^4)R^5$, wherein each m is independently 0, 1, or 2 and each n is independently 1 or 2;

or $R^{3a}$ and $R^{3b}$, together with the carbon ring atoms to which they are directly attached, form a fused ring selected from cycloalkyl, heterocyclyl, aryl or heteroaryl, and $R^{3c}$ and $R^{3d}$ are as defined above;

or $R^{3b}$ and $R^{3c}$, together with the carbon ring atoms to which they are directly attached, may form a fused ring selected from cycloalkyl, heterocyclyl, aryl or heteroaryl, and $R^{3a}$ and $R^{3d}$ are as defined above;

or $R^{3c}$ and $R^{3d}$, together with the carbon ring atoms to which they are directly attached, may form a fused ring selected from cycloalkyl, heterocyclyl, aryl or heteroaryl, and $R^{3a}$ and $R^{3b}$ are as defined above;

each $R^4$ and $R^5$ is independently selected from the group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when $R^4$ and $R^5$ are each attached to the same nitrogen atom, then $R^4$ and $R^5$, together with the nitrogen atom to which they are attached, may form a heterocyclyl or heteroaryl;

each $R^8$ is a direct bond or a straight or branched alkylene chain, a straight or branched alkenylene chain or a straight or branched alkynylene chain; and each $R^9$ is a straight or branched alkylene chain, a straight or branched alkenylene chain or a straight or branched alkynylene chain.

Another embodiment of the invention are the compounds of formula (I) as set forth above in the Summary of the invention wherein:

j is 0 and k is 1;

Q is —O—;

$R^1$ is aralkyl optionally substituted by one or more substituents selected from the group consisting of —$R^8$—$OR^5$, —$C(O)OR^5$, halo, haloalkyl, alkyl, nitro, cyano, aryl, aralkyl, heterocyclyl and heteroaryl;

$R^{2a}$, $R^{2b}$, $R^{2c}$ and $R^{2d}$ are each independently selected from hydrogen, alkyl or halo;

$R^{3a}$, $R^{3b}$, $R^{3c}$ and $R^{3d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—$NO_2$, —$R^8$—$OR^5$, —$R^8$—$N(R^4)R^5$, —N=$C(R^4)R^5$, —$S(O)_m R^4$, —$OS(O)_2 CF_3$, —$R^8$—C(O)$R^4$, —$C(S)R^4$, —$C(R^4)_2 C(O)R^5$, —$R^8$—$C(O)OR^4$, —$C(S)OR^4$, —$R^8$—$C(O)N(R^4)R^5$, —$C(S)N(R^4)R^5$, —$N(R^5)C(O)R^4$, —$N(R^5)C(S)R^4$, —$N(R^5)C(O)OR^4$, —$N(R^5)C(S)OR^4$, —$N(R^5)C(O)N(R^4)R^5$, —$N(R^5)C(S)N(R^4)R^5$, —$N(R^5)S(O)_n R^4$, —$N(R^5)S(O)_n N(R^4)R^5$, —$R^8$—$S(O)_n N(R^4)R^5$, —$N(R^5)C(=NR^5)N(R^4)R^5$, and —$N(R^5)C(N=C(R^4)R^5)N(R^4)R^5$, wherein each m is independently 0, 1, or 2 and each n is independently 1 or 2;

or $R^{3a}$ and $R^{3b}$, together with the carbon ring atoms to which they are directly attached, form a fused ring selected from cycloalkyl, heterocyclyl, aryl or heteroaryl, and $R^{3c}$ and $R^{3d}$ are as defined above;

or $R^{3b}$ and $R^{3c}$, together with the carbon ring atoms to which they are directly attached, may form a fused ring selected from cycloalkyl, heterocyclyl, aryl or heteroaryl, and $R^{3a}$ and $R^{3d}$ are as defined above;

or $R^{3c}$ and $R^{3d}$, together with the carbon ring atoms to which they are directly attached, may form a fused ring selected from cycloalkyl, heterocyclyl, aryl or heteroaryl, and $R^{3a}$ and $R^{3b}$ are as defined above;

each $R^5$ is independently selected from the group consisting of hydrogen, alkyl, alkenyl, alkynyl, haloalkyl, alkoxyalkyl, cycloalkyl, cycloalkylalkyl, aryl, aralkyl, heterocyclyl and heteroaryl; and each $R^8$ is a direct bond or a straight or branched alkylene chain, a straight or branched alkenylene chain or a straight or branched alkynylene chain.

Another embodiment of the invention are the compounds of formula (I) as set forth above in the Summary of the invention wherein:

j is 0 and k is 1;

Q is —O—;

$R^1$ is aralkyl optionally substituted by one or more substituents selected from the group consisting of —$R^8$—$OR^5$, —C(O)$OR^5$, halo, haloalkyl, alkyl, nitro, cyano, aryl, aralkyl, heterocyclyl and heteroaryl;

$R^{2a}$, $R^{2b}$, $R^{2c}$ and $R^{2d}$ are each independently selected from hydrogen, alkyl or halo;

$R^{3a}$, $R^{3b}$, $R^{3c}$ and $R^{3d}$ are each independently selected from the group consisting of hydrogen, halo, and —$R^8$—$OR^5$ or $R^{3b}$ and $R^{3c}$, together with the carbon ring atoms to which they are directly attached, form a fused ring selected from cycloalkyl, dioxolyl, tetrahydrofuranyl, and heteroaryl, and $R^{3a}$ and $R^{3d}$ are each hydrogen;

each $R^5$ is independently selected from the group consisting of hydrogen, alkyl, alkenyl, alkynyl, haloalkyl, alkoxyalkyl, cycloalkyl, cycloalkylalkyl, aryl, aralkyl, heterocyclyl and heteroaryl; and each $R^8$ is a direct bond or a straight or branched alkylene chain, a straight or branched alkenylene chain or a straight or branched alkynylene chain.

Another embodiment of the invention are the compounds of formula (I) as set forth above in the Summary of the invention wherein:

at least one of j and k is 1 and the other is 0 or 1;

Q is —O—;

$R^1$ is —$R^9$—N($R^{10}$)$R^{11}$, —$R^9$—N($R^{12}$)C(O)$R^{11}$ or —$R^9$—N($R^{10}$)C(O)N($R^{10}$)$R^{11}$ where:

each $R^{10}$ is hydrogen, alkyl, aryl, aralkyl or heteroaryl;

each $R^{11}$ is hydrogen, alkyl, haloalkyl, cycloalkyl, cycloalkylalkyl, aryl, aralkyl, heterocyclyl, heterocyclylalkyl, heteroaryl, heteroarylalkyl, —$R^9$—OC(O)$R^5$, —$R^9$—C(O)$OR^5$, —$R^9$—C(O)N($R^4$)$R^5$, —$R^9$—C(O)$R^5$, —$R^9$—N($R^4$)$R^5$, —$R^9$—$OR^5$, or —$R^9$—CN; and $R^{12}$ is hydrogen, alkyl, aryl, aralkyl or —C(O)$R^5$;

and wherein each aryl, aralkyl, cycloalkyl, cycloalkylalkyl, heterocyclyl, heterocyclylalkyl, heteroaryl and heteroarylalkyl group for $R^{10}$ and $R^{11}$ may be optionally substituted by one or more substituents selected from the group consisting of alkyl, cycloalkyl, aryl, aralkyl, halo, haloalkyl, nitro, —$R^8$—CN, —$R^8$—$OR^5$, —$R^8$—C(O)$R^5$, heterocyclyl and heteroaryl;

$R^{2a}$, $R^{2b}$, $R^{2c}$ and $R^{2d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—$NO_2$, —$R^8$—$OR^5$, —$R^8$—N($R^4$)$R^5$, —N=C($R^4$)$R^5$, —S(O)$_m R^4$, —$R^8$—C(O)$R^4$, —C(S)$R^4$, —C($R^4$)$_2$C(O)$R^5$, —$R^8$—C(O)$OR^4$, —C(S)$OR^4$, —$R^8$—C(O)N($R^4$)$R^5$, —C(S)N($R^4$)$R^5$, —N($R^5$)C(O)$R^4$, —N($R^5$)C(S)$R^4$, —N($R^5$)C(O)$OR^4$, —N($R^5$)C(S)$OR^4$, —N($R^5$)C(O)N($R^4$)$R^5$, —N($R^5$)C(S)N($R^4$)$R^5$, —N($R^5$)S(O)$_n R^4$, —N($R^5$)S(O)$_n$N($R^4$)$R^5$, —$R^8$—S(O)$_n$N($R^4$)$R^5$, —N($R^5$)C(=N$R^5$)N($R^4$)$R^5$, and —N($R^5$)C(=N—CN)N($R^4$)$R^5$, wherein each m is independently 0, 1, or 2 and each n is independently 1 or 2;

and wherein each of the cycloalkyl, cycloalkylalkyl, aryl, aralkyl, aralkenyl, heterocyclyl, heterocyclylalkyl, heteroaryl and heteroarylalkyl groups for $R^{2a}$, $R^{2b}$, $R^{2c}$ and $R^{2d}$ may be optionally substituted by one or more substituents selected from the group consisting of alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—$NO_2$, —$R^8$—$OR^5$, —$R^8$—N($R^4$)$R^5$, —S(O)$_m R^4$, —$R^8$—S(O)$_n$N($R^4$)$R^5$, —$R^8$—C(O)$R^4$, —$R^8$—C(O)$OR^4$, —$R^8$—C(O)N($R^4$)$R^5$, —N($R^5$)C(O)$R^4$, and —N($R^5$)S(O)$_n R^4$, wherein each m is independently 0, 1, or 2 and each n is independently 1 or 2;

or $R^{2a}$ and $R^{2b}$, together with the carbon ring atoms to which they are directly attached, may form a fused ring selected from cycloalkyl, aryl, heterocyclyl and heteroaryl, and $R^{2c}$ and $R^{2d}$ are as defined above;

or $R^{2b}$ and $R^{2c}$, together with the carbon ring atoms to which they are directly attached, may form a fused ring selected from cycloalkyl, aryl, heterocyclyl and heteroaryl, and $R^{2a}$ and $R^{2d}$ are as defined above;

or $R^{2c}$ and $R^{2d}$, together with the carbon ring atoms to which they are directly attached, may form a fused ring selected from cycloalkyl, aryl, heterocyclyl and heteroaryl, and $R^{2a}$ and $R^{2b}$ are as defined above;

$R^{3a}$, $R^{3b}$, $R^{3c}$ and $R^{3d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—$NO_2$, —$R^8$—$OR^5$, —$R^8$—N($R^4$)$R^5$, —N=C($R^4$)$R^5$, —S(O)$_m R^4$, —OS(O)$_2 CF_3$, —$R^8$—C(O)$R^4$, —C(S)$R^4$, —C($R^4$)$_2$C(O)$R^5$, —$R^8$—C(O)$OR^4$, —O(S)$OR^4$, —$R^8$—C(O)N($R^4$)$R^5$, —C(S)N($R^4$)$R^5$, —N($R^5$)C(O)$R^4$, —N($R^5$)C(S)$R^4$, —N($R^5$)C(O)$OR^4$, —N($R^5$)C(S)$OR^4$, —N($R^5$)C(O)N($R^4$)$R^5$, —N($R^5$)C(S)N($R^4$)$R^5$, —N($R^5$)S(O)$_n R^4$, —N($R^5$)S(O)$_n$N($R^4$)$R^5$, —$R^8$—S(O)$_n$N($R^4$)$R^5$, —N($R^5$)C(=N$R^5$)N($R^4$)$R^5$, and —N($R^5$)C(N=C($R^4$)$R^5$)N($R^4$)$R^5$, wherein each m is independently 0, 1, or 2 and each n is independently 1 or 2;

or $R^{3a}$ and $R^{3b}$, together with the carbon ring atoms to which they are directly attached, form a fused ring selected from cycloalkyl, heterocyclyl, aryl or heteroaryl, and $R^{3c}$ and $R^{3d}$ are as defined above;

or $R^{3b}$ and $R^{3c}$, together with the carbon ring atoms to which they are directly attached, may form a fused ring selected from cycloalkyl, heterocyclyl, aryl or heteroaryl, and $R^{3a}$ and $R^{3d}$ are as defined above;

or $R^{3c}$ and $R^{3d}$, together with the carbon ring atoms to which they are directly attached, may form a fused ring selected from cycloalkyl, heterocyclyl, aryl or heteroaryl, and $R^{3a}$ and $R^{3b}$ are as defined above;

each $R^4$ and $R^5$ is independently selected from the group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when $R^4$ and $R^5$ are each attached to the same nitrogen atom, then $R^4$ and $R^5$, together with the nitrogen atom to which they are attached, may form a heterocyclyl or heteroaryl;

each $R^8$ is a direct bond or a straight or branched alkylene chain, a straight or branched alkenylene chain or a straight or branched alkynylene chain; and each $R^9$ is a straight or branched alkylene chain, a straight or branched alkenylene chain or a straight or branched alkynylene chain.

Another embodiment of the invention are the compounds of formula (I) as set forth above in the Summary of the invention wherein:
j is 0 and k is 1;
Q is —O—;
$R^1$ is —$R^9$—N($R^{10}$)$R^{11}$, $R^9$—N($R^{12}$)C(O)$R^{11}$ or —$R^9$—N($R^{10}$)C(O)N($R^{10}$)$R^{11}$ where:
  each $R^{10}$ is hydrogen, alkyl, aryl, aralkyl or heteroaryl;
  each $R^{11}$ is hydrogen, alkyl, haloalkyl, cycloalkyl, cycloalkylalkyl, aryl, aralkyl, heterocyclyl, heterocyclylalkyl, heteroaryl, heteroarylalkyl, —$R^9$—OC(O)$R^5$, —$R^9$—C(O)O$R^5$, —$R^9$—C(O)N($R^4$)$R^5$, —$R^9$—C(O)$R^5$, —$R^9$—N($R^4$)$R^5$, —$R^9$—O$R^5$, or —$R^9$—CN; and
  $R^{12}$ is hydrogen, alkyl, aryl, aralkyl or —C(O)$R^5$;
  and wherein each aryl, aralkyl, cycloalkyl, cycloalkylalkyl, heterocyclyl, heterocyclylalkyl, heteroaryl and heteroarylalkyl group for $R^{10}$ and $R^{11}$ may be optionally substituted by one or more substituents selected from the group consisting of alkyl, cycloalkyl, aryl, aralkyl, halo, haloalkyl, nitro, —$R^8$—CN, —$R^8$—O$R^5$, —$R^8$—C(O)$R^5$, heterocyclyl and heteroaryl;
$R^{2a}$, $R^{2b}$, $R^{2c}$ and $R^{2d}$ are each hydrogen;
$R^{3a}$ and $R^{3d}$ are each hydrogen;
$R^{3b}$ and $R^{3c}$, together with the carbon ring atoms to which they are directly attached, form a fused ring selected from cycloalkyl, heterocyclyl, aryl or heteroaryl;
each $R^4$ and $R^5$ is independently selected from the group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;
or when $R^4$ and $R^5$ are each attached to the same nitrogen atom, then $R^4$ and $R^5$, together with the nitrogen atom to which they are attached, may form a heterocyclyl or heteroaryl;
each $R^8$ is a direct bond or a straight or branched alkylene chain, a straight or branched alkenylene chain or a straight or branched alkynylene chain; and
each $R^9$ is a straight or branched alkylene chain, a straight or branched alkenylene chain or a straight or branched alkynylene chain.

Another embodiment of the invention are the compounds of formula (I) as set forth above in the Summary of the invention wherein:
j is 0 and k is 1;
Q is —O—;
$R^1$ is —$R^9$—N($R^{10}$)$R^{11}$ where:
  each $R^{10}$ is hydrogen, alkyl, aryl, aralkyl or heteroaryl;
  each $R^{11}$ is hydrogen, alkyl, haloalkyl, cycloalkyl, cycloalkylalkyl, aryl, aralkyl, heterocyclyl, heterocyclylalkyl, heteroaryl, heteroarylalkyl, —$R^9$—OC(O)$R^5$, —$R^9$—C(O)O$R^5$, —$R^9$—C(O)N($R^4$)$R^5$, —$R^9$—C(O)$R^5$, —$R^9$—N($R^4$)$R^9$, —$R^9$—O$R^5$, or —$R^9$—CN;
  and wherein each aryl, aralkyl, cycloalkyl, cycloalkylalkyl, heterocyclyl, heterocyclylalkyl, heteroaryl and heteroarylalkyl group for $R^{10}$ and $R^{11}$ may be optionally substituted by one or more substituents selected from the group consisting of alkyl, cycloalkyl, aryl, aralkyl, halo, haloalkyl, nitro, —$R^8$—CN, —$R^8$—O$R^5$, —$R^8$—C(O)$R^5$, heterocyclyl and heteroaryl;
$R^{2a}$, $R^{2b}$, $R^{2c}$ and $R^{2d}$ are each hydrogen;
$R^{3a}$ and $R^{3d}$ are each hydrogen;
$R^{3b}$ and $R^{3c}$, together with the carbon ring atoms to which they are directly attached, form a fused dioxolyl ring;
each $R^4$ and $R^5$ is independently selected from the group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;
or when $R^4$ and $R^5$ are each attached to the same nitrogen atom, then $R^4$ and $R^5$, together with the nitrogen atom to which they are attached, may form a heterocyclyl or heteroaryl;
each $R^8$ is a direct bond or a straight or branched alkylene chain, a straight or branched alkenylene chain or a straight or branched alkynylene chain; and
each $R^9$ is a straight or branched alkylene chain, a straight or branched alkenylene chain or a straight or branched alkynylene chain.

Another embodiment of the invention are the compounds of formula (I) as set forth above in the Summary of the invention wherein:
j is 0 and k is 1;
Q is —O—;
$R^1$ is —$R^9$—N($R^{12}$)C(O)$R^{11}$ where:
  each $R^{10}$ is hydrogen, alkyl, aryl, aralkyl or heteroaryl;
  each $R^{11}$ is hydrogen, alkyl, haloalkyl, cycloalkyl, cycloalkylalkyl, aryl, aralkyl, heterocyclyl, heterocyclylalkyl, heteroaryl, heteroarylalkyl, —$R^9$—OC(O)$R^5$, —$R^9$—C(O)O$R^5$, —$R^9$—C(O)N($R^4$)$R^5$, —$R^9$—C(O)$R^5$, —$R^9$—N($R^4$)$R^5$, —$R^9$—O$R^5$, or —$R^9$—CN; and
  $R^{12}$ is hydrogen, alkyl, aryl, aralkyl or —C(O)$R^5$;
  and wherein each aryl, aralkyl, cycloalkyl, cycloalkylalkyl, heterocyclyl, heterocyclylalkyl, heteroaryl and heteroarylalkyl group for $R^{10}$ and $R^{11}$ may be optionally substituted by one or more substituents selected from the group consisting of alkyl, cycloalkyl, aryl, aralkyl, halo, haloalkyl, nitro, —$R^8$—CN, —$R^8$—O$R^5$, —$R^8$—C(O)$R^5$, heterocyclyl and heteroaryl;
$R^{2a}$, $R^{2b}$, $R^{2c}$ and $R^{2d}$ are each hydrogen;
$R^{3a}$ and $R^{3d}$ are each hydrogen;
$R^{3b}$ and $R^{3c}$, together with the carbon ring atoms to which they are directly attached, form a fused dioxolyl ring;
each $R^4$ and $R^5$ is independently selected from the group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;
or when $R^4$ and $R^5$ are each attached to the same nitrogen atom, then $R^4$ and $R^5$, together with the nitrogen atom to which they are attached, may form a heterocyclyl or heteroaryl;
each $R^8$ is a direct bond or a straight or branched alkylene chain, a straight or branched alkenylene chain or a straight or branched alkynylene chain; and
each $R^9$ is a straight or branched alkylene chain, a straight or branched alkenylene chain or a straight or branched alkynylene chain.

Another embodiment of the invention are the compounds of formula (I) as set forth above in the Summary of the invention wherein:
j is 0 and k is 1;
Q is —O—;
$R^1$ is —$R^9$—N($R^{10}$)C(O)N($R^{10}$)$R^{11}$ where:
  each $R^{10}$ is hydrogen, alkyl, aryl, aralkyl or heteroaryl;
  each $R^{11}$ is hydrogen, alkyl, haloalkyl, cycloalkyl, cycloalkylalkyl, aryl, aralkyl, heterocyclyl, heterocyclylalkyl, heteroaryl, heteroarylalkyl, —$R^9$—OC(O)$R^5$, —$R^9$—C(O)O$R^5$, —$R^9$—C(O)N($R^4$)$R^5$, —$R^9$—C(O)$R^5$, —$R^9$—N($R^4$)$R^5$, —$R^9$—O$R^5$, or —$R^9$—CN;

and wherein each aryl, aralkyl, cycloalkyl, cycloalkylalkyl, heterocyclyl, heterocyclylalkyl, heteroaryl and heteroarylalkyl group for $R^{10}$ and $R^{11}$ may be optionally substituted by one or more substituents selected from the group consisting of alkyl, cycloalkyl, aryl, aralkyl, halo, haloalkyl, nitro, —$R^8$—CN, —$R^8$—$OR^5$, —$R^8$—C(O)$R^5$, heterocyclyl and heteroaryl;

$R^{2a}$, $R^{2b}$, $R^{2c}$ and $R^{2d}$ are each hydrogen;

$R^{3a}$ and $R^{3d}$ are each hydrogen;

$R^{3b}$ and $R^{3c}$, together with the carbon ring atoms to which they are directly attached, form a fused dioxolyl ring;

each $R^4$ and $R^5$ is independently selected from the group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when $R^4$ and $R^5$ are each attached to the same nitrogen atom, then $R^4$ and $R^5$, together with the nitrogen atom to which they are attached, may form a heterocyclyl or heteroaryl;

each $R^8$ is a direct bond or a straight or branched alkylene chain, a straight or branched alkenylene chain or a straight or branched alkynylene chain; and each $R^9$ is a straight or branched alkylene chain, a straight or branched alkenylene chain or a straight or branched alkynylene chain.

Another embodiment of the invention are the compounds of formula (I) as set forth above in the Summary of the invention wherein:

at least one of j and k is 1 and the other is 0 or 1;

Q is —O—;

$R^1$ is heterocyclylalkyl or heteroarylalkyl where the heterocyclylalkyl or the heteroarylalkyl group is optionally substituted by one or more substituents selected from the group consisting of oxo, alkyl, halo, haloalkyl, cycloalkyl, cycloalkylalkyl, aryl, aralkyl, heterocyclyl, heterocyclylalkyl, heteroaryl, heteroarylalkyl, —$R^8$—$OR^5$, —$R^8$—C(O)$OR^5$, —$R^8$—N($R^4$)$R^5$, —$R^8$—C(O)N($R^4$)$R^5$, —$R^8$—N($R^5$)C(O)$R^4$, —$R^8$—S(O)$_m R^4$ (where m is 0, 1 or 2), —$R^8$—CN, or —$R^8$—$NO_2$;

$R^{2a}$, $R^{2b}$, $R^{2c}$ and $R^{2d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—$NO_2$, —$R^8$—$OR^5$, —$R^8$—N($R^4$)$R^5$, —N=C($R^4$)$R^5$, —S(O)$_m R^4$, —OS(O)$_2 CF_3$, —$R^8$—C(O)$R^4$, —C(S)$R^4$, —C($R^4$)$_2$C(O)$R^5$, —$R^8$—C(O)$OR^4$, —C(S)$OR^4$, —$R^8$—C(O)N($R^4$)$R^5$, —C(S)N($R^4$)$R^5$, —N($R^5$)C(O)$R^4$, —N($R^5$)C(S)$R^4$, —N($R^5$)C(O)$OR^4$, —N($R^5$)C(S)$OR^4$, —N($R^5$)C(O)N($R^4$)$R^5$, —N($R^5$)C(S)N($R^4$)$R^5$, —N($R^5$)S(O)$_n R^4$, —N($R^5$)S(O)$_n$N($R^4$)$R^5$, —$R^8$—S(O)$_n$N($R^4$)$R^5$, —N($R^5$)C(=N$R^5$)N($R^4$)$R^5$, and —N($R^5$)C(=N—CN)N($R^4$)$R^5$, wherein each m is independently 0, 1, or 2 and each n is independently 1 or 2;

and wherein each of the cycloalkyl, cycloalkylalkyl, aryl, aralkyl, aralkenyl, heterocyclyl, heterocyclylalkyl, heteroaryl and heteroarylalkyl groups for $R^{2a}$, $R^{2b}$, $R^{2c}$ and $R^{2d}$ may be optionally substituted by one or more substituents selected from the group consisting of alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—$NO_2$, —$R^8$—$OR^5$, —$R^8$—N($R^4$)$R^5$, —S(O)$_m R^4$, —$R^8$—S(O)$_n$N($R^4$)$R^5$, —$R^8$—C(O)$R^4$, —$R^8$—C(O)$OR^4$, —$R^8$—C(O)N($R^4$)$R^5$, —N($R^5$)C(O)$R^4$, and —N($R^5$)S(O)$_n R^4$, wherein each m is independently 0, 1, or 2 and each n is independently 1 or 2;

or $R^{2a}$ and $R^{2b}$, together with the carbon ring atoms to which they are directly attached, may form a fused ring selected from cycloalkyl, aryl, heterocyclyl and heteroaryl, and $R^{2c}$ and $R^{2d}$ are as defined above;

or $R^{2b}$ and $R^{2c}$, together with the carbon ring atoms to which they are directly attached, may form a fused ring selected from cycloalkyl, aryl, heterocyclyl and heteroaryl, and $R^{2a}$ and $R^{2d}$ are as defined above;

or $R^{2c}$ and $R^{2d}$, together with the carbon ring atoms to which they are directly attached, may form a fused ring selected from cycloalkyl, aryl, heterocyclyl and heteroaryl, and $R^{2a}$ and $R^{2b}$ are as defined above;

$R^{3a}$, $R^{3b}$, $R^{3c}$ and $R^{3d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—$NO_2$, —$R^8$—$OR^5$, —$R^8$—N($R^4$)$R^5$, —N=C($R^4$)$R^5$, —S(O)$_m R^4$, —OS(O)$_2 CF_3$, —$R^8$—C(O)$R^4$, —C(S)$R^4$, —C($R^4$)$_2$C(O)$R^5$, —$R^8$—C(O)$OR^4$, —C(S)$OR^4$, —$R^8$—C(O)N($R^4$)$R^5$, —C(S)N($R^4$)$R^5$, —N($R^5$)C(O)$R^4$, —N($R^5$)C(S)$R^4$, —N($R^5$)C(O)$OR^4$, —N($R^5$)C(S)$OR^4$, —N($R^5$)C(O)N($R^4$)$R^5$, —N($R^5$)C(S)N($R^4$)$R^5$, —N($R^5$)S(O)$_n R^4$, —N($R^5$)S(O)$_n$N($R^4$)$R^5$, —$R^8$—S(O)$_n$N($R^4$)$R^5$, —N($R^5$)C(=N$R^5$)N($R^4$)$R^5$, and —N($R^5$)C(N=C($R^4$)$R^5$)N($R^4$)$R^5$, wherein each m is independently 0, 1, or 2 and each n is independently 1 or 2;

or $R^{3a}$ and $R^{3b}$, together with the carbon ring atoms to which they are directly attached, form a fused ring selected from cycloalkyl, heterocyclyl, aryl or heteroaryl, and $R^{3c}$ and $R^{3d}$ are as defined above;

or $R^{3b}$ and $R^{3c}$, together with the carbon ring atoms to which they are directly attached, may form a fused ring selected from cycloalkyl, heterocyclyl, aryl or heteroaryl, and $R^{3a}$ and $R^{3d}$ are as defined above;

or $R^{3c}$ and $R^{3d}$, together with the carbon ring atoms to which they are directly attached, may form a fused ring selected from cycloalkyl, heterocyclyl, aryl or heteroaryl, and $R^{3a}$ and $R^{3b}$ are as defined above;

each $R^4$ and $R^5$ is independently selected from the group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when $R^4$ and $R^5$ are each attached to the same nitrogen atom, then $R^4$ and $R^5$, together with the nitrogen atom to which they are attached, may form a heterocyclyl or heteroaryl;

each $R^8$ is a direct bond or a straight or branched alkylene chain, a straight or branched alkenylene chain or a straight or branched alkynylene chain; and each $R^9$ is a straight or branched alkylene chain, a straight or branched alkenylene chain or a straight or branched alkynylene chain.

Another embodiment of the invention are the compounds of formula (I) as set forth above in the Summary of the invention wherein:

j is 0 and k is 1;

Q is —O—;

$R^1$ is heterocyclylalkyl or heteroarylalkyl where the heterocyclylalkyl or the heteroarylalkyl group is optionally substituted by one or more substituents selected from the group consisting of oxo, alkyl, halo, haloalkyl, cycloalkyl, cycloalkylalkyl, aryl, aralkyl, heterocyclyl, heterocyclylalkyl, heteroaryl, heteroarylalkyl, —R$^8$—OR$^5$, —R$^8$—C(O)OR$^5$, —R$^8$—N(R$^4$)R$^5$, —R$^8$—C(O)N(R$^4$)R$^5$, —R$^8$—N(R$^5$)C(O)R$^4$, —R$^8$—S(O)$_m$R$^4$ (where m is 0, 1 or 2), —R$^8$—CN, or —R$^8$—NO$_2$;

R$^{2a}$, R$^{2b}$, R$^{2c}$ and a R$^{2d}$ are each independently selected from hydrogen, halo, alkyl or —R$^8$—OR$^5$;

R$^{3a}$, R$^{3b}$, R$^{3c}$ and R$^{3d}$ are each independently selected from hydrogen, halo, alkyl or —R$^8$—OR$^5$;

or R$^{3b}$ and R$^{3c}$, together with the carbon ring atoms to which they are directly attached, form a fused ring selected from cycloalkyl, heterocyclyl, aryl or heteroaryl, and R$^{3a}$ and R$^{3d}$ are each hydrogen;

each R$^5$ is independently selected from the group consisting of hydrogen, alkyl, alkenyl, alkynyl, haloalkyl, alkoxyalkyl, cycloalkyl, cycloalkylalkyl, aryl, aralkyl, heterocyclyl and heteroaryl; and each R$^8$ is a direct bond or a straight or branched alkylene chain, a straight or branched alkenylene chain or a straight or branched alkynylene chain.

Another embodiment of the invention are the compounds of formula (I) as set forth above in the Summary of the invention wherein:

j is 0 and k is 1;

Q is —O—;

R$^1$ is heterocyclylalkyl or heteroarylalkyl where the heterocyclylalkyl or the heteroarylalkyl group is optionally substituted by one or more substituents selected from the group consisting of oxo, alkyl, halo, haloalkyl, cycloalkyl, cycloalkylalkyl, aryl, aralkyl, heterocyclyl, heterocyclylalkyl, heteroaryl, heteroarylalkyl, —R$^8$—OR$^5$, —R$^8$—C(O)OR$^5$, —R$^8$—N(R$^4$)R$^5$, —R$^8$—C(O)N(R$^4$)R$^5$, —R$^8$—N(R$^5$)C(O)R$^4$, —R$^8$—S(O)$_m$R$^4$ (where m is 0, 1 or 2), —R$^8$—CN, or —R$^8$—NO$_2$;

R$^{2a}$, R$^{2b}$, R$^{2c}$ and R$^{2d}$ are each independently selected from hydrogen, halo, alkyl or —R$^8$—OR$^5$;

R$^{3a}$, R$^{3b}$, R$^{3c}$ and R$^{3d}$ are each independently selected from hydrogen, halo, alkyl or —R$^8$—OR$^5$;

or R$^{3b}$ and R$^{3c}$, together with the carbon ring atoms to which they are directly attached, form a fused ring selected from dioxolyl or tetrahydrofuranyl, and R$^{3a}$ and R$^{3d}$ are each hydrogen;

each R$^5$ is independently selected from the group consisting of hydrogen, alkyl, alkenyl, alkynyl, haloalkyl, alkoxyalkyl, cycloalkyl, cycloalkylalkyl, aryl, aralkyl, heterocyclyl and heteroaryl; and each R$^8$ is a direct bond or a straight or branched alkylene chain, a straight or branched alkenylene chain or a straight or branched alkynylene chain.

Another embodiment of the invention are the compounds of formula (I) as set forth above in the Summary of the invention wherein:

at least one of j and k is 1 and the other is 0 or 1;

Q is —O—;

R$^1$ is heterocyclylalkyl or heteroarylalkyl where the heterocyclylalkyl or the heteroarylalkyl group is optionally substituted by one or more substituents selected from the group consisting of oxo, alkyl, halo, haloalkyl, cycloalkyl, cycloalkylalkyl, aryl, aralkyl, heterocyclyl, heterocyclylalkyl, heteroaryl, heteroarylalkyl, —R$^8$—OR$^5$, —R$^8$—C(O)OR$^5$, —R$^8$—N(R$^4$)R$^5$, —R$^8$—C(O)N(R$^4$)R$^5$, —R$^8$—N(R$^5$)C(O)R$^4$, —R$^8$—S(O)$_m$R$^4$ (where m is 0, 1 or 2), —R$^8$—CN, or —R$^8$—NO$_2$;

R$^{2a}$, R$^{2b}$, R$^{2c}$ and R$^{2d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —R$^8$—CN, —R$^8$—NO$_2$, —R$^8$—OR$^5$, —R$^8$—N(R$^4$)R$^5$, —N=C(R$^4$)R$^5$, —S(O)$_m$R$^4$, —OS(O)$_2$CF$_3$, —R$^8$—C(O)R$^4$, —C(S)R$^4$, —C(R$^4$)$_2$C(O)R$^5$, —R$^8$—C(O)OR$^4$, —C(S)OR$^4$, —R$^8$—C(O)N(R$^4$)R$^5$, —C(S)N(R$^4$)R$^5$, —N(R$^5$)C(O)R$^4$, —N(R$^5$)C(S)R$^4$, —N(R$^5$)C(O)OR$^4$, —N(R$^5$)C(S)OR$^4$, —N(R$^5$)C(O)N(R$^4$)R$^5$, —N(R$^5$)C(S)N(R$^4$)R$^5$, —N(R$^5$)S(O)$_n$R$^4$, —N(R$^5$)S(O)$_n$N(R$^4$)R$^5$, —R$^8$—S(O)$_n$N(R$^4$)R$^5$, —N(R$^5$)C(=NR$^5$)N(R$^4$)R$^5$, and —N(R$^5$)C(=N—CN)N(R$^4$)R$^5$, wherein each m is independently 0, 1, or 2 and each n is independently 1 or 2;

and wherein each of the cycloalkyl, cycloalkylalkyl, aryl, aralkyl, aralkenyl, heterocyclyl, heterocyclylalkyl, heteroaryl and heteroarylalkyl groups for R$^{2a}$, R$^{2b}$, R$^{2c}$ and R$^{2d}$ may be optionally substituted by one or more substituents selected from the group consisting of alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —R$^8$—CN, —R$^8$—NO$_2$, —R$^8$—OR$^5$, —R$^8$—N(R$^4$)R$^5$, —S(O)$_m$R$^4$, —R$^8$—S(O)$_n$N(R$^4$)R$^5$, —R$^8$—C(O)R$^4$, —R$^8$—C(O)OR$^4$, —R$^8$—C(O)N(R$^4$)R$^5$, —N(R$^5$)C(O)R$^4$, and —N(R$^5$)S(O)$_n$R$^4$, wherein each m is independently 0, 1, or 2 and each n is independently 1 or 2;

R$^{3a}$ and R$^{3d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —R$^8$—CN, —R$^8$—NO$_2$, —R$^8$—OR$^5$, —R$^8$—N(R$^4$)R$^5$, —N=C(R$^4$)R$^5$, —S(O)$_m$R$^4$, —OS(O)$_2$CF$_3$, —R$^8$—C(O)R$^4$, —C(S)R$^4$, —C(R$^4$)$_2$C(O)R$^5$, —R$^8$—C(O)OR$^4$, —C(S)OR$^4$, —R$^8$—C(O)N(R$^4$)R$^5$, —C(S)N(R$^4$)R$^5$, —N(R$^5$)C(O)R$^4$, —N(R$^5$)C(S)R$^4$, —N(R$^5$)C(O)OR$^4$, —N(R$^5$)C(S)OR$^4$, —N(R$^5$)C(O)N(R$^4$)R$^5$, —N(R$^5$)C(S)N(R$^4$)R$^5$, —N(R$^5$)S(O)$_n$R$^4$, —N(R$^5$)S(O)$_n$N(R$^4$)R$^5$, —R$^8$—S(O)$_n$N(R$^4$)R$^5$, —N(R$^5$)C(=NR$^5$)N(R$^4$)R$^5$, and —N(R$^5$)C(N=C(R$^4$)R$^5$)N(R$^4$)R$^5$, wherein each m is independently 0, 1, or 2 and each n is independently 1 or 2;

or R$^{3b}$ and R$^{3c}$, together with the carbon ring atoms to which they are directly attached, may form a fused ring selected from dioxolyl or tetrahydrofuranyl, and R$^{3a}$ and R$^{3d}$ are as defined above;

each R$^4$ and R$^5$ is independently selected from the group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when R$^4$ and R$^5$ are each attached to the same nitrogen atom, then R$^4$ and R$^5$, together with the nitrogen atom to which they are attached, may form a heterocyclyl or heteroaryl;

each R$^8$ is a direct bond or a straight or branched alkylene chain, a straight or branched alkenylene chain or a straight or branched alkynylene chain; and each R$^9$ is a straight or branched alkylene chain, a straight or branched alkenylene chain or a straight or branched alkynylene chain.

Another embodiment of the invention are the compounds of formula (I) as set forth above in the Summary of the invention wherein:

at least one of j and k is 1 and the other is 0 or 1;

Q is —O—;

R$^1$ is heterocyclylalkyl or heteroarylalkyl where the heterocyclylalkyl or the heteroarylalkyl group is optionally substituted by one or more substituents selected from the group consisting of oxo, alkyl, halo, haloalkyl, cycloalkyl, cycloalkylalkyl, aryl, aralkyl, heterocyclyl, heterocyclylalkyl, heteroaryl, heteroarylalkyl, —$R^8$—$OR^5$, —$R^8$—C(O)$OR^5$, —$R^8$—N($R^4$)$R^5$, —$R^8$—C(O)N($R^4$)$R^5$, —$R^8$—N($R^5$)C(O)$R^4$, —$R^8$—S(O)$_m R^4$ (where m is 0, 1 or 2), —$R^8$—CN, or —$R^8$—$NO_2$;

$R^{2a}$, $R^{2b}$, $R^{2c}$ and $R^{2d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—$NO_2$, —$R^8$—$OR^5$, —$R^8$—N($R^4$)$R^5$, —N=C($R^4$)$R^5$, —S(O)$_m R^4$, —OS(O)$_2 CF_3$, —$R^8$—C(O)$R^4$, —C(S)$R^4$, —C($R^4$)$_2$C(O)$R^5$, —$R^8$—C(O)$OR^4$, —C(S)$OR^4$, —$R^8$—C(O)N($R^4$)$R^5$, —C(S)N($R^4$)$R^5$, —N($R^5$)C(O)$R^4$, —N($R^5$)C(S)$R^4$, —N($R^5$)C(O)$OR^4$, —N($R^5$)C(S)$OR^4$, —N($R^5$)C(O)N($R^4$)$R^5$, —N($R^5$)C(S)N($R^4$)$R^5$, —N($R^5$)S(O)$_n R^4$, —N($R^5$)S(O)$_n$N($R^4$)$R^5$, —$R^8$—S(O)$_n$N($R^4$)$R^5$, —N($R^5$)C(=N$R^5$)N($R^4$)$R^5$, and —N($R^5$)C(=N—CN)N($R^4$)$R^5$, wherein each m is independently 0, 1, or 2 and each n is independently 1 or 2;

and wherein each of the cycloalkyl, cycloalkylalkyl, aryl, aralkyl, aralkenyl, heterocyclyl, heterocyclylalkyl, heteroaryl and heteroarylalkyl groups for $R^{2a}$, $R^{2b}$, $R^{2c}$ and $R^{2d}$ may be optionally substituted by one or more substituents selected from the group consisting of alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—$NO_2$, —$R^8$—$OR^5$, —$R^8$—N($R^4$)$R^5$, —S(O)$_m R^4$, —$R^8$—S(O)$_n$N($R^4$)$R^5$, —$R^8$—C(O)$R^4$, —$R^8$—C(O)$OR^4$, —$R^8$—C(O)N($R^4$)$R^5$, —N($R^5$)C(O)$R^4$, and —N($R^5$)S(O)$_n R^4$, wherein each m is independently 0, 1, or 2 and each n is independently 1 or 2;

$R^{3a}$, $R^{3b}$, $R^{3c}$ and $R^{3d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—$NO_2$, —$R^8$—$OR^5$, —$R^8$—N($R^4$)$R^5$, —N=C($R^4$)$R^5$, —S(O)$_m R^4$, —OS(O)$_2 CF_3$, —$R^8$—C(O)$R^4$, —C(S)$R^4$, —C($R^4$)$_2$C(O)$R^5$, —$R^8$—C(O)$OR^4$, —C(S)$OR^4$, —$R^8$—C(O)N($R^4$)$R^5$, —C(S)N($R^4$)$R^5$, —N($R^5$)C(O)$R^4$, —N($R^5$)C(S)$R^4$, —N($R^5$)C(O)$OR^4$, —N($R^5$)C(S)$OR^4$, —N($R^5$)C(O)N($R^4$)$R^5$, —N($R^5$)C(S)N($R^4$)$R^5$, —N($R^5$)S(O)$_n R^4$, —N(R)S(O)$_n$N($R^4$)$R^5$, —$R^8$—S(O)$_n$N($R^4$)$R^5$, —N($R^5$)C(=N$R^5$)N($R^4$)$R^5$, and —N($R^5$)C(N=C($R^4$)$R^5$)N($R^4$)$R^5$, wherein each m is independently 0, 1, or 2 and each n is independently 1 or 2;

each $R^4$ and $R^5$ is independently selected from the group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when $R^4$ and $R^5$ are each attached to the same nitrogen atom, then $R^4$ and $R^5$, together with the nitrogen atom to which they are attached, may form a heterocyclyl or heteroaryl;

each $R^8$ is a direct bond or a straight or branched alkylene chain, a straight or branched alkenylene chain or a straight or branched alkynylene chain; and each $R^9$ is a straight or branched alkylene chain, a straight or branched alkenylene chain or a straight or branched alkynylene chain.

Another embodiment of the invention are the compounds of formula (I) as set forth above in the Summary of the invention wherein:

j is 0 and k is 1 or 2;

Q is —O—;

$R^1$ is hydrogen, alkyl, alkenyl, alkynyl, haloalkyl, aryl, cycloalkyl, cycloalkylalkyl, heteroaryl, heterocyclyl, —$R^8$—C(O)$R^5$, —$R^8$—C(O)$OR^5$, —$R^8$—C(O)N($R^4$)$R^5$, —S(O)$_2$—$R^5$, —$R^9$—S(O)$_m$—$R^5$ (where m is 0, 1 or 2), —$R^8$—$OR^5$, —$R^8$—CN, —$R^9$—P(O)($OR^5$)$_2$, or —$R^9$—O—$R^9$—$OR^5$;

$R^{2a}$, $R^{2b}$, $R^{2c}$ and $R^{2d}$ are each hydrogen;

$R^{3a}$ and $R^{3d}$ are each hydrogen;

$R^{3b}$ and $R^{3c}$, together with the carbon ring atoms to which they are directly attached, form a fused ring selected from cycloalkyl, heterocyclyl, aryl or heteroaryl;

each $R^4$ and $R^5$ is independently selected from the group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when $R^4$ and $R^5$ are each attached to the same nitrogen atom, then $R^4$ and $R^5$, together with the nitrogen atom to which they are attached, may form a heterocyclyl or heteroaryl;

each $R^8$ is a direct bond or a straight or branched alkylene chain, a straight or branched alkenylene chain or a straight or branched alkynylene chain; and each $R^9$ is a straight or branched alkylene chain, a straight or branched alkenylene chain or a straight or branched alkynylene chain.

Another embodiment of the invention are the compounds of formula (I) as set forth above in the Summary of the invention wherein:

j is 0 and k is 1 or 2;

Q is —C($R^{1a}$)H—, —C(O)—, —$CF_2$—, —C(O)O— or —N($R^5$)C(O)—;

$R^{1a}$ is hydrogen or —$OR^5$;

$R^1$ is hydrogen, alkyl, alkenyl, alkynyl, haloalkyl, aryl, cycloalkyl, cycloalkylalkyl, heteroaryl, heterocyclyl, —$R^8$—C(O)$R^5$, —$R^8$—C(O)$OR^5$, —$R^8$—C(O)N($R^4$)$R^5$, —S(O)$_2$—$R^5$, —$R^9$—S(O)$_m$—$R^5$ (where m is 0, 1 or 2), —$R^8$—$OR^5$, —$R^8$—CN, —$R^9$—P(O)($OR^5$)$_2$, or —$R^9$—O—$R^9$—$OR^5$;

or $R^1$ is aralkyl substituted by —C(O)N($R^6$)$R^7$ where:

$R^6$ is hydrogen, alkyl, aryl or aralkyl; and $R^7$ is hydrogen, alkyl, haloalkyl, —$R^9$—CN, —$R^9$—$OR^5$, —$R^9$—N($R^4$)$R^5$, aryl, aralkyl, cycloalkyl, cycloalkylalkyl, heterocyclyl, heterocyclylalkyl, heteroaryl or heteroarylalkyl;

or $R^6$ and $R^7$, together with the nitrogen to which they are attached, form a heterocyclyl or heteroaryl;

and wherein each aryl, aralkyl, cycloalkyl, cycloalkylalkyl, heterocyclyl, heterocyclylalkyl, heteroaryl and heteroarylalkyl group for $R^6$ and $R^7$ may be optionally substituted by one or more substituents selected from the group consisting of alkyl, cycloalkyl, aryl, aralkyl, halo, haloalkyl, —$R^8$—CN, —$R^8$—$OR^5$, heterocyclyl and heteroaryl;

or $R^1$ is aralkyl optionally substituted by one or more substituents selected from the group consisting of —$R^8$—$OR^5$, —C(O)$OR^5$, halo, haloalkyl, alkyl, nitro, cyano, aryl, aralkyl, heterocyclyl and heteroaryl;

or $R^1$ is —$R^9$—N($R^{10}$)$R^{11}$, —$R^9$—N($R^{12}$)C(O)$R^{11}$ or —$R^9$—N($R^{10}$)C(O)N($R^{10}$)$R^{11}$ where:

each $R^{10}$ is hydrogen, alkyl, aryl, aralkyl or heteroaryl;

each $R^{11}$ is hydrogen, alkyl, haloalkyl, cycloalkyl, cycloalkylalkyl, aryl, aralkyl, heterocyclyl, heterocyclylalkyl, heteroaryl, heteroarylalkyl, —$R^9$—OC(O)$R^5$, —$R^9$—C(O)O$R^5$, —$R^9$—C(O)N($R^4$)$R^5$, —$R^9$—C(O)$R^5$, —$R^9$—N($R^4$)$R^5$, —$R^9$—O$R^5$, or —$R^9$—CN; and $R^{12}$ is hydrogen, alkyl, aryl, aralkyl or —C(O)$R^5$;

and wherein each aryl, aralkyl, cycloalkyl, cycloalkylalkyl, heterocyclyl, heterocyclylalkyl, heteroaryl and heteroarylalkyl group for $R^{10}$ and $R^{11}$ may be optionally substituted by one or more substituents selected from the group consisting of alkyl, cycloalkyl, aryl, aralkyl, halo, haloalkyl, nitro, —$R^8$—CN, —$R^8$—O$R^5$, —$R^8$—C(O)$R^5$, heterocyclyl and heteroaryl;

or $R^1$ is heterocyclylalkyl or heteroarylalkyl where the heterocyclylalkyl or the heteroarylalkyl group is optionally substituted by one or more substituents selected from the group consisting of oxo, alkyl, halo, haloalkyl, cycloalkyl, cycloalkylalkyl, aryl, aralkyl, heterocyclyl, heterocyclylalkyl, heteroaryl, heteroarylalkyl, —$R^8$—O$R^5$, —$R^8$—C(O)O$R^5$, —$R^8$—N($R^4$)$R^5$, —$R^8$—C(O)N($R^4$)$R^5$, —$R^8$—N($R^5$)C(O)$R^4$, —$R^8$—S(O)$_m R^4$ (where m is 0, 1 or 2), —$R^8$—CN, or —$R^8$—NO$_2$;

$R^{2a}$, $R^{2b}$, $R^{2c}$ and $R^{2d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—NO$_2$, —$R^8$—O$R^5$, —$R^8$—N($R^4$)$R^5$, —N=C($R^4$)$R^5$, —S(O)$_m R^4$, —OS(O)$_2$CF$_3$, —$R^8$—C(O)$R^4$, —C(S)$R^4$, —C($R^4$)$_2$C(O)$R^5$, —$R^8$—C(O)O$R^4$, —C(S)O$R^4$, —$R^8$—C(O)N($R^4$)$R^5$, —C(S)N($R^4$)$R^5$, —N($R^5$)C(O)$R^4$, —N($R^5$)C(S)$R^4$, —N($R^5$)C(O)O$R^4$, —N($R^5$)C(S)O$R^4$, —N($R^5$)C(O)N($R^4$)$R^5$, —N($R^5$)C(S)N($R^4$)$R^5$, —N($R^5$)S(O)$_n R^4$, —N($R^5$)S(O)$_n$N($R^4$)$R^5$, —$R^8$—S(O)$_n$N($R^4$)$R^5$, —N($R^5$)C(=N$R^5$)N($R^4$)$R^5$, and —N($R^8$)C(=N—CN)N($R^4$)$R^5$, wherein each m is independently 0, 1, or 2 and each n is independently 1 or 2;

and wherein each of the cycloalkyl, cycloalkylalkyl, aryl, aralkyl, aralkenyl, heterocyclyl, heterocyclylalkyl, heteroaryl and heteroarylalkyl groups for $R^{2a}$, $R^{2b}$, $R^{2c}$ and $R^{2d}$ may be optionally substituted by one or more substituents selected from the group consisting of alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—NO$_2$, —$R^8$—O$R^5$, —$R^8$—N($R^4$)$R^5$, —S(O)$_m R^4$, —$R^8$—S(O)$_n$N($R^4$)$R^5$, —$R^8$—C(O)$R^4$, —$R^8$—C(O)O$R^4$, —$R^8$—C(O)N($R^4$)$R^5$, —N($R^5$)C(O)$R^4$, and —N($R^5$)S(O)$_n R^4$, wherein each m is independently 0, 1 or 2 and each n is independently 1 or 2;

or $R^{2a}$ and $R^{2b}$, together with the carbon ring atoms to which they are directly attached, may form a fused ring selected from cycloalkyl, aryl, heterocyclyl and heteroaryl, and $R^{2c}$ and $R^{2d}$ are as defined above;

or $R^{2b}$ and $R^{2c}$, together with the carbon ring atoms to which they are directly attached, may form a fused ring selected from cycloalkyl, aryl, heterocyclyl and heteroaryl, and $R^{2a}$ and $R^{2d}$ are as defined above;

or $R^{2c}$ and $R^{2d}$, together with the carbon ring atoms to which they are directly attached, may form a fused ring selected from cycloalkyl, aryl, heterocyclyl and heteroaryl, and $R^{2a}$ and $R^{2b}$ are as defined above;

$R^{3a}$, $R^{3b}$, $R^{3c}$ and $R^{3d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—NO$_2$, —$R^8$—O$R^5$, —$R^8$—N($R^4$)$R^5$, —N=C($R^4$)$R^5$, —S(O)$_m R^4$, —OS(O)$_2$CF$_3$, —$R^8$—C(O)$R^4$, —C(S)$R^4$, —C($R^4$)$_2$C(O)$R^5$, —$R^8$—C(O)O$R^4$, —O(S)O$R^4$, —$R^8$—C(O)N($R^4$)$R^5$, —C(S)N($R^4$)$R^5$, —N($R^5$)C(O)$R^4$, —N($R^5$)C(S)$R^4$, —N($R^5$)C(O)O$R^4$, —N($R^5$)C(S)O$R^4$, —N($R^5$)C(O)N($R^4$)$R^5$, —N($R^5$)C(S)N($R^4$)$R^5$, —N($R^8$)S(O)$_n R^4$, —N($R^8$)S(O)$_n$N($R^4$)$R^5$, —$R^8$—S(O)$_n$N($R^4$)$R^5$, —N($R^5$)C(=N$R^5$)N($R^4$)$R^5$, and —N($R^5$)C(N=C($R^4$)$R^5$)N($R^4$)$R^5$, wherein each m is independently 0, 1, or 2 and each n is independently 1 or 2;

or $R^{3a}$ and $R^{3b}$, together with the carbon ring atoms to which they are directly attached, form a fused ring selected from cycloalkyl, heterocyclyl, aryl or heteroaryl, and $R^{3c}$ and $R^{3d}$ are as defined above;

or $R^{3b}$ and $R^{3c}$, together with the carbon ring atoms to which they are directly attached, may form a fused ring selected from cycloalkyl, heterocyclyl, aryl or heteroaryl, and $R^{3a}$ and $R^{3d}$ are as defined above;

or $R^{3c}$ and $R^{3d}$, together with the carbon ring atoms to which they are directly attached, may form a fused ring selected from cycloalkyl, heterocyclyl, aryl or heteroaryl, and $R^{3a}$ and $R^{3b}$ are as defined above;

each $R^4$ and $R^5$ is independently selected from the group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when $R^4$ and $R^5$ are each attached to the same nitrogen atom, then $R^4$ and $R^5$, together with the nitrogen atom to which they are attached, may form a heterocyclyl or heteroaryl;

each $R^8$ is a direct bond or a straight or branched alkylene chain, a straight or branched alkenylene chain or a straight or branched alkynylene chain; and each $R^9$ is a straight or branched alkylene chain, a straight or branched alkenylene chain or a straight or branched alkynylene chain.

Another embodiment of the invention are the compounds of formula (I) as set forth above in the Summary of the invention wherein:

j is 0 and k is 1 or 2;

Q is —C($R^{1a}$)H—;

$R^{1a}$ is hydrogen or —O$R^5$;

$R^1$ is hydrogen, alkyl, alkenyl, alkynyl, haloalkyl, aryl, cycloalkyl, cycloalkylalkyl, heteroaryl, heterocyclyl, —$R^8$—C(O)$R^5$, —$R^8$—C(O)O$R^5$, —$R^8$—C(O)N($R^4$)$R^5$, —S(O)$_2$—$R^5$, —$R^9$—S(O)$_m$—$R^5$ (where m is 0, 1 or 2), —$R^8$—O$R^5$, —$R^8$—CN, —$R^9$—P(O)(O$R^5$)$_2$, or —$R^9$—O—$R^9$—O$R^5$;

$R^{2a}$, $R^{2b}$, $R^{2c}$ and $R^{2d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—NO$_2$, —$R^8$—O$R^5$, —$R^8$—N($R^4$)$R^5$, —N=C($R^4$)$R^5$, —S(O)$_m R^4$, —OS(O)$_2$CF$_3$, —$R^8$—C(O)$R^4$, —C(S)$R^4$, —C($R^4$)$_2$C(O)$R^5$, —$R^8$—C(O)O$R^4$, —C(S)O$R^4$, —$R^8$—C(O)N($R^4$)$R^5$, —C(S)N($R^4$)$R^5$, —N($R^5$)C(O)$R^4$, —N($R^5$)C(S)$R^4$, —N($R^5$)C(O)O$R^4$, —N($R^5$)C(S)O$R^4$, —N($R^5$)C(O)N($R^4$)$R^5$, —N($R^5$)C(S)N($R^4$)$R^5$, —N($R^5$)S(O)$_n R^4$, —N($R^5$)S(O)$_n$N($R^4$)$R^5$, —$R^8$—S(O)$_n$N($R^4$)$R^5$, —N($R^5$)C(=N$R^5$)N($R^4$)$R^5$, and —N($R^5$)C(=N—CN)N($R^4$)$R^5$, wherein each m is independently 0, 1, or 2 and each n is independently 1 or 2;

and wherein each of the cycloalkyl, cycloalkylalkyl, aryl, aralkyl, aralkenyl, heterocyclyl, heterocyclylalkyl, heteroaryl and heteroarylalkyl groups for $R^{2a}$, $R^{2b}$, $R^{2c}$ and $R^{2d}$ may be optionally substituted by one or more substituents selected from the group consisting of alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —R$^8$—CN, —R$^8$—NO$_2$, —R$^8$—OR$^5$, —R$^8$—N(R$^4$)R$^5$, —S(O)$_m$R$^4$, —R$^8$—S(O)$_n$N(R$^4$)R$^5$, —R$^8$—C(O)R$^4$, —R$^8$—C(O)OR$^4$, —R$^8$—C(O)N(R$^4$)R$^5$, —N(R$^5$)C(O)R$^4$, and —N(R$^5$)S(O)$_n$R$^4$, wherein each m is independently 0, 1, or 2 and each n is independently 1 or 2;

or R$^{2a}$ and R$^{2b}$, together with the carbon ring atoms to which they are directly attached, may form a fused ring selected from cycloalkyl, aryl, heterocyclyl and heteroaryl, and R$^{2c}$ and R$^{2d}$ are as defined above;

or R$^{2b}$ and R$^{2c}$, together with the carbon ring atoms to which they are directly attached, may form a fused ring selected from cycloalkyl, aryl, heterocyclyl and heteroaryl, and R$^{2a}$ and R$^{2d}$ are as defined above;

or R$^{2c}$ and R$^{2d}$, together with the carbon ring atoms to which they are directly attached, may form a fused ring selected from cycloalkyl, aryl, heterocyclyl and heteroaryl, and R$^{2a}$ and R$^{2b}$ are as defined above;

R$^{3a}$, R$^{3b}$, R$^{3c}$ and R$^{3d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —R$^8$—CN, —R$^8$—NO$_2$, —R$^8$—OR$^5$, —R$^8$—N(R$^4$)R$^5$, —N═C(R$^4$)R$^5$, —S(O)$_m$R$^4$, —OS(O)$_2$CF$_3$, —R$^8$—C(O)R$^4$, —C(S)R$^4$, —C(R$^4$)$_2$C(O)R$^5$, —R$^8$—C(O)OR$^4$, —C(S)OR$^4$, —R$^8$—C(O)N(R$^4$)R$^5$, —C(S)N(R$^4$)R$^5$, —N(R$^5$)C(O)R$^4$, —N(R$^5$)C(S)R$^4$, —N(R$^5$)C(O)OR$^4$, —N(R$^5$)C(S)OR$^4$, —N(R$^5$)C(O)N(R$^4$)R$^5$, —N(R$^5$)C(S)N(R$^4$)R$^5$, —N(R$^5$)S(O)$_n$R$^4$, —N(R$^5$)S(O)$_n$N(R$^4$)R$^5$, —R$^8$—S(O)$_n$N(R$^4$)R$^5$, —N(R$^5$)C(═NR$^5$)N(R$^4$)R$^5$, and —N(R$^5$)C(N═C(R$^4$)R$^5$)N(R$^4$)R$^5$, wherein each m is independently 0, 1, or 2 and each n is independently 1 or 2;

or R$^{3a}$ and R$^{3b}$, together with the carbon ring atoms to which they are directly attached, form a fused ring selected from cycloalkyl, heterocyclyl, aryl or heteroaryl, and R$^{3c}$ and R$^{3d}$ are as defined above;

or R$^{3b}$ and R$^{3c}$, together with the carbon ring atoms to which they are directly attached, may form a fused ring selected from cycloalkyl, heterocyclyl, aryl or heteroaryl, and R$^{3a}$ and R$^{3d}$ are as defined above;

or R$^{3c}$ and R$^{3d}$, together with the carbon ring atoms to which they are directly attached, may form a fused ring selected from cycloalkyl, heterocyclyl, aryl or heteroaryl, and R$^{3a}$ and R$^{3b}$ are as defined above;

each R$^4$ and R$^5$ is independently selected from the group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when R$^4$ and R$^5$ are each attached to the same nitrogen atom, then R$^4$ and R$^5$, together with the nitrogen atom to which they are attached, may form a heterocyclyl or heteroaryl;

each R$^8$ is a direct bond or a straight or branched alkylene chain, a straight or branched alkenylene chain or a straight or branched alkynylene chain; and each R$^9$ is a straight or branched alkylene chain, a straight or branched alkenylene chain or a straight or branched alkynylene chain.

Another embodiment of the invention are the compounds of formula (I) as set forth above in the Summary of the invention wherein:

j is 0 and k is 1 or 2;

Q is —C(R$^{1a}$)H—;

R$^{1a}$ is hydrogen or —OR$^5$;

R$^1$ is hydrogen, alkyl, alkenyl, alkynyl, haloalkyl, aryl, cycloalkyl, cycloalkylalkyl, heteroaryl, heterocyclyl, —R$^8$—C(O)R$^5$, —R$^8$—C(O)OR$^5$, —R$^8$—C(O)N(R$^4$)R$^5$, —S(O)$_2$—R$^5$, —R$^9$—S(O)$_m$—R$^5$ (where m is 0, 1 or 2), —R$^8$—OR$^5$, —R$^8$—CN, —R$^9$—P(O)(OR$^5$)$_2$, or —R$^9$—O—R$^9$—OR$^5$;

R$^{2a}$, R$^{2b}$, R$^{2c}$ and R$^{2d}$ are each hydrogen;

R$^{2a}$, R$^{2b}$, R$^{2c}$ and R$^{2d}$ are each hydrogen;

R$^{3a}$ and R$^{3d}$ are each hydrogen;

R$^{3b}$ and R$^{3c}$, together with the carbon ring atoms to which they are directly attached, form a fused ring selected from cycloalkyl, heterocyclyl, aryl or heteroaryl;

each R$^5$ is independently selected from the group consisting of hydrogen, alkyl, alkenyl, alkynyl, haloalkyl, alkoxyalkyl, cycloalkyl, cycloalkylalkyl, aryl, aralkyl, heterocyclyl and heteroaryl;

each R$^8$ is a direct bond or a straight or branched alkylene chain, a straight or branched alkenylene chain or a straight or branched alkynylene chain; and each R$^9$ is a straight or branched alkylene chain, a straight or branched alkenylene chain or a straight or branched alkynylene chain.

Another embodiment of the invention are the compounds of formula (I) as set forth above in the Summary of the invention wherein:

j is 0 and k is 1 or 2;

Q is —C(R$^{1a}$)H—;

R$^{1a}$ is hydrogen or —OR$^5$;

R$^1$ is pentyl;

R$^{2a}$, R$^{2b}$, R$^{2c}$ and R$^{2d}$ are each hydrogen;

R$^{3a}$ and R$^{3d}$ are each hydrogen;

R$^{3b}$ and R$^{3c}$, together with the carbon ring atoms to which they are directly attached, form a fused dioxolyl ring; and each R$^5$ is independently selected from the group consisting of hydrogen, alkyl, alkenyl, alkynyl, haloalkyl, alkoxyalkyl, cycloalkyl, cycloalkylalkyl, aryl, aralkyl, heterocyclyl and heteroaryl.

Another embodiment of the invention are the compounds of formula (I) as set forth above in the Summary of the invention wherein:

j is 0 and k is 1 or 2;

Q is —C(O)—, —CF$_2$—, —C(O)O— or —N(R$^5$)C(O)—;

R$^1$ is hydrogen, alkyl, alkenyl, alkynyl, haloalkyl, aryl, cycloalkyl, cycloalkylalkyl, heteroaryl, heterocyclyl, —R$^8$—C(O)R$^5$, —R$^8$—C(O)OR$^5$, —R$^8$—C(O)N(R$^4$)R$^5$, —S(O)$_2$—R$^5$, —R$^9$—S(O)$_m$—R$^5$ (where m is 0, 1 or 2), —R$^8$—OR$^5$, —R$^8$—CN, —R$^9$—P(O)(OR$^5$)$_2$, or —R$^9$—O—R$^9$—OR$^5$;

or R$^1$ is aralkyl substituted by —C(O)N(R$^6$)R$^7$ where:

R$^6$ is hydrogen, alkyl, aryl or aralkyl; and

R$^7$ is hydrogen, alkyl, haloalkyl, —R$^9$—CN, —R$^9$—OR$^5$, —R$^9$—N(R$^4$)R$^5$, aryl, aralkyl, cycloalkyl, cycloalkylalkyl, heterocyclyl, heterocyclylalkyl, heteroaryl or heteroarylalkyl;

or R$^6$ and R$^7$, together with the nitrogen to which they are attached, form a heterocyclyl or heteroaryl;

and wherein each aryl, aralkyl, cycloalkyl, cycloalkylalkyl, heterocyclyl, heterocyclylalkyl, heteroaryl and heteroarylalkyl group for R$^6$ and R$^7$ may be optionally substituted by one or more substituents selected from the group consisting of alkyl, cycloalkyl, aryl, aralkyl, halo, haloalkyl, —R$^8$—CN, —R$^8$—OR$^5$, heterocyclyl and heteroaryl;

or R$^1$ is aralkyl optionally substituted by one or more substituents selected from the group consisting of —R$^8$—

OR$^5$, —C(O)OR$^5$, halo, haloalkyl, alkyl, nitro, cyano, aryl, aralkyl, heterocyclyl and heteroaryl;

or R$^1$ is —R$^9$—N(R$^{10}$)R$^{11}$, —R$^9$—N(R$^{12}$)C(O)R$^{11}$ or —R$^9$-N(R$^{10}$)C(O)N(R$^{10}$)R$^{11}$ where:
- each R$^{10}$ is hydrogen, alkyl, aryl, aralkyl or heteroaryl;
- each R$^{11}$ is hydrogen, alkyl, haloalkyl, cycloalkyl, cycloalkylalkyl, aryl, aralkyl, heterocyclyl, heterocyclylalkyl, heteroaryl, heteroarylalkyl, —R$^9$—OC(O)R$^5$, —R$^9$—C(O)OR$^5$, —R$^9$—C(O)N(R$^4$)R$^5$, —R$^9$—C(O)R$^5$, —R$^9$—N(R$^4$)R$^5$, —R$^9$—OR$^5$, or —R$^9$—CN; and
- R$^{12}$ is hydrogen, alkyl, aryl, aralkyl or —C(O)R$^5$;
- and wherein each aryl, aralkyl, cycloalkyl, cycloalkylalkyl, heterocyclyl, heterocyclylalkyl, heteroaryl and heteroarylalkyl group for R$^{10}$ and R$^{11}$ may be optionally substituted by one or more substituents selected from the group consisting of alkyl, cycloalkyl, aryl, aralkyl, halo, haloalkyl, nitro, —R$^8$—CN, —R$^8$—OR$^5$, —R$^8$—C(O)R$^5$, heterocyclyl and heteroaryl;

or R$^1$ is heterocyclylalkyl or heteroarylalkyl where the heterocyclylalkyl or the heteroarylalkyl group is optionally substituted by one or more substituents selected from the group consisting of oxo, alkyl, halo, haloalkyl, cycloalkyl, cycloalkylalkyl, aryl, aralkyl, heterocyclyl, heterocyclylalkyl, heteroaryl, heteroarylalkyl, —R$^8$—OR$^5$, —R$^8$—C(O)OR$^5$, —R$^8$—N(R$^4$)R$^5$, —R$^8$—C(O)N(R$^4$)R$^5$, —R$^8$—N(R$^5$)C(O)R$^4$, —R$^8$—S(O)$_m$R$^4$ (where m is 0, 1 or 2), —R$^8$—CN, or —R$^8$—NO$_2$;

R$^{2a}$, R$^{2b}$, R$^{2c}$ and R$^{2d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —R$^8$—CN, —R$^8$—NO$_2$, —R$^8$—OR$^5$, —R$^8$—N(R$^4$)R$^5$, —N=C(R$^4$)R$^5$, —S(O)$_m$R$^4$, —OS(O)$_2$CF$_3$, —R$^8$—C(O)R$^4$, —C(S)R$^4$, —C(R$^4$)$_2$C(O)R$^5$, —R$^8$—C(O)OR$^4$, —C(S)OR$^4$, —R$^8$—C(O)N(R$^4$)R$^5$, —C(S)N(R$^4$)R$^5$, —N(R$^5$)C(O)R$^4$, —N(R$^5$)C(S)R$^4$, —N(R$^5$)C(O)OR$^4$, —N(R$^5$)C(S)OR$^4$, —N(R$^5$)C(O)N(R$^4$)R$^5$, —N(R$^5$)C(S)N(R$^4$)R$^5$, —N(R$^5$)S(O)$_n$R$^4$, —N(R$^5$)S(O)$_n$N(R$^4$)R$^5$, —R$^8$—S(O)$_n$N(R$^4$)R$^5$, —N(R$^5$)C(=NR$^5$)N(R$^4$)R$^5$, and —N(R$^5$)C(=N—CN)N(R$^4$)R$^5$, wherein each m is independently 0, 1, or 2 and each n is independently 1 or 2;

and wherein each of the cycloalkyl, cycloalkylalkyl, aryl, aralkyl, aralkenyl, heterocyclyl, heterocyclylalkyl, heteroaryl and heteroarylalkyl groups for R$^{2a}$, R$^{2b}$, R$^{2c}$ and R$^{2d}$ may be optionally substituted by one or more substituents selected from the group consisting of alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —R$^8$—CN, —R$^8$—NO$_2$, —R$^8$—OR$^5$, —R$^8$—N(R$^4$)R$^5$, —S(O)$_m$R$^4$, —R$^8$—S(O)$_n$N(R$^4$)R$^5$, —R$^8$—C(O)R$^4$, —R$^8$—C(O)OR$^4$, —R$^8$—C(O)N(R$^4$)R$^5$, —N(R$^5$)C(O)R$^4$, and —N(R$^5$)S(O)$_n$R$^4$, wherein each m is independently 0, 1, or 2 and each n is independently 1 or 2;

or R$^{2a}$ and R$^{2b}$, together with the carbon ring atoms to which they are directly attached, may form a fused ring selected from cycloalkyl, aryl, heterocyclyl and heteroaryl, and R$^{2c}$ and R$^{2d}$ are as defined above;

or R$^{2b}$ and R$^{2c}$, together with the carbon ring atoms to which they are directly attached, may form a fused ring selected from cycloalkyl, aryl, heterocyclyl and heteroaryl, and R$^{2a}$ and R$^{2b}$ are as defined above;

or R$^{2c}$ and R$^{2d}$, together with the carbon ring atoms to which they are directly attached, may form a fused ring selected from cycloalkyl, aryl, heterocyclyl and heteroaryl, and R$^{2a}$ and R$^{2b}$ are as defined above;

R$^{3a}$, R$^{3b}$, R$^{3c}$ and R$^{3d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —R$^8$—CN, —R$^8$—NO$_2$, —R$^8$—OR$^5$, —R$^8$—N(R$^4$)R$^5$, —N=C(R$^4$)R$^5$, —S(O)$_m$R$^4$, —OS(O)$_2$CF$_3$, —R$^8$—C(O)R$^4$, —C(S)R$^4$, —C(R$^4$)$_2$C(O)R$^5$, —R$^8$—C(O)OR$^4$, —C(S)OR$^4$, —R$^8$—C(O)N(R$^4$)R$^5$, —C(S)N(R$^4$)R$^5$, —N(R$^5$)C(O)R$^4$, —N(R$^5$)C(S)R$^4$, —N(R$^5$)C(O)OR$^4$, —N(R$^5$)C(S)OR$^4$, —N(R$^5$)C(O)N(R$^4$)R$^5$, —N(R$^5$)C(S)N(R$^4$)R$^5$, —N(R$^5$)S(O)$_n$R$^4$, —N(R$^5$)S(O)$_n$N(R$^4$)R$^5$, —R$^8$—S(O)$_n$N(R$^4$)R$^5$, —N(R$^5$)C(=NR$^5$)N(R$^4$)R$^5$, and —N(R$^5$)C(N=C(R$^4$)R$^5$)N(R$^4$)R$^5$, wherein each m is independently 0, 1, or 2 and each n is independently 1 or 2;

or R$^{3a}$ and R$^{3b}$, together with the carbon ring atoms to which they are directly attached, form a fused ring selected from cycloalkyl, heterocyclyl, aryl or heteroaryl, and R$^{3c}$ and R$^{3d}$ are as defined above;

or R$^{3b}$ and R$^{3c}$, together with the carbon ring atoms to which they are directly attached, may form a fused ring selected from cycloalkyl, heterocyclyl, aryl or heteroaryl, and R$^{3a}$ and R$^{3d}$ are as defined above;

or R$^{3c}$ and R$^{3d}$, together with the carbon ring atoms to which they are directly attached, may form a fused ring selected from cycloalkyl, heterocyclyl, aryl or heteroaryl, and R$^{3a}$ and R$^{3b}$ are as defined above;

each R$^4$ and R$^5$ is independently selected from the group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when R$^4$ and R$^5$ are each attached to the same nitrogen atom, then R$^4$ and R$^5$, together with the nitrogen atom to which they are attached, may form a heterocyclyl or heteroaryl;

each R$^8$ is a direct bond or a straight or branched alkylene chain, a straight or branched alkenylene chain or a straight or branched alkynylene chain; and each R$^9$ is a straight or branched alkylene chain, a straight or branched alkenylene chain or a straight or branched alkynylene chain.

Another embodiment of the invention are the compounds of formula (I) as set forth above in the Summary of the invention wherein:

j is 0 and k is 1 or 2;

Q is —C(O)—, —CF$_2$—, —C(O)O— or —N(R$^5$)C(O)—;

R$^1$ is hydrogen, alkyl, alkenyl, alkynyl, haloalkyl, aryl, cycloalkyl, cycloalkylalkyl, heteroaryl, heterocyclyl, —R$^8$—C(O)R$^5$, —R$^8$—C(O)OR$^5$, —R$^8$—C(O)N(R$^4$)R$^5$, —S(O)$_2$—R$^5$, —R$^9$—S(O)$_m$—R$^5$ (where m is 0, 1 or 2), —R$^8$—OR$^5$, —R$^8$—P(O)(OR$^5$)$_2$, or —R$^9$—O—R$^9$—OR$^5$;

R$^{2a}$, R$^{2b}$, R$^{2c}$ and R$^{2d}$ are each hydrogen;

R$^{2a}$, R$^{2b}$, R$^{2c}$ and R$^{2d}$ are each hydrogen;

R$^{3a}$ and R$^{3d}$ are each hydrogen;

R$^{3b}$ and R$^{3c}$, together with the carbon ring atoms to which they are directly attached, form a fused ring selected from cycloalkyl, heterocyclyl, aryl or heteroaryl;

each R$^5$ is independently selected from the group consisting of hydrogen, alkyl, alkenyl, alkynyl, haloalkyl, alkoxyalkyl, cycloalkyl, cycloalkylalkyl, aryl, aralkyl, heterocyclyl and heteroaryl;

each $R^8$ is a direct bond or a straight or branched alkylene chain, a straight or branched alkenylene chain or a straight or branched alkynylene chain; and each $R^9$ is a straight or branched alkylene chain, a straight or branched alkenylene chain or a straight or branched alkynylene chain.

Another embodiment of the invention are the compounds of formula (I) as set forth above in the Summary of the invention wherein:

j is 0 and k is 1 or 2;

Q is —C(O)—, —CF$_2$—, —C(O)O— or —N(R$^5$)C(O)—;

$R^1$ is pentyl;

$R^{2a}$, $R^{2b}$, $R^{2c}$ and $R^{2d}$ are each hydrogen;

$R^{3a}$ and $R^{3d}$ are each hydrogen;

$R^{3b}$ and $R^{3c}$, together with the carbon ring atoms to which they are directly attached, form a fused dioxolyl ring; and each $R^5$ is independently selected from the group consisting of hydrogen, alkyl, alkenyl, alkynyl, haloalkyl, alkoxyalkyl, cycloalkyl, cycloalkylalkyl, aryl, aralkyl, heterocyclyl and heteroaryl.

Specific embodiments of the compounds of formula (I) are described in more detail below in the Preparation of the Compounds of the Invention.

Utility and Testing of the Compounds of the Invention

The present invention relates to compounds, pharmaceutical compositions and methods of using the compounds and pharmaceutical compositions for the treatment of sodium channel-mediated diseases, preferably diseases related to pain, central nervous conditions such as epilepsy, anxiety, depression and bipolar disease; cardiovascular conditions such as arrhythmias, atrial fibrillation and ventricular fibrillation; neuromuscular conditions such as restless leg syndrome and muscle paralysis or tetanus; neuroprotection against stroke, neural trauma and multiple sclerosis; and channelopathies such as erythromyalgia and familial rectal pain syndrome, by administering to a patient in need of such treatment an effective amount of a sodium channel blocker modulating, especially inhibiting, agent.

In general, the present invention provides a method for treating a patient for, or protecting a patient from developing, a sodium channel-mediated disease, especially pain, comprising administering to an animal, such as a mammal, especially a human patient in need thereof, a therapeutically effective amount of a compound of the invention or a pharmaceutical composition comprising a compound of the invention wherein the compound modulates the activity of one or more voltage-dependent sodium channels.

The general value of the compounds of the invention in mediating, especially inhibiting, the sodium channel ion flux can be determined using the assays described below in the Biological Assays section. Alternatively, the general value of the compounds in treating conditions and diseases may be established in industry standard animal models for demonstrating the efficacy of compounds in treating pain. Animal models of human neuropathic pain conditions have been developed that result in reproducible sensory deficits (allodynia, hyperalgesia, and spontaneous pain) over a sustained period of time that can be evaluated by sensory testing. By establishing the degree of mechanical, chemical, and temperature induced allodynia and hyperalgesia present, several physiopathological conditions observed in humans can be modeled allowing the evaluation of pharmacotherapies.

In rat models of peripheral nerve injury, ectopic activity in the injured nerve corresponds to the behavioural signs of pain. In these models, intravenous application of the sodium channel blocker and local anesthetic lidocaine can suppress the ectopic activity and reverse the tactile allodynia at concentrations that do not affect general behaviour and motor function (Mao, J. and Chen, L. L, *Pain* (2000), 87:7-17). Allimetric scaling of the doses effective in these rat models, translates into doses similar to those shown to be efficacious in humans (Tanelian, D. L. and Brose, W. G., *Anesthesiology* (1991), 74(5):949-951). Furthermore, Lidoderm®, lidocaine applied in the form of a dermal patch, is currently an FDA approved treatment for post-herpetic neuralgia (Devers, A. and Glaler, B. S., *Clin. J. Pain* (2000), 16(3):205-8).

Sodium channel blockers have clinical uses in addition to pain. Epilepsy and cardiac arrhythmias are often targets of sodium channel blockers. Recent evidence from animal models suggest that sodium channel blockers may also be useful for neuroprotection under ischaemic conditions caused by stroke or neural trauma and in patients with multiple sclerosis (MS) (Clare, J. J. et al., op. cit. and Anger, T. et al., op. cit.).

The compounds of the invention modulate, preferably inhibit, ion flux through a voltage-dependent sodium channel in a mammal, especially in a human. Any such modulation, whether it be partial or complete inhibition or prevention of ion flux, is sometimes referred to herein as "blocking" and corresponding compounds as "blockers". In general, the compounds of the invention modulates the activity of a sodium channel downwards, inhibits the voltage-dependent activity of the sodium channel, and/or reduces or prevents sodium ion flux across a cell membrane by preventing sodium channel activity such as ion flux.

The compounds of the instant invention are sodium channel blockers and are therefore useful for treating diseases and conditions in humans and other organisms, including all those human diseases and conditions which are the result of aberrant voltage-dependent sodium channel biological activity or which may be ameliorated by modulation of voltage-dependent sodium channel biological activity.

As defined herein, a sodium channel-mediated disease or condition refers to a disease or condition which is ameliorated upon modulation of the sodium channel and includes, but is not limited to, pain, central nervous conditions such as epilepsy, anxiety, depression and bipolar disease; cardiovascular conditions such as arrhythmias, atrial fibrillation and ventricular fibrillation; neuromuscular conditions such as restless leg syndrome and muscle paralysis or tetanus; neuroprotection against stroke, neural trauma and multiple sclerosis; and channelopathies such as erythromyalgia and familial rectal pain syndrome.

A sodium channel-mediated disease or condition also includes pain associated with HIV, HIV treatment induced neuropathy, trigeminal neuralgia, glossopharyngeal neuralgia, neuropathy secondary to metastatic infiltration, adiposis dolorosa, thalamic lesions, hypertension, autoimmune disease, asthma, drug addiction (e.g. opiate, benzodiazepine, amphetamine, cocaine, alcohol, butane inhalation), Alzheimer, dementia, age-related memory impairment, Korsakoff syndrome, restenosis, urinary dysfunction, incontinence, parkinson's disease, cerebrovascular ischemia, neurosis, gastrointestinal disease, sickle cell anemia, transplant rejection, heart failure, myocardial infarction, reperfusion injury, intermittant claudication, angina, convulsion, respiratory disorders, cerebral or myocardial ischemias, long-QT syndrome, Catecholeminergic polymorphic ventricular tachycardia, ophthalmic diseases, spasticity, spastic paraplegia, myopathies, myasthenia gravis, paramyotonia congenita, hyperkalemic periodic paralysis, hypokalemic periodic paralysis, alopecia, anxiety disorders, psychotic disorders, mania, paranoia, seasonal affective disorder, panic disorder, obsessive compulsive disorder (OCD), phobias, autism, Aspergers Syndrome, Retts syndrome, disintegrative disorder, attention deficit disorder, aggressivity, impulse control disorders, thrombosis, pre clampsia, congestive cardiac failure, cardiac arrest, Freidrich's ataxia, Spinocerebellear ataxia, myelopathy, radiculopathy, systemic lupus erythamatosis, granulomatous disease, olivo-ponto-cerebellar atrophy, spinocerebellar ataxia, episodic ataxia, myokymia, progressive pallidal atrophy, progressive supranuclear palsy and spasticity, traumatic brain injury, cerebral oedema, hydrocephalus injury, spinal cord injury, anorexia nervosa, bulimia, Prader-Willi syndrome, obesity, optic neuritis, cataract, retinal haemorrhage, ischaemic retinopathy, retinitis pigmentosa, acute and chronic glaucoma, macular degeneration, retinal artery occlusion, Chorea, Huntington's chorea, cerebral edema, proctitis, post-herpetic neuralgia, eudynia, heat sensitivity, sarcoidosis, irritable bowel syndrome, Tourette syndrome, Lesch-Nyhan Syndrome, Brugado syndrome, Liddle syndrome, Crohns disease, multiple sclerosis and the pain associated with multiple sclerosis (MS), amyotrophic lateral sclerosis (ALS), disseminated sclerosis, diabetic neuropathy, peripheral neuropathy, charcot marie tooth syndrome, arthritic, rheumatoid arthritis, osteoarthritis, chondrocalcinosis, atherosclerosis, paroxysmal dystonia, myasthenia syndromes, myotonia, myotonic dystrophy, muscular dystrophy, malignant hyperthermia, cystic fibrosis, pseudoaldosteronism, rhabdomyolysis, mental handicap, hypothyroidism, bipolar depression, anxiety, schizophrenia, sodium channel toxin related illnesses, familial erythromelalgia, primary erythromelalgia, rectal pain, cancer, epilepsy, partial and general tonic seizures, febrile seizures, absence seizures (petit mal), myoclonic seizures, atonic seizures, clonic seizures, Lennox Gastaut, West Syndome (infantile spasms), multiresistant seizures, seizure prophylaxis (anti-epileptogenic), familial Mediterranean fever syndrome, gout, restless leg syndrome, arrhythmias, fibromyalgia, neuroprotection under ischaemic conditions caused by stroke or neural trauma, tachy-arrhythmias, atrial fibrillation and ventricular fibrillation and as a general or local anaesthetic.

As used herein, the term "pain" refers to all categories of pain and is recognized to include, but is not limited to, neuropathic pain, inflammatory pain, nociceptive pain, idiopathic pain, neuralgic pain, orofacial pain, burn pain, burning mouth syndrome, somatic pain, visceral pain, myofacial pain, dental pain, cancer pain, chemotherapy pain, trauma pain, surgical pain, post-surgical pain, childbirth pain, labor pain, reflex sympathetic dystrophy, brachial plexus avulsion, neurogenic bladder, acute pain (e.g. musculoskeletal and post-operative pain), chronic pain, persistent pain, peripherally mediated pain, centrally mediated pain, chronic headache, migraine headache, familial hemiplegic migraine, conditions associated with cephalic pain, sinus headache, tension headache, phantom limb pain, peripheral nerve injury, pain following stroke, thalamic lesions, radiculopathy, HIV pain, post-herpetic pain, non-cardiac chest pain, irritable bowel syndrome and pain associated with bowel disorders and dyspepsia, and combinations thereof.

The compounds identified in the instant specification inhibit the ion flux through a voltage-dependent sodium channel. Preferably, the compounds are state or frequency dependent modifiers of the sodium channels, having a low affinity for the rested/closed state and a high affinity for the inactivated state. These compounds are likely to interact with overlapping sites located in the inner cavity of the sodium conducting pore of the channel similar to that described for other state-dependent sodium channel blockers (Cestèle, S., et al., op. cit.). These compounds may also be likely to interact with sites outside of the inner cavity and have allosteric effects on sodium ion conduction through the channel pore.

Any of these consequences may ultimately be responsible for the overall therapeutic benefit provided by these compounds.

The present invention readily affords many different means for identification of sodium channel modulating agents that are useful as therapeutic agents. Identification of modulators of sodium channel can be assessed using a variety of in vitro and in vivo assays, e.g. measuring current, measuring membrane potential, measuring ion flux, (e.g. sodium or guanidinium), measuring sodium concentration, measuring second messengers and transcription levels, and using e.g., voltage-sensitive dyes, radioactive tracers, and patch=clamp electrophysiology.

One such protocol involves the screening of chemical agents for ability to modulate the activity of a sodium channel thereby identifying it as a modulating agent.

A typical assay described in Bean et al., *J. General Physiology* (1983), 83:613-642, and Leuwer, M., et al., *Br. J. Pharmacol* (2004), 141(1):47-54, uses patch-clamp techniques to study the behaviour of channels. Such techniques are known to those skilled in the art, and may be developed, using current technologies, into low or medium throughput assays for evaluating compounds for their ability to modulate sodium channel behaviour.

A competitive binding assay with known sodium channel toxins such as tetrodotoxin, alpha-scorpion toxins, aconitine, BTX and the like, may be suitable for identifying potential therapeutic agents with high selectivity for a particular sodium channel. The use of BTX in such a binding assay is well known and is described in McNeal, E. T., et al., *J. Med. Chem.* (1985), 28(3):381-8; and Creveling, C. R., et al., *Methods in Neuroscience, Vol.* 8: *Neurotoxins* (Conn PM Ed) (1992), pp. 25-37, Academic Press, New York.

These assays can be carried out in cells, or cell or tissue extracts expressing the channel of interest in a natural endogenous setting or in a recombinant setting. The assays that can be used include plate assays which measure Na+ influx through surrogate markers such as $^{14}$C-guanidine influx or determine cell depolarization using fluorescent dyes such as the FRET based and other fluorescent assays or a radiolabelled binding assay employing radiolabelled aconitine, BTX, TTX or STX. More direct measurements can be made with manual or automated electrophysiology systems. The guanidine influx assay is explained in more detail below in the Biological Assays section.

Throughput of test compounds is an important consideration in the choice of screening assay to be used. In some strategies, where hundreds of thousands of compounds are to be tested, it is not desirable to use low throughput means. In other cases, however, low throughput is satisfactory to identify important differences between a limited number of compounds. Often it will be necessary to combine assay types to identify specific sodium channel modulating compounds.

Electrophysiological assays using patch clamp techniques is accepted as a gold standard for detailed characterization of sodium channel compound interactions, and as described in Bean et al., op. cit. and Leuwer, M., et al., op. cit. There is a manual low-throughput screening (LTS) method which can compare 2-10 compounds per day; a recently developed system for automated medium-throughput screening (MTS) at 20-50 patches (i.e. compounds) per day; and a technology from Molecular Devices Corporation (Sunnyvale, Calif.) which permits automated high-throughput screening (HTS) at 1000-3000 patches (i.e. compounds) per day.

One automated patch-clamp system utilizes planar electrode technology to accelerate the rate of drug discovery. Planar electrodes are capable of achieving high-resistance, cells-attached seals followed by stable, low-noise whole-cell recordings that are comparable to conventional recordings. A suitable instrument is the PatchXpress 7000A (Axon Instruments Inc, Union City, Calif.). A variety of cell lines and culture techniques, which include adherent cells as well as cells growing spontaneously in suspension are ranked for seal success rate and stability. Immortalized cells (e.g. HEK and CHO) stably expressing high levels of the relevant sodium ion channel can be adapted into high-density suspension cultures.

Other assays can be selected which allow the investigator to identify compounds which block specific states of the channel, such as the open state, closed state or the resting state, or which block transition from open to closed, closed to resting or resting to open. Those skilled in the art are generally familiar with such assays.

Binding assays are also available, however these are of only limited functional value and information content. Designs include traditional radioactive filter based binding assays or the confocal based fluorescent system available from Evotec OAI group of companies (Hamburg, Germany), both of which are HTS.

Radioactive flux assays can also be used. In this assay, channels are stimulated to open with veratridine or aconitine and held in a stabilized open state with a toxin, and channel blockers are identified by their ability to prevent ion influx. The assay can use radioactive $^{22}$[Na] and $^{14}$[C] guanidinium ions as tracers. FlashPlate & Cytostar-T plates in living cells avoids separation steps and are suitable for HTS. Scintillation plate technology has also advanced this method to HTS suitability. Because of the functional aspects of the assay, the information content is reasonably good.

Yet another format measures the redistribution of membrane potential using the FLIPR system membrane potential kit (HTS) available from Molecular Dynamics (a division of Amersham Biosciences, Piscataway, N.J.). This method is limited to slow membrane potential changes. Some problems may result from the fluorescent background of compounds. Test compounds may also directly influence the fluidity of the cell membrane and lead to an increase in intracellular dye concentrations. Still, because of the functional aspects of the assay, the information content is reasonably good.

Sodium dyes can be used to measure the rate or amount of sodium ion influx through a channel. This type of assay provides a very high information content regarding potential channel blockers. The assay is functional and would measure Na+ influx directly. CoroNa Red, SBFI and/or sodium green (Molecular Probes, Inc. Eugene Oreg.) can be used to measure Na influx; all are Na responsive dyes. They can be used in combination with the FLIPR instrument. The use of these dyes in a screen has not been previously described in the literature. Calcium dyes may also have potential in this format.

In another assay, FRET based voltage sensors are used to measure the ability of a test compound to directly block Na influx. Commercially available HTS systems include the VIPR™ II FRET system (Aurora Biosciences Corporation, San Diego, Calif., a division of Vertex Pharmaceuticals, Inc.) which may be used in conjunction with FRET dyes, also available from Aurora Biosciences. This assay measures sub-second responses to voltage changes. There is no requirement for a modifier of channel function. The assay measures depolarization and hyperpolarizations, and provides ratiometric outputs for quantification. A somewhat less expensive MTS version of this assay employs the FLEXstation™ (Molecular Devices Corporation) in conjunction with FRET dyes from Aurora Biosciences. Other methods of testing the compounds disclosed herein are also readily known and available to those skilled in the art.

These results provide the basis for analysis of the structure-activity relationship (SAR) between test compounds and the sodium channel. Certain substituents on the core structure of the test compound tend to provide more potent inhibitory compounds. SAR analysis is one of the tools those skilled in the art may now employ to identify preferred embodiments of the compounds of the invention for use as therapeutic agents.

Modulating agents so identified are then tested in a variety of in vivo models so as to determine if they alleviate pain, especially chronic pain or other conditions such as arrhythmias and epilepsy with minimal adverse events. The assays described below in the Biological Assays Section are useful in assessing the biological activity of the instant compounds.

Typically, a successful therapeutic agent of the present invention will meet some or all of the following criteria. Oral availability should be at or above 20%. Animal model efficacy is less than about 0.1 μg to about 100 mg/Kg body weight and the target human dose is between 0.1 μg to about 100 mg/Kg body weight, although doses outside of this range may be acceptable ("mg/Kg" means milligrams of compound per kilogram of body mass of the subject to whom it is being administered). The therapeutic index (or ratio of toxic dose to therapeutic dose) should be greater than 100. The potency (as expressed by $IC_{50}$ value) should be less than 10 μM, preferably below 1 μM and most preferably below 50 nM. The $IC_{50}$ ("Inhibitory Concentration—50%") is a measure of the amount of compound required to achieve 50% inhibition of ion flux through a sodium channel, over a specific time period, in an assay of the invention. Compounds of the present invention in the guanidine influx assay have demonstrated IC-50s ranging from less than a nanomolar to less than 10 micromolar.

In an alternative use of the invention, the compounds of the invention can be used in in vitro or in vivo studies as exemplary agents for comparative purposes to find other compounds also useful in treatment of, or protection from, the various diseases disclosed herein.

Another aspect of the invention relates to inhibiting $Na_v1.1$, $Na_v1.2$, $Na_v1.3$, $Na_v1.4$, $Na_v1.5$, $Na_v1.6$, $Na_v1.7$, $Na_v1.8$, or $Na_v1.9$ activity in a biological sample or a patient, which method comprises administering to the patient, or contacting said biological sample with a compound of formula I or a composition comprising said compound. The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition of $Na_v1.1$, $Na_v1.2$, $Na_v1.3$, $Na_v1.4$, $Na_v1.5$, $Na_v1.6$, $Na_v1.7$, $Na_v1.8$, or $Na_v1.9$ activity in a biological sample is useful for a variety of purposes that are known to one of skill in the art. Examples of such purposes include, but are not limited to, the study of sodium ion channels in biological and pathological phenomena; and the comparative evaluation of new sodium ion channel inhibitors.

Pharmaceutical Compositions of the Invention and Administration

The present invention also relates to pharmaceutical composition containing the compounds of the invention disclosed herein. In one embodiment, the present invention relates to a composition comprising compounds of the invention in a pharmaceutically acceptable carrier and in an amount effective to modulate, preferably inhibit, ion flux through a voltage-dependent sodium channel to treat sodium channel mediated diseases, such as pain, when administered to an animal, preferably a mammal, most preferably a human patient.

The pharmaceutical compositions useful herein also contain a pharmaceutically acceptable carrier, including any suitable diluent or excipient, which includes any pharmaceutical agent that does not itself induce the production of antibodies harmful to the individual receiving the composition, and which may be administered without undue toxicity. Pharmaceutically acceptable carriers include, but are not limited to, liquids, such as water, saline, glycerol and ethanol, and the like. A thorough discussion of pharmaceutically acceptable carriers, diluents, and other excipients is presented in REMINGTON'S PHARMACEUTICAL SCIENCES (Mack Pub. Co., N.J. current edition).

Those skilled in the art know how to determine suitable doses of the compounds for use in treating the diseases and conditions contemplated herein. Therapeutic doses are generally identified through a dose ranging study in humans based on preliminary evidence derived from animal studies. Doses must be sufficient to result in a desired therapeutic benefit without causing unwanted side effects for the patient.

A typical regimen for treatment of sodium channel-mediated disease comprises administration of an effective amount over a period of one or several days, up to and including between one week and about six months, or it may be chronic. It is understood that the dosage of a diagnostic/pharmaceutical compound or composition of the invention administered in vivo or in vitro will be dependent upon the age, sex, health, and weight of the recipient, severity of the symptoms, kind of concurrent treatment, if any, frequency of treatment, the response of the individual, and the nature of the diagnostic/pharmaceutical effect desired. The ranges of effective doses provided herein are not intended to be limiting and represent preferred dose ranges. However, the most preferred dosage will be tailored to the individual subject, as is understood and determinable by one skilled in the relevant arts. (see, e.g., Berkow et al., eds., The Merck Manual, $16^{th}$ edition, Merck and Co., Rahway, N. J., 1992; Goodmanetna., eds., Goodman and Cilman's The Pharmacological Basis of Therapeutics, $10^{th}$ edition, Pergamon Press, Inc., Elmsford, N.Y., (2001); Avery's Drug Treatment: Principles and Practice of Clinical Pharmacology and Therapeutics, 3rd edition, ADIS Press, LTD., Williams and Wilkins, Baltimore, Md. (1987), Ebadi, Pharmacology, Little, Brown and Co., Boston, (1985); Osolci al., eds., Remington's Pharmaceutical Sciences, $18^{th}$ edition, Mack Publishing Co., Easton, Pa. (1990); Katzung, Basic and Clinical Pharmacology, Appleton and Lange, Norwalk, Conn. (1992)).

The total dose required for each treatment can be administered by multiple doses or in a single dose over the course of the day, if desired. Generally, treatment is initiated with smaller dosages, which are less than the optimum dose of the compound. Thereafter, the dosage is increased by small increments until the optimum effect under the circumstances is reached. The diagnostic pharmaceutical compound or composition can be administered alone or in conjunction with other diagnostics and/or pharmaceuticals directed to the pathology, or directed to other symptoms of the pathology. Effective amounts of a diagnostic pharmaceutical compound or composition of the invention are from about 0.1 μg to about 100 mg/Kg body weight, administered at intervals of 4-72 hours, for a period of 2 hours to 1 year, and/or any range or value therein, such as 0.0001-0.001, 0.001-0.01, 0.01-0.1, 0.1-1.0,1.0-10, 5-10, 10-20, 20-50 and 50-100 mg/Kg, at intervals of 1-4, 4-10, 10-16, 16-24, 24-36, 24-36, 36-48, 48-72 hours, for a period of 1-14, 14-28, or 30-44 days, or 1-24 weeks, or any range or value therein. The recipients of administration of compounds and/or compositions of the invention can be any vertebrate animal, such as mammals. Among mammals, the preferred recipients are mammals of the Orders Primate (including humans, apes and monkeys), Arteriodactyla (including horses, goats, cows, sheep, pigs), Rodenta (including mice, rats, rabbits, and hamsters), and Carnivora (including cats, and dogs). Among birds, the preferred recipients are turkeys, chickens and other members of the same order. The most preferred recipients are humans.

For topical applications, it is preferred to administer an effective amount of a pharmaceutical composition according to the invention to target area, e.g., skin surfaces, mucous membranes, and the like, which are adjacent to peripheral neurons which are to be treated. This amount will generally range from about 0.0001 mg to about 1 g of a compound of the invention per application, depending upon the area to be treated, whether the use is diagnostic, prophylactic or therapeutic, the severity of the symptoms, and the nature of the topical vehicle employed. A preferred topical preparation is an ointment, wherein about 0.001 to about 50 mg of active ingredient is used per cc of ointment base. The pharmaceutical composition can be be formulated as transdermal compositions or transdermal delivery devices ("patches"). Such compositions include, for example, a backing, active compound reservoir, a control membrane, liner and contact adhesive. Such transdermal patches may be used to provide continuous pulsatile, or on demand delivery of the compounds of the present invention as desired.

The composition may be intended for rectal administration, in the form, e.g., of a suppository which will melt in the rectum and release the drug. A typical suppository formulation will generally consist of active ingredient with a binding and/or lubricating agent such as a gelatine or cocoa butter or other low melting vegetable or synthetic wax or fat.

A typical formulation for intramuscular or intrathecal administration will consist of a suspension or solution of active in an oil or solution of active ingredient in an oil, for example arachis oil or seasame oil. A typical formulation for intravenous or intrathecal administration will consist of sterile isotonic aqueous solution containing, for example active ingredient and dextrose or sodium chloride or a mixture of dextrose and sodium chloride.

The compositions of the invention can be formulated so as to provide quick, sustained or delayed release of the active ingredient after administration to the patient by employing procedures known in the art. Controlled release drug delivery systems include osmotic pump systems and dissolutional systems containing polymer-coated reservoirs or drug-polymer matrix formulations. Examples of controlled release systems are given in U.S. Pat. Nos. 3,845,770 and 4,326,525 and in P. J. Kuzma et al, Regional Anesthesia 22 (6): 543-551 (1997), all of which are incorporated herein by reference.

The compositions of the invention can also be delivered through intra-nasal drug delivery systems for local, systemic, and nose-to-brain medical therapies. Controlled Particle Dispersion (CPD)™ technology, traditional nasal spray bottles, inhalers or nebulizers are known by those skilled in the art to provide effective local and systemic delivery of drugs by targeting the olfactory region and paranasal sinuses.

The invention also relates to an intravaginal shell or core drug delivery device suitable for administration to the human or animal female. The device may be comprised of the active pharmaceutical ingredient in a polymer matrix, surrounded by a sheath, and capable of releasing the compound in a substantially zero order pattern on a daily basis similar to devises used to apply testosterone as described in PCT Patent No. WO 98/50016.

Current methods for ocular delivery include topical administration (eye drops), subconjunctival injections, periocular injections, intravitreal injections, surgical implants and iontophoresis (uses a small electrical current to transport ionized drugs into and through body tissues) Those skilled in the art would combine the best suited excipients with the compound for safe and effective intra-occular administration.

The most suitable route will depend on the nature and severity of the condition being treated. Those skilled in the art are also familiar with determining administration methods (oral, intravenous, inhalation, sub-cutaneous, rectal etc.), dosage forms, suitable pharmaceutical excipients and other matters relevant to the delivery of the compounds to a subject in need thereof.

Combination Therapy

The compounds of the invention may be usefully combined with one or more other compounds of the invention or one or more other therapeutic agent or as any combination thereof, in the treatment of sodium channel-mediated diseases and conditions. For example, a compound of formula (I) may be administered simultaneously, sequentially or separately in combination with other therapeutic agents, including, but not limited to:

opiates analgesics, e.g. morphine, heroin, cocaine, oxymorphine, levorphanol, levallorphan, oxycodone, codeine, dihydrocodeine, propoxyphene, nalmefene, fentanyl, hydrocodone, hydromorphone, meripidine, methadone, nalorphine, naloxone, naltrexone, buprenorphine, butorphanol, nalbuphine and pentazocine;

non-opiate analgesics, e.g. acetaminophen, salicylates (e.g. aspirin);

nonsteroidal antiinflammatory drugs (NSAIDs), e.g. ibuprofen, naproxen, fenoprofen, ketoprofen, celecoxib, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac;

anticonvulsants, e.g. carbamazepine, oxcarbazepine, lamotrigine, valproate, topiramate, gabapentin and pregabalin;

antidepressants such as tricyclic antidepressants, e.g. amitriptyline, clomipramine, despramine, imipramine and nortriptyline;

COX-2 selective inhibitors, e.g. celecoxib, rofecoxib, parecoxib, valdecoxib, deracoxib, etoricoxib, and lumiracoxib;

alpha-adrenergics, e.g. doxazosin, tamsulosin, clonidine, guanfacine, dexmetatomidine, modafinil, and 4-amino-6,7-dimethoxy-2-(5-methane sulfonamido-1,2,3,4-tetrahydroisoquinol-2-yl)-5-(2-pyridyl)quinazoline;

barbiturate sedatives, e.g. amobarbital, aprobarbital, butabarbital, butabital, mephobarbital, metharbital, methohexital, pentobarbital, phenobartital, secobarbital, talbutal, theamylal and thiopental;

tachykinin (NK) antagonist, particularly an NK-3, NK-2 or NK-1 antagonist, e.g. (αR,9R)-7-[3,5-bis(trifluoromethyl)benzyl)]-8,9,10,11-tetrahydro-9-methyl-5-(4-methylphenyl)-7H-[1,4]diazocino[2,1-g][1,7]-naphthyridine-6-13-dione (TAK-637), 5-[[2R,3S)-2-[(1R)-1-[3,5-bis(trifluoromethylphenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy5-(trifluoromethoxy)phenyl]-methylamino]-2-phenylpiperidine (2S,3S);

coal-tar analgesics, in particular paracetamol;

serotonin reuptake inhibitors, e.g. paroxetine, sertraline, norfluoxetine (fluoxetine desmethyl metabolite), metabolite demethylsertraline, '3 fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine, trazodone and fluoxetine;

noradrenaline (norepinephrine) reuptake inhibitors, e.g. maprotiline, lofepramine, mirtazepine, oxaprotiline, fezolamine, tomoxetine, mianserin, buprorion, buprorion metabolite hydroxybuprorion, nomifensine and viloxazine (Vivalan®)), especially a selective noradrenaline reuptake inhibitor such as reboxetine, in particular (S,S)-reboxetine, and venlafaxine duloxetine neuroleptics sedative/anxiolytics;

dual serotonin-noradrenaline reuptake inhibitors, such as venlafaxine, venlafaxine metabolite O-desmethylvenlafaxine, clomipramine, clomipramine metabolite desmethylclomipramine, duloxetine, milnacipran and imipramine;

acetylcholinesterase inhibitors such as donepezil;

5-HT3 antagonists such as ondansetron;

metabotropic glutamate receptor (mGluR) antagonists;

local anaesthetic such as mexiletine and lidocaine;

corticosteroid such as dexamethasone;

antiarrhythimics, e.g. mexiletine and phenytoin;

muscarinic antagonists, e.g., tolterodine, propiverine, tropsium t chloride, darifenacin, solifenacin, temiverine and ipratropium;

cannabinoids;

vanilloid receptor agonists (e.g. resinferatoxin) or antagonists (e.g. capsazepine);

sedatives, e.g. glutethimide, meprobamate, methaqualone, and dichloralphenazone;

anxiolytics such as benzodiazepines, antidepressants such as mirtazapine, topical agents (e.g. lidocaine, capsacin and resiniferotoxin);

muscle relaxants such as benzodiazepines, baclofen, carisoprodol, chlorzoxazone, cyclobenzaprine, methocarbamol and orphrenadine;

anti-histamines or H1 antagonists;

NMDA receptor antagonists;

5-HT receptor agonists/antagonists;

PDEV inhibitors;

Tramadol®;

cholinergic (nicotine) analgesics;

alpha-2-delta ligands;

prostaglandin E2 subtype antagonists;

leukotriene B4 antagonists; and 5-lipoxygenase inhibitors.

Sodium channel-mediated diseases and conditions that may be treated and/or prevented using such combinations include but not limited to, pain, central and peripherally mediated, acute, chronic, neuropathic as well as other diseases with associated pain and other central nervous disorders such as epilepsy, anxiety, depression and bipolar disease; or cardiovascular disorders such as arrhythmias, atrial fibrillation and ventricular fibrillation; neuromuscular disorders such as restless leg syndrome and muscle paralysis or tetanus; neuroprotection against stroke, neural trauma and multiple sclerosis; and channelopathies such as erythromyalgia and familial rectal pain syndrome.

As used herein "combination" refers to any mixture or permutation of one or more compounds of the invention and one or more other compounds of the invention or one or more additional therapeutic agent. Unless the context makes clear otherwise, "combination" may include simultaneous or sequentially delivery of a compound of the invention with one or more therapeutic agents. Unless the context makes clear otherwise, "combination" may include dosage forms of a compound of the invention with another therapeutic agent. Unless the context makes clear otherwise, "combination" may include routes of administration of a compound of the invention with another therapeutic agent. Unless the context makes clear otherwise, "combination" may include formulations of a compound of the invention with another therapeutic agent. Dosage forms, routes of administration and pharmaceutical compositions include, but are not limited to, those described herein.

Kits-of-Parts

The present invention also provides kits that contain a pharmaceutical composition which includes one or more compounds of the above formulae. The kit also includes instructions for the use of the pharmaceutical composition for modulating the activity of ion channels, for the treatment of pain, as well as other utilities as disclosed herein. Preferably, a commercial package will contain one or more unit doses of the pharmaceutical composition. For example, such a unit dose may be an amount sufficient for the preparation of an intravenous injection. It will be evident to those of ordinary skill in the art that compounds which are light and/or air sensitive may require special packaging and/or formulation. For example, packaging may be used which is opaque to light, and/or sealed from contact with ambient air, and/or formulated with suitable coatings or excipients.

PREPARATION OF THE COMPOUNDS OF THE INVENTION

The following Reaction Schemes illustrate methods to make compounds of this invention, i.e., compounds of formula (I):

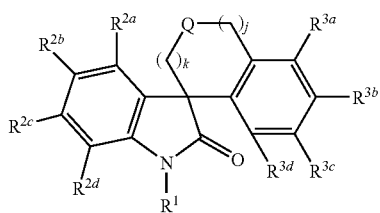

(I)

wherein k, j, Q, $R^1$, $R^{2a}$, $R^{2b}$, $R^{2c}$, $R^{2d}$, $R^{3a}$, $R^{3b}$, $R^{3c}$, and $R^{3d}$ are as defined herein, as a stereoisomer, enantiomer, tautomer thereof or mixtures thereof; or a pharmaceutically acceptable salt, solvate or prodrug thereof.

It is understood that in the following description, combinations of substituents and/or variables of the depicted formulae are permissible only if such contributions result in stable compounds.

It will also be appreciated by those skilled in the art that in the process described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters.

Protecting groups may be added or removed in accordance with standard techniques, which are known to one skilled in the art and as described herein.

The use of protecting groups is described in detail in Greene, T. W. and P. G. M. Wuts, *Protective Groups in Organic Synthesis* (1999), 3rd Ed., Wiley. The protecting group may also be a polymer resin such as a Wang resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

The following Reaction Schemes illustrate methods to make compounds of this invention. It is understood that one skilled in the art would be able to make these compounds by similar methods or by methods known to one skilled in the art. It is also understood that one skilled in the art would be able to make in a similar manner as described below other compounds of formula (I) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, e.g., Smith, M. B. and J. March, *Advanced Organic Chemistry: Reactions*, Mechanisms, and Structure, 5th edition (Wiley, December 2000)) or prepared as described herein.

In the following Reaction Schemes, $R^1$, $R^{2a}$, $R^{2b}$, $R^{2c}$, $R^{2d}$, $R^{3a}$, $R^{3b}$, $R^{3c}$ and $R^{3d}$ are defined as in the Specification unless specifically defined otherwise. X is Cl or Br. $R^{11}$ is an alkyl group.

In general, the compounds of formula (I) of the invention where Q is —O—, j is 0 and k is 1 can be synthesized following the general procedure as described below in REACTION SCHEME 1. As set forth below, an isatin compound of formula (101) is alkylated with the chloro or bromo compound of formula (102) to afford the product of formula (103). The phenol compound of formula (104) is treated with a Grignard reagent of formula (105) at low temperature (0° C.) to form the phenoxymagnesium halide intermediate which reacts with the keto-carbonyl group of the isatin compound of formula (103) in a solvent, such as, but not limited to, methylene chloride or toluene, to afford the oxindole of formula (106). The compound of formula (107) is obtained after the removal of the hydroxyl group at C-3 position of the oxindole by treating the compound of formula (106) with silane such as triethylsilane. The compound of formula (107)

can also be achieved by treating the compound of formula (106) with SOCl$_2$/NEt$_3$ then reduction with Zn dust. Compound of formula (107) is treated with a silyl compound, such as, but not limited to, trimethylsilyl chloride, to generate the silyl ether intermediate which is treated with ytterbium (III) trifluoromethanesulfonate and formaldehyde to afford the compound of formula (108). Alternatively, compound of formula (108) can be obtained by treating the compound of formula (107) with a base, such as, but not limited to, LiOH, iPr$_2$NH, LDA, and subsequently reacting with formaldehyde. Intramolecular cyclization via Mitsunobu reaction affords the compound of formula (I) of the invention where Q is —O—, j is 0 and k is 1.

REACTION SCHEME 1

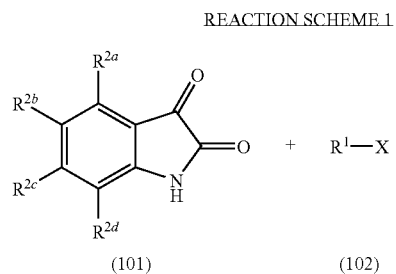

(101)  (102)

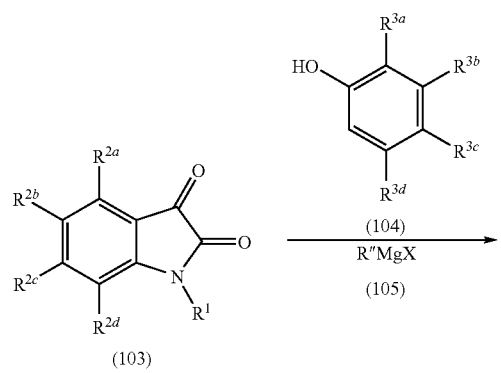

(103)  (104)/R″MgX (105)

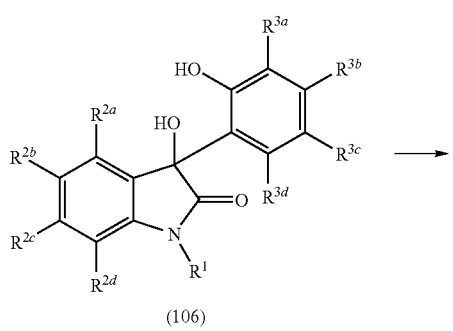

(106)

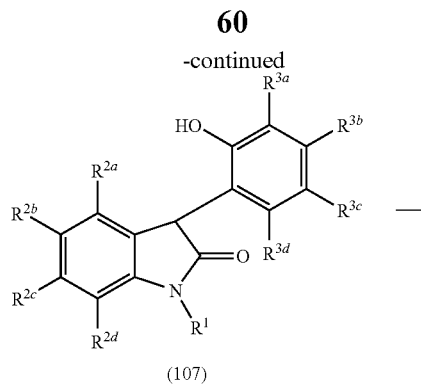

(107)

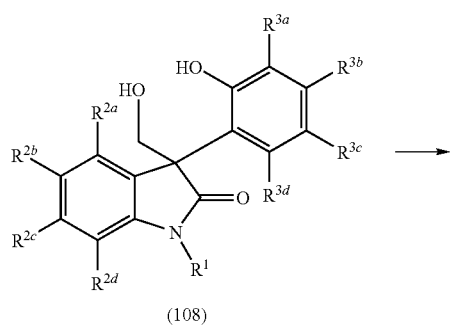

(108)

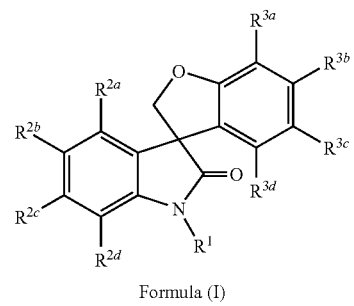

Formula (I)

REACTION SCHEME 1.1 below illustrates a schematic synthesis of amide and heterocyclic compounds as compounds of formula (I). When R$^1$ consists of an ester group, a compound such as a compound of formula (109) (in which A is alkyl or aralkyl) can be converted to the corresponding carboxylic acid compound of formula (110) by treatment of a compound of formula (109) with a base such as, but not limited to, lithium hydroxide, sodium hydroxide or potassium hydroxide, in a mixed solvent such as, but not limited to, tetrahydrofuran or methanol with water. The acid compound of formula (110) can be converted to a mixed anhydride, by treatment with iso-butyl chloroformate in the presence of a base such as, but not limited to, N-methylmorpholine, or to the corresponding acid chloride, by treatment with oxalyl chloride in the presence of catalytic amount of N,N-dimethylformamide in a solvent such as, but not limited to, toluene, dichloromethane or chloroform. The mixed anhydride can react directly with, or the acid chloride can react with, in the presence of a base such as, but not limited to, triethylamine or diisopropyl ethylamine, a primary or secondary amine to form the amide compound of formula (111) as a compound of formula (I). The acid compound of formula (110) can react with an aromatic diamine compound in a solvent such as, but not limited to, toluene to form the benzimidazole compound of formula (111.1) as a compound of formula (I).

REACTION SCHEME 1.1

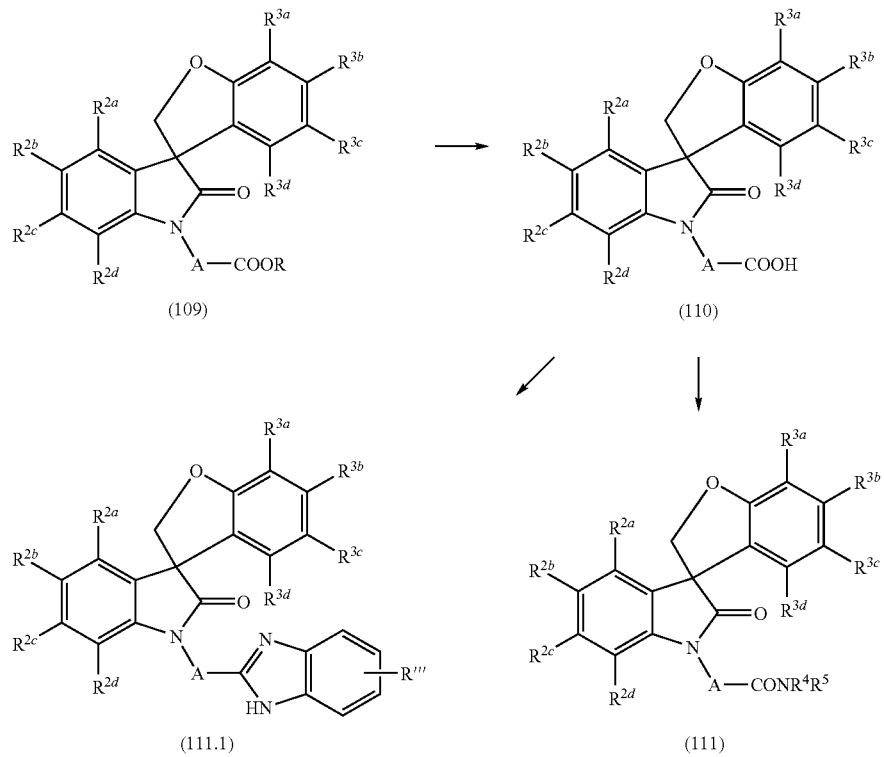

REACTION SCHEME 1.2 below illustrates a schematic synthesis of amine compounds as compounds of formula (I). From compound (112), after removal of the protecting group (PG) such as, but not limited to, phthalimido or tert-butyloxycarbonyl, either the primary or secondary amino compound of formula (113) can be formed. Reaction of the amino compound of formula (113) with an acyl chloride in the presence of a base such as, but not limited to, triethylamine or diisopropyl ethylamine, in a solvent such as, but not limited to, toluene, dichloromethane or chloroform provides the amide compound of formula (114) as a compound of formula (I). Treatment of amino compound of formula (113) with an isocyanate in the presence of a base such as, but not limited to, triethylamine or diisopropyl ethylamine, in a solvent such as, but not limited to, dichloromethane or chloroform leads to the formation of the urea compound of formula (115) as a compound of formula (I). When the primary or secondary amino compound of formula (113) is treated with an aldehyde or a ketone in the presence of a reducing agent such as, but not limited to, sodium cyanoborohydride or sodium triacetoxyborohydride, in a solvent such as, but not limited to, dichloromethane, a high order functionalized amine (116) is produced as a compound of formula (I).

REACTION SCHEME 1.2

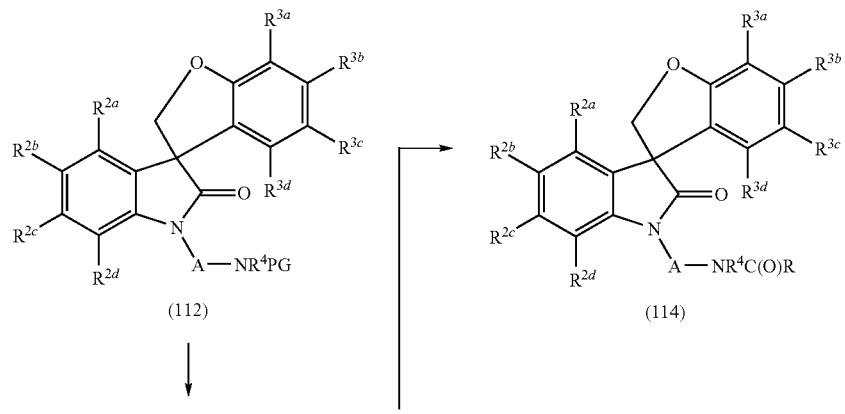

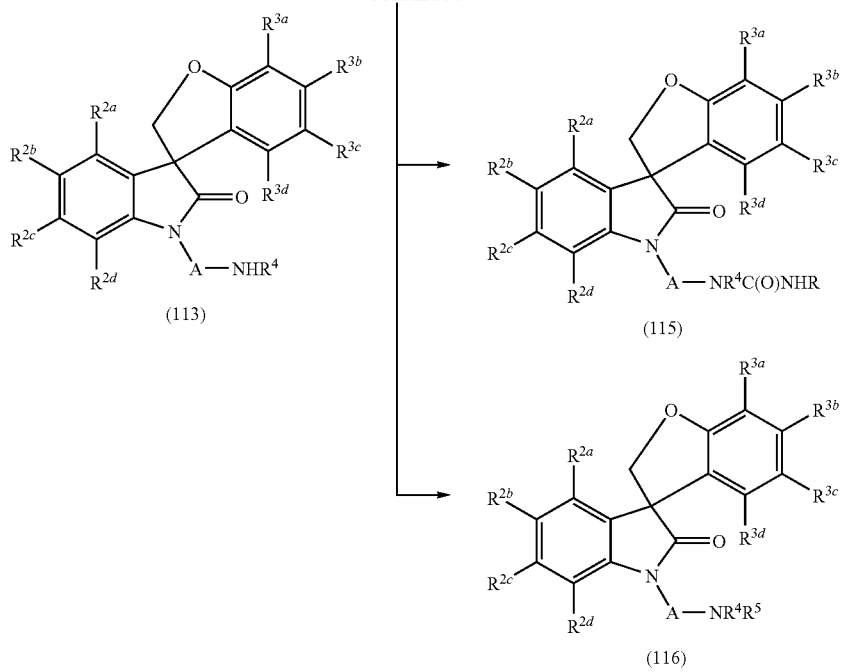

REACTION SCHEME 1.3 below illustrates a schematic synthesis of amine compounds as compounds of formula (I). The alcohol compound of formula (118), upon removal of the protecting group in compound of formula (117), can be oxidized to the aldehyde compound of (119) by using an oxidant such as, but not limited to, pyridinium dichromate or Dess-Martin's reagent. Similarly to the transformation of the compound of formula (113) to the compound of formula (116) as illustrated in REACTION SCHEME 1.2, the amine compound of formula (120) can be obtained as a compound of formula (I) through the reductive amination of the aldehyde compound of formula (119) with a primary or secondary amine.

REACTION SCHEME 1.3

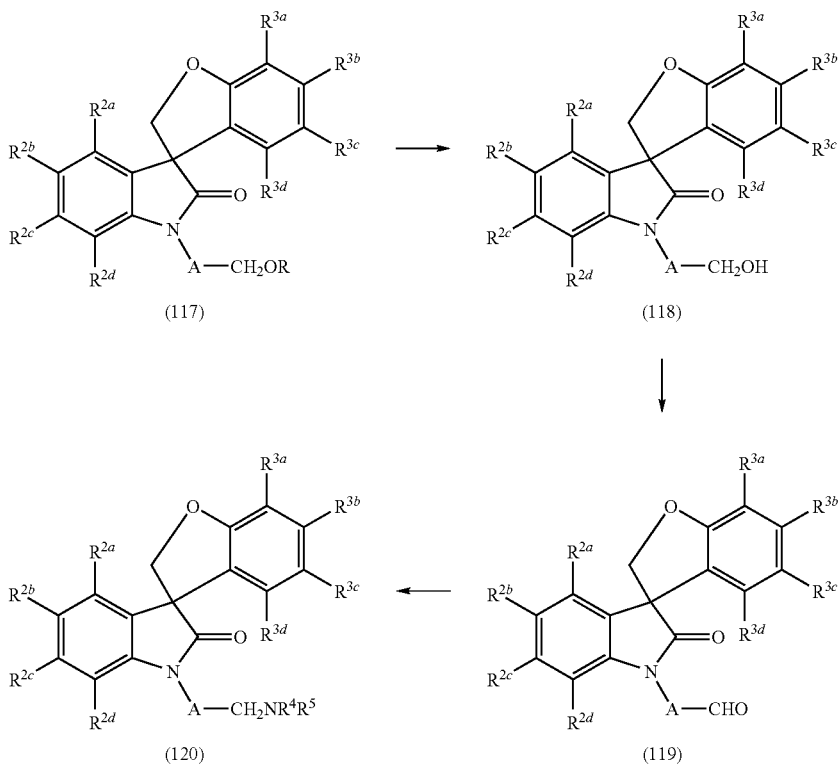

REACTION SCHEME 1.4 below illustrates an alternative synthesis of compounds of formula (I) with the introduction of a variety of $R^1$ groups. Compound of formula (121) where PG is a protecting group such as, but not limited to, diphenylmethyl, can be synthesized through the sequence as shown in REACTION SCHEME 1 above. The protecting group can be removed under a high pressure of hydrogen such as 60 psi to form the oxindole compound of formula (122). The formation of a compound of formula (I) can be achieved by alkylation of the compound of formula (122) with a halide reagent $XR^1$ (where X is chloro, bromo or iodo) in the presence of a base such as, but not limited to, sodium hydride, sodium bis(trimethylsilyl)amide, and lithium hydroxide, in a solvent such as, but not limited to, N,N-dimethylformamide, tetrahydrofuran, acetone or acetonitrile. Alternatively, reaction of compound of formula (122) with an alcohol under Mitsunobu reaction conditions in the presence of a phosphine reagent such as, but not limited to, triphenylphosphine, tributylphosphine or trimethyl phosphine, and azadicarboxylate of diethyl, diisopropyl or di-tert-butyl in a solvent such as, but not limited to, tetrahydrofuran, ethyl acetate or dichloromethane, provides the compound of formula (I). Alternatively, treatment of compound of formula (122) with a base such as, but not limited to, sodium hydride or lithium hydroxide, followed by reacting with an acyl chloride or anhydride, or with a sulfonyl chloride reagent, provides the corresponding acyl or sulfonyl ($R^1$) compound of formula (I) respectively.

dium catalyst followed by sequential oxidation with hydrogen peroxide/sodium hydroxide and reaction with trifluoromethanesulfonyl anhydride. Compounds of formula (123) or (129) (with either a bromo or a trifluoromethylsulfonyloxy group for $R^{2a}$, $R^{2b}$, $R^{2c}$, $R^{2d}$, $R^{3a}$, $R^{3b}$, $R^{3c}$ or $R^{3d}$) can react with zinc cyanide or tributyltin cyanide and potassium cyanide in the presence of a palladium catalyst such as, but not limited to, palladium acetate or tris(dibenzylideneacetone)dipalladium(0), and a ligand such as, but not limited to, tri(o-olyl)phosphine, 1,1'-bis(diphenylphosphino)ferrocene or 2-(di-tert-butylphosphino)biphenyl in a solvent such as, but not limited to, N,N-dimethylformamide or acetonitrile to provide the cyano compounds of formula (124) or formula (130) as compounds of formula (I) (see Marcantonio, K. M., et al, *Org. Lett.* (2004), 6:3723-5 and Yang, C., et al, *Org. Lett.* (2004), 6:2837-40). Reaction of compounds of formula (123) or formula (129) (with either a bromo or a trifluoromethylsulfonyloxy group for $R^{2a}$, $R^{2b}$, $R^{2c}$, $R^{2d}$, $R^{3a}$, $R^{3b}$, $R^{3c}$ or $R^{3d}$) with a primary or secondary amine in the presence of a palladium catalyst such as, but not limited to, palladium acetate, tetrakis(triphenylphosphine)palladium(0), or tris(dibenzylideneacetone)dipalladium(0), under a pressure of carbon monoxide in a solvent such as, but not limited to, N,N-dimethylformamide or acetonitrile leads to the formation of the amide compound of formula (125) or formula (131) as compounds of formula formula (I) (See Takahashi, T., et al, *Tetrahedron Lett.* (1999), 40:7843-6 and Schnyder, A., et al, *J. Org. Chem.* (2001), 66:4311-5). Under a typical

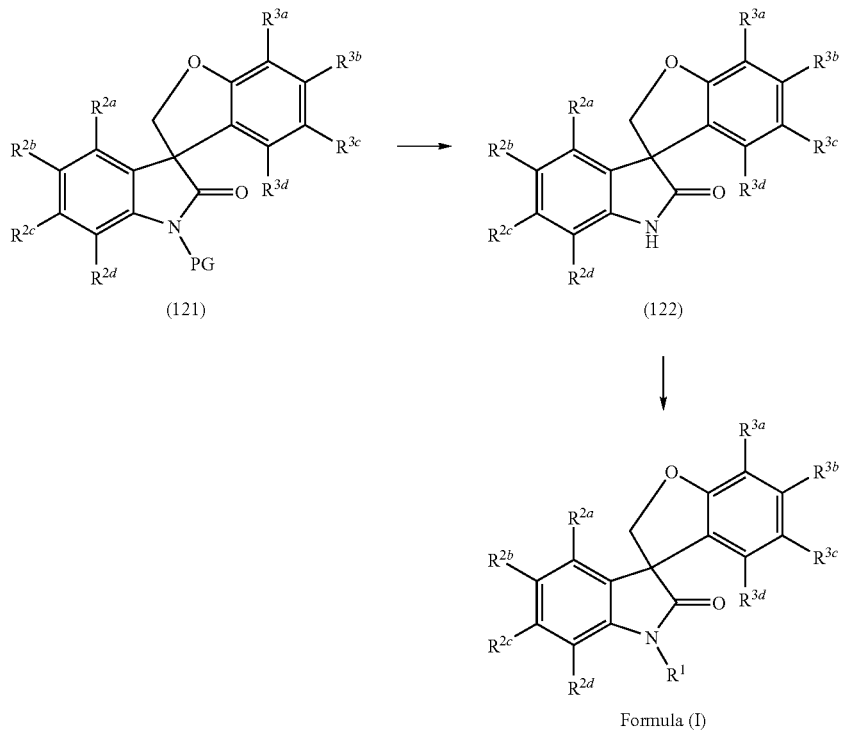

REACTION SCHEME 1.4

Formula (I)

When $R^{2a}$, $R^{2b}$, $R^{2c}$, $R^{2d}$, $R^{3a}$, $R^{3b}$, $R^{3c}$ or $R^{3d}$ of the compound of formula (I) is a bromo or trifluoromethylsulfonyloxy group, further derivatives can be synthesized as shown in REACTION SCHEME 1.5 and REACTION SCHEME 1.6 below. The triflate compound can be obtained by treating the bromo compound with diborane in the presence of a palladium catalyst followed by sequential oxidation with hydrogen peroxide/sodium hydroxide and reaction with trifluoromethanesulfonyl anhydride.

Ullmann coupling reaction conditions, compounds of formula (123) or formula (129) (with either bromo or trifluoromethylsulfonyloxy group for $R^{2a}$, $R^{2b}$, $R^{2c}$, $R^{2d}$, $R^{3a}$, $R^{3b}$, $R^{3c}$ or $R^{3d}$) can react with a phenol compound in the presence of a copper reagent such as, but not limited to, copper iodide or copper bromide, a base such as, but not limited to, cesium carbonate or potassium carbonate, an amino acid such as, but not limited to, N,N-dimethylglycine, in a solvent such as, but not limited to, dimethyl sulfoxide, dioxane or acetonitrile, to form the diaryl ether compounds of formula (126) or formula (132) as compounds of formula (I) (see Sawyer, J. S. *Tetrahedron* (2000), 56:5045-65 and Ma, D., et al, *Org. Lett.* (2003), 5(21):3799-802). Compounds of formula (123) or formula (129) (with either bromo or trifluoromethylsulfonyloxy group for $R^{2a}$, $R^{2b}$, $R^{2c}$, $R^{2d}$, $R^{3a}$, $R^{3b}$, $R^{3c}$ or $R^{3d}$) can react with an arylboronic acid in the presence of a palladium catalyst such as, but not limited to, palladium acetate, tetrakis(triphenylphosphine)palladium(0), or tris(dibenzylideneacetone)dipalladium(0), with or without a ligand such as, but not limited to, triphenylphosphine, tri(o-tolyl)phosphine, 1,1'-bis(diphenylphosphino)ferrocene or 2-(di-tert-butylphosphino)biphenyl, a base such as, but not limited to, sodium carbonate, cesium carbonate, or sodium bicarbonate, in a solvent such as, but not limited to, dimethoxyethane, dioxane, or tetrahydrofuran to provide the coupled product of formula (127) or formula (133) as compounds of formula (I) (see Kotha, S., et al, *Tetrahedron* (2002), 58:9633 and Miyaura, N., et al, *Chem. Rev.* (1995), 95:2457). Compound of formula (123) or formula (129) (with either a bromo or a trifluoromethylsulfonyloxy group for $R^{2a}$, $R^{2b}$, $R^{2c}$, $R^{2d}$, $R^{3a}$, $R^{3b}$, $R^{3c}$ or $R^{3d}$) can react with a primary or secondary amine in the presence of a palladium catalyst such as, but not limited to, tetrakis(triphenylphosphine)palladium(0) or tris(dibenzylideneacetone)dipalladium(0), with or without a ligand such as, but not limited to, triphenylphosphine, tri(o-tolyl) phosphine, 1,1'-bis(diphenylphosphino)ferrocene or 2-(di-tert-butylphosphino)biphenyl, a base such as, but not limited to, sodium carbonate, cesium carbonate or sodium tert-butoxide, in a solvent such as, but not limited to, dioxane or tetrahydrofuran, to provide the amino compound of formula (128) or formula (134) as compounds of formula (I) (see Muci, A. R., et al, *Topics in Current Chemistry* (2002), 219: 131).

REACTION SCHEME 1.5

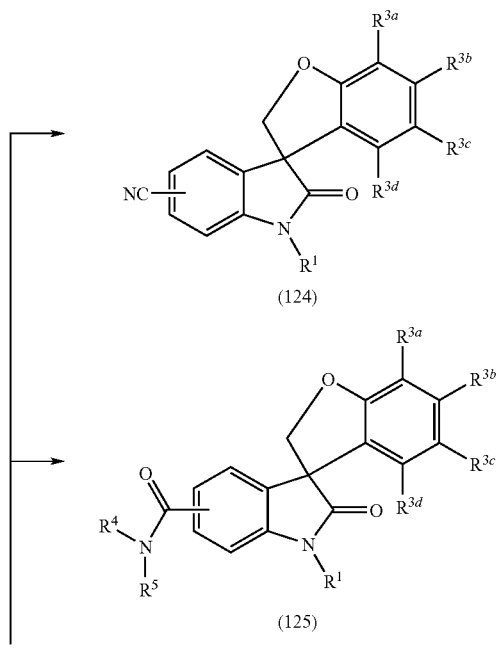

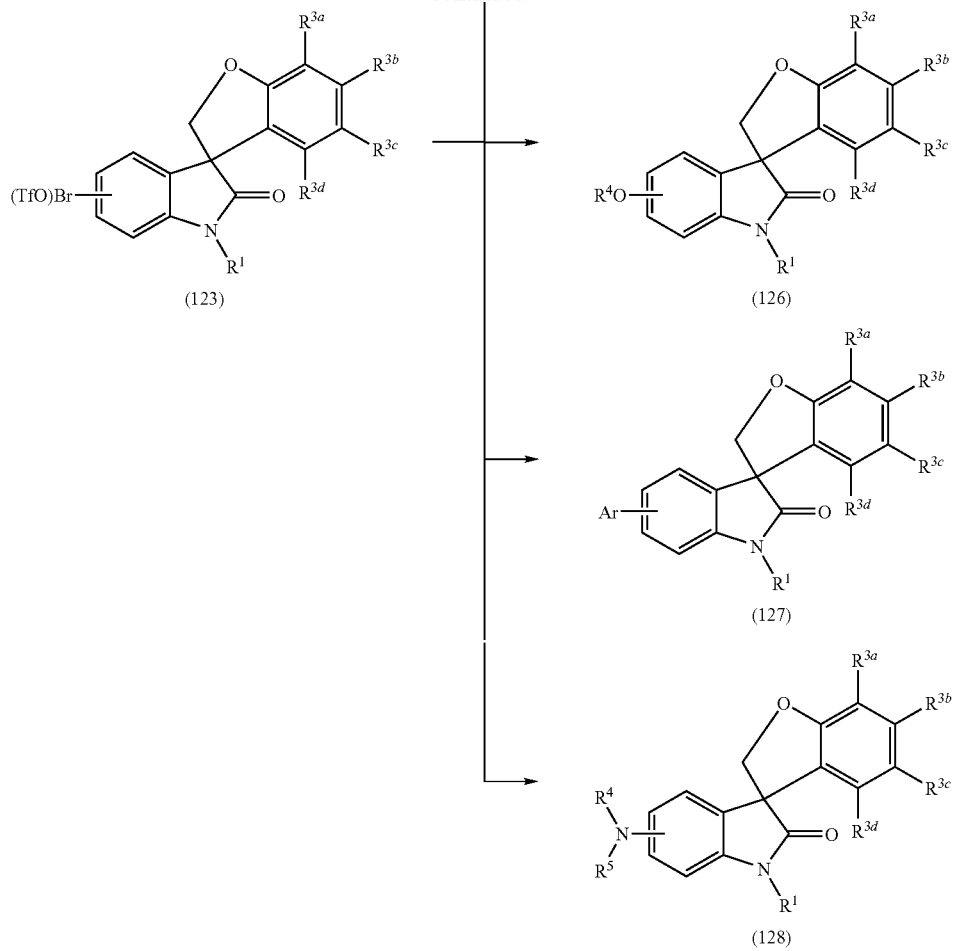
REACTION SCHEME 1.6
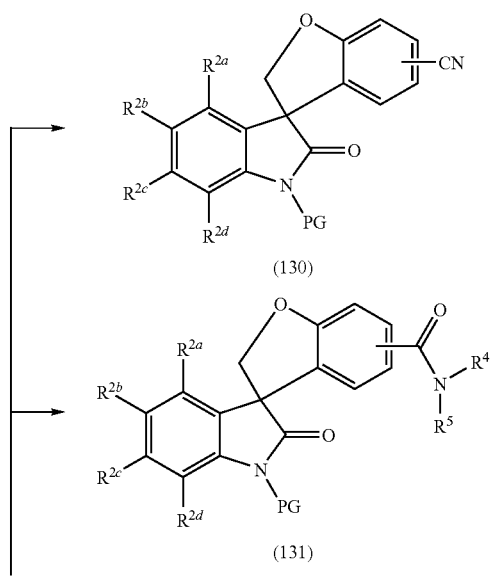

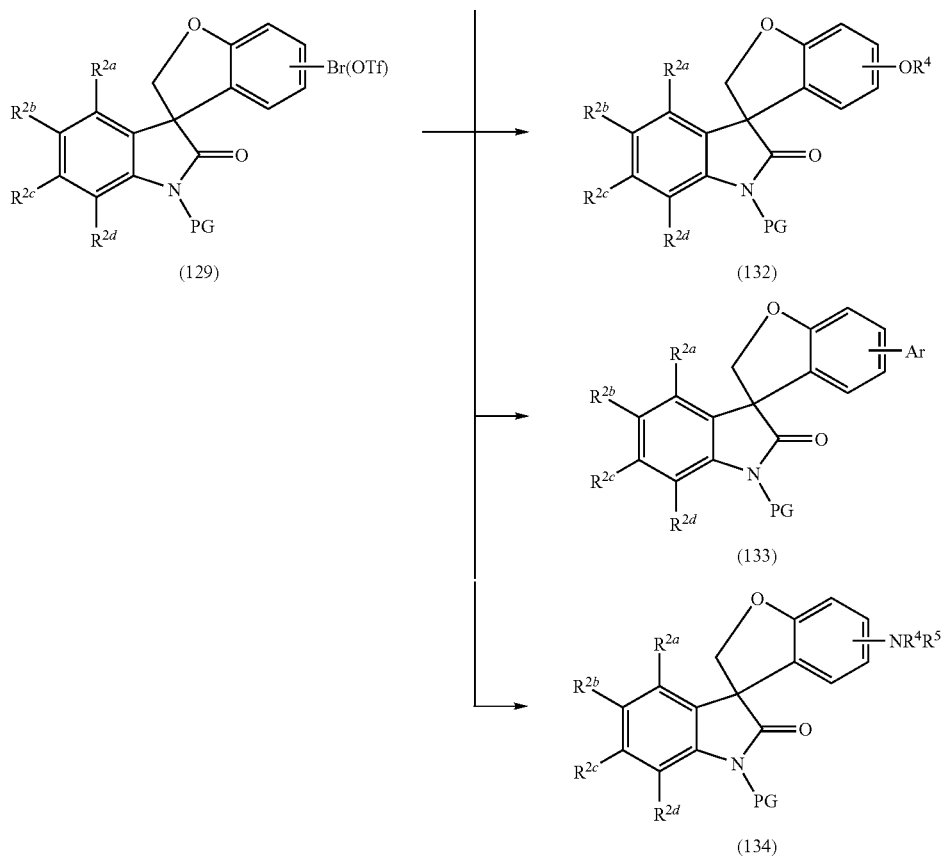

(129) (132) (133) (134)

Alternatively, the compound of formula (I) of the invention where Q is —O— and k is 1 can be synthesized following the general procedure as described below in REACTION SCHEME 2. As set forth below, a compound of formula (201) is treated with a lithium reagent of formula (202), such as, but not limited to, n-BuLi at low temperature followed by the reaction with keto-carbonyl group of the isatin compound of formula (103) in a solvent, such as, but not limited to, THF to afford the oxindole of formula (203). The compound of formula (204) is obtained after the removal of the hydroxyl group at C-3 position of the oxindole by treating the compound of formula (203) with silane such as triethylsilane. The compound of formula (204) can also be achieved by treating the compound of formula (203) with $SOCl_2/NEt_3$ then reduction with Zn dust. Compound of formula (204) is treated with a silyl compound, such as, but not limited to, trimethylsilyl chloride to generate the silyl ether intermediate which is treated with ytterbium (III) trifluoromethanesulfonate and formaldehyde to afford the compound of formula (205). Alternatively, a compound of formula (205) can be obtained by treating the compound of formula (204) with a base, such as, but not limited to, LiOH, $iPr_2NH$, or LDA, and subsequently reacting with formaldehyde. Intramolecular cyclization via Mitsunobu reaction affords the compound of formula (I) of the invention where Q is —O— and k is 1.

REACTION SCHEME 2

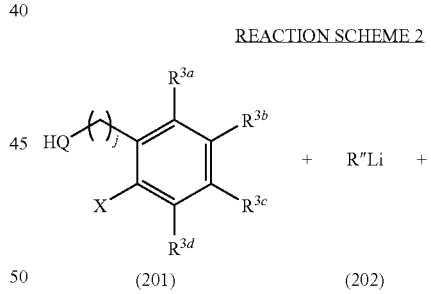

(201)    (202)

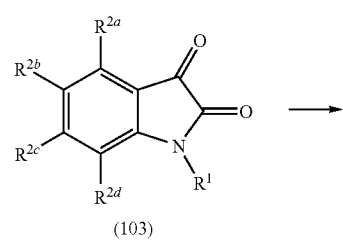

(103)

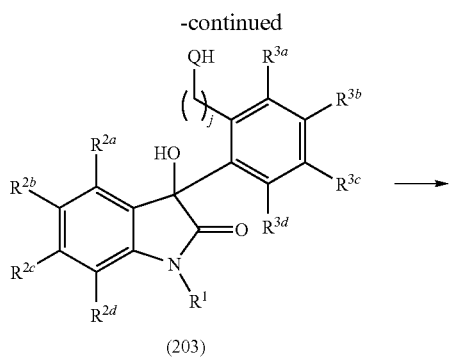

(203)

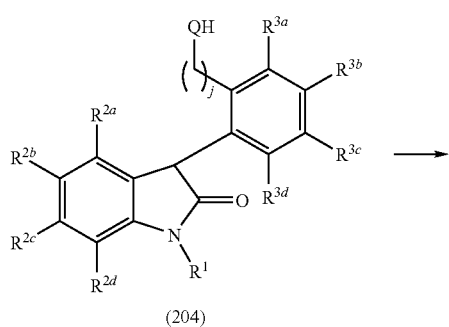

(204)

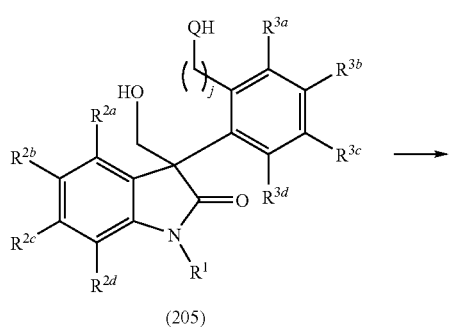

(205)

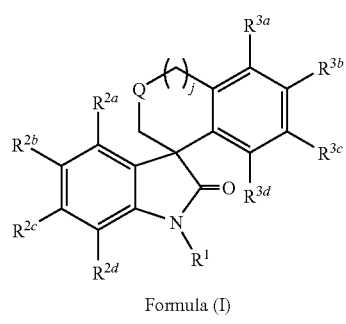

Formula (I)

Alternatively, the compound of formula (I) of the invention where Q is —O— or —S— and k is 0 can be synthesized following the general procedure as described below in REACTION SCHEME 3 wherein intramolecular cyclization of the compound of formula (203) via Mitsunobu reaction affords the compound of formula (I) of the invention where Q is —O— or —S— and k is 0.

REACTION SCHEME 3

(203) →

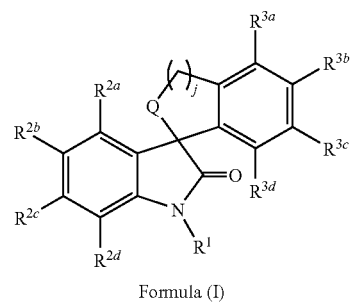

Formula (I)

Alternatively, the compound of formula (I) of the invention where Q is —C(O)—, —(CH$_2$)— or —(CF$_2$)— and j is 0 can be synthesized following the general procedure as described in REACTION SCHEME 4. As set forth below, the Grignard reagent of formula (401) reacts with keto-carbonyl group of the isatin compound of formula (103) in a solvent, such as, but not limited to, methylene chloride or toluene to afford the oxindole of formula (402). The compound of formula (403) is obtained after the removal of the hydroxyl group at C-3 position of the oxindole by treating the compound of formula (402) with silane such as triethylsilane. The compound of formula (403) can also be achieved by treating the compound of formula (402) with SOCl$_2$/NEt$_3$, followed by reduction with Zn dust. Compound of formula (403) is alkylated at C-3 position of oxindole ring with a compound of formula (404) to afford the compound of formula (405) which is subjected to saponification to generate the carboxylic acid of formula (406). This carboxylic acid is then converted to an acid chloride of formula (407) following procedures known to one skilled in the art. Intramolecular cyclization in the presence of an Lewis acid, such as, but not limited to, tin(IV) chloride, yields the compound of formula (I) of the invention where Q is —C(O)— and j is 0. The removal of the carbonyl group of the compound of formula (I) using a silane, such as triethylsilane, or other reagents known to the one skilled in the art, yields the compound of formula (I) of the invention where Q is —CH$_2$— and j is 0. Reaction of the carbonyl group of the compound (408) of formula (I) with a fluorinating reagent such as, but not limited to, bis(2-methoxyethyl)amino sulfur trifluoride leads to the formation of di-fluoro compound of formula (I) of the invention where Q is —CF$_2$— and j is 0. Reduction of the carbonyl group of the compound (408) of formula (I) with a reducing agent such as, but not limited to, sodium borohydride provides the hydroxy compound of formula (I) of the invention where Q is —CH(OH)— and j is 0. Further alkylation of the hydroxy compound of formula (I) by the method known to one skilled in the art gives the alkylated compound of formula (I) of the invention where Q is —CH(OR$^5$)— and j is 0.

REACTION SCHEME 4
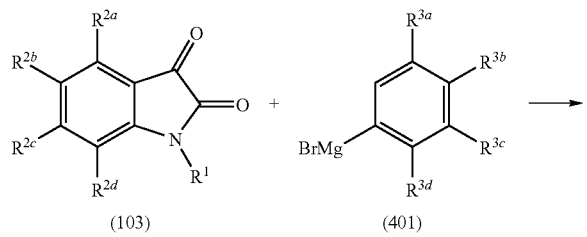
(103) + (401)
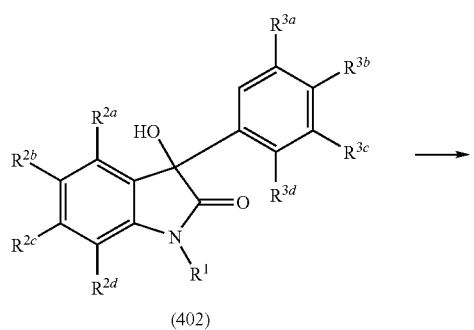
(402)
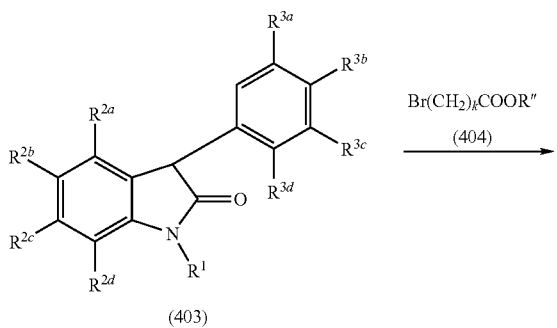
(403) → Br(CH₂)ₖCOOR″ (404)
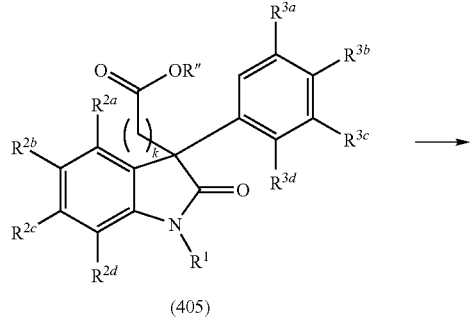
(405)
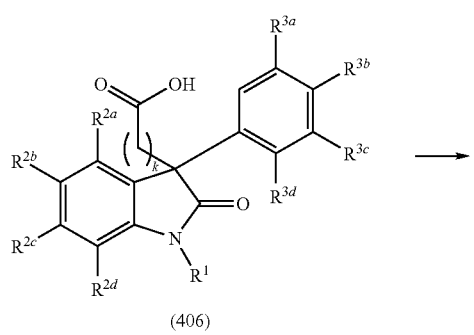
(406)
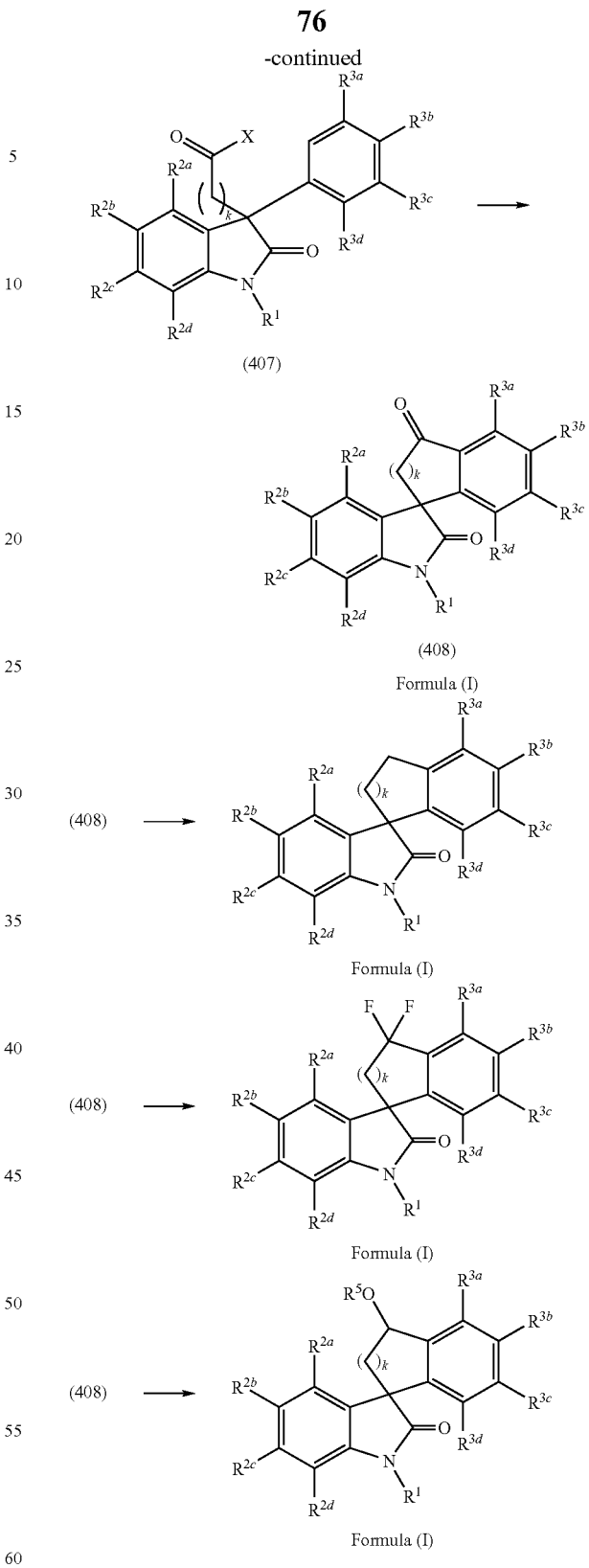
Alternatively, the compound of formula (I) of the invention where Q is —O—, j is 0 and k is 1 can be synthesized following the general procedure as described below in REACTION SCHEME 5. As set forth below, the phenol compound of formula (104) is treated with a Grignard reagent of formula (105) at low temperature (0° C.) to form the phenoxymagnesium halide intermediate which reacts with the keto-carbonyl group of the isatin compound of formula (101) in a solvent, such as, but not limited to, tetrahydrofuran, methylene chloride or toluene, to afford the heterocyclic compound of formula (501). The compound of formula (502) can be obtained after the removal of the hydroxyl group of the heterocyclic compound by treating the compound of formula (501) with a silane such as triethylsilane. The compound of formula (502) can also be achieved by treating the compound of formula (501) with $SOCl_2/NEt_3$ followed by reduction with Zn dust. Compound of formula (502) is treated with a silyl compound such as, but not limited to, trimethylsilyl chloride, to generate the silyl ether intermediate which is treated with ytterbium (III) trifluoromethanesulfonate and formaldehyde to afford the compound of formula (503). Alternatively, compound of formula (503) can be obtained by treating the compound of formula (502) with a base such as, but not limited to, LiOH, $iPr_2NH$, or LDA, and by subsequently reacting with formaldehyde. Intramolecular cyclization via Mitsunobu reaction affords the compound of formula (504) which can be alkylated with a chloro or bromo compound of formula (102) to afford the compound of formula (I) of the invention where Q is —O—, j is 0 and k is 1.

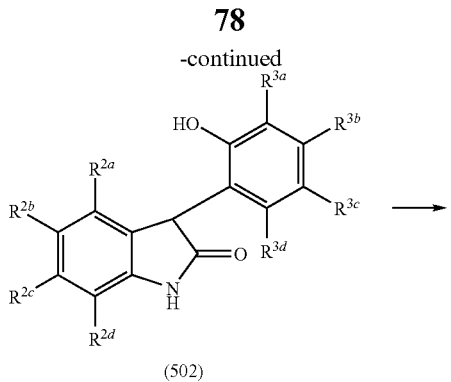

(502)

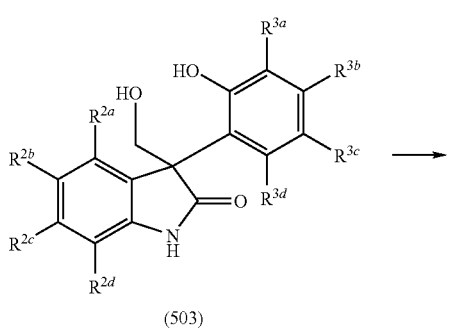

(503)

REACTION SCHEME 5

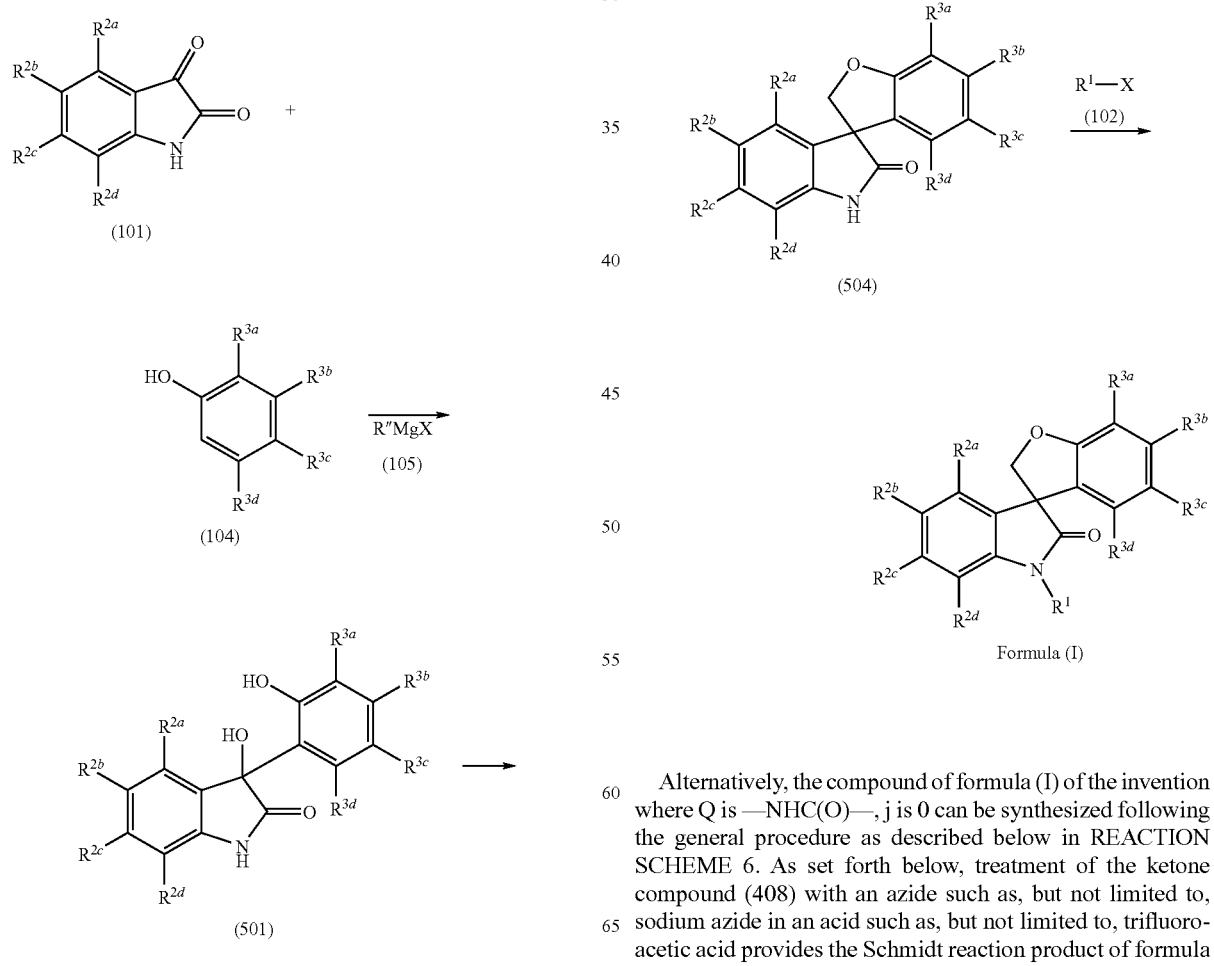

Alternatively, the compound of formula (I) of the invention where Q is —NHC(O)—, j is 0 can be synthesized following the general procedure as described below in REACTION SCHEME 6. As set forth below, treatment of the ketone compound (408) with an azide such as, but not limited to, sodium azide in an acid such as, but not limited to, trifluoroacetic acid provides the Schmidt reaction product of formula (I) of the invention where Q is —NHC(O)—, j is 0.

REACTION SCHEME 6

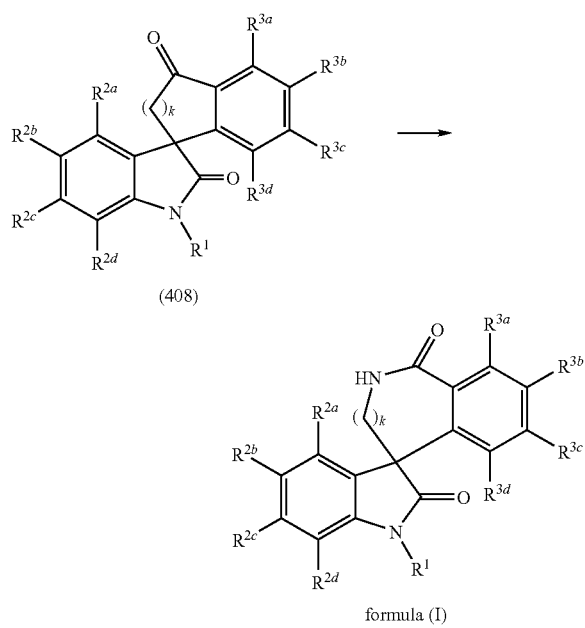

(408)

Alternatively, the compound of formula (I) of the invention where Q is —C(O)O—, j is 0 can be synthesized following the general procedure as described below in REACTION SCHEME 7. As set forth below, treatment of the compound of formula (701), which can be obtained following a similar procedure as for the synthesis of compound of formula (405) as described in REACTION SCHEME 4, with a base such as, but not limited to, lithium hydroxide, sodium hydroxide or potassium hydroxide, in a mixed solvent such as, but not limited to, tetrahydrofuran or methanol with water, leads to the formation of the lactone product of formula (I) of the invention where Q is —C(O)O—, j is 0.

REACTION SCHEME 7

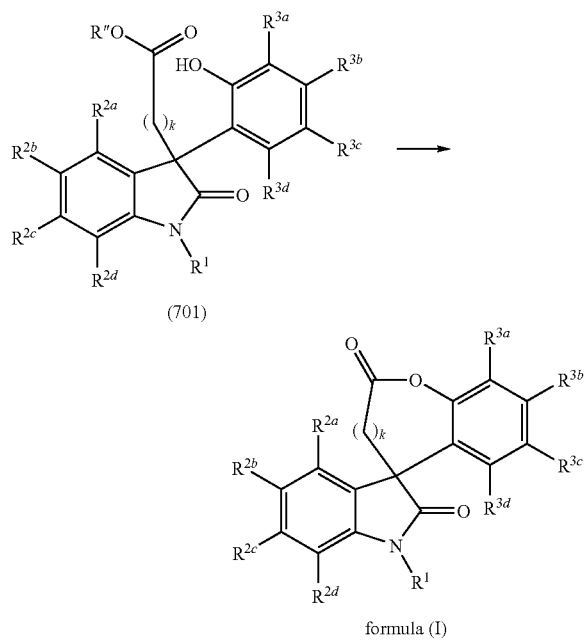

In the following Preparations, which are directed to intermediates used in the preparation of the compounds of formula (I), and in the following Examples, which are directed to compounds of formula (I), the compound numbers presented therein do not correspond to the compound numbers in the above REACTION SCHEMES.

PREPARATION 1

Synthesis of 4-bromo-3-(6-hydroxy-1,3-benzodioxol-5-yl)-3-(hydroxymethyl)-1-pentyl-1,3-dihydro-2H-indol-2-one

A. Synthesis of 4-bromo-1-pentyl-1H-indole

To a mixture of sodium hydride (2.54 g, 66.3 mmol, 60% dispersion in mineral oil) in anhydrous N,N-dimethylformamide (50.0 mL) was added 4-bromoindole (10.0 g, 51.0 mmol) at 0° C. The reaction mixture was stirred for 0.5 h followed by the addition of 1-bromopentane (9.25 g, 61.2 mmol) at 0° C. The reaction mixture was stirred at ambient temperature for 6 h and quenched with brine solution (20.0 mL). The reaction mixture was diluted with water (100 mL) and extracted with ether (3×200 mL). The combined organic layers was washed with brine (100 mL), dried over anhydrous sodium sulfate and filtered. The filtrate was concentrated in vacuo to dryness. The residue was subjected to column chromatography eluting with hexane (100%) to give the title compound (13.3 g, 98%) as a yellow oil: $^1$H NMR (300 MHz, CDCl$_3$) δ 7.30-7.27 (m, 2H), 7.14 (t, 1H), 6.88 (t, 1H), 6.55 (d, 1H), 4.08 (t, 2H), 1.87-1.77 (m, 2H), 1.39-1.22 (m, 4H), 0.89 (t, 3H); $^{13}$C NMR (75 MHz, CDCl$_3$) δ 136.3, 129.2, 128.4, 122.2, 122.1, 114.9, 108.7, 101.3, 46.8, 29.9, 29.1, 22.3, 13.9.

B. Synthesis of 4-bromo-1-pentyl-1H-indole-2,3-dione

To a solution of 4-bromo-1-pentyl-1H-indole (25.0 g, 93.9 mmol) in anhydrous dimethylsulfoxide (350 mL) was added N-bromosuccinimide (50.2 g, 282 mmol) in portions over 30 min. The reaction mixture was heated at 60° C. for 3 h, upon which time the internal temperature increased to 120° C. After cooling down to ambient temperature, the reaction mixture was poured onto ethyl acetate/water (1/1, 600 mL). The organic layer was separated and the aqueous layer was extracted with ethyl acetate (3×500 mL). The combined organic layers was washed with water (3×500 mL), dried over anhydrous sodium sulfate and filtered. The filtrate was concentrated in vacuo to dryness to yield the title compound (25.7 g, 92%) as a yellow solid: $^1$H NMR (300 MHz, CDCl$_3$) δ 7.38 (t, 1H), 7.21 (t, 1H), 6.82 (d, 1H), 3.68 (t, 2H), 1.72-1.59 (m, 2H), 1.39-1.25 (m, 4H), 0.86 (t, 3H); $^{13}$C NMR (75 MHz, CDCl$_3$) δ 180.9, 157.2, 152.6, 138.4, 128.3, 121.7, 116.3, 108.9, 40.4, 28.9, 26.9, 22.3, 13.9.

C. Synthesis of 4-bromo-3-hydroxy-3-(6-hydroxy-1,3-benzodioxol-5-yl)-1-pentyl-1,3-dihydro-2H-indol-2-one To a solution of 1,3-benzodioxol-5-ol (12.8 g, 92.9 mmol) in tetrahydrofuran (200 mL) was added isopropylmagnesium chloride solution (50.7 mL, 101 mmol, 2.0 M in ether) at 0° C. The reaction mixture was stirred at 0° C. for 0.5 h, upon which time the colorless precipitate was formed. After the solvent was removed under reduced pressure, the residue was dissolved in methylene chloride (100 mL) and added to a solution of 4-bromo-1-pentyl-1H-indole-2,3-dione (25.0 g, 84.5 mmol) in dichloromethane (100 mL) via a canula over 10 min at 0° C. The reaction mixture was stirred at ambient temperature for 16 h, quenched with saturated ammonium chloride solution (100 mL) and the organic layer was separated. The aqueous layer was extracted with dichloromethane (100 mL). The combined organic layers was washed with brine, dried over anhydrous sodium sulfate and filtered. The filtrate was concentrated in vacuo to dryness. The residue was subjected to column chromatography eluting with ethyl acetate-hexane to give the title compound (34.9 g, 97%) as a brown gummy material: $^1$H NMR (300 MHz, DMSO-$d_6$) δ 8.95 (s, 1H), 7.29-7.21 (m, 2H), 6.88-6.81 (m, 1H), 6.55, (s, 1H), 6.14 (s, 1H), 5.86 (dd, 2H), 4.24 (s, 1H), 3.70-3.52 (m, 2H), 1.69-1.55 (m, 2H), 1.31-1.24 (m, 4H), 0.83 (t, 3H); $^{13}$C NMR (75 MHz, DMSO-$d_6$) δ 177.6, 152.6, 149.1, 144.8, 141.2, 131.7, 127.7, 127.6, 121.0, 113.8, 108.3, 106.7, 101.7, 101.4, 80.5 40.5, 28.8, 26.7 22.2, 13.9.

D. Synthesis of 4-bromo-3-(6-hydroxy-1,3-benzodioxol-5-yl)-1-pentyl-1,3-dihydro-2H-indol-2-one To a solution of 4-bromo-3-hydroxy-3-(6-hydroxy-1,3-benzodioxol-5-yl)-1-pentyl-1,3-dihydro-2H-indol-2-one (34.9 g, 80.4 mmol) in dichloromethane (100 mL) was added trifluoroacetic acid (18.7 g, 161 mmol) and triethylsilane (18.3 g, 161 mmol). The brown solution was stirred at ambient temperature for 3 h and concentrated in vacuo to dryness. The residue was diluted with dichloromethane (200 mL), washed with saturated ammonium chloride solution (50.0 mL), brine (3×50.0 mL), dried over anhydrous sodium sulfate and filtered. The filtrate was concentrated in vacuo to dryness. The residue was crystallized from ether to give the title compound (16.5 g, 49%) as a brown solid: $^1$H NMR (300 MHz, CDCl$_3$) δ 7.29-7.21 (m, 2H), 7.14 (dd, 1H), 6.58 (s, 1H), 6.10 (s, 1H), 5.85 (dd, 2H), 5.01 (s, 1H), 3.75-3.55 (m, 2H), 1.69-1.56 (m, 2H), 1.35-1.21 (m, 4H), 0.86 (t, 3H); $^{13}$C NMR (75 MHz, CDCl$_3$) δ 177.9, 150.9, 147.6, 145.4, 141.6, 130.3 127.1 126.8, 120.8, 113.3 108.0, 106.7, 101.5, 101.2, 59.9, 48.6, 40.7, 28.9, 26.9, 22.3 13.9; MS (ES+) m/z 418.3 (M+1), 420.3 (M+1).

E. Synthesis of 4-bromo-3-(6-hydroxy-1,3-benzodioxol-5-yl)-3-(hydroxymethyl)-1-pentyl-1,3-dihydro-2H-indol-2-one To a solution of 4-bromo-3-(6-hydroxy-1,3-benzodioxol-5-yl)-1-pentyl-1,3-dihydro-2H-indol-2-one (7.50 g, 17.9 mmol) in dry dichloromethane (150 mL) was added triethylamine (10.9 g, 108 mmol) and chlorotrimethylsilane (7.80 g, 71.8 mmol) at 0° C. The reaction mixture was stirred at 0° C. for 2 h and diluted with dichloromethane (100 mL). The mixture was washed with water (3×50.0 mL), dried over anhydrous magnesium sulfate and filtered. The filtrate was concentrated in vacuo to dryness. The residue was dissolved in THF (150 mL) followed by the additions of formaldehyde solution (4.90 mL, 179 mmol, 37 wt % in water) and ytterbium (III) trifluoromethanesulfonate (1.11 g, 1.79 mmol). The resulting mixture was stirred at ambient temperature for 36 h. After the solvent was removed under reduced pressure, the residue was diluted with dichloromethane (200 mL), washed with saturated sodium bicarbonate (50.0 mL), saturated ammonium chloride (50.0 mL) and water (100 mL). The organic layer was dried over anhydrous sodium sulfate and filtered. The filtrate was concentrated in vacuo to dryness to yield the title compound (6.32 g, 79%) as a fluffy solid: $^1$H NMR (300 MHz, CDCl$_3$) δ 8.28 (s, 1H), 7.10 (t, 1H), 7.00 (dd, 1H), 6.89 (dd, 1H), 6.83 (s, 1H), 6.27 (s, 1H), 6.85 (dd, 2H), 4.52-4.41 (m, 2H), 3.90 (dd, 1H), 3.70-3.65 (m, 2H), 1.68-1.57 (m, 2H), 1.36-1.29 (m, 4H), 0.83 (t, 3H); $^{13}$C NMR (75 MHz, CDCl$_3$) δ 178.1, 150.3, 147.2, 147.2, 140.5, 129.6, 129.2, 125.6, 118.4, 114.8, 109.2, 106.9, 101.0, 98.2, 62.6, 57.6, 39.9, 28.9, 26.7, 22.2, 13.5.

PREPARATION 2

Synthesis of 1-(2-cyclopropylethyl)-3-(6-hydroxy-1,3-benzodioxol-5-yl)-3-(hydroxymethyl)-1,3-dihydro-2H-indol-2-one

A. Synthesis of 1-(2-cyclopropylethyl)-1H-indole-2,3-dione

To a suspension of sodium hydride (1.61 g, 41.9 mmol, 60% dispersion in mineral oil) in anhydrous N,N-dimethylformamide (25.0 mL) was added isatin (6.17 g, 41.9 mmol) at 0° C. The reaction mixture was stirred for 0.5 h followed by the addition of (2-bromoethyl)cyclopropane (Maercker, A., et al, *Justus Liebigs Ann. Chem.* (1972), 759:132-157) (9.25 g, 61.2 mmol). The resulting mixture was stirred at ambient temperature for 16 h and quenched with water (50.0 mL). The mixture was extracted with ethyl acetate (3×100 mL). The combined organic layers was washed with water (3×50.0 mL), dried over anhydrous sodium sulfate and filtered. The filtrate was concentrated in vacuo to dryness to yield the title compound (6.50 g, 90%) as a viscous gum: $^1$H NMR (300 MHz, CDCl$_3$) δ 7.57-7.51 (m, 2H), 7.05 (t, 1H), 6.88 (d, 1H), 3.79-3.74 (m, 2H), 1.59-1.52 (m, 2H), 0.70-0.61 (m, 1H), 0.44-0.38 (m, 2H), 0.05-0.02 (m, 2H); $^{13}$C NMR (75 MHz, CDCl$_3$) δ 183.7, 158.2, 151.2, 138.4, 125.4, 123.6, 117.5, 110.3, 40.3, 32.2, 8.6, 4.3.

B. Synthesis of 1-(2-cyclopropylethyl)-3-hydroxy-3-(6-hydroxy-1,3-benzodioxol-5-yl)-1,3-dihydro-2H-indol-2-one To a solution of 1,3-benzodioxol-5-ol (1.25 g, 9.06 mmol) in THF (20.0 mL) was added dropwise a solution of isopropylmagnesium chloride solution (4.53 mL, 9.06 mmol, 2.0 M in THF) at 0° C. over 5 min. The reaction mixture was stirred for 0.5 h upon which time colorless precipitate was formed. After the solvent was removed under reduced pressure, the residue was dissolved in dichloromethane (20.0 mL) and cooled to 0° C. A solution of 1-(2-cyclopropylethyl)-1H-indole-2,3-dione (1.77 g, 8.23 mmol) in dichloromethane (20.0 mL) was added to the above solution at 0° C. The resulting mixture was stirred at ambient temperature for 16 h and quenched with saturated ammonium chloride solution (30.0 mL). The organic layer was separated and washed with water (3×25.0 mL), dried over anhydrous sodium sulfate and filtered. The filtrate was concentrated in vacuo to dryness. The residue was crystallized from ethyl acetate and ether to give the title compound (2.22 g, 76%) as a colorless solid: $^1$H NMR (300 MHz, CDCl$_3$) δ 9.52 (s, 1H), 7.46 (d, 1H), 7.37 (dt, 1H), 7.18 (dt, 1H), 6.90 (d, 1H), 6.56 (s, 1H), 6.23 (s, 1H), 5.84 (dd, 2H), 4.55 (s, 1H), 3.87-3.63 (m, 2H), 1.64-1.44 (m, 2H), 0.68-0.55 (m, 1H), 0.41-0.27 (m, 2H), −0.02-(−0.07) (m, 2H); $^{13}$C NMR (75 MHz, CDCl$_3$) δ 179.1, 152.4, 148.8, 142.7, 141.3, 130.3, 129.1, 126.3, 123.7, 117.3, 109.5, 106.9, 101.9, 101.4, 79.3, 40.6, 32.2, 8.6, 4.3, 4.2; MS (ES+) m/z 337.6 (M−17).

C. Synthesis of 1-(2-cyclopropylethyl)-3-(6-hydroxy-1,3-benzodioxol-5-yl)-1,3-dihydro-2H-indol-2-one To a solution of 1-(2-cyclopropylethyl)-3-hydroxy-3-(6-hydroxy-1,3-benzodioxol-5-yl)-1,3-dihydro-2H-indol-2- one (2.22 g, 6.27 mmol) in dichloromethane (30.0 mL) was added trifluoroacetic acid (2.12 g, 18.8 mmol) and triethylsilane (2.14 g, 18.8 mmol). The brown solution was stirred at ambient temperature for 0.5 h and concentrated in vacuo to dryness. The residue was diluted with dichloromethane (100 mL), washed with water (3×50.0 mL), dried over anhydrous sodium sulfate and filtered. The filtrate was concentrated in vacuo to dryness. The residue was subjected to column chromatography eluting with ethyl acetate/hexane (20/80) to give the title compound (1.69 g, 80%) as a brown solid: $^1$H NMR (300 MHz, CDCl$_3$) δ 9.21-9.10 (br, 1H), 7.38-7.30 (m, 2H), 7.16 (t, 1H), 6.96 (d, 1H), 6.63 (s, 1H), 6.33 (s, 1H), 5.84 (dd, 2H), 5.01 (s, 1H), 3.87-3.72 (m, 2H), 1.66-1.46 (m, 2H), 0.69-0.59 (m, 1H), 0.43-0.30 (m, 2H), 0.09-0.06 (m, 2H); $^{13}$C NMR (75 MHz, CDCl$_3$) δ 178.8, 151.3, 147.6, 144.1, 141.5, 128.7, 126.2, 123.1, 115.2, 109.5, 109.4, 106.5, 101.5, 101.2, 47.4, 40.5, 32.2, 8.6, 4.3, 4.2; MS (ES+) m/z 338.3 (M+1).

D. Synthesis of 1-(2-cyclopropylethyl)-3-(6-hydroxy-1,3-benzodioxol-5-yl)-3-(hydroxymethyl)-1,3-dihydro-2H-indol-2-one Following the procedure as described in PREPARATION 1E, making variations to replace 4-bromo-3-(6-hydroxy-1,3-benzodioxol-5-yl)-1-pentyl-1,3-dihydro-2H-indol-2-one with 1-(2-cyclopropylethyl)-3-(6-hydroxy-1,3-benzodioxol-5-yl)-1,3-dihydro-2H-indol-2-one, the title compound was obtained (53%): R$_f$=0.28 (EtOAc/Hexanes, 1/1).

PREPARATION 3

Synthesis of ethyl [3-(6-hydroxy-1,3-benzodioxol-5-yl)-3-(hydroxymethyl)-2-oxo-2,3-dihydro-1H-indol-1-yl]acetate A. Synthesis of ethyl (2,3-dioxo-2,3-dihydro-1H-indol-1-yl)acetate Following the procedure as described in PREPARATION 2A, and making non-critical variations to replace (2-bromoethyl)cyclopropane with ethyl bromoacetate, the title compound was obtained (79%) as a light yellow powder: $^1$H NMR (300 MHz, CDCl$_3$) δ 7.64-7.54 (m, 2H), 7.16-7.11 (m, 1H), 6.77 (d, 1H), 4.47 (s, 2H), 4.22 (q, 2H), 1.26 (t, 3H); MS(ES+) m/z 256.2 (M+23).

B. Synthesis of ethyl [3-hydroxy-3-(6-hydroxy-1,3-benzodioxol-5-yl)-2-oxo-2,3-dihydro-1H-indol-1-yl]acetate Following the procedure as described in PREPARATION 2B, and making non-critical variations to replace 1-(2-cyclopropylethyl)-1H-indole-2,3-dione with ethyl (2,3-dioxo-2,3-dihydro-1H-indol-1-yl)acetate, the title compound was obtained (95%): $^1$H NMR (300 MHz, DMSO-d$_6$) δ 9.08 (s, 1H), 7.21-7.13 (m, 2H), 6.93-6.86 (m, 3H), 6.57 (s, 1H), 6.19 (s, 1H), 5.88 (m, 2H), 4.47 (m, 2H), 4.13 (q, 2H), 1.19 (t, 3H); MS (ES−) m/z 370.2 (M−1).

C. Synthesis of ethyl [3-(6-hydroxy-1,3-benzodioxol-5-yl)-2-oxo-2,3-dihydro-1H-indol-1-yl]acetate Following the procedure as described in PREPARATION 1D, and making non-critical variations to replace 4-bromo-3-hydroxy-3-(6-hydroxy-1,3-benzodioxol-5-yl)-1-pentyl-1,3-dihydro-2H-indol-2-one with ethyl [3-hydroxy-3-(6-hydroxy-1,3-benzodioxol-5-yl)-2-oxo-2,3-dihydro-1H-indol-1-yl]acetate, the title compound was obtained (84%) as a white powder: $^1$H NMR (300 MHz, DMSO-d$_6$) δ 9.37 (s, 1H), 7.19 (m, 1H), 7.01-6.90 (m, 3H), 6.43 (s, 2H), 5.84 (m, 2H), 4.86 (s, 1H), 4.56 (s, 2H), 4.13 (q, 2H), 1.18 (t, 3H); MS (ES+) m/z 378.2 (M+23).

D. Synthesis of ethyl [3-(6-hydroxy-1,3-benzodioxol-5-yl)-3-(hydroxymethyl)-2-oxo-2,3-dihydro-1H-indol-1-yl]acetate Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with ethyl [3-(6-hydroxy-1,3-benzodioxol-5-yl)-2-oxo-2,3-dihydro-1H-indol-1-yl]acetate, the title compound was obtained as a white powder: $^1$H NMR (300 MHz, DMSO-d$_6$) δ 9.03 (s, 1H), 7.17-6.85 (m, 5H), 6.22 (s, 1H), 5.83 (s, 2H), 5.04 (t, 1H), 4.56-4.08 (m, 5H), 3.69 (m, 1H), 1.18 (t, 3H); MS (ES+) m/z 408.1 (M+23).

PREPARATION 4

Synthesis of methyl 3-{[3-(6-hydroxy-1,3-benzodioxol-5-yl)-3-(hydroxymethyl)-2-oxo-2,3-dihydro-1H-indol-1-yl]methyl}benzoate A. Synthesis of methyl 3-[(2,3-dioxo-2,3-dihydro-1H-indol-1-yl)methyl]benzoate Following the procedure as described in PREPARATION 2A, and making non-critical variations to replace (2-bromoethyl)cyclopropane with methyl 3-(bromomethyl)benzoate, the title compound was obtained (84%) as a orange solid: $^1$H NMR (300 MHz, CDCl$_3$) δ 7.99-7.95 (m, 2H), 7.60 (d, 1H), 7.53-7.47 (m, 2H), 7.43 (d, 1H), 7.09 (t, 1H), 6.43 (d, 1H), 4.95 (s, 2H), 3.89 (s, 3H).

B. Synthesis of methyl 3-{[3-hydroxy-3-(6-hydroxy-1,3-benzodioxol-5-yl)-2-oxo-2,3-dihydro-1H-indol-1-yl]methyl}benzoate Following the procedure as described in PREPARATION 2B, and making non-critical variations to replace 1-(2-cyclopropylethyl)-1H-indole-2,3-dione with methyl 3-[(2,3-dioxo-2,3-dihydro-1H-indol-1-yl)methyl]benzoate, the title compound was obtained (96%): $^1$H NMR (300 MHz, CDCl$_3$) δ 8.65 (s, 1H), 7.92 (s, 1H), 7.85 (d, 1H), 7.41-7.38 (m, 1H), 7.32-7.24 (m, 2H), 7.19-7.13 (m, 1H), 7.04-6.9 (m, 1H), 6.63 (d, 1H), 6.44 (s, 1H), 6.39 (s, 1H), 5.79 (s, 2H), 5.05 (s, 1H), 4.83 (dd, 2H), 3.80 (s, 3H); $^{13}$C NMR (75 MHz, CDCl$_3$) δ 178.7, 167.0, 151.0, 148.5, 142.1, 141.1, 135.7, 131.6, 130.5, 130.1, 129.1, 129.0, 128.4, 125.5, 123.9, 116.7, 109.7, 106.5, 101.3, 100.5, 78.6, 60.6, 52.4, 43.6; MS (ES+) m/z 456.1 (M+23).

C. Synthesis of methyl 3-{[3-(6-hydroxy-1,3-benzodioxol-5-yl)-2-oxo-2,3-dihydro-1H-indol-1-yl]methyl}benzoate Following the procedure as described in PREPARATION 2C, and making non-critical variations to replace 1-(2-cyclopropylethyl)-3-hydroxy-3-(6-hydroxy-1,3-benzodioxol-5-yl)-1,3-dihydro-2H-indol-2-one with methyl 3-{[3-hydroxy-3-(6-hydroxy-1,3-benzodioxol-5-yl)-2-oxo-2,3-dihydro- 1H-indol-1-yl]methyl}benzoate, the title compound was obtained (98%): MS (ES+) m/z 418.2 (M+1).

D. Synthesis of methyl 3-{[3-(6-hydroxy-1,3-benzodioxol-5-yl)-3-(hydroxymethyl)-2-oxo-2,3-dihydro-1H-indol-1-yl]methyl}benzoate Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with methyl 3-{[3-(6-hydroxy-1,3-benzodioxol-5-yl)-2-oxo-2,3-dihydro-1H-indol-1-yl]methyl}benzoate, the title compound was obtained (81%) as a white powder: MS (ES+) m/z 470.3 (M+23), 448.3 (M+1).

PREPARATION 5

Synthesis of methyl 4-{[3-(6-hydroxy-1,3-benzodioxol-5-yl)-3-(hydroxymethyl)-2-oxo-2,3-dihydro-1H-indol-1-yl]methyl}benzoate A. Synthesis of methyl 4-[(2,3-dioxo-2,3-dihydro-1H-indol-1-yl)methyl]benzoate Following the procedure as described in PREPARATION 2A, and making non-critical variations to replace (2-bromoethyl)cyclopropane with methyl 4-(bromomethyl)benzoate, the title compound was obtained (84%) as an orange solid: $^1$H-NMR (300 MHz, CDCl$_3$) δ 8.00 (d, 2H), 7.61 (d, 1H), 7.46 (t, 1H), 7.38 (d, 2H), 7.09 (t, 1H), 6.69 (d, 1H), 4.96 (s, 2H), 3.88 (s, 3H); MS (ES+) m/z 296.1 (M+1).

B. Synthesis of methyl 4-{[3-hydroxy-3-(6-hydroxy-1,3-benzodioxol-5-yl)-2-oxo-2,3-dihydro-1H-indol-1-yl]methyl}benzoate Following the procedure as described in PREPARATION 2B, and making non-critical variations to replace 1-(2-cyclopropylethyl)-1H-indole-2,3-dione with methyl 4-[(2,3-dioxo-2,3-dihydro-1H-indol-1-yl)methyl]benzoate, the title compound was obtained (79%): MS (ES+) m/z 416.1 (M−17).

C. Synthesis of methyl 4-{[3-(6-hydroxy-1,3-benzodioxol-5-yl)-2-oxo-2,3-dihydro-1H-indol-1-yl]methyl}benzoate Following the procedure as described in PREPARATION 2C, and making the variations to replace 1-(2-cyclopropylethyl)-3-hydroxy-3-(6-hydroxy-1,3-benzodioxol-5-yl)-1,3-dihydro-2H-indol-2-one with methyl 4-{[3-hydroxy-3-(6-hydroxy-1,3-benzodioxol-5-yl)-2-oxo-2,3-dihydro-1H-indol-1-yl]methyl}benzoate, the title compound was obtained (98%) as a solid: MS (ES+) m/z 418.1 (M+1).

D. Synthesis of methyl 4-{[3-(6-hydroxy-1,3-benzodioxol-5-yl)-3-(hydroxymethyl)-2-oxo-2,3-dihydro-1H-indol-1-yl]methyl}benzoate Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with methyl 4-{[3-(6-hydroxy-1,3-benzodioxol-5-yl)-2-oxo-2,3-dihydro-1H-indol-1-yl]methyl}benzoate, the title compound was obtained (81%): MS (ES+) m/z 448.1 (M+1).

PREPARATION 6

Synthesis of 2-{3-[3-(6-hydroxy-1,3-benzodioxol-5-yl)-3-(hydroxymethyl)-2-oxo-2,3-dihydro-1H-indol-1-yl]propyl}-1H-isoindole-1,3(2H)-dione A. Synthesis of 1-[3-(1,3-dioxo-1,3-dihydro-isoindol-2-yl)-propyl]-1H-indole-2,3-dione Following the procedure as described in PREPARATION 2A, and making non-critical variations to replace (2-bromoethyl)cyclopropane with 2-(3-bromopropyl)-1H-isoindole-1,3(2H)-dione, the title compound was obtained (92%): $^1$H NMR (300 MHz, CDCl$_3$) δ 7.80-7.79 (m, 4H), 7.61-7.56 (m, 1H), 7.49-7.46 (m, 1H), 7.18-7.16 (m, 1H), 7.07-7.05 (m, 1H), 3.72-3.60 (m, 4H), 1.97-1.92 (m, 2H).

B. Synthesis of 2-{3-[3-hydroxy-3-(6-hydroxy-1,3-benzodioxol-5-yl)-2-oxo-2,3-dihydro-1H-indol-1-yl]propyl}-1H-isoindole-1,3(2H)-dione Following the procedure as described in PREPARATION 2B, and making non-critical variations to replace 1-(2-cyclopropylethyl)-1H-indole-2,3-dione with 1-[3-(1,3-dioxo-1,3-dihydro-isoindol-2-yl)-propyl]-1H-indole-2,3-dione, the title compound was obtained (96%): $^1$H NMR (300 MHz, CDCl$_3$) δ 7.86-7.78 (m, 4H), 7.21-7.13 (m, 2H), 7.00-6.97 (m, 1H), 6.87-6.85 (m, 2H), 6.15 (s, 1H), 5.86-5.84 (m, 2H), 3.69-3.65 (m, 4H), 2.46-2.45 (m, 1H), 1.94-1.87 (m, 2H); MS (ES+) m/z 473.4 (M−17).

C. Synthesis of 2-{3-[3-(6-hydroxy-1,3-benzodioxol-5-yl)-2-oxo-2,3-dihydro-1H-indol-1-yl]propyl}-1H-isoindole-1,3(2H)-dione Following the procedure as described in PREPARATION 1D, and making non-critical variations to replace 4-bromo-3-hydroxy-3-(6-hydroxy-1,3-benzodioxol-5-yl)-1-pentyl-1,3-dihydro-2H-indol-2-one with 2-{3-[3-hydroxy-3-(6-hydroxy-1,3-benzodioxol-5-yl)-2-oxo-2,3-dihydro-1H-indol-1-yl]propyl}-1H-isoindole-1,3(2H)-dione, the title compound was obtained (94%): $^1$H NMR (300 MHz, CDCl$_3$,) δ 7.81-7.78 (m, 2H), 7.70-7.67 (m, 2H), 7.32-7.27 (m, 2H), 7.12-7.07 (m, 1H), 6.90-6.87 (m, 1H), 6.54 (s, 1H), 6.45 (s, 1H), 5.86 (dd, 2H), 4.82 (s, 1H), 3.96-3.66 (m, 4H), 2.17-2.04 (m, 2H); MS (ES+) m/z 457.0 (M+1).

D. Synthesis of 2-{3-[3-(6-hydroxy-1,3-benzodioxol-5-yl)-3-(hydroxymethyl)-2-oxo-2,3-dihydro-1H-indol-1-yl]propyl}-1H-isoindole-1,3(2H)-dione Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with 2-{3-[3-(6-hydroxy-1,3-benzodioxol-5-yl)-2-oxo-2,3-dihydro-1H-indol-1-yl]propyl}-1H-isoindole-1,3(2H)-dione, the title compound was obtained (94%) as a foam solid: $^1$H NMR (300 MHz, CDCl$_3$) δ 9.20 (s, 1H), 7.81-7.79 (m, 2H), 7.68-7.61 (m, 2H), 7.35-7.25 (m, 2H), 7.16-7.14 (m, 1H), 6.90 (d, 1H), 6.80 (s, 1H), 6.48 (s, 1H), 5.86 (dd, 2H), 4.64 (d, 1H), 3.67-4.13 (m, 5H), 2.18-2.05-(m, 2H);
$^{13}$C NMR (75 MHz, CDCl$_3$) δ 180.6, 168.6, 151.2, 147.8, 143.2, 141.2, 134.2, 134.2, 131.9, 130.0, 128.7, 125.1, 123.2, 113.9, 108.7, 108.3, 101.3, 100.6, 64.9, 58.0, 37.6, 36.1, 26.5; MS (ES+) m/z 487.3 (M+1).

PREPARATION 7

Synthesis of 2-{2-[3-(6-hydroxy-1,3-benzodioxol-5-yl)-3-(hydroxymethyl)-2-oxo-2,3-dihydro-1H-indol-1-yl]ethyl}-1H-isoindole-1,3(2H)-dione

A. Synthesis of 1-[2-(1,3-dioxo-1,3-dihydro-isoindol-2-yl)-ethyl]-1H-indole-2,3-dione Following the procedure as described in PREPARATION 2A, and making non-critical variations to replace (2-bromoethyl)cyclopropane with 2-(2-bromoethyl)-1H-isoindole-1,3 (2H)-dione, the title compound was obtained (75%): $^1$H NMR (300 MHz, CDCl$_3$) δ 7.85-7.78 (m, 4H), 7.65 (td, 1H), 7.55 (dd, 1H), 7.25(d, 1H), 7.12 (t, 1H), 4.00-3.80 (m, 4H); MS (ES+) m/z 321 (M+1), 343 (M+23).

B. Synthesis of 2-{2-[3-hydroxy-3-(6-hydroxy-1,3-benzodioxol-5-yl)-2-oxo-2,3-dihydro-1H-indol-1-yl]ethyl}-1H-isoindole-1,3(2H)-dione Following the procedure as described in PREPARATION 2B, and making non-critical variations to replace 1-(2-cyclopropylethyl)-1H-indole-2,3-dione with 1-[2-(1,3-dioxo-1,3-dihydro-isoindol-2-yl)-ethyl]-1H-indole-2,3-dione, the title compound was obtained (99%): $^1$H NMR (300 MHz, CD$_3$OD) δ 7.85-7.68 (m, 4H), 7.29 (td, 1H), 7.18-6.96 (m, 3H), 6.88 (s, 1H), 6.16 (s, 1H), 5.85 (s, 1H), 5.82 (s, 1H), 3.81-4.01 (m, 4H); MS (ES+) m/z 441 (M−17), 458 (M+23).

C. Synthesis of 2-{2-[3-(6-hydroxy-1,3-benzodioxol-5-yl)-2-oxo-2,3-dihydro-1H-indol-1-yl]ethyl}-1H-isoindole-1,3(2H)-dione Following the procedure as described in PREPARATION 1D, and making non-critical variations to replace 4-bromo-3-hydroxy-3-(6-hydroxy-1,3-benzodioxol-5-yl)-1-pentyl-1,3-dihydro-2H-indol-2-one with 2-{2-[3-hydroxy-3-(6-hydroxy-1,3-benzodioxol-5-yl)-2-oxo-2,3-dihydro-1H-indol-1-yl]ethyl}-1H-isoindole-1,3(2H)-dione, the title compound was obtained (90%) as a white solid: $^1$H NMR (300 MHz, CD$_3$OD) δ 10.15-10.05 (br, 1H), 8.66-8.58 (m, 4H), 8.07-7.70 (m, 4H), 7.12 (s, 1H), 7.18 (s, 1H), 6.70 (s, 1H), 6.69 (s, 1H), 5.50 (s, 1H), 4.91-4.56 (m, 4H); MS (ES+) m/z 443 (M+1).

D. Synthesis of 2-{2-[3-(6-hydroxy-1,3-benzodioxol-5-yl)-3-(hydroxymethyl)-2-oxo-2,3-dihydro-1H-indol-1-yl]ethyl}-1H-isoindole-1,3(2H)-dione Following the procedure as described in PREPARATION 1E, making variation to replace 4-bromo-3-(6-hydroxy-1,3-benzodioxol-5-yl)-1-pentyl-1,3-dihydro-2H-indol-2-one with 2-{2-[3-(6-hydroxy-1,3-benzodioxol-5-yl)-2-oxo-2,3-dihydro-1H-indol-1-yl]ethyl}-1H-isoindole-1,3(2H)-dione, the title compound was obtained (56%): $^1$H NMR (300 MHz, CD$_3$OD) δ 9.97 (s, 1H), 8.72-8.62 (m, 4H), 8.07-7.67 (m, 5H), 7.01 (s, 1H), 6.71 (s, 1H), 6.70 (s, 1H), 5.79 (t, 1H), 4.88-4.50 (m, 6H); MS (ES+) m/z 455 (M−17), 473 (M+1), 495 (M+23).

PREPARATION 8

Synthesis of 1-(diphenylmethyl)-3-(6-hydroxy-1,3-benzodioxol-5-yl)-3-(hydroxymethyl)-1,3-dihydro-2H-indol-2-one

A. Synthesis of 1-(diphenylmethyl)-1H-indole-2,3-dione

Following the procedure as described in PREPARATION 2A, and making non-critical variations to replace (2-bromoethyl)cyclopropane with 1,1'-(bromomethylene)dibenzene, the title compound was obtained (68%) as an orange solid: MS (ES+) m/z 336.4 (M+23).

B. Synthesis of 1-(diphenylmethyl)-3-hydroxy-3-(6-hydroxy-1,3-benzodioxol-5-yl)-1,3-dihydro-2H-indol-2-one Following the procedure as described in PREPARATION 2B, and making non-critical variations to replace 1-(2-cyclopropylethyl)-1H-indole-2,3-dione with 1-(diphenylmethyl)-1H-indole-2,3-dione, the title compound was obtained (99%) as an off-white powder: MS (ES+) m/z 474.5 (M+23).

C. Synthesis of 1-(diphenylmethyl)-3-(6-hydroxy-1,3-benzodioxol-5-yl)-1,3-dihydro-2H-indol-2-one Following the procedure as described in PREPARATION 2C, and making the variations to replace 1-(2-cyclopropylethyl)-3-hydroxy-3-(6-hydroxy-1,3-benzodioxol-5-yl)-1,3-dihydro-2H-indol-2-one with 1-(diphenylmethyl)-3-hydroxy-3-(6-hydroxy-1,3-benzodioxol-5-yl)-1,3-dihydro-2H-indol-2-one, the title compound was obtained (84%) as an off-white solid: MS (ES+) m/z 458.4 (M+23).

D. Synthesis of 1-(diphenylmethyl)-3-(6-hydroxy-1,3-benzodioxol-5-yl)-3-(hydroxymethyl)-1,3-dihydro-2H-indol-2-one Following the procedure as described in PREPARATION 1E, and making non-critical variations using 1-(diphenylmethyl)-3-(6-hydroxy-1,3-benzodioxol-5-yl)-1,3-dihydro-2H-indol-2-one to replace 4-bromo-3-(6-hydroxy-1,3-benzodioxol-5-yl)-1-pentyl-1,3-dihydro-2H-indol-2-one, the title compound was obtained (56%): MS (ES+) m/z 488.3 (M+23).

PREPARATION 9

Synthesis of 1-[3-(benzyloxy)propyl]-3-(6-hydroxy-1,3-benzodioxol-5-yl)-3-(hydroxymethyl)-1,3-dihydro-2H-indol-2-one

A. Synthesis of 1-[3-(benzyloxy)propyl]-1H-indole-2,3-dione

Following the procedure as described in PREPARATION 1A, and making non-critical variations to replace 4-bromoindole with isatin, and 1-bromopentane with benzyl 3-bromopropyl ether, the title compound was obtained (95%) as a pale yellow syrup: $^1$H NMR (300 MHz, CDCl$_3$) δ 7.57-6.92 (m, 9H), 4.50 (s, 2H), 3.84 (t, 2H), 3.54 (t, 2H), 2.03-1.94 (m, 2H); MS (ES$^+$) m/z 296.3 (M+1), 318.3 (M+23).

B. Synthesis of 1-[3-(benzyloxy)propyl]-3-hydroxy-3-(6-hydroxy-1,3-benzodioxol-5-yl)-1,3-dihydro-2H-indol-2-one Following the procedure as described in PREPARATION 10, and making non-critical variations to replace 4-bromo-1-pentyl-1H-indole-2,3-dione with 1-[3-(benzyloxy)propyl]-1H-indole-2,3-dione, the title compound was obtained (70%): $^1$H NMR (300 MHz, CDCl$_3$) δ 9.42 (s, 1H), 7.32-7.16 (m, 8H), 6.96 (d,), 6.61 (s, 1H), 6.23 (s, 1H), 5.86-5.83 (m, 2H), 4.44 (s, 2H), 3.88-3.73(m, 2H), 3.46 (t, 2H), 2.06-1.85 (m, 2H); MS (ES+) m/z 416.3 (M−17), 456.3 (M+23).

C. Synthesis of 1-[3-(benzyloxy)propyl]-3-(6-hydroxy-1,3-benzodioxol-5-yl)-1,3-dihydro-2H-indol-2-one Following the procedure as described in PREPARATION 1D, and making non-critical variations to replace 4-bromo-3-hydroxy-3-(6-hydroxy-1,3-benzodioxol-5-yl)-1-pentyl-1,3-dihydro-2H-indol-2-one with 1-[3-(benzyloxy)propyl]-3-hydroxy-3-(6-hydroxy-1,3-benzodioxol-5-yl)-1,3-dihydro-2H-indol-2-one, the title compound was obtained (92%): $^1$H NMR (300 MHz, CDCl$_3$) δ 7.42-6.95 (m, 9H), 6.56 (s, 1H), 6.24 (s, 1H), 5.86 (ABq, 1H), 5.81(ABq, 1H), 4.99 (s, 1H), 4.42 (s, 2H), 3.91-3.76 (m, 2H), 3.46 (t, 2H), 2.03-1.93 (m, 2H); MS (ES+) m/z 418.3 (M+1).

D. Synthesis of 1-[3-(benzyloxy)propyl]-3-(6-hydroxy-1,3-benzodioxol-5-yl)-3-(hydroxymethyl)-1,3-dihydro-2H-indol-2-one Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with 1-[3-(benzyloxy)propyl]-3-(6-hydroxy-1,3-benzodioxol-5-yl)-1,3-dihydro-2H-indol-2-one, the title compound was obtained (93%): MS (ES+) m/z 448.2 (M+1).

PREPARATION 10

Synthesis of methyl 2-{[3-(6-hydroxy-1,3-benzodioxol-5-yl)-3-(hydroxymethyl)-2-oxo-2,3-dihydro-1H-indol-1-yl]methyl}benzoate

A. Synthesis of methyl 2-[(2,3-dioxo-2,3-dihydro-1H-indol-1-yl)methyl]benzoate Following the procedure as described in PREPARATION 2A, and making non-critical variations to replace (2-bromoethyl)cyclopropane with methyl 2-(bromomethyl) benzoate, the title compound was obtained (68%) as a yellow solid: $^1$H NMR (300 MHz, CDCl$_3$) δ 8.05 (dd, 1H), 7.64 (dd, 1H),7.50-7.31 (m, 3H), 7.22 (d, 1H), 7.10 (t, 1H), 6.72 (d, 1H), 5.41 (s, 2H), 3.95 (s, 3H).

B. Synthesis of methyl 2-{[3-hydroxy-3-(6-hydroxy-1,3-benzodioxol-5-yl)-2-oxo-2,3-dihydro-1H-indol-1-yl]methyl}benzoate Following the procedure as described in PREPARATION 2B, and making non-critical variations to replace 1-(2-cyclopropylethyl)-1H-indole-2,3-dione with methyl 2-[(2,3-dioxo-2,3-dihydro-1H-indol-1-yl)methyl]benzoate, the title compound was obtained (97%) as a colorless solid: $^1$H NMR (300 MHz, DMSO-d$_6$) δ 9.29 (s, 1H), 7.97 (dd, 1H), 7.53-7.36 (m, 3H), 7.28 (s, 1H), 7.10 (td, 1H), 6.96-6.83 (m, 2H), 6.59 (d, 2H), 6.25 (s, 1H), 5.95-5.86 (m, 2H), 5.31-5.07 (m, 2H), 3.88 (s, 3H); MS (ES+) m/z 456.1 (M+23).

C. Synthesis of methyl 2-{[3-(6-hydroxy-1,3-benzodioxol-5-yl)-2-oxo-2,3-dihydro-1H-indol-1-yl]methyl}benzoate Following the procedure as described in PREPARATION 2C, and making non-critical variations to replace 1-(2-cyclopropylethyl)-3-hydroxy-3-(6-hydroxy-1,3-benzodioxol-5-yl)-1,3-dihydro-2H-indol-2-one with methyl 2-{[3-hydroxy-3-(6-hydroxy-1,3-benzodioxol-5-yl)-2-oxo-2,3-dihydro-1H-indol-1-yl]methyl}benzoate, the title compound was obtained (100%) as a white solid: $^1$H NMR (300 MHz, DMSO-d$_6$) δ 9.32 (s, 1H), 7.94 (dd, 1H), 7.50-7.34 (m, 2H), 7.26 (d, 1H), 7.08 (t, 1H), 7.00-6.86 (m, 2H), 6.76 (s, 1H), 6.64 (d, 1H), 6.38 (s, 1H), 5.93-5.86 (m, 2H), 5.34-5.12 (m, 2H), 4.83 (s, 1H), 3.87 (s, 3H); MS (ES+) m/z 418.2 (M+1).

D. Synthesis of methyl 2-{[3-(6-hydroxy-1,3-benzodioxol-5-yl)-3-(hydroxymethyl)-2-oxo-2,3-dihydro-1H-indol-1-yl]methyl}benzoate A solution of methyl 2-{[3-(6-hydroxy-1,3-benzodioxol-5-yl)-2-oxo-2,3-dihydro-1H-indol-1-yl]methyl}benzoate (17.1 g, 40.0 mmol) and paraformaldehyde (10.3 g, 330 mmol) in THF (500 mL) was degassed by bubbling through argon for 2 hours. To this solution was added lithium diisopropylamide solution (45.1 mL, 2 M solution, 90.0 mmol) slowly at −78° C. The mixture was stirred at ambient temperature overnight and quenched with saturated ammonium chloride solution. The mixture was concentrated in vacuo to remove THF followed by the addition of ethyl acetate (500 mL). The organic layer was washed with water, dried over sodium sulfate and filtered. The filtrate was concentrated in vacuo to dryness. The residue was recrystallized from ethyl acetate/hexanes to give the title compound (13.7 g, 75%): $^1$H NMR (300 MHz, DMSO-d$_6$) δ 9.20 (s, 1H), 7.95 (dd, 1H), 7.53-7.33 (m, 3H), 7.08-6.82 (m, 4H), 6.53 (d, 1H), 6.25 (s, 1H), 5.93-5.86 (m, 2H), 5.31-5.07 (m, 3H), 4.26-4.17 (m, 1H), 4.00-3.92 (m, 1H), 3.88 (s, 3H); MS (ES+) m/z 448.3 (M+1).

PREPARATION 11

Synthesis of [3-(1,3-benzodioxol-5-yl)-2-oxo-1-pentyl-2,3-dihydro-1H-indol-3-yl]acetic acid

A. Synthesis of 1-pentyl-1H-indole-2,3-dione

Following the procedure as described in PREPARATION 2A, and making non-critical variations to replace (2-bromoethyl)cyclopropane with 1-bromopentane, the title compound was obtained (85%) as an orange solid: $^1$H NMR (300 MHz, CDCl$_3$) δ 7.60-7.52 (m, 2H), 7.08 (td, 1H), 6.87 (d, 1H), 3.69 (t, 2H), 1.74-1.61 (m, 2H), 1.40-1.28 (m, 4H), 0.88 (t, 3H).

B. Synthesis of 3-(1,3-benzodioxol-5-yl)-3-hydroxy-1-pentyl-1,3-dihydro-2H-indol-2-one To a solution of 1-pentyl-1H-indole-2,3-dione (2.80 g, 12.8 mmol) in THF (50.0 mL) was added 3,4-(methylenedioxy)phenylmagnesium bromide (14.0 mL, 1 M THF solution, 14.0 mmol) slowly at −78° C. The mixture was stirred at 0° C. for 1 h and quenched with ammonium chloride solution. The mixture was poured into water (150 mL) and extracted with ethyl acetate (200 mL). The organic layer was washed with water, dried over sodium sulfate and filtered. The filtrate was concentrated in vacuo to dryness. The residue was subjected to flash column chromatography to afford the title compound (3.10 g, 71%) as an orange oil: $^1$H NMR (300 MHz, CDCl$_3$) δ 7.34-7.23 (m, 2H), 7.05 (t, 1H), 6.91-6.85 (m, 2H), 6.83-6.78 (m, 1H), 6.71 (d, 1H), 5.92-5.89 (m, 2H), 3.82-3.55 (m, 2H), 3.40 (br, 1H), 1.76-1.61 (m, 2H), 1.39-1.28 (m, 4H), 0.87 (t, 3H).

C. Synthesis of 3-(1,3-benzodioxol-5-yl)-1-pentyl-1,3-dihydro-2H-indol-2-one Following the procedure as described in PREPARATION 2C, and making non-critical variations to replace 1-(2-cyclopropylethyl)-3-hydroxy-3-(6-hydroxy-1,3-benzodioxol-5-yl)-1,3-dihydro-2H-indol-2-one with 3-(1,3-benzodioxol-5-yl)-3-hydroxy-1-pentyl-1,3-dihydro-2H-indol-2-one, the title compound was obtained (90%) as an oil: $^1$H NMR (300 MHz, CDCl$_3$) δ 7.30 (td, 1H), 7.14 (d, 1H), 7.03 (td, 1H), 6.89 (d, 1H), 6.75 (d, 1H), 6.67 (dd, 1H), 6.57 (d, 1H), 5.90 (s, 2H), 4.50 (s, 1H), 3.81-3.62 (m, 2H), 1.76-1.62 (m, 2H), 1.41-1.28 (m, 4H), 0.88 (t, 3H); $^{13}$C NMR (75 MHz, CDCl$_3$) δ 176.8, 148.1, 147.2, 143.5, 130.0, 129.4, 128.4, 125.1, 122.9, 122.0, 108.7, 108.6, 101.1, 51.9, 40.4, 29.0, 27.1, 22.3, 14.0.

D. Synthesis of methyl [3-(1,3-benzodioxol-5-yl)-2-oxo-1-pentyl-2,3-dihydro-1H-indol-3-yl]acetate A solution of 3-(1,3-benzodioxol-5-yl)-1-pentyl-1,3-dihydro-2H-indol-2-one (1.00 g, 3.10 mmol) and methyl bromoacetate (0.44 mL, 4.60 mmol) in THF (20.0 mL) was degassed by bubbling through argon for one hour. Sodium hydride (0.19 g, 4.60 mmol) was added at 0° C. The mixture was stirred at 0° C. for 1 h and quenched with ammonium chloride solution. The mixture was poured into water (150 mL), and extracted with ethyl acetate (200 mL). The organic layer was washed with water, dried over sodium sulfate and filtered. The filtrate was concentrated in vacuo to dryness. The residue was subjected to flash column chromatography to afford the title compound (0.94 g, 76%) as a colorless oil: $^1$H NMR (300 MHz, CDCl$_3$) δ 7.30 (td, 1H), 7.25 (dd, 1H), 7.06 (td, 1H), 6.89 (d, 1H), 6.81 (d, 1H), 6.74-6.65 (m, 2H), 5.90-5.87 (m, 2H), 3.71-3.64 (m, 2H), 3.45 (d, 1H), 3.41 (s, 3H), 3.18 (d, 1H), 1.74-1.60 (m, 2H), 1.39-1.22 (m, 4H), 0.85 (t, 3H); $^{13}$C NMR (75 MHz, CDCl$_3$,) δ 177.8, 170.0, 147.9, 147.0, 143.9, 133.1, 131.3, 128.6, 124.6, 122.3, 119.9, 108.7, 108.1, 107.4, 101.2, 52.8, 51.6, 41.8, 40.4, 29.0, 26.8, 22.3, 14.0; MS (ES+) m/z 418.1 (M+23), 396.1 (M+1).

E. Synthesis of [3-(1,3-benzodioxol-5-yl)-2-oxo-1-pentyl-2,3-dihydro-1H-indol-3-yl]acetic acid To a solution of methyl [3-(1,3-benzodioxol-5-yl)-2-oxo-1-pentyl-2,3-dihydro-1H-indol-3-yl]acetate (5.90 g, 15.0 mmol) in THF/water (2/1 v/v, 120 mL) was added lithium hydroxide monohydrate (1.26 g, 28.0 mmol). The mixture was stirred at ambient temperature overnight. Most THF was removed under vacuum and water (150 mL) was added. The solution was extracted with ethyl acetate/hexanes (1/3 v/v, 50.0 mL). The water layer was acidified with 1 N HCl solution until the pH value reached 2 and extracted with ethyl acetate (200 mL). The organic layer was washed with water, dried over sodium sulfate and filtered. The filtrate was concentrated in vacuo to dryness to afford the title compound (5.00 g, 88%) as a white solid: $^1$H NMR (300 MHz, CDCl$_3$) δ 7.29 (td, 1H), 7.21 (dd, 1H), 7.05 (td, 1H), 6.87 (d, 1H), 6.76 (d, 1H), 6.72-6.64 (m, 2H), 5.90-5.86 (m, 2H), 3.65 (t, 2H), 3.43 (d, 1H), 3.11 (d, 1H), 1.70-1.55 (m, 2H), 1.36-1.22 (m, 4H), 0.85 (t, 3H); $^{13}$C NMR (75 MHz, CDCl$_3$) δ 178.2, 174.0, 148.0, 147.1, 143.4, 132.6, 131.4, 128.7, 124.4, 122.7, 119.8, 108.9, 108.2, 107.2, 101.2, 52.6, 41.5, 40.4, 29.0, 26.6, 22.3, 14.0; MS (ES+) m/z 404.0 (M+23), 382.0 (M+1).

PREPARATION 12

Synthesis of 3-[3-(1,3-benzodioxol-5-yl)-2-oxo-1-pentyl-2,3-dihydro-1H-indol-3-yl]propanoic acid A. Synthesis of methyl 3-[3-(1,3-benzodioxol-5-yl)-2-oxo-1-pentyl-2,3-dihydro-1H-indol-3-yl]propanoate Following the procedure as described in PREPARATION 11D, and making non-critical variations to replace methyl bromoacetate with methyl 3-bromopropionate, the title compound was obtained (76%) as a colorless oil: $^1$H NMR (300 MHz, CDCl$_3$) δ 7.28 (td, 1H), 7.17 (dd, 1H), 7.06 (td, 1H), 6.89 (d, 1H), 6.84 (d, 1H), 6.77 (dd, 1H), 6.68 (d, 1H), 5.89-5.84 (m, 2H), 3.67 (t, 2H), 3.53 (s, 3H), 2.69-2.56 (m, 1H), 2.54-2.41 (m, 1H), 2.21-2.08 (m, 1H), 1.99-1.86 (m, 1H), 1.72-1.59 (m, 2H), 1.38-1.24 (m, 4H), 0.85 (t, 3H); $^{13}$C NMR (75 MHz, CDCl$_3$) δ 177.8, 173.1, 147.9, 146.9, 143.2, 133.5, 131.6, 128.5, 124.9, 122.6, 120.1, 108.7, 108.1, 107.6, 101.1, 55.2, 51.6, 40.2, 32.4, 29.5, 29.1, 27.1, 22.3, 14.0; MS (ES+) m/z 410.1 (M+1), 432.0 (M+23).

B. Synthesis of 3-[3-(1,3-benzodioxol-5-yl)-2-oxo-1-pentyl-2,3-dihydro-1H-indol-3-yl]propanoic acid Following the procedure as described in PREPARATION 11E, and making non-critical variations to replace methyl [3-(1,3-benzodioxol-5-yl)-2-oxo-1-pentyl-2,3-dihydro-1H-indol-3-yl]acetate with methyl 3-[3-(1,3-benzodioxol-5-yl)-2-oxo-1-pentyl-2,3-dihydro-1H-indol-3-yl]propanoate, the title compound was obtained (92%) as a colorless solid: MS (ES−) m/z 394.2 (M−1).

PREPARATION 13

Synthesis of 3-(4,5-difluoro-2-hydroxyphenyl)-3-(hydroxymethyl)-1-pentyl-1,3-dihydro-2H-indol-2-one A. Synthesis of 3-(4,5-difluoro-2-hydroxyphenyl)-3-hydroxy-1-pentyl-1,3-dihydro-2H-indol-2-one Following the procedure as described in PREPARATION 2B, and making non-critical variations to replace 1-(2-cyclopropylethyl)-1H-indole-2,3-dione with 1-pentyl-1H-indole-2,3-dione, and 1,3-benzodioxol-5-ol with 3,4-difluorophenol, the title compound was obtained (31%): $^1$H NMR (300 MHz, CDCl$_3$) δ 9.69-9.65 (br, 1H), 7.51-7.41 (m, 2H), 7.26-7.21 (m, 1H), 6.99-6.57 (m, 3H), 4.18-4.14 (br, 1H), 3.78-3.58 (m, 2H), 1.76-1.62 (m, 2H), 1.40-1.28 (m, 4H), 0.87 (t, 3H); MS (ES+) m/z 330 (M−17), 370 (M+23).

B. Synthesis of 3-(4,5-difluoro-2-hydroxyphenyl)-1-pentyl-1,3-dihydro-2H-indol-2-one Following the procedure as described in PREPARATION 2C, and making non-critical variations to replace 1-(2-cyclopropylethyl)-3-hydroxy-3-(6-hydroxy-1,3-benzodioxol-5-yl)-1,3-dihydro-2H-indol-2-one with 3-(4,5-difluoro-2-hydroxyphenyl)-3-hydroxy-1-pentyl-1,3-dihydro-2H-indol-2-one, the title compound was obtained (98%): $^1$H NMR (300 MHz, CDCl$_3$) δ 7.46-7.19 (m, 3H), 7.03-6.68 (m, 3H), 5.03 (s, 1H), 3.76-3.67 (m, 2H), 1.76-1.62 (m, 2H), 1.40-1.28 (m, 4H), 0.87 (t, 3H); MS (ES+) m/z 332 (M+1).

C. Synthesis of 3-(4,5-difluoro-2-hydroxyphenyl)-3-(hydroxymethyl)-1-pentyl-1,3-dihydro-2H-indol-2-one Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with 3-(4,5-difluoro-2-hydroxyphenyl)-1-pentyl-1,3-dihydro-2H-indol-2-one, the title compound was obtained (96%): MS (ES+) m/z 344 (M−17), 384 (M+23).

PREPARATION 14

Synthesis of 3-(5-fluoro-2-hydroxyphenyl)-3-(hydroxymethyl)-1-pentyl-1,3-dihydro-2H-indol-2-one

A. Synthesis of 3-(5-fluoro-2-hydroxyphenyl)-3-hydroxy-1-pentyl-1,3-dihydro-2H-indol-2-one Following the procedure as described in PREPARATION 1C, and making non-critical variations to replace 4-bromo-1-pentyl-1H-indole-2,3-dione with 1-pentyl-1H-indole-2,3-dione, and 1,3-benzodioxol-5-ol with 4-fluorophenol, the title compound was obtained (53%): $^1$H NMR (300 MHz, CDCl$_3$) δ 9.42-9.14 (br, 1H), 7.53-6.86 (m, 6H), 6.56-6.48 (m, 1H), 4.58-4.28 (br, 1H), 3.79-3.58 (m, 2H), 1.77-1.61 (m, 2H), 1.41-1.24 (m, 4H), 0.87 (t, 3H); MS (ES+) m/z 312 (M−17), 352 (M+23).

B. Synthesis of 3-(5-fluoro-2-hydroxyphenyl)-1-pentyl-1,3-dihydro-2H-indol-2-one To a solution of 3-(5-fluoro-2-hydroxyphenyl)-3-hydroxy-1-pentyl-1,3-dihydro-2H-indol-2-one (2.42 g, 7.35 mmol) in dichloromethane (10.0 mL) were added trifluoroacetic acid (1.00 mL) and triethylsilane (1.00 mL) at ambient temperature. The reaction mixture was stirred at 40° C. for 15 hrs and concentrated in vacuo to dryness. The residue was triturated with ether to give the title compound (2.10 g, 91%) as a solid: MS (ES+) m/z 314 (M+1).

C. Synthesis of 3-(5-fluoro-2-hydroxyphenyl)-3-(hydroxymethyl)-1-pentyl-1,3-dihydro-2H-indol-2-one To a solution of 3-(5-fluoro-2-hydroxyphenyl)-1-pentyl-1,3-dihydro-2H-indol-2-one (2.10 g, 6.70 mmol) in THF (20.0 mL) were added paraformaldehyde (1.76 g, 58.8 mmol) and lithium diisopropylamide (7.35 mL, 2.0 M in THF, 14.7 mmol) at 0° C. The reaction mixture was stirred at 0° C. for 2 hrs followed by the addition of ammonium chloride solution (10.0 mL) and ethyl acetate (100 mL). The organic layer was washed with water and brine, dried over Na$_2$SO$_4$ and filtered. The filtrate was concentrated in vacuo to dryness to give the title compound: $^1$H NMR (300 MHz, CDCl$_3$) δ 9.55-9.10 (br, 1H), 7.53-6.86 (m, 6H), 6.57-6.49 (m, 1H), 4.74-4.30 (br, 1H), 4.18-4.07 (m, 2H), 3.79-3.60 (m, 2H), 1.77-1.61 (m, 2H), 1.41-1.24 (m, 4H), 0.87 (t, 3H); MS (ES+) m/z 326 (M−17), 366 (M+23).

PREPARATION 15

Synthesis of 3-(5-bromo-2-hydroxyphenyl)-3-(hydroxymethyl)-1-pentyl-1,3-dihydro-2H-indol-2-one

A. Synthesis of 3-(5-bromo-2-hydroxyphenyl)-3-hydroxy-1-pentyl-1,3-dihydro-2H-indol-2-one Following the procedure as described in PREPARATION 1C, and making non-critical variations to replace 4-bromo-1-pentyl-1H-indole-2,3-dione with 1-pentyl-1H-indole-2,3-dione, and 1,3-benzodioxol-5-ol with 4-bromophenol, the title compound was obtained (41%): $^1$H NMR (300 MHz, CDCl$_3$) δ 9.46-9.25 (br, 1H), 7.51-6.80 (m, 7H), 4.73-4.51(br, 1H), 3.79-3.56 (m, 2H), 1.76-1.60 (m, 2H), 1.41-1.22 (m, 4H), 0.87 (t, 3H); MS (ES+) m/z 377 (M−17), 379 (M−17), 412 (M+23), 414 (M+23).

B. Synthesis of 3-(5-bromo-2-hydroxyphenyl)-1-pentyl-1,3-dihydro-2H-indol-2-one To a solution of 3-(5-bromo-2-hydroxyphenyl)-3-hydroxy-1-pentyl-1,3-dihydro-2H-indol-2-one (2.22 g, 5.64 mmol) in dichloromethane (10.0 mL) were added trifluoroacetic acid (1.00 mL) and triethylsilane (1.00 mL) at ambient temperature. The reaction mixture was stirred at 50° C. for 15 hrs and concentrated in vacuo to dryness to give the title compound: MS (ES+) m/z 374 (M+1), 376 (M+1).

C. Synthesis of 3-(5-bromo-2-hydroxyphenyl)-3-(hydroxymethyl)-1-pentyl-1,3-dihydro-2H-indol-2-one Following the procedure as described in PREPARATION 14C, and making non-critical variations to replace 3-(5-fluoro-2-hydroxyphenyl)-1-pentyl-1,3-dihydro-2H-indol-2-one with 3-(5-bromo-2-hydroxyphenyl)-1-pentyl-1,3-dihydro-2H-indol-2-one, the title compound was obtained: MS (ES+) m/z 386 (M−17), 388 (M−17), 426 (M+23), 428 (M+23).

PREPARATION 16

Synthesis of 3-(5-chloro-4-fluoro-2-hydroxyphenyl)-3-(hydroxymethyl)-1-pentyl-1,3-dihydro-2H-indol-2-one

A. Synthesis of 3-(5-chloro-4-fluoro-2-hydroxyphenyl)-3-hydroxy-1-pentyl-1,3-dihydro-2H-indol-2-one Following the procedure as described in PREPARATION 1C, and making non-critical variations to replace 4-bromo-1-pentyl-1H-indole-2,3-dione with 1-pentyl-1H-indole-2,3-dione, and 1,3-benzodioxol-5-ol with 4-chloro-3-fluorophenol, the title compound was obtained (33%): $^1$H NMR (300 MHz, CDCl$_3$) δ 9.80 (s, 1H), 7.52-7.41 (m, 2H), 7.23 (t, 1H), 6.96 (d, 1H), 6.84 (d, 1H), 6.80 (d, 1H), 4.15 (s, 1H), 3.79-3.58 (m, 2H), 1.76-1.62 (m, 2H), 1.40-1.28 (m, 4H), 0.87 (t, 3H); MS (ES+) m/z 346 (M−17), 386 (M+23).

B. Synthesis of 3-(5-chloro-4-fluoro-2-hydroxyphenyl)-1-pentyl-1,3-dihydro-2H-indol-2-one Following the procedure as described in PREPARATION 15B, and making non-critical variations to replace 3-(5-bromo-2-hydroxyphenyl)-3-hydroxy-1-pentyl-1,3-dihydro-2H-indol-2-one with 3-(5-chloro-4-fluoro-2-hydroxyphenyl)-3-hydroxy-1-pentyl-1,3-dihydro-2H-indol-2-one, the title compound was obtained (99%): $^1$H NMR (300 MHz, CDCl$_3$) δ 10.0-9.70 (br, 1H), 7.45-7.18 (m, 3H), 6.98 (d, 1H), 6.90-6.82 (m, 2H), 5.01 (s, 1H), 3.75-3.66 (m, 2H), 1.76-1.62 (m, 2H), 1.40-1.28 (m, 4H), 0.87 (t, 3H); MS (ES+) m/z 348 (M+1).

C. Synthesis of 3-(5-chloro-4-fluoro-2-hydroxyphenyl)-3-(hydroxymethyl)-1-pentyl-1,3-dihydro-2H-indol-2-one Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with 3-(5-chloro-4-fluoro-2-hydroxyphenyl)-1-pentyl-1,3-dihydro-2H-indol-2-one, the title compound was obtained (46%): MS (ES+) m/z 360 (M−17), 400 (M+23).

PREPARATION 17

Synthesis of 3-(4-chloro-5-fluoro-2-hydroxyphenyl)-3-(hydroxymethyl)-1-pentyl-1,3-dihydro-2H-indol-2-one

A. Synthesis of 3-(4-chloro-5-fluoro-2-hydroxyphenyl)-3-hydroxy-1-pentyl-1,3-dihydro-2H-indol-2-one Following the procedure as described in PREPARATION 1C, and making non-critical variations to replace 4-bromo-1-pentyl-1H-indole-2,3-dione with 1-pentyl-1H-indole-2,3-dione, and 1,3-benzodioxol-5-ol with 3-chloro-4-fluorophenol, the title compound was obtained (14%): MS (ES+) m/z 346 (M−17), 386 (M+23).

B. Synthesis 3-(4-chloro-5-fluoro-2-hydroxyphenyl)-1-pentyl-1,3-dihydro-2H-indol-2-one Following the procedure as described in PREPARATION 15B, and making non-critical variations to replace 3-(5-bromo-2-hydroxyphenyl)-3-hydroxy-1-pentyl-1,3-dihydro-2H-indol-2-one with 3-(4-chloro-5-fluoro-2-hydroxyphenyl)-3-hydroxy-1-pentyl-1,3-dihydro-2H-indol-2-one, the title compound was obtained: MS (ES+) m/z 348 (M+1).

C. Synthesis of 3-(4-chloro-5-fluoro-2-hydroxyphenyl)-3-(hydroxymethyl)-1-pentyl-1,3-dihydro-2H-indol-2-one Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with 3-(4-chloro-5-fluoro-2-hydroxyphenyl)-1-pentyl-1,3-dihydro-2H-indol-2-one, the title compound was obtained (50% for two steps): MS (ES+) m/z 360 (M−17), 400 (M+23).

PREPARATION 18

Synthesis of 3-(4,5-dichloro-2-hydroxyphenyl)-3-(hydroxymethyl)-1-pentyl-1,3-dihydro-2H-indol-2-one

A. Synthesis of 3-(4,5-dichloro-2-hydroxyphenyl)-3-hydroxy-1-pentyl-1,3-dihydro-2H-indol-2-one Following the procedure as described in PREPARATION 1C, and making non-critical variations to replace 4-bromo-1-pentyl-1H-indole-2,3-dione with 1-pentyl-1H-indole-2,3-dione, and 1,3-benzodioxol-5-ol with 3,4-dichlorophenol, the title compound was obtained (26%): $^1$H NMR (300 MHz, CDCl$_3$) δ 9.60 (s, 1H), 7.50-7.40 (m, 2H), 7.22 (td, 1H), 7.11 (s, 1H), 6.95 (d, 1H), 6.86 (s, 1H), 4.31-4.12 (br, 1H), 3.79-3.59 (m, 2H), 1.76-1.62 (m, 2H), 1.40-1.27 (m, 4H), 0.88 (t, 3H); MS (ES+) m/z 363 (M−17), 403 (M+23).

B. Synthesis of 3-(4,5-dichloro-2-hydroxyphenyl)-1-pentyl-1,3-dihydro-2H-indol-2-one Following the procedure as described in PREPARATION 15B, and making non-critical variations to replace 3-(5-bromo-2-hydroxyphenyl)-3-hydroxy-1-pentyl-1,3-dihydro-2H-indol-2-one with 3-(4,5-dichloro-2-hydroxyphenyl)-3-hydroxy-1-pentyl-1,3-dihydro-2H-indol-2-one, the title compound was obtained (86%): $^1$H NMR (300 MHz, CDCl$_3$) δ 10.0-9.50 (br, 1H), 7.42 (t, 1H), 7.32 (d, 1H), 7.22 (td, 1H), 7.09 (s, 1H), 6.95 (d, 1H), 6.93 (s, 1H), 5.04(s, 1H), 3.77-3.68 (m, 2H), 1.77-1.62 (m, 2H), 1.40-1.27 (m, 4H), 0.88 (t, 3H); MS (ES+) m/z 348 (M+1).

C. Synthesis of 3-(4,5-dichloro-2-hydroxyphenyl)-3-(hydroxymethyl)-1-pentyl-1,3-dihydro-2H-indol-2-one Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with 3-(4,5-dichloro-2-hydroxyphenyl)-1-pentyl-1,3-dihydro-2H-indol-2-one, the title compound was obtained: MS (ES+) m/z 376 (M−17), 416 (M+23).

PREPARATION 19

Synthesis of 3-(hydroxymethyl)-3-[2-hydroxy-5-(trifluoromethyl)phenyl]-1-pentyl-1,3-dihydro-2H-indol-2-one

A. Synthesis of 3-hydroxy-3-[2-hydroxy-5-(trifluoromethyl)phenyl]-1-pentyl-1,3-dihydro-2H-indol-2-one Following the procedure as described in PREPARATION 1C, and making non-critical variations to replace 4-bromo-1-pentyl-1H-indole-2,3-dione with 1-pentyl-1H-indole-2,3-dione, and 1,3-benzodioxol-5-ol with α,α,α-trifluorocresol, the title compound was obtained (46%): $^1$H NMR (300 MHz, CDCl$_3$) δ 9.75 (s, 1H), 7.50-7.39 (m, 3H), 7.21 (td, 1H), 7.10-7.02 (m, 2H), 6.96 (d, 1H), 4.26 (s, 1H), 3.82-3.59 (m, 2H), 1.77-1.63 (m, 2H), 1.40-1.27 (m, 4H), 0.88 (t, 3H); MS (ES+) m/z 362 (M−17), 402 (M+23).

B. Synthesis of 3-[2-hydroxy-5-(trifluoromethyl)phenyl]-1-pentyl-1,3-dihydro-2H-indol-2-one Following the procedure as described in PREPARATION 15B, and making non-critical variations to replace 3-(5-bromo-2-hydroxyphenyl)-3-hydroxy-1-pentyl-1,3-dihydro-2H-indol-2-one with 3-hydroxy-3-[2-hydroxy-5-(trifluoromethyl)phenyl]-1-pentyl-1,3-dihydro-2H-indol-2-one, the title compound was obtained (78%): $^1$H NMR (300 MHz, CDCl$_3$) δ 8.20-8.00 (br, 1H), 7.43-7.14 (m, 5H), 7.02 (d, 1H), 6.95 (d, 1H), 5.11(s, 1H), 3.82-3.72 (m, 2H), 1.79-1.66 (m, 2H), 1.40-1.27 (m, 4H), 0.88 (t, 3H); MS (ES+) m/z 364 (M+1).

C. Synthesis of 3-(hydroxymethyl)-3-[2-hydroxy-5-(trifluoromethyl)phenyl]-1-pentyl-1,3-dihydro-2H-indol-2-one Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with 3-[2-hydroxy-5-(trifluoromethyl)phenyl]-1-pentyl-1,3-dihydro-2H-indol-2-one, the title compound was obtained: MS (ES+) m/z 376 (M−17), 416 (M+23).

PREPARATION 20

Synthesis of 3-(2-hydroxy-4-methoxyphenyl)-3-(hydroxymethyl)-1-pentyl-1,3-dihydro-2H-indol-2-one

A. Synthesis of 3-(5-bromo-2-hydroxy-4-methoxyphenyl)-3-hydroxy-1-pentyl-1,3-dihydro-2H-indol-2-one Following the procedure as described in PREPARATION 1C, and making non-critical variations to replace 4-bromo- 1-pentyl-1H-indole-2,3-dione with 1-pentyl-1H-indole-2,3-dione, and 1,3-benzodioxol-5-ol with 4-bromo-3-methoxyphenol, the title compound was obtained (48%): ¹H NMR (300 MHz, CDCl₃) δ 9.85 (s, 1H), 7.52-7.38 (m, 2H), 7.22 (td, 1H), 6.94 (d, 1H), 6.89 (s, 1H), 6.63 (s, 1H), 4.13-4.03 (br, 1H)3.86(s, 3H), 3.80-3.57 (m, 2H), 1.75-1.63 (m, 2H), 1.40-1.25 (m, 4H), 0.88 (t, 3H); MS (ES+) m/z 402 (M−17), 404 (M−17), 442 (M+23), 444 (M+23).

B. Synthesis of 3-(2-hydroxy-4-methoxyphenyl)-1-pentyl-1,3-dihydro-2H-indol-2-one Following the procedure as described in PREPARATION 15B, and making non-critical variations to replace 3-(5-bromo-2-hydroxyphenyl)-3-hydroxy-1-pentyl-1,3-dihydro-2H-indol-2-one with 3-(5-bromo-2-hydroxy-4-methoxyphenyl)-3-hydroxy-1-pentyl-1,3-dihydro-2H-indol-2-one, the title compound was obtained (83%): ¹H NMR (300 MHz, CDCl₃) δ 9.78-9.20 (br, 1H), 7.43-7.31 (m, 2H), 7.19 (t, 1H), 6.97 (d, 1H), 6.79 (d, 1H), 6.70-6.64 (m, 1H), 6.38 (dd, 1H), 5.02 (s, 1H), 3.77 (s, 3H), 3.70 (t, 2H), 1.75-1.63 (m, 2H), 1.40-1.25 (m, 4H), 0.87 (t, 3H); MS (ES+) m/z 326 (M+1).

C. Synthesis of 3-(2-hydroxy-4-methoxyphenyl)-3-(hydroxymethyl)-1-pentyl-1,3-dihydro-2H-indol-2-one Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with 3-(2-hydroxy-4-methoxyphenyl)-1-pentyl-1,3-dihydro-2H-indol-2-one, the title compound was obtained (41%): ¹H NMR (300 MHz, CDCl₃) δ 10.79 (s, 1H), 7.51-7.37 (m, 2H), 7.26 (td, 1H), 6.99 (d, 1H), 6.95 (d, 1H), 6.59 (d, 1H), 6.34 (dd, 1H), 4.67 (d, 1H), 4.14 (d, 1H), 3.76 (s, 3H), 3.78-3.69 (m, 2H), 1.75-1.63 (m, 2H), 1.40-1.25 (m, 4H), 0.87 (t, 3H); MS (ES+) m/z 338 (M−17), 378 (M+23).

PREPARATION 21

Synthesis of ethyl [3-(6-hydroxy-2,3-dihydro-1H-inden-5-yl)-3-(hydroxymethyl)-2-oxo-2,3-dihydro-1H-indol-1-yl]acetate A. Synthesis of ethyl [3-hydroxy-3-(6-hydroxy-2,3-dihydro-1H-inden-5-yl)-2-oxo-2,3-dihydro-1H-indol-1-yl]acetate Following the procedure as described in PREPARATION 1C, and making non-critical variations to replace 4-bromo-1-pentyl-1H-indole-2,3-dione with ethyl (2,3-dioxo-2,3-dihydro-1H-indol-1-yl)acetate, and 1,3-benzodioxol-5-ol with 5-indanol, the title compound was obtained (84%): ¹H NMR (300 MHz, CDCl₃) δ 8.76 (s, 1H), 7.55 (d, 1H), 7.38 (td, 1H), 7.20 (t, 1H), 6.9 (s, 1H), 6.80 (d, 1H), 6.65 (s, 1H), 4.45 (ABq, 2H), 4.32-4.25 (br, 1H), 4.20 (q, 2H), 2.83 (t, 2H), 2.74-2.65 (m, 2H), 2.06-1.94 (m, 2H), 1.27 (t, 3H); MS (ES+) m/z 350 (M−17), 390 (M+23).

B. Synthesis of ethyl [3-(6-hydroxy-2,3-dihydro-1H-inden-5-yl)-2-oxo-2,3-dihydro-1H-indol-1-yl]acetate Following the procedure as described in PREPARATION 15B, and making non-critical variations to replace 3-(5-bromo-2-hydroxyphenyl)-3-hydroxy-1-pentyl-1,3-dihydro-2H-indol-2-one with ethyl [3-hydroxy-3-(6-hydroxy-2,3-dihydro-1H-inden-5-yl)-2-oxo-2,3-dihydro-1H-indol-1-yl] acetate, the title compound was obtained: ¹H NMR (300 MHz, CDCl₃) δ 8.50-7.90 (br, 1H), 7.40-7.32 (m, 2H), 7.38 (td, 1H), 6.94 (s, 1H), 6.84 (d, 1H), 6.75 (s, 1H), 5.16 (s, 1H), 4.48 (ABq, 2H), 4.21 (q, 2H), 2.85 (t, 2H), 2.81-2.61 (m, 2H), 2.09-1.92 (m, 2H), 1.25 (t, 3H); MS (ES+) m/z 352 (M+1).

C. Synthesis of ethyl [3-(6-hydroxy-2,3-dihydro-1H-inden-5-yl)-3-(hydroxymethyl)-2-oxo-2,3-dihydro-1H-indol-1-yl]acetate Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with ethyl [3-(6-hydroxy-2,3-dihydro-1H-inden-5-yl)-2-oxo-2,3-dihydro-1H-indol-1-yl]acetate, the title compound was obtained: MS (ES+) m/z 364 (M−17), 404 (M+23).

PREPARATION 22

Synthesis of ethyl [3-(hydroxymethyl)-3-(3-hydroxy-5,6,7,8-tetrahydronaphthalen-2-yl)-2-oxo-2,3-dihydro-1H-indol-1-yl]acetate A. Synthesis of ethyl [3-hydroxy-3-(3-hydroxy-5,6,7,8-tetrahydronaphthalen-2-yl)-2-oxo-2,3-dihydro-1H-indol-1-yl]acetate Following the procedure as described in PREPARATION 1C, and making non-critical variations to replace 4-bromo-1-pentyl-1H-indole-2,3-dione with ethyl (2,3-dioxo-2,3-dihydro-1H-indol-1-yl)acetate, and 1,3-benzodioxol-5-ol with 5,6,7,8-tetrahydronapthalen-2-ol, the title compound was obtained (81%): ¹H NMR (300 MHz, CDCl₃) δ 8.61 (s, 1H), 7.54 (dd, 1H), 7.38 (td, 1H), 7.20 (t, 1H), 6.80 (d, 1H), 6.76 (s, 1H), 6.50 (s, 1H), 4.45 (ABq, 2H), 4.21 (q, 2H), 4.18-4.14 (br, 1H), 2.73-2.47 (m, 4H), 1.77-1.63 (m, 4H), 1.24 (t, 3H); MS (ES+) m/z 364 (M−17), 404 (M+23)

B. Synthesis of ethyl [3-(3-hydroxy-5,6,7,8-tetrahydronaphthalen-2-yl)-2-oxo-2,3-dihydro-1H-indol-1-yl]acetate Following the procedure as described in PREPARATION 15B, and making non-critical variations to replace 3-(5-bromo-2-hydroxyphenyl)-3-hydroxy-1-pentyl-1,3-dihydro-2H-indol-2-one with ethyl [3-hydroxy-3-(3-hydroxy-5,6,7,8-tetrahydronaphthalen-2-yl)-2-oxo-2,3-dihydro-1H-indol-1-yl]acetate, the title compound was obtained: ¹H NMR (300 MHz, CDCl₃) δ 7.42-7.32 (m, 2H), 7.20 (t, 1H), 6.84 (d, 1H), 6.78 (s, 1H), 6.61 (s, 1H), 5.12 (s, 1H), 4.47 (ABq, 2H), 4.21 (q, 2H), 2.76-2.44 (m, 4H), 1.78-1.64 (m, 4H), 1.24 (t, 3H); MS (ES+) m/z 366 (M+1).

C. Synthesis of ethyl [3-(hydroxymethyl)-3-(3-hydroxy-5,6,7,8-tetrahydronaphthalen-2-yl)-2-oxo-2,3-dihydro-1H-indol-1-yl]acetate Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with ethyl [3-(3-hydroxy-5,6,7,8-tetrahydronaphthalen-2-yl)-2-oxo-2,3-dihydro-1H-indol-1-yl]acetate, the title compound was obtained: MS (ES+) m/z 378 (M−17), 418 (M+23).

PREPARATION 23

Synthesis of ethyl [4-bromo-3-(4,5-difluoro-2-hydroxyphenyl)-3-(hydroxymethyl)-2-oxo-2,3-dihydro-1H-indol-1-yl]acetate

A. Synthesis of ethyl (4-bromo-2,3-dioxo-2,3-dihydro-1H-indol-1-yl)acetate

Following the procedure as described in PREPARATION 2A, and making non-critical variations to replace isatin with 4-bromoisatin and (2-bromoethyl)cyclopropane with ethyl bromoacetate, the title compound was obtained as a yellow solid (68%): $^1$H NMR (300 MHz, CDCl$_3$) δ 7.39 (t, 1H), 7.27(dd, 1H), 6.71 (dd, 1H), 4.47 (s, 2H), 4.23 (q, 2H), 1.27 (t, 3H); MS (ES+) m/z 312 (M+1), 314 (M+1), 334 (M+23) 336 (M+23).

B. Synthesis of ethyl [4-bromo-3-(4,5-difluoro-2-hydroxyphenyl)-3-hydroxy-2-oxo-2,3-dihydro-1H-indol-1-yl]acetate Following the procedure as described in PREPARATION 2B, and making non-critical variations to replace 1-(2-cyclopropylethyl)-1H-indole-2,3-dione with ethyl (4-bromo-2,3-dioxo-2,3-dihydro-1H-indol-1-yl)acetate and 1,3-benzodioxol-5-ol with 3,4-difluorophenol, the title compound was obtained as a white solid (42%); MS (ES+) m/z 424 (M−17), 426 (M−17), 464 (M+23), 466 (M+23).

C. Synthesis of ethyl [4-bromo-3-(4,5-difluoro-2-hydroxyphenyl)-2-oxo-2,3-dihydro-1H-indol-1-yl]acetate A mixture of ethyl [4-bromo-3-(4,5-difluoro-2-hydroxyphenyl)-3-hydroxy-2-oxo-2,3-dihydro-1H-indol-1-yl]acetate (0.90 g, 2.00 mmol), triethylsilane (2.00 mL, 12.2 mmol) and trifluroacetic acid (0.94 mL, 12.2 mmol) was heated at 90° C. for two days. After cooling down to ambient temperature, the mixture was diluted with ethyl acetate (200 mL), washed with water, dried over anhydrous sodium sulfate and filtered. The filtrate was concentrated in vacuo to dryness. The residue was subjected to column chromatography (ethyl acetate/hexanes, 1/3) to give the title compound (0.37 g, 43%): $^1$H NMR (300 MHz, CDCl$_3$) δ 7.35-7.22 (m, 3H), 6.82-6.71 (m, 2H), 6.52 (t, 1H), 5.10 (s, 1H), 4.45 (s, 2H), 4.21 (q, 2H), 1.23 (t, 3H); MS (ES+) m/z 426.4 (M+1), 428.4 (M+1).

D. Synthesis of ethyl [4-bromo-3-(4,5-difluoro-2-hydroxyphenyl)-3-(hydroxymethyl)-2-oxo-2,3-dihydro-1H-indol-1-yl]acetate Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with ethyl [4-bromo-3-(4,5-difluoro-2-hydroxyphenyl)-2-oxo-2,3-dihydro-1H-indol-1-yl]acetate, the title compound was obtained (83%): MS (ES+) m/z 456.3 (M+1), 458.3 (M+1).

PREPARATION 24

Synthesis of ethyl [4-bromo-3-(6-hydroxy-2,2-dimethyl-2,3-dihydro-1-benzofuran-5-yl)-3-(hydroxymethyl)-2-oxo-2,3-dihydro-1H-indol-1-yl]acetate

A. Synthesis of 6-(benzyloxy)-2,2-dimethylbenzofuran-3(2H)-one

To a solution of 6-(benzyloxy)benzofuran-3(2H)-one (Adams, J. L., et al., *J. Med. Chem.* (1996), 39(26):5035-46) (1.60 g, 6.67 mmol) in DMF (50.0 mL) were added sodium hydride (0.59 g, 14.7 mmol) and iodomethane (1.46 mL, 23.3 mmol) at 0° C. The reaction mixture was stirred at ambient temperature for 16 h and quenched with saturated ammonium chloride (50.0 mL). The aqueous mixture was extracted with ethyl acetate (3×50.0 mL). The combined organic layers was dried over anhydrous sodium sulfate and filtered. The filtrate was concentrated in vacuo to dryness. The residue was subjected to column chromatography (ethyl acetate/hexane, 1/10) to give the title compound (0.85 g, 47%): $^1$H NMR (300 MHz, CDCl$_3$) δ 7.55 (d, 1H), 7.44-7.30 (m, 5H), 6.69 (dd, 1H), 6.54 (d, 1H), 5.10 (s, 2H), 1.43 (s, 6H); MS (ES+) m/z 269.5 (M+1).

B. Synthesis of 2,2-dimethyl-2,3-dihydrobenzofuran-6-ol

To a solution of 6-(benzyloxy)-2,2-dimethylbenzofuran-3(2H)-one (0.85 g, 3.20 mmol) in methanol (100 mL) was added palladium hydroxide (0.22 g, 20 wt. % loading, 0.32 mmol). The resulting mixture was hydrogenated for 16 hours under 60 psi of hydrogen. The reaction mixture was filtered through celite, washed with methanol. The filtrate was concentrated in vacuo to dryness. The residue was subjected to column chromatography (ethyl acetate/hexane, 1/5) to give the title compound (0.46 g, 88%): $^1$H NMR (300 MHz, CDCl$_3$) δ 6.92 (d, 1H), 6.30-6.21 (m, 2H), 4.77 (s, 1H), 2.90 (s, 2H), 1.44 (s, 6H).

C. Synthesis of ethyl [4-bromo-3-hydroxy-3-(6-hydroxy-2,2-dimethyl-2,3-dihydro-1-benzofuran-5-yl)-2-oxo-2,3-dihydro-1H-indol-1-yl]acetate Following the procedure as described in PREPARATION 2B, and making non-critical variations to replace 1-(2-cyclopropylethyl)-1H-indole-2,3-dione with ethyl (4-bromo-2,3-dioxo-2,3-dihydro-1H-indol-1-yl)acetate and 1,3-benzodioxol-5-ol with 2,2-dimethyl-2,3-dihydrobenzofuran-6-ol, the title compound was obtained: MS (ES+) m/z 498.5 (M+23), 500.5 (M+23).

D. Synthesis of ethyl [4-bromo-3-(6-hydroxy-2,2-dimethyl-2,3-dihydro-1-benzofuran-5-yl)-2-oxo-2,3-dihydro-1H-indol-1-yl]acetate A mixture of ethyl [4-bromo-3-hydroxy-3-(6-hydroxy-2,2-dimethyl-2,3-dihydro-1-benzofuran-5-yl)-2-oxo-2,3-dihydro-1H-indol-1-yl]acetate (1.32 g, 2.80 mmol), triethylsilane (2.00 mL, 12.2 mmol) and trifluoroacetic acid (0.94 mL, 12.2 mmol) in dichloromethane (50.0 mL) was stirred at 35° C. for 3 hours. The mixture was diluted with dichloromethane (100 mL), washed with water, dried over anhydrous sodium sulfate and filtered. The filtrate was concentrated in vacuo to dryness. The residue was subjected to column chromatography (ethyl acetate/hexane, 1/3) to give the title compound (1.04 g, 81%): $^1$H NMR (300 MHz, CDCl$_3$) δ 7.32-7.15 (m, 2H), 6.74 (d, 1H), 6.50-6.36 (br, 2H), 5.04 (s, 1H), 4.51-4.34 (m, 2H), 4.25-4.14 (m, 2H), 2.92-2.69 (m, 2H), 1.43 (s, 3H), 1.37 (s, 3H), 1.23 (t, 3H); MS (ES+) m/z 460.5 (M+1), 462.5 (M+1).

E. Synthesis of ethyl [4-bromo-3-(6-hydroxy-2,2-dimethyl-2,3-dihydro-1-benzofuran-5-yl)-3-(hydroxymethyl)-2-oxo-2,3-dihydro-1H-indol-1-yl]acetate Following the procedure as described in PREPARATION 1E, and making non-critical variations to replace 4-bromo-3-

(6-hydroxy-1,3-benzodioxol-5-yl)-1-pentyl-1,3-dihydro-2H-indol-2-one with ethyl [4-bromo-3-(6-hydroxy-2,2-dimethyl-2,3-dihydro-1-benzofuran-5-yl)-2-oxo-2,3-dihydro-1H-indol-1-yl]acetate, the title compound was obtained (25%): MS (ES+) m/z 490.5 (M+1), 492.5 (M+1).

PREPARATION 25

Synthesis of
3,3-dimethyl-2,3-dihydro-1-benzofuran-6-ol

A. Synthesis of
4-(benzyloxy)-1-bromo-2-(2-methylallyloxy)benzene

To a solution of 5-(benzyloxy)-2-bromophenol (Simas, A. B. C., et al, *Synthesis*, (1999):1017-21) (8.15 g, 29.3 m mol) in DMF (150 mL) was added potassium carbonate (4.46 g, 32.2 mmol) slowly at 0° C. The mixture was stirred at ambient temperature for half an hour, followed by the addition of 3-bromo-2-methylpropene (3.35 mL, 32.2 mmol) during half an hour at 0° C. The mixture was stirred at ambient temperature overnight and quenched with saturated ammonium chloride (50 mL). The aqueous mixture was extracted with ethyl acetate (3×200 mL). The combined organic layers was dried over anhydrous sodium sulfate and filtered. The filtrate was concentrated in vacuo. The residue was subjected to column chromatography (ethyl acetate/hexane, 1/20) to give the title compound (10.0 g, 94%): $^1$H NMR (300 MHz, CDCl$_3$) δ 7.43-7.29 (m, 5H), 6.53 (d, 1H), 6.45 (dd, 1H), 5.15-4.94 (m, 4H), 4.43 (s, 2H), 1.82 (s, 3H); $^{13}$C NMR (75 MHz, CDCl$_3$) δ 159.1, 155.6, 140.1, 136.5, 133.1, 128.6, 128.1, 127.5, 112.9, 107.2, 103.3, 102.0, 72.4, 70.3, 19.3.

B. Synthesis of
6-(benzyloxy)-3,3-dimethyl-2,3-dihydrobenzofuran

To a solution of 4-(benzyloxy)-1-bromo-2-(2-methylallyloxy)benzene (5.00 g, 15.1 mmol) in benzene (400 mL) was added tributyltin hydride (7.42 mL, 27.2 mmol) and benzoyl peroxide (0.70 g, 2.90 mmol) at 0° C. The resulting mixture was refluxed at 100° C. overnight. After cooling down to ambient temperature, the mixture was washed with water, dried over anhydrous sodium sulfate and filtered. The filtrate was concentrated in vacuo to dryness. The residue was subjected to column chromatography (ethyl acetate/hexane, 1/20) to give the title compound (3.48 g, 91%): MS (ES+) m/z 255.6 (M+1).

C. Synthesis of
3,3-dimethyl-2,3-dihydro-1-benzofuran-6-ol

To a solution of 6-(benzyloxy)-3,3-dimethyl-2,3-dihydrobenzofuran (3.48 g, 13.7 mmol) in methanol (200 mL) was added Pd/C (1.45 g) and the mixture was hydrogenated under 40 psi of hydrogen overnight. The reaction mixture was filtered through celite, washed with methanol. The filtrate was concentrated in vacuo to dryness. The residue was subjected to column chromatography (ethyl acetate/hexane, 1/7) to give the title compound (1.66 g, 74%): MS (ES+) m/z 165.4 (M+1).

PREPARATION 26

Synthesis of 1-(diphenylmethyl)-3-(5-hydroxy-2,3-dihydro-1-benzofuran-6-yl)-3-(hydroxymethyl)-1,3-dihydro-2H-indol-2-one A. Synthesis of 1-(diphenylmethyl)-3-hydroxy-3-(5-hydroxy-2,3-dihydro-1-benzofuran-6-yl)-1,3-dihydro-2H-indol-2-one Following the procedure as described in PREPARATION 2B, and making non-critical variations to replace 1,3-benzodioxol-5-ol with 2,3-dihydrobenzofuran-5-ol, (Alabaster, R. J., et al.; *Synthesis* (1988), 12:950-2) and 1-(2-cyclopropylethyl)-1H-indole-2,3-dione with 1-(diphenylmethyl)-1H-indole-2,3-dione, the title compound was obtained: MS (ES+) m/z 472.2 (M+23).

B. Synthesis of 1-(diphenylmethyl)-3-(5-hydroxy-2,3-dihydro-1-benzofuran-6-yl)-1,3-dihydro-2H-indol-2-one Following the procedure as described in PREPARATION 2C, and making non-critical variations to replace 1-(2-cyclopropylethyl)-3-hydroxy-3-(6-hydroxy-1,3-benzodioxol-5-yl)-1,3-dihydro-2H-indol-2-one with 1-(diphenylmethyl)-3-hydroxy-3-(5-hydroxy-2,3-dihydro-1-benzofuran-6-yl)-1,3-dihydro-2H-indol-2-one, the title compound was obtained: MS (ES+) m/z 434.4 (M+1).

C. Synthesis of 1-(diphenylmethyl)-3-(5-hydroxy-2,3-dihydro-1-benzofuran-6-yl)-3-(hydroxymethyl)-1,3-dihydro-2H-indol-2-one To a solution of 1-(diphenylmethyl)-3-(5-hydroxy-2,3-dihydro-1-benzofuran-6-yl)-1,3-dihydro-2H-indol-2-one (1.01 g, 2.30 mmol) in THF (50.0 mL) was added paraformaldehyde (1.00 g, 30.0 mmol). Argon was bubbled through the reaction mixture for one hour followed by the addition of diisopropylamine (1.00 g, 10.0 mmol) at 0° C. The reaction mixture was stirred at ambient temperature for 20 hours and diluted with ethyl acetate (100 mL). The resulting mixture was washed with water (2×50.0 mL), dried over sodium sulfate and filtered. The filtrate was concentrated in vacuo to dryness to give 0.67 g (65%) of the title compound: MS (ES+) m/z 486.4 (M+23).

PREPARATION 27

Synthesis of 3-(6-hydroxy-1,3-benzodioxol-5-yl)-3-(hydroxymethyl)-4-methoxy-1-{[5-(trifluoromethyl)-2-furyl]methyl}-1,3-dihydro-2H-indol-2-one A. Synthesis of ethyl 2-(2-(tert-butoxycarbonylamino)-6-methoxyphenyl)-2-oxoacetate To a solution of tert-butyl 3-methoxyphenylcarbamate (25.6 g, 0.11 mol) in THF (300 mL) was added n-BuLi (0.25 mol, 1.6 M solution in pentane) at −78° C. The resulted solution was stirred at 0° C. for 3 hours and re-cooled to −78° C. followed by the addition of diethyl oxalate (20.1 g, 0.14 mol). The mixture was stirred at −78° C. for 45 min and at ambient temperature for one hour, and quenched with 1 N HCl. The mixture was extracted with ether. The organic solution was dried over sodium sulfate and filtered. The filtrate was concentrated in vacuo to dryness. The residue was subjected to column chromatography to give 3.70 g (27% based on recovered starting material) of the title compound: MS (ES+) m/z 324.3 (M+1).

B. Synthesis of 4-methoxy-1H-indole-2,3-dione

A mixture of ethyl 2-(2-(tert-butoxycarbonylamino)-6-methoxyphenyl)-2-oxoacetate (3.70 g, 110 mmol) and 10% $H_2SO_4$ (100 mL) was heated at 100° C. for 10 hours. After cooling down to ambient temperature, the reaction mixture was extracted with ether (3×100 mL). The combined ether solution was washed with water (2×50.0 mL), dried over sodium sulfate and filtered. The filtrate was concentrated in vacuo to dryness. The residue was subjected to column chromatography to give 0.37 g (19%) of the title compound: MS (ES+) m/z 200.1 (M+23).

C. Synthesis of 4-methoxy-1-{[5-(trifluoromethyl)-2-furyl]methyl}-1H-indole-2,3-dione Following the procedure as described in PREPARATION 1A, and making non-critical variations to replace 4-bromoindole with 4-methoxy-1H-indole-2,3-dione, and 1-bromopentane with 2-(bromomethyl)-5-(trifloromethyl)furan, the title compound was obtained (26%): MS (ES+) m/z 348.2 (M+23).

D. Synthesis of 3-hydroxy-3-(6-hydroxy-1,3-benzodioxol-5-yl)-4-methoxy-1-{[5-(trifluoromethyl)-2-furil]methyl}-1,3-dihydro-2H-indol-2-one Following the procedure as described in PREPARATION 2B, and making non-critical variations to replace 1-(2-cyclopropylethyl)-1H-indole-2,3-dione with 4-methoxy-1-{[5-(trifluoromethyl)-2-furyl]methyl}-1H-indole-2,3-dione, the title compound was obtained (56%): MS (ES+) m/z 486.4 (M+23).

E. Synthesis of 3-(6-hydroxy-1,3-benzodioxol-5-yl)-4-methoxy-1-{[5-(trifluoromethyl)-2-furyl]methyl}-1,3-dihydro-2H-indol-2-one Following the procedure as described in PREPARATION 2C, and making non-critical variations to replace 1-(2-cyclopropylethyl)-3-hydroxy-3-(6-hydroxy-1,3-benzodioxol-5-yl)-1,3-dihydro-2H-indol-2-one with 3-hydroxy-3-(6-hydroxy-1,3-benzodioxol-5-yl)-4-methoxy-1-{[5-(trifluoromethyl)-2-furil]methyl}-1,3-dihydro-2H-indol-2-one, the title compound was obtained (86%): MS (ES+) m/z 448.4 (M+1).

F. Synthesis of 3-(6-hydroxy-1,3-benzodioxol-5-yl)-3-(hydroxymethyl)-4-methoxy-1-{[5-(trifluoromethyl)-2-furyl]methyl}-1,3-dihydro-2H-indol-2-one Following the procedure as described in PREPARATION 26C, and making non-critical variations to replace 1-(diphenylmethyl)-3-(5-hydroxy-2,3-dihydro-1-benzofuran-6-yl)-1,3-dihydro-2H-indol-2-one with 3-(6-hydroxy-1,3-benzodioxol-5-yl)-4-methoxy-1-{[5-(trifluoromethyl)-2-furyl]methyl}-1,3-dihydro-2H-indol-2-one, the title compound was obtained (64%): MS (ES+) m/z 500.4 (M+23).

PREPARATION 28

Synthesis of 4,7-dichloro-3-(6-hydroxy-1,3-benzodioxol-5-yl)-3-(hydroxymethyl)-1-pentyl-1,3-dihydro-2H-indol-2-one

A. Synthesis of 4,7-dichloro-1-pentyl-1H-indole-2,3-dione

To a mixture of sodium hydride (0.17 g, 6.94 mmol, 60% dispersion in mineral oil) in anhydrous N,N-dimethylformamide (5.00 mL) was added a solution of 4,7-dichloro-1H-indole-2,3-dione (1.00 g, 4.60 mmol) in N,N-dimethylformamide (5.00 mL) at 0° C. The brown reaction mixture was stirred for 0.5 h followed by the addition of a solution of 1-bromopentane (0.84 g, 5.55 mmol) in anhydrous N,N-dimethylformamide (5.00 mL). The reaction mixture was stirred at ambient temperature for 16 h and poured into wet ethyl ether (30.0 mL). After the organic layer was separated, it was washed with water (2×20.0 mL), dried over anhydrous sodium sulfate and filtered. The filtrate was concentrated in vacuo to dryness. The gummy residue was dried under vacuum and the solid was triturated with ether to give the title compound (0.98 g, 98%): MS (ES+) m/z 286.2 (M+1).

B. Synthesis of 4,7-dichloro-3-hydroxy-3-(6-hydroxy-1,3-benzodioxol-5-yl)-1-pentyl-1,3-dihydro-2H-indol-2-one Following the procedure as described in PREPARATION 2B, and making non-critical variations to replace 1-(2-cyclopropylethyl)-1H-indole-2,3-dione with 4,7-dichloro-1-pentyl-1H-indole-2,3-dione, the title compound was obtained (68%) as a white solid: $^1$H NMR (300 MHz, CDCl$_3$) δ 8.61 (s, br, 1H), 7.26 (t, 1H), 7.03 (d, 1H), 6.52 (s, 1H), 6.12 (s, 1H), 5.86 (dd, 2H), 4.21 (s, br, 1H), 4.01-3.96 (m, 2H), 1.73-1.58 (m, 2H), 1.34-1.21 (m, 4H), 0.84 (t, 3H); MS (ES+) m/z 408.2 (M−17).

C. Synthesis of 4,7-dichloro-3-(6-hydroxy-1,3-benzodioxol-5-yl)-1-pentyl-1,3-dihydro-2H-indol-2-one Following the procedure as described in PREPARATION 2C, and making non-critical variations to replace 1-(2-cyclopropylethyl)-3-hydroxy-3-(6-hydroxy-1,3-benzodioxol-5-yl)-1,3-dihydro-2H-indol-2-one with 4,7-dichloro-3-hydroxy-3-(6-hydroxy-1,3-benzodioxol-5-yl)-1-pentyl-1,3-dihydro-2H-indol-2-one, the title compound was obtained (72%) as a white solid: $^1$H NMR (300 MHz, CDCl$_3$) δ 7.27-7.23 (m, 1H), 7.03 (d, 1H), 6.55 (s, 1H), 6.04 (s, 1H), 5.84 (dd, 2H), 5.03 (s, 1H), 4.09-3.99 (m, 2H), 1.72-1.62 (m, 2H), 1.33-1.24 (m, 4H), 0.86 (t, 3H); MS (ES+) m/z 409.2 (M+1).

D. Synthesis of 4,7-dichloro-3-(6-hydroxy-1,3-benzodioxol-5-yl)-3-(hydroxymethyl)-1-pentyl-1,3-dihydro-2H-indol-2-one Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with 4,7-dichloro-3-(6-hydroxy-1,3-benzodioxol-5-yl)-1-pentyl-1,3-dihydro-2H-indol-2-one, the title compound was obtained (94%) as a gummy solid: MS (ES+) m/z 439.3 (M+1).

PREPARATION 29

Synthesis of ethyl 2-(4-chloro-3-(6-hydroxy-2,3-dihydrobenzofuran-5-yl)-3-(hydroxymethyl)-2-oxoindolin-1-yl)acetate

A. Synthesis of ethyl (4-chloro-2,3-dioxo-2,3-dihydro-1H-indol-1-yl)acetate

Following the procedure as described in PREPARATION 2A, and making non-critical variations to replace isatin with 4-chloro-1H-indole-2,3-dione, and (2-bromoethyl)cyclopropane with ethyl bromoacetate, the title compound was obtained (95%) as a colorless solid: $^1$H NMR (300 MHz, CDCl$_3$) δ 7.48 (t, 1H), 7.08 (d, 1H), 6.67 (d, 1H), 4.47 (s, 2H), 4.23 (q, 2H), 1.27 (t, 3H); MS (ES+) m/z 268.6 (M+1).

B. Synthesis of ethyl [4-chloro-3-hydroxy-3-(6-hydroxy-2,3-dihydro-1-benzofuran-5-yl)-2-oxo-2,3-dihydro-1H-indol-1-yl]acetate Following the procedure as described in PREPARATION 2B, and making non-critical variations to replace 1-(2-cyclopropylethyl)-1H-indole-2,3-dione with ethyl (4-chloro-2,3-dioxo-2,3-dihydro-1H-indol-1-yl)acetate, the title compound was obtained (75%) as a white solid: $^1$H NMR (300 MHz, CDCl$_3$) δ 8.70 (br, 1H), 7.31 (t, 1H), 7.12 (d, 1H), 6.68 (d, 1H), 6.46 (d, 2H), 4.53-4.46 (m, 2H), 4.18 (q, 2H), 3.08-2.88 (m, 2H), 1.23 (t, 3H); MS (ES+) m/z 387.8 (M−17).

C. Synthesis ethyl [4-chloro-3-(6-hydroxy-2,3-dihydro-1-benzofuran-5-yl)-2-oxo-2,3-dihydro-1H-indol-1-yl]acetate Following the procedure as described in PREPARATION 2C, and making non-critical variations to replace 1-(2-cyclopropylethyl)-3-hydroxy-3-(6-hydroxy-1,3-benzodioxol-5-yl)-1,3-dihydro-2H-indol-2-one with ethyl [4-chloro-3-hydroxy-3-(6-hydroxy-2,3-dihydro-1-benzofuran-5-yl)-2-oxo-2,3-dihydro-1H-indol-1-yl]acetate, the title compound was obtained (75%) as a white solid: $^1$H NMR (300 MHz, CDCl$_3$) δ 7.33-7.27 (m, 2H), 7.12 (d, 1H), 6.71 (d, 1H), 6.50-6.48 (m, 1H), 5.10 (s, 1H), 4.54-4.42 (m, 4H), 4.19 (q, 2H), 3.11-2.90 (m, 2H), 1.23 (t, 3H); MS (ES+) m/z 388.8 (M+1).

D. Synthesis of ethyl [4-chloro-3-(6-hydroxy-2,3-dihydro-1-benzofuran-5-yl)-3-(hydroxymethyl)-2-oxo-2,3-dihydro-1H-indol-1-yl]acetate Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with ethyl [4-chloro-3-(6-hydroxy-2,3-dihydro-1-benzofuran-5-yl)-2-oxo-2,3-dihydro-1H-indol-1-yl]acetate, the title compound was obtained (99%) as a gummy solid: MS (ES+) m/z 418.7 (M+1).

PREPARATION 30

Synthesis of 3-hydroxy-3-[6-(hydroxymethyl)-1,3-benzodioxol-5-yl]-1-pentyl-1,3-dihydro-2H-indol-2-one To a solution of (6-bromo-1,3-benzodioxol-5-yl)methanol (Mann, J., et al, *J. Chem. Soc. Perkin Trans.* 1 (1984):2081-8) (1.27 g, 5.50 mmol) in THF (45.0 mL) was added n-BuLi (5.00 mL, 2.0 M, 10.0 mmol) dropwise at −75° C. The reaction mixture was stirred at −75° C. for 45 min followed by the addition of a solution of 1-pentyl-1H-indole-2,3-dione (1.00 g, 4.60 mmol) in THF (20.0 mL) at −75° C. The resulting mixture was stirred at ambient temperature for 12 hrs and quenched with ammonium chloride solution (5.00 mL). More ethyl acetate and water were added and separated. The organic layer was concentrated in vacuo to dryness. The residue was subjected to column chromatography eluting with 50% EtOAc:Hexanes to yield the title compound (0.29 g, 25%) as a solid: $^1$H NMR (300 MHz, CDCl$_3$) δ 7.38-7.24 (m, 2H), 7.11 (t, 1H), 6.91 (d, 1H), 6.81(s, 1H), 6.43 (s, 1H), 5.90-5.87 (m, 2H), 4.77 (dd, 2H), 3.75-3.56 (m, 2H), 1.75-1.58 (m, 2H), 1.26-1.35 (m, 2H), 0.89-0.83 (m, 3H); $^{13}$C NMR (75 MHz, CDCl$_3$) δ 177.8, 147.4, 147.2, 142.8, 133.5, 132.2, 131.1, 130.1, 125.3, 123.8, 111.4, 109.2, 108.1, 101.5, 79.5, 64.7, 40.4, 29.0, 26.8, 22.3, 13.9; MS (ES+) m/z 352.1 (M−17).

PREPARATION 31

Synthesis of ethyl [1-hexyl-3-(6-hydroxy-1,3-benzodioxol-5-yl)-2-oxo-2,3-dihydro-1H-indol-3-yl]acetate

A. Synthesis of 1-hexyl-1H-indole-2,3-dione

Following the procedure as described in PREPARATION 2A, and making non-critical variations to replace (2-bromoethyl)cyclopropane with n-bromohexane, the title compound was obtained (90%) as a viscous gum: $^1$H NMR (300 MHz, CDCl$_3$) δ 7.58-7.51 (m, 2H), 7.08 (t, 1H), 6.87 (d, 1H), 3.68 (t, 2H), 1.71-1.62 (m, 2H), 1.41-1.22 (m, 6H), 0.85 (t, 3H).

B. Synthesis of 1-hexyl-3-hydroxy-3-(6-hydroxy-1,3-benzodioxol-5-yl)-1,3-dihydro-2H-indol-2-one Following the procedure as described in PREPARATION 2B, and making non-critical variations to replace 1-(2-cyclopropylethyl)-1H-indole-2,3-dione with 1-hexyl-1H-indole-2,3-dione, the title compound was obtained (53%) as a colorless solid: $^1$H NMR (300 MHz, CDCl$_3$) δ 9.44 (br, 1H), 7.47-7.44 (m, 1H), 7.40-7.34 (m, 1H),7.17 (t, 1H), 6.89 (d, 1H), 6.55 (s, 1H), 6.21 (s, 1H), 5.84-5.82 (m, 2H), 4.58 (br, 1H), 3.71-3.56 (m, 2H), 1.67-1.62 (m, 2H), 1.32-1.21 (m, 6H), 0.84-0.80 (m, 3H); $^{13}$C NMR (75 MHz, CDCl$_3$) δ 179.0, 152.3, 148.8, 142.5, 141.3, 130.3, 129.2, 126.1, 123.7, 117.2, 109.5, 106.8, 101.9, 101.4, 79.2, 40.4, 31.3, 27.1, 26.4, 22.4, 13.9; MS (ES+) m/z 352.5 (M−17).

C. Synthesis of 1-hexyl-3-(6-hydroxy-1,3-benzodioxol-5-yl)-1,3-dihydro-2H-indol-2-one Following the procedure as described in PREPARATION 2C, and making non-critical variations to replace 1-(2-cyclopropylethyl)-3-hydroxy-3-(6-hydroxy-1,3-benzodioxol-5-yl)-1,3-dihydro-2H-indol-2-one with 1-hexyl-3-hydroxy-3-(6-hydroxy-1,3-benzodioxol-5-yl)-1,3-dihydro-2H-indol-2-one, the title compound was obtained (98%) as a white solid: $^1$H NMR (300 MHz, CDCl$_3$) δ 7.38-7.13 (m, 3H), 6.94 (d, 1H), 6.60 (s, 1H), 6.32 (s, 1H), 5.84 (dd, 2H), 5.02 (s, 1H), 3.74-3.63 (m, 2H), 1.70-1.61 (m, 2H), 1.37-1.19 (m, 6H), 0.83 (t, 3H); MS (ES+) m/z 354.2 (M+1).

D. Synthesis of ethyl [1-hexyl-3-(6-hydroxy-1,3-benzodioxol-5-yl)-2-oxo-2,3-dihydro-1H-indol-3-yl]acetate To a solution of diisopropylamine (1.14 g, 11.0 mmol) in THF (10.0 mL) was added n-butyl lithium (7.00 mL, 11.0 mmol, 1.6 M solution in hexane) at −75° C. The resulting mixture was stirred at −75° C. for half an hour and added slowly to a solution of 1-hexyl-3-(6-hydroxy-1,3-benzodioxol-5-yl)-1,3-dihydro-2H-indol-2-one in THF (20.0 mL) at −75° C. After stirring at −75° C. for another half an hour, ethyl bromoacetate was added. The mixture was stirred at ambient temperature for 18 hrs and quenched with saturated ammonium chloride solution. The organic solvent was removed in vacuo and the aqueous residue was diluted with ethyl acetate (100 mL). The organic layer was washed with saturated ammonium chloride (25.0 mL), brine (50.0 mL), dried over anhydrous sodium sulfate and filtered. The filtrate was concentrated in vacuo to dryness. The residue was subjected to column chromatography eluting with 40% EtOAc/Hexanes to yield the title compound (0.19 g, 8%) as an oil: MS (ES+) m/z 440.5 (M+1).

PREPARATION 32

Synthesis of 4-bromo-3-(6-hydroxy-1,3-benzodioxol-5-yl)-3-(hydroxymethyl)-1,3-dihydro-2H-indol-2-one A. Synthesis of 4-bromo-3-hydroxy-3-(6-hydroxy-1,3-benzodioxol-5-yl)-1,3-dihydro-2H-indol-2-one Following the procedure as described in PREPARATION 2B, and making non-critical variations to replace 1-(2-cyclopropylethyl)-1H-indole-2,3-dione with 4-bromoisatin, the title compound was obtained (95%) as a beige solid: $^1$H NMR (300 MHz, DMSO-d$_6$) δ 10.40 (s, 1H), 9.09 (s, 1H), 7.22 (s, 1H), 7.04 (t, 1H), 6.90 (d, 1H), 6.75 (d, 1H), 6.43 (br, 1H), 6.21 (s, 1H), 5.88 (d, 2H); $^{13}$C NMR (75 MHz, DMSO-d$_6$) δ 178.0, 148.7, 147.0, 145.8, 139.5, 131.3, 130.8, 125.4, 118.8, 118.4, 109.4, 108.9, 101.0, 97.4, 76.6; MS (ES+) m/z 366.4 (M+1), 364.5 (M+1).

B. Synthesis of 4-bromo-3-(6-hydroxy-1,3-benzodioxol-5-yl)-1,3-dihydro-2H-indol-2-one Following the procedure as described in PREPARATION 1D, and making non-critical variations to replace 4-bromo-3-hydroxy-3-(6-hydroxy-1,3-benzodioxol-5-yl)-1-pentyl-1,3-dihydro-2H-indol-2-one with 4-bromo-3-hydroxy-3-(6-hydroxy-1,3-benzodioxol-5-yl)-1,3-dihydro-2H-indol-2-one, the title compound was obtained (95%) as a cream solid: MS (ES+) m/z 348.5 (M+1), 346.3 (M+1).

C. Synthesis of 4-bromo-3-(6-hydroxy-1,3-benzodioxol-5-yl)-3-(hydroxymethyl)-1,3-dihydro-2H-indol-2-one Following the procedure as described in PREPARATION 31D, and making non-critical variations to replace 1-hexyl-3-(6-hydroxy-1,3-benzodioxol-5-yl)-1,3-dihydro-2H-indol-2-one with 4-bromo-3-(6-hydroxy-1,3-benzodioxol-5-yl)-1,3-dihydro-2H-indol-2-one, and ethyl bromoacetate with para-formaldehyde, the title compound was obtained (70%) as a colorless solid: $^1$H NMR (300 MHz, DMSO-d$_6$) δ 9.00 (br, 1H), 7.13-6.95 (m, 3H), 6.84 (d, 1H), 6.16 (d, 1H), 5.90-5.84 (m, 2H), 5.16-4.83 (m, 2H); $^{13}$C NMR (75 MHz, DMSO-d$_6$) δ 177.8, 150.4, 147.1, 146.8, 139.8, 130.2, 129.3, 125.8, 117.7, 115.8, 109.3, 107.9, 101.2, 97.6, 63.5, 57.4.

PREPARATION 33

Synthesis of 4-bromo-3-(6-hydroxy-2,3-dihydro-1-benzofuran-5-yl)-3-(hydroxymethyl)-1,3-dihydro-2H-indol-2-one A. Synthesis of 4-bromo-3-hydroxy-3-(6-hydroxy-2,3-dihydro-1-benzofuran-5-yl)-1,3-dihydro-2H-indol-2-one Following the procedure as described in PREPARATION 2B, and making non-critical variations to replace 1-(2-cyclopropylethyl)-1H-indole-2,3-dione with 4-bromoisatin, and 1,3-benzodioxol-5-ol with 2,3-dihydrobenzofuran-6-ol, the title compound was obtained (78%) as a colorless solid: $^1$H NMR (300 MHz, DMSO-d$_6$) δ 10.36 (s, 1H), 9.15 (s, 1H), 7.49 (1H), 7.04 (t, 1H), 6.89 (d, 1H), 6.74 (d, 1H), 6.35 (br, 1H), 5.90 (s, 1H), 4.45 (t, 2H), 3.05 (t, 2H); $^{13}$C NMR (75 MHz, DMSO-d$_6$) δ 178.4, 160.2, 154.0, 145.7, 131.6, 130.7, 125.5, 125.4, 118.9, 117.7, 116.1, 108.8, 96.8, 76.9, 71.8, 29.1; MS (ES−) m/z 344.4 (M−17), 360.4 (M−1).

B. Synthesis of 4-bromo-3-(6-hydroxy-2,3-dihydro-1-benzofuran-5-yl)-1,3-dihydro-2H-indol-2-one Following the procedure as described in PREPARATION 1D, and making non-critical variations to replace 4-bromo-3-hydroxy-3-(6-hydroxy-1,3-benzodioxol-5-yl)-1-pentyl-1,3-dihydro-2H-indol-2-one with 4-bromo-3-hydroxy-3-(6-hydroxy-2,3-dihydro-1-benzofuran-5-yl)-1,3-dihydro-2H-indol-2-one, the title compound was obtained (62%) as a solid: MS (ES+) m/z 346.5 (M+1), 348.5 (M+1).

C. Synthesis of 4-bromo-3-(6-hydroxy-2,3-dihydro-1-benzofuran-5-yl)-3-(hydroxymethyl)-1,3-dihydro-2H-indol-2-one Following the procedure as described in PREPARATION 31D, and making non-critical variations to replace 1-hexyl-3-(6-hydroxy-1,3-benzodioxol-5-yl)-1,3-dihydro-2H-indol-2-one with 4-bromo-3-(6-hydroxy-2,3-dihydro-1-benzofuran-5-yl)-1,3-dihydro-2H-indol-2-one, and ethyl bromoacetate with para-formaldehyde, the title compound was obtained that was used directly for further reaction.

PREPARATION 34

Synthesis of 4-bromo-3-(6-hydroxy-2,3-dihydro-1-benzofuran-5-yl)-3-(hydroxymethyl)-1-(pyridin-2-ylmethyl)-1,3-dihydro-2H-indol-2-one A. Synthesis of 4-bromo-1-(pyridin-2-ylmethyl)-1H-indole-2,3-dione To a solution of 4-bromoisatin (8.94 g, 39.5 mmol) in anhydrous N,N-dimethylformamide (100 mL) was added sodium hydride (3.34 g, 86.9 mmol, 60% dispersion in mineral oil) in portions at 0° C. The brown reaction mixture was stirred for 30 min followed by the addition of a solution of 2-(bromomethyl)pyridine hydrobromide (10.0 g, 39.5 mmol) neutralized with sodium hydride (1.52 g, 39.5 mmol, 60% dispersion in mineral oil) in N,N-dimethylformamide at 0° C. The reaction mixture was stirred for 16 h and quenched with water (100 mL). The reaction mixture was extracted with diethyl ether (3×100 mL) and the aqueous layer was extracted with ethyl acetate (3×100 mL). The combined organic layers was washed with water (5×200 mL), dried over anhydrous sodium sulfate and filtered. The filtrate was concentrated in vacuo to dryness. The residue was triturated with ether to afford the title compound (10.6 g, 85%) as a brown solid: $^1$H NMR (300 MHz, DMSO-$d_6$) δ 8.53 (d, 1H), 7.67 (t, 1H), 7.30 (t, 2H), 7.25-7.19 (m, 2H), 6.94 (d, 1H), 5.04 (s, 2H); $^{13}$C NMR (75 MHz, DMSO-$d_6$) δ 180.5, 157.3, 154.2, 152.3, 149.5, 138.4, 137.5, 128.6, 123.3, 122.3, 121.5, 116.4, 110.3, 45.8.

B. Synthesis of 4-bromo-3-hydroxy-3-(6-hydroxy-2,3-dihydro-1-benzofuran-5-yl)-1-(pyridin-2-ylmethyl)-1,3-dihydro-2H-indol-2-one Following the procedure as described in PREPARATION 2B, and making non-critical variations to replace 1-(2-cyclopropylethyl)-1H-indole-2,3-dione with 4-bromo-1-(pyridin-2-ylmethyl)-1H-indole-2,3-dione, and 1,3-benzodioxol-5-ol with 2,3-dihydrobenzofuran-6-ol, the title compound was obtained (91%) as a colorless solid: mp>225° C.; $^1$H NMR (300 MHz, DMSO-$d_6$) δ 9.29 (s, 1H), 8.54 (d, 1H), 7.70 (dt, 1H); 7.61 (br, 1H), 7.32-7.26 (m, 2H), 7.07 (d, 1H), 7.00 (d, 1H), 6.72 (d, 1H), 6.60 (br, 1H), 6.02 (s, 1H), 4.91 (ABq, 2H), 4.47 (t, 2H), 3.06 (d, 2H); $^{13}$C NMR (75 MHz, DMSO-$d_6$) δ 176.9, 160.4, 156.3, 153.8, 149.6, 146.1, 137.5, 130.9, 130.8, 126.5, 125.8, 123.1, 121.5, 118.8, 117.3, 116.4, 108.3, 96.7, 76.6, 71.9, 45.7, 29.1; MS (ES+) m/z 455.4 (M+1), 437.4 (M−17).

C. Synthesis of 4-bromo-3-(6-hydroxy-2,3-dihydro-1-benzofuran-5-yl)-1-(pyridin-2-ylmethyl)-1,3-dihydro-2H-indol-2-one To a solution of 4-bromo-3-hydroxy-3-(6-hydroxy-2,3-dihydro-1-benzofuran-5-yl)-1-(pyridin-2-ylmethyl)-1,3-dihydro-2H-indol-2-one (1.12 g, 2.48 mmol) in anhydrous dichloromethane (25.0 mL) was added triethylamine (1.40 mL, 9.91 mmol) and SOCl$_2$ (0.40 mL, 4.96 mmol) at 0° C. The reaction mixture was stirred at 0° C. for 2 h and quenched with water (30.0 mL). The organic layer was separated, washed with water (3×30.0 mL), dried over anhydrous sodium sulfate and filtered. The filtrate was concentrated in vacuo to dryness to give a gummy material. The residue was dissolved in acetic acid/tetrahydrofuran (3.00 mL/22.0 mL) followed by the addition of zinc dust (0.81 g, 12.4 mmol) in one portion. The reaction mixture was stirred at ambient temperature for 16 h. After the solid was filtered, the solvent was removed in vacuo. The residue was dissolved in ethyl acetate (100 mL), washed with water (3×30.0 mL), dried over anhydrous sodium sulfate and filtered. The filtrate was concentrated in vacuo to dryness to give the title compound (1.50 g, 77%) as a gummy material: MS (ES+) m/z 437.3 (M+1).

D. Synthesis of 4-bromo-3-(6-hydroxy-2,3-dihydro-1-benzofuran-5-yl)-3-(hydroxymethyl)-1-(pyridin-2-ylmethyl)-1,3-dihydro-2H-indol-2-one Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with 4-bromo-3-(6-hydroxy-2,3-dihydro-1-benzofuran-5-yl)-1-(pyridin-2-ylmethyl)-1,3-dihydro-2H-indol-2-one, the title compound was obtained (34%): MS (ES+) m/z 468.4 (M+1).

PREPARATION 35

Synthesis of 5-fluoro-3-(6-hydroxy-1,3-benzodioxol-5-yl)-3-(hydroxymethyl)-1-{[5-(trifluoromethyl)-2-furyl]methyl}-1,3-dihydro-2H-indol-2-one A. Synthesis of 5-fluoro-1-{[5-(trifluoromethyl)-2-furyl]methyl}-1H-indole-2,3-dione Following the procedure as described in PREPARATION 2A, and making non-critical variations to replace isatin with 5-fluoroisatin, and (2-bromoethyl)cyclopropane with 2-(bromomethyl)-5-(trifluoromethyl)furan, the title compound was obtained (59%) as a red solid: $^1$H NMR (300 MHz, DMSO-$d_6$) δ 7.54-7.50 (m, 1H), 7.47-7.44 (m, 1H), 7.20 (dd, 1H), 7.14-7.13 (m, 1H), 6.75 (d, 1H), 4.99 (s, 2H); $^{13}$C NMR (75 MHz, DMSO-$d_6$) δ 182.4 (d), 160.7, 158.5 (d), 157.5, 153.0 (d), 146.5 (d), 139.9 (q), 124.3, 119.3 (d), 114.5 (d), 112.7 (d), 112.0 (d), 110.5, 36.8.

B. Synthesis of 5-fluoro-3-hydroxy-3-(6-hydroxy-1,3-benzodioxol-5-yl)-1-{[5-(trifluoromethyl)-2-furyl]methyl}-1,3-dihydro-2H-indol-2-one Following the procedure as described in PREPARATION 2B, and making non-critical variations to replace 1-(2-cyclopropylethyl)-1H-indole-2,3-dione with 5-fluoro-1-{[5-(trifluoromethyl)-2-furyl]methyl}-1H-indole-2,3-dione, the title compound was obtained (66%) as a pale yellow solid: $^1$H NMR (300 MHz, DMSO-$d_6$) δ 9.15 (s, 1H), 7.21 (s,1H), 7.15 (dd, 1H), 7.08-6.95 (m, 2H), 6.74 (s, 1H), 6.54 (s, 1H), 6.22 (d, 1H), 5.90 (d, 2H), 4.96 (s, 2H); $^{13}$C NMR (75 MHz, DMSO-$d_6$) δ 176.7, 160.57, 157.4, 154.0, 148.6, 147.4, 140.1 (m), 139.6 (m), 134.7 (d, $^2J_{CF}$=29.4 Hz), 121.3, 119.5, 117.7, 115.1 (d, $^1J_{CF}$=92.1 Hz), 114.5, 111.8 (d, $^1J_{CF}$=97.5 Hz), 109.7, 109.6, 107.2, 101.3, 97.8, 75.1, 36.9; MS (ES+) m/z 450.3 (M+1)

C. Synthesis of 5-fluoro-3-(6-hydroxy-1,3-benzodioxol-5-yl)-1-{[5-(trifluoromethyl)-2-furyl]methyl}-1,3-dihydro-2H-indol-2-one Following the procedure as described in PREPARATION 1D, and making non-critical variations to replace 4-bromo-3-hydroxy-3-(6-hydroxy-1,3-benzodioxol-5-yl)-1-pentyl-1,3-dihydro-2H-indol-2-one with 5-fluoro-3-hydroxy-3-(6-hydroxy-1,3-benzodioxol-5-yl)-1-{[5-(trifluoromethyl)-2-furyl]methyl}-1,3-dihydro-2H-indol-2-one, the title compound was obtained (72%) as a pale yellow solid: $^1$H NMR (300 MHz, DMSO-$d_6$) δ 9.31 (s, 1H), 7.13 (dd, 1H), 7.02 (dd, 2H), 6.82 (d, 1H), 6.59 (d, 2H), 6.39 (s, 1H), 5.87 (d, 2H), 5.07-4.96 (m, 2H), 4.84 (s, 1H); $^{13}$C NMR (75 MHz, DMSO-$d_6$) δ 176.1, 160.5, 157.4, 153.9, 150.5, 147.5, 140.2, 139.6, 139.1, 132.3 (d, $^2J_{CF}$=33.3 Hz), 115.3, 114.5 (m), 114.2, 113.9, 111.9 (d, $^1J_{CF}$=98.7 Hz), 109.9, 109.7 (d, $^2J_{CF}$=32.7 Hz), 101.3, 98.3, 48.5, 36.8; MS (ES+) m/z 436.2 (M+1).

D. Synthesis of 5-fluoro-3-(6-hydroxy-1,3-benzodioxol-5-yl)-3-(hydroxymethyl)-1-{[5-(trifluoromethyl)-2-furyl]methyl}-1,3-dihydro-2H-indol-2-one A mixture of 5-fluoro-3-(6-hydroxy-1,3-benzodioxol-5-yl)-1-{[5-(trifluoromethyl)-2-furyl]methyl}-1,3-dihydro-2H-indol-2-one (3.64 g, 8.41 mmol), para-formaldehyde (2.52 g, 84.1 mmol) and lithium hydroxide monohydrate (1.06 g, 25.2 mmol) in tetrahydrofuran (84.0 mL) and water (10.0 mL) was stirred at 0° C. for 4 h. After the solvent was removed in vacuo, the residue was dissolved in ethyl acetate (100 mL), washed with 10% aqueous HCl (3×25.0 mL), dried over anhydrous sodium sulfate and filtered. The filtrate was concentrated in vacuo to dryness. The residue was subjected to column chromatography eluting with ethyl acetate/hexanes (50%) to give the title compound (0.65 g, 59%) as a colorless solid: $^1$H NMR (300 MHz, DMSO-$d_6$) δ 9.11 (s, 1H), 7.12 (d, 1H), 6.99-6.87 (m, 3H), 6.80 (dd, 1H), 6.48 (d, 1H), 6.23 (s, 1H), 5.89 (d, 2H), 5.09 (br, 1H), 4.97 (ABq, 2H), 4.01(ABq, 2H); $^{13}$C NMR (75 MHz, DMSO-$d_6$) δ 176.1, 160.5; MS (ES+) m/z 466.2 (M+1), 448.2 (M−17).

PREPARATION 36

Synthesis of tert-butyl-(2-chloromethyl-5-trifluoromethylthiophen-3-yloxy)dimethylsilane A. Synthesis of methyl 3-tert-butyl dimethylsilanyloxy-5-trifluoromethyl-2-thiophenecarboxylate To a solution of methyl 3-hydroxy-5-trifluoromethyl-2-thiophenecarboxylate (Karp, G. M., et al, *Synthesis* (2000), 8:1078-1080) (19.4 g, 85.8 mmol) in N,N-dimethylformamide (50.0 mL) was added imidazole (8.77 g, 129 mmol) followed by tert-butyl dimethylsilyl chloride (19.4 g, 129 mmol) at 0° C. The reaction mixture was stirred at ambient temperature overnight. More imidazole (7.50 g) and tert-butyl dimethylsilyl chloride (10.5 g) were added. The reaction mixture was stirred for another 4 h and quenched with water (100 mL). The reaction mixture was extracted with ether (3×500 mL). The combined organic layers was washed with water (3×500 mL), dried over anhydrous sodium sulfate and filtered. The filtrate was concentrated in vacuo to dryness. The residue was subjected to column chromatography eluting with ethyl acetate/hexanes (1/9) to give the titlew compound (26.5 g, 90%) as a yellow oil: $^1$H NMR (300 MHz, CDCl$_3$) δ 6.91 (s, 1H), 3.82 (s, 3H), 0.21 (s, 6H), 0.06 (s, 9H); $^{13}$C NMR (75 MHz, CDCl$_3$) δ 161.5, 155.5, 133.7, 133.2, 123.6 (q, $^1J_{CF}$=14.4 Hz), 119.8, 51.9, 25.4, 18.2, −4.6.

B. Synthesis of [3-(tert-butyldimethylsilanyloxy)-5-trifluoromethylthiophen-2-yl]methanol To a mixture of lithium aluminum hydride (1.67 g, 43.9 mmol) in anhydrous ether (75.0 mL) was added a solution of methyl 3-tert-butyl dimethylsilanyloxy-5-trifluoromethyl-2-thiophenecarboxylate (10.0 g, 29.3 mmol) in anhydrous ether (25.0 mL) at 0° C. The reaction mixture was stirred at 0° C. for 30 min and quenched by the slow addition of water (50.0 mL). After the aqueous layer was separated, the organic layer was washed with saturated ammonium chloride (3×20.0 mL), dried over anhydrous sodium sulfate and filtered. The filtrate was concentrated in vacuo to dryness. The residue was subjected to column chromatography eluting with ethyl acetate/hexanes (1/9) to give the title compound (6.95 g, 76%) as a yellow oil: $^1$H NMR (300 MHz, CDCl$_3$) δ 6.89 (s, 1H), 4.68 (s, 2H), 2.11 (br, 1H), 0.96 (s, 9H), 0.88 (s, 6H); $^{13}$C NMR (75 MHz, CDCl$_3$) δ 148.0, 127.0, 124.0, 122.4 (q, $^1J_{CF}$=14.7 Hz), 120.5, 56.1, 25.5, 18.1, −4.6.

C. Synthesis of tert-butyl-(2-chloromethyl-5-trifluoromethylthiophen-3-yloxy)dimethylsilane To a solution of [3-(tert-butyldimethylsilanyloxy)-5-trifluoromethylthiophen-2-yl]methanol in anhydrous dichloromethane (100 mL) was added triethylamine (4.05 g, 40.0 mmol) followed by thionyl chloride (2.38 g, 20.0 mmol) at 0° C. The reaction mixture was stirred for 30 min and quenched with water (50.0 mL). After separation, the organic layer was washed with water (3×50.0 mL), dried over anhydrous sodium sulfate and filtered. The filtrate was concentrated in vacuo to dryness. The residue was subjected to column chromatography eluting with hexane to afford the title compound (2.31 g, 70%) as a yellow oil, which was directly used.

PREPARATION 37

Synthesis of 1-(diphenylmethyl)-3-(6-hydroxy-1,3-benzodioxol-5-yl)-3-(hydroxymethyl)-5-methyl-1,3-dihydro-2H-indol-2-one A. Synthesis of 1-(diphenylmethyl)-5-methyl-1H-indole-2,3-dione Following the procedure as described in PREPARATION 2A, and making non-critical variations to replace isatin with 5-methylisatin, and (2-bromoethyl)cyclopropane with 1,1'-(bromomethylene)dibenzene, the title compound was obtained (74%) as a bright orange solid: $^1$H NMR (300 MHz, CDCl$_3$) δ 7.42-7.26 (m, 11H), 7.09 (d, 1H), 6.95 (s, 1H), 6.37 (d, 1H), 2.24 (s, 3H).

B. Synthesis of 1-(diphenylmethyl)-3-hydroxy-3-(6-hydroxy-1,3-benzodioxol-5-yl)-5-methyl-1,3-dihydro-2H-indol-2-one Following the procedure as described in PREPARATION 2B, and making non-critical variations to replace 1-(2-cyclopropylethyl)-1H-indole-2,3-dione with 1-(diphenylmethyl)-5-methyl-1H-indole-2,3-dione, the title compound was obtained (92%) as a colorless solid: $^1$H NMR (300 MHz, CDCl$_3$) δ 9.23 (br, 1H), 7.40-7.15 (m, 11H), 6.90-6.85 (m, 2H), 6.57 (s, 1H), 6.33 (d, 1H), 6.31 (s, 1H), 5.87 (s, 2H), 4.46 (br s, 1H), 2.28 (s, 3H); MS (ES+) m/z 448.4 (M−17).

C. Synthesis of 1-(diphenylmethyl)-3-(6-hydroxy-1,3-benzodioxol-5-yl)-5-methyl-1,3-dihydro-2H-indol-2-one Following the procedure as described in PREPARATION 2C, and making non-critical variations to replace 1-(2-cyclopropylethyl)-3-hydroxy-3-(6-hydroxy-1,3-benzodioxol-5-yl)-1,3-dihydro-2H-indol-2-one with 1-(diphenylmethyl)-3-hydroxy-3-(6-hydroxy-1,3-benzodioxol-5-yl)-5-methyl-1,3-dihydro-2H-indol-2-one, the title compound was obtained (84%) as a colorless solid: $^1$H NMR (300 MHz, CDCl$_3$) δ 7.37-7.25 (m, 9H), 7.22-7.17 (m, 2H), 7.10 (s, 1H), 6.91 (s, 1H), 6.86 (d, 1H), 6.63 (s, 1H), 6.40 (s, 1H), 6.38 (d, 1H), 5.88 (ABq, 2H), 5.07 (s, 1H), 2.23 (s, 3H); MS (ES+) m/z 450.3 (M+1).

D. Synthesis of 1-(diphenylmethyl)-3-(6-hydroxy-1,3-benzodioxol-5-yl)-3-(hydroxymethyl)-5-methyl-1,3-dihydro-2H-indol-2-one To a solution of 1-(diphenylmethyl)-3-(6-hydroxy-1,3-benzodioxol-5-yl)-5-methyl-1,3-dihydro-2H-indol-2-one (1.61 g, 3.60 mmol) and para-formaldehyde (0.43 g, 14.6 mmol) in dichloromethane (60.0 mL) was added diisopropylamine (7.20 mmol). After stirring at ambient temperature for 3 h, the reaction was quenched with saturated aqueous ammonium chloride (60.0 mL). The organic layer was separated and washed with water (3×100 mL), dried over sodium sulfate and filtered. The filtrate was concentrated in vacuo to dryness. The residue was subjected to column chromatography eluting with ethyl acetate/hexanes (20-60%) to afford the title compound (1.07 g, 63%) as a colorless solid: $^1$H NMR (300 MHz, CDCl$_3$) δ 10.09 (br, 1H), 7.37-7.16 (m, 12H), 6.99 (s, 1H), 6.87 (d, 1H), 6.62 (s, 1H) 6.54 (s, 1H), 6.37 (d, 1H), 5.87 (d, 2H), 4.45 (ABq, 2H), 2.33 (s, 3H); MS (ES+) m/z 480.4 (M+1).

PREPARATION 38

Synthesis of 3-(hydroxymethyl)-3-(5-hydroxy-2-methyl-1,3-benzothiazol-6-yl)-1-pentyl-1,3-dihydro-2H-indol-2-one A. Synthesis of 3-hydroxy-3-(5-hydroxy-2-methyl-1,3-benzothiazol-6-yl)-1-pentyl-1,3-dihydro-2H-indol-2-one Following the procedure as described in PREPARATION 2B, and making non-critical variations to replace 1-(2-cyclopropylethyl)-1H-indole-2,3-dione with 1-pentyl-1H-indole-2,3-dione, and 1,3-benzodioxol-5-ol with 2-methyl-1,3-benzothiazol-5-ol, the title compound was obtained (81%) as a colorless solid: $^1$H NMR (300 MHz, DMSO-d$_6$) δ 9.90 (br, 1H), 9.05 (br, 1H), 7.78 (d, 1H), 7.25 (dd, 1H), 7.10-6.95 (m, 2H), 6.90-6.80 (m, 2H), 3.81-3.58 (m, 2H), 2.75 (br, 3H), 1.80-1.60 (m, 2H), 1.50-1.31 (m, 4H), 0.90 (t, 3H); MS (ES+) m/z 383.4 (M+1).

B. Synthesis of 3-(5-hydroxy-2-methyl-1,3-benzothiazol-6-yl)-1-pentyl-1,3-dihydro-2H-indol-2-one A suspension of 3-hydroxy-3-(5-hydroxy-2-methyl-1,3-benzothiazol-6-yl)-1-pentyl-1,3-dihydro-2H-indol-2-one (0.50 g, 1.31 mmol) in hydroiodic acid (10.0 mL) was refluxed for 1.5 days. The reaction mixture was concentrated in vacuo to dryness. The residue was used directly in next step.

C. Synthesis of 3-(hydroxymethyl)-3-(5-hydroxy-2-methyl-1,3-benzothiazol-6-yl)-1-pentyl-1,3-dihydro-2H-indol-2-one Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with 3-(5-hydroxy-2-methyl-1,3-benzothiazol-6-yl)-1-pentyl-1,3-dihydro-2H-indol-2-one, the title compound was obtained: MS (ES+) m/z 367.5 (M+1).

PREPARATION 39

Synthesis of (5-chloro-1,3,4-thiadiazol-2-yl)methanol

To a a solution of ethyl 5-chloro-1,3,4-thiadiazole-2-carboxylate (0.51 g, 2.60 mmol) in anhydrous methanol (5.00 mL) was added sodium borohydride (0.30 g, 7.99 mmol) at 0° C. The reaction mixture was stirred at ambient temperature for 16 h, diluted with acetic acid (3.00 mL) and extracted with ethyl acetate (2×150 mL). The combined organics was washed with aqueous saturated sodium bicarbonate (3×25.0 mL) and aqueous saturated sodium chloride (2×25.0 mL). The organic layer was dried over anhydrous sodium sulfate and filtered. The filtrate was concentrated in vacuo to dryness to give the title compound (0.30 g, 75%) as a light yellow semi-solid: $^1$H NMR (300 MHz, CDCl$_3$) δ 5.04 (s, 2H), 2.80 (br, 1H); MS (ES+) 151.1 (M+1), 153.1 (M+1).

PREPARATION 40

Synthesis of 1-(diphenylmethyl)-3-(6-hydroxy-3,3-dimethyl-2,3-dihydro-1-benzofuran-5-yl)-3-(hydroxymethyl)-1,3-dihydro-2H-indol-2-one A. Synthesis of 1-(diphenylmethyl)-3-hydroxy-3-(6-hydroxy-3,3-dimethyl-2,3-dihydro-1-benzofuran-5-yl)-1,3-dihydro-2H-indol-2-one Following the procedure as described in PREPARATION 2B, and making non-critical variations to replace 1-(2-cyclopropylethyl)-1H-indole-2,3-dione with 1-(diphenylmethyl)-1H-indole-2,3-dione, and 1,3-benzodioxol-5-ol with 3,3-dimethyl-2,3-dihydro-1-benzofuran-6-ol, the title compound was obtained: MS (ES+) m/z 478.5 (M+1).

B. Synthesis of 1-(diphenylmethyl)-3-(6-hydroxy-3,3-dimethyl-2,3-dihydro-1-benzofuran-5-yl)-1,3-dihydro-2H-indol-2-one Following the procedure as described in PREPARATION 2C, and making non-critical variations to replace 1-(2-cyclopropylethyl)-3-hydroxy-3-(6-hydroxy-1,3-benzodioxol-5-yl)-1,3-dihydro-2H-indol-2-one with 1-(diphenylmethyl)-3-hydroxy-3-(6-hydroxy-3,3-dimethyl-2,3-dihydro-1-benzofuran-5-yl)-1,3-dihydro-2H-indol-2-one, the title compound was obtained (73% for two steps): $^1$H NMR (300 MHz, CDCl$_3$) δ 7.38-7.20 (m, 12H), 7.11-7.04 (m, 2H), 6.97 (s, 1H), 6.58 (s, 1H), 6.57-6.51 (m, 1H), 6.50 (s, 1H), 5.08 (s, 1H), 4.19 (s, 2H), 1.25 (s, 3H), 1.18 (s, 3H); MS (ES+) m/z 426.6 (M+1).

C. Synthesis of 1-(diphenylmethyl)-3-(6-hydroxy-3,3-dimethyl-2,3-dihydro-1-benzofuran-5-yl)-3-(hydroxymethyl)-1,3-dihydro-2H-indol-2-one Following the procedure as described in PREPARATION 26C, and making non-critical variations to replace 1-(diphenylmethyl)-3-(5-hydroxy-2,3-dihydro-1-benzofuran-6-yl)-1,3-dihydro-2H-indol-2-one with 1-(diphenylmethyl)-3-(6-hydroxy-3,3-dimethyl-2,3-dihydro-1-benzofuran-5-yl)-1,3-dihydro-2H-indol-2-one, the title compound was obtained: MS (ES+) m/z 492.5 (M+1)

PREPARATION 41

Synthesis of 7-fluoro-3-(6-hydroxy-1,3-benzodioxol-5-yl)-1,3-dihydro-2H-indol-1-one A. Synthesis of 7-fluoro-3-hydroxy-3-(6-hydroxy-1,3-benzodioxol-5-yl)-1,3-dihydro-2H-indol-2-one Following the procedure as described in PREPARATION 2B, and making non-critical variations to replace 1-(2-cyclopropylethyl)-1H-indole-2,3-dione with 7-fluoro-1H-indole-2,3-dione, the title compound was obtained (80%): $^1$H NMR (300 MHz, DMSO-d$_6$) δ 10.66 (s, 1H), 9.11 (s, 1H), 7.18 (s, 1H), 7.07-6.98 (m, 1H), 6.83-6.74 (m, 1H), 6.66 (d, 1H), 6.48 (s, 1H), 6.18 (s, 1H), 5.92-5.85 (m, 2H); MS (ES+) m/z 304.5 (M+1).

B. Synthesis of 7-fluoro-3-(6-hydroxy-1,3-benzodioxol-5-yl)-1,3-dihydro-2H-indol-2-one Following the procedure as described in PREPARATION 2C, and making non-critical variations to replace 1-(2-cyclopropylethyl)-3-hydroxy-3-(6-hydroxy-1,3-benzodioxol-5-yl)-1,3-dihydro-2H-indol-2-one with 7-fluoro-3-hydroxy-3-(6-hydroxy-1,3-benzodioxol-5-yl)-1,3-dihydro-2H-indol-2-one, the title compound was obtained (100%): $^1$H NMR (300 MHz, DMSO-d$_6$) δ 10.84 (s, 1H), 9.22 (s, 1H), 7.01 (t, 1H), 6.87-6.78 (m, 1H), 6.71 (d, 1H), 6.62 (s, 1H), 6.35 (s, 1H), 5.90-5.85 (m, 2H), 4.67 (s, 1H); MS (ES+) m/z 288.5 (M+1).

PREPARATION 42

Synthesis of ethyl [4-bromo-3-(6-hydroxy-2,3-dihydro-1-benzofuran-5-yl)-3-(hydroxymethyl)-2-oxo-2,3-dihydro-1H-indol-1-yl]acetate

A. Synthesis of ethyl [4-bromo-3-hydroxy-3-(6-hydroxy-2,3-dihydro-1-benzofuran-5-yl)-2-oxo-2,3-dihydro-1H-indol-1-yl]acetate Following the procedure as described in PREPARATION 2B, and making non-critical variations to replace 1-(2-cyclopropylethyl)-1H-indole-2,3-dione with ethyl (4-bromo-2,3-dioxo-2,3-dihydro-1H-indol-1-yl)acetate, and 1,3-benzodioxol-5-ol with 2,3-dihydrobenzofuran-6-ol, the title compound was obtained (68%) as a white solid: $^1$H NMR (300 MHz, CDCl$_3$) δ 8.66 (br, 1H), 7.31-7.19 (m, 3H), 6.73 (dd, 1H), 6.49-6.45 (m, 1H), 5.09-4.36 (m, 4H), 4.20 (q, 2H), 3.14-2.90 (m, 2H), 1.23 (t, 3H); MS (ES+) m/z 432.2 (M−17).

B. Synthesis of ethyl [4-bromo-3-(6-hydroxy-2,3-dihydro-1-benzofuran-5-yl)-2-oxo-2,3-dihydro-1H-indol-1-yl]acetate Following the procedure as described in PREPARATION 2C, and making non-critical variations to replace 1-(2-cyclopropylethyl)-3-hydroxy-3-(6-hydroxy-1,3-benzodioxol-5-yl)-1,3-dihydro-2H-indol-2-one with ethyl [4-bromo-3-hydroxy-3-(6-hydroxy-2,3-dihydro-1-benzofuran-5-yl)-2-oxo-2,3-dihydro-1H-indol-1-yl]acetate, the title compound was obtained (81%) as a white solid: $^1$H NMR (CDCl$_3$, 300 MHz) δ 7.31-7.19 (m, 3H), 6.75 (d, 1H), 6.50-6.45 (m, 1H), 5.08 (s, 1H), 5.09-4.36 (m, 4H), 4.20 (q, 2H), 3.14-2.90 (m, 2H), 1.23 (t, 3H); MS (ES+) m/z 433.3 (M+1).

C. Synthesis of ethyl [4-bromo-3-(6-hydroxy-2,3-dihydro-1-benzofuran-5-yl)-3-(hydroxymethyl)-2-oxo-2,3-dihydro-1H-indol-1-yl]acetate Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with ethyl [4-bromo-3-(6-hydroxy-2,3-dihydro-1-benzofuran-5-yl)-2-oxo-2,3-dihydro-1H-indol-1-yl]acetate, the title compound was obtained (99%): MS (ES+) m/z 463.2 (M+1).

PREPARATION 43

Synthesis of ethyl [5-chloro-3-(6-hydroxy-2,3-dihydro-1-benzofuran-5-yl)-3-(hydroxymethyl)-2-oxo-2,3-dihydro-1H-indol-1-yl]acetate

A. Synthesis of ethyl (5-chloro-2,3-dioxo-2,3-dihydro-1H-indol-1-yl)acetate

Following the procedure as described in PREPARATION 2A, and making non-critical variations to replace isatin with 5-chloro-1H-indole-2,3-dione, and (2-bromoethyl)cyclopropane with ethyl 2-bromoacetate, the title compound was obtained (98%) as solid: $^1$H NMR (300 MHz, CDCl$_3$) δ 7.60 (d, 1H), 7.54 (dd, 1H), 6.74 (d, 1H), 4.46 (s, 2H), 4.23 (q, 2H), 1.27 (t, 3H); MS (ES+) m/z 268.6 (M+1).

B. Synthesis of ethyl [5-chloro-3-hydroxy-3-(6-hydroxy-2,3-dihydro-1-benzofuran-5-yl)-2-oxo-2,3-dihydro-1H-indol-1-yl]acetate Following the procedure as described in PREPARATION 1C, and making non-critical variations to replace 4-bromo-1-pentyl-1H-indole-2,3-dione with ethyl (5-chloro-2,3-dioxo-2,3-dihydro-1H-indol-1-yl)acetate, and 1,3-benzodioxol-5-ol with 2,3-dihydrobenzofuran-6-ol, the title compound was obtained (85%) as a white solid: $^1$H NMR (300 MHz, CDCl$_3$) δ 8.70 (br, 1H), 7.31-7.24 (m, 2H), 6.92 (d, 1H), 6.68 (s, 1H), 6.46 (s, 1H), 4.53-4.46 (m, 2H), 5.09-4.40 (d, 2H), 4.18 (q, 2H), 3.08-2.88 (m, 2H), 1.23 (t, 3H); MS (ES+) m/z 387.8 (M−17).

C. Synthesis of ethyl [5-chloro-3-(6-hydroxy-2,3-dihydro-1-benzofuran-5-yl)-2-oxo-2,3-dihydro-1H-indol-1-yl]acetate Following the procedure as described in PREPARATION 1D, and making non-critical variations to replace 4-bromo-3-hydroxy-3-(6-hydroxy-1,3-benzodioxol-5-yl)-1-pentyl-1,3-dihydro-2H-indol-2-one with ethyl [5-chloro-3-hydroxy-3-(6-hydroxy-2,3-dihydro-1-benzofuran-5-yl)-2-oxo-2,3-dihydro-1H-indol-1-yl]acetate, the title compound was obtained (94%) as a white solid: $^1$H NMR (300 MHz, CDCl$_3$) δ 7.30-7.24 (m, 2H), 6.72 (d, 1H), 6.66 (s, 1H), 6.39 (s, 1H), 5.05 (s, 1H), 4.53-4.46 (m, 4H), 4.21 (q, 2H), 3.14-2.94 (m, 2H), 1.25 (t, 3H); MS (ES+) m/z 388.8 (M+1).

D. Synthesis of ethyl [5-chloro-3-(6-hydroxy-2,3-dihydro-1-benzofuran-5-yl)-3-(hydroxymethyl)-2-oxo-2,3-dihydro-1H-indol-1-yl]acetate Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with ethyl [5-chloro-3-(6-hydroxy-2,3-dihydro-1-benzofuran-5-yl)-2-oxo-2,3-dihydro-1H-indol-1-yl]acetate, the title compound was obtained (99%): MS (ES+) m/z 418.7 (M+1).

PREPARATION 44

Synthesis of methyl [3-(4-chloro-2-hydroxyphenyl)-3-(hydroxymethyl)-2-oxo-2,3-dihydro-1H-indol-1-yl]acetate

A. Synthesis of methyl (2,3-dioxo-2,3-dihydro-1H-indol-1-yl)acetate

Following the procedure as described in PREPARATION 2A, and making non-critical variations to replace (2-bromoethyl)cyclopropane with methyl bromoacetate, the title compound was obtained (72%): $^1$H NMR (300 MHz, CDCl$_3$) δ 7.64-7.53 (m, 2H), 7.14 (t, 1H), 6.77 (d, 1H), 4.48 (s, 2H), 3.76 (s, 3H); MS (ES+) m/z 220.4 (M+1).

B. Synthesis of methyl [3-(4-chloro-2-hydroxyphenyl)-3-hydroxy-2-oxo-2,3-dihydro-1H-indol-1-yl]acetate Following the procedure as described in PREPARATION 1C, and making non-critical variations to replace 4-bromo- 1-pentyl-1H-indole-2,3-dione with methyl (2,3-dioxo-2,3-dihydro-1H-indol-1-yl)acetate, and 1,3-benzodioxol-5-ol with 3-chlorophenol, the title compound was obtained (29%) as a yellow solid: $^1$H NMR (300 MHz, CDCl$_3$) δ 9.10 (s, 1H), 7.48 (d, 1H), 7.38 (t, 1H), 7.19 (t, 1H), 7.01 (br, 1H), 6.80-6.64 (m, 3H), 5.28 (br s, 1H), 4.51 (d, 1H), 4.44 (d, 1H), 3.75 (s, 3H); MS (ES+) m/z 370.5 (M+23), 372.4 (M+23).

C. Synthesis of methyl [3-(4-chloro-2-hydroxyphenyl)-2-oxo-2,3-dihydro-1H-indol-1-yl]acetate Following the procedure as described in PREPARATION 2C, and making non-critical variations to replace 1-(2-cyclopropylethyl)-3-hydroxy-3-(6-hydroxy-1,3-benzodioxol-5-yl)-1,3-dihydro-2H-indol-2-one with methyl [3-(4-chloro-2-hydroxyphenyl)-3-hydroxy-2-oxo-2,3-dihydro-1H-indol-1-yl]acetate, the title compound was obtained (83%) as a semisolid; $^1$H NMR (300 MHz, CDCl$_3$) δ 7.36 (t, 1H), 7.29 (bd, 1H), 7.18 (t, 1H), 6.95 (br, 1H), 6.86-6.78 (m, 3H), 5.13 (br, 1H), 4.55 (d, 1H), 4.45 (d, 1H), 3.75 (s, 3H); MS (ES+) m/z 332.5 (M+1), 334.5 (M+1).

D. Synthesis of methyl [3-(4-chloro-2-hydroxyphenyl)-3-(hydroxymethyl)-2-oxo-2,3-dihydro-1H-indol-1-yl]acetate Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with methyl [3-(4-chloro-2-hydroxyphenyl)-2-oxo-2,3-dihydro-1H-indol-1-yl]acetate, the title compound was obtained: MS (ES+) m/z 362.5 (M+1) 364.5 (M+1).

PREPARATION 45

Synthesis of ethyl [3-(4,5-difluoro-2-hydroxyphenyl)-3-(hydroxymethyl)-2-oxo-2,3-dihydro-1H-indol-1-yl]acetate

A. Synthesis of ethyl [3-(4,5-difluoro-2-hydroxyphenyl)-3-hydroxy-2-oxo-2,3-dihydro-1H-indol-1-yl]acetate Following the procedure as described in PREPARATION 2B, and non-critical variations to replace 1-(2-cyclopropylethyl)-1H-indole-2,3-dione with ethyl (2,3-dioxo-2,3-dihydro-1H-indol-1-yl)acetate, the title compound was obtained as a brown oil: MS (ES+) m/z 364.3 (M+1), 348.5 (M−17).

B. Synthesis of ethyl [3-(4,5-difluoro-2-hydroxyphenyl)-2-oxo-2,3-dihydro-1H-indol-1-yl]acetate Following the procedure as described in PREPARATION 2C, and making non-critical variations to replace 1-(2-cyclopropylethyl)-3-hydroxy-3-(6-hydroxy-1,3-benzodioxol-5-yl)-1,3-dihydro-2H-indol-2-one with ethyl [3-(4,5-difluoro-2-hydroxyphenyl)-3-hydroxy-2-oxo-2,3-dihydro-1H-indol-1-yl]acetate, the title compound was obtained (83%) as a light yellow oil: $^1$H NMR (300 MHz, CDCl$_3$) δ 7.39 (t, 1H), 7.34 (d, 1H), 7.26-7.22 (m, 1H), 6.92-6.82 (m, 2H), 6.73 (dd, 1H), 5.11 (br, 1H), 4.50 (d, 1H), 4.43 (d, 1H), 4.21 (q, 2H), 1.23 (t, 3H); MS (ES+) m/z 448.5 (M+1).

C. Synthesis of ethyl [3-(4,5-difluoro-2-hydroxyphenyl)-3-(hydroxymethyl)-2-oxo-2,3-dihydro-1H-indol-1-yl]acetate Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with methyl [3-(4-chloro-2-hydroxyphenyl)-2-oxo-2,3-dihydro-1H-indol-1-yl]acetate, the title compound was obtained: MS (ES+) m/z 378.3 (M+1), 361.3 (M−17).

PREPARATION 46

Synthesis of 3-(4-bromo-2-hydroxyphenyl)-3-(hydroxymethyl)-1-pentyl-1,3-dihydro-2H-indol-2-one

A. Synthesis of 3-(4-bromo-2-hydroxyphenyl)-3-hydroxy-1-pentyl-1,3-dihydro-2H-indol-2-one Following the procedure as described in PREPARATION 10, and making non-critical variations to replace 4-bromo-1-pentyl-1H-indole-2,3-dione with 1-pentyl-1H-indole-2,3-dione, and 1,3-benzodioxol-5-ol with 3-bromophenol, the title compound was obtained (48%) as a white solid: $^1$H NMR (300 MHz, CDCl$_3$) δ 9.66 (br, 1H), 7.50-7.38 (m, 2H), 7.24-7.16 (m, 2H), 6.98-6.86 (m, 2H), 6.64 (d, 1H), 4.15 (br, 1H), 3.80-3.55 (m, 2H), 1.75-1.62 (m, 2H), 1.40-1.34 (m, 4H), 0.89 (t, 3H); MS (ES+) m/z 391.4 (M+1), 393.4 (M+1).

B. Synthesis of 3-(4-bromo-2-hydroxyphenyl)-1-pentyl-1,3-dihydro-2H-indol-2-one Following the procedure as described in PREPARATION 1D, and making non-critical variations to replace 4-bromo-3-hydroxy-3-(6-hydroxy-1,3-benzodioxol-5-yl)-1-pentyl-1,3-dihydro-2H-indol-2-one with 3-(4-bromo-2-hydroxyphenyl)-3-hydroxy-1-pentyl-1,3-dihydro-2H-indol-2-one, the title compound was obtained (91%) as a white powder: $^1$H NMR (300 MHz, CDCl$_3$) δ 7.40 (t, 1H), 7.31 (d, 1H) 7.24-7.23 (m, 2H), 7.01-6.91 (m, 2H), 6.74 (d, 1H), 5.05 (br, 1H), 3.80-3.65 (m, 2H), 1.75-1.63 (m, 2H), 1.38-1.29 (m, 4H), 0.88 (t, 3H); MS (ES+) m/z 374.4 (M+1), 376.4 (M+1).

C. Synthesis of 3-(4-bromo-2-hydroxyphenyl)-3-(hydroxymethyl)-1-pentyl-1,3-dihydro-2H-indol-2-one Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with 3-(4-bromo-2-hydroxyphenyl)-1-pentyl-1,3-dihydro-2H-indol-2-one, the title compound was obtained: R$_f$=0.5 (EtOAc/Hexanes, ¼).

PREPARATION 47

Synthesis of 3-(5-bromo-2-hydroxyphenyl)-3-(hydroxymethyl)-1,3-dihydro-2H-indol-2-one

A. Synthesis of 3-(5-bromo-2-hydroxyphenyl)-3-hydroxy-1,3-dihydro-2H-indol-2-one Following the procedure as described in PREPARATION 2B, and making non-critical variations to replace 1-(2-cyclopropylethyl)-1H-indole-2,3-dione with isatin, 1,3-benzodioxol-5-ol with 4-bromophenol, the title compound was obtained (71%) as a yellowish solid: MS (ES+) m/z 319.4 (M+1), 321.4 (M+1).

B. Synthesis of 3-(5-bromo-2-hydroxyphenyl)-1,3-dihydro-2H-indol-2-one

Following the procedure as described in PREPARATION 1D, and making non-critical variations to replace 4-bromo- 3-hydroxy-3-(6-hydroxy-1,3-benzodioxol-5-yl)-1-pentyl-1,3-dihydro-2H-indol-2-one with 3-(5-bromo-2-hydroxyphenyl)-3-hydroxy-1,3-dihydro-2H-indol-2-one, the title compound was obtained (98%) as a white powder: MS (ES+) m/z 306.2 (M+1), 304.2 (M+1).

C. Synthesis of 3-(5-bromo-2-hydroxyphenyl)-3-(hydroxymethyl)-1,3-dihydro-2H-indol-2-one Following the procedure as described in PREPARATION 35D, and making non-critical variations to replace 5-fluoro-3-(6-hydroxy-1,3-benzodioxol-5-yl)-1-{[5-(trifluoromethyl)-2-furyl]methyl}-1,3-dihydro-2H-indol-2-one with 3-(5-bromo-2-hydroxyphenyl)-1,3-dihydro-2H-indol-2-one, the title compound was obtained: MS (ES+) m/z 334.2 (M+1), 336.2 (M+1).

PREPARATION 48

Synthesis of 1-(diphenylmethyl)-3-(hydroxymethyl)-3-[2-hydroxy-4-(trifluoromethoxy)phenyl]-1,3-dihydro-2H-indol-2-one A. Synthesis of 1-(diphenylmethyl)-3-hydroxy-3-[2-hydroxy-4-(trifluoromethoxy)phenyl]-1,3-dihydro-2H-indol-2-one Following the procedure as described in PREPARATION 2B, and making non-critical variations to replace 1-(2-cyclopropylethyl)-1H-indole-2,3-dione with 1-(diphenylmethyl)-1H-indole-2,3-dione, and 1,3-benzodioxol-5-ol with 3-(trifluoromethoxy)phenol, the title compound was obtained (75%): MS (ES+) m/z 514.5 (M+23).

B. Synthesis of 1-(diphenylmethyl)-3-[2-hydroxy-4-(trifluoromethoxy)phenyl]-1,3-dihydro-2H-indol-2-one Following the procedure as described in PREPARATION 2C, and making non-critical variations to replace 1-(2-cyclopropylethyl)-3-hydroxy-3-(6-hydroxy-1,3-benzodioxol-5-yl)-1,3-dihydro-2H-indol-2-one with 1-(diphenylmethyl)-3-hydroxy-3-[2-hydroxy-4-(trifluoromethoxy)phenyl]-1,3-dihydro-2H-indol-2-one, the title compound was obtained (82%): MS (ES+) m/z 498.4 (M+23).

C. Synthesis of 1-(diphenylmethyl)-3-(hydroxymethyl)-3-[2-hydroxy-4-(trifluoromethoxy)phenyl]-1,3-dihydro-2H-indol-2-one Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with 1-(diphenylmethyl)-3-[2-hydroxy-4-(trifluoromethoxy)phenyl]-1,3-dihydro-2H-indol-2-one, the title compound was obtained: MS (ES+) m/z 488 (M−17), 528 (M+23).

PREPARATION 49

Synthesis of 1-(diphenylmethyl)-3-(6-hydroxy-2,3-dihydro-1-benzofuran-5-yl)-3-(hydroxymethyl)-1,3-dihydro-2H-indol-2-one A. Synthesis of 1-(diphenylmethyl)-3-hydroxy-3-(6-hydroxy-2,3-dihydro-1-benzofuran-5-yl)-1,3-dihydro-2H-indol-2-one Following the procedure as described in PREPARATION 2B, and making non-critical variations to replace 1,3-benzodioxol-5-ol with 2,3-dihydrobenzofuran-6-ol (Foster et al., *J. Chem. Soc.* 1948:2254-2258) and 1-(2-cyclopropylethyl)-1H-indole-2,3-dione with 1-(diphenylmethyl)-1H-indole-2,3-dione, the title compound was obtained (68%) as a white solid: MS (ES+) m/z 450.4 (M+1).

B. Synthesis of 1-(diphenylmethyl)-3-(6-hydroxy-2,3-dihydro-1-benzofuran-5-yl)-1,3-dihydro-2H-indol-2-one Following the procedure as described in PREPARATION 2C, and making non-critical variations to replace 1-(2-cyclopropylethyl)-3-hydroxy-3-(6-hydroxy-1,3-benzodioxol-5-yl)-1,3-dihydro-2H-indol-2-one with 1-(diphenylmethyl)-3-hydroxy-3-(6-hydroxy-2,3-dihydro-1-benzofuran-5-yl)-1,3-dihydro-2H-indol-2-one, the title compound was obtained (67%) as a white solid: MS (ES+) m/z 434.3 (M+1).

C. Synthesis of 1-(diphenylmethyl)-3-(6-hydroxy-2,3-dihydro-1-benzofuran-5-yl)-(3-hydroxymethyl)-1,3-dihydro-2H-indol-2-one Following the procedure as described in PREPARATION 26C, and making non-critical variations to replace 1-(diphenylmethyl)-3-(5-hydroxy-2,3-dihydro-1-benzofuran-6-yl)-1,3-dihydro-2H-indol-2-one with 1-(diphenylmethyl)-3-(6-hydroxy-2,3-dihydro-1-benzofuran-5-yl)-1,3-dihydro-2H-indol-2-one, the title compound was obtained (45%) as a white solid: MS (ES+) m/z 464.5 (M+1).

PREPARATION 50

Synthesis of 4-bromo-3-(6-hydroxy-2,3-dihydro-1-benzofuran-5-yl)-3-(hydroxymethyl)-1,3-dihydro-2H-indol-2-one A. Synthesis of 4-bromo-3-hydroxy-3-(6-hydroxy-2,3-dihydro-1-benzofuran-5-yl)-1,3-dihydro-2H-indol-2-one Following the procedure as described in PREPARATION 2B, and making non-critical variations to replace 1,3-benzodioxol-5-ol with 2,3-dihydrobenzofuran-6-ol and 1-(2-cyclopropylethyl)-1H-indole-2,3-dione with 4-bromo-1H-indole-2,3-dione, the title compound was obtained (78%) as a white solid: $^1$H NMR (300 MHz, DMSO-d$_6$) δ 10.36 (s, 1H), 9.15 (s, 1H), 7.49 (1H), 7.04 (t, 1H), 6.89 (d, 1H), 6.74 (d, 1H), 6.35 (br, 1H), 5.90 (s, 1H), 4.45 (t, 2H), 3.05 (t, 2H); $^{13}$C NMR (75 MHz, DMSO-d$_6$) δ 178.4, 160.2, 154.0, 145.7, 131.6, 130.7, 125.5, 125.4, 118.9, 117.7, 116.1, 108.8, 96.8, 76.9, 71.8, 29.1; MS (ES−) m/z 344.4 (M−17), 360.4 (M−1).

B. Synthesis of 4-bromo-3-(6-hydroxy-2,3-dihydro-1-benzofuran-5-yl)-1,3-dihydro-2H-indol-2-one Following the procedure as described in PREPARATION 2C, and making non-critical variations to replace 1-(2-cyclopropylethyl)-3-hydroxy-3-(6-hydroxy-1,3-benzodioxol-5-yl)-1,3-dihydro-2H-indol-2-one with 4-bromo-3-hydroxy-3-(6-hydroxy-2,3-dihydro-1-benzofuran-5-yl)-1,3-dihydro-2H-indol-2-one, the title compound was obtained (62%) as a white solid: MS (ES+) m/z 346.5 (M+1), 348.5 (M+1).

C. Synthesis of 4-bromo-3-(6-hydroxy-2,3-dihydro-1-benzofuran-5-yl)-3-(hydroxymethyl)-1,3-dihydro-2H-indol-2-one Following the procedure as described in PREPARATION 14C, and making non-critical variations to replace 3-(5- fluoro-2-hydroxyphenyl)-1-pentyl-1,3-dihydro-2H-indol-2-one with 4-bromo-3-(6-hydroxy-2,3-dihydro-1-benzofuran-5-yl)-1,3-dihydro-2H-indol-2-one, the title compound was obtained (16%): R$_f$=0.21 (EtOAc/Hexanes, 7/3).

PREPARATION 51

Synthesis of 7-fluoro-3-(6-hydroxy-1,3-benzodioxol-5-yl)-3-(hydroxymethyl)-1-{[5-(trifluoromethyl)-2-furyl]methyl}-1,3-dihydro-2H-indol-2-one A. Synthesis of 7-fluoro-1-{[5-(trifluoromethyl)-2-furyl]methyl}-1H-indole-2,3-dione Following the procedure as described in PREPARATION 1A, and making tnon-critical variations to replace 4-bromoindole with 7-fluoroisatin, and 1-bromopentane with 2-(bromomethyl)-5-(trifluoromethyl)furan, the title compound was obtained (34%): MS (ES+) m/z 336.2 (M+23).

B. Synthesis of 7-fluoro-3-hydroxy-3-(6-hydroxy-1,3-benzodioxol-5-yl)-1-{[5-(trifluoromethyl)-2-furyl]methyl}-1,3-dihydro-2H-indol-2-one Following the procedure as described in PREPARATION 2B, and making non-critical variations to replace 1-(2-cyclopropylethyl)-1H-indole-2,3-dione with 7-fluoro-1-{[5-(trifluoromethyl)-2-furyl]methyl}-1H-indole-2,3-dione, the title compound was obtained (75%): MS (ES+) m/z 474.3 (M+23).

C. Synthesis of 7-fluoro-3-(6-hydroxy-1,3-benzodioxol-5-yl)-1-{[5-(trifluoromethyl)-2-furyl]methyl}-1,3-dihydro-2H-indol-2-one Following the procedure as described in PREPARATION 2C, and making non-critical variations to replace 1-(2-cyclopropylethyl)-3-hydroxy-3-(6-hydroxy-1,3-benzodioxol-5-yl)-1,3-dihydro-2H-indol-2-one with 7-fluoro-3-hydroxy-3-(6-hydroxy-1,3-benzodioxol-5-yl)-1-{[5-(trifluoromethyl)-2-furyl]methyl}-1,3-dihydro-2H-indol-2-one, the title compound was obtained (65%): MS (ES+) m/z 436.4 (M+1).

D. Synthesis of 7-fluoro-3-(6-hydroxy-1,3-benzodioxol-5-yl)-3-(hydroxymethyl)-1-{[5-(trifluoromethyl)-2-furyl]methyl}-1,3-dihydro-2H-indol-2-one Following the procedure as described in PREPARATION 26C, and making non-critical variations to replace 1-(diphenylmethyl)-3-(5-hydroxy-2,3-dihydro-1-benzofuran-6-yl)-1,3-dihydro-2H-indol-2-one with 7-fluoro-3-(6-hydroxy-1,3-benzodioxol-5-yl)-1-{[5-(trifluoromethyl)-2-furyl]methyl}-1,3-dihydro-2H-indol-2-one, the title compound was obtained (67%): MS (ES+) m/z 488.4 (M+23).

PREPARATION 52

Synthesis of 3-(6-hydroxy-2,3-dihydro-1-benzofuran-5-yl)-3-(hydroxymethyl)-1-pentyl-1,3-dihydro-2H-indol-2-one A. Synthesis of 3-hydroxy-3-(6-hydroxy-2,3-dihydro-1-benzofuran-5-yl)-1-pentyl-1,3-dihydro-2H-indol-2-one Following the procedure as described in PREPARATION 2B, and making non-critical variations to replace1-(2-cyclopropylethyl)-1H-indole-2,3-dione with 1-pentyl-1H-indole-2,3-dione, and 1,3-benzodioxol-5-ol with 2,3-dihydrobenzofuran-6-ol, the title compound was obtained (90%) as a white powder: MS (ES+) m/z 376.3 (M+23).

B. Synthesis of 3-(6-hydroxy-2,3-dihydro-1-benzofuran-5-yl)-1-pentyl-1,3-dihydro-2H-indol-2-one Following the procedure as described in PREPARATION 2C, and making non-critical variations to replace 1-(2-cyclopropylethyl)-3-hydroxy-3-(6-hydroxy-1,3-benzodioxol-5-yl)-1,3-dihydro-2H-indol-2-one with 3-hydroxy-3-(6-hydroxy-2,3-dihydro-1-benzofuran-5-yl)-1-pentyl-1,3-dihydro-2H-indol-2-one, the title compound was obtained (76%): MS (ES+) m/z 338.3 (M+1).

C. Synthesis of 3-(6-hydroxy-2,3-dihydro-1-benzofuran-5-yl)-3-(hydroxymethyl)-1-pentyl-1,3-dihydro-2H-indol-2-one Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with 3-(6-hydroxy-2,3-dihydro-1-benzofuran-5-yl)-1-pentyl-1,3-dihydro-2H-indol-2-one, the title compound was obtained (46%): MS (ES+) m/z 368.3 (M+1), 380.4 (M+23).

PREPARATION 53

Synthesis of 3-(5-bromo-2-hydroxyphenyl)-1-(diphenylmethyl)-3-(hydroxymethyl)-1,3-dihydro-2H-indol-2-one A. Synthesis of 3-(5-bromo-2-hydroxyphenyl)-1-(diphenylmethyl)-3-hydroxy-1,3-dihydro-2H-indol-2-one Following the procedure as described in PREPARATION 2B, and making non-critical variations to replace1-(2-cyclopropylethyl)-1H-indole-2,3-dione with 1-(diphenylmethyl)-1H-indole-2,3-dione, and 1,3-benzodioxol-5-ol with 4-bromophenol, the title compound was obtained (90%) as an orange solid: MS (ES+) m/z 486.2 (M+1), 488.2 (M+1).

B. Synthesis of 3-(5-bromo-2-hydroxyphenyl)-1-(diphenylmethyl)-1,3-dihydro-2H-indol-2-one Following the procedure as described in PREPARATION 15B, and making non-critical variations to replace 3-(5-bromo-2-hydroxyphenyl)-3-hydroxy-1-pentyl-1,3-dihydro-2H-indol-2-one with 3-(5-bromo-2-hydroxyphenyl)-1-(diphenylmethyl)-3-hydroxy-1,3-dihydro-2H-indol-2-one, the title compound was obtained (99%) as a white powder: $^1$H NMR (300 MHz, CDCl$_3$) δ 7.39-7.20 (m, 11H), 7.11-7.06 (m, 4H), 6.82 (d, 1H), 6.57-6.51 (m, 1H), 5.04 (s, 1H); MS (ES+) m/z 471.2 (M+1), 473.2 (M+1).

C. Synthesis of 3-(5-bromo-2-hydroxyphenyl)-1-(diphenylmethyl)-3-(hydroxymethyl)-1,3-dihydro-2H-indol-2-one Following the procedure as described in PREPARATION 26C, and making non-critical variations to replace 1-(diphenylmethyl)-3-(5-hydroxy-2,3-dihydro-1-benzofuran-6-yl)-1,3-dihydro-2H-indol-2-one with 3-(5-bromo-2-hydroxyphenyl)-1-(diphenylmethyl-1,3-dihydro-2H-indol-2-one, the title compound was obtained: MS (ES+) m/z 500.4 (M+1), 502.4 (M+1).

PREPARATION 54

Synthesis of 3-(6-hydroxy-1,3-benzodioxol-5-yl)-3-(hydroxymethyl)-1-pentyl-1,3-dihydro-2H-indol-2-one A. Synthesis of 1-pentyl-1H-indole-2,3-dione Following the procedure as described in PREPARATION 2A, and making non-critical variations to replace (2-bromoethyl)cyclopropane with 1-bromopentane, the title compound was obtained (72%) as a red solid: $^1$H NMR (300 MHz, CDCl$_3$) δ 7.90 (d, 1H), 7.53-7.45 (m, 1H), 7.03-6.97 (m, 1H), 6.82 (d, 1H), 3.64-3.57 (m, 2H), 1.68-1.52 (m, 2H), 1.34-1.21 (m, 4H), 0.79 (t, 3H); $^{13}$C NMR (75 MHz, CDCl$_3$) δ 183.6, 158.1, 151.0, 138.4, 125.3, 123.5, 117.5, 110.2, 40.2, 28.9, 26.9, 22.2, 13.9.

B. Synthesis of 3-hydroxy-3-(6-hydroxy-1,3-benzodioxol-5-yl)-1-pentyl-1,3-dihydro-2H-indol-2-one Following the procedure as described in PREPARATION 2B, and making non-critical variations to replace1-(2-cyclopropylethyl)-1H-indole-2,3-dione with 1-pentyl-1H-indole-2,3-dione, the title compound was obtained (47%) as a colorless solid: $^1$H NMR (300 MHz, CDCl$_3$) δ 9.41 (s, 1H), 7.46 (dd, 1H), 7.37 (dt, 1H), 7.16 (dt, 1H), 6.89 (d, 1H), 6.53 (s, 1H), 6.22 (s, 1H), 5.83 (dd, 2H), 4.70 (br, 1H), 3.73-3.54 (m, 2H), 1.69-1.60 (m, 2H), 1.34-1.26 (m, 4H), 0.85 (t, 3H); $^{13}$C NMR (75 MHz, CDCl$_3$) δ 178.9, 152.2, 148.8, 142.5, 141.3, 130.3, 129.3, 126.1, 123.8, 117.1, 109.5, 106.8, 101.8, 101.4, 79.3, 40.4, 28.9, 26.8, 22.3, 13.9; MS (ES+1) m/z 355.5 (M+1).

C. Synthesis of 3-(6-hydroxy-1,3-benzodioxol-5-yl)-1-pentyl-1,3-dihydro-2H-indol-2-one Following the procedure as described in PREPARATION 2C, and making non-critical variations to replace 1-(2-cyclopropylethyl)-3-hydroxy-3-(6-hydroxy-1,3-benzodioxol-5-yl)-1,3-dihydro-2H-indol-2-one with 3-hydroxy-3-(6-hydroxy-1,3-benzodioxol-5-yl)-1-pentyl-1,3-dihydro-2H-indol-2-one, the title compound was obtained (81%) as a colorless solid: $^1$H NMR (300 MHz, CDCl$_3$) δ 9.67 (br, 1H), 7.39-7.29 (m, 2H), 7.18-7.13 (m, 1H), 6.94 (d, 1H), 6.62 (s, 1H), 6.32 (s, 1H), 5.84 (dd, 2H), 5.01 (s, 1H), 3.71-3.63 (m, 2H), 1.71-1.61 (m, 2H), 1.35-1.27 (m, 4H), 0.86 (t, 3H); $^{13}$C NMR (75 MHz, CDCl$_3$) δ 178.8, 151.3, 147.6, 143.9, 141.53, 128.7, 126.4, 126.2, 123.1, 115.3, 109.4, 106.5, 101.5, 101.2, 47.4, 40.5, 28.9, 26.9, 22.3, 13.9; MS (ES+) m/z 340 (M+1).

D. Synthesis of 3-(6-hydroxy-1,3-benzodioxol-5-yl)-3-(hydroxymethyl)-1-pentyl-1,3-dihydro-2H-indol-2-one Following the procedure as described in PREPARATION 1E, and making non-critical variations to replace 4-bromo-3-(6-hydroxy-1,3-benzodioxol-5-yl)-1-pentyl-1,3-dihydro-2H-indol-2-one with 3-(6-hydroxy-1,3-benzodioxol-5-yl)-1-pentyl-1,3-dihydro-2H-indol-2-one, the title compound was obtained (67%): $^1$H NMR (300 MHz, CDCl$_3$) δ 10.85-10.63 (br, 1H), 7.48-7.35 (m, 2H), 7.28-7.19 (m, 1H), 6.96 (d, 1H), 6.52 (d, 2H), 5.82 (dd, 2H), 4.63 (d, 1H), 4.11 (d, 1H), 3.70 (d, 2H), 2.04-1.74 (br, 1H), 1.65-162 (m, 2H), 1.31-1.24 (m, 4H), 0.84 (t, 3H); $^{13}$C NMR (75 MHz, CDCl$_3$) δ 180.3, 152.6, 148.1, 143.2, 141.3, 129.2, 129.1, 126.2, 123.3, 112.4, 109.6, 108.2, 101.9, 101.3, 64.6, 59.8, 40.6, 28.9, 26.9, 22.2, 13.9; MS (ES+) m/z 370.1 (M+1).

EXAMPLE 1

Synthesis of 1'-(2-cyclopropylethyl)spiro[furo[2,3-f][1,3]benzodioxole-7,3'-indol]-2'(1'H)-one

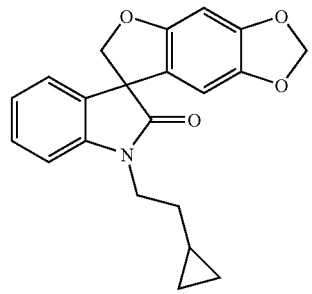

To a solution of 1-(2-cyclopropylethyl)-3-(6-hydroxy-1,3-benzodioxol-5-yl)-3-(hydroxymethyl)-1,3-dihydro-2H-indol-2-one (0.92 g, 2.51 mmol) in anhydrous THF (20.0 mL) was added triphenylphosphine (0.82 g, 3.13 mmol) and diethyl azodicarboxylate (0.55, 3.13 mmol) at −78° C. The brown reaction solution was stirred at ambient temperature for 16 h, and quenched with saturated ammonium chloride (50.0 mL). The organic solvent was removed under reduced pressure and the aqueous mixture was extracted with ethyl acetate (3×50.0 mL). The combined organic layers were dried over anhydrous sodium sulfate and filtered. The filtrate was concentrated in vacuo to dryness. The brown residue was subjected to column chromatography eluting with ethyl acetate/hexane (5% to 20%, gradient) to give the title compound (0.63 g, 72%) which was crystallized from ether to afford a colorless solid: mp 125-127° C.; $^1$H NMR (300 MHz, CDCl$_3$) δ 7.30-7.25 (m, 1H), 7.14 (d, 1H), 7.02 (t, 1H), 6.89 (d, 1H), 6.49 (s, 1H), 6.11 (s, 1H), 5.84 (m, 2H), 4.76 (m, 2H), 3.93-3.74 (m, 2H), 1.65-1.57 (m, 2H), 0.76-0.56 (m, 1H), 0.48-0.41 (m, 2H), 0.08-0.03 (m, 2H); $^{13}$C NMR (75 MHz, CDCl$_3$) δ 177.4, 155.9, 148.8, 142.6, 142.3, 132.4, 128.8, 124.0, 123.1, 119.5, 108.6, 103.1, 101.5, 93.6, 80.6, 58.2, 40.5, 32.5, 30.8, 8.7, 4.4; MS (ES+) m/z 350.3 (M+1).

EXAMPLE 1.1

Synthesis of 1'-pentylspiro[furo[2,3-f][1,3]benzodioxole-7,3'-indol]-2'(1'H)-one

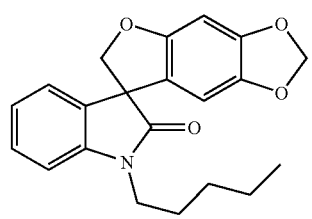

Following the procedure as described in Example 1, and making non-critical variations using 3-(6-hydroxy-1,3-benzodioxol-5-yl)-3-(hydroxymethyl)-1-pentyl-1,3-dihydro-2H-indol-2-one to replace 1-(2-cyclopropylethyl)-3-(6-hydroxy-1,3-benzodioxol-5-yl)-3-(hydroxymethyl)-1,3-dihydro-2H-indol-2-one, the title compound was obtained (80%) as a white solid: mp 85-87° C.; $^1$H NMR (300 MHz, CDCl$_3$)δ 7.28 (t, 1H), 7.15(d, 1H), 7.02 (t, 1H), 6.89 (d, 1H), 6.49 (s, 1H), 6.11 (s, 1H), 5.84 (dd, 2H),4.77(ABq, 2H),3.85-3.62 (m, 2H), 1.76-1.66 (m, 2H), 1.40-1.33 (m, 4H), 0.89 (t, 3H); $^{13}$C NMR (75 MHz, CDCl$_3$) δ 177.3, 155.9, 148.8, 142.4, 142.3, 132.5, 128.9, 123.9, 119.6, 108.6, 103.0, 101.5, 93.6, 80.5, 58.2, 40.4, 29.0, 27.1, 22.3, 14.0; MS (ES+) m/z 352 (M+1).

EXAMPLE 1.2

Synthesis of 4'-bromo-1-pentylspiro[furo[2,3-f][1,3]benzodioxole-7,3'-indol]-2'(1'H)-one

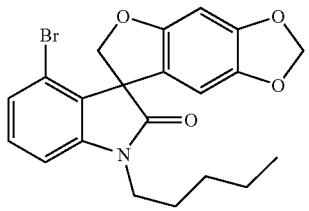

Following the procedure as described in EXAMPLE 1, and making non-critical variations using 4-bromo-3-(6-hydroxy-1,3-benzodioxol-5-yl)-3-(hydroxymethyl)-1-pentyl-1,3-dihydro-2H-indol-2-one to replace 1-(2-cyclopropylethyl)-3-(6-hydroxy-1,3-benzodioxol-5-yl)-3-(hydroxymethyl)-1,3-dihydro-2H-indol-2-one, the title compound was obtained as a colorless solid: $^1$H NMR (300 MHz, CDCl$_3$) δ 7.16 (d, 1H), 7.15 (s, 1H), 6.84 (dd, 1H), 6.45 (s, 1H), 6.06 (s, 1H), 5.86 (dd, 2H), 4.90 (ABq, 2H), 3.83-3.60 (m, 2H), 1.74-1.64 (m, 2H), 1.39-1.28 (m, 4H), 0.89 (t, 3H); $^{13}$C NMR (75 MHz, CDCl$_3$) δ 177.1, 157.2, 149.1, 144.6, 142.0, 130.3, 130.1, 127.0, 120.0, 116.5, 107.6, 102.5, 101.5, 93.3, 77.3, 59.6, 40.6, 29.0, 27.0, 22.3, 14.0; MS (ES+) m/z 430 (M+1).

EXAMPLE 1.3

Synthesis of ethyl (2'-oxospiro[furo[2,3-f][1,3]benzodioxole-7,3'-indol]-1'(2'H)-yl)acetate

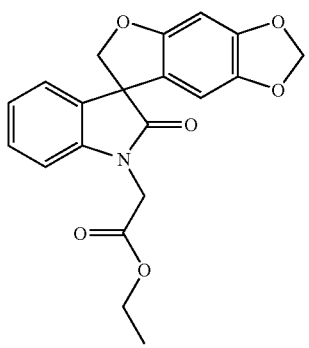

Following the procedure as described in EXAMPLE 1, and making non-critical variations using ethyl [3-(6-hydroxy-1,3-benzodioxol-5-yl)-3-(hydroxymethyl)-2-oxo-2,3-dihydro-1H-indol-1-yl]acetate to replace 1-(2-cyclopropylethyl)-3-(6-hydroxy-1,3-benzodioxol-5-yl)-3-(hydroxymethyl)-1,3-dihydro-2H-indol-2-one, the title compound was obtained as a white powder in 90% yield: $^1$H NMR (300 MHz, DMSO-d$_6$) δ 7.31-7.26 (m, 1H), 7.17-7.00 (m, 3H), 6.67 (s, 1H), 6.18 (s, 1H), 5.90-5.89 (m, 2H), 4.76-4.66 (m, 2H), 4.59 (s, 2H), 4.13 (q, 2H), 1.17 (t, 3H); $^{13}$C NMR (75 MHz, DMSO-d$_6$) δ 177.3, 168.3, 155.6, 148.8, 142.4, 142.1, 132.0, 129.3, 124.1, 123.7, 120.4, 109.6, 103.3, 101.9, 93.8, 79.8, 61.8, 57.8, 41.8, 14.5; MS (ES+) m/z 390.2 (M+23).

EXAMPLE 1.4

Synthesis of methyl 2-[(2'-oxospiro[furo[2,3-f][1,3]benzodioxole-7,3'-indol]-1'(2'H)-yl)methyl]benzoate

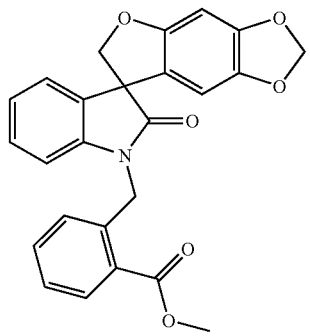

Following the procedure as described in EXAMPLE 1, and making non-critical variations using methyl 2-{[3-(6-hydroxy-1,3-benzodioxol-5-yl)-3-(hydroxymethyl)-2-oxo-2,3-dihydro-1H-indol-1-yl]methyl}benzoate to replace 1-(2-cyclopropylethyl)-3-(6-hydroxy-1,3-benzodioxol-5-yl)-3-(hydroxymethyl)-1,3-dihydro-2H-indol-2-one, the title compound was obtained as a white powder in 74% yield: mp 166-167° C.; $^1$H NMR (300 MHz, CDCl$_3$) δ 8.05 (m, 1H), 7.44 (m, 1H), 7.34 (t, 1H), 7.22-7.10 (m, 3H), 7.03 (m, 1H), 6.70 (d, 1H), 6.52 (s, 1H), 6.21 (s, 1H), 5.90-5.84 (m, 2H), 5.52-5.33 (m, 2H), 4.99 (d, 1H), 4.72 (d, 1H), 3.95 (s, 3H); $^{13}$C NMR (75 MHz, CDCl$_3$) δ 177.8, 167.5, 156.0, 148.9, 142.4, 142.3, 137.4, 132.8, 132.1, 131.4, 129.0, 128.6, 127.4, 126.5, 123.9, 123.6, 119.4, 109.5, 103.1, 101.5, 93.7, 80.7, 58.4, 52.3, 42.4; MS (ES+) m/z 430.3 (M+1), 452.3 (M+23).

EXAMPLE 1.5

Synthesis of methyl 3-[(2'-oxospiro[furo[2,3-f][1,3]benzodioxole-7,3'-indol]-1'(2'H)-yl)methyl]benzoate

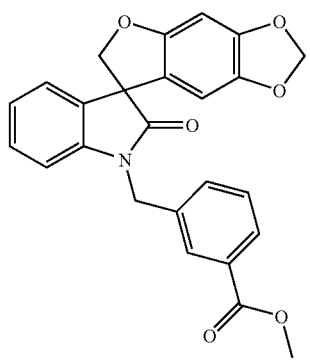

Following the procedure as described in EXAMPLE 1, and making non-critical variations using methyl 3-{[3-(6-hydroxy-1,3-benzodioxol-5-yl)-3-(hydroxymethyl)-2-oxo-2,3-dihydro-1H-indol-1-yl]methyl}benzoate to replace 1-(2-cyclopropylethyl)-3-(6-hydroxy-1,3-benzodioxol-5-yl)-3-(hydroxymethyl)-1,3-dihydro-2H-indol-2-one, the title compound was obtained as a white powder in 73% yield; $^1$H NMR (300 MHz, CDCl$_3$) δ 7.97-7.95 (m, 2H), 7.53-7.50 (m, 1H), 7.45-7.40 (m, 1H), 7.21-7.15 (m, 2H), 7.04-6.99 (m, 1H), 6.73-6.71 (m, 1H), 6.52 (s, 1H), 6.20 (s, 1H), 5.86 (s, 1H), 5.18 (d, 1H), 4.72 (d, 1H), 4.80 (d, 1H), 4.69 (d, 1H), 3.89 (s, 1H); $^{13}$C NMR (75 MHz, CDCl$_3$) δ 177.7, 166.6, 156.0, 149.0, 142.4, 141.7, 136.1, 132.2, 131.7, 130.9, 129.2, 128.1, 124.0, 123.7, 119.4, 109.2, 103.1, 101.6, 93.7, 80.5, 64.3, 58.3, 52.3, 43.7; MS (ES+) m/z 430 (M+1).

EXAMPLE 1.6

Synthesis of methyl 4-[(2'-oxospiro[furo[2,3-f][1,3]benzodioxole-7,3'-indol]-1'(2'H)-yl)methyl]benzoate

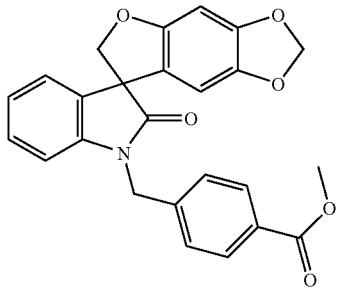

Following the procedure as described in EXAMPLE 1, and making non-critical variations using methyl 4-{[3-(6-hydroxy-1,3-benzodioxol-5-yl)-3-(hydroxymethyl)-2-oxo-2,3-dihydro-1H-indol-1-yl]methyl}benzoate to replace 1-(2-cyclopropylethyl)-3-(6-hydroxy-1,3-benzodioxol-5-yl)-3-(hydroxymethyl)-1,3-dihydro-2H-indol-2-one, the title compound was obtained as a white powder in 87% yield: $^1$H NMR (300 MHz, CDCl$_3$) δ 8.01 (d, 2H), 7.38 (d, 2H), 7.18 (t, 2H), 7.02 (t, 1H), 6.72 (d, 1H), 6.52 (s, 1H), 6.12 (s, 1H), 5.86 (m, 2H), 5.11 (d, 1H), 4.96 (d, 1H), 4.86 (d, 1H), 4.69 (d, 1H), 3.89 (s, 1H); $^{13}$C NMR (75 MHz, CDCl$_3$) δ 177.7, 166.6, 156.0, 149.0, 142.4, 141.8, 140.8, 132.1, 130.3, 129.8, 129.0 127.3, 124.1, 123.7, 119.3, 109.2, 103.0, 102.0, 93.7, 80.5, 58.3, 52.2, 43.9; MS (ES+) m/z 430.1 (M+1).

EXAMPLE 1.7

Synthesis of 1'-(diphenylmethyl)spiro[furo[2,3-f][1,3]benzodioxole-7,3'-indol]-2'(1'H)-one

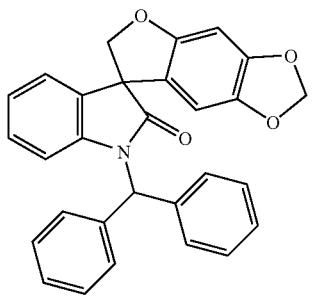

Following the procedure as described in EXAMPLE 1, and making non-critical variations using 1-(diphenylmethyl)-3-(6-hydroxy-1,3-benzodioxol-5-yl)-3-(hydroxymethyl)-1,3-dihydro-2H-indol-2-one to replace 1-(2-cyclopropylethyl)-3-(6-hydroxy-1,3-benzodioxol-5-yl)-3-(hydroxymethyl)-1,3-dihydro-2H-indol-2-one, the title compound was obtained as a white powder in 26% yield: MS (ES+) m/z 462.3 (M+1).

EXAMPLE 1.8

Synthesis of spiro[furo[2,3-f][1,3]benzodioxole-7,3'-indol]-2'(1'H)-one

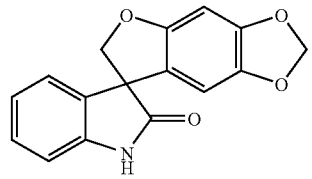

To a solution of 1'-(diphenylmethyl)spiro[furo[2,3-f][1,3]benzodioxole-7,3'-indol]-2'(1'H)-one (2.10 g, 4.70 mmol) in EtOAc (100 mL) and acetic acid (0.10 mL) was added palladium on carbon (1.00 g). The reaction mixture was hydrogenated under 60 psi of hydrogen at ambient temperature for 5 days and filtered. The filtrate was concentrated in vacuo to dryness. The residue was subjected to column chromatography to yield the title compound (0.87 g, 66%) as a white powder: mp 252° C. (dec.); $^1$H NMR (300 MHz, CDCl$_3$) δ 10.55 (s, 1H), 7.25-6.84 (m, 4H), 6.64 (s, 1H), 6.22 (s, 1H), 5.88 (s, 2H), 4.76-4.57 (dd, 2H); MS (ES+) m/z 282.2 (M+1).

EXAMPLE 1.9

Synthesis of 2-[3-(2'-oxospiro[furo[2,3-f][1,3]benzodioxole-7,3'-indol]-1'(2'H)-yl)propyl]-1H-isoindole-1,3(2H)-dione

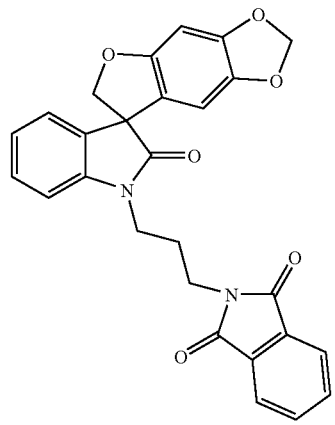

Following the procedure as described in EXAMPLE 1, and making non-critical variations using 2-{3-[3-(6-hydroxy-1,3-benzodioxol-5-yl)-3-(hydroxymethyl)-2-oxo-2,3-dihydro-1H-indol-1-yl]propyl}-1H-isoindole-1,3(2H)-dione to replace 1-(2-cyclopropylethyl)-3-(6-hydroxy-1,3-benzodioxol-5-yl)-3-(hydroxymethyl)-1,3-dihydro-2H-indol-2-one, the title compound was obtained in 45% yield: $^1$H NMR (300 MHz, CDCl$_3$) δ 7.83-7.80 (m, 2H), 7.70-7.68 (m, 2H), 7.28-7.26 (m, 1H), 7.15 (d, 1H), 7.05-7.00 (m, 1H), 6.86 (d, 1H), 6.48 (s, 1H), 6.23 (s, 1H), 5.85-5.83 (m, 2H), 4.91 (d, 1H), 4.65 (d, 1H), 3.94-3.68-(m, 4H), 2.15-2.10-(m, 2H); $^{13}$C NMR (75 MHz, CDCl$_3$) δ 177.4, 168.2, 155.9, 148.8, 142.4, 141.9, 134.0, 132.5, 132.0, 128.9, 124.1, 123.4, 123.3, 119.4, 108.4, 103.2, 101.5, 93.6, 80.4, 58.2, 38.0, 35.6, 26.8; MS (ES+) m/z 469.3 (M+1), 491.3 (M+23).

EXAMPLE 1.10

Synthesis of 2-[2-(2'-oxospiro[furo[2,3-f][1,3]benzodioxole-7,3'-indol]-1'(2'H)-yl)ethyl]-1H-isoindole-1,3(2H)-dione

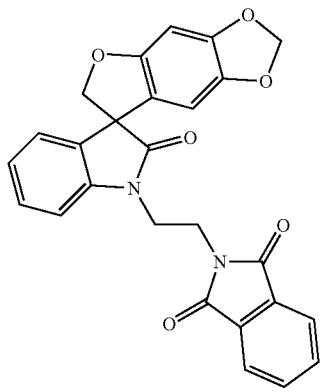

Following the procedure as described in EXAMPLE 1, and making non-critical variations using 2-{2-[3-(6-hydroxy-1,3-benzodioxol-5-yl)-3-(hydroxymethyl)-2-oxo-2,3-dihydro-1H-indol-1-yl]ethyl}-1H-isoindole-1,3(2H)-dione to replace 1-(2-cyclopropylethyl)-3-(6-hydroxy-1,3-benzodioxol-5-yl)-3-(hydroxymethyl)-1,3-dihydro-2H-indol-2-one, the title compound was obtained in 61% yield: $^1$H NMR (300 MHz, CDCl$_3$) δ 7.81-7.73 (m, 2H), 7.71-7.62 (m, 2H), 7.18-7.08 (m, 2H), 6.98 (t, 1H), 6.87 (d, 1H), 6.43 (s, 1H), 6.29 (s, 1H), 5.91-5.81 (ABq, 2H), 4.79 (d, 1H), 4.58 (d, 1H), 4.18-3.92 (m, 4H), 3.06 (t, 2H), 1.59-1.35 (br, 2H); $^{13}$C NMR (75 MHz, CDCl$_3$) δ 178, 168.2, 156.1, 148.7, 142.2, 141.9, 134.1, 132.4, 131.8, 128.7, 124.1, 123.4, 123.3, 119.0, 107.8, 103.7, 101.4, 93.4, 80.9, 58.1, 39.0, 35.6; MS (ES+) m/z 455 (M+1), 477 (M+23).

EXAMPLE 1.11

Synthesis of 1'-[3-(Benzyloxy)propyl]spiro[furo[2,3-f][1,3]benzodioxole-7,3'-indol]-2'(1'H)-one

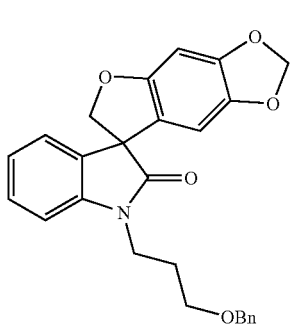

Following the procedure as described in EXAMPLE 1, and making non-critical variations using 1-[3-(benzyloxy)propyl]-3-(6-hydroxy-1,3-benzodioxol-5-yl)-3-(hydroxymethyl)-1,3-dihydro-2H-indol-2-one to replace 1-(2-cyclopropylethyl)-3-(6-hydroxy-1,3-benzodioxol-5-yl)-3-(hydroxymethyl)-1,3-dihydro-2H-indol-2-one, the title compound was obtained in 98% yield as a pale yellow syrup: $^1$H NMR (300 MHz, CDCl$_3$) δ 7.38-6.95 (m, 9H), 6.49 (s, 1H), 6.08 (s, 1H), 5.83 (dd, 2H), 5.86 (ABq, 1H), 4.58 (ABq, 1H), 3.96-3.79 (m, 2H), 3.53 (t, 2H), 2.06-2.00 (m, 2H); $^{13}$C NMR (75 MHz, CDCl$_3$) δ 177.4, 155.9, 148.8, 142.5, 142.2, 138.1, 132.3, 128.9, 127.9, 127.6, 123.9, 123.1, 119.5, 108.7, 103.0, 101.4, 93.6, 80.4, 73.1, 67.4, 58.1, 37.7, 27.9; MS (ES+) m/z 430.3 (M+1).

EXAMPLE 1.12

Synthesis of 5,6-difluoro-1'-pentylspiro[1-benzofuran-3,3'-indol]-2'(1'H)-one

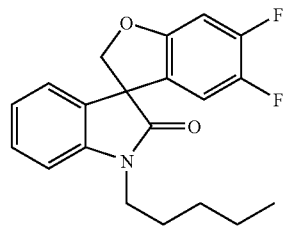

Following the procedure as described in EXAMPLE 1, and making non-critical variations using 3-(4,5-difluoro-2-hydroxyphenyl)-3-(hydroxymethyl)-1-pentyl-1,3-dihydro-2H-indol-2-one to replace 1-(2-cyclopropylethyl)-3-(6-hydroxy-1,3-benzodioxol-5-yl)-3-(hydroxymethyl)-1,3-dihydro-2H-indol-2-one, the title compound was obtained in 71% yield: mp 48-50° C.; $^1$H NMR (300 MHz, CDCl$_3$) δ 7.33 (td, 1H), 7.18-7.12 (m, 2H), 6.93 (d, 1H), 6.77 (dd, 1H), 6.51 (dd, 1H), 4.96 (d, 1H), 4.71 (d, 1H), 3.87-3.64 (m, 2H), 1.82-1.65 (m, 2H), 1.46-1.28 (m, 4H), 0.92 (t, 3H); $^{13}$C NMR (75 MHz, CDCl$_3$) δ 176.6, 156.8, 152.9, 149.8, 144.2, 142.6, 131.8, 129.4, 124.1, 123.5, 111.7, 109.0, 100.2, 80.9, 57.9, 40.6, 29.1, 27.2, 22.5, 14.1; MS (ES+) m/z 344 (M+1).

EXAMPLE 1.13

Synthesis of 5-fluoro-1'-pentylspiro[1-benzofuran-3,3'-indol]-2'(1'H)-one

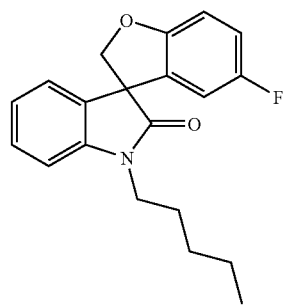

Following the procedure as described in EXAMPLE 1, and making non-critical variations using 3-(5-fluoro-2-hydroxyphenyl)-3-(hydroxymethyl)-1-pentyl-1,3-dihydro-2H-indol-2-one to replace 1-(2-cyclopropylethyl)-3-(6-hydroxy-1,3-benzodioxol-5-yl)-3-(hydroxymethyl)-1,3-dihydro-2H-indol-2-one, the title compound was obtained in 3% yield: ¹H NMR (300 MHz, CDCl₃) δ 7.37-7.28 (m, 1H), 7.18-7.11 (m, 1H), 7.09-7.01 (m, 1H), 6.98-6.82 (m, 3H), 6.45-6.37 (m, 1H), 4.95 (d, 1H), 4.69 (d, 1H), 3.89-3.63 (m, 2H), 1.81-1.65 (m, 2H), 1.48-1.28 (m, 4H), 0.92 (t, 3H); ¹³C NMR (75 MHz, CDCl₃) δ 176.7, 159.4, 156.6, 132.2, 130.1, 129.3, 124.1, 123.4, 116.3, 110.8, 110.5, 108.9, 80.4, 58.4, 40.6, 29.2, 27.3, 22.5, 14.1; MS (ES+) m/z 326 (M+1).

EXAMPLE 1.14

Synthesis of 5-bromo-1'-pentylspiro[1-benzofuran-3,3'-indol]-2'(1'H)-one

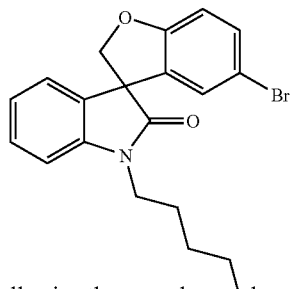

Following the procedure as described in EXAMPLE 1, and making non-critical variations using 3-(5-bromo-2-hydroxyphenyl)-3-(hydroxymethyl)-1-pentyl-1,3-dihydro-2H-indol-2-one to replace 1-(2-cyclopropylethyl)-3-(6-hydroxy-1,3-benzodioxol-5-yl)-3-(hydroxymethyl)-1,3-dihydro-2H-indol-2-one, the title compound was obtained in 4% yield: ¹H NMR (300 MHz, CDCl₃) δ 7.38-7.23 (m, 2H), 7.17-7.01 (m, 2H), 6.93 (d, 1H), 6.84 (d, 1H), 6.79 (d, 1H), 4.95 (d, 1H), 4.69 (d, 1H), 3.89-3.64 (m, 2H), 1.81-1.65 (m, 2H), 1.48-1.28 (m, 4H), 0.92 (t, 3H); ¹³C NMR (75 MHz, CDCl₃) δ 176.7, 160.1, 142.6, 132.7, 132.1, 131.4, 129.3, 126.5, 124.1, 123.5, 113.1, 112.2, 108.9, 80.3, 58.0, 40.6, 29.2, 27.3, 22.5, 14.2; MS (ES+) m/z 386 (M+1), 388 (M+23).

EXAMPLE 1.15

Synthesis of 5-chloro-6-fluoro-1'-pentylspiro[1-benzofuran-3,3'-indol]-2'(1'H)-one

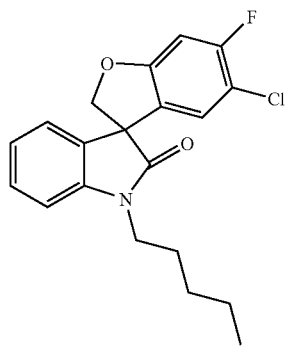

Following the procedure as described in EXAMPLE 1, and making non-critical variations using 3-(5-chloro-4-fluoro-2-hydroxyphenyl)-3-(hydroxymethyl)-1-pentyl-1,3-dihydro-2H-indol-2-one to replace 1-(2-cyclopropylethyl)-3-(6-hydroxy-1,3-benzodioxol-5-yl)-3-(hydroxymethyl)-1,3-dihydro-2H-indol-2-one, the title compound was obtained in 80% yield; mp 74-76° C.; ¹H NMR (300 MHz, CDCl₃) δ 7.38-7.27 (m, 1H), 7.18-7.02 (m, 2H), 6.94 (d, 1H), 6.77 (d, 1H), 6.69 (d, 1H), 4.98 (d, 1H), 4.72 (d, 1H), 3.87-3.64 (m, 2H), 1.82-1.65 (m, 2H), 1.47-1.28 (m, 4H), 0.92 (t, 3H); ¹³C NMR (75 MHz, CDCl₃) δ 176.5, 160.6, 157.4, 142.6, 133.9, 131.8, 129.5, 124.6, 124.1, 123.5, 113.1, 109.0, 100.0, 81.2, 57.5, 40.6, 29.2, 27.2, 22.5, 14.1; MS (ES+) m/z 360 (M+1).

EXAMPLE 1.16

Synthesis of 6-methoxy-1'-pentylspiro[1-benzofuran-3,3'-indol]-2'(1'H)-one

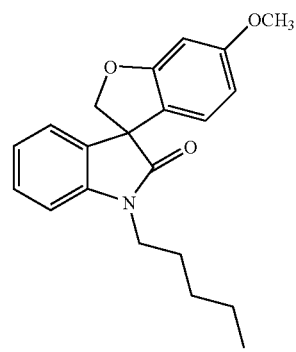

Following the procedure as described in EXAMPLE 1, and making non-critical variations using 3-(2-hydroxy-4-methoxyphenyl)-3-(hydroxymethyl)-1-pentyl-1,3-dihydro-2H-indol-2-one to replace 1-(2-cyclopropylethyl)-3-(6-hydroxy-1,3-benzodioxol-5-yl)-3-(hydroxymethyl)-1,3-dihydro-2H-indol-2-one, the title compound was obtained in 99% yield: ¹H NMR (300 MHz, CDCl₃) δ 7.30 (td, 1H), 7.14 (dd, 1H), 7.03 (t, 1H), 6.91 (d, 1H), 6.58 (d, 1H), 6.52 (d, 1H), 6.36 (dd, 1H), 4.93 (d, 1H), 4.69 (d, 1H), 3.91-3.63 (m, 2H), 3.77 (s, 3H), 1.81-1.65 (m, 2H), 1.46-1.29 (m, 4H), 0.91 (t, 3H); ¹³C NMR (75 MHz, CDCl₃) δ 177.4, 162.1, 161.5, 142.5, 132.9, 128.8, 123.9, 123.5, 123.1, 121.0, 108.5, 107.5, 96.6, 80.5, 57.6, 55.6, 40.3, 29.0, 27.1, 22.3, 14.0; MS (ES+) m/z 338 (M+1).

EXAMPLE 1.17

Synthesis of 6-chloro-5-fluoro-1'-pentylspiro[1-benzofuran-3,3'-indol]-2'(1'H)-one

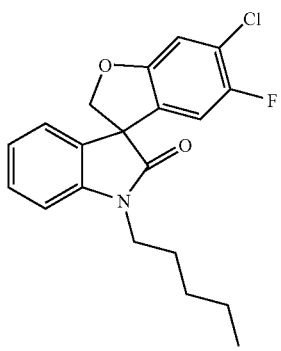

Following the procedure as described in EXAMPLE 1, and making non-critical variations using 3-(4-chloro-5-fluoro-2-hydroxyphenyl)-3-(hydroxymethyl)-1-pentyl-1,3-dihydro-2H-indol-2-one to replace 1-(2-cyclopropylethyl)-3-(6-hydroxy-1,3-benzodioxol-5-yl)-3-(hydroxymethyl)-1,3-dihydro-2H-indol-2-one, the title compound was obtained in 44% yield: $^1$H NMR (300 MHz, CDCl$_3$) δ 7.34 (td, 1H), 7.14 (dd, 1H), 7.06 (td, 1H), 6.98 (d, 1H), 6.93 (d, 1H), 6.50 (d, 1H), 4.96 (d, 1H), 4.70 (d, 1H), 3.87-3.63 (m, 2H), 1.81-1.65 (m, 2H), 1.47-1.29 (m, 4H), 0.91 (t, 3H); $^{13}$C NMR (75 MHz, CDCl$_3$) δ 176.2, 156,9, 154.8, 151.6, 142.5, 131.5, 129.4, 128.6, 123.7, 121.7, 121.9, 111.2, 108.9, 80.6, 57.9, 40.5, 29.0, 27.1, 22.3, 14.0; MS (ES+) m/z 360 (M+1).

EXAMPLE 1.18

Synthesis of 1'-pentyl-5-(trifluoromethyl)spiro[1-benzofuran-3,3'-indol]-2'(1'H)-one

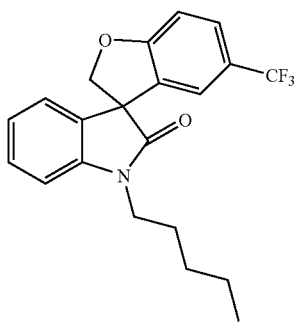

Following the procedure as described in Example 1, and making non-critical variations using 3-(hydroxymethyl)-3-[2-hydroxy-5-(trifluoromethyl)phenyl]-1-pentyl-1,3-dihydro-2H-indol-2-one to replace 1-(2-cyclopropylethyl)-3-(6-hydroxy-1,3-benzodioxol-5-yl)-3-(hydroxymethyl)-1,3-dihydro-2H-indol-2-one, the title compound was obtained in 27% yield: $^1$H NMR (300 MHz, CDCl$_3$) δ 7.48 (dd, 1H), 7.35 (td, 1H), 7.16-6.90 (m, 5H), 5.02 (d, 1H), 4.76 (d, 1H), 3.91-3.65 (m, 2H), 1.82-1.67 (m, 2H), 1.47-1.29 (m, 4H), 0.91 (t, 3H); $^{13}$C NMR (75 MHz, CDCl$_3$) δ 176.5, 163.3, 142.6, 131.8, 129.8, 129.3, 127.7, 124.1, 124.0, 123.9, 123.6, 121.0, 110.6, 108.9, 80.5, 57.6, 40.5, 29.0, 27.1, 22.3, 13.9; MS (ES+) m/z 376 (M+1).

EXAMPLE 1.19

Synthesis of 5,6-dichloro-1'-pentylspiro[1-benzofuran-3,3'-indol]-2'(1'H)-one

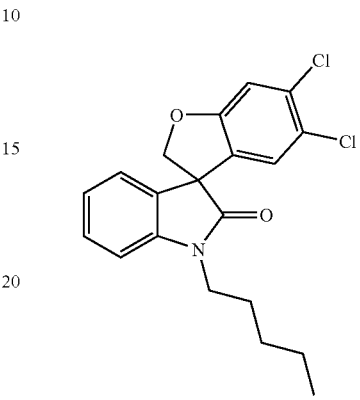

Following the procedure as described in EXAMPLE 1, and making non-critical variations using 3-(4,5-dichloro-2-hydroxyphenyl)-3-(hydroxymethyl)-1-pentyl-1,3-dihydro-2H-indol-2-one to replace 1-(2-cyclopropylethyl)-3-(6-hydroxy-1,3-benzodioxol-5-yl)-3-(hydroxymethyl)-1,3-dihydro-2H-indol-2-one, the title compound was obtained in 43% yield. $^1$H NMR (300 MHz, CDCl$_3$) δ 7.35 (td, 1H), 7.17-7.03 (m, 3H), 6.94 (d, 1H), 6.76 (s, 1H), 4.98 (d, 1H), 4.72 (d, 1H), 3.88-3.65 (m, 2H), 1.82-1.67 (m, 2H), 1.47-1.29 (m, 4H), 0.92 (t, 3H). $^{13}$C NMR (75 MHz, CDCl$_3$) δ 176.2, 159.9, 142.5, 133.3, 131.5, 129.4, 124.6, 124.5, 123.9, 123.4, 112.4, 108.9, 80.8, 57.5, 40.5, 29.0, 27.1, 22.3, 14.0; MS (ES+) m/z 376 (M+1), 378 (M+1).

EXAMPLE 1.20

Synthesis of 1'-(diphenylmethyl)-5,5-dimethyl-5,6-dihydrospiro[benzo[1,2-b:5,4-b']difuran-3,3'-indol]-2'(1'H)-one

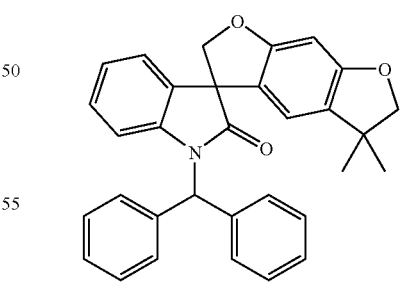

Following the procedure as described in EXAMPLE1, and making non-critical variations using 1-(diphenylmethyl)-3-(6-hydroxy-3,3-dimethyl-2,3-dihydro-1-benzofuran-5-yl)-3-(hydroxymethyl)-1,3-dihydro-2H-indol-2-one to replace 1-(2-cyclopropylethyl)-3-(6-hydroxy-1,3-benzodioxol-5-yl)-3-(hydroxymethyl)-1,3-dihydro-2H-indol-2-one, the title compound was obtained: mp 190-192° C.; $^1$H NMR (300 MHz, CDCl$_3$) δ 7.40-7.26 (m, 10H), 7.19-7.15 (m, 1H), 7.07-

6.93 (m, 3H), 6.55-6.51 (m, 1H), 6.38 (s, 1H), 6.20 (s, 1H), 4.98 (d, 1H), 4.71 (d, 1H), 4.17 (s, 2H), 1.17 (s, 3H), 1.14 (s, 3H); $^{13}$C NMR (75 MHz, CDCl$_3$) δ 178.1, 161.1, 161.0, 141.8, 137.9, 137.2, 132.8, 130.0, 128.6, 128.5, 128.4, 128.2, 128.0, 127.8, 123.9, 123.1, 120.8, 116.1, 112.1, 93.4, 85.4, 80.4, 58.7, 57.4, 41.3, 27.7, 27.6; MS (ES+) m/z 474.5 (M+1).

EXAMPLE 1.21

Synthesis of 5,5-dimethyl-5,6-dihydrospiro[benzo[1,2-b:5,4-b]difuran-3,3'-indol]-2'(1'H)-one

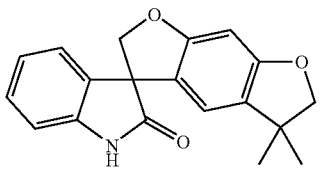

To a solution of 1'-(diphenylmethyl)-5,5-dimethyl-5,6-dihydrospiro[benzo[1,2-b:5,4-b]difuran-3,3'-indol]-2'(1'H)-one (0.23 g, 0.49 mmol) in methanol (50.0 mL) was added palladium on carbon (0.10 g). The mixture was hydrogenated under 120 psi of hydrogen at ambient temperature overnight. The reaction mixture was filtered through celite, washed with methanol. The filtrate was concentrated in vacuo to dryness. The residue was subjected to column chromatography (ethyl acetate/hexane, ½) to give the title compound (0.10 g, 68%): mp 95-100° C.; $^1$H NMR (300 MHz, CDCl$_3$) δ 8.74 (s, 1H), 7.28-7.20 (m, 1H), 7.15 (d, 1H), 7.03 (t, 1H), 6.95 (d, 1H), 6.43 (s, 1H), 6.40 (s, 1H), 4.94 (d, 1H), 4.66 (d, 1H), 4.19 (s, 2H), 1.20 (s, 3H), 1.16 (3H); $^{13}$C NMR (75 MHz, CDCl$_3$) δ 180.4, 161.3, 161.0, 140.3, 133.0, 130.1, 128.8, 124.2, 123.4, 120.0, 116.6, 110.1, 93.4, 85.5, 80.6, 58.3, 41.4, 27.7, 27.6; MS (ES+) m/z 308.6 (M+1).

EXAMPLE 1.22

Synthesis of 4',7'-dichloro-1'-pentylspiro[furo[2,3-f][1,3]benzodioxole-7,3'-indol]-2'(1'H)-one

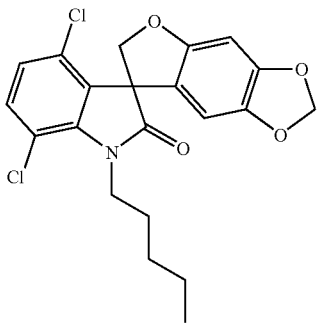

To a solution of 4,7-dichloro-3-(6-hydroxy-1,3-benzodioxol-5-yl)-3-(hydroxymethyl)-1-pentyl-1,3-dihydro-2H-indol-2-one (0.69 g, 1.57 mmol) in anhydrous tetrahydrofuran (15.0 mL) was added triphenylphosphine (0.54 g, 2.04 mmol) followed by slow addition of diisopropyl azodicarboxylate (0.41 g, 2.04 mmol) at 0° C. The brown reaction mixture was stirred at ambient temperature for 16 h and quenched with ammonium chloride solution (2.00 mL). The organic solvent was removed in vacuo. The residue was dissolved in ethyl acetate (20.0 mL), washed with 10% aqueous HCl solution (10.0 mL), dried over anhydrous sodium sulfate and filtered. The filtrate was concentrated in vacuo to dryness. The residue was subjected to column chromatography eluting with ethyl acetate/hexane (35%) to give a solid, which was crystallized from ethyl acetate/ether to give the title compound (0.13 g, 20%) as a colorless solid: mp 106-108° C.; $^1$H NMR (300 MHz, CDCl$_3$) δ 7.24-7.16 (m, 1H), 6.81 (d, 1H), 6.44 (s, 1H), 6.07 (s, 1H), 5.86 (dd, 2H), 4.87 (dd, 2H), 4.12-4.07 (m, 2H), 1.76-1.66 (m, 2H) 1.36-1.31 (m, 4H), 0.89 (t, 3H); $^{13}$C NMR (75 MHz, CDCl$_3$) δ 177.5, 157.0, 149.2, 142.1, 140.0, 132.3, 131.0, 130.2, 124.6, 116.0, 113.8, 102.3, 101.5, 93.3, 77.2, 58.5, 42.1, 29.5, 28.7, 22.3, 14.0; MS (ES+) m/z 420.4 (M+1).

EXAMPLE 1.23

Synthesis of 4'-bromospiro[furo[2,3-f][1,3]benzodioxole-7,3'-indol]-2'(1'H)-one

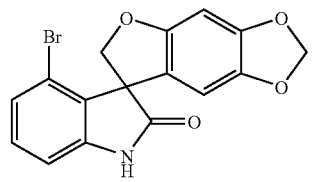

Following the procedure as described in EXAMPLE 1.22, and making non-critical variations using 4-bromo-3-(6-hydroxy-1,3-benzodioxol-5-yl)-3-(hydroxymethyl)-1,3-dihydro-2H-indol-2-one to replace 4,7-dichloro-3-(6-hydroxy-1,3-benzodioxol-5-yl)-3-(hydroxymethyl)-1-pentyl-1,3-dihydro-2H-indol-2-one, the title compound was obtained in 71% yield as a colorless solid: $^1$H NMR (300 MHz, DMSO-d$_6$) δ 10.79 (s, 1H), 7.19-7.08 (m, 2H), 6.90 (dd, 1H), 6.58 (s, 1H), 6.25 (s, 1H), 5.90 (d, 2H), 4.74 (ABq, 2H); $^{13}$C NMR (75 MHz, DMSO-d$_6$) δ 178.5, 157.0, 148.8, 144.5, 141.9, 131.2, 130.6, 126.1, 119.2, 117.5, 109.8, 103.3, 101.8, 93.3, 77.6, 59.7; MS (ES−) m/z 360.4 (M−1), 358.4 (M−1).

EXAMPLE 1.24

Synthesis of 4'-bromo-5,6-dihydrospiro[benzo[1,2-b:5,4-b]difuran-3,3'-indol]-2'(1'H)-one

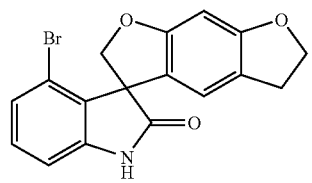

To a solution of 4-bromo-3-(6-hydroxy-2,3-dihydro-1-benzofuran-5-yl)-3-(hydroxymethyl)-1,3-dihydro-2H-indol-2-one (1.80 g, 4.80 mmol) in anhydrous ethyl acetate (50 mL) was added tributylphosphine (1.26 g, 1.54 mL, 6.24 mmol) at 0° C. under nitrogen. A solution of di-tert-butyl azodicarboxylate (1.44 g, 6.24 mmol) in anhydrous ethyl acetate (15.0 mL) was added over 10 min. The reaction solution was stirred for 2 h, and then quenched with saturated ammonium chloride solution (30.0 mL). After the aqueous layer was separated, the organic layer was washed with 10% aqueous HCl solution (2×25.0 mL), dried over anhydrous sodium sulfate and filtered. The filtrate was concentrated in vacuo to dryness. The residue was subjected to column chromatography eluting with ethyl acetate-hexane (70%) to obtain a solid which was triturated with diethyl ether to give the title compound (0.64 g, 37%) as a colorless solid: $^1$H NMR (300 MHz, DMSO-$d_6$) δ 10.77 (s, 1H), 7.18-7.13 (m, 1H), 7.08 (d, 1H), 6.90 (d, 1H), 6.47 (s, 1H), 6.30 (s, 1H), 4.80 (ABq, 2H), 4.46 (t, 2H), 2.92 (t, 2H); $^{13}$C NMR (75 MHz, DMSO-$d_6$) δ 178.7, 162.2, 161.7, 144.5, 131.1, 131.0, 126.1, 119.8, 119.2, 119.1, 118.3, 109.7, 92.4, 77.6, 72.5, 59.2, 28.8; MS (ES−) m/z 358.4 (M−1), 356.3 (M−1).

EXAMPLE 1.25

Synthesis of 4'-bromo-1'-(pyridin-2-ylmethyl)-5,6-dihydrospiro[benzo[1,2-b:5,4-b']difuran-3,3'-indol]-2'(1'H)-one

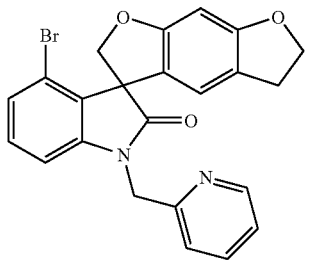

A mixture of 4-bromo-3-(6-hydroxy-2,3-dihydro-1-benzofuran-5-yl)-3-(hydroxymethyl)-1-(pyridin-2-ylmethyl)-1,3-dihydro-2H-indol-2-one (1.81 g, 3.88 mmol), triphenylphosphine (2.04 g, 7.77 mmol) and diisopropyl azodicarboxylate (1.57 g, 7.77 mmol) in anhydrous dioxane (60 mL) was heated at reflux for 16 h. After cooling down to ambient temperature, the solvent was removed in vacuo. The gummy residue was diluted with ethyl acetate (50.0 mL), washed with water (3×25.0 mL), brine (3×25.0 mL), dried over anhydrous sodium sulfate and filtered. The filtrate was concentrated in vacuo to dryness. The residue was subjected to column chromatography eluting with ethyl acetate/hexane (80%) to give the title compound (0.64 g, 37%) as colorless solid: mp>200° C.; $^1$H NMR (300 MHz, DMSO-$d_6$) δ 8.47 (d, 1H), 7.77 (dt, 1H), 7.37 (d, 1H), 7.27 (dt, 1H), 7.19-7.13 (m, 2H), 6.94 (dd, 1H), 6.61 (s, 1H), 6.33 (s, 1H), 5.08 (d, 1H), 5.03 (d, 1H), 4.93 (d, 1H), 4.74 (d, 1H), 4.48 (t, J=8.6 Hz, 2H), 2.96 (t, 2H); $^{13}$C NMR (75 MHz, DMSO-$d_6$) δ 177.4, 162.2, 161.8, 155.3, 149.8, 145.3, 137.6, 131.0, 130.5, 126.8, 123.3, 122.2, 119.9, 119.5, 119.0, 118.1, 109.3, 92.4, 77.5, 72.5, 58.8, 45.3, 28.8; MS (ES+) m/z 451.3 (M+1).

EXAMPLE 1.26

Synthesis of 5'-fluoro-1'-{[5-(trifluoromethyl)-2-furyl]methyl}spiro[furo[2,3-f][1,3]benzodioxole-7,3'-indol]-2'(1'H)-one

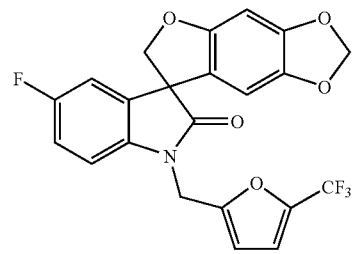

To a solution of 5-fluoro-3-(6-hydroxy-1,3-benzodioxol-5-yl)-3-(hydroxymethyl)-1-{[5-(trifluoromethyl)-2-furyl]methyl}-1,3-dihydro-2H-indol-2-one (3.34 g, 7.18 mmol) in anhydrous tetrahydrofuran (80.0 mL) was added tributylphosphine (2.18 g, 2.70 mL, 10.8 mmol) under nitrogen. A solution of di-tert-butyl azodicarboxylate (2.49 g, 10.8 mmol) in anhydrous tetrahydrofuran (25.0 mL) was added over 10 min. The reaction solution was stirred for 1 h, and quenched with saturated ammonium chloride (30.0 mL). After the solvent was removed under reduced pressure, the gummy material was extracted with ethyl acetate (3×75.0 mL). The organic layer was washed with 10% aqueous HCl solution (2×25.0 mL), saturated aqueous sodium hydrogen carbonate (3×25.0 mL), brine (3×25.0 mL), dried over anhydrous sodium sulfate and filtered. The filtrate was concentrated in vacuo to dryness. The residue was subjected to column chromatography eluting with ethyl acetate/hexane (30%) to afforded the title compound (1.10 g, 34%) as a colorless solid: mp 139-141° C.; $^1$H NMR (300 MHz, CDCl$_3$) δ 7.02-6.96 (m, 1H), 6.93-6.89 (m, 2H), 6.74-6.73 (m, 1H), 6.50 (s, 1H), 6.38 (d, 1H), 6.09 (s, 1H), 5.87 (dd, 2H), 4.95 (ABq, 2H), 4.78 (Abq, 2H); $^{13}$C NMR (75 MHz, CDCl$_3$) δ 176.9, 161.5, 158.3, 155.9, 151.7, 149.2, 142.6, 137.1, 137.1, 133.7, 118.6, 115.6, 115.3, 112.7, 112.4, 112.0, 109.7, 109.6, 109.4, 102.8, 101.7, 93.8, 80.1, 58.6, 37.1; MS (ES+) m/z 448.2 (M+1).

EXAMPLE 1.27

Synthesis of 1'-(diphenylmethyl)-5'-methylspiro[furo[2,3-f][1,3]benzodioxole-7,3'-indol]-2'(1'H)-one

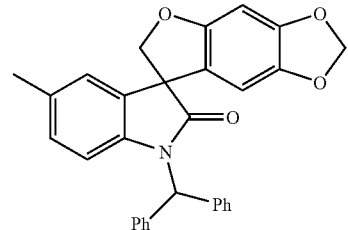

To a solution of 1-(diphenylmethyl)-3-(6-hydroxy-1,3-benzodioxol-5-yl)-3-(hydroxymethyl)-5-methyl-1,3-dihydro-2H-indol-2-one (1.31 g, 2.72 mmol) in ethyl acetate (50.0 mL) was added tributylphosphine (0.82 g, 4.07 mmol). A solution of di-tert-butyl azodicarboxylate (0.94 g, 4.07 mmol) in ethyl acetate (45.0 mL) was added to the above reaction mixture over a period of 5 minutes. After stirring for 10 minutes under $N_2$, the reaction was quenched with saturated aqueous ammonium chloride (60.0 mL). The organic layer was separated and washed with 1.0 N hydrochloric acid solution (3×100 mL), dried over sodium sulfate and filtered. The filtrate was concentrated in vacuo to dryness. The residue was subjected to column chromatography eluting with ethyl acetate/hexane (10-50%) to afford the title compound (0.98 g, 78% yield): $^1$H NMR (300 MHz, CDCl$_3$) δ 7.40-7.25 (m, 10H), 7.02, (s, 1H), 6.96 (s, 1H), 6.79 (d, 1H), 6.50 (s, 1H), 6.36 (d, 1H), 6.08 (s, 1H), 5.86 (d,2H), (4.82 (ABq, 2H), 2.20 (s, 3H).

EXAMPLE 1.28

Synthesis of 5'-methylspiro[furo[2,3-f][1,3]benzo-dioxole-7,3'-indol]-2'(1'H)-one

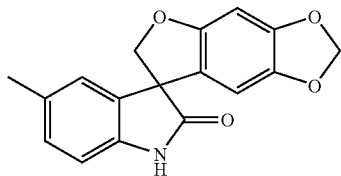

A stainless steel hydrogenating vessel was successively charged with 1'-(diphenylmethyl)-5'-methylspiro[furo[2,3-f][1,3]benzodioxole-7,3'-indol]-2'(1'H)-one (0.90 g, 1.95 mmol), glacial acetic acid (50.0 mL) and palladium hydroxide (0.10 g, 1.35 mmol, 20 wt % on carbon). The vessel was flushed with nitrogen, sealed then heated to 60° C. and placed under 120 Psi of $H_2$. After 4 days of stirring, the reaction mixture was diluted with ethyl acetate and passed through a bed of celite. The filtrate was washed with water (6×100 mL), dried over sodium sulfate and filtered. The filtrate was concentrated in vacuo to dryness. The residue was subjected to column chromatography eluting with ethyl acetate/hexane (40-50%) to afford the title compound (0.25 g, 43%): mp 269-271° C.; $^1$H NMR (300 MHz, DMSO-d$_6$)δ 10.45 (s, 1H), 7.00 (d, 1H), 6.87 (s, 1H), 6.76 (d, 1H), 6.63 (s, 1H), 6.21 (s, 1H), 5.87 (d, 2H); 4.64 (ABq, 2H), 2.17 (s, 3H); MS (ES+) m/z 296.28 (M+1).

EXAMPLE 1.29

Synthesis of 5'-methyl-1'-{[5-(trifluoromethyl)-2-furyl]methyl}spiro[furo[2,3-f][1,3]benzodioxole-7, 3'-indol]-2'(1'H)-one

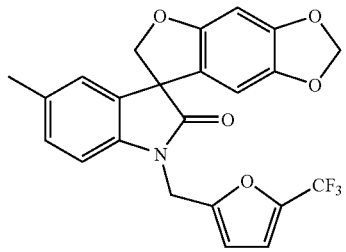

To a suspension of sodium hydride (0.03 g, 0.63 mmol, 60% dispersion in mineral oil) in N,N-dimethylformamide (5.00 mL) was slowly added a solution of 5'-methylspiro[furo[2,3-f][1,3]benzodioxole-7,3'-indol]-2'(1'H)-one (0.10 g, 0.33 mmol) in N,N-dimethylformamide (5.00 mL) at 0° C. After stirring for 15 minutes at 0° C., a solution of 2-(bromomethyl)-5-(trifluoromethyl)furan (0.11 g, 0.49 mmol) in N,N-dimethylformamide (40.0 mL) was added. The resulting mixture was stirred at ambient temperature for 4 h and quenched with water (20.0 mL). The mixture was extracted with ethyl acetate (3×25.0 mL). The combined organic layers was washed with water (50.0 mL) and brine (2×25.0 mL), dried over sodium sulfate and filtered. The filtrated was concentrated in vacuo. The residue was subjected to column chromatography eluting with ethyl acetate/hexane (15-50%) to afford the title compound (0.11 g, 77% yield): mp 96-98° C.; $^1$H NMR (300 MHz, CDCl$_3$) δ 7.09 (d, 1H), 7.00 (s, 1H), 6.87 (d, 1H), 6.74 (d, 1H), 6.52 (s, 1H), 6.38 (d, 1H), 6.11 (s, 1H), 5.88 (d, 2H), 4.96 (ABq, 2H), 4.80 (ABq, 2H), 2.29 (s, 3H); MS (ES+) m/z 444.2 (M+1).

EXAMPLE 1.30

Synthesis of 6-bromo-1'-pentylspiro[1-benzofuran-3, 3'-indol]-2'(1'H)-one

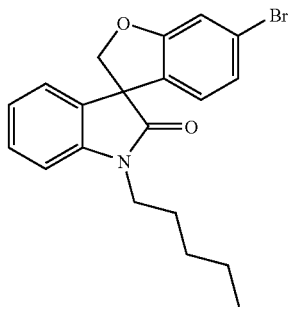

Following the procedure as described in EXAMPLE 1.22, and making non-critical variations using 3-(4-bromo-2-hydroxyphenyl)-3-(hydroxymethyl)-1-pentyl-1,3-dihydro-2H-indol-2-one to replace 4,7-dichloro-3-(6-hydroxy-1,3-benzodioxol-5-yl)-3-(hydroxymethyl)-1-pentyl-1,3-dihydro-2H-indol-2-one, the title compound was obtained in 82% yield as a colorless solid: $^1$H NMR (300 MHz, CDCl$_3$) δ 7.33 (td, 1H), 7.15-7.14 (m, 2H), 7.04 (dd, 1H), 6.96-6.90 (m, 2H), 6.56 (d, 1H), 4.95 (d, 1H), 4.69 (d, 1H), 3.89-3.64 (m, 2H), 1.80-1.68 (m, 2H), 1.43-1.34 (m, 4H), 0.92 (t, 3H); $^{13}$C NMR (75 MHz, CDCl$_3$) δ 176.6, 161.6, 142.5, 132.1, 129.1, 128.4, 124.4, 123.9, 123.3, 122.8, 114.1, 108.8, 80.4, 57.6, 40.4, 29.0, 27.1, 22.3, 14.0; MS (ES+) m/z 386.3 (M+1), 388.3 (M+1).

EXAMPLE 1.31

Synthesis of 5-bromo-1'-(diphenylmethyl)spiro[1-benzofuran-3,3'-indol]-2'(1'H)-one

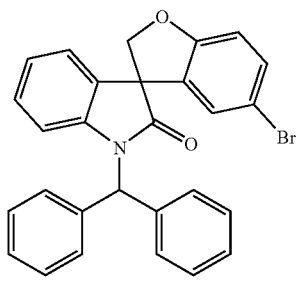

Following the procedure as described in Example 1, and making non-critical variations using 3-(5-bromo-2-hydroxyphenyl)-1-(diphenylmethyl)-3-(hydroxymethyl)-1,3-dihydro-2H-indol-2-one to replace 1-(2-cyclopropylethyl)-3-(6-hydroxy-1,3-benzodioxol-5-yl)-3-(hydroxymethyl)-1,3-dihydro-2H-indol-2-one, the title compound was obtained (72%) as a white solid: $^1$H NMR (300 MHz, CDCl$_3$) δ 7.43-7.25 (m, 11H), 7.14-6.93 (m, 4H), 6.83 (d, 1H), 6.71 (d, 1H), 6.52 (d, 1H), 5.0 (d, 1H), 4.73 (d, 1H); MS (ES+) m/z 484.4 (M+1), 482.4 (M+1).

EXAMPLE 1.32

Synthesis of 2-methyl-1'-pentylspiro[furo[2,3-f][1,3]benzothiazole-7,3'-indol]-2'(1'H)-one

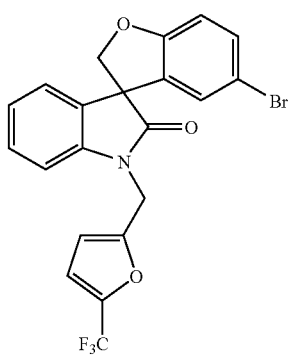

Following the procedure as described in EXAMPLE 1.22, and making non-critical variations using 3-(hydroxymethyl)-3-(5-hydroxy-2-methyl-1,3-benzothiazol-6-yl)-1-pentyl-1,3-dihydro-2H-indol-2-one to replace 4,7-dichloro-3-(6-hydroxy-1,3-benzodioxol-5-yl)-3-(hydroxymethyl)-1-pentyl-1,3-dihydro-2H-indol-2-one, the title compound was obtained (50%) as a white solid: mp 105-107° C.; $^1$H NMR (300 MHz, CDCl$_3$) δ 7.59 (d, 1H), 7.28 (dt, 1H), 7.02-6.92 (m, 2H), 5.02 (d, 1H), 4.77 (d, 1H), 4.01 (m, 1H), 3.64 (m, 1H), 2.54 (s, 3H), 1.92-1.71 (m, 2H), 1.54-1.34 (m, 4H), 0.92 (t, 3H); $^{13}$C NMR (75 MHz, CDCl$_3$) δ 176.7, 169.2, 160.2, 149.2, 142.7, 138.3, 132.7, 129.0, 128.6, 123.5, 122.7, 122.1, 120.2, 108.6, 108.3, 80.1, 58.1, 40.7, 29.1, 27.0, 22.5, 20.2, 14.1; MS (ES+) m/z 379.5 (M+1).

EXAMPLE 1.33

Synthesis of 5-bromo-1-{[5-(trifluoromethyl)-2-furyl]methyl}spiro[1-benzofuran-3,3'-indol]-2'(1'H)-one

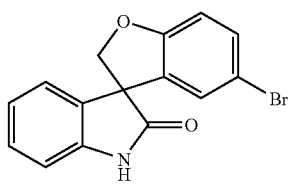

Following the procedure as described in EXAMPLE1.22, and making non-critical variations using 3-(hydroxymethyl)-3-(5-hydroxy-2-methyl-1,3-benzothiazol-6-yl)-1-pentyl-1,3-dihydro-2H-indol-2-one to replace 4,7-dichloro-3-(6-hydroxy-1,3-benzodioxol-5-yl)-3-(hydroxymethyl)-1-pentyl-1,3-dihydro-2H-indol-2-one, the title compound was obtained (30%) as a white solid: mp 143-145° C.; $^1$H NMR (300 MHz, CDCl$_3$) δ 7.35-7.27 (m, 2H), 7.17-6.98 (m, 3H), 6.84 (d, 1H), 6.78-6.73 (m, 2H), 6.40 (d, 1H),5.07-4.87(m 3H), 4.69 (d,1H); MS (ES+) m/z 464.2 (M+1), 466.2 (M+1).

EXAMPLE 1.34

Synthesis of 5-bromospiro[1-benzofuran-3,3'-indol]-2'(1'H)-one

Following the procedure as described in Example 1, and making non-critical variations using 3-(5-bromo-2-hydroxyphenyl)-3-(hydroxymethyl)-1,3-dihydro-2H-indol-2-one to replace 1-(2-cyclopropylethyl)-3-(6-hydroxy-1,3-benzodioxol-5-yl)-3-(hydroxymethyl)-1,3-dihydro-2H-indol-2-one, the title compound was obtained (25%) as a white solid: mp 225-228° C.; $^1$H NMR (300 MHz, CDCl$_3$) δ 10.65 (s, 1H), 7.35 (dd, 1H), 7.24 (dt, 1H), 7.11 (d, 1H), 6.99-6.88 (m, 3H), 6.83 (d, 1H), 4.81 (d, 1H), 4.69 (d, 1H); MS (ES+) m/z 316.1 (M+1), 318.1 (M+1).

EXAMPLE 1.35

Synthesis of 1'-(diphenylmethyl)-6-(trifluoromethoxy)spiro[1-benzofuran-3,3'-indol]-2'(1'H)-one

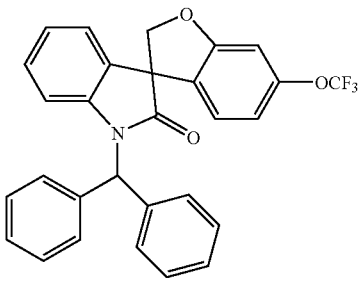

To a solution of 1-(diphenylmethyl)-3-(hydroxymethyl)-3-[2-hydroxy-4-(trifluoromethoxy)phenyl]-1,3-dihydro-2H-indol-2-one (17.3 mmol) in anhydrous THF (200 mL) was added triphenylphosphine (6.34 g, 24.2 mmol) followed by diethyl azodicarboxylate (4.39 mL, 24.2 mmol) at 0° C. The reaction mixture was stirred at ambient temperature for 16 h, quenched with saturated ammonium chloride (40.0 mL). The aqueous mixture was extracted with ethyl acetate (3×150 mL). The combined organic layers was dried over anhydrous sodium sulfate and filtered. The filtrate was concentrated in vacuo. The residue was subjected to column chromatography (ethyl acetate/hexane, ¼) to give the title compound (6.00 g, 71%): $^1$H NMR (300 MHz, CDCl$_3$) δ 7.45-6.51 (m, 18H), 5.08 (d, 1H), 4.81 (d, 1H); MS (ES+) m/z 488 (M+1).

EXAMPLE 1.36

Synthesis of 6-(trifluoromethoxy)spiro[1-benzofuran-3,3'-indol]-2'(1'H)-one

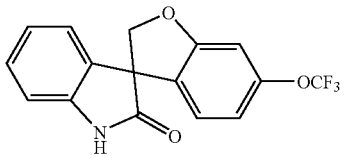

To a suspension of 1-(diphenylmethyl)-6-(trifluoromethoxy)spiro[1-benzofuran-3,3'-indol]-2'(1'H)-one (6.00 g, 12.3 mmol) in methanol (100 mL) and acetic acid (1.00 mL) was added 10% palladium on carbon (0.65 g, 0.62 mmol), and the mixture was hydrogenated at ambient temperature under 130 psi of hydrogen for 5 days. The reaction mixture was filtered over celite and the filtrate was concentrated in vacuo to dryness. The residue was subjected to flash chromatography eluting with 30% ethyl acetate in hexane to give the title compound (2.95 g, 75%) as a white solid: mp 180-182° C.; $^1$H NMR (300 MHz, CDCl$_3$) δ 9.19 (s, 1H), 7.29-6.92 (m., 4H), 6.86-6.64 (m, 3H), 5.03 (d, 1H), 4.75 (d, 1H); $^{13}$C NMR(75 MHz, CDCl$_3$) δ 179.9, 161.9, 150.6, 132.3, 129.4, 127.4, 125.6, 124.3, 124.2, 123.8, 120.5, 114.1, 110.7, 104.3, 80.8, 58.2; MS (ES+) m/z 322 (M+1).

EXAMPLE 1.37

Synthesis of ethyl (4'-bromo-2'-oxo-5,6-dihydrospiro[benzo[1,2-b:5,4-b']difuran-3,3'-indol]-1'(2'H)-yl)acetate

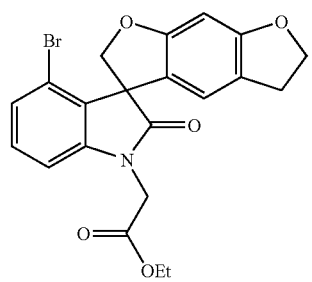

Following the procedure as described in EXAMPLE 1.22, and making non-critical variations using ethyl [4-bromo-3-(6-hydroxy-2,3-dihydro-1-benzofuran-5-yl)-3-(hydroxymethyl)-2-oxo-2,3-dihydro-1H-indol-1-yl]acetate to replace 4,7-dichloro-3-(6-hydroxy-1,3-benzodioxol-5-yl)-3-(hydroxymethyl)-1-pentyl-1,3-dihydro-2H-indol-2-one, the title compound was obtained (41%) as a colorless solid: MS (ES+) m/z 445.5 (M+1).

EXAMPLE 1.38

Synthesis of ethyl (4'-chloro-2'-oxo-5,6-dihydrospiro[benzo[1,2-b:5,4-b']difuran-3,3'-indol]-1'(2'H)-yl)acetate

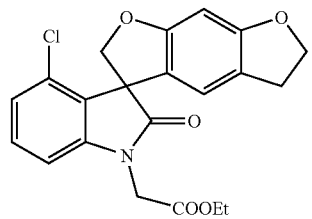

Following the procedure as described in EXAMPLE 1.22, and making non-critical variations using ethyl [4-chloro-3-(6-hydroxy-2,3-dihydro-1-benzofuran-5-yl)-3-(hydroxymethyl)-2-oxo-2,3-dihydro-1H-indol-1-yl]acetate to replace 4,7-dichloro-3-(6-hydroxy-1,3-benzodioxol-5-yl)-3-(hydroxymethyl)-1-pentyl-1,3-dihydro-2H-indol-2-one, the title compound was obtained in 63% yield as a colorless solid: MS (ES+) m/z 400.8 (M+1).

EXAMPLE 1.39

Synthesis of ethyl (4'-bromo-6,6-dimethyl-2'-oxo-5,6-dihydrospiro[benzo[1,2-b:5,4-b']difuran-3,3'-indol]-1'(2'H)-yl)acetate

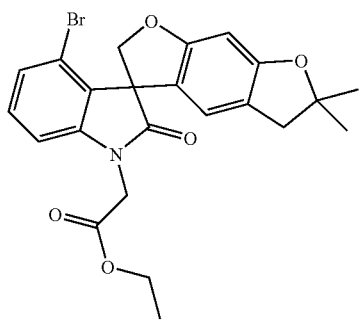

Following the procedure as described in EXAMPLE 1, and making non-critical variations using ethyl [4-bromo-3-(6-hydroxy-2,2-dimethyl-2,3-dihydro-1-benzofuran-5-yl)-3-(hydroxymethyl)-2-oxo-2,3-dihydro-1H-indol-1-yl]acetate to replace 1-(2-cyclopropylethyl)-3-(6-hydroxy-1,3-benzodioxol-5-yl)-3-(hydroxymethyl)-1,3-dihydro-2H-indol-2-one, the title compound was obtained in 52% yield: $^1$H NMR (300 MHz, CDCl$_3$) δ 7.22-7.10 (m, 2H), 6.70 (d, 1H), 6.48 (s, 1H), 6.30 (s, 1H), 5.0 (d, 1H); 4.86 (d, 1H), 4.63 (d, 1H), 4.35 (d, 1H), 4.28-4.18 (m, 2H), 2.79 (s, 2H), 1.43 (s, 3H); 1.39 (s, 3H), 1.28 (t, 3H); MS (ES+) m/z 472.5 (M+1), 474.5 (M+1).

EXAMPLE 1.40

Synthesis of ethyl (4'-bromo-5,6-difluoro-2'-oxospiro[1-benzofuran-3,3'-indol]-1'(2'H)-yl)acetate

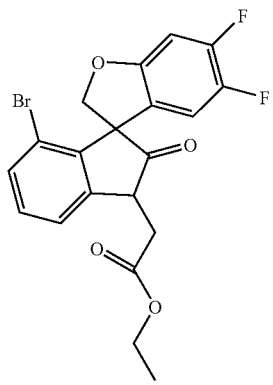

Following the procedure as described in EXAMPLE 1, and making non-critical variations using ethyl [4-bromo-3-(4,5-difluoro-2-hydroxyphenyl)-3-(hydroxymethyl)-2-oxo-2,3-dihydro-1H-indol-1-yl]acetate to replace 1-(2-cyclopropylethyl)-3-(6-hydroxy-1,3-benzodioxol-5-yl)-3-(hydroxymethyl)-1,3-dihydro-2H-indol-2-one, the title compound was obtained in 81% yield: MS (ES+) m/z 438.4 (M+1), 440.4 (M+1).

EXAMPLE 1.41

Synthesis of ethyl (5'-chloro-2'-oxo-5,6-dihydrospiro[benzo[1,2-b:5,4-b']difuran-3,3'-indol]-1'(2'H)-yl)acetate

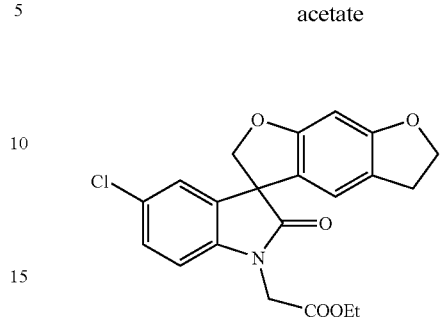

Following the procedure as described in EXAMPLE 1.22, and making non-critical variations using ethyl [5-chloro-3-(6-hydroxy-2,3-dihydro-1-benzofuran-5-yl)-3-(hydroxymethyl)-2-oxo-2,3-dihydro-1H-indol-1-yl]acetate to replace 4,7-dichloro-3-(6-hydroxy-1,3-benzodioxol-5-yl)-3-(hydroxymethyl)-1-pentyl-1,3-dihydro-2H-indol-2-one, the title compound was obtained in 90% yield as a colorless solid: MS (ES$_+$) m/z 400.8 (M+1).

EXAMPLE 1.42

Synthesis of 7'-fluorospiro[furo[2,3-f][1,3]benzodioxole-7,3'-indol]-2'(1'H)-one

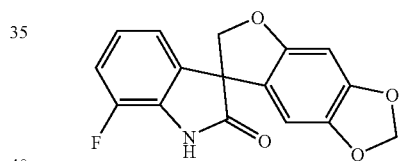

A solution of 7-fluoro-3-(6-hydroxy-1,3-benzodioxol-5-yl)-1,3-dihydro-2H-indol-2-one (2.00 g, 7.00 mmol) and paraformaldehyde (2.10 g, 61.0 mmol) in THF (50 mL) was degassed by bubbling through argon for one hour, followed by the slow addition of lithium diisopropylamide (48.8 mL, freshly made 0.50 M solution, 25 mmol) at −78° C. The mixture was stirred at ambient temperature overnight and quenched with saturated ammonium chloride (50.0 mL). The mixture was extracted with ethyl acetate (3×100 mL). The combined organic layers was dried over anhydrous sodium sulfate and filtered. The filtrate was concentrated in vacuo to dryness. The residue was dissolved in anhydrous ethyl acetate (50 mL) followed by the addition of tributylphosphine (2.10 mL, 8.00 mmol) and di-tert-butyl azodicarboxylate (1.90 g, 8.00 mmol) at 0° C. The reaction mixture was stirred at ambient temperature for 16 h and quenched with saturated ammonium chloride (30.0 mL). The organic layer was separated, dried over anhydrous sodium sulfate and filtered. The filtrate was concentrated in vacuo to dryness. The residue was dissolved in methanol (70.0 mL) followed by the addition of saturated sodium bicarbonate solution (30.0 mL). The resulted mixture was refluxed at 100° C. for one hour. After cooling down to ambient temperature, the mixture was extracted with ethyl acetate (3×50.0 mL). The combined organic layers was dried over anhydrous sodium sulfate and filtered. The filtrate was concentrated in vacuo to dryness. The residue was subjected to column chromatography (ethyl acetate/hexane, 1/5) to give the title compound (0.27 g, 17%): $^1$H NMR (300 MHz, DMSO-d$_6$) δ 11.06 (s, 1H), 7.17-7.08 (m, 1H), 7.00-6.88 (m, 2H), 6.64 (s, 1H), 6.33 (s, 1H), 5.92-5.85 (m, 2H), 4.74 (d, 1H), 4.62 (d, 1H).

EXAMPLE 1.43

Synthesis of methyl (6-chloro-2'-oxospiro[1-benzofuran-3,3'-indol]-1(2'H)-yl)acetate

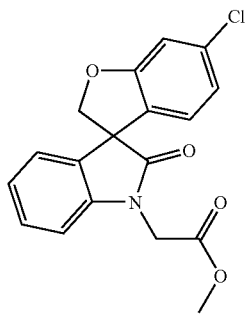

Following the procedure as described in EXAMPLE1.22, and making non-critical variations using methyl [3-(4-chloro-2-hydroxyphenyl)-3-(hydroxymethyl)-2-oxo-2,3-dihydro-1H-indol-1-yl]acetate to replace 4,7-dichloro-3-(6-hydroxy-1,3-benzodioxol-5-yl)-3-(hydroxymethyl)-1-pentyl-1,3-dihydro-2H-indol-2-one, the title compound was obtained in 74% yield as a colorless solid: $^1$H NMR (300 MHz, CDCl$_3$) δ 7.29 (dt, 1H), 7.14 (dd, 1H), 7.06 (t, 1H), 6.95 (d, 1H), 6.81-6.74 (m, 3H), 5.03 (d, 1H), 4.74 (d, 1H), 4.65 (d, 1H), 4.44 (d, 1H), 3.75 (s, 3H); MS (ES+) m/z 344.5 (M+1), 346.5 (M+1).

EXAMPLE 1.44

Synthesis of ethyl (5,6-difluoro-2'-oxospiro[1-benzofuran-3,3'-indol]-1'(2'H)-yl)acetate

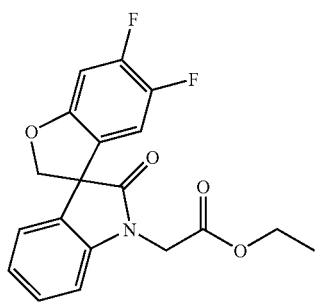

Following the procedure as described in EXAMPLE 1.22, and making non-critical variations using ethyl [3-(4,5-difluoro-2-hydroxyphenyl)-3-(hydroxymethyl)-2-oxo-2,3-dihydro-1H-indol-1-yl]acetate to replace 4,7-dichloro-3-(6-hydroxy-1,3-benzodioxol-5-yl)-3-(hydroxymethyl)-1-pentyl-1,3-dihydro-2H-indol-2-one, the title compound was obtained in 46% yield as a light yellow oil: $^1$H NMR (300 MHz, CDCl$_3$) δ 7.31 (dt, 1H), 7.16 (dd, 1H), 7.08 (dt, 1H), 6.81-6.71 (m, 2H), 6.67 (dd, 1H), 4.98 (d, 1H), 4.74 (d, 1H), 4.64 (d, 1H), 4.37 (d, 4.24 (q, 7.1 Hz), 1.28 (t, 3H); MS (ES+) m/z 360.5 (M+1).

EXAMPLE 1.45

Synthesis of ethyl (2'-oxo-6,7-dihydro-5H-spiro[indeno[5,6-b]furan-3,3'-indol]-1(2'H)-yl)acetate

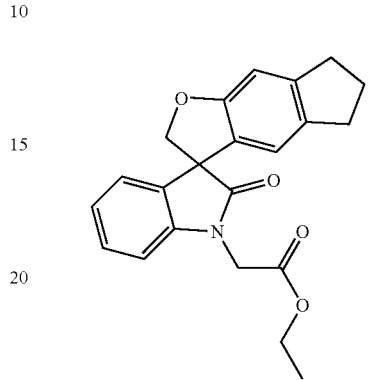

To a solution of ethyl [3-(6-hydroxy-2,3-dihydro-1H-inden-5-yl)-3-(hydroxymethyl)-2-oxo-2,3-dihydro-1H-indol-1-yl]acetate (4.20 mmol) in anhydrous THF (60.0 mL) was added triphenylphosphine (1.43 g, 5.46 mmol) and diethyl azodicarboxylate (0.95 g, 5.46 mmol) at 0° C. The reaction mixture was stirred at ambient temperature for 16 h and quenched with saturated ammonium chloride (20.0 mL). The mixture was extracted with ethyl acetate (3×50.0 mL). The combined organic layers was dried over anhydrous sodium sulfate and filtered. The filtrate was concentrated in vacuo to dryness. The residue was subjected to column chromatography (ethyl acetate/hexane, 1/4) to give the title compound (0.25 g, 16% in three steps): $^1$H NMR (300 MHz, CDCl$_3$) δ 7.29 (td, 1H), 7.22-7.17 (m, 1H), 7.07 (t, 1H), 6.81 (s, 1H), 6.78 (d, 1H), 6.65 (s, 1H), 4.95 (d, 1H), 4.71 (d, 1H), 4.64 (d, 1H), 4.42 (d, 1H), 4.24 (q, 2H), 2.84 (t, 2H), 2.73-2.65 (m, 2H), 2.10-1.95 (m, 2H), 1.29 (t, 3H); MS (ES+) m/z 364 (M+1).

EXAMPLE 1.46

Synthesis of ethyl (2-oxo-5',6',7',8'-tetrahydrospiro[indole-3,3'-naphtho[2,3-b]furan]-1(2H)-yl)acetate

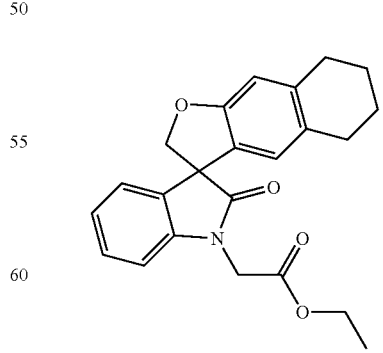

Following the procedure as described in EXAMPLE 1.45, and making non-critical variations using ethyl [3-(hydroxymethyl)-3-(3-hydroxy-5,6,7,8-tetrahydronaphthalen-2-yl)-2- oxo-2,3-dihydro-1H-indol-1-yl]acetate to replace ethyl [3-(6-hydroxy-2,3-dihydro-1H-inden-5-yl)-3-(hydroxymethyl)-2-oxo-2,3-dihydro-1H-indol-1-yl]acetate, the title compound was obtained (24% in three steps): $^1$H NMR (300 MHz, CDCl$_3$) δ 7.29 (td, 1H), 7.19 (d, 1H), 7.07 (t, 1H), 6.79 (d, 1H), 6.66 (s, 1H), 6.51 (s, 1H),), 4.91 (d, 1H), 4.67 (d, 1H), 4.52 (ABq, 2H), 4.24 (q, 2H), 2.77-2.51 (m, 4H), 1.77-1.64 (m, 4H), 1.29 (t, 3H); MS (ES+) m/z 378 (M+1).

EXAMPLE 1.47

Synthesis of ethyl (4'-bromo-5,6-difluoro-2'-oxospiro[1-benzofuran-3,3'-indol]-1'(2'H)-yl)acetate

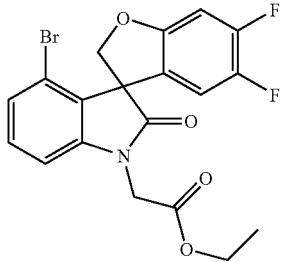

Following the procedure as described in EXAMPLE 1.45, and making non-critical variations using ethyl [4-bromo-3-(4,5-difluoro-2-hydroxyphenyl)-3-(hydroxymethyl)-2-oxo-2,3-dihydro-1H-indol-1-yl]acetate to replace ethyl [3-(6-hydroxy-2,3-dihydro-1H-inden-5-yl)-3-(hydroxymethyl)-2-oxo-2,3-dihydro-1H-indol-1-yl]acetate, the title compound was obtained (41%): mp 133-134° C.; $^1$H NMR (300 MHz, CDCl$_3$) δ 7.26-7.15 (m, 3 H), 6.78-6.58 (m, 2H), 5.08 (d, 1H), 4.91 (d, 1H), 4.63 (d, 1H), 4.35 (d, 1H), 4.24 (q, 2H), 1.29 (t, 3H); $^{13}$C NMR (75 MHz, CDCl$_3$) δ 176.5, 166.8, 157.1, 143.7, 130.7, 129.0, 127.8, 120.0, 111.8, 111.6, 107.5, 99.8, 99.5, 62.2, 59.1, 41.7, 14.1; MS (ES+) m/z 438 (M+1), 440 (M+1), 460 (M+23), 462 (M+23).

EXAMPLE 1.48

Synthesis of 1'-(diphenylmethyl)-6,7-dihydrospiro[benzo[1,2-b:4,5-b']difuran-3,3'-indol]-2'(1'H)-one

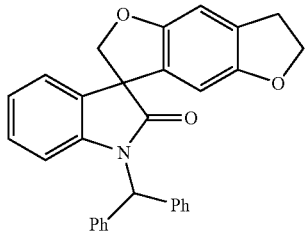

Following the procedure described in EXAMPLE 1, and making non-critical variations using 1-(diphenylmethyl)-3-(5-hydroxy-2,3-dihydro-1-benzofuran-6-yl)-3-(hydroxymethyl)-1,3-dihydro-2H-indol-2-one to replace 1-(2-cyclopropylethyl)-3-(6-hydroxy-1,3-benzodioxol-5-yl)-3-(hydroxymethyl)-1,3-dihydro-2H-indol-2-one, the title compound was obtained (43%): MS (ES+) m/z 446.4 (M+1).

EXAMPLE 1.49

Synthesis of 6,7-dihydrospiro[benzo[1,2-b:4,5-b']difuran-3,3'-indol]-2'(1'H)-one

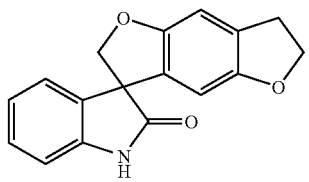

A mixture of 1'-(diphenylmethyl)-6,7-dihydrospiro[benzo[1,2-b:4,5-b']difuran-3,3'-indol]-2'(1'H)-one (0.29 g, 0.65 mmol) and palladium hydroxide (0.10 g, 20% on activated carbon) in acetic acid (20.0 mL) was hydrogenated at 60° C. under normal pressure of hydrogen for 20 hours. The reaction mixture was filtered through celite and washed with acetone (50.0 mL). The filtrate was concentrated in vacuo to dryness to give the title compound (0.13 g, 69%): MS (ES+) m/z 280.2 (M+1).

EXAMPLE 1.50

Synthesis of 1-(diphenylmethyl)-5,6-dihydrospiro[benzo[1,2-b:5,4-b']difuran-3,3'-indol]-2'(1'H)-one

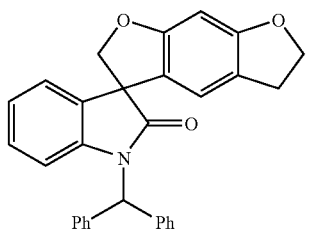

Following the procedure described in EXAMPLE 1, and making non-critical variations using 1-(diphenylmethyl)-3-(6-hydroxy-2,3-dihydro-1-benzofuran-5-yl)-3-(hydroxymethyl)-1,3-dihydro-2H-indol-2-one to replace 1-(2-cyclopropylethyl)-3-(6-hydroxy-1,3-benzodioxol-5-yl)-3-(hydroxymethyl)-1,3-dihydro-2H-indol-2-one, the title compound was obtained (51%) as a white solid: MS (ES+) m/z 446.3 (M+1).

EXAMPLE 1.51

Synthesis of 5,6-dihydrospiro[benzo[1,2-b:5,4-b']difuran-3,3'-indol]-2'(1'H)-one

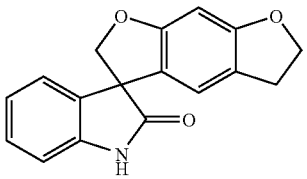

Following the procedure as described in EXAMPLE 1.49, and making non-critical variations using 1-(diphenylmethyl)-5,6-dihydrospiro[benzo[1,2-b:5,4-b']difuran-3,3'-indol]-2'(1'H)-one to replace 1'-(diphenylmethyl)-6,7-dihydrospiro[benzo[1,2-b:4,5-b']difuran-3,3'-indol]-2'(1'H)-one, the title compound was obtained (68%): mp 208-210° C.; $^1$H NMR (300 MHz, DMSO-$d_6$) δ 10.53 (s, 1H), 7.39-6.76 (m, 4H), 6.45 (s, 1H), 6.35 (s, 1H), 4.68 (ABq, 2H), 4.45 (t, 2H), 2.92 (t, 2H); MS (ES+) m/z 280.2 (M+1).

EXAMPLE 1.52

Synthesis of ethyl (2'-oxo-5,6-dihydrospiro[benzo[1,2-b:5,4-b']difuran-3,3'-indol]-1'(2'H)-yl)acetate

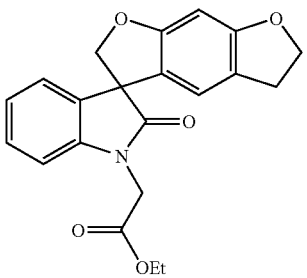

A mixture of 5,6-dihydrospiro[benzo[1,2-b:5,4-b']difuran-3,3'-indol]2'(1'H)-one (0.28 g, 1.00 mmol), ethyl 2-bromoacetate (0.17 g, 1.00 mmol) and cesium carbonate (0.98 g, 3.00 mmol) in acetone (20.0 mL) was stirred at reflux for 5 hours. After cooling down to ambient temperature, the mixture was filtered. The filtrate was evaporated under reduced pressure and the residue was subjected to column chromatography to give the title compound (0.23 g, 63%) as a white solid: MS (ES+) m/z 366.4 (M+1).

EXAMPLE 1.53

Synthesis of 4'-methoxy-1'-{[5-(trifluoromethyl)-2-furyl]methyl}spiro[furo[2,3-f][1,3]benzodioxole-7,3'-indol]-2'(1'H)-one

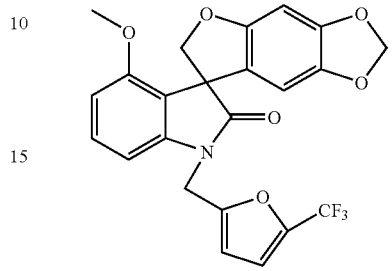

Following the procedure described in EXAMPLE 1, and making non-critical variations using 3-(6-hydroxy-1,3-benzodioxol-5-yl)-3-(hydroxymethyl)-4-methoxy-1-{[5-(trifluoromethyl)-2-furyl]methyl}-1,3-dihydro-2H-indol-2-one to replace 1-(2-cyclopropylethyl)-3-(6-hydroxy-1,3-benzodioxol-5-yl)-3-(hydroxymethyl)-1,3-dihydro-2H-indol-2-one, the title compound was obtained (33%) as a white solid: mp 149-153° C.; $^1$H NMR (300 MHz, DMSO-$d_6$) δ 7.32-7.24 (m, 1H), 6.82-6.62 (m, 3H), 6.46 (s, 1H), 6.40 (d, 1H), 6.08 (s, 1H), 5.87 (ABq, 2H), 4.92 (ABq, 2H), 4.82 (ABq, 2H), 3.70 (s, 3H); MS (ES+) m/z 460.3 (M+1).

EXAMPLE 1.54

Synthesis of 7'-fluoro-1'-{[5-(trifluoromethyl)-2-furyl]methyl}spiro[furo[2,3-f][1,3]benzodioxole-7,3'-indol]-2'(1'H)-one

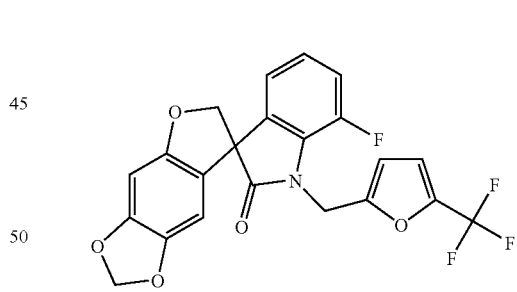

Following the procedure described in EXAMPLE 1, and making non-critical variations using 7-fluoro-3-(6-hydroxy-1,3-benzodioxol-5-yl)-3-(hydroxymethyl)-1-{[5-(trifluoromethyl)-2-furyl]methyl}-1,3-dihydro-2H-indol-2-one to replace 1-(2-cyclopropylethyl)-3-(6-hydroxy-1,3-benzodioxol-5-yl)-3-(hydroxymethyl)-1,3-dihydro-2H-indol-2-one, the title compound was obtained (32%) as a white solid: mp 116-118° C.; $^1$H NMR (300 MHz, DMSO-$d_6$) δ 7.36-6.88 (m, 4H), 6.67 (s, 1H), 6.62 (d, 1H), 6.19 (s, 1H), 5.90 (d, 2H), 5.07 (q, 2H), 4.75 (dd, 2H); $^{13}$C NMR (75 MHz, DMSO-$d_6$) δ 176.9, 155.8, 154.1, 149.1, 148.8, 145.6, 142.4, 140.9, 140.3, 139.2, 139.2, 135.2, 135.2, 128.5, 128.4, 124.9, 128.4, 124.9, 124.8, 124.7, 121.2, 120.4, 120.4, 119.8, 117.6, 117.2, 117.0, 114.5, 114.5, 109.5, 103.2, 102.0, 93.8, 80.1, 58.3, 58.2, 39.0, 38.9; MS (ES+) m/z 448.3 (M+1).

EXAMPLE 2

Synthesis of (2'-oxospiro[furo[2,3-f][1,3]benzodioxole-7,3'-indol]-1'(2'H)-yl)acetic acid

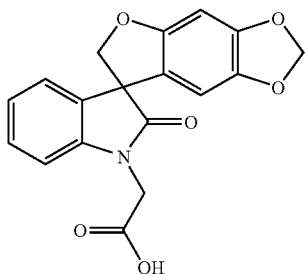

To a suspension of ethyl (2'-oxospiro[furo[2,3-f][1,3]benzodioxole-7,3'-indol]-1'(2'H)-yl)acetate (10.5 g, 24.5 mmol) in THF (200 mL) and water (100 mL) was added lithium hydroxide monohydrate (3.98 g, 95.0 mmol) at 0° C. The reaction mixture was stirred at 0° C. for 30 min and at ambient temperature for 17 h. The mixture was neutralized with of 4 M HCl (15.0 mL). The residue obtained upon removing the solvent was acidified by the addition of 4 M HCl (6.2 mL) to pH 3. The solid was filtered, washed with water and hexane, and dried under the reduced pressure to give the title compound (8.48 g, 87%) as a white solid: $^1$H NMR (300 MHz, CDCl$_3$) δ 7.32-7.06 (m, 4H), 6.79 (d, 1H), 6.49 (s, 1H), 6.23 (s, 1H), 5.84 (m, 2H), 4.92 (m, 1H), 4.69-4.63 (m, 2H), 4.45 (m, 1H); $^{13}$C NMR (75 MHz, CDCl$_3$) δ 177.8, 171.8, 155.8, 149.0, 142.4, 141.2, 132.0, 129.0, 124.1, 124.0, 119.2, 108.3, 103.4, 101.5, 93.5, 80.2, 58.2, 41.1; MS (ES−) m/z 338.2 (M−1).

EXAMPLE 2.1

Synthesis of (2'-oxo-6,7-dihydro-5H-spiro[indeno[5,6-b]furan-3,3'-indol]-1'(2'H)-yl)acetic acid

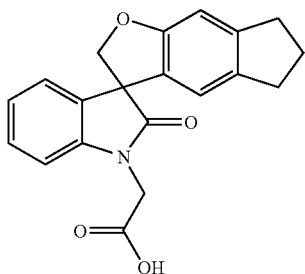

Following the procedure as described in EXAMPLE 2, and making non-critical variations using ethyl (2'-oxo-6,7-dihydro-5H-spiro[indeno[5,6-b]furan-3,3'-indol]-1'(2'H)-yl)acetate to replace ethyl (2'-oxospiro[furo[2,3-f][1,3]benzodioxole-7,3'-indol]-1'(2'H)-yl)acetate, the title compound was obtained in 74% yield; MS (ES−) m/z 354 (M−1).

EXAMPLE 2.2

Synthesis of (4'-chloro-2'-oxo-5,6-dihydrospiro[benzo[1,2-b:5,4-b']difuran-3,3'-indol]-1'(2'H)-yl)acetic acid

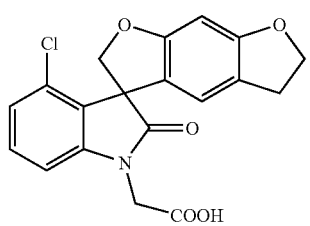

Following the procedure as described in EXAMPLE 2, and making non-critical variations using ethyl (4'-chloro-2'-oxo-5,6-dihydrospiro[benzo[1,2-b:5,4-b']difuran-3,3'-indol]-1'(2'H)-yl)acetate to replace ethyl (2'-oxospiro[furo[2,3-f][1,3]benzodioxole-7,3'-indol]-1'(2'H)-yl)acetate, the title compound was obtained in 92% yield as a colorless solid: mp 228-229° C.; $^1$H NMR (300 MHz, CDCl$_3$) δ 7.26-7.21 (m, 1H), 7.03 (dd, 1H), 6.71 (dd, 1H), 6.52 (s, 1H), 6.36 (s, 1H), 4.93 (dd, 2H), 4.69-4.63 (m, 1H), 4.54-4.51 (m, 3H), 2.95 (t, 2H); $^{13}$C NMR (75 MHz, CDCl$_3$) δ 177.8, 170.9, 162.1, 162.1, 143.1, 131.7, 130.0, 128.6, 124.7, 119.6, 118.7, 117.0, 106.7, 92.8, 77.2, 72.3, 58.1, 41.2, 28.9; MS (ES−) m/z 370.4 (M−1).

EXAMPLE 2.3

Synthesis of (4'-bromo-2'-oxo-5,6-dihydrospiro[benzo[1,2-b:5,4-b']difuran-3,3'-indol]-1'(2'H)-yl)acetic acid

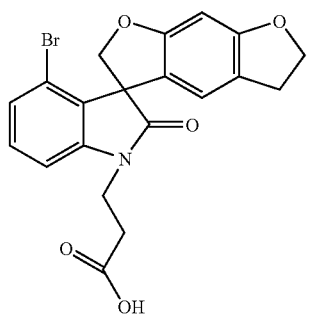

Following the procedure as described in EXAMPLE 2, and making non-critical variations using ethyl (4'-bromo-2'-oxo-5,6-dihydrospiro[benzo[1,2-b:5,4-b']difuran-3,3'-indol]-1'(2'H)-yl)acetate to replace ethyl (2'-oxospiro[furo[2,3-f][1,3]

benzodioxole-7,3'-indol]-1'(2'H)-yl)acetate, the title compound was obtained (98%) as a colorless solid: MS (ES−) m/z 415.2 (M−1).

EXAMPLE 2.4

Synthesis of (5'-chloro-2'-oxo-5,6-dihydrospiro [benzo[1,2-b:5,4-b']difuran-3,3'-indol]-1'(2'H)-yl) acetic acid

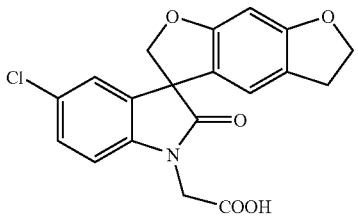

Following the procedure as described in EXAMPLE 2, and making non-critical variations using ethyl (5'-chloro-2'-oxo-5,6-dihydrospiro[benzo[1,2-b:5,4-b']difuran-3,3'-indol]-1 (2'H)-yl)acetate to replace ethyl (2'-oxospiro[furo[2,3-f][1,3] benzodioxole-7,3'-indol]-1(2'H)-yl)acetate, the title compound was obtained in 98% yield as a colorless solid: $^1$H NMR (300 MHz, CDCl$_3$) δ 7.27-7.25 (m, 1H), 7.16 (d, 1H), 6.72 (d, 1H), 6.54 (s, 1H), 6.39 (s, 1H), 4.93 (dd, 2H), 4.69-4.63 (m, 1H), 4.54-4.51 (m, 3H), 2.95 (t, 2H); $^{13}$C NMR (75 MHz, CDCl$_3$) δ 177.8, 170.9, 162.1, 162.1, 143.1, 131.7, 130.0, 128.6, 124.7, 119.6, 118.7, 117.0, 106.7, 92.8, 77.2, 72.3, 58.1, 41.2, 28.9; MS (ES−) m/z 370.4 (M−1).

EXAMPLE 2.5

Synthesis of (2-oxo-5',6',7',8'-tetrahydrospiro[indole-3,3'-naphtho[2,3-b]furan]-1(2H)-yl)acetic acid

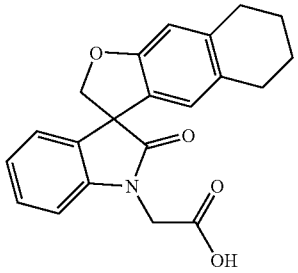

Following the procedure as described in Example 2, and making non-critical variations using ethyl (2-oxo-5',6',7',8'-tetrahydrospiro[indole-3,3'-naphtho[2,3-b]furan]-1(2H)-yl) acetate to replace ethyl (2'-oxospiro[furo[2,3-f][1,3]benzo-dioxole-7,3'-indol]-1(2'H)-yl)acetate, the title compound was obtained (99%): MS (ES−) m/z 348 (M−1).

EXAMPLE 2.6

Synthesis of (2'-oxo-5,6-dihydrospiro[benzo[1,2-b:5, 4-b']difuran-3,3'-indol]-1'(2'H)-yl)acetic acid

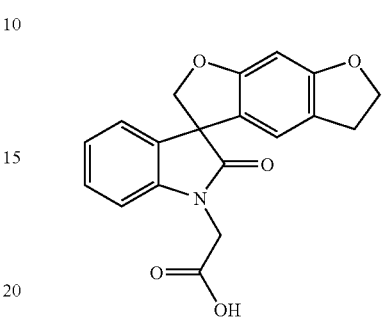

A mixture of ethyl (2'-oxo-5,6-dihydrospiro[benzo[1,2-b: 5,4-b']difuran-3,3'-indol]-1(2'H)-yl)acetate (0.23 g, 0.63 mmol) and LiOH (0.10 g, 4.20 mmol) in MeOH/H$_2$O (1/1, 20.0 mL) was stirred at ambient temperature for 20 hours. The mixture was acidified with 0.1 M HCl until pH 2-3. The solid was filtered off and dried to give the title compound (0.15 g, 70%): MS (ES−) m/z 336.3 (M−1).

EXAMPLE 3

Synthesis of N-(4-chlorobenzyl)-2-(2'-oxospiro[furo [2,3-f][1,3]benzodioxole-7,3'-indol]-1(2'H)-yl)aceta-mide

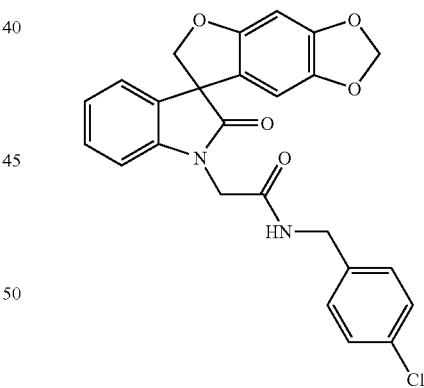

A. Preparation of stock solution of isobutyl (2'-ox-ospiro[furo[2,3-f][1,3]benzodioxole-7,3'-indol]-1' (2'H)-yl)acetyl carbonate To a solution of (2'-oxospiro[furo[2,3-f][1,3]benzodiox-ole-7,3'-indol]-1'(2'H)-yl)acetic acid (0.30 g, 0.88 mmol) in dichloromethane (12.5 mL) was added N-methylmorpholine (0.09 g, 0.88 mmol) and iso-butyl chloroformate (0.12 g, 0.88 mmol) dropwise at 0° C. The mixture was stirred at 0° C. for 1.5 h and at ambient temperature for 3 h. This mixture was used as a mixed anhydride for the next step amide formation.

B. Synthesis of N-(4-chlorobenzyl)-2-(2'-oxospiro[furo[2,3-f][1,3]benzodioxole-7,3'-indol]-1'(2'H)-yl)acetamide To the above mixed anhydride stock solution (2.50 mL, 0.18 mmol) was added a solution of 4-chlorobenzylamine in dichloromethane (0.35 mL, 0.50 M, 0.18 mmol) at ambient temperature. The reaction mixture was stirred at ambient temperature for 23 h, washed with saturated aqueous sodium carbonate and water. After removal of the solvent, diethyl ether was added and the precipitate was collected by filtration to give the title compound (0.04 g, 46%): $^1$H NMR (300 MHz, CDCl$_3$) δ 7.39-6.97 (m, 8H), 6.49 (s, 1H), 6.29 (br, 1H), 6.01 (s, 1H), 5.85 (m, 2H), 4.87 (m, 1H), 4.65 (m, 1H), 4.53-4.29 (m, 4H); MS (ES+), m/z 485.2 (M+23).

EXAMPLE 3.1

The compounds listed in the following table were synthesized using similar conditions as described in Example 3. The compound numbers listed below do not correspond to the compound numbers provided in the general Reaction Schemes above.

| Compound Number | Name | MS (m/z, M + 1) |
| --- | --- | --- |
| 1 | N-(3-fluorophenyl)-2-(2'-oxospiro[furo[2,3-f][1,3]benzodioxole-7,3'-indol]-1'(2'H)-yl)acetamide | 433.2 |
| 2 | N-butyl-2-(2'-oxospiro[furo[2,3-f][1,3]benzodioxole-7,3'-indol]-1'(2'H)-yl)acetamide | 395.2 |
| 3 | 1'-(2-oxo-2-piperidin-1-ylethyl)spiro[furo[2,3-f][1,3]benzodioxole-7,3'-indol]-2'(1'H)-one | 407.2 |
| 4 | N-butyl-N-methyl-2-(2'-oxospiro[furo[2,3-f][1,3]benzodioxole-7,3'-indol]-1'(2'H)-yl)acetamide | 409.3 |
| 5 | 2-(2'-oxospiro[furo[2,3-f][1,3]benzodioxole-7,3'-indol]-1'(2'H)-yl)-N-phenylacetamide | 415.2 |
| 6 | N-(4-fluorophenyl)-2-(2'-oxospiro[furo[2,3-f][1,3]benzodioxole-7,3'-indol]-1'(2'H)-yl)acetamide | 433.3 |
| 7 | N-(3-fluorobenzyl)-2-(2'-oxospiro[furo[2,3-f][1,3]benzodioxole-7,3'-indol]-1'(2'H)-yl)acetamide | 447.3 |
| 8 | N-(3-chlorophenyl)-2-(2'-oxospiro[furo[2,3-f][1,3]benzodioxole-7,3'-indol]-1'(2'H)-yl)acetamide | 449.2 |
| 9 | N-(2-fluorophenyl)-2-(2'-oxospiro[furo[2,3-f][1,3]benzodioxole-7,3'-indol]-1'(2'H)-yl)acetamide | 433.3 |
| 10 | N-(2-ethylphenyl)-2-(2'-oxospiro[furo[2,3-f][1,3]benzodioxole-7,3'-indol]-1'(2'H)-yl)acetamide | 443.2 |
| 11 | N-(4-ethylphenyl)-2-(2'-oxospiro[furo[2,3-f][1,3]benzodioxole-7,3'-indol]-1'(2'H)-yl)acetamide | 443.3 |
| 12 | N-(3-methylphenyl)-2-(2'-oxospiro[furo[2,3-f][1,3]benzodioxole-7,3'-indol]-1'(2'H)-yl)acetamide | 429.3 |
| 13 | N-(2,3-dimethylphenyl)-2-(2'-oxospiro[furo[2,3-f][1,3]benzodioxole-7,3'-indol]-1'(2'H)-yl)acetamide | 443.3 |
| 14 | N-(3,5-dimethylphenyl)-2-(2'-oxospiro[furo[2,3-f][1,3]benzodioxole-7,3'-indol]-1'(2'H)-yl)acetamide | 443.4 |
| 15 | 2-(2'-oxospiro[furo[2,3-f][1,3]benzodioxole-7,3'-indol]-1'(2'H)-yl)-N-pentylacetamide | 409.4 |
| 16 | 2-(2'-oxospiro[furo[2,3-f][1,3]benzodioxole-7,3'-indol]-1'(2'H)-yl)-N-propylacetamide | 381.3 |
| 17 | N-isopropyl-2-(2'-oxospiro[furo[2,3-f][1,3]benzodioxole-7,3'-indol]-1'(2'H)-yl)acetamide | 381.4 |
| 18 | N-(3-methylbutyl)-2-(2'-oxospiro[furo[2,3-f][1,3]benzodioxole-7,3'-indol]-1'(2'H)-yl)acetamide | 409.3 |
| 19 | N-isobutyl-2-(2'-oxospiro[furo[2,3-f][1,3]benzodioxole-7,3'-indol]-1'(2'H)-yl)acetamide | 395.3 |
| 20 | N-hexyl-2-(2'-oxospiro[furo[2,3-f][1,3]benzodioxole-7,3'-indol]-1'(2'H)-yl)acetamide | 423.4 |
| 21 | N-cyclohexyl-2-(2'-oxospiro[furo[2,3-f][1,3]benzodioxole-7,3'-indol]-1'(2'H)-yl)acetamide | 421.4 |
| 22 | N-cyclopentyl-2-(2'-oxospiro[furo[2,3-f][1,3]benzodioxole-7,3'-indol]-1'(2'H)-yl)acetamide | 407.3 |
| 23 | N-heptyl-2-(2'-oxospiro[furo[2,3-f][1,3]benzodioxole-7,3'-indol]-1'(2'H)-yl)acetamide | 437.5 |
| 24 | N-(2-chlorobenzyl)-2-(2'-oxospiro[furo[2,3-f][1,3]benzodioxole-7,3'-indol]-1'(2'H)-yl)acetamide | 463.2 |
| 25 | N-(2,6-dimethylphenyl)-2-(2'-oxospiro[furo[2,3-f][1,3]benzodioxole-7,3'-indol]-1'(2'H)-yl)acetamide | 443.3 |
| 26 | N-(2-methoxyphenyl)-2-(2'-oxospiro[furo[2,3-f][1,3]benzodioxole-7,3'-indol]-1'(2'H)-yl)acetamide | 445.3 |
| 27 | N-[(5-methyl-2-furyl)methyl]-2-(2'-oxospiro[furo[2,3-f][1,3]benzodioxole-7,3'-indol]-1'(2'H)-yl)acetamide | 433.2 |
| 28 | N-ethyl-2-(2'-oxospiro[furo[2,3-f][1,3]benzodioxole-7,3'-indol]-1'(2'H)-yl)acetamide | 367.4 |
| 29 | N-methyl-2-(2'-oxospiro[furo[2,3-f][1,3]benzodioxole-7,3'-indol]-1'(2'H)-yl)acetamide | 353.3 |
| 30 | N-(2-fluorobenzyl)-2-(2'-oxospiro[furo[2,3-f][1,3]benzodioxole-7,3'-indol]-1'(2'H)-yl)acetamide | 447.2 |

-continued

| Compound Number | Name | MS (m/z, M + 1) |
|---|---|---|
| 31 | N-[2-(3-methoxyphenyl)ethyl]-2-(2'-oxospiro[furo[2,3-f][1,3]benzodioxole-7,3'-indol]-1'(2'H)-yl)acetamide | 473.3 |
| 32 | N-(2-ethoxyethyl)-2-(2'-oxospiro[furo[2,3-f][1,3]benzodioxole-7,3'-indol]-1'(2'H)-yl)acetamide | 411.3 |
| 33 | N-(4-methoxybenzyl)-2-(2'-oxospiro[furo[2,3-f][1,3]benzodioxole-7,3'-indol]-1'(2'H)-yl)acetamide | 459.3 |
| 34 | N-(2,4-dimethylphenyl)-2-(2'-oxospiro[furo[2,3-f][1,3]benzodioxole-7,3'-indol]-1'(2'H)-yl)acetamide | 443.3 |
| 35 | N-(3-isopropoxypropyl)-2-(2'-oxospiro[furo[2,3-f][1,3]benzodioxole-7,3'-indol]-1'(2'H)-yl)acetamide | 439.4 |
| 36 | N-(2-furylmethyl)-2-(2'-oxospiro[furo[2,3-f][1,3]benzodioxole-7,3'-indol]-1'(2'H)-yl)acetamide | 419.3 |
| 37 | N-(cyclohexylmethyl)-2-(2'-oxospiro[furo[2,3-f][1,3]benzodioxole-7,3'-indol]-1'(2'H)-yl)acetamide | 435.3 |
| 38 | N-(3-fluoro-2-methylphenyl)-2-(2'-oxospiro[furo[2,3-f][1,3]benzodioxole-7,3'-indol]-1'(2'H)-yl)acetamide | 447.3 |
| 39 | N-(4-methoxyphenyl)-2-(2'-oxospiro[furo[2,3-f][1,3]benzodioxole-7,3'-indol]-1'(2'H)-yl)acetamide | 445.3 |
| 40 | N-cyclobutyl-2-(2'-oxospiro[furo[2,3-f][1,3]benzodioxole-7,3'-indol]-1'(2'H)-yl)acetamide | 393.4 |
| 41 | N-(2,5-difluorophenyl)-2-(2'-oxospiro[furo[2,3-f][1,3]benzodioxole-7,3'-indol]-1'(2'H)-yl)acetamide | 451.3 |
| 42 | N-benzyl-2-(2'-oxospiro[furo[2,3-f][1,3]benzodioxole-7,3'-indol]-1'(2'H)-yl)acetamide | 429.3 |
| 43 | N-(cyclopropylmethyl)-2-(2'-oxospiro[furo[2,3-f][1,3]benzodioxole-7,3'-indol]-1'(2'H)-yl)acetamide | 393.2 |
| 44 | N-butyl-N-ethyl-2-(2'-oxospiro[furo[2,3-f][1,3]benzodioxole-7,3'-indol]-1'(2'H)-yl)acetamide | 423.3 |
| 45 | N-octyl-2-(2'-oxospiro[furo[2,3-f][1,3]benzodioxole-7,3'-indol]-1'(2'H)-yl)acetamide | 451.2 |
| 46 | N-(3,3-dimethylbutyl)-2-(2'-oxospiro[furo[2,3-f][1,3]benzodioxole-7,3'-indol]-1'(2'H)-yl)acetamide | 423.2 |
| 47 | N-(4-chloro-2-methylphenyl)-2-(2'-oxospiro[furo[2,3-f][1,3]benzodioxole-7,3'-indol]-1'(2'H)-yl)acetamide | 463.1 |
| 48 | N-(3-methoxyphenyl)-2-(2'-oxospiro[furo[2,3-f][1,3]benzodioxole-7,3'-indol]-1'(2'H)-yl)acetamide | 445.0 |
| 49 | N-(2-fluoro-4-methylphenyl)-2-(2'-oxospiro[furo[2,3-f][1,3]benzodioxole-7,3'-indol]-1'(2'H)-yl)acetamide | 447.0 |
| 50 | N-(3,4-dimethylphenyl)-2-(2'-oxospiro[furo[2,3-f][1,3]benzodioxole-7,3'-indol]-1'(2'H)-yl)acetamide | 443.1 |
| 51 | N-(3-chlorobenzyl)-2-(2'-oxospiro[furo[2,3-f][1,3]benzodioxole-7,3'-indol]-1'(2'H)-yl)acetamide | 463.1 |
| 52 | N-(3-methoxybenzyl)-2-(2'-oxospiro[furo[2,3-f][1,3]benzodioxole-7,3'-indol]-1'(2'H)-yl)acetamide | 459.1 |
| 53 | N-(3,4-difluorophenyl)-2-(2'-oxospiro[furo[2,3-f][1,3]benzodioxole-7,3'-indol]-1'(2'H)-yl)acetamide | 451.1 |
| 54 | N-(3-methylbenzyl)-2-(2'-oxospiro[furo[2,3-f][1,3]benzodioxole-7,3'-indol]-1'(2'H)-yl)acetamide | 443.1 |
| 55 | N-(2-methoxybenzyl)-2-(2'-oxospiro[furo[2,3-f][1,3]benzodioxole-7,3'-indol]-1'(2'H)-yl)acetamide | 459.2 |
| 56 | N-(4-isopropylphenyl)-2-(2'-oxospiro[furo[2,3-f][1,3]benzodioxole-7,3'-indol]-1'(2'H)-yl)acetamide | 457.2 |
| 57 | N-(2,3-difluorophenyl)-2-(2'-oxospiro[furo[2,3-f][1,3]benzodioxole-7,3'-indol]-1'(2'H)-yl)acetamide | 451.1 |
| 58 | 2-(2'-oxospiro[furo[2,3-f][1,3]benzodioxole-7,3'-indol]-1'(2'H)-yl)-N-(tetrahydrofuran-2-ylmethyl)acetamide | 423.1 |
| 59 | N-[2-(4-methylphenyl)ethyl]-2-(2'-oxospiro[furo[2,3-f][1,3]benzodioxole-7,3'-indol]-1'(2'H)-yl)acetamide | 457.1 |
| 60 | N-[2-(3-chlorophenyl)ethyl]-2-(2'-oxospiro[furo[2,3-f][1,3]benzodioxole-7,3'-indol]-1'(2'H)-yl)acetamide | 477.1 |
| 61 | N-(4-cyanophenyl)-2-(2'-oxospiro[furo[2,3-f][1,3]benzodioxole-7,3'-indol]-1'(2'H)-yl)acetamide | 440.1 |
| 62 | N-(2,3-dihydro-1H-inden-1-yl)-2-(2'-oxospiro[furo[2,3-f][1,3]benzodioxole-7,3'-indol]-1'(2'H)-yl)acetamide | 455.1 |
| 63 | N-(2-methoxyethyl)-2-(2'-oxospiro[furo[2,3-f][1,3]benzodioxole-7,3'-indol]-1'(2'H)-yl)acetamide | 397.1 |
| 64 | N-[2-(4-methoxyphenyl)ethyl]-2-(2'-oxospiro[furo[2,3-f][1,3]benzodioxole-7,3'-indol]-1'(2'H)-yl)acetamide | 473.1 |
| 65 | N-(2-cyanoethyl)-2-(2'-oxospiro[furo[2,3-f][1,3]benzodioxole-7,3'-indol]-1'(2'H)-yl)acetamide | 392.1 |
| 66 | N-(2,4-dichlorobenzyl)-2-(2'-oxospiro[furo[2,3-f][1,3]benzodioxole-7,3'-indol]-1'(2'H)-yl)acetamide | 497.0 |
| 67 | N-(3,5-difluorobenzyl)-2-(2'-oxospiro[furo[2,3-f][1,3]benzodioxole-7,3'-indol]-1'(2'H)-yl)acetamide | 465.0 |
| 68 | N-(2,4-difluorobenzyl)-2-(2'-oxospiro[furo[2,3-f][1,3]benzodioxole-7,3'-indol]-1'(2'H)-yl)acetamide | 465.0 |

-continued

| Compound Number | Name | MS (m/z, M + 1) |
|---|---|---|
| 69 | N-(2-methylbenzyl)-2-(2'-oxospiro[furo[2,3-f][1,3]benzodioxole-7,3'-indol]-1'(2'H)-yl)acetamide | 443.1 |
| 70 | N-(3,4-difluorobenzyl)-2-(2'-oxospiro[furo[2,3-f][1,3]benzodioxole-7,3'-indol]-1'(2'H)-yl)acetamide | 465.1 |
| 71 | N-(2,5-difluorobenzyl)-2-(2'-oxospiro[furo[2,3-f][1,3]benzodioxole-7,3'-indol]-1'(2'H)-yl)acetamide | 465.1 |
| 72 | 2-(2'-oxospiro[furo[2,3-f][1,3]benzodioxole-7,3'-indol]-1'(2'H)-yl)-N,N-dipropylacetamide | 423.2 |
| 73 | N,N-dibutyl-2-(2'-oxospiro[furo[2,3-f][1,3]benzodioxole-7,3'-indol]-1'(2'H)-yl)acetamide | 451.2 |
| 74 | N-(2,6-difluorobenzyl)-2-(2'-oxospiro[furo[2,3-f][1,3]benzodioxole-7,3'-indol]-1'(2'H)-yl)acetamide | 465.1 |
| 75 | N-[2-(methylthio)phenyl]-2-(2'-oxospiro[furo[2,3-f][1,3]benzodioxole-7,3'-indol]-1'(2'H)-yl)acetamide | 461.1 |
| 76 | N-(2-isopropylphenyl)-2-(2'-oxospiro[furo[2,3-f][1,3]benzodioxole-7,3'-indol]-1'(2'H)-yl)acetamide | 457.2 |
| 77 | N-(4-bromophenyl)-2-(2'-oxospiro[furo[2,3-f][1,3]benzodioxole-7,3'-indol]-1'(2'H)-yl)acetamide | 493.0 |
| 78 | N-(4-chlorophenyl)-2-(2'-oxospiro[furo[2,3-f][1,3]benzodioxole-7,3'-indol]-1'(2'H)-yl)acetamide | 449.0 |
| 79 | N-(2,4-dichlorophenyl)-2-(2'-oxospiro[furo[2,3-f][1,3]benzodioxole-7,3'-indol]-1'(2'H)-yl)acetamide | 483.0 |
| 80 | N-(3,5-dichlorophenyl)-2-(2'-oxospiro[furo[2,3-f][1,3]benzodioxole-7,3'-indol]-1'(2'H)-yl)acetamide | 483.1 |
| 81 | N,N-diethyl-2-(2'-oxospiro[furo[2,3-f][1,3]benzodioxole-7,3'-indol]-1'(2'H)-yl)acetamide | 395.1 |
| 82 | N-methyl-2-(2'-oxospiro[furo[2,3-f][1,3]benzodioxole-7,3'-indol]-1'(2'H)-yl)-N-phenylacetamide | 429.1 |
| 83 | N-(4-hydroxybutyl)-2-(2'-oxospiro[furo[2,3-f][1,3]benzodioxole-7,3'-indol]-1'(2'H)-yl)acetamide | 411.1 |
| 84 | N-allyl-2-(2'-oxospiro[furo[2,3-f][1,3]benzodioxole-7,3'-indol]-1'(2'H)-yl)acetamide | 379.1 |
| 85 | N-(2-fluoro-5-methylphenyl)-2-(2'-oxospiro[furo[2,3-f][1,3]benzodioxole-7,3'-indol]-1'(2'H)-yl)acetamide | 447.1 |
| 86 | N-(1,3-benzodioxol-5-ylmethyl)-2-(2'-oxospiro[furo[2,3-f][1,3]benzodioxole-7,3'-indol]-1'(2'H)-yl)acetamide | 473.1 |
| 87 | N-cyclopropyl-2-(2'-oxospiro[furo[2,3-f][1,3]benzodioxole-7,3'-indol]-1'(2'H)-yl)acetamide | 379.1 |
| 88 | N-(2-cyclopropylethyl)-2-(2'-oxospiro[furo[2,3-f][1,3]benzodioxole-7,3'-indol]-1'(2'H)-yl)acetamide | 407.2 |
| 89 | N-(3,4-dichlorobenzyl)-2-(2'-oxospiro[furo[2,3-f][1,3]benzodioxole-7,3'-indol]-1'(2'H)-yl)acetamide | 497.1 |
| 90 | N-(2,3-dichlorobenzyl)-2-(2'-oxospiro[furo[2,3-f][1,3]benzodioxole-7,3'-indol]-1'(2'H)-yl)acetamide | 497.1 |
| 91 | N-(2,5-dimethylphenyl)-2-(2'-oxospiro[furo[2,3-f][1,3]benzodioxole-7,3'-indol]-1'(2'H)-yl)acetamide | 443.1 |
| 92 | N-(3,4-dichlorophenyl)-2-(2'-oxospiro[furo[2,3-f][1,3]benzodioxole-7,3'-indol]-1'(2'H)-yl)acetamide | 483.3 |
| 93 | N,N-dimethyl-2-(2'-oxospiro[furo[2,3-f][1,3]benzodioxole-7,3'-indol]-1'(2'H)-yl)acetamide | 367.2 |
| 94 | N-methyl-2-(2'-oxospiro[furo[2,3-f][1,3]benzodioxole-7,3'-indol]-1'(2'H)-yl)-N-(2-phenylethyl)acetamide | 457.2 |
| 95 | 2-(2'-oxospiro[furo[2,3-f][1,3]benzodioxole-7,3'-indol]-1'(2'H)-yl)-N-(2-phenylpropyl)acetamide | 457.2 |
| 96 | N-[(1R)-1-cyclohexylethyl]-2-(2'-oxospiro[furo[2,3-f][1,3]benzodioxole-7,3'-indol]-1'(2'H)-yl)acetamide | 449.2 |
| 97 | N-[(1S)-1-cyclohexylethyl]-2-(2'-oxospiro[furo[2,3-f][1,3]benzodioxole-7,3'-indol]-1'(2'H)-yl)acetamide | 449.2 |
| 98 | 2-(2'-oxospiro[furo[2,3-f][1,3]benzodioxole-7,3'-indol]-1'(2'H)-yl)-N-(2-piperidin-1-ylethyl)acetamide | 451.4 |
| 99 | 2-(2'-oxospiro[furo[2,3-f][1,3]benzodioxole-7,3'-indol]-1'(2'H)-yl)-N-[3-(trifluoromethyl)phenyl]acetamide | 483.1 |
| 100 | N-(3-cyanophenyl)-2-(2'-oxospiro[furo[2,3-f][1,3]benzodioxole-7,3'-indol]-1'(2'H)-yl)acetamide | 440.1 |
| 101 | 1'-(2-morpholin-4-yl-2-oxoethyl)spiro[furo[2,3-f][1,3]benzodioxole-7,3'-indol]-2'(1'H)-one | 409.1 |
| 102 | 2-(2'-oxospiro[furo[2,3-f][1,3]benzodioxole-7,3'-indol]-1'(2'H)-yl)-N-(2-phenylethyl)acetamide | 443.1 |
| 103 | N-(4-bromo-2-chlorophenyl)-2-(2'-oxospiro[furo[2,3-f][1,3]benzodioxole-7,3'-indol]-1'(2'H)-yl)acetamide | 527.0 |
| 104 | N-(2-biphenyl-4-ylethyl)-2-(2'-oxospiro[furo[2,3-f][1,3]benzodioxole-7,3'-indol]-1'(2'H)-yl)acetamide | 519.2 |

EXAMPLE 3.2

Synthesis of N-(2-fluorophenyl)-2-(2'-oxo-6,7-dihydro-5H-spiro[indeno[5,6-b]furan-3,3'-indol]-1'(2'H)-yl)acetamide

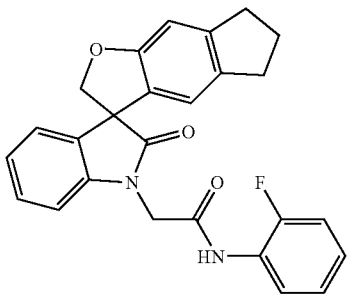

To a solution of 2'-oxo-6,7-dihydro-5H-spiro[indeno[5,6-b]furan-3,3'-indol]-1'(2'H)-yl)acetic acid (0.18 g, 0.54 mmol) in chloroform (5.00 mL) was added oxalyl chloride (0.09 mL, 1.07 mmol) with one drop of DMF. The mixture was refluxed for 2 hours, and evaporated under reduced vacuum to dryness. To the above residue were added Et$_3$N (0.66 mL, 4.72 mmol), 2-fluoroaniline (0.10 mL, 1.00 mmol) and THF (5.00 mL). The reaction mixture was stirred at ambient temperature overnight, evaporated to dryness. The residue was subjected to column chromatography (25% ethyl acetate in hexane) to yield the title compound (0.04 g, 17%): $^1$H NMR (300 MHz, CDCl$_3$) δ 8.26 (t, 1H), 8.05-7.90 (br, 1H), 7.33 (td, 1H), 7.26-6.96 (m, 6H), 6.83 (s, 1H), 6.61 (s, 1H), 4.98 (d, 1H), 4.73 (d, 1H), 4.71 (d, 1H), 4.52 (d, 1H), 2.85 (t, 2H), 2.69 (t, 2H), 2.12-1.94 (m, 2H); $^{13}$C NMR (75 MHz, CDCl$_3$) δ 178.6, 165.0, 159.8, 146.9, 141.5, 137.5, 132.5, 129.2, 126.3, 125.2, 124.8, 124.4, 124.3, 121.9, 118.9, 115.2, 114.9, 109.0, 106.8, 79.9, 58.2, 45.3, 33.2, 32.0, 26.1; MS (ES+) m/z 429 (M+1), 451 (M+23).

EXAMPLE 3.3

Synthesis of N-(2-fluorophenyl)-2-(2-oxo-5',6',7',8'-tetrahydrospiro[indole-3,3'-naphtho[2,3-b]furan]-1(2H)-yl)acetamide

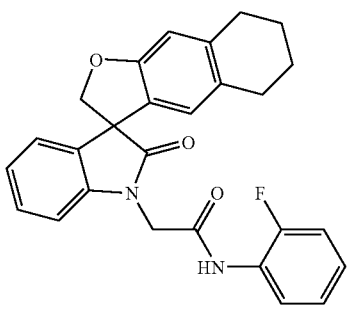

Following the procedure as described in EXAMPLE 3.2, and making non-critical variations using (2-oxo-5',6',7',8'-tetrahydrospiro[indole-3,3'-naphtho[2,3-b]furan]-1(2H)-yl) acetic acid to replace 2'-oxo-6,7-dihydro-5H-spiro[indeno[5,6-b]furan-3,3'-indol]-1'(2'H)-yl)acetic acid, the title compound was obtained in 5% yield: $^1$H NMR (300 MHz, CDCl$_3$) δ 8.27 (t, 1H), 8.04-7.90 (br, 1H), 7.33 (td, 1H), 7.26-6.97 (m, 6H), 6.69 (s, 1H), 6.48 (s, 1H), 4.94 (d, 1H), 4.69 (d, 1H), 4.71 (d, 1H), 4.52 (d, 1H), 2.81-2.45 (m, 4H), 1.82-1.60 (m, 4H); MS (ES+) m/z 443 (M+1), 465 (M+23).

EXAMPLE 3.4

Synthesis of 2-(4'-bromo-5,6-difluoro-2'-oxospiro[1-benzofuran-3,3'-indol]-1'(2'H)-yl)-N-(2-fluorophenyl)acetamide

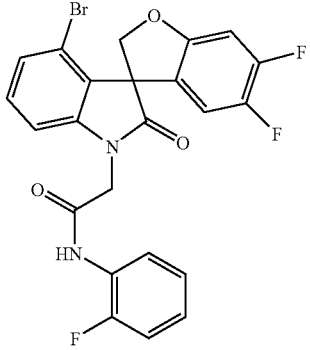

A. Synthesis of (4'-bromo-5,6-difluoro-2'-oxospiro [1-benzofuran-3,3'-indol]-1'(2' H)-yl)acetic acid Following the procedure as described in EXAMPLE 2, and making non-critical variations using ethyl (4'-bromo-5,6-difluoro-2'-oxospiro[1-benzofuran-3,3'-indol]-1'(2' H)-yl)acetate to replace ethyl (2'-oxospiro[furo[2,3-f][1,3]benzodioxole-7,3'-indol]-1'(2'H)-yl)acetate, the title compound was obtained in 100% yield. The product was used directly in the next step.

B. Synthesis of 2-(4'-bromo-5,6-difluoro-2'-oxospiro [1-benzofuran-3,3'-indol]-1'(2' H)-yl)-N-(2-fluorophenyl)acetamide To a solution of (4'-bromo-5,6-difluoro-2'-oxospiro[1-benzofuran-3,3'-indol]-1'(2'H)-yl)acetic acid (0.24 g, 0.59 mmol) and oxalyl chloride (0.15 mL, 1.76 mmol) in toluene (7.00 mL) was added one drop of DMF and the resulted mixture was stirred at ambient temperature overnight. The mixture was concentrated under vacuum. The residue was dissolved in dichloromethane (5.00 mL) and 2-fluoroaniline (0.18 mL, 1.89 mmol) was added at ambient temperature. The mixture was stirred at ambient temperature for one hour. More dichloromethane (100 mL) was added. The organic layer was washed with water, dried over anhydrous sodium sulfate and filtered. The filtrate was concentrated in vacuo. The residue was subjected to column chromatography (ethyl acetate/hexane, 1/5) to give the title compound (0.23 g, 76%): $^1$H NMR (300 MHz, CDCl$_3$) δ 8.20 (t, 1H), 7.80 (br, 1H), 7.27-7.17 (m, 2H), 7.16-7.03 (m, 3H), 6.97-6.88 (m, 1H), 6.78-6.60 (m, 2H), 5.08 (d, 1H), 4.93 (d, 1H), 4.68 (d, 1H), 4.49 (d, 1H); $^{13}$C NMR (75 MHz, CDCl$_3$) δ 177.1, 163.9, 157.8, 143.6, 131.0, 128.8, 128.1, 124.7, 121.8, 120.0, 115.0, 111.6, 108.1, 99.8, 77.5, 59.2, 44.7; MS (ES+) m/z 503.4 (M+1), 505.4 (M+1).

EXAMPLE 3.5

Synthesis of 2-(4'-bromo-6,6-dimethyl-2'-oxo-5,6-dihydrospiro[benzo[1,2-b:5,4-b']difuran-3,3'-indol]-1'(2'H)-yl)-N-(2-fluorophenyl)acetamide

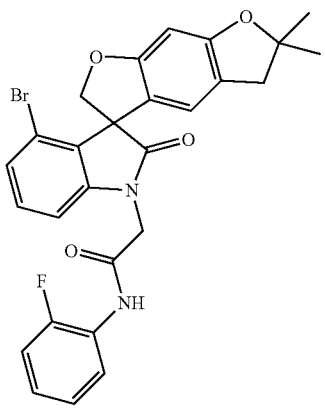

A. Synthesis of (4'-bromo-6,6-dimethyl-2'-oxo-5,6-dihydrospiro[benzo[1,2-b:5,4-b']difuran-3,3'-indol]-1'(2'H)-yl)acetic acid Following the procedure as described in EXAMPLE 2, and making non-critical variations using ethyl (4'-bromo-6,6-dimethyl-2'-oxo-5,6-dihydrospiro[benzo[1,2-b:5,4-b']difuran-3,3'-indol]-1'(2'H)-yl)acetate to replace ethyl (2'-oxospiro[furo[2,3-f][1,3]benzodioxole-7,3'-indol]-1'(2'H)-yl)acetate, the title compound was obtained. The product was used directly in the next step.

B. Synthesis of 2-(4'-bromo-6,6-dimethyl-2'-oxo-5,6-dihydrospiro[benzo[1,2-b:5,4-b']difuran-3,3'-indol]-1'(2'H)-yl)-N-(2-fluorophenyl)acetamide Following the procedure as described in EXAMPLE 3.4B, and making non-critical variations using (4'-bromo-6,6-dimethyl-2'-oxo-5,6-dihydrospiro[benzo[1,2-b:5,4-b']difuran-3,3'-indol]-1'(2'H)-yl)acetic acid to replace (4'-bromo-5,6-difluoro-2'-oxospiro[1-benzofuran-3,3'-indol]-1'(2' H)-yl)acetic acid, the title compound was obtained (61% for two steps): MS (ES+) m/z 537.4 (M+1), 539.4 (M+1).

EXAMPLE 3.6

Synthesis of 2-(4'-chloro-2'-oxo-5,6-dihydrospiro[benzo[1,2-b:5,4-b']difuran-3,3'-indol]-1'(2'H)-yl)-N-(2-fluorophenyl)acetamide

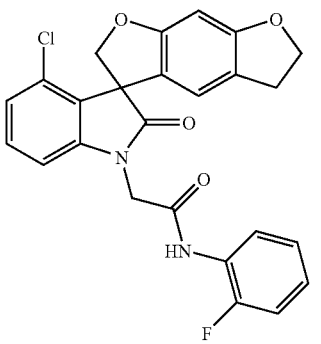

Following the procedure as described in EXAMPLE 3.4B, and making non-critical variations using (4'-chloro-2'-oxo-5,6-dihydrospiro[benzo[1,2-b:5,4-b']difuran-3,3'-indol]-1'(2'H)-yl)acetic acid to replace (4'-bromo-5,6-difluoro-2'-oxospiro[1-benzofuran-3,3'-indol]-1'(2' H)-yl)acetic acid, the title compound was obtained (69%) as a colorless solid: mp 243-245° C.; $^1$H NMR (300 MHz, CDCl$_3$) δ 8.19 (t, 1H), 7.96 (s, 1H), 7.21-7.27 (m, 1H), 7.10-7.02 (m, 4H), 6.88 (d, 1H), 6.55 (s, 1H), 6.35 (s, 1H), 4.96 (dd, 2H), 4.70 (d, 1H), 4.57-4.53 (m, 3H), 2.97 (t, 2H); $^{13}$C NMR (75 MHz, CDCl$_3$) δ 178.2, 164.4, 162.2, 162.1, 143.2, 131.6, 130.2, 128.5, 125.2, 125.1, 124.9, 124.6, 121.9, 119.7, 118.6, 116.8, 115.1, 114.8, 107.3, 92.9, 77.2, 72.4, 58.2, 44.9, 28.9; MS (ES+) m/z 465.5 (M+1).

EXAMPLE 3.7

Synthesis of 2-(5'-chloro-2'-oxo-5,6-dihydrospiro[benzo[1,2-b:5,4-b']difuran-3,3'-indol]-1'(2'H)-yl)-N-(2-fluorophenyl)acetamide

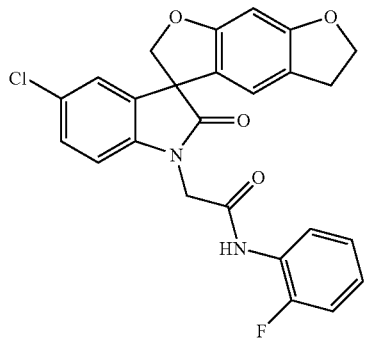

Following the procedure as described in EXAMPLE 3.4B, and making non-critical variations using (5'-chloro-2'-oxo-5,6-dihydrospiro[benzo[1,2-b:5,4-b']difuran-3,3'-indol]-1'(2'H)-yl)acetic acid to replace (4'-bromo-5,6-difluoro-2'-oxospiro[1-benzofuran-3,3'-indol]-1'(2' H)-yl)acetic acid, the title compound was obtained (91%) as a colorless solid: mp 229-230° C.; $^1$H NMR (300 MHz, CDCl$_3$) δ 8.21 (t, 1H), 7.88 (s, 1H), 7.28-7.25 (m, 1H), 7.18 (d, 1H), 7.13-7.04 (m, 3H), 6.90 (d, 1H), 6.57 (s, 1H), 6.40 (s, 1H), 4.95 (d, 1H), 4.70-4.66 (m, 2H), 4.56-4.43 (m, 3H), 2.99 (t, 2H); $^{13}$CNMR (75 MHz, CDCl$_3$) δ 177.8, 170.9, 162.1, 162.1, 143.1, 131.7, 130.0, 128.6, 124.7, 119.6, 118.7, 117.0, 106.7, 92.8, 77.2, 72.3, 58.1, 41.2, 28.9; MS (ES+) m/z 465.4 (M+1).

EXAMPLE 3.8

Synthesis of 2-(6-chloro-2'-oxospiro[1-benzofuran-3,3'-indol]-1'(2'H)-yl)-N-(2-fluorophenyl)acetamide

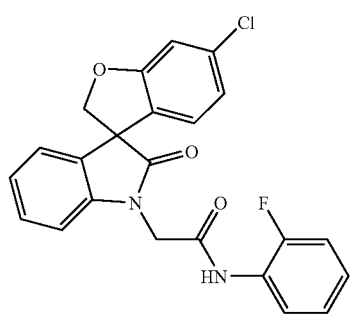

Following the procedure as described in EXAMPLE 3.4B, and making non-critical variations using (6-chloro-2'-oxospiro[1-benzofuran-3,3'-indol]-1'(2'H)-yl)acetic acid to replace (4'-bromo-5,6-difluoro-2'-oxospiro[1-benzofuran-3,3'-indol]-1'(2' H)-yl)acetic acid, the title compound was obtained (10%) as a white solid: mp 70-75° C.; $^1$H NMR (300 MHz, CDCl$_3$) δ 8.21 (t, 1H), 7.99 (br, 1H), 7.32 (dt, 1H), 7.19-6.93 (m, 7H), 6.80 (dd, 1H), 6.73 (d, 1H), 5.01 (d, 1H), 4.75 (d, 1H), 4.69 (d, 1H), 4.50 (d, 1H); $^{13}$C NMR (75 MHz, CDCl$_3$) δ 177.7, 164.6, 161.4, 141.4, 135.5, 131.6, 129.4, 127.3, 125.2, 125.0, 124.7, 124.6, 124.4, 124.3, 124.1, 121.9, 121.8, 115.1, 114.8, 111.3, 109.0, 80.3, 57.6, 44.9; MS (ES+) m/z 423.4 (M+1).

EXAMPLE 3.9

Synthesis of 2-(5,6-difluoro-2'-oxospiro[1-benzofuran-3,3'-indol]-1'(2'H)-yl)-N-(2-fluorophenyl)acetamide

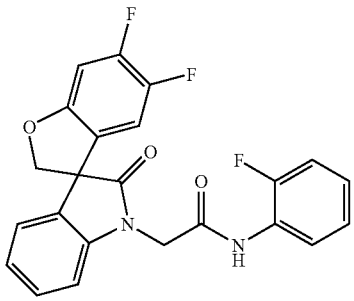

Following the procedure as described in EXAMPLE 3.4B, and making non-critical variations using (5,6-difluoro-2'-oxospiro[1-benzofuran-3,3'-indol]-1'(2'H)-yl)acetic acid to replace (4'-bromo-5,6-difluoro-2'-oxospiro[1-benzofuran-3,3'-indol]-1'(2'H)-yl)acetic acid, the title compound was obtained (35%) as a white solid: mp 97-100° C.; $^1$H NMR (300 MHz, CDCl$_3$) δ 8.20-8.10 (m, 2H), 7.31 (dt, 1H), 7.19-7.00 (m, 5H), 6.95 (d, 1H), 6.77-6.40 (m, 2H), 5.02 (d, 1H), 4.74 (d, 1H), 4.69 (d, 1H), 4.51 (d, 1H); $^{13}$C NMR (75 MHz, CDCl$_3$) δ 177.4, 164.3, 141.4, 131.2, 129.7, 125.6, 125.5, 125.3, 125.2, 125.1, 124.7, 124.4, 124.1, 121.8, 115.1, 114.9, 112.1, 111.8, 109.1, 100.3, 100.0, 80.7, 57.9; MS (ES+) m/z 425.5 (M+1).

EXAMPLE 3.10

Synthesis of 2-(5-bromo-2'-oxospiro[1-benzofuran-3,3'-indol]-1'(2'H)-yl)-N-(2-fluorophenyl)acetamide

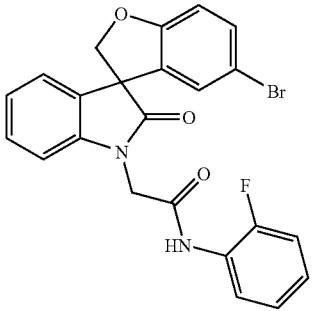

Following the procedure as described in EXAMPLE 3.4B, and making non-critical variations using (5-bromo-2'-oxospiro[1-benzofuran-3,3'-indol]-1'(2'H)-yl)acetic acid to replace (4'-bromo-5,6-difluoro-2'-oxospiro[1-benzofuran-3,3'-indol]-1'(2'H)-yl)acetic acid, the title compound was obtained (94%) as a light yellow solid: mp 100-103° C.; $^1$H NMR (300 MHz, CDCl$_3$) δ 8.26 (dd, 1H), 7.92 (br, 1H), 7.39-7.31 (m, 2H), 7.22-7.01 (m, 6H), 6.91 (d, 1H), 6.87 (d, 1H), 5.02 (d, 1H), 4.76 (d, 1H), 4.67 (d, 1H), 4.57 (d, 1H); MS (ES+) m/z 467.3 (M+1).

EXAMPLE 3.11

Synthesis of 2-(4'-fluoro-2'-oxo-5,6-dihydrospiro[benzo[1,2-b:5,4-b]difuran-3,3'-indol]-1'(2'H)-yl)-N-(2-fluorophenyl)acetamide

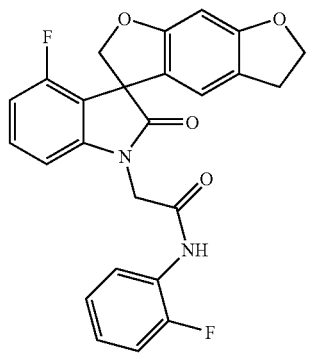

Following the procedure as described in EXAMPLE 3.4B, and making non-critical variations using (4'-fluoro-2'-oxo-5,6-dihydrospiro[benzo[1,2-b:5,4-b]difuran-3,3'-indol]-1'(2'H)-yl)acetic acid to replace (4'-bromo-5,6-difluoro-Z-oxospiro[1-benzofuran-3,3'-indol]-1(2'H)-yl)acetic acid, the title compound was obtained: $^1$H NMR (300 MHz, CDCl$_3$) δ 8.20 (t, 1H), 7.91 (s, 1H), 7.29 (dt, 1H), 7.13-7.04 (m, 3H), 6.81-6.75 (m, 2H), 6.61 (s, 1H), 6.39 (s, 1H), 4.95-4.87 (m, 2H), 4.70 (d, 1H), 4.55-4.44 (m, 3H), 2.98 (t, 2H); MS (ES+) m/z 449.5 (M+1)

EXAMPLE 3.12

Synthesis of 2-(4'-bromo-2'-oxo-5,6-dihydrospiro[benzo[1,2-b:5,4-b]difuran-3,3'-indol]-1'(2'H)-yl)-N-(2-fluorophenyl)acetamide

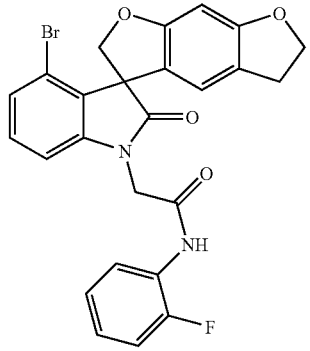

Following the procedure as described in EXAMPLE 3.4B, and making non-critical variations using (4'-bromo-2'-oxo-5,6-dihydrospiro[benzo[1,2-b:5,4-b]difuran-3,3'-indol]-1'(2'H)-yl)acetic acid to replace (4'-bromo-5,6-difluoro-2'-oxospiro[1-benzofuran-3,3'-indol]-1'(2'H)-yl)acetic acid, the title compound was obtained (75%) as a colorless solid: mp 245-246° C.; $^1$H NMR (300 MHz, CDCl$_3$) δ 8.20 (t, 1H), 7.90 (s, 1H), 7.20-7.03 (m, 5H), 6.92 (dd, 1H), 6.53 (s, 1H), 6.36 (s, 1H), 5.05 (d, 1H), 4.90 (d, 1H), 4.69 (d, 1H), 4.55-4.43 (m, 3H), 2.97 (t, 2H); $^{13}$C NMR (75 MHz, CDCl$_3$) δ 178.3, 164.3, 162.4, 162.2, 143.4, 130.4, 130.0, 128.0, 125.5, 125.2, 124.7, 121.9, 120.0, 119.7, 118.6, 116.7, 115.1, 114.8, 107.8, 92.8, 77.2, 72.4, 59.1, 44.9, 28.9; MS (ES+) m/z 509 (M+1), 511 (M+1).

EXAMPLE 3.13

Synthesis of N-(2-fluorophenyl)-2-(2'-oxo-5,6-dihydrospiro[benzo[1,2-b:5,4-b']difuran-3,3'-indol]-1'(2'H)-yl)acetamide

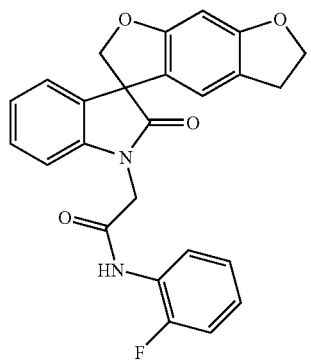

Following the procedure as described in EXAMPLE 3.4B, and making non-critical variations using (2'-oxo-5,6-dihydrospiro[benzo[1,2-b:5,4-b']difuran-3,3'-indol]-1'(2'H)-yl) acetic acid to replace (4'-bromo-5,6-difluoro-2'-oxospiro[1-benzofuran-3,3'-indol]-1(2'H)-yl)acetic acid, the title compound was obtained (68%) as a white solid: mp 210-212° C.; $^1$H NMR (300 MHz, DMSO-d$_6$) δ 10.18 (s, 1H), 8.17-7.67 (m, 1H), 7.55-6.90 (m, 7H), 6.54 (s, 1H), 6.38 (s, 1H), 4.68 (m, 4H), 4.46 (t, 2H), 2.93 (t, 2H); MS (ES+) m/z 431.4 (M+1).

EXAMPLE 3.14

Synthesis of 2-(4'-fluoro-7'-methyl-2'-oxo-5,6-dihydrospiro[benzo[1,2-b:5,4-b']difuran-3,3'-indol]-1'(2'H)-yl)-N-(2-fluorophenyl)acetamide

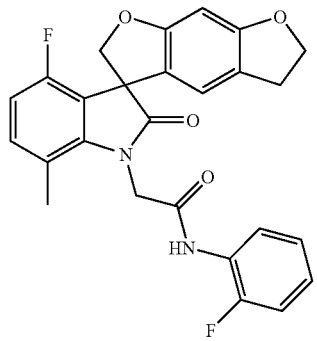

Following the procedure as described in EXAMPLE 3.4B and making non-critical variations using (4'-fluoro-7'-methyl-2'-oxo-5,6-dihydrospiro[benzo[1,2-b:5,4-b']difuran-3,3'-indol]-1'(2'H)-yl)acetic acid to replace (4'-bromo-5,6-difluoro-2'-oxospiro[1-benzofuran-3,3'-indol]-1'(2'H)-yl)acetic acid, the title compound was obtained (21%) as a white solid: mp 250-255° C.; $^1$H NMR (300 MHz, DMSO-d$_6$) δ 10.23 (s, 1H), 7.99-7.69 (m, 1H), 7.36-7.01 (m, 4H), 6.74 (t, 1H), 6.63 (s, 1H), 6.42 (s, 1H), 5.90 (d, 2H), 4.88 (t, 2H), 4.76 (ABq, 2H), 3.30 (s, 3H); MS (ES+) m/z 463.4 (M+1).

EXAMPLE 4

Synthesis of 4'-[6-(dimethylamino)pyridin-3-yl]-1'-pentylspiro[furo[2,3-f][1,3]benzodioxole-7,3'-indol]-2'(1'H)-one

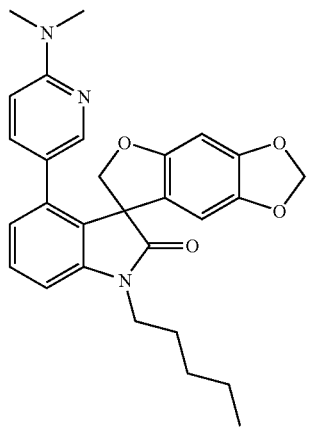

To an oven-dried flask was charged with [6-(dimethylamino)pyridin-3-yl]boronic acid (37.0 mg, 0.17 mmol), Pd(PPh$_3$)$_4$ (13.5 mg, 0.012 mmol) followed by flashing with nitrogen. To the flask was added a solution of 4'-bromo-1'-pentylspiro[furo[2,3-f][1,3]benzodioxole-7,3'-indol]-2'(1'H)-one (50.0 mg, 0.12 mmol) in anhydrous dioxane (2.00 mL) followed by the addition of 2.0 M Na$_2$CO$_3$ (0.24 mL). The reaction mixture was heated at reflux for 48 h. After cooling down to ambient temperature, the solvent was removed under reduced pressure. The residue was diluted with ethyl acetate (2.00 mL), washed with saturated ammonium chloride (2.00 mL), and concentrated in vacuo to dryness. The residue was subjected to column chromatography to yield the title compounds: $^1$H NMR (300 MHz, CDCl$_3$) δ 7.77 (d, 1H), 7.32 (t, 1H), 6.87 (dd, 2H), 6.71 (dd, 1H), 6.23 (d, 1H), 6.20 (s, 1H), 5.88 (d, 2H), 4.56 (ABq, 2H), 3.89-3.80 (m, 1H), 3.69-3.59 (m, 1H), 3.05 (s, 6H), 1.78-1.69 (m, 2H), 1.39-1.35 (m, 4H), 0.90 (t, 3H); $^{13}$C NMR (75 MHz, CDCl$_3$) δ 177.9, 158.3, 156.1, 148.8, 147.3, 142.9, 142.0, 137.8, 137.2, 129.9, 128.9, 125.6, 122.0, 121.0, 107.6, 104.3, 102.5, 101.5, 93.6, 77.8, 58.5, 40.5, 38.2, 29.1, 27.2, 22.4, 14.0; MS (ES+, m/z) 472.0 (M+1).

EXAMPLE 4.1

The compounds listed in the following table were synthesized using similar conditions as described in EXAMPLE 4. As previously noted, the compound numbers listed below do not correspond to the compound numbers provided in the general Reaction Schemes above.

| Compound Number | Name | MS (m/z, M + 1) |
|---|---|---|
| 105 | 4'-(3,5-dimethoxyphenyl)-1'-pentylspiro[furo[2,3-f][1,3]benzodioxole-7,3'-indol]-2'(1'H)-one | 488.4 |
| 106 | 4'-(4-fluorophenyl)-1'-pentylspiro[furo[2,3-f][1,3]benzodioxole-7,3'-indol]-2'(1'H)-one | 447.3 |
| 107 | 4'-(3,5-dichlorophenyl)-1'-pentylspiro[furo[2,3-f][1,3]benzodioxole-7,3'-indol]-2'(1'H)-one | 496.3 |
| 108 | 4'-[4-(dimethylamino)phenyl]-1'-pentylspiro[furo[2,3-f][1,3]benzodioxole-7,3'-indol]-2'(1'H)-one | 471.3 |
| 109 | 1'-pentyl-4'-(3,4,5-trimethoxyphenyl)spiro[furo[2,3-f][1,3]benzodioxole-7,3'-indol]-2'(1'H)-one | 518.3 |
| 110 | 4-(2'-oxo-1'-pentyl-1',2'-dihydrospiro[furo[2,3-f][1,3]benzodioxole-7,3'-indol]-4'-yl)benzonitrile | 453.3 |
| 111 | 4'-dibenzo[b,d]furan-4-yl-1'-pentylspiro[furo[2,3-f][1,3]benzodioxole-7,3'-indol]-2'(1'H)-one | 518.3 |
| 112 | 4'-(1-benzyl-1H-pyrazol-4-yl)-1'-pentylspiro[furo[2,3-f][1,3]benzodioxole-7,3'-indol]-2'(1'H)-one | 508.4 |
| 113 | 4'-(2-methoxypyrimidin-5-yl)-1'-pentylspiro[furo[2,3-f][1,3]benzodioxole-7,3'-indol]-2'(1'H)-one | 460.3 |
| 114 | 4'-(2,4-dimethoxypyrimidin-5-yl)-1'-pentylspiro[furo[2,3-f][1,3]benzodioxole-7,3'-indol]-2'(1'H)-one | 490.4 |
| 115 | 4-(2'-oxo-1'-pentyl-1',2'-dihydrospiro[furo[2,3-f][1,3]benzodioxole-7,3'-indol]-4'-yl)benzamide | 471.3 |
| 116 | 4'-{4-[(dimethylamino)methyl]phenyl}-1'-pentylspiro[furo[2,3-f][1,3]benzodioxole-7,3'-indol]-2'(1'H)-one | 484.6 |
| 117 | 4'-(1-benzofuran-2-yl)-1'-pentylspiro[furo[2,3-f][1,3]benzodioxole-7,3'-indol]-2'(1'H)-one | 467.5 |
| 118 | 4'-(6-methoxypyridin-3-yl)-1'-pentylspiro[furo[2,3-f][1,3]benzodioxole-7,3'-indol]-2'(1'H)-one | 458.5 |
| 119 | N,N-dimethyl-4-(2'-oxo-1'-pentyl-1',2'-dihydrospiro[furo[2,3-f][1,3]benzodioxole-7,3'-indol]-4'-yl)benzamide | 498.6 |
| 120 | 4'-dibenzo[b,d]thien-4-yl-1'-pentylspiro[furo[2,3-f][1,3]benzodioxole-7,3'-indol]-2'(1'H)-one | 533.6 |
| 121 | 3-(2'-oxo-1'-pentyl-1',2'-dihydrospiro[furo[2,3-f][1,3]benzodioxole-7,3'-indol]-4'-yl)benzonitrile | 452.5 |
| 122 | 1'-pentyl-4'-pyridin-3-ylspiro[furo[2,3-f][1,3]benzodioxole-7,3'-indol]-2'(1'H)-one | 428.5 |
| 123 | 4'-(3-fluoro-4-methoxyphenyl)-1'-pentylspiro[furo[2,3-f][1,3]benzodioxole-7,3'-indol]-2'(1'H)-one | 475.5 |
| 124 | 1'-pentyl-4'-[2-(trifluoromethoxy)phenyl]spiro[furo[2,3-f][1,3]benzodioxole-7,3'-indol]-2'(1'H)-one | 511.5 |
| 125 | 4'-[3,5-bis(trifluoromethyl)phenyl]-1'-pentylspiro[furo[2,3-f][1,3]benzodioxole-7,3'-indol]-2'(1'H)-one | 563.5 |
| 126 | 1'-pentyl-4'-[4-(trifluoromethyl)pyridin-3-yl]spiro[furo[2,3-f][1,3]benzodioxole-7,3'-indol]-2'(1'H)-one | 496.5 |
| 127 | 4'-(2-fluoro-5-methoxyphenyl)-1'-pentylspiro[furo[2,3-f][1,3]benzodioxole-7,3'-indol]-2'(1'H)-one | 475.5 |
| 128 | 4'-(4-ethoxy-3-fluorophenyl)-1'-pentylspiro[furo[2,3-f][1,3]benzodioxole-7,3'-indol]-2'(1'H)-one | 489.5 |
| 129 | 4'-(1-benzothien-2-yl)-1'-pentylspiro[furo[2,3-f][1,3]benzodioxole-7,3'-indol]-2'(1'H)-one | 483.6 |
| 130 | 4'-isobutyl-1'-pentylspiro[furo[2,3-f][1,3]benzodioxole-7,3'-indol]-2'(1'H)-one | 407.5 |
| 131 | 1'-pentyl-4'-[4-(trifluoromethoxy)phenyl]spiro[furo[2,3-f][1,3]benzodioxole-7,3'-indol]-2'(1'H)-one | 511.5 |
| 132 | 4'-(5-fluoro-2-methoxyphenyl)-1'-pentylspiro[furo[2,3-f][1,3]benzodioxole-7,3'-indol]-2'(1'H)-one | 475.5 |
| 133 | 4'-(1,3-benzodioxol-5-yl)-1'-pentylspiro[furo[2,3-f][1,3]benzodioxole-7,3'-indol]-2'(1'H)-one | 471.5 |
| 134 | 1'-pentyl-4'-phenylspiro[furo[2,3-f][1,3]benzodioxole-7,3'-indol]-2'(1'H)-one | 427.5 |
| 135 | 1'-pentyl-4'-[2-(trifluoromethyl)phenyl]spiro[furo[2,3-f][1,3]benzodioxole-7,3'-indol]-2'(1'H)-one | 495.5 |
| 136 | 4'-(4-chlorophenyl)-1'-pentylspiro[furo[2,3-f][1,3]benzodioxole-7,3'-indol]-2'(1'H)-one | 461.9 |
| 137 | 4'-(2,3-dihydro-1,4-benzodioxin-6-yl)-1'-pentylspiro[furo[2,3-f][1,3]benzodioxole-7,3'-indol]-2'(1'H)-one | 485.5 |
| 138 | 1'-pentyl-4'-quinolin-3-ylspiro[furo[2,3-f][1,3]benzodioxole-7,3'-indol]-2'(1'H)-one | 478.5 |
| 139 | 4'-(3,5-difluorophenyl)-1'-pentylspiro[furo[2,3-f][1,3]benzodioxole-7,3'-indol]-2'(1'H)-one | 463.5 |

-continued

| Compound Number | Name | MS (m/z, M + 1) |
|---|---|---|
| 140 | 4'-isoquinolin-4-yl-1'-pentylspiro[furo[2,3-f][1,3]benzodioxole-7,3'-indol]-2'(1'H)-one | 478.5 |
| 141 | 4'-(6-methoxypyridin-2-yl)-1'-pentylspiro[furo[2,3-f][1,3]benzodioxole-7,3'-indol]-2'(1'H)-one | 458.5 |
| 142 | 4'-(1H-indol-5-yl)-1'-pentylspiro[furo[2,3-f][1,3]benzodioxole-7,3'-indol]-2'(1'H)-one | 466.5 |
| 143 | N-[2-(2'-oxo-1'-pentyl-1',2'-dihydrospiro[furo[2,3-f][1,3]benzodioxole-7,3'-indol]-4'-yl)phenyl]acetamide | 484.5 |
| 144 | 4'-(4-fluoro-2-methylphenyl)-1'-pentylspiro[furo[2,3-f][1,3]benzodioxole-7,3'-indol]-2'(1'H)-one | 459.5 |
| 145 | 1'-pentyl-4'-quinolin-6-ylspiro[furo[2,3-f][1,3]benzodioxole-7,3'-indol]-2'(1'H)-one | 478.5 |
| 146 | N-[4-(2'-oxo-1'-pentyl-1',2'-dihydrospiro[furo[2,3-f][1,3]benzodioxole-7,3'-indol]-4'-yl)phenyl]methanesulfonamide | 520.6 |
| 147 | 4'-(5-chloro-2-methoxyphenyl)-1'-pentylspiro[furo[2,3-f][1,3]benzodioxole-7,3'-indol]-2'(1'H)-one | 492.0 |
| 148 | 1'-pentyl-4'-[3-(trifluoromethoxy)phenyl]spiro[furo[2,3-f][1,3]benzodioxole-7,3'-indol]-2'(1'H)-one | 511.5 |
| 149 | 1'-pentyl-4'-(4-phenoxyphenyl)spiro[furo[2,3-f][1,3]benzodioxole-7,3'-indol]-2'(1'H)-one | 519.6 |
| 150 | 4'-(2,4-dimethoxyphenyl)-1'-pentylspiro[furo[2,3-f][1,3]benzodioxole-7,3'-indol]-2'(1'H)-one | 487.5 |
| 151 | 4'-(3-furyl)-1'-pentylspiro[furo[2,3-f][1,3]benzodioxole-7,3'-indol]-2'(1'H)-one | 417.5 |
| 152 | 4'-(3,4-dimethoxyphenyl)-1'-pentylspiro[furo[2,3-f][1,3]benzodioxole-7,3'-indol]-2'(1'H)-one | 487.5 |
| 153 | N-[4-(2'-oxo-1'-pentyl-1',2'-dihydrospiro[furo[2,3-f][1,3]benzodioxole-7,3'-indol]-4'-yl)phenyl]acetamide | 484.5 |
| 154 | 1'-pentyl-4'-[(E)-2-phenylvinyl]spiro[furo[2,3-f][1,3]benzodioxole-7,3'-indol]-2'(1'H)-one | 453.5 |
| 155 | 4'-(4-methoxyphenyl)-1'-pentylspiro[furo[2,3-f][1,3]benzodioxole-7,3'-indol]-2'(1'H)-one | 457.5 |
| 156 | 4'-(6-fluoropyridin-3-yl)-1'-pentylspiro[furo[2,3-f][1,3]benzodioxole-7,3'-indol]-2'(1'H)-one | 446.5 |
| 157 | 4'-(3-chloro-4-fluorophenyl)-1'-pentylspiro[furo[2,3-f][1,3]benzodioxole-7,3'-indol]-2'(1'H)-one | 479.9 |
| 158 | 4'-(3-chlorophenyl)-1'-pentylspiro[furo[2,3-f][1,3]benzodioxole-7,3'-indol]-2'(1'H)-one | 461.9 |
| 159 | 4'-(1-benzothien-3-yl)-1'-pentylspiro[furo[2,3-f][1,3]benzodioxole-7,3'-indol]-2'(1'H)-one | 483.6 |
| 160 | 1'-pentyl-4'-(2-phenoxyphenyl)spiro[furo[2,3-f][1,3]benzodioxole-7,3'-indol]-2'(1'H)-one | 519.6 |
| 161 | 4'-(4-isopropoxyphenyl)-1'-pentylspiro[furo[2,3-f][1,3]benzodioxole-7,3'-indol]-2'(1'H)-one | 485.6 |
| 162 | 4'-[(E)-2-(4-fluorophenyl)vinyl]-1'-pentylspiro[furo[2,3-f][1,3]benzodioxole-7,3'-indol]-2'(1'H)-one | 471.5 |
| 163 | 4'-(6-fluoropyridin-2-yl)-1'-pentylspiro[furo[2,3-f][1,3]benzodioxole-7,3'-indol]-2'(1'H)-one | 446.5 |
| 164 | 1'-pentyl-4'-[1-(phenylsulfonyl)-1H-indol-3-yl]spiro[furo[2,3-f][1,3]benzodioxole-7,3'-indol]-2'(1'H)-one | 606.7 |
| 165 | 4'-(3-fluorophenyl)-1'-pentylspiro[furo[2,3-f][1,3]benzodioxole-7,3'-indol]-2'(1'H)-one | 445.5 |
| 166 | 4'-(3-acetylphenyl)-1'-pentylspiro[furo[2,3-f][1,3]benzodioxole-7,3'-indol]-2'(1'H)-one | 469.5 |
| 167 | 4'-(2-furyl)-1'-pentylspiro[furo[2,3-f][1,3]benzodioxole-7,3'-indol]-2'(1'H)-one | 417.5 |
| 168 | 4'-(4-methylphenyl)-1'-pentylspiro[furo[2,3-f][1,3]benzodioxole-7,3'-indol]-2'(1'H)-one | 441.5 |
| 169 | 4'-(1-methyl-1H-pyrrol-3-yl)-1'-pentylspiro[furo[2,3-f][1,3]benzodioxole-7,3'-indol]-2'(1'H)-one | 430.5 |
| 170 | 4'-(2,5-difluorophenyl)-1'-pentylspiro[furo[2,3-f][1,3]benzodioxole-7,3'-indol]-2'(1'H)-one | 463.5 |
| 171 | 4'-(2-fluorophenyl)-1'-pentylspiro[furo[2,3-f][1,3]benzodioxole-7,3'-indol]-2'(1'H)-one | 445.5 |
| 172 | 4'-(2-chlorophenyl)-1'-pentylspiro[furo[2,3-f][1,3]benzodioxole-7,3'-indol]-2'(1'H)-one | 461.9 |
| 173 | 4'-(2,4-difluorophenyl)-1'-pentylspiro[furo[2,3-f][1,3]benzodioxole-7,3'-indol]-2'(1'H)-one | 463.5 |
| 174 | 4'-(4-morpholin-4-ylphenyl)-1'-pentylspiro[furo[2,3-f][1,3]benzodioxole-7,3'-indol]-2'(1'H)-one | 512.6 |
| 175 | tert-butyl 5-methoxy-3-(2'-oxo-1'-pentyl-1',2'-dihydrospiro[furo[2,3-f][1,3]benzodioxole-7,3'-indol]-4'-yl)-1H-indole-1-carboxylate | 596.7 |

-continued

| Compound Number | Name | MS (m/z, M + 1) |
|---|---|---|
| 176 | 1'-pentyl-4'-pyrimidin-5-ylspiro[furo[2,3-f][1,3]benzodioxole-7,3'-indol]-2'(1'H)-one | 429.5 |
| 177 | tert-butyl 4-[2-(2'-oxo-1'-pentyl-1',2'-dihydrospiro[furo[2,3-f][1,3]benzodioxole-7,3'-indol]-4'-yl)phenyl]piperazine-1-carboxylate | 611.7 |
| 178 | 4'-(2-methoxypyridin-3-yl)-1'-pentylspiro[furo[2,3-f][1,3]benzodioxole-7,3'-indol]-2'(1'H)-one | 458.5 |
| 179 | 4'-(5-methoxypyridin-3-yl)-1'-pentylspiro[furo[2,3-f][1,3]benzodioxole-7,3'-indol]-2'(1'H)-one | 458.5 |
| 180 | 4'-(4-butoxy-3-fluorophenyl)-1'-pentylspiro[furo[2,3-f][1,3]benzodioxole-7,3'-indol]-2'(1'H)-one | 517.6 |
| 181 | 1'-pentyl-4'-pyridin-4-ylspiro[furo[2,3-f][1,3]benzodioxole-7,3'-indol]-2'(1'H)-one | 428.5 |
| 182 | 1'-pentyl-4'-phenoxathiin-4-ylspiro[furo[2,3-f][1,3]benzodioxole-7,3'-indol]-2'(1'H)-one | 549.6 |
| 183 | 4'-[(1Z)-3-chloroprop-1-en-1-yl]-1'-pentylspiro[furo[2,3-f][1,3]benzodioxole-7,3'-indol]-2'(1'H)-one | 425.9 |
| 184 | 1'-pentyl-4'-(3-thienyl)spiro[furo[2,3-f][1,3]benzodioxole-7,3'-indol]-2'(1'H)-one | 433.5 |
| 185 | 4'-(2,3-dimethoxyphenyl)-1'-pentylspiro[furo[2,3-f][1,3]benzodioxole-7,3'-indol]-2'(1'H)-one | 487.5 |
| 186 | 4'-(4-butylphenyl)-1'-pentylspiro[furo[2,3-f][1,3]benzodioxole-7,3'-indol]-2'(1'H)-one | 483.6 |
| 187 | 4'-(3-fluoro-5-methoxyphenyl)-1'-pentylspiro[furo[2,3-f][1,3]benzodioxole-7,3'-indol]-2'(1'H)-one | 475.5 |
| 188 | 4'-[3-fluoro-4-(pentyloxy)phenyl]-1'-pentylspiro[furo[2,3-f][1,3]benzodioxole-7,3'-indol]-2'(1'H)-one | 531.6 |
| 189 | 4'-(2-butoxy-5-fluorophenyl)-1'-pentylspiro[furo[2,3-f][1,3]benzodioxole-7,3'-indol]-2'(1'H)-one | 517.6 |
| 190 | 4'-(3-butoxyphenyl)-1'-pentylspiro[furo[2,3-f][1,3]benzodioxole-7,3'-indol]-2'(1'H)-one | 499.6 |
| 191 | 4'-(4-butoxyphenyl)-1'-pentylspiro[furo[2,3-f][1,3]benzodioxole-7,3'-indol]-2'(1'H)-one | 499.6 |
| 192 | 4'-(4-isobutoxyphenyl)-1'-pentylspiro[furo[2,3-f][1,3]benzodioxole-7,3'-indol]-2'(1'H)-one | 499.6 |
| 193 | 4'-{2-chloro-4-[(3,5-dimethoxybenzyl)oxy]phenyl}-1'-pentylspiro[furo[2,3-f][1,3]benzodioxole-7,3'-indol]-2'(1'H)-one | 628.1 |
| 194 | 4'-[4-(benzyloxy)-3-chlorophenyl]-1'-pentylspiro[furo[2,3-f][1,3]benzodioxole-7,3'-indol]-2'(1'H)-one | 568.1 |
| 195 | 4'-(1-methyl-1H-indol-5-yl)-1'-pentylspiro[furo[2,3-f][1,3]benzodioxole-7,3'-indol]-2'(1'H)-one | 480.6 |
| 196 | 4'-(4-methoxypyridin-3-yl)-1'-pentylspiro[furo[2,3-f][1,3]benzodioxole-7,3'-indol]-2'(1'H)-one | 458.5 |
| 197 | 4'-[(6-methoxypyridin-3-yl)amino]-1'-pentylspiro[furo[2,3-f][1,3]benzodioxole-7,3'-indol]-2'(1'H)-one | 473.5 |

EXAMPLE 4.2

Synthesis of 2-(5,6-difluoro-2'-oxo-4'-pyrimidin-5-ylspiro[1-benzofuran-3,3'-indol]-1'(2'H)-yl)-N-(2-fluorophenyl)acetamide

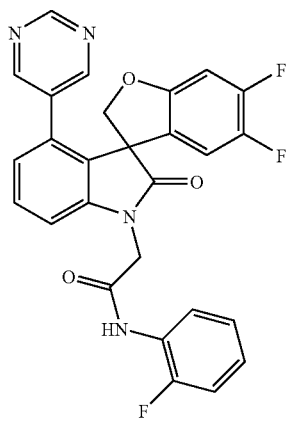

To a solution of 2-(4'-bromo-5,6-difluoro-2'-oxospiro[1-benzofuran-3,3'-indol]-1'(2'H)-yl)-N-(2-fluorophenyl)acetamide (0.15 g, 0.30 mmol) in anhydrous 1,4-dioxane (5.00 mL) was added Pd(PPh$_3$)$_4$ (0.03 g, 0.03 mmol) and stirred at ambient temperature for 10 min. Pyrimidine-5-boronic acid (0.06 g, 0.45 mmol) and sodium carbonate (0.90 mL of 2 M solution, 1.80 mmol) were added. The reaction mixture was reluxed at 120° C. for 16 h, diluted with ethyl acetate (50.0 mL). The organic layer was washed with water, dried over anhydrous sodium sulfate and filtered. The filtrate was concentrated in vacuo. The residue was subjected to column chromatography (ethyl acetate/hexane, 1/1) to give the title compound (0.13 g, 84%): $^1$H NMR (300 MHz, CDCl$_3$) δ 9.13 (s, 1H), 8.29-8.10 (m, 3H), 7.62 (s, 1H), 7.44 (t, 1H), 7.16-7.03 (m, 4H), 6.91 (d, 1H), 6.85-6.76 (m, 1H), 6.46-6.37 (m, 1H), 4.85-4.73 (m, 2H), 4.61-4.47 (m, 2H); $^{13}$C NMR (75 MHz, CDCl$_3$) δ 177.1, 163.9, 157.7, 156.4, 155.7, 141.9, 132.9, 130.0, 126.0, 124.7, 121.9, 115.0, 111.6, 109.8, 100.2, 79.4, 57.9, 44.7; MS (ES+) m/z 503.5 (M+1).

EXAMPLE 4.3

Synthesis of 2-(6,6-dimethyl-2'-oxo-4'-pyrimidin-5-yl-5,6-dihydrospiro[benzo[1,2-b:5,4-b']difuran-3,3'-indol]-1'(2'H)-yl)-N-(2-fluorophenyl)acetamide

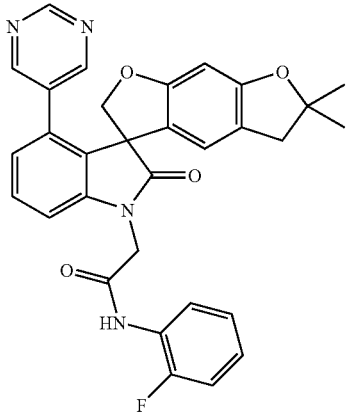

Following the procedure as described in EXAMPLE 4.2, making variation using 2-(4'-bromo-6,6-dimethyl-2'-oxo-5,6-dihydrospiro[benzo[1,2-b:5,4-b']difuran-3,3'-indol]-1'(2'H)-yl)-N-(2-fluorophenyl)acetamide to replace 2-(4'-bromo-5,6-difluoro-2'-oxospiro[1-benzofuran-3,3'-indol]-1'(2'H)-yl)-N-(2-fluorophenyl)acetamide, the title compound was obtained (95%): mp>250° C.; $^1$H NMR (300 MHz, CDCl$_3$) δ 9.10 (s, 1H), 8.24 (t, 1H), 8.15 (s, 2H), 8.00 (s, 1H), 7.40 (t, 1H), 7.16-7.03 (m, 4H), 6.88 (d, 1H), 6.61 (s, 1H), 5.99 (s, 1H), 4.84-4.73 (m, 2H), 4.54 (d, 1H), 4.44 (d, 1H), 2.79 (s, 2H), 1.45 (s, 3H), 1.39 (s, 3H); $^{13}$C NMR (75 MHz, CDCl$_3$) δ 178.4, 164.5, 161.1, 157.4, 155.8, 154.1, 150.8, 141.7, 132.9, 132.2, 131.3, 129.4, 125.9, 125.5, 125.2, 124.7, 121.9, 120.8, 119.3, 118.8, 115.0, 109.5, 93.5, 88.5, 78.9, 58.0, 45.0, 42.0, 28.0, 27.9; MS (ES+) m/z 537.5 (M+1).

EXAMPLE 4.4

Synthesis of 4'-(3-furyl)spiro[furo[2,3-f][1,3]benzo-dioxole-7,3'-indol]-2'(1'H)-one

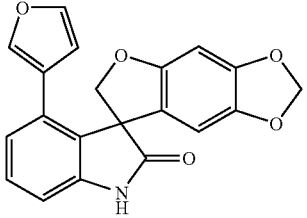

Following the procedure as described in EXAMPLE 4, making variations using 4'-bromospiro[furo[2,3-f][1,3]benzodioxole-7,3'-indol]-2'(1'H)-one to replace 4'-bromo-1'-pentylspiro[furo[2,3-f][1,3]benzodioxole-7,3'-indol]-2'(1'H)-one, and 3-furanboronic acid to replace [6-(dimethylamino)pyridin-3-yl]boronic acid, the title compound was obtained (66%) as a colorless solid: mp 270-272° C.; $^1$H NMR (300 MHz, CDCl$_3$) δ 7.32 (t, 1H), 7.25 (d, 2H), 6.97 (d, 1H), 6.91 (d, 1H), 6.83 (s, 1H), 6.44 (s, 1H), 6.30 (s, 1H), 6.04 (d, 1H), 5.89 (dd, 2H), 4.68 (ABq, 2H); $^{13}$C NMR (75 MHz, CDCl$_3$) δ 180.4, 156.2, 149.2, 142.9, 142.1, 141.2, 140.4, 131.3, 129.2, 128.5, 125.3, 122.6, 120.6, 111.0, 109.5, 102.9, 101.6, 94.0, 77.2, 59.0; MS (ES+) m/z 348.4 (M+1).

EXAMPLE 4.5

Synthesis of 4'-dibenzo[b,d]furan-4-ylspiro[furo[2,3-f][1,3]benzodioxole-7,3'-indol]-2'(1'H)-one

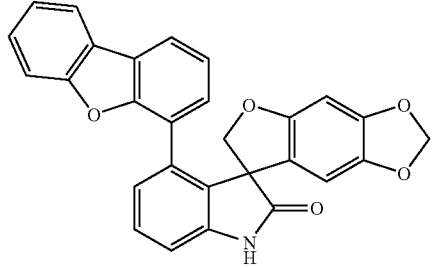

Following the procedure as described in EXAMPLE 4, and making non-critical variations using 4'-bromospiro[furo[2,3-f][1,3]benzodioxole-7,3'-indol]-2'(1'H)-one to replace 4'-bromo-1'-pentylspiro[furo[2,3-f][1,3]benzodioxole-7,3'-indol]-2'(1'H)-one, and dibenzo[b,d]furan-4-ylboronic acid to replace [6-(dimethylamino)pyridin-3-yl]boronic acid, the title compound was obtained (10%) as a colorless solid: mp>230° C.; $^1$H NMR (300 MHz, DMSO-d$_6$) δ 10.77 (s, 1H), 8.04 (d, 1H), 7.97 (dd, 1H), 7.43-7.42 (m, 3H), 7.34-7.29 (m, 3H), 7.16 (t, 1H), 6.98 (d, 1H), 6.89 (d, 1H), 6.25 (s, 1H), 5.69 (d, 2H), 4.41 (ABq, 2H); MS (ES+) m/z 448.5 (M+1).

EXAMPLE 4.6

Synthesis of 4'-(6-methoxypyridin-3-yl)-1'-{[5-(trifluoromethyl)-2-furyl]methyl}spiro[furo[2,3-f][1,3]benzodioxole-7,3'-indol]-2'(1'H)-one

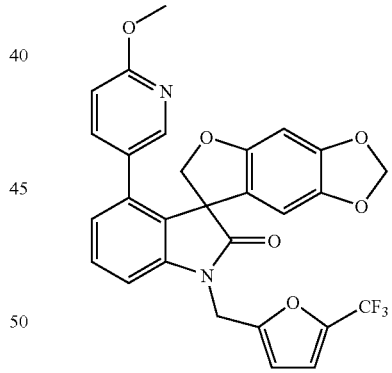

Following the procedure as described in EXAMPLE 4, and making non-critical variations using 4'-bromo-1'-{[5-(trifluoromethyl)-2-furyl]methyl}spiro[furo[2,3-f][1,3]benzodioxole-7,3'-indol]-2'(1'H)-one to replace 4'-bromo-1'-pentylspiro[furo[2,3-f][1,3]benzodioxole-7,3'-indol]-2'(1'H)-one, and (6-methoxypyridin-3-yl)boronic acid to replace [6-(dimethylamino)pyridin-3-yl]boronic acid, the title compound was obtained (51%) as a colorless solid: mp 174-176° C.; $^1$H NMR (300 MHz, CDCl$_3$) δ 7.73 (d, 1H), 7.69 (d, 1H), 7.34 (t, 1H), 7.03 (d, 1H), 6.89-6.86 (m, 2H), 6.65 (d, 1H), 6.61 (d, 1H), 6.56 (d, 1H), 6.17 (d, 2H), 5.87 (d, 2H), 4.99 (ABq, 2H), 4.56 (ABq, 2H), 3.90 (s, 3H); $^{13}$C NMR (75 MHz, CDCl$_3$) δ 177.7, 163.5, 158.4, 156.1, 151.8, 151.8, 149.2, 147.8, 146.1, 142.3, 141.6, 138.8, 136.9, 132.6, 130.0, 129.1, 127.8, 127.2, 126.2, 119.9, 112.7, 112.7, 110.9, 109.6, 109.5, 108.5, 102.3, 101.6, 93.6, 78.2, 58.5, 53.6, 37.0; MS (ES+) m/z 537.4 (M+1).

EXAMPLE 4.7

Synthesis of 4'-[6-(dimethylamino)pyridin-3-yl]-1'-{[5-(trifluoromethyl)-2-furyl]methyl}spiro[furo[2,3-f][1,3]benzodioxole-7,3'-indol]-2'(1'H)-one

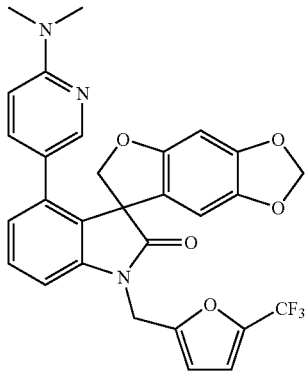

Following the procedure as described in EXAMPLE 4, and making non-critical variations using 4'-bromo-1'-{[5-(trifluoromethyl)-2-furyl]methyl}spiro[furo[2,3-f][1,3]benzodioxole-7,3'-indol]-2'(1'H )-one to replace 4'-bromo-1'-pentylspiro[furo[2,3-f][1,3]benzodioxole-7,3'-indol]-2'(1'H)-one, the title compound was obtained (37%) as a colorless solid: mp 174-176° C.; MS (ES+) m/z 550.4 (M+1).

EXAMPLE 4.8

Synthesis of 4'-pyrimidin-5-ylspiro[furo[2,3-f][1,3]benzodioxole-7,3'-indol]-2'(1'H)-one

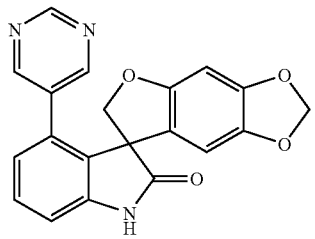

Following the procedure as described in EXAMPLE 4, and making non-critical variations using 4'-bromospiro[furo[2,3-f][1,3]benzodioxole-7,3'-indol]-2'(1'H)-one to replace 4'-bromo-1'-pentylspiro[furo[2,3-f][1,3]benzodioxole-7,3'-indol]-2'(1'H)-one, and pyrimidin-5-ylboronic acid to replace [6-(dimethylamino)pyridin-3-yl]boronic acid, the title compound was obtained (32%) as a colorless solid: mp 185-187° C.; $^1$H NMR (300 MHz, DMSO-$d_6$) δ 10.85 (s, 1H), 9.02 (s, 1H), 8.19 (s, 2H), 7.33 (t, 1H), 7.00 (d, 1H), 6.83 (d, 1H), 6.37 (s, 1H), 6.19 (s, 1H), 5.89 (d, 2H); $^{13}$C NMR (75 MHz, DMSO-$d_6$) δ 178.7, 157.5, 156.0, 155.6, 148.8, 142.3, 133.1, 132.6, 131.8, 129.5, 124.5, 120.3, 110.9, 103.2, 101.9, 93.3, 79.5, 66.8, 58.5; MS (ES+) m/z 360.4 (M+1).

EXAMPLE 4.9

Synthesis of 4'-(3-furyl)-1'-(pyridin-2-ylmethyl)-5,6-dihydrospiro[benzo[1,2-b:5,4-b']difuran-3,3'-indol]-2'(1'H)-one

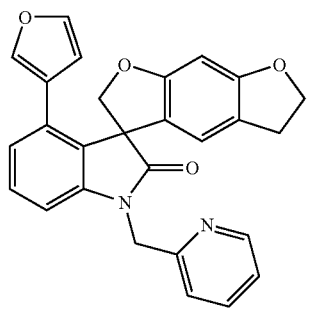

Following the procedure as described in EXAMPLE 4, and making non-critical variations using 4'-bromo-1'-(pyridin-2-ylmethyl)-5,6-dihydrospiro[benzo[1,2-b:5,4-b']difuran-3,3'-indol]-2'(1'H)-one to replace 4'-bromo-1'-pentylspiro[furo[2,3-f][1,3]benzodioxole-7,3'-indol]-2'(1'H)-one, and 3-furanboronic acid to replace [6-(dimethylamino)pyridin-3-yl]boronic acid, the title compound was obtained (75%) as a colorless solid: mp 195-197° C.; $^1$H NMR (300 MHz, CDCl$_3$) δ 8.58 (d, 1H), 7.68 (t, 1H), 7.32-7.21 (m, 4H), 6.97 (d, 1H), 6.92 (d, 1H), 6.77 (s, 1H), 6.60 (s, 1H), 6.35 (s, 1H), 5.99 (s, 1H), 5.12 (ABq, 2H), 4.71 (ABq, 2H), 4.57 (t, 2H), 3.03 (t, 2H); MS (ES+) m/z 437.4 (M+1).

EXAMPLE 4.10

Synthesis of 1'-(pyridin-2-ylmethyl)-4'-pyrimidin-5-yl-5,6-dihydrospiro[benzo[1,2-b:5,4-b']difuran-3,3'-indol]-2M -1)-one

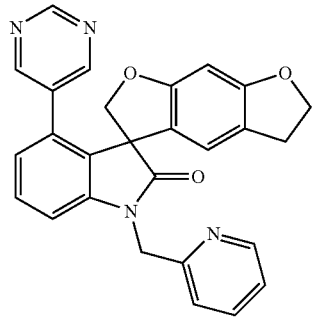

Following the procedure as described in EXAMPLE 4, and making non-critical variations using 4'-bronno-1'-(pyridin-2-ylmethyl)-5,6-dihydrospiro[benzo[1,2-b:5,4-b']difuran-3,3'-indol]-2'(1H)-one to replace 4'-bromo-1'-pentylspiro[furo[2,3-f][1,3]benzodioxole-7,3'-indol]-2'(1'H)-one, and pyrimidin-5-ylboronic acid to replace [6-(dimethylamino)pyridin-3-yl]boronic acid, the title compound was obtained (16%) as a colorless solid: mp>200° C.; $^1$H NMR (300 MHz, CDCl₃) δ 9.09 (s, 1H), 8.59 (d, 1H), 8.14 (s, 2H), 7.74 (t, 1H), 7.67 (d, 1H), 7.63 (d, 1H), 7.52 (d, 1H), 7.47-7.42 (m, 1H), 7.37 (d, 1H), 7.30 (d, 1H), 7.09 (d, 1H), 6.82 (d, 1H), 6.62 (s, 1H), 6.07 (s, 1H), 5.18 (ABq, 2H), 4.62 (ABq, 2H), 4.62-4.48 (m, 2H), 3.02 (t, 2H); MS (ES+) m/z 449.5 (M+1).

EXAMPLE 4.11

Synthesis of 4'-pyridin-3-yl-1'-(pyridin-2-ylmethyl)-5,6-dihydrospiro[benzo[1,2-b:5,4-b']difuran-3,3'-indol]-2'(1'H)-one

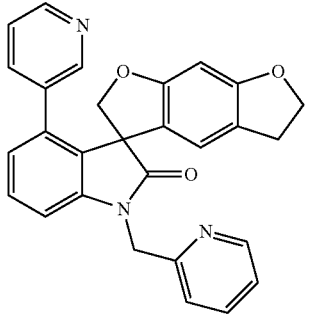

Following the procedure as described in EXAMPLE 4, and making non-critical variations using 4'-bromo-1'-(pyridin-2-ylmethyl)-5,6-dihydrospiro[benzo[1,2-b:5,4-b']difuran-3,3'-indol]-2'(1'H)-one to replace 4'-bromo-1'-pentylspiro[furo[2,3-f][1,3]benzodioxole-7,3'-indol]-2'(1'H)-one, and pyridin-3-ylboronic acid to replace [6-(dimethylamino)pyridin-3-yl]boronic acid, the title compound was obtained (9%) as a colorless solid: mp>200° C.; ¹H NMR (300 MHz, DMSO-d₆) δ 8.52 (d, 1H), 8.42 (d, 1H), 7.96 (s, 1H), 7.79 (t, 1H), 7.40 (d, 1H), 7.29 (t, 2H), 7.18-7.08 (m, 2H), 7.00 (d, 1H), 6.81 (d, 1H), 6.72 (s, 1H), 5.98 (s, 1H), 5.08 (ABq, 2H), 4.56-4.40 (m, 4H), 3.10-2.90 (m, 2H); MS (ES+) m/z 448.5 (M+1).

EXAMPLE 4.12

Synthesis of 4'-(3-furyl)-1'-{[5-(trifluoromethyl)-2-furyl]methyl}-5,6-dihydrospiro[benzo[1,2-b:5,4-b']difuran-3,3'-indol]-2'(1'H)-one

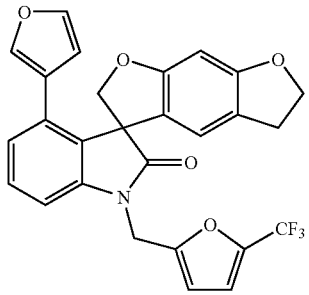

Following the procedure as described in EXAMPLE 4, and making non-critical variations using 4'-bromo-1'-{[5-(trifluoromethyl)-2-furyl]methyl}-5,6-dihydrospiro[benzo[1,2-b:5,4-b']difuran-3,3'-indol]-2'(1'H)-one to replace 4'-bromo-1'-pentylspiro[furo[2,3-f][1,3]benzodioxole-7,3'-indol]-2'(1'H)-one, and 3-furylboronic acid to replace [6-(dimethylamino)pyridin-3-yl]boronic acid, the title compound was obtained (27%) as a colorless solid: mp 167-169° C.; ¹H NMR (300 MHz, CDCl₃) δ 7.34-7.29 (m, 2H), 7.01 (dd, 1H), 6.95 (dd, 1H), 6.77 (dd, 1H), 6.74 (dd, 1H), 6.51 (s, 1H), 6.41 (d, 1H), 6.34 (s, 1H), 6.00 (dd, 1H), 4.97 (ABq, 2H), 4.67 (ABq, 2H), 4.56 (t, 2H), 3.01 (t, 2H); MS (ES+) m/z 494.4 (M+1).

EXAMPLE 4.13

Synthesis of 4'-quinolin-3-yl-1'-{[5-(trifluoromethyl)-2-furyl]methyl}spiro[furo[2,3-f][1,3]benzodioxole-7,3'-indol]-2'(1'H)-one

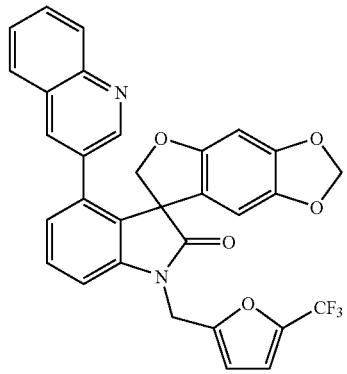

Following the procedure as described in EXAMPLE 4, and making non-critical variations using 4'-bromo-1'-{[5-(trifluoromethyl)-2-furyl]methyl}spiro[furo[2,3-f][1,3]benzodioxole-7,3'-indol]-2'(1'H)-one to replace 4'-bromo-1'-pentylspiro[furo[2,3-f][1,3]benzodioxole-7,3'-indol]-2'(1'H)-one, quinolin-3-ylboronic acid to replace [6-(dimethylamino)pyridin-3-yl]boronic acid, the title compound was obtained (50%) as a colorless solid: ¹H NMR (300 MHz, CDCl₃) δ 8.52 (d, 1H), 8.09 (d, 1H), 7.74-7.68 (m, 1H), 7.56-7.50 (m, 1H), 7.42-7.39 (m, 2H), 7.32 (s, 1H), 7.09 (d, 1H), 7.01 (d, 1H), 6.78-6.77 (m, 1H), 6.45 (d, 1H), 6.26 (s, 1H), 5.94 (d, 1H), 5.91 (s, 1H), 5.89 (d, 1H), 5.03 (ABq, 2H), 4.52 (ABq, 2H); ¹³C NMR (75 MHz, CDCl₃) δ 177.4, 156.0, 151.8, 150.0, 149.3, 147.0, 142.4, 141.8, 136.8, 135.8, 131.1, 130.2, 129.9, 129.3, 129.0, 128.8, 128.0, 127.1, 127.0, 126.4, 126.0, 120.4, 112.7, 109.5, 108.8, 102.5, 101.7, 93.7, 78.3, 58.5, 37.1; MS (ES+) m/z 557.4 (M+1).

EXAMPLE 4.14

Synthesis of 4'-pyrimidin-5-yl-1'-{[5-(trifluoromethyl)-2-furyl]methyl}-5,6-dihydrospiro[benzo[1,2-b:5,4-b']difuran-3,3'-indol]-2'(1'H)-one

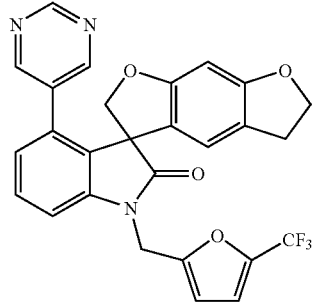

A mixture of 4'-bromo-1'-{[5-(trifluoromethyl)-2-furyl]methyl}-5,6-dihydrospiro[benzo[1,2-b:5,4-b']difuran-3,3'-indol]-2'(1'H)-one (0.11 g, 0.21 mmol), pyrimidine-5-boronic acid (0.04 g, 0.33 mmol), tetrakis(triphenylphosphine)palladium(0) (0.03 g, 0.02 mmol), 2.00 M sodium carbonate (1.00 mL) and 1,2-dimethoxyethane (10.0 mL) was heated at reflux for 16 h under nitrogen. After the organic solvent was evaporated in vacuo, the black residue was extracted with ethyl acetate (3×35.0 mL). The combined organic layers was dried over anhydrous sodium sulfate and filtered. The filtrate was concentrated in vacuo. The residue was subjected to column chromatography eluting with ethyl acetate:hexane (35%) to afford the title compound (0.03 g, 26%): mp 263-266° C.; $^1$H NMR (300 MHz, CDCl$_3$) δ 9.10 (s, 1H), 8.14 (s, 2H), 7.39 (t, 1H), 7.10, (d, 1H), 6.87 (d, 1H), 6.76 (s, 1H), 6.51 (s, 1H), 6.46 (s, 1H), 6.07 (s, 1H), 5.03 (ABq, 2H), 4.62-4.48 (m, 2H), 4.58 (ABq, 2H), 3.01 (t, 2H); $^{13}$C NMR (75 MHz, CDCl$_3$) δ 177.3, 162.5, 161.0, 157.4, 155.9, 151.6, 142.2, 141.7, 132.8, 132.3, 131.3, 129.3, 125.7, 120.6, 120.2, 118.3, 117.0, 112.7, 109.7, 109.4, 93.5, 78.9, 72.5, 57.7, 37.1, 28.9; MS (ES+) m/z 506.5 (M+1).

EXAMPLE 4.15

Synthesis of tert-butyl 4-[(2'-oxo-4'-pyrimidin-5-ylspiro[furo[2,3-f][1,3]benzodioxole-7,3'-indol]-1'(2'H)-yl)methyl]piperidine-1'-carboxylate

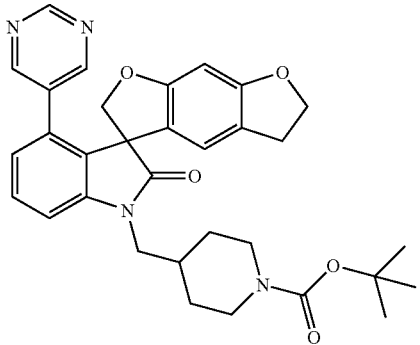

Following the procedure as described in EXAMPLE 4.14, and making non-critical variations using tert-butyl 4-[(4'-bromo-2'-oxospiro[furo[2,3-f][1,3]benzodioxole-7,3'-indol]-1'(2'H)yl)methyl]piperidine-1'-carboxylate to replace 4'-bromo-1'-{[5-(trifluoromethyl)-2-furyl]methyl}-5,6-dihydrospiro[benzo[1,2-b:5,4-b']difuran-3,3'-indol]-2'(1'H)-one, the title compound was obtained (91%) as a colorless solid: $^1$H NMR (300 MHz, CDCl$_3$) δ 9.13 (s, 1H), 8.23 (s, 2H), 8.24-7.37 (m, 5H), 7.01 (d, 1H), 6.85 (d, 1H), 6.14 (dd2H), 5.91 (d, 2H), 4.55 (ABq, 2H), 4.15 (d, 2H), 3.84-3.58 (m, 3H), 2.69 (t, 2H), 1.44 (s, 9H); MS (ES+) m/z 557.5 (M+1).

EXAMPLE 4.16

Synthesis of 1'-methyl-4'-pyrimidin-5-ylspiro[furo[2,3-f][1,3]benzodioxole-7,3'-indol]-2'(1'H)-one

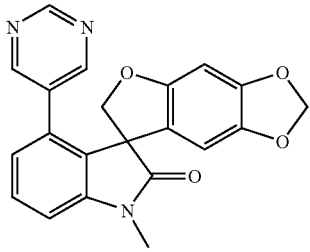

Following the procedure as described in EXAMPLE 4.14, and making non-critical variations using 4'-bromo-1'-methylspiro[furo[2,3-f][1,3]benzodioxole-7,3'-indol]-2'(1'H)-one to replace 4'-bromo-1'-{[5-(trifluoromethyl)-2-furyl]methyl}-5,6-dihydrospiro[benzo[1,2-b:5,4-b']difuran-3,3'-indol]-2'(1'H)-one, the title compound was obtained (22%) as a colorless solid: $^1$H NMR (300 MHz, CDCl$_3$) δ 9.10 (s, 1H), 8.18 (s, 2H), 7.41 (t, 1H), 7.00 (d, 1H), 6.85 (d, 1H), 6.20 (s, 1H), 6.12 (s, 1H), 5.87 (d, 2H), 4.54 (ABq, 2H), 3.32 (s, 1H); MS (ES+) m/z 374.5 (M+1).

EXAMPLE 4.17

Synthesis of 4'-(3-furyl)-1'-methylspiro[furo[2,3-f][1,3]benzodioxole-7,3'-indol]-2'(1'H)-one

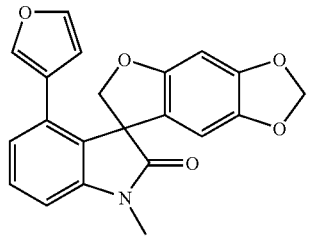

Following the procedure as described in EXAMPLE 4.14, and making non-critical variations using 4'-bromo-1'-methylspiro[furo[2,3-f][1,3]benzodioxole-7,3'-indol]-2'(1'H)-one to replace 4'-bromo-1'-{[5-(trifluoromethyl)-2-furyl]methyl}-5,6-dihydrospiro[benzo[1,2-b:5,4-b']difuran-3,3'-indol]-2'(1'H)-one, and 3-furanboronic acid to replace pyrimidine-5-boronic acid, the title compound was obtained (81%) as a colorless solid: $^1$H NMR (300 MHz, CDCl$_3$) δ 7.40-7.28 (m, 2H), 7.05-6.95 (m, 1H), 6.90-6.78 (m, 2H), 6.45-6.38 (m, 1H), 6.23-6.16 (m, 1H), 6.07-5.97 (m, 1H), 5.97-5.80 (m, 2H), 4.75-4.50 (m, 2H), 3.30-3.22 (m, 3H); MS (ES+) m/z 362.4 (M+1).

EXAMPLE 4.18

Synthesis of 4'-(6-fluoropyridin-3-yl)-1'-methylspiro[furo[2,3-f][1,3]benzodioxole-7,3'-indol]-2'(1'H)-one

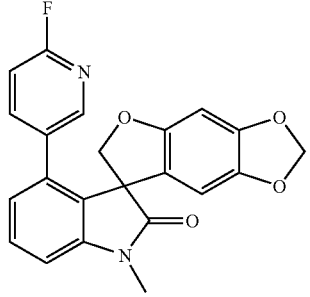

Following the procedure as described in EXAMPLE 4.14, and making non-critical variations using 4'-bromo-1'-methylspiro[furo[2,3-f][1,3]benzodioxole-7,3'-indol]-2'(1'H)-one to replace 4'-bromo-1'-{[5-(trifluoromethyl)-2-furyl]methyl}-5,6-dihydrospiro[benzo[1,2-b:5,4-b']difuran-3,3'-indol]-2'(1'H)-one, and (6-fluoropyridin-3-yl)boronic acid to replace pyrimidine-5-boronic acid, the title compound was obtained (100%) as a colorless solid: $^1$H NMR (300 MHz, CDCl$_3$) δ 7.75-7.65 (m, 1H), 7.42-7.30 (m, 1H), 7.19-7.05 (m, 1H), 7.00-6.90 (m, 1H), 6.90-6.80 (m, 1H), 6.78-6.64 (m, 1H), 6.24-6.12 (m, 2H), 5.92-5.79 (m, 2H), 4.74-4.63 (m, 1H), 4.40-4.29 (m, 1H), 3.34-3.26 (m, 3H); MS (ES+) m/z 391.4 (M+1).

EXAMPLE 4.19

Synthesis of 1'-(2-cyclopropylethyl)-4'-quinolin-3-ylspiro[furo[2,3-f][1,3]benzodioxole-7,3'-indol]-2'(1H)-one

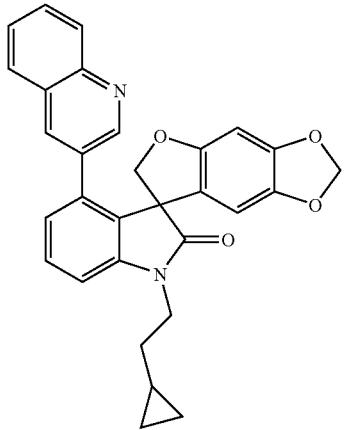

Following the procedure as described in EXAMPLE 4, and making non-critical variations using 4'-bromo-1'-(2-cyclopropylethyl)spiro[furo[2,3-f][1,3]benzodioxole-7,3'-indol]-2'(1'H)-one to replace 4'-bromo-1'-pentylspiro[furo[2,3-f][1,3]benzodioxole-7,3'-indol]-2'(1'H)-one, and quinolin-3-ylboronic acid to replace [6-(dimethylamino)pyridin-3-yl]boronic acid, the title compound was obtained: MS (ES+) m/z 477.5 (M+1)

EXAMPLE 4.20

Synthesis of N-(2-fluorophenyl)-2-(2'-oxo-4'-pyrimidin-5-yl-5,6-dihydrospiro[benzo[1,2-b:5,4-b']difuran-3,3'-indol]-1'(2'H)-yl)acetamide

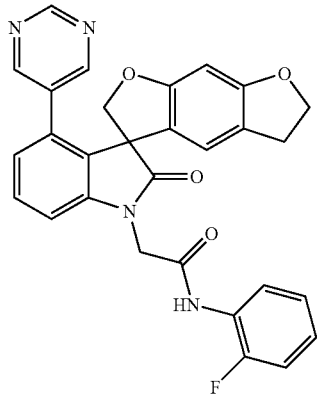

Following the procedure as described in EXAMPLE 4, and making non-critical variations using 2-(4'-bromo-2'-oxo-5,6-dihydrospiro[benzo[1,2-b:5,4-b']difuran-3,3'-indol]-1(2'H)-yl)-N-(2-fluorophenyl)acetamide to replace 4'-bromo-1'-pentylspiro[furo[2,3-f][1,3]benzodioxole-7,3'-indol]-2'(1'H)-one, and pyrimidine-5-boronic acid to replace [6-(dimethylamino)pyridin-3-yl]boronic acid, the title compound was obtained (53%) as a colorless solid: mp 229-230° C.; $^1$H NMR (300 MHz, CDCl$_3$) δ 9.10 (s, 1H), 8.26-8.15 (m, 3H), 7.98 (s, 1H), 7.41 (t, 1H), 7.15-7.05 (m, 4H), 6.89 (d, 1H), 6.68 (s, 1H), 6.06 (s, 1H), 4.81-4.76 (m, 2H), 4.59-4.42 (m, 4H), 3.00 (t, 2H); $^{13}$C NMR (75 MHz, CDCl$_3$) δ 178.2, 164.4, 162.5, 161.0, 157.0, 155.8, 141.8, 132.6, 131.1, 129.4, 125.8, 125.5, 125.4, 125.2, 125.1, 124.7, 121.9, 120.6, 119.9, 118.7, 115.1, 114.8, 109.5, 93.4, 79.0, 72.4, 57.8, 44.9, 28.9; MS (ES+) m/z 509.5 (M+1).

EXAMPLE 5

Synthesis of 4'-[(6-methoxypyridin-3-yl)amino]-1'-pentylspiro[furo[2,3-f][1,3]benzodioxole-7,3'-indol]-2'(1'H)-one

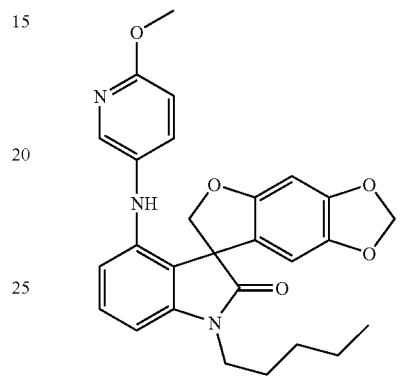

To an oven-dried 2-neck 25 mL round bottom flask equipped with a condenser was charged with 4'-bromo-1'-pentylspiro-(6,7-dihydrofuro-[2,3-f][1,3]benzodioxole-7,3'-indole)-2'-(1'H)-one (50.5 mg, 0.12 mmol), 5-amino-2-methoxypyridine (22.3 mg, 0.18 mmol), Pd$_2$(dba)$_3$ (10 mole %), BINAP (10 mole %) and sodium methoxide (12.9 mg, 0.24 mmol). The flask was flushed with nitrogen for 5 min followed by the addition of degassed toluene (5.00 mL). The reaction mixture was heated at reflux for 16 h. After cooling to ambient temperature, the reaction mixture was diluted with ethyl acetate (20.0 mL) and washed with saturated ammonium chloride (10.0 mL), brine (10.0 mL), dried over anhydrous sodium sulfate and filtered. The filtrate was concentrated in vacuo to dryness. The brown residue was subjected to column chromatography eluting with ethyl acetate-hexane (20% to 50%) to yield the title compound (30.0 mg) in 54% yield: MS (ES+), m/z 474.3 (M+1).

EXAMPLE 5.1

The compounds listed in the following table were synthesized using similar conditions as described in EXAMPLE 5. As previously noted, the compound numbers listed below do not correspond to the compound numbers provided in the general Reaction Schemes above.

| Compound Number | Name | MS (m/z, M + 1) |
|---|---|---|
| 198 | 4'-[(3,5-difluorophenyl)amino]-1'-pentylspiro[furo[2,3-f][1,3]benzodioxole-7,3'-indol]-2'(1'H)-one | 479.1 |
| 199 | 4'-[(4,6-dimethylpyridin-2-yl)amino]-1'-pentylspiro[furo[2,3-f][1,3]benzodioxole-7,3'-indol]-2'(1'H)-one | 473.3 (M + 2) |
| 200 | 4'-[(4-methyl-1,3-thiazol-2-yl)amino]-1'-pentylspiro[furo[2,3-f][1,3]benzodioxole-7,3'-indol]-2'(1'H)-one | 464.1 |

EXAMPLE 5.2
Synthesis of 1'-pentyl-4'-{[3-trifluoromethyl)phenyl]amino}spiro[furo[2,3-f][1,3]benzodioxole-7,3'-indol]-2'(1'H)-one

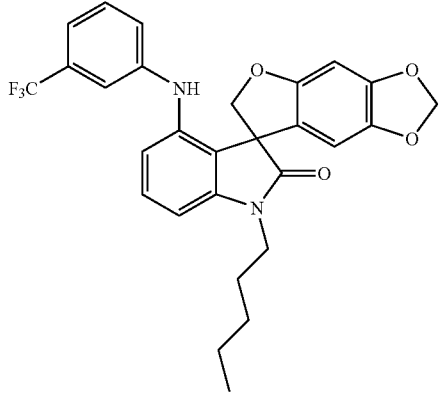

A mixture of 4'-bromo-1'-pentylspiro[furo[2,3-f][1,3]benzodioxole-7,3'-indol]-2'(1'H)-one (0.05 g, 0.12 mmol), 3-(trifluoromethyl)aniline (0.03 g, 0.17 mmol), Pd$_2$(dba)$_3$ (0.02 g, 0.01 mmol), xanthphos (0.007 g, 0.01 mmol), and sodium tert-butoxide (0.02 g, 0.17 mmol) in toluene (5.00 mL) was heated at 110° C. for 4 days. After cooling down to ambient temperature, the mixture was extracted with ethyl acetate. The organic phase was dried over anhydrous sodium sulfate and filtered. The filtrate was concentrated in vacuo to dryness. The residue was subjected to column chromatography eluting with ethyl acetate/hexane to give the title compound (0.06 g, 71%) as a solid: MS (ES+) m/z 511.5 (M+1).

EXAMPLE 5.3

The compounds listed in the following table were synthesized using similar conditions as described in EXAMPLE 5.2. As previously noted, the compound numbers listed below do not correspond to the compound numbers provided in the general Reaction Schemes above.

| Compound Number | Name | MS (m/z, M + 1) |
|---|---|---|
| 201 | 4'-morpholino-1'-pentyl-6H-spiro[benzofuro[6,5-d][1,3]dioxole-7,3'-indolin]-2'-one | 437.5 |
| 202 | 4'-(4-methylpiperazin-1-yl)-1'-pentyl-6H-spiro[benzofuro[6,5-d][1,3]dioxole-7,3'-indolin]-2'-one | 450.5 |
| 203 | 1'-pentyl-4'-(pyrimidin-4-ylamino)-6H-spiro[benzofuro[6,5-d][1,3]dioxole-7,3'-indolin]-2'-one | 445.5 |
| 204 | 1'-pentyl-4'-(pyridin-3-ylamino)-6H-spiro[benzofuro[6,5-d][1,3]dioxole-7,3'-indolin]-2'-one | 444.5 |
| 205 | 4'-(4-chloro-2-(trifluoromethyl)phenylamino)-1'-pentyl-6H-spiro[benzofuro[6,5-d][1,3]dioxole-7,3'-indolin]-2'-one | 545.5 |
| 206 | 1'-pentyl-4'-(pyrimidin-2-ylamino)-6H-spiro[benzofuro[6,5-d][1,3]dioxole-7,3'-indolin]-2'-one | 444.5 |
| 207 | 4'-(benzo[d][1,3]dioxol-5-ylamino)-1'-pentyl-6H-spiro[benzofuro[6,5-d][1,3]dioxole-7,3'-indolin]-2'-one | 487.5 |
| 208 | 4'-(3-fluorophenylamino)-1'-pentyl-6H-spiro[benzofuro[6,5-d][1,3]dioxole-7,3'-indolin]-2'-one | 461.5 |
| 209 | 4'-(naphthalen-2-ylamino)-1'-pentyl-6H-spiro[benzofuro[6,5-d][1,3]dioxole-7,3'-indolin]-2'-one | 493.5 |
| 210 | 4'-(2-methoxyphenylamino)-1'-pentyl-6H-spiro[benzofuro[6,5-d][1,3]dioxole-7,3'-indolin]-2'-one | 473.2 |
| 211 | 4'-(4-methylthiazol-2-ylamino)-1'-pentyl-6H-spiro[benzofuro[6,5-d][1,3]dioxole-7,3'-indolin]-2'-one | 464.1 |
| 212 | 4'-(4,6-dimethylpyridin-2-ylamino)-1'-pentyl-6H-spiro[benzofuro[6,5-d][1,3]dioxole-7,3'-indolin]-2'-one | 473.3 |
| 213 | 4'-(3,5-difluorophenylamino)-1'-pentyl-6H-spiro[benzofuro[6,5-d][1,3]dioxole-7,3'-indolin]-2'-one | 479.1 |
| 214 | 4'-(6-methoxypyridin-3-ylamino)-1'-pentyl-6H-spiro[benzofuro[6,5-d][1,3]dioxole-7,3'-indolin]-2'-one | 474.3 |

EXAMPLE 6
Synthesis of 2-[(2'-oxospiro[furo[2,3-f][1,3]benzodioxole-7,3'-indol]-1'(2'H)-yl)methyl]benzoic acid

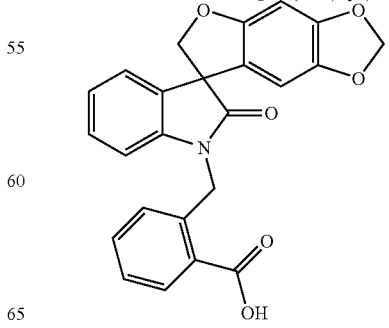

To a solution of methyl 2-[(2'-oxospiro[furo[2,3-f][1,3]benzodioxole-7,3'-indol]-1'(2'H)-yl)methyl]benzoate (7.56 g, 17.6 mmol) in a mixture of THF/water (2/1 v/v, 180 mL) was added lithium hydroxide monohydrate (1.48 g, 35.2 mmol). The resulting mixture was stirred at ambient temperature overnight and concentrated in vacuo followed by the addition of water (150 mL). The mixture was extracted with of ethyl acetate/hexanes, 1/3 v/v, 50.0 mL). The water layer was acidified with 1 N HCl solution until the pH value reached 2. The precipitate was filtered and dried to give the title compound (7.30 g, 100%) as a white solid: mp>250° C.; $^1$H NMR (300 MHz, DMSO-$d_6$) δ 13.25 (s, 1H), 7.95 (dd, 1H), 7.49 (dt, 1H), 7.37 (t, 1H), 7.24-7.16 (m, 2H), 7.11-6.98 (m, 2H), 6.80 (d, 1H), 6.68 (s, 1H), 6.36 (s, 1H), 5.91 (s, 2H), 5.37-5.19 (m, 2H), 4.88-4.68 (m, 2H); $^{13}$C NMR (75 MHz, DMSO-$d_6$) δ 177.6, 168.8, 156.0, 148.8, 143.0, 142.3, 137.6, 133.1, 132.1, 131.5, 129.9, 129.4, 127.7, 126.5, 124.2, 123.6, 120.1, 109.8, 103.8, 101.9, 93.8, 80.5, 58.0, 42.6.

EXAMPLE 7

Synthesis of N-[2-(4-chlorophenyl)ethyl]-2-[(2'-oxospiro[furo[2,3-f][1,3]benzodioxole-7,3'-indol]-1'(2'H)-yl)methyl]benzamide

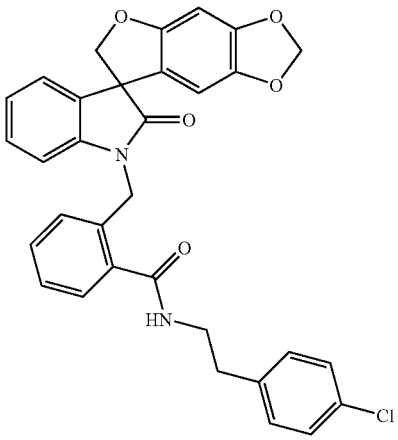

A. Preparation of Stock Solution of 2-[(2'-oxospiro[furo[2,3-f][1,3]benzodioxole-7,3'-indol]-1'(2'H)-yl)methyl]benzoyl chloride A solution of 2-[(2'-oxospiro[furo[2,3-f][1,3]benzodioxole-7,3'-indol]-1'(2'H)-yl)methyl]benzoic acid (0.21 g, 0.50 mmol), oxalyl chloride (0.09 mL, 1.00 mmol) and one drop of DMF in toluene (10.0 mL) was stirred at ambient temperature overnight. The mixture was concentrated under vacuum to afford a solid, which was dissolved in dichloromethane (5.00 mL) to form an acid chloride stock solution (0.10 mmol/mL) for use.

B. Synthesis of N-[2-(4-chlorophenyl)ethyl]-2-[(2'-oxospiro[furo[2,3-f][1,3]benzodioxole-7,3'-indol]-1'(2'H)-yl)methyl]benzamide The acid chloride stock solution obtained above (1.00 mL, 0.10 mmol) was added to a mixture of 2-(4-chlorophenyl)ethylamine (0.02 g, 0.13 mmol), triethylamine (0.14 mL, 1.00 mmol) in dichloromethane (1.00 mL). The resulting mixture was stirred at ambient temperature overnight and diluted with dichloromethane (5.00 mL). The mixture was washed with 1 N HCl, saturated sodium bicarbonate solution, dried over sodium sulfate and filtered. The filtrate was concentrated under vacuum to dryness to give the title compound as a white powder: $^1$H NMR (300 MHz, CDCl$_3$) δ 7.70-7.13 (m, 10H), 7.10-6.96 (m, 2H), 6.65-6.54 (br, 1H), 6.50 (s, 1H), 6.11 (s, 1H), 5.89-5.82 (m, 2H), 5.09-4.88 (m, 3H), 4.68 (d, 1H), 3.79-3.66 (m, 2H), 2.93 (t, 2H); MS (ES+), m/z 553.3 (M+1), 575.3 (M+23).

EXAMPLE 7.1

The compounds listed in the following table were synthesized using similar conditions as described in EXAMPLE 7. As previously noted, the compound numbers listed below do not correspond to the compound numbers provided in the general Reaction Schemes above.

| Compound Number | Name | MS (m/z, M + 1) |
|---|---|---|
| 215 | N-(3-methylbutyl)-2-[(2'-oxospiro[furo[2,3-f][1,3]benzodioxole-7,3'-indol]-1'(2'H)-yl)methyl]benzamide | 485.3 |
| 216 | 2-[(2'-oxospiro[furo[2,3-f][1,3]benzodioxole-7,3'-indol]-1'(2'H)-yl)methyl]-N-phenylbenzamide | 491.2 |
| 217 | N,N-diisopropyl-2-[(2'-oxospiro[furo[2,3-f][1,3]benzodioxole-7,3'-indol]-1'(2'H)-yl)methyl]benzamide | 499.4 |
| 218 | N-(3-fluorophenyl)-2-[(2'-oxospiro[furo[2,3-f][1,3]benzodioxole-7,3'-indol]-1'(2'H)-yl)methyl]benzamide | 509.3 |
| 219 | N-(4-chlorobenzyl)-2-[(2'-oxospiro[furo[2,3-f][1,3]benzodioxole-7,3'-indol]-1'(2'H)-yl)methyl]benzamide | 539.3 |
| 220 | N-butyl-2-[(2'-oxospiro[furo[2,3-f][1,3]benzodioxole-7,3'-indol]-1'(2'H)-yl)methyl]benzamide | 471.3 |
| 221 | 2-[(2'-oxospiro[furo[2,3-f][1,3]benzodioxole-7,3'-indol]-1'(2'H)-yl)methyl]-N-pentylbenzamide | 485.3 |
| 222 | N-hexyl-2-[(2'-oxospiro[furo[2,3-f][1,3]benzodioxole-7,3'-indol]-1'(2'H)-yl)methyl]benzamide | 499.4 |
| 223 | 2-[(2'-oxospiro[furo[2,3-f][1,3]benzodioxole-7,3'-indol]-1'(2'H)-yl)methyl]-N-propylbenzamide | 457.3 |
| 224 | N-isopropyl-2-[(2'-oxospiro[furo[2,3-f][1,3]benzodioxole-7,3'-indol]-1'(2'H)-yl)methyl]benzamide | 457.3 |

-continued

| Compound Number | Name | MS (m/z, M + 1) |
|---|---|---|
| 225 | N-cyclohexyl-2-[(2'-oxospiro[furo[2,3-f][1,3]benzodioxole-7,3'-indol]-1'(2'H)-yl)methyl]benzamide | 497.3 |
| 226 | N-cyclopentyl-2-[(2'-oxospiro[furo[2,3-f][1,3]benzodioxole-7,3'-indol]-1'(2'H)-yl)methyl]benzamide | 483.3 |
| 227 | N-heptyl-2-[(2'-oxospiro[furo[2,3-f][1,3]benzodioxole-7,3'-indol]-1'(2'H)-yl)methyl]benzamide | 513.4 |
| 228 | N-(4-fluorophenyl)-2-[(2'-oxospiro[furo(2,3-f][1,3]benzodioxole-7,3'-indol]-1'(2'H)-yl)methyl]benzamide | 509.1 |
| 229 | N-(3-fluorobenzyl)-2-[(2'-oxospiro[furo[2,3-f][1,3]benzodioxole-7,3'-indol]-1'(2'H)-yl)methyl]benzamide | 523.1 |
| 230 | N-(3-chlorophenyl)-2-[(2'-oxospiro[furo[2,3-f][1,3]benzodioxole-7,3'-indol]-1'(2'H)-yl)methyl]benzamide | 525.0 |
| 231 | N-(2-fluorophenyl)-2-[(2'-oxospiro[furo[2,3-f][1,3]benzodioxole-7,3'-indol]-1'(2'H)-yl)methyl]benzamide | 509.1 |
| 232 | N-(2-ethylphenyl)-2-[(2'-oxospiro[furo[2,3-f][1,3]benzodioxole-7,3'-indol]-1'(2'H)-yl)methyl]benzamide | 519.1 |
| 233 | N-(4-ethylphenyl)-2-[(2'-oxospiro[furo[2,3-f][1,3]benzodioxole-7,3'-indol]-1'(2'H)-yl)methyl]benzamide | 519.2 |
| 234 | N-(3-methylphenyl)-2-[(2'-oxospiro[furo[2,3-f][1,3]benzodioxole-7,3'-indol]-1'(2'H)-yl)methyl]benzamide | 505.2 |
| 235 | N-(2,3-dimethylphenyl)-2-[(2'-oxospiro[furo[2,3-f][1,3]benzodioxole-7,3'-indol]-1'(2'H)-yl)methyl]benzamide | 519.2 |
| 236 | N-(3,5-dimethylphenyl)-2-[(2'-oxospiro[furo[2,3-f][1,3]benzodioxole-7,3'-indol]-1'(2'H)-yl)methyl]benzamide | 519.1 |
| 237 | 1'-[2-(piperidin-1-ylcarbonyl)benzyl]spiro[furo[2,3-f][1,3]benzodioxole-7,3'-indol]-2'(1'H)-one | 483.1 |
| 238 | N-isobutyl-2-[(2'-oxospiro[furo[2,3-f][1,3]benzodioxole-7,3'-indol]-1'(2'H)-yl)methyl]benzamide | 471.2 |
| 239 | N-(2-chlorobenzyl)-2-[(2'-oxospiro[furo[2,3-f][1,3]benzodioxole-7,3'-indol]-1'(2'H)-yl)methyl]benzamide | 539.1 |
| 240 | N-(2,6-dimethylphenyl)-2-[(2'-oxospiro[furo[2,3-f][1,3]benzodioxole-7,3'-indol]-1'(2'H)-yl)methyl]benzamide | 519.1 |
| 241 | N-(2-methoxyphenyl)-2-[(2'-oxospiro[furo[2,3-f][1,3]benzodioxole-7,3'-indol]-1'(2'H)-yl)methyl]benzamide | 521.1 |
| 242 | N-(3-methoxypropyl)-2-[(2'-oxospiro[furo[2,3-f][1,3]benzodioxole-7,3'-indol]-1'(2'H)-yl)methyl]benzamide | 487.2 |
| 243 | N-[2-(4-methylphenyl)ethyl]-2-[(2'-oxospiro[furo[2,3-f][1,3]benzodioxole-7,3'-indol]-1'(2'H)-yl)methyl]benzamide | 533.2 |
| 244 | 2-[(2'-oxospiro[furo[2,3-f][1,3]benzodioxole-7,3'-indol]-1'(2'H)-yl)methyl]-N-(tetrahydrofuran-2-ylmethyl)benzamide | 499.2 |
| 245 | N,N-dibenzyl-2-[(2'-oxospiro[furo[2,3-f][1,3]benzodioxole-7,3'-indol]-1'(2'H)-yl)methyl]benzamide | 595.2 |
| 246 | 2-[(2'-oxospiro[furo[2,3-f][1,3]benzodioxole-7,3'-indol]-1'(2'H)-yl)methyl]-N-(3-phenylpropyl)benzamide | 533.2 |
| 247 | N-[2-(3-chlorophenyl)ethyl]-2-[(2'-oxospiro[furo[2,3-f][1,3]benzodioxole-7,3'-indol]-1'(2'H)-yl)methyl]benzamide | 553.1 |
| 248 | N-[2-(4-fluorophenyl)ethyl]-2-[(2'-oxospiro[furo[2,3-f][1,3]benzodioxole-7,3'-indol]-1'(2'H)-yl)methyl]benzamide | 537.1 |
| 249 | N-(4-fluorobenzyl)-2-[(2'-oxospiro[furo[2,3-f][1,3]benzodioxole-7,3'-indol]-1'(2'H)-yl)methyl]benzamide | 523.1 |
| 250 | N-(3-ethoxypropyl)-2-[(2'-oxospiro[furo[2,3-f][1,3]benzodioxole-7,3'-indol]-1'(2'H)-yl)methyl]benzamide | 501.1 |
| 251 | N-hexyl-N-methyl-2-[(2'-oxospiro[furo[2,3-f][1,3]benzodioxole-7,3'-indol]-1'(2'H)-yl)methyl]benzamide | 513.2 |
| 252 | N-(3-isopropoxypropyl)-2-[(2'-oxospiro[furo[2,3-f][1,3]benzodioxole-7,3'-indol]-1'(2'H)-yl)methyl]benzamide | 515.2 |

-continued

| Compound Number | Name | MS (m/z, M + 1) |
|---|---|---|
| 253 | N-(4-methoxybenzyl)-2-[(2'-oxospiro[furo[2,3-f][1,3]benzodioxole-7,3'-indol]-1'(2'H)-yl)methyl]benzamide | 535.2 |
| 254 | N-(cyclopropylmethyl)-2-[(2'-oxospiro[furo[2,3-f][1,3]benzodioxole-7,3'-indol]-1'(2'H)-yl)methyl]benzamide | 469.1 |
| 255 | N-(2-ethoxyethyl)-2-[(2'-oxospiro[furo[2,3-f][1,3]benzodioxole-7,3'-indol]-1'(2'H)-yl)methyl]benzamide | 487.2 |
| 256 | N-(cyclohexylmethyl)-2-[(2'-oxospiro[furo[2,3-f][1,3]benzodioxole-7,3'-indol]-1'(2'H)-yl)methyl]benzamide | 511.2 |
| 257 | N-(2-furylmethyl)-2-[(2'-oxospiro[furo[2,3-f][1,3]benzodioxole-7,3'-indol]-1'(2'H)-yl)methyl]benzamide | 495.0 |
| 258 | N-(2,4-dimethylphenyl)-2-[(2'-oxospiro[furo[2,3-f][1,3]benzodioxole-7,3'-indol]-1'(2'H)-yl)methyl]benzamide | 519.2 |
| 259 | N-(4-cyanophenyl)-2-[(2'-oxospiro[furo[2,3-f][1,3]benzodioxole-7,3'-indol]-1'(2'H)-yl)methyl]benzamide | 516.2 |
| 260 | N-(3,5-dichlorophenyl)-2-[(2'-oxospiro[furo[2,3-f][1,3]benzodioxole-7,3'-indol]-1'(2'H)-yl)methyl]benzamide | 559.0 |
| 261 | N-(3-fluoro-2-methylphenyl)-2-[(2'-oxospiro[furo[2,3-f][1,3]benzodioxole-7,3'-indol]-1'(2'H)-yl)methyl]benzamide | 523.1 |
| 262 | N-(4-methoxyphenyl)-2-[(2'-oxospiro[furo[2,3-f][1,3]benzodioxole-7,3'-indol]-1'(2'H)-yl)methyl]benzamide | 521.1 |
| 263 | N-(5-chloro-2-methylphenyl)-2-[(2'-oxospiro[furo[2,3-f][1,3]benzodioxole-7,3'-indol]-1'(2'H)-yl)methyl]benzamide | 539.1 |
| 264 | 2-[(2'-oxospiro[furo[2,3-f][1,3]benzodioxole-7,3'-indol]-1'(2'H)-yl)methyl]-N-[3-(trifluoromethyl)phenyl]benzamide | 559.1 |
| 265 | 2-[(2'-oxospiro[furo[2,3-f][1,3]benzodioxole-7,3'-indol]-1'(2'H)-yl)methyl]-N-(pyridin-4-ylmethyl)benzamide | 506.1 |
| 266 | N-cyclobutyl-2-[(2'-oxospiro[furo[2,3-f][1,3]benzodioxole-7,3'-indol]-1'(2'H)-yl)methyl]benzamide | 469.1 |
| 267 | N-methyl-2-[(2'-oxospiro[furo[2,3-f][1,3]benzodioxole-7,3'-indol]-1'(2'H)-yl)methyl]benzamide | 429.1 |
| 268 | N-ethyl-2-[(2'-oxospiro[furo[2,3-f][1,3]benzodioxole-7,3'-indol]-1'(2'H)-yl)methyl]benzamide | 443.1 |
| 269 | 2-[(2'-oxospiro[furo[2,3-f][1,3]benzodioxole-7,3'-indol]-1'(2'H)-yl)methyl]-N-(2,2,2-trifluoroethyl)benzamide | 497.1 |
| 270 | N-(2,2-diphenylethyl)-2-[(2'-oxospiro[furo[2,3-f][1,3]benzodioxole-7,3'-indol]-1'(2'H)-yl)methyl]benzamide | 595.2 |
| 271 | N-[2-(diethylamino)ethyl]-2-[(2'-oxospiro[furo[2,3-f][1,3]benzodioxole-7,3'-indol]-1'(2'H)-yl)methyl]benzamide | 514.2 |
| 272 | N-(3,3-dimethylbutyl)-2-[(2'-oxospiro[furo[2,3-f][1,3]benzodioxole-7,3'-indol]-1'(2'H)-yl)methyl]benzamide | 499.2 |
| 273 | N-(2-ethylbutyl)-2-[(2'-oxospiro[furo[2,3-f][1,3]benzodioxole-7,3'-indol]-1'(2'H)-yl)methyl]benzamide | 499.2 |
| 274 | 2-[(2'-oxospiro[furo[2,3-f][1,3]benzodioxole-7,3'-indol]-1'(2'H)-yl)methyl]-N-(2-pyrrolidin-1-ylethyl)benzamide | 512.4 |
| 275 | N-[(1-ethylpyrrolidin-2-yl)methyl]-2-[(2'-oxospiro[furo[2,3-f][1,3]benzodioxole-7,3'-indol]-1'(2'H)-yl)methyl]benzamide | 526.4 |
| 276 | 2-[(2'-oxospiro[furo[2,3-f][1,3]benzodioxole-7,3'-indol]-1'(2'H)-yl)methyl]-N-(2-piperidin-1-ylethyl)benzamide | 526.5 |
| 277 | N-(2-morpholin-4-ylethyl)-2-[(2'-oxospiro[furo[2,3-f][1,3]benzodioxole-7,3'-indol]-1'(2'H)-yl)methyl]benzamide | 528.4 |
| 278 | N-[(1S)-1-cyclohexylethyl]-2-[(2'-oxospiro[furo[2,3-f][1,3]benzodioxole-7,3'-indol]-1'(2'H)-yl)methyl]benzamide | 525.5 |
| 279 | N-(2-fluoro-5-methylphenyl)-2-[(2'-oxospiro[furo[2,3-f][1,3]benzodioxole-7,3'-indol]-1'(2'H)-yl)methyl]benzamide | 523.4 |
| 280 | N-(2,4-difluorophenyl)-2-[(2'-oxospiro[furo[2,3-f][1,3]benzodioxole-7,3'-indol]-1'(2'H)-yl)methyl]benzamide | 527.3 |

-continued

| Compound Number | Name | MS (m/z, M + 1) |
|---|---|---|
| 281 | 2-[(2'-oxospiro[furo[2,3-f][1,3]benzodioxole-7,3'-indol]-1'(2'H)-yl)methyl]-N-(4-propylphenyl)benzamide | 533.4 |
| 282 | N-(3,3-diphenylpropyl)-2-[(2'-oxospiro[furo[2,3-f][1,3]benzodioxole-7,3'-indol]-1'(2'H)-yl)methyl]benzamide | 609.4 |
| 283 | N-(2-methoxyethyl)-2-[(2'-oxospiro[furo[2,3-f][1,3]benzodioxole-7,3'-indol]-1'(2'H)-yl)methyl]benzamide | 473.4 |
| 284 | N-(2,5-difluorobenzyl)-2-[(2'-oxospiro[furo[2,3-f][1,3]benzodioxole-7,3'-indol]-1'(2'H)-yl)methyl]benzamide | 541.3 |
| 285 | 2-[(2'-oxospiro[furo[2,3-f][1,3]benzodioxole-7,3'-indol]-1'(2'H)-yl)methyl]-N-(2-thienylmethyl)benzamide | 511.4 |
| 286 | N-[4-chloro-2-(trifluoromethyl)phenyl]-2-[(2'-oxospiro[furo[2,3-f][1,3]benzodioxole-7,3'-indol]-1'(2'H)-yl)methyl]benzamide | 593.3 |
| 287 | N-[2-(4-methoxyphenyl)ethyl]-2-[(2'-oxospiro[furo[2,3-f][1,3]benzodioxole-7,3'-indol]-1'(2'H)-yl)methyl]benzamide | 549.4 |
| 288 | N-(3,5-dichlorobenzyl)-2-[(2'-oxospiro[furo[2,3-f][1,3]benzodioxole-7,3'-indol]-1'(2'H)-yl)methyl]benzamide | 573.2 |
| 289 | N-(3-chlorobenzyl)-2-[(2'-oxospiro[furo[2,3-f][1,3]benzodioxole-7,3'-indol]-1'(2'H)-yl)methyl]benzamide | 539.3 |
| 290 | 2-[(2'-oxospiro[furo[2,3-f][1,3]benzodioxole-7,3'-indol]-1'(2'H)-yl)methyl]-N-[2-(2-thienyl)ethyl]benzamide | 525.4 |
| 291 | N-(2,3-dihydro-1H-inden-1-yl)-2-[(2'-oxospiro[furo[2,3-f][1,3]benzodioxole-7,3'-indol]-1'(2'H)-yl)methyl]benzamide | 531.4 |
| 292 | 2-[(2'-oxospiro[furo[2,3-f][1,3]benzodioxole-7,3'-indol]-1'(2'H)-yl)methyl]-N-[4-(trifluoromethyl)benzyl]benzamide | 573.3 |
| 293 | N-[4-fluoro-2-(trifluoromethyl)phenyl]-2-[(2'-oxospiro[furo[2,3-f][1,3]benzodioxole-7,3'-indol]-1'(2'H)-yl)methyl]benzamide | 577.5 |
| 294 | 2-[(2'-oxospiro[furo[2,3-f][1,3]benzodioxole-7,3'-indol]-1'(2'H)-yl)methyl]-N-(pyridin-3-ylmethyl)benzamide | 506.4 |
| 295 | 2-[(2'-oxospiro[furo[2,3-f][1,3]benzodioxole-7,3'-indol]-1'(2'H)-yl)methyl]-N-[2-(trifluoromethyl)benzyl]benzamide | 573.3 |
| 296 | N-(3-methylpyridin-2-yl)-2-[(2'-oxospiro[furo[2,3-f][1,3]benzodioxole-7,3'-indol]-1'(2'H)-yl)methyl]benzamide | 506.4 |
| 297 | N-(1-benzylpiperidin-4-yl)-2-[(2'-oxospiro[furo[2,3-f][1,3]benzodioxole-7,3'-indol]-1'(2'H)-yl)methyl]benzamide | 588.4 |
| 298 | 2-[(2'-oxospiro[furo[2,3-f][1,3]benzodioxole-7,3'-indol]-1'(2'H)-yl)methyl]-N-[2-(trifluoromethyl)phenyl]benzamide | 559.4 |
| 299 | N-[(1R)-1-cyclohexylethyl]-2-[(2'-oxospiro[furo[2,3-f][1,3]benzodioxole-7,3'-indol]-1'(2'H)-yl)methyl]benzamide | 525.5 |
| 300 | N-(2-cyanoethyl)-2-[(2'-oxospiro[furo[2,3-f][1,3]benzodioxole-7,3'-indol]-1'(2'H)-yl)methyl]benzamide | 468.3 |
| 301 | N-(6-methoxypyridin-3-yl)-2-[(2'-oxospiro[furo[2,3-f][1,3]benzodioxole-7,3'-indol]-1'(2'H)-yl)methyl]benzamide | 522.4 |
| 302 | 2-[(2'-oxospiro[furo[2,3-f][1,3]benzodioxole-7,3'-indol]-1'(2'H)-yl)methyl]-N-1,3-thiazol-2-ylbenzamide | 498.3 |
| 303 | 2-[(2'-oxospiro[furo[2,3-f][1,3]benzodioxole-7,3'-indol]-1'(2'H)-yl)methyl]-N-1,3,4-thiadiazol-2-ylbenzamide | 499.3 |
| 304 | N-(4,6-dimethylpyridin-2-yl)-2-[(2'-oxospiro[furo[2,3-f][1,3]benzodioxole-7,3'-indol]-1'(2'H)-yl)methyl]benzamide | 520.3 |
| 305 | N-(2,3-dihydro-1H-inden-5-yl)-2-[(2'-oxospiro[furo[2,3-f][1,3]benzodioxole-7,3'-indol]-1'(2'H)-yl)methyl]benzamide | 531.4 |
| 306 | 1'-{2-[(4-pyrimidin-2-ylpiperazin-1-yl)carbonyl]benzyl}spiro[furo[2,3-f][1,3]benzodioxole-7,3'-indol]-2'(1'H)-one | 562.4 |
| 307 | 1'-(2-{[4-(1,3-benzodioxol-5-ylmethyl)piperazin-1-yl]carbonyl}benzyl)spiro[furo[2,3-f][1,3]benzodioxole-7,3'-indol]-2'(1'H)-one | 618.4 |
| 308 | N-2-adamantyl-2-[(2'-oxospiro[furo[2,3-f][1,3]benzodioxole-7,3'-indol]-1'(2'H)-yl)methyl]benzamide | 549.5 |

-continued

| Compound Number | Name | MS (m/z, M + 1) |
|---|---|---|
| 309 | N-1-adamantyl-2-[(2'-oxospiro[furo[2,3-f][1,3]benzodioxole-7,3'-indol]-1'(2'H)-yl)methyl]benzamide | 549.5 |
| 310 | N-1-naphthyl-2-[(2'-oxospiro[furo[2,3-f][1,3]benzodioxole-7,3'-indol]-1'(2'H)-yl)methyl]benzamide | 541.4 |
| 311 | N-(3,5-difluorophenyl)-2-[(2'-oxospiro[furo[2,3-f][1,3]benzodioxole-7,3'-indol]-1'(2'H)-yl)methyl]benzamide | 527.3 |
| 312 | 1'-[2-(morpholin-4-ylcarbonyl)benzyl]spiro[furo[2,3-f][1,3]benzodioxole-7,3'-indol]-2'(1'H)-one | 485.4 |
| 313 | N-[3-(dimethylamino)propyl]-N-methyl-2-[(2'-oxospiro[furo[2,3-f][1,3]benzodioxole-7,3'-indol]-1'(2'H)-yl)methyl]benzamide | 514.4 |

EXAMPLE 8

Synthesis of 3-[(2'-oxospiro[furo[2,3-f][1,3]benzodioxole-7,3'-indol]-1'(2'H)-yl)methyl]benzoic acid

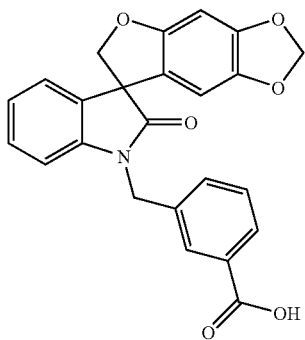

Following the procedure described in EXAMPLE 6, and making non-critical variations using methyl 3-[(2'-oxospiro[furo[2,3-f][1,3]benzodioxole-7,3'-indol]-1'(2'H)-yl)methyl]benzoate to replace methyl 2-[(2'-oxospiro[furo[2,3-f][1,3]benzodioxole-7,3'-indol]-1'(2'H)-yl)methyl]benzoate, the title compound was obtained (100%): $^1$H NMR (300 MHz, CDCl$_3$) δ 13.03 (s, 1H), 7.86-7.80 (m, 2H), 7.59-7.57 (m, 1H), 7.48-7.44 (m, 1H), 7.25-7.16 (m, 2H), 7.03-6.95 (m, 2H), 6.68 (s, 1H), 6.18 (s, 1H), 5.90 (s, 2H), 5.05 (ABq, 2H), 4.75 (ABq, 2H); $^{13}$C NMR (75 MHz, CDCl$_3$) δ 177.4, 167.5, 155.9, 148.9, 142.5, 142.3, 137.3, 132.2, 131.7, 129.6, 129.4, 128.8, 128.1, 124.3, 123.7, 120.1, 109.9, 103.3, 101.9, 93.9, 80.3, 58.0, 43.2; MS (ES+) m/z 416.2 (M+1).

EXAMPLE 9

Synthesis of N-[2-(3-chlorophenyl)ethyl]-3-[(2'-oxospiro[furo[2,3-f][1,3]benzodioxole-7,3'-indol]-1'(2'H)-yl)methyl]benzamide

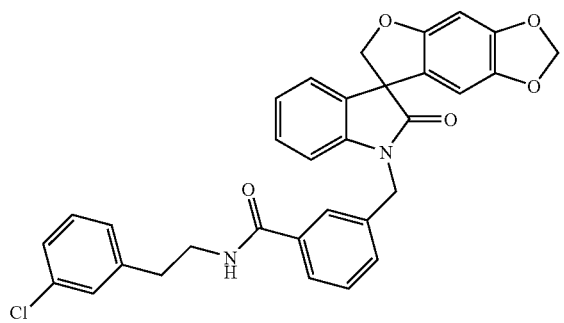

A. Preparation of Stock Solution of 3-[(2'-oxospiro[furo[2,3-f][1,3]benzodioxole-7,3'-indol]-1'(2'H)-yl)methyl]benzoyl chloride To a stirred slurry of 3-[(2'-oxospiro[furo[2,3-f][1,3]benzodioxole-7,3'-indol]-1'(2'H)-yl)methyl]benzoic acid (2.08 g, 5.00 mmol) in dry chloroform (50.0 mL) was added oxalyl chloride (0.95 g, 7.5 mmol) at ambient temperature followed by 1 drop of DMF. The mixture was stirred at ambient temperature overnight and evaporated to dryness in vacuo. The residue was dissolved in dry dichlormethane (60.0 mL) to form an acid chloride stock solution for use.

B. Synthesis of N-[2-(3-Chlorophenyl)ethyl]-3-[(2'-oxospiro[furo[2,3-f][1,3]benzodioxole-7,3'-indol]-1'(2'H)-yl)methyl]benzamide To a solution of 2-(3-chlorophenyl)ethylamine (0.02 mL, 0.24 mmol) in dry dichloromethane (2.00 mL) and triethylamine (0.05 mL, 0.32 mmol) was added the acid chloride stock solution (2.0 mL, 0.081 M in dichloromethane) obtained above at ambient temperature. The mixture was stirred for 2 h, washed with 15% HCl solution and water. The organic layer was separated, dried over Na$_2$SO$_4$ and filtered. The filtrate was concentrated in vacuo to dryness. The residue was dissolved in ethyl acetate, and the product was precipitated by the addition of hexane. The white solid was filtered and collected to yield the title compound (0.06 g) in 65% yield: $^1$H NMR (300 MHz, CDCl$_3$) δ 7.97-7.95 (m, 2H), 7.53-7.50 (m, 1H), 7.45-7.40 (m, 1H), 7.21-7.15 (m, 2H), 7.04-6.99 (m, 1H), 6.73-6.71 (m, 1H), 6.52 (s, 1H), 6.20 (s, 1H), 5.86 (s, 1H), 5.18 (d, 1H), 4.72 (d, 1H), 4.80 (d, 1H), 4.69 (d, 1H), 3.89 (s, 1H); MS (ES+) m/z 554.0 (M+1).

EXAMPLE 9.1

The compounds listed in the following table were synthesized using the similar procedure as described in EXAMPLE 9. As previously noted, the compound numbers listed below do not correspond to the compound numbers provided in the general Reaction Schemes above.

| Compound Number | Name | MS (m/z, M + 1) |
|---|---|---|
| 314 | N-(3-methylbutyl)-3-[(2'-oxospiro[furo[2,3-f][1,3]benzodioxole-7,3'-indol]-1'(2'H)-yl)methyl]benzamide | 485.5 |
| 315 | 3-[(2'-oxospiro[furo[2,3-f][1,3]benzodioxole-7,3'-indol]-1'(2'H)-yl)methyl]-N-phenylbenzamide | 491.5 |
| 316 | N,N-diisopropyl-3-[(2'-oxospiro[furo[2,3-f][1,3]benzodioxole-7,3'-indol]-1'(2'H)-yl)methyl]benzamide | 499.6 |
| 317 | N-(3-fluorophenyl)-3-[(2'-oxospiro[furo[2,3-f][1,3]benzodioxole-7,3'-indol]-1'(2'H)-yl)methyl]benzamide | 509.5 |
| 318 | N-(4-chlorobenzyl)-3-[(2'-oxospiro[furo[2,3-f][1,3]benzodioxole-7,3'-indol]-1'(2'H)-yl)methyl]benzamide | 540.0 |
| 319 | N-butyl-3-[(2'-oxospiro[furo[2,3-f][1,3]benzodioxole-7,3'-indol]-1'(2'H)-yl)methyl]benzamide | 471.5 |
| 320 | N-(3-fluorobenzyl)-3-[(2'-oxospiro[furo[2,3-f][1,3]benzodioxole-7,3'-indol]-1'(2'H)-yl)methyl]benzamide | 523.5 |
| 321 | N-(3-chlorophenyl)-3-[(2'-oxospiro[furo[2,3-f][1,3]benzodioxole-7,3'-indol]-1'(2'H)-yl)methyl]benzamide | 526.0 |
| 322 | N-(2-fluorophenyl)-3-[(2'-oxospiro[furo[2,3-f][1,3]benzodioxole-7,3'-indol]-1'(2'H)-yl)methyl]benzamide | 509.5 |
| 323 | N-(2-ethylphenyl)-3-[(2'-oxospiro[furo[2,3-f][1,3]benzodioxole-7,3'-indol]-1'(2'H)-yl)methyl]benzamide | 519.6 |
| 324 | N-(4-ethylphenyl)-3-[(2'-oxospiro[furo[2,3-f][1,3]benzodioxole-7,3'-indol]-1'(2'H)-yl)methyl]benzamide | 519.6 |
| 325 | N-(3-methylphenyl)-3-[(2'-oxospiro[furo[2,3-f][1,3]benzodioxole-7,3'-indol]-1'(2'H)-yl)methyl]benzamide | 505.5 |
| 326 | N-(2,3-dimethylphenyl)-3-[(2'-oxospiro[furo[2,3-f][1,3]benzodioxole-7,3'-indol]-1'(2'H)-yl)methyl]benzamide | 519.6 |
| 327 | N-(3,5-dimethylphenyl)-3-[(2'-oxospiro[furo[2,3-f][1,3]benzodioxole-7,3'-indol]-1'(2'H)-yl)methyl]benzamide | 519.6 |
| 328 | 3-[(2'-oxospiro[furo[2,3-f][1,3]benzodioxole-7,3'-indol]-1'(2'H)-yl)methyl]-N-pentylbenzamide | 485.5 |
| 329 | 3-[(2'-oxospiro[furo[2,3-f][1,3]benzodioxole-7,3'-indol]-1'(2'H)-yl)methyl]-N-propylbenzamide | 457.5 |
| 330 | N-isopropyl-3-[(2'-oxospiro[furo[2,3-f][1,3]benzodioxole-7,3'-indol]-1'(2'H)-yl)methyl]benzamide | 457.5 |
| 331 | 1'-[3-(piperidin-1-ylcarbonyl)benzyl]spiro[furo[2,3-f][1,3]benzodioxole-7,3'-indol]-2'(1'H)-one | 483.5 |
| 332 | N-isobutyl-3-[(2'-oxospiro[furo[2,3-f][1,3]benzodioxole-7,3'-indol]-1'(2'H)-yl)methyl]benzamide | 471.5 |
| 333 | N-hexyl-3-[(2'-oxospiro[furo[2,3-f][1,3]benzodioxole-7,3'-indol]-1'(2'H)-yl)methyl]benzamide | 499.6 |
| 334 | N-cyclohexyl-3-[(2'-oxospiro[furo[2,3-f][1,3]benzodioxole-7,3'-indol]-1'(2'H)-yl)methyl]benzamide | 497.6 |
| 335 | N-cyclopentyl-3-[(2'-oxospiro[furo[2,3-f][1,3]benzodioxole-7,3'-indol]-1'(2'H)-yl)methyl]benzamide | 483.5 |
| 336 | N-heptyl-3-[(2'-oxospiro[furo[2,3-f][1,3]benzodioxole-7,3'-indol]-1'(2'H)-yl)methyl]benzamide | 513.6 |
| 337 | N-(2-methoxybenzyl)-3-[(2'-oxospiro[furo[2,3-f][1,3]benzodioxole-7,3'-indol]-1'(2'H)-yl)methyl]benzamide | 535.6 |
| 338 | N-(2-methoxyphenyl)-3-[(2'-oxospiro[furo[2,3-f][1,3]benzodioxole-7,3'-indol]-1'(2'H)-yl)methyl]benzamide | 521.5 |
| 339 | N-cyclopropyl-3-[(2'-oxospiro[furo[2,3-f][1,3]benzodioxole-7,3'-indol]-1'(2'H)-yl)methyl]benzamide | 455.5 |
| 340 | N-(3-methoxypropyl)-3-[(2'-oxospiro[furo[2,3-f][1,3]benzodioxole-7,3'-indol]-1'(2'H)-yl)methyl]benzamide | 487.5 |
| 341 | N-(2,4-dimethylphenyl)-3-[(2'-oxospiro[furo[2,3-f][1,3]benzodioxole-7,3'-indol]-1'(2'H)-yl)methyl]benzamide | 519.6 |

-continued

| Compound Number | Name | MS (m/z, M + 1) |
| --- | --- | --- |
| 342 | 3-[(2'-oxospiro[furo[2,3-f][1,3]benzodioxole-7,3'-indol]-1'(2'H)-yl)methyl]-N-(tetrahydrofuran-2-ylmethyl)benzamide | 499.5 |
| 343 | N,N-dibenzyl-3-[(2'-oxospiro[furo[2,3-f][1,3]benzodioxole-7,3'-indol]-1'(2'H)-yl)methyl]benzamide | 595.7 |
| 344 | N-[2-(diethylamino)ethyl]-3-[(2'-oxospiro[furo[2,3-f][1,3]benzodioxole-7,3'-indol]-1'(2'H)-yl)methyl]benzamide | 514.6 |
| 345 | N-methyl-3-[(2'-oxospiro[furo[2,3-f][1,3]benzodioxole-7,3'-indol]-1'(2'H)-yl)methyl]benzamide | 429.4 |
| 346 | 3-[(2'-oxospiro[furo[2,3-f][1,3]benzodioxole-7,3'-indol]-1'(2'H)-yl)methyl]-N-[3-(trifluoromethyl)phenyl]benzamide | 559.5 |
| 347 | N-ethyl-3-[(2'-oxospiro[furo[2,3-f][1,3]benzodioxole-7,3'-indol]-1'(2'H)-yl)methyl]benzamide | 443.5 |
| 348 | N-(3-ethoxypropyl)-3-[(2'-oxospiro[furo[2,3-f][1,3]benzodioxole-7,3'-indol]-1'(2'H)-yl)methyl]benzamide | 501.5 |
| 349 | N-(4-methoxybenzyl)-3-[(2'-oxospiro[furo[2,3-f][1,3]benzodioxole-7,3'-indol]-1'(2'H)-yl)methyl]benzamide | 535.6 |
| 350 | N-(3,5-dichlorophenyl)-3-[(2'-oxospiro[furo[2,3-f][1,3]benzodioxole-7,3'-indol]-1'(2'H)-yl)methyl]benzamide | 560.4 |
| 351 | 3-[(2'-oxospiro[furo[2,3-f][1,3]benzodioxole-7,3'-indol]-1'(2'H)-yl)methyl]-N-pyridin-3-ylbenzamide | 492.5 |
| 352 | 3-[(2'-oxospiro[furo[2,3-f][1,3]benzodioxole-7,3'-indol]-1'(2'H)-yl)methyl]-N-(pyridin-4-ylmethyl)benzamide | 506.5 |
| 353 | N-(2-furylmethyl)-3-[(2'-oxospiro[furo[2,3-f][1,3]benzodioxole-7,3'-indol]-1'(2'H)-yl)methyl]benzamide | 495.5 |
| 354 | N-(3-fluoro-2-methylphenyl)-3-[(2'-oxospiro[furo[2,3-f][1,3]benzodioxole-7,3'-indol]-1'(2'H)-yl)methyl]benzamide | 523.5 |
| 355 | N-hexyl-N-methyl-3-[(2'-oxospiro[furo[2,3-f][1,3]benzodioxole-7,3'-indol]-1'(2'H)-yl)methyl]benzamide | 513.6 |
| 356 | N-(3-isopropoxypropyl)-3-[(2'-oxospiro[furo[2,3-f][1,3]benzodioxole-7,3'-indol]-1'(2'H)-yl)methyl]benzamide | 515.6 |
| 357 | N-(2-ethoxyethyl)-3-[(2'-oxospiro[furo[2,3-f][1,3]benzodioxole-7,3'-indol]-1'(2'H)-yl)methyl]benzamide | 487.5 |
| 358 | N-(cyclopropylmethyl)-3-[(2'-oxospiro[furo[2,3-f][1,3]benzodioxole-7,3'-indol]-1'(2'H)-yl)methyl]benzamide | 469.5 |
| 359 | N-(4-methoxyphenyl)-3-[(2'-oxospiro[furo[2,3-f][1,3]benzodioxole-7,3'-indol]-1'(2'H)-yl)methyl]benzamide | 521.5 |
| 360 | N-cyclobutyl-3-[(2'-oxospiro[furo[2,3-f][1,3]benzodioxole-7,3'-indol]-1'(2'H)-yl)methyl]benzamide | 469.5 |
| 361 | N-[2-(4-fluorophenyl)ethyl]-3-[(2'-oxospiro[furo[2,3-f][1,3]benzodioxole-7,3'-indol]-1'(2'H)-yl)methyl]benzamide | 537.5 |
| 362 | N-(cyclohexylmethyl)-3-[(2'-oxospiro[furo[2,3-f][1,3]benzodioxole-7,3'-indol]-1'(2'H)-yl)methyl]benzamide | 511.6 |
| 363 | N-[2-(4-methylphenyl)ethyl]-3-[(2'-oxospiro[furo[2,3-f][1,3]benzodioxole-7,3'-indol]-1'(2'H)-yl)methyl]benzamide | 533.6 |
| 364 | N-(2-ethylbutyl)-3-[(2'-oxospiro[furo[2,3-f][1,3]benzodioxole-7,3'-indol]-1'(2'H)-yl)methyl]benzamide | 499.6 |
| 365 | N-benzyl-3-[(2'-oxospiro[furo[2,3-f][1,3]benzodioxole-7,3'-indol]-1'(2'H)-yl)methyl]benzamide | 505.5 |
| 366 | N-(2-methoxyethyl)-3-[(2'-oxospiro[furo[2,3-f][1,3]benzodioxole-7,3'-indol]-1'(2'H)-yl)methyl]benzamide | 473.5 |
| 367 | 1'-[3-(morpholin-4-ylcarbonyl)benzyl]spiro[furo[2,3-f][1,3]benzodioxole-7,3'-indol]-2'(1'H)-one | 485.5 |
| 368 | N-(1-benzylpiperidin-4-yl)-3-[(2'-oxospiro[furo[2,3-f][1,3]benzodioxole-7,3'-indol]-1'(2'H)-yl)methyl]benzamide | 588.7 |

-continued

| Compound Number | Name | MS (m/z, M + 1) |
|---|---|---|
| 369 | N-[2-(4-methoxyphenyl)ethyl]-3-[(2'-oxospiro[furo[2,3-f][1,3]benzodioxole-7,3'-indol]-1'(2'H)-yl)methyl]benzamide | 549.6 |
| 370 | 3-[(2'-oxospiro[furo[2,3-f][1,3]benzodioxole-7,3'-indol]-1'(2'H)-yl)methyl]-N-(2-piperidin-1-ylethyl)benzamide | 526.6 |
| 371 | N-(1-cyclohexylethyl)-3-[(2'-oxospiro[furo[2,3-f][1,3]benzodioxole-7,3'-indol]-1'(2'H)-yl)methyl]benzamide | 525.6 |
| 372 | 3-[(2'-oxospiro[furo[2,3-f][1,3]benzodioxole-7,3'-indol]-1'(2'H)-yl)methyl]-N-(2-thienylmethyl)benzamide | 511.6 |
| 373 | 3-[(2'-oxospiro[furo[2,3-f][1,3]benzodioxole-7,3'-indol]-1'(2'H)-yl)methyl]-N-(4-propylphenyl)benzamide | 533.6 |
| 374 | N-(2,4-difluorobenzyl)-3-[(2'-oxospiro[furo[2,3-f][1,3]benzodioxole-7,3'-indol]-1'(2'H)-yl)methyl]benzamide | 541.5 |
| 375 | N-(3,5-difluorophenyl)-3-[(2'-oxospiro[furo[2,3-f][1,3]benzodioxole-7,3'-indol]-1'(2'H)-yl)methyl]benzamide | 527.5 |
| 376 | N-(2,3-dihydro-1H-inden-5-yl)-3-[(2'-oxospiro[furo[2,3-f][1,3]benzodioxole-7,3'-indol]-1'(2'H)-yl)methyl]benzamide | 531.6 |
| 377 | 3-[(2'-oxospiro[furo[2,3-f][1,3]benzodioxole-7,3'-indol]-1'(2'H)-yl)methyl]-N-[4-(trifluoromethyl)benzyl]benzamide | 573.5 |
| 378 | 3-[(2'-oxospiro[furo[2,3-f][1,3]benzodioxole-7,3'-indol]-1'(2'H)-yl)methyl]-N-[2-(2-thienyl)ethyl]benzamide | 525.6 |
| 379 | 3-[(2'-oxospiro[furo[2,3-f][1,3]benzodioxole-7,3'-indol]-1'(2'H)-yl)methyl]-N-(pyridin-3-ylmethyl)benzamide | 506.5 |
| 380 | 3-[(2'-oxospiro[furo[2,3-f][1,3]benzodioxole-7,3'-indol]-1'(2'H)-yl)methyl]-N-[2-(trifluoromethyl)benzyl]benzamide | 573.5 |
| 381 | N-[2-(4-chlorophenyl)ethyl]-3-[(2'-oxospiro[furo[2,3-f][1,3]benzodioxole-7,3'-indol]-1'(2'H)-yl)methyl]benzamide | 554.0 |
| 382 | 3-[(2'-oxospiro[furo[2,3-f][1,3]benzodioxole-7,3'-indol]-1'(2'H)-yl)methyl]-N-(2-pyrrolidin-1-ylethyl)benzamide | 512.6 |
| 383 | N-(3-methylpyridin-2-yl)-3-[(2'-oxospiro[furo[2,3-f][1,3]benzodioxole-7,3'-indol]-1'(2'H)-yl)methyl]benzamide | 506.5 |
| 384 | N-1,3-benzodioxol-5-yl-3-[(2'-oxospiro[furo[2,3-f][1,3]benzodioxole-7,3'-indol]-1'(2'H)-yl)methyl]benzamide | 535.5 |
| 385 | N-(2-morpholin-4-ylethyl)-3-[(2'-oxospiro[furo[2,3-f][1,3]benzodioxole-7,3'-indol]-1'(2'H)-yl)methyl]benzamide | 528.6 |
| 386 | 1'-{3-[(4-pyrimidin-2-ylpiperazin-1-yl)carbonyl]benzyl}spiro[furo[2,3-f][1,3]benzodioxole-7,3'-indol]-2'(1'H)-one | 562.6 |
| 387 | 3-[(2'-oxospiro[furo[2,3-f][1,3]benzodioxole-7,3'-indol]-1'(2'H)-yl)methyl]-N-1,3-thiazol-2-ylbenzamide | 498.5 |
| 388 | N-(6-methoxypyridin-3-yl)-3-[(2'-oxospiro[furo[2,3-f][1,3]benzodioxole-7,3'-indol]-1'(2'H)-yl)methyl]benzamide | 522.5 |
| 389 | N-(3,5-dichlorobenzyl)-3-[(2'-oxospiro[furo[2,3-f][1,3]benzodioxole-7,3'-indol]-1'(2'H)-yl)methyl]benzamide | 574.4 |
| 390 | N-1-naphthyl-3-[(2'-oxospiro[furo[2,3-f][1,3]benzodioxole-7,3'-indol]-1'(2'H)-yl)methyl]benzamide | 541.6 |
| 391 | N-(4,6-dimethylpyridin-2-yl)-3-[(2'-oxospiro[furo[2,3-f][1,3]benzodioxole-7,3'-indol]-1'(2'H)-yl)methyl]benzamide | 520.5 |
| 392 | 3-[(2'-oxospiro[furo[2,3-f][1,3]benzodioxole-7,3'-indol]-1'(2'H)-yl)methyl]-N-pyrimidin-4-ylbenzamide | 493.5 |
| 393 | N-(5-methyl-1,3-thiazol-2-yl)-3-[(2'-oxospiro[furo[2,3-f][1,3]benzodioxole-7,3'-indol]-1'(2'H)-yl)methyl]benzamide | 512.5 |
| 394 | N-(4-methylbenzyl)-3-[(2'-oxospiro[furo[2,3-f][1,3]benzodioxole-7,3'-indol]-1'(2'H)-yl)methyl]benzamide | 519.6 |
| 395 | N-[3-(1H-imidazol-1-yl)propyl]-3-[(2'-oxospiro[furo[2,3-f][1,3]benzodioxole-7,3'-indol]-1'(2'H)-yl)methyl]benzamide | 523.6 |

-continued

| Compound Number | Name | MS (m/z, M + 1) |
|---|---|---|
| 396 | 1'-{3-[(4-methylpiperazin-1-yl)carbonyl]benzyl}spiro[furo[2,3-f][1,3]benzodioxole-7,3'-indol]-2'(1'H)-one | 498.5 |
| 397 | N-(5-cyclopropyl-1,3,4-thiadiazol-2-yl)-3-[(2'-oxospiro[furo[2,3-f][1,3]benzodioxole-7,3'-indol]-1'(2'H)-yl)methyl]benzamide | 539.6 |
| 398 | 3-[(2'-oxospiro[furo[2,3-f][1,3]benzodioxole-7,3'-indol]-1'(2'H)-yl)methyl]-N-1,3,4-thiadiazol-2-ylbenzamide | 499.5 |
| 399 | N-(3,3-dimethylbutyl)-3-[(2'-oxospiro[furo[2,3-f][1,3]benzodioxole-7,3'-indol]-1'(2'H)-yl)methyl]benzamide | 499.6 |
| 400 | N-(4-morpholin-4-ylphenyl)-3-[(2'-oxospiro[furo[2,3-f][1,3]benzodioxole-7,3'-indol]-1'(2'H)-yl)methyl]benzamide | 576.6 |
| 401 | N-[(1-ethylpyrrolidin-2-yl)methyl]-3-[(2'-oxospiro[furo[2,3-f][1,3]benzodioxole-7,3'-indol]-1'(2'H)-yl)methyl]benzamide | 526.6 |
| 402 | N-(2-cyanoethyl)-3-[(2'-oxospiro[furo[2,3-f][1,3]benzodioxole-7,3'-indol]-1'(2'H)-yl)methyl]benzamide | |
| 403 | N-(2,2-diphenylethyl)-3-[(2'-oxospiro[furo[2,3-f][1,3]benzodioxole-7,3'-indol]-1'(2'H)-yl)methyl]benzamide | 595.4 |

EXAMPLE 10

Synthesis of 1'-(4-fluorobenzyl)spiro[furo[2,3-f][1,3]benzodioxole-7,3'-indol]-2'(1'H)-one

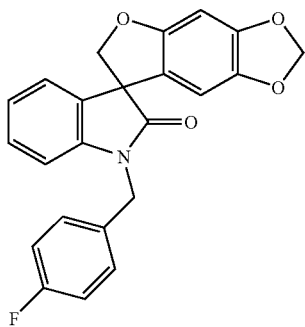

To a solution of spiro[furo[2,3-f][1,3]benzodioxole-7,3'-indol]-2'(1'H)-one (0.16 g, 0.57 mmol) in ethylmethylketone (5.00 mL) was added $Cs_2CO_3$ (0.40 g, 1.20 mmol). The reaction mixture was stirred at ambient temperature for 15 min followed by the addition of 4-fluorobenzyl bromide (0.20 g, 1.0 mmol). The reaction mixture was refluxed for 4 h. After the completion of the reaction, the mixture was filtered and the solvent was removed under reduced pressure. The residue was recrystallized from EtOAc/Hexane to yield the title compound (0.111 g) as a white solid in 50% yield: MS (ES+) m/z 390.3 (M+1).

EXAMPLE 10.1

The compounds listed in the following table were synthesized using the similar procedure as described in EXAMPLE 10. As previously noted, the compound numbers listed below do not correspond to the compound numbers provided in the general Reaction Schemes above.

| Compound Number | Name | MS (m/z, M + 1) |
|---|---|---|
| 404 | 1'-{[1-(2,6-difluorobenzyl)-1H-1,2,3-triazol-4-yl]methyl}spiro[furo[2,3-f][1,3]benzodioxole-7,3'-indol]-2'(1'H)-one | 489.3 |
| 405 | 1'-prop-2-yn-1-ylspiro[furo[2,3-f][1,3]benzodioxole-7,3'-indol]-2'(1'H)-one | 320.3 |
| 406 | 1'-benzylspiro[furo[2,3-f][1,3]benzodioxole-7,3'-indol]-2'(1'H)-one | 372.2 |
| 407 | 1'-{[6-(trifluoromethyl)pyridin-3-yl]methyl}spiro[furo[2,3-f][1,3]benzodioxole-7,3'-indol]-2'(1'H)-one | 441.2 |
| 408 | 1'-(3,5-difluorobenzyl)spiro[furo[2,3-f][1,3]benzodioxole-7,3'-indol]-2'(1'H)-one | 408.3 |
| 409 | 1'-(3-nitrobenzyl)spiro[furo[2,3-f][1,3]benzodioxole-7,3'-indol]-2'(1'H)-one | 417.2 |
| 410 | 1'-[(6-chloropyridin-3-yl)methyl]spiro[furo[2,3-f][1,3]benzodioxole-7,3'-indol]-2'(1'H)-one | 407.2 |
| 411 | 1'-(tetrahydro-2H-pyran-2-ylmethyl)spiro[furo[2,3-f][1,3]benzodioxole-7,3'-indol]-2'(1'H)-one | 380.2 |
| 412 | 1'-(3-fluorobenzyl)spiro[furo[2,3-f][1,3]benzodioxole-7,3'-indol]-2'(1'H)-one | 390.3 |
| 413 | 1'-(tetrahydrofuran-2-ylmethyl)spiro[furo[2,3-f][1,3]benzodioxole-7,3'-indol]-2'(1'H)-one | 365.2 |
| 414 | 3-[(2'-oxospiro[furo[2,3-f][1,3]benzodioxole-7,3'-indol]-1'(2'H)-yl)methyl]benzonitrile | 397.2 |
| 415 | 1'-(2,3-dihydro-1,4-benzodioxin-2-ylmethyl)spiro[furo[2,3-f][1,3]benzodioxole-7,3'-indol]-2'(1'H)-one | 430.3 |
| 416 | 1'-(2-ethoxyethyl)spiro[furo[2,3-f][1,3]benzodioxole-7,3'-indol]-2'(1'H)-one | 354.2 |
| 417 | 1'-[(2E)-pent-2-en-1-yl]spiro[furo[2,3-f][1,3]benzodioxole-7,3'-indol]-2'(1'H)-one | 350.2 |
| 418 | 1'-hex-5-en-1-ylspiro[furo[2,3-f][1,3]benzodioxole-7,3'-indol]-2'(1'H)-one | 364.3 |
| 419 | 1'-(cyclobutylmethyl)spiro[furo[2,3-f][1,3]benzodioxole-7,3'-indol]-2'(1'H)-one | 350.2 |
| 420 | 1'-pent-2-yn-1-ylspiro[furo[2,3-f][1,3]benzodioxole-7,3'-indol]-2'(1'H)-one | 348.2 |
| 421 | 1'-(5-chloropentyl)spiro[furo[2,3-f][1,3]benzodioxole-7,3'-indol]-2'(1'H)-one | 386.2 |
| 422 | 1'-[4-(1H-pyrazol-1-yl)benzyl]spiro[furo[2,3-f][1,3]benzodioxole-7,3'-indol]-2'(1'H)-one | 438.3 |

| Compound Number | Name | MS (m/z, M + 1) |
|---|---|---|
| 423 | 1'-[(7-methoxy-2-oxo-2H-1,4-benzoxazin-3-yl)methyl]spiro[furo[2,3-f][1,3]benzodioxole-7,3'-indol]-2'(1'H)-one | 471.3 |
| 424 | 1'-(4-fluorobutyl)spiro[furo[2,3-f][1,3]benzodioxole-7,3'-indol]-2'(1'H)-one | 356.2 |
| 425 | 1'-(5-methylhexyl)spiro[furo[2,3-f][1,3]benzodioxole-7,3'-indol]-2'(1'H)-one | 380.3 |
| 426 | 1'-[(3Z)-4-methylhex-3-en-1-yl]spiro[furo[2,3-f][1,3]benzodioxole-7,3'-indol]-2'(1'H)-one | 378.2 |
| 427 | 1'-[(5-methyl-2-phenyl-2H-1,2,3-triazol-4-yl)methyl]spiro[furo[2,3-f][1,3]benzodioxole-7,3'-indol]-2'(1'H)-one | 453.2 |
| 428 | 1'-{[5-(trifluoromethyl)-2-furyl]methyl}spiro[furo[2,3-f][1,3]benzodioxole-7,3'-indol]-2'(1'H)-one | 430.2 |
| 429 | 1'-(3,4-dihydro-2H-1,5-benzodioxepin-7-ylmethyl)spiro[furo[2,3-f][1,3]benzodioxole-7,3'-indol]-2'(1'H)-one | 444.3 |
| 430 | 1'-(biphenyl-4-ylmethyl)spiro[furo[2,3-f][1,3]benzodioxole-7,3'-indol]-2'(1'H)-one | 448.2 |
| 431 | 4'-[(2'-oxospiro[furo[2,3-f][1,3]benzodioxole-7,3'-indol]-1'(2'H)-yl)methyl]biphenyl-2-carbonitrile | 473.3 |
| 432 | 1'-(2-bromoethyl)spiro[furo[2,3-f][1,3]benzodioxole-7,3'-indol]-2'(1'H)-one | 389.1 |
| 433 | 1'-(1H-1,2,3-triazol-4-ylmethyl)spiro[furo[2,3-f][1,3]benzodioxole-7,3'-indol]-2'(1'H)-one | 363.2 |
| 434 | 1'-(biphenyl-2-ylmethyl)spiro[furo[2,3-f][1,3]benzodioxole-7,3'-indol]-2'(1'H)-one | 448.3 |
| 435 | 1'-(diphenylmethyl)spiro[furo[2,3-f][1,3]benzodioxole-7,3'-indol]-2'(1'H)-one | 448.3 |
| 436 | 5-(2'-oxospiro[furo[2,3-f][1,3]benzodioxole-7,3'-indol]-1'(2'H)-yl)pentanenitrile | 363.2 |
| 437 | 1'-[2-(2-methoxyethoxy)ethyl]spiro[furo[2,3-f][1,3]benzodioxole-7,3'-indol]-2'(1'H)-one | 384.2 |
| 438 | 1'-(cyclopropylmethyl)spiro[furo[2,3-f][1,3]benzodioxole-7,3'-indol]-2'(1'H)-one | 336.2 |
| 439 | 1'-(4,4,4-trifluorobutyl)spiro[furo[2,3-f][1,3]benzodioxole-7,3'-indol]-2'(1'H)-one | 392.2 |
| 440 | ethyl 1-[2-(2'-oxospiro[furo[2,3-f][1,3]benzodioxole-7,3'-indol]-1'(2'H)-yl)ethyl]-1H-1,2,3-triazole-5-carboxylate | 449.3 |
| 441 | ethyl 1-[2-(2'-oxospiro[furo[2,3-f][1,3]benzodioxole-7,3'-indol]-1'(2'H)-yl)ethyl]-1H-1,2,3-triazole-4-carboxylate | 449.3 |
| 442 | diethyl [2-(2'-oxospiro[furo[2,3-f][1,3]benzodioxole-7,3'-indol]-1'(2'H)-yl)ethyl]phosphonate | 446.1 |
| 443 | 1'-(1,3-thiazol-4-ylmethyl)spiro[furo[2,3-f][1,3]benzodioxole-7,3'-indol]-2'(1'H)-one | 379.3 |
| 444 | 1'-[(5-chloro-1-benzothien-3-yl)methyl]spiro[furo[2,3-f][1,3]benzodioxole-7,3'-indol]-2'(1'H)-one | 462.1 |
| 445 | 1'-(pyridin-2-ylmethyl)spiro[furo[2,3-f][1,3]benzodioxole-7,3'-indol]-2'(1'H)-one | 373.1 |
| 446 | 1'-(pyridin-4-ylmethyl)spiro[furo[2,3-f][1,3]benzodioxole-7,3'-indol]-2'(1'H)-one | 373.1 |
| 447 | 1'-(pyridin-3-ylmethyl)spiro[furo[2,3-f][1,3]benzodioxole-7,3'-indol]-2'(1'H)-one | 373.1 |
| 448 | 1'-[2-(1H-pyrrol-1-yl)ethyl]spiro[furo[2,3-f][1,3]benzodioxole-7,3'-indol]-2'(1'H)-one | 375.2 |
| 449 | 1'-{[4-chloro-2-(trifluoromethyl)quinolin-6-yl]methyl}spiro[furo[2,3-f][1,3]benzodioxole-7,3'-indol]-2'(1'H)-one | 525.1 |
| 450 | 1'-(4-fluoro-3-methylbenzyl)spiro[furo[2,3-f][1,3]benzodioxole-7,3'-indol]-2'(1'H)-one | 404.3 |
| 451 | 1'-(5-fluoro-2-methylbenzyl)spiro[furo[2,3-f][1,3]benzodioxole-7,3'-indol]-2'(1'H)-one | 404.3 |
| 452 | 1'-[(2-methyl-1,3-thiazol-4-yl)methyl]spiro[furo[2,3-f][1,3]benzodioxole-7,3'-indol]-2'(1'H)-one | 393.2 |
| 453 | 1'-(1,3-benzothiazol-2-ylmethyl)spiro[furo[2,3-f][1,3]benzodioxole-7,3'-indol]-2'(1'H)-one | 329.3 |
| 454 | 1'-(2,5-difluorobenzyl)spiro[furo[2,3-f][1,3]benzodioxole-7,3'-indol]-2'(1'H)-one | 408.2 |
| 455 | 1'-[4-(1H-pyrrol-1-yl)benzyl]spiro[furo[2,3-f][1,3]benzodioxole-7,3'-indol]-2'(1'H)-one | 437.3 |
| 456 | 1'-[3-(1H-pyrrol-1-yl)benzyl]spiro[furo[2,3-f][1,3]benzodioxole-7,3'-indol]-2'(1'H)-one | 437.3 |
| 457 | 1'-(2,1,3-benzothiadiazol-4-ylmethyl)spiro[furo[2,3-f][1,3]benzodioxole-7,3'-indol]-2'(1'H)-one | 430.3 |
| 458 | 1'-(2,1,3-benzothiadiazol-5-ylmethyl)spiro[furo[2,3-f][1,3]benzodioxole-7,3'-indol]-2'(1'H)-one | 430.3 |
| 459 | 1'-[(1-methyl-1H-1,2,3-benzotriazol-5-yl)methyl]spiro[furo[2,3-f][1,3]benzodioxole-7,3'-indol]-2'(1'H)-one | 427.2 |
| 460 | 1'-[(4-chlorophenoxy)methyl]spiro[furo[2,3-f][1,3]benzodioxole-7,3'-indol]-2'(1'H)-one | 422.2 |
| 461 | 1'-[2-fluoro-3-(trifluoromethyl)benzyl]spiro[furo[2,3-f][1,3]benzodioxole-7,3'-indol]-2'(1'H)-one | 458.1 |
| 462 | 1'-[2-fluoro-6-(trifluoromethyl)benzyl]spiro[furo[2,3-f][1,3]benzodioxole-7,3'-indol]-2'(1'H)-one | 458.1 |
| 463 | 1'-[3-fluoro-4-(trifluoromethyl)benzyl]spiro[furo[2,3-f][1,3]benzodioxole-7,3'-indol]-2'(1'H)-one | 458.1 |
| 464 | 1'-[4-fluoro-3-(trifluoromethyl)benzyl]spiro[furo[2,3-f][1,3]benzodioxole-7,3'-indol]-2'(1'H)-one | 458.1 |
| 465 | 1'-[2-fluoro-5-(trifluoromethyl)benzyl]spiro[furo[2,3-f][1,3]benzodioxole-7,3'-indol]-2'(1'H)-one | 458.1 |
| 466 | 1'-[4-fluoro-2-(trifluoromethyl)benzyl]spiro[furo[2,3-f][1,3]benzodioxole-7,3'-indol]-2'(1'H)-one | 458.1 |
| 467 | 1'-[5-fluoro-2-(trifluoromethyl)benzyl]spiro[furo[2,3-f][1,3]benzodioxole-7,3'-indol]-2'(1'H)-one | 458.1 |
| 468 | 1'-[2-fluoro-4-(trifluoromethyl)benzyl]spiro[furo[2,3-f][1,3]benzodioxole-7,3'-indol]-2'(1'H)-one | 458.1 |
| 469 | 1'-[3-(1H-pyrrol-1-yl)propyl]spiro[furo[2,3-f][1,3]benzodioxole-7,3'-indol]-2'(1'H)-one | 389.2 |
| 470 | 1'-[(2,2,3,3-tetrafluorocyclobutyl)methyl]spiro[furo[2,3-f][1,3]benzodioxole-7,3'-indol]-2'(1'H)-one | 422.1 |
| 471 | 1'-[(3-methyl-5-phenylisoxazol-4-yl)methyl]spiro[furo[2,3-f][1,3]benzodioxole-7,3'-indol]-2'(1'H)-one | 453.3 |
| 472 | 1'-[2-(diethylamino)ethyl]spiro[furo[2,3-f][1,3]benzodioxole-7,3'-indol]-2'(1'H)-one | 381.2 |
| 473 | 1'-(2,3-difluorobenzyl)spiro[furo[2,3-f][1,3]benzodioxole-7,3'-indol]-2'(1'H)-one | 408.1 |
| 474 | 1'-[(1-bromo-2-naphthyl)methyl]spiro[furo[2,3-f][1,3]benzodioxole-7,3'-indol]-2'(1'H)-one | 501.2 |
| 475 | 1'-[(7-methoxy-2-oxo-2H-chromen-4-yl)methyl]spiro[furo[2,3-f][1,3]benzodioxole-7,3'-indol]-2'(1'H)-one | 470.3 |
| 476 | 1'-[(benzyloxy)methyl]spiro[furo[2,3-f][1,3]benzodioxole-7,3'-indol]-2'(1'H)-one | 402.3 |
| 477 | 1'-[2-(2,5,5-trimethyl-1,3-dioxan-2-yl)ethyl]spiro[furo[2,3-f][1,3]benzodioxole-7,3'-indol]-2'(1'H)-one | 438.2 |
| 478 | 1'-[(6-fluoro-4H-1,3-benzodioxin-8-yl)methyl]spiro[furo[2,3-f][1,3]benzodioxole-7,3'-indol]-2'(1'H)-one | 448.2 |
| 479 | 1'-allylspiro[furo[2,3-f][1,3]benzodioxole-7,3'-indol]-2'(1'H)-one | 322.3 |
| 480 | 1'-(1-naphthylmethyl)spiro[furo[2,3-f][1,3]benzodioxole-7,3'-indol]-2'(1'H)-one | 423.3 |
| 481 | 1'-[3-fluoro-5-(trifluoromethyl)benzyl]spiro[furo[2,3-f][1,3]benzodioxole-7,3'-indol]-2'(1'H)-one | 458.1 |
| 482 | 1'-(2,4-difluorobenzyl)spiro[furo[2,3-f][1,3]benzodioxole-7,3'-indol]-2'(1'H)-one | 408.1 |
| 483 | 1'-(2,6-difluorobenzyl)spiro[furo[2,3-f][1,3]benzodioxole-7,3'-indol]-2'(1'H)-one | 408.3 |
| 484 | 1'-[(5-phenyl-1,3-oxazol-4-yl)methyl]spiro[furo[2,3-f][1,3]benzodioxole-7,3'-indol]-2'(1'H)-one | 439.2 |
| 485 | 1'-(3,5,5-trimethylhexyl)spiro[furo[2,3-f][1,3]benzodioxole-7,3'-indol]-2'(1'H)-one | 408.3 |
| 486 | 1'-(2-ethylbutyl)spiro[furo[2,3-f][1,3]benzodioxole-7,3'-indol]-2'(1'H)-one | 366.3 |
| 487 | 1'-(4-methylpentyl)spiro[furo[2,3-f][1,3]benzodioxole-7,3'-indol]-2'(1'H)-one | 366.3 |
| 488 | 1'-(3-methoxybenzyl)spiro[furo[2,3-f][1,3]benzodioxole-7,3'-indol]-2'(1'H)-one | 402.3 |
| 489 | 1'-(3-methylbutyl)spiro[furo[2,3-f][1,3]benzodioxole-7,3'-indol]-2'(1'H)-one | 352.2 |
| 490 | 1'-(3-methylbut-2-en-1-yl)spiro[furo[2,3-f][1,3]benzodioxole-7,3'-indol]-2'(1'H)-one | 350.2 |
| 491 | 1'-pent-4-en-1-ylspiro[furo[2,3-f][1,3]benzodioxole-7,3'-indol]-2'(1'H)-one | 350.2 |
| 492 | 4-(2'-oxospiro[furo[2,3-f][1,3]benzodioxole-7,3'-indol]-1'(2'H)-yl)butanenitrile | 349.1 |

-continued

| Compound Number | Name | MS (m/z, M + 1) |
|---|---|---|
| 493 | 1'-[4-(1H-1,2,4-triazol-1-yl)benzyl]spiro[furo[2,3-f][1,3]benzodioxole-7,3'-indol]-2'(1'H)-one | 439.2 |
| 494 | 1'-(1,3-benzodioxol-5-ylmethyl)spiro[furo[2,3-f][1,3]benzodioxole-7,3'-indol]-2'(1'H)-one | 416.2 |
| 495 | 1'-[4,4-bis(4-fluorophenyl)butyl]spiro[furo[2,3-f][1,3]benzodioxole-7,3'-indol]-2'(1'H)-one | 526.2 |
| 496 | 1'-[(2-methylcyclopropyl)methyl]spiro[furo[2,3-f][1,3]benzodioxole-7,3'-indol]-2'(1'H)-one | 350.4 |
| 497 | 1'-(3-cyclopropylpropyl)spiro[furo[2,3-f][1,3]benzodioxole-7,3'-indol]-2'(1'H)-one | 364.3 |
| 498 | 1'-hexylspiro[furo[2,3-f][1,3]benzodioxole-7,3'-indol]-2'(1'H)-one | 366.3 |
| 499 | 1'-[(2-cyclopropyl-6-hydroxypyrimidin-4-yl)methyl]spiro[furo[2,3-f][1,3]benzodioxole-7,3'-indol]-2'(1'H)-one | 430.3 |

EXAMPLE 10.2

Synthesis of 1'-(piperidin-4-ylmethyl)spiro[furo[2,3-f][1,3]benzodioxole-7,3'-indol]-2'(1'H)-one

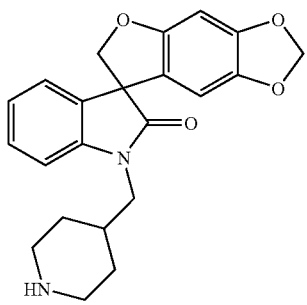

Following the procedure as described in EXAMPLE 10, and making non-critical variations using tert-butyl 4-(bromomethyl)peridine-1-carboxylate to replace 4-fluorobenzyl bromide, the title compound was obtained in 67% yield as a white solid upon acidification of the intermediate with 33% HBr: MS (ES+) m/z 379.3 (M+1).

EXAMPLE 10.3

Synthesis of 1'-[(1-methylpiperidin-4-yl)methyl]spiro[furo[2,3-f][1,3]benzodioxole-7,3'-indol]-2'(1'H)-one hydrochloride

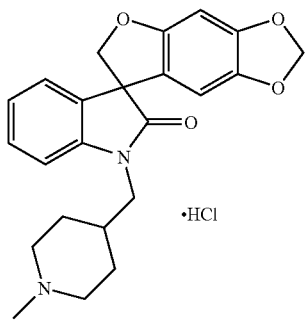

To a solution of 1'-(piperidin-4-ylmethyl)spiro[furo[2,3-f][1,3]benzodioxole-7,3'-indol]-2'(1'H)-one (0.19 g, 0.50 mmol) in dichloroethane (5.00 mL) was added formaldehyde (0.10 mL, 33% solution, 0.03 g, 1.10 mmol) and sodium triacetoxyborohydride (0.30 g, 1.40 mmol). After stirring at ambient temperature for 20 hours, the reaction mixture was diluted with of dichloromethane (20.0 mL) and washed with water (2×20.0 mL). The organic layer was dried over sodium sulfate and filtered. The filtrate was concentrated in vacuo to dryness. The residue was subjected to column chromatography and the product was dissolved in dichloromethane (5.00 mL) and excess of HCl in ether was added. The precipitate was filtered to give the title compound in 20% yield: MS (ES+) m/z 393.3 (M+1).

EXAMPLE 10.4

Synthesis of 1'-[(1-ethylpiperidin-4-yl)methyl]spiro[furo[2,3-f][1,3]benzodioxole-7,3'-indol]-2'(1'H)-one hydrochloride

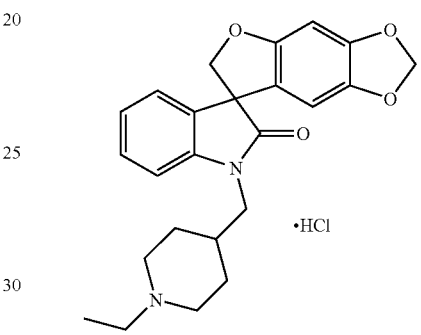

Following the procedure as described in EXAMPLE 10.3, and making non-critical variations using acetaldehyde to replace formalin, the title compound was obtained in 20% yield as a white solid: MS (ES+) m/z 407.3 (M+1).

EXAMPLE 10.5

Synthesis of 1'-[(1-cyclohexyllpiperidin-4-yl)methyl]spiro[furo[2,3-f][1,3]benzodioxole-7,3'-indol]-2'(1'H)-one hydrochloride

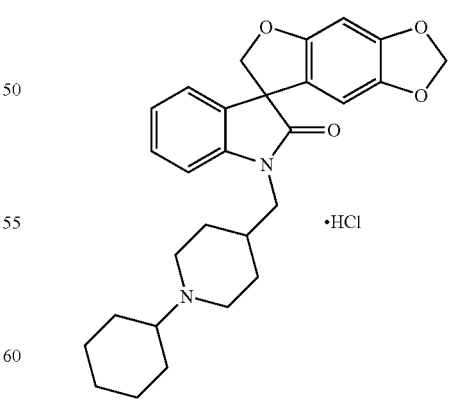

Following the procedure as described in EXAMPLE 10.3, and making non-critical variations using cyclohexanone to replace formalin, the title compound was obtained 24% yield as a white solid: MS (ES+) m/z 461.5 (M+1).

EXAMPLE 10.6

Synthesis of 1'-{[1-cyclopropylmethyl)piperidin-4-yl]methyl}spiro[furo[2,3-f][1,3]benzodioxole-7,3'-indol]-2'(1'H)-one hydrochloride

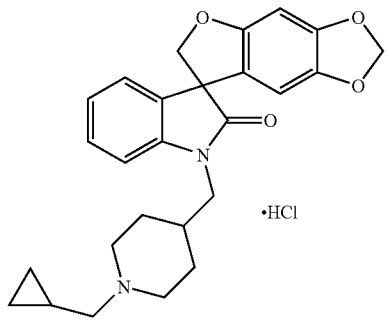

Following the procedure as described in EXAMPLE 10.3, and making non-critical variations using cyclopropanecarbaldehyde to replace formalin, the title compound was obtained in 14% yield as a white solid: MS (ES+) m/z 433.5 (M+1).

EXAMPLE 10.7

Synthesis of 1'-[(1-cyclopentylpiperidin-4-yl)methyl]spiro[furo[2,3-f][1,3]benzodioxole-7,3'-indol]-2'(1'H)-one hydrochloride

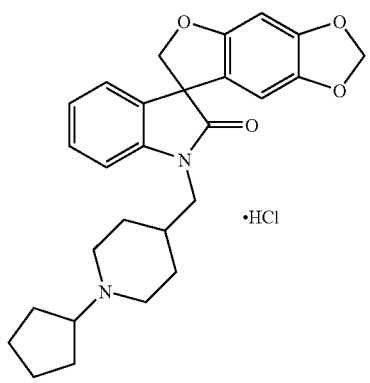

Following the procedure as described in EXAMPLE 10.3, and making non-critical variations using cyclopentanone to replace formalin, the title compound was obtained in 37% yield as a white solid: MS (ES+) m/z 447.3 (M+1).

EXAMPLE 10.8

Synthesis of 1-{[1-(pyridine-3-ylmethyl)piperidin-4-yl]methyl}spiro[furo[2,3-f][1,3]benzodioxole-7,3'-indol]-2'(1'H)-one hydrochloride

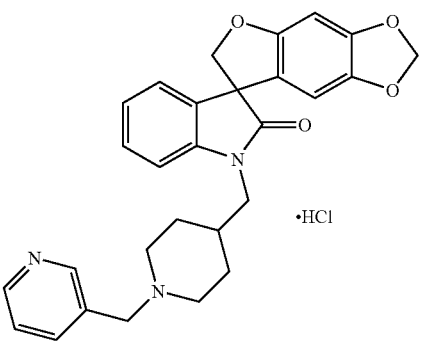

Following the procedure as described in EXAMPLE 10.3, and making non-critical variations using nicotinaldehyde to replace formalin, the title compound was obtained in 11% yield as a white solid: MS (ES+) m/z 470.4 (M+1).

EXAMPLE 10.9

Synthesis of 1'-{[1-(3-methylbutyl)piperidin-4-yl]methyl}spiro[furo[2,3-f][1,3]benzodioxole-7,3'-indol]-2'(1'H)-one hydrochloride

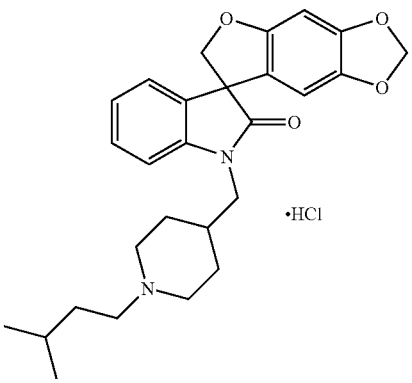

Following the procedure as described in EXAMPLE 10.3, and making non-critical variations using 3-methylbutanal to replace formalin, the title compound was obtained in 15% yield as a white solid: MS (ES+) m/z 449.5 (M+1).

EXAMPLE 10.10

Synthesis of 1'-{[1-(1-ethylpropyl)piperidin-4-yl]methyl}spiro[furo[2,3-f][1,3]benzodioxole-7,3'-indol]-2'(1'H)-one hydrochloride

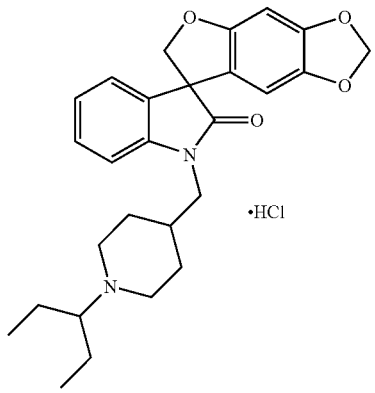

Following the procedure as described in EXAMPLE 10.3, and making non-critical variations using pentan-3-one to replace formalin, the title compound was obtained in 17% yield as a white solid: MS (ES+) m/z 449.4 (M+1).

EXAMPLE 10.11

Synthesis of 1'-[(1-cyclobutylpiperidin-4-yl)methyl]spiro[furo[2,3-f][1,3]benzodioxole-7,3'-indol]-2'(1'H)-one hydrochloride

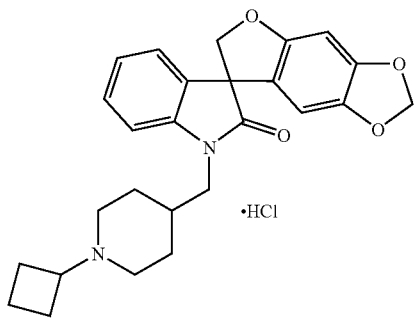

Following the procedure as described in EXAMPLE 10.3, and making non-critical variations using cyclobutanone to replace formalin, the title compound was obtained in 31% yield as a white solid: MS (ES+) m/z 433.4 (M+1).

EXAMPLE 10.12

Synthesis of 1'-[(1-isopropyllpiperidin-4-yl)methyl]spiro[furo[2,3-f][1,3]benzodioxole-7,3'-indol]-2'(1'H)-one hydrochloride

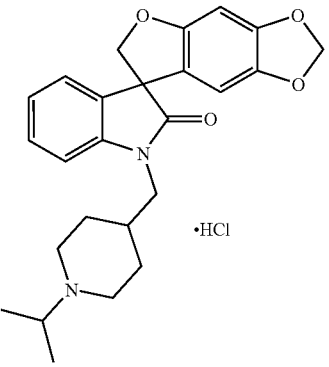

Following the procedure as described in EXAMPLE 10.3, and making non-critical variations using acetone to replace formalin, the title compound was obtained in 31% yield as a white solid: $^1$H NMR (300 MHz, DMSO-$d_6$) δ 10.36 (s, 1H), 7.79-6.87 (m, 4H), 6.82-6.48 (m, 1H), 6.38-6.15 (m, 1H), 5.89 (s, 2H), 4.67 (ABq, 2H), 4.12 (s, 1H), 3.79-0.60 (m, 16H); MS (ES+) m/z 421.4 (M+1).

EXAMPLE 10.13

Synthesis of 1'-{[1-(pyridin-2-ylmethyl)piperidin-4-yl]methyl}spiro[furo[2,3-f][1,3]benzodioxole-7,3'-indol]-2'(1'H)-one hydrochloride

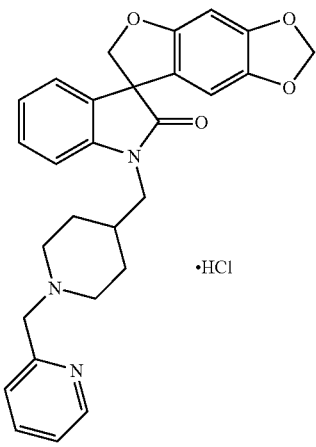

Following the procedure as described in EXAMPLE 10.3, and making non-critical variations using picolinaldehyde to replace formalin, the title compound was obtained in 15% yield as a white solid: MS (ES+) m/z 470.4 (M+1).

EXAMPLE 10.14

Synthesis of 1'-{[1-(2-thienylmethyl)piperidin-4-yl]methyl}spiro[furo[2,3-f][1,3]benzodioxole-7,3'-indol]-2'(1'H)-one hydrochloride

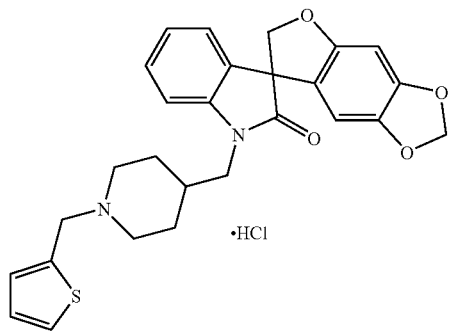

Following the procedure as described in EXAMPLE 10.3, and making non-critical variations using thiophene-2-carbaldehyde to replace formalin, the title compound was obtained in 21% yield as a white solid: MS (ES+) m/z 475.3 (M+1).

EXAMPLE 10.15

Synthesis of 1'-({1-[3-(methylthio)propyl]piperidin-4-yl}methyl)spiro[furo[2,3-f][1,3]benzodioxole-7,3'-indol]-2'(1'H)-one hydrochloride

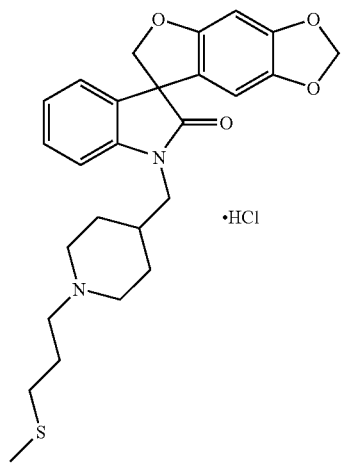

Following the procedure as described in EXAMPLE 10.3, and making non-critical variations using 3-(methylthio)propanal to replace formalin, the title compound was obtained in 7% yield as a white solid: MS (ES+) m/z 467.5 (M+1).

EXAMPLE 10.16

Synthesis of 1'-{[1-(tetrahydro-2H-pyran-4-yl)piperidin-4-yl]methyl}spiro[furo[2,3-f][1,3]benzodioxole-7,3'-indol]-2'(1'H)-one hydrochloride

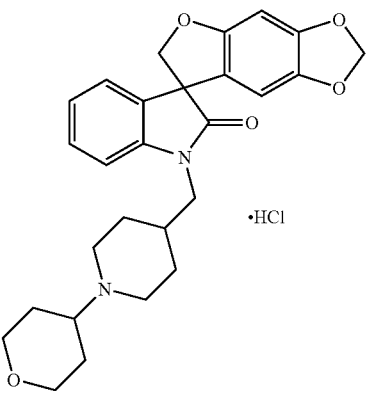

Following the procedure as described in EXAMPLE 10.3, and making non-critical variations using tetrahydro-4H-pyran-4-one to replace formalin, the title compound was obtained in 33% yield as a white solid: MS (ES+) m/z 463.4 (M+1).

EXAMPLE 10.17

Synthesis of 1'-{[1-(3,3-dimethylbutyl)piperidin-4-yl]methyl}spiro[furo[2,3-f][1,3]benzodioxole-7,3'-indol]-2'(1'H)-one hydrochloride

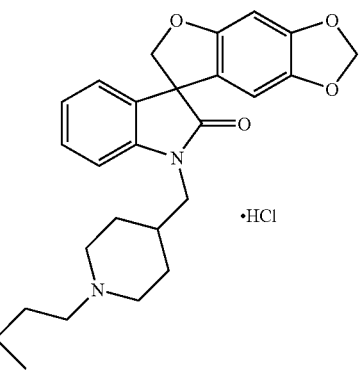

Following the procedure as described in EXAMPLE 10.3, and making non-critical variations using 3,3-dimethylbutanal to replace formalin, the title compound was obtained in 19% yield as a white solid: MS (ES+) m/z 463.5 (M+1).

EXAMPLE 10.18

Synthesis of tert-butyl 4-[(5,5-dimethyl-2'-oxo-5,6-dihydrospiro[benzo[1,2-b:5,4-b']difuran-3,3'-indol]-1'(2'H)-yl)methyl]piperidine-1-carboxylate

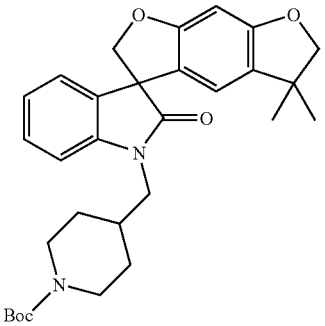

Following the procedure as described in EXAMPLE 10, and making non-critical variations using 5,5-dimethyl-5,6-dihydrospiro[benzo[1,2-b:5,4-b']difuran-3,3'-indol]-2'(1'H)-one to replace spiro[furo[2,3-f][1,3]benzodioxole-7,3'-indol]-2'(1'H)-one, and tert-butyl 4-(tosyloxymethyl)piperidine-1'-carboxylate to replace 4-fluorobenzyl bromide, the title compound was obtained in 70% yield: mp 65-75° C.; $^1$H NMR (300 MHz, CDCl$_3$) δ 7.30 (td, 1H), 7.18 (d, 1H), 7.05 (t, 1H), 6.89 (d, 1H), 6.38 (s, 1H), 6.28 (s, 1H), 4.88 (d, 1H), 4.64 (d, 1H), 4.18 (s, 2H), 4.17-4.01 (br, 2H), 3.74-3.53 (m, 2H), 2.74-2.59 (m, 2H), 2.11-1.92 (m, 1H), 1.70-1.59 (m, 2H), 1.43 (s, 9H), 1.37-1.19 (m, 2H), 1.17 (s, 3H), 1.14 (s, 3H); $^{13}$C NMR (75 MHz, CDCl$_3$) δ 178.0, 161.3, 161.0, 154.7, 142.8, 132.6, 129.9, 128.7, 124.2, 123.3, 120.3, 116.2, 108.5, 93.4, 85.4, 80.6, 79.5, 57.7, 45.7, 41.3, 35.0, 30.0, 28.4, 27.8, 27.5; MS (ES+) m/z 527.5 (M+23).

EXAMPLE 10.19

Synthesis of 5,5-dimethyl-1'-(piperidin-4-ylmethyl)-5,6-dihydrospiro[benzo[1,2-b:5,4-b']difuran-3,3'-indol]-2'(1'H)-one hydrochloride

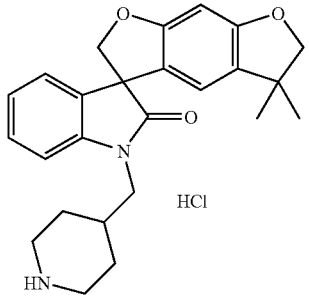

To a stirred solution of tert-butyl 4-[(5,5-dimethyl-2'-oxo-5,6-dihydrospiro[benzo[1,2-b:5,4-b]difuran-3,3'-indol]-1'(2'H)-yl)methyl]piperidine-1'-carboxylate (80 mg, 0.16 mmol) in 10.0 mL dichloromethane was added hydrobromic acid (0.50 mL of hydrobromic acid ≧33% in glacial acetic acid, 1.60 mmol) slowly at 0° C. The mixture was stirred at ambient temperature for one hour and concentrated in vacuo to dryness. The residue was treated with 10.0 mL of 2 N sodium hydroxide solution and extracted with dichloromethane (3×30.0 mL). The combined organic layers was washed with brine (100 mL), dried over anhydrous sodium sulfate and filtered. The filtrate was concentrated in vacuo to dryness. The residue was subjected to column chromatography (2% methanol in ethyl acetate) to give 5,5-dimethyl-1'-(piperidin-4-ylmethyl)-5,6-dihydrospiro[benzo[1,2-b:5,4-b']difuran-3,3'-indol]-2'(1'H)-one (0.03 g, 46%), which was treated with 2.0 M HCl in diethyl ether to give the title compound: $^1$H NMR (300 MHz, CD$_3$OD) δ 7.41 (td, 1H), 7.25-7.12 (m, 3H), 6.43 (s, 1H), 6.37 (s, 1H), 4.87 (d, 1H), 4.72 (d, 1H), 4.23 (s, 2H), 3.80 (d, 2H), 3.51-3.38 (m, 2H), 3.11-2.94 (m, 2H), 2.39-2.19 (m, 1H), 2.06-1.94 (m, 2H), 1.67-1.49 (m, 2H), 1.22 (s, 3H), 1.19 (s, 3H); $^{13}$C NMR (75 MHz, CD$_3$OD) δ 181.4, 163.9, 163.4, 144.7, 134.7, 132.3, 131.0, 125.9, 125.8, 122.6, 118.4, 111.3, 94.9, 87.4, 82.6, 60.2, 46.7, 45.7, 45.6, 43.3, 34.6, 28.8, 28.7, 28.6; MS (ES+) m/z 405.4 (M+1).

EXAMPLE 10.20

Synthesis of 7'-fluoro-1'-[(1-isopropylpiperidin-4-yl)methyl]spiro[furo[2,3-f][1,3]benzodioxole-7,3'-indol]-2'(1'H)-one hydrochloride

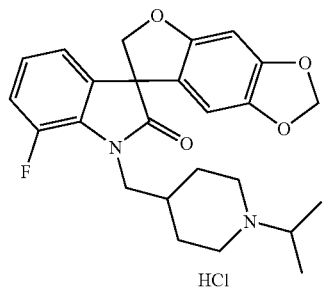

A. Following the procedure as described in EXAMPLES 10.18 and 10.19, and making non-critical variations using 7'-fluorospiro[furo[2,3-f][1,3]benzodioxole-7,3'-indol]-2'(1'H)-one to replace 5,5-dimethyl-5,6-dihydrospiro[benzo[1,2-b:5,4-b']difuran-3,3'-indol]-2'(1'H)-one, 7'-fluoro-1'-(piperidin-4-ylmethyl)spiro[furo[2,3-f][1,3]benzodioxole-7,3'-indol]-2'(1'H)-one was obtained and used in the next step.

B. To a stirred solution of 7'-fluoro-1'-(piperidin-4-ylmethyl)spiro[furo[2,3-f][1,3]benzodioxole-7,3'-indol]-2'(1H)-one (120 mg, 0.28 mmol) and triethylamine (3.9 µL, 0.028 mmol) in 5.00 mL dichloromethane was added acetone (4.1 µL, 0.56 mmol) followed with sodium triacetoxyborohydride (124 mg, 0.56 mmol) at ambient temperature. The mixture was stirred at ambient temperature overnight, quenched with water (10.0 mL). The mixture was extracted with dichloromethane (3×30.0 mL). The combined organic layers was dried over anhydrous sodium sulfate and filtered. The filtrate was concentrated in vacuo. The residue was subjected to column chromatography (2% methanol in ethyl acetate/hexane) to give 7'-fluoro-1'-[(1-isopropylpiperidin-4-yl)methyl]spiro[furo[2,3-f][1,3]benzodioxole-7,3'-indol]-2'(1'H)-one (85 mg, 69%) as a white solid, which was treated with 2.0 M HCl in diethyl ether to give the title compound: mp 157-160° C.; $^1$H NMR (300 MHz, CD$_3$OD) δ 7.22-7.05 (m, 2H), 7.05-6.98 (m, 1H), 6.52 (s, 1H), 6.21 (s, 1H), 5.86 (s, 2H), 4.83 (d, 1H), 4.68 (d, 1H), 3.95-3.77 (m, 2H), 3.55-3.42 (m, 3H), 3.12-2.96 (m, 2H), 2.30-2.10 (m, 1H), 2.10-1.97 (m, 2H), 1.76-1.52 (m, 2H), 1.34 (d, 6H); $^{13}$C NMR (75 MHz, CD$_3$OD) δ 179.7, 157.6, 150.6, 150.4, 147.1, 143.9, 136.6, 125.8, 121.2, 120.3, 118.0, 103.9, 103.0, 94.3, 81.8, 60.1, 59.7, 47.6, 35.33, 35.30, 28.6, 28.5, 16.98, 16.96; MS (ES+) m/z 439.27 (M+1).

EXAMPLE 10.21

Synthesis of 5,5-dimethyl-1'-{[5-(trifluoromethyl)-2-furyl]methyl}-5,6-dihydrospiro[benzo[1,2-b:5,4-b']difuran-3,3'-indol]-2'(1'H)-one

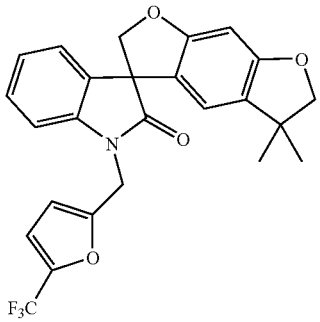

To a solution of 5,5-dimethyl-5,6-dihydrospiro[benzo[1,2-b:5,4-b']difuran-3,3'-indol]-2'(1'H)-one (0.09 g, 0.29 mmol) in 2-butanone (10.0 mL) was added 2-bromomethyl-5-(trifluoromethyl)furan (0.08 g, 0.35 mmol) followed by cesium carbonate (0.19 g, 0.58 mmol) at 0° C. The mixture was stirred at ambient temperature overnight. The reaction mixture was filtered and the filtrate was concentrated in vacuo. The residue was subjected to column chromatography (ethyl acetate/hexane, 1/5) to give the title compound (0.06 g, 45%): mp 155-160° C.; $^1$H NMR (300 MHz, CDCl$_3$,) δ 7.29 (t, 1H), 7.19 (d, 1H), 7.07 (t, 1H), 6.97 (d, 1H), 6.73 (t, 1H), 6.42-6.37 (m, 2H), 6.30 (s, 1H), 5.08 (d, 1H), 4.94-4.84 (m, 2H), 4.65 (d, 1H), 4.18 (s, 2H), 1.19 (s, 3H), 1.14 (s, 3H); $^{13}$C NMR (75 MHz, CDCl$_3$) δ 177.5, 161.2, 161.0, 152.0, 141.4, 132.5, 130.1, 128.8, 124.2, 123.8, 120.1, 116.4, 112.6, 109.3, 108.7, 93.4, 85.5, 80.6, 57.7, 41.4, 36.9, 27.6, 27.5; MS (ES+) m/z 456.5 (M+1).

EXAMPLE 10.22

Synthesis of 5,5-dimethyl-1'-(pyridin-3-ylmethyl)-5,6-dihydrospiro[benzo[1,2-b:5,4-b']difuran-3,3'-indol]-2'(1'H)-one hydrochloride

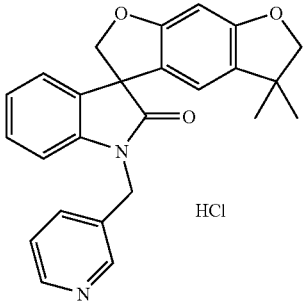

To a solution of 5,5-dimethyl-5,6-dihydrospiro[benzo[1,2-b:5,4-b']difuran-3,3'-indol]-2'(1'H)-one (0.08 g, 0.26 mmol) in DMF (10 mL) was added sodium hydride (0.03 g, 0.78 mmol) slowly at 0° C. After 30 min, 3-(bromomethyl)-pyridine hydrobromide (0.10 g, 0.39 mmol) was added. The mixture was stirred at ambient temperature overnight, quenched with saturated ammonium chloride (10.0 mL). The mixture was extracted with ethyl acetate (3×20.0 mL). The combined organic layers was dried over anhydrous sodium sulfate and filtered. The filtrate was concentrated in vacuo. The residue was subjected to column chromatography (ethyl acetate/hexane, 2/1) to give 5,5-dimethyl-1'-(pyridin-3-ylmethyl)-5,6-dihydrospiro[benzo[1,2-b:5,4-b']difuran-3,3'-indol]-2'(1'H)-one as a white solid (0.05 g, 48%), which was treated with 2.0 M HCl in diethyl ether to give the title compound: mp 124-126° C.; $^1$H NMR (300 MHz, CD$_3$OD) δ 8.96 (br, 1H), 8.82 (br, 1H), 8.62 (d, 1H), 7.3 (t, 1H), 7.32 (td, 1H), 7.23-7.17 (m, 1H), 7.16-7.08 (m, 2H), 6.42 (s, 1H), 6.32 (s, 1H), 5.35-5.14 (m, 2H), 4.93-4.84 (m, 1H), 4.74 (d, 1H), 4.18 (s, 2H), 1.18 (s, 3H), 1.14 (s, 3H); $^{13}$C NMR (75 MHz, CD$_3$OD) δ 178.9, 161.6, 161.1, 145.4, 141.3, 141.1, 132.5, 130.1, 128.8, 124.0, 123.9, 120.1, 116.2, 108.8, 92.6, 85.1, 80.2, 57.8, 41.0, 40.5, 26.5, 26.4; MS (ES+) m/z 399.5 (M+1).

EXAMPLE 10.23

Synthesis of 5,5-dimethyl-1'-(pyridin-2-ylmethyl)-5,6-dihydrospiro[benzo[1,2-b:5,4-b']difuran-3,3'-indol]-2'(1'H)-one hydrochloride

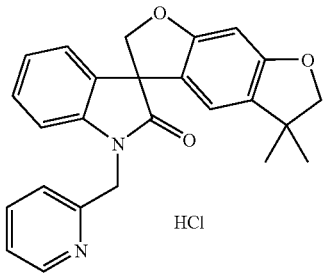

Following the procedure as described in EXAMPLE 10.22, and making non-critical variations using 2-(bromomethyl)-pyridine hydrobromide to replace 3-(bromomethyl)-pyridine hydrobromide, the title compound was obtained (45%): mp 145-147° C.; $^1$H NMR (300 MHz, CD$_3$OD) δ 8.86 (dd, 1H), 8.56 (td, 1H), 8.05-7.97 (m, 2H), 7.37 (td, 1H), 7.31-7.25 (m, 1H), 7.24-7.16 (m, 1H), 7.11 (d, 1H), 6.55 (s, 1H), 6.37 (s, 1H), 5.52 (d, 1H), 5.38 (d, 1H), 4.97 (d, 1H), 4.79 (d, 1H), 4.23 (s, 2H), 1.24 (s, 3H), 1.20 (s, 3H); $^{13}$C NMR (75 MHz, CD$_3$OD) δ 177.4, 160.0, 159.6, 150.3, 144.7, 141.0, 139.7, 131.0, 128.6, 127.2, 124.3, 123.7, 122.6, 122.4, 118.5, 114.8, 107.2, 91.0, 83.6, 78.7, 56.3, 40.1, 39.4, 24.9, 24.8; MS (ES+) m/z 399.5 (M+1).

EXAMPLE 10.24

Synthesis of 1'-[(6-methylpyridin-3-yl)methyl]spiro[furo[2,3-f][1,3]benzodioxole-7,3'-indol]-2'(1'H)-one hydrochloride

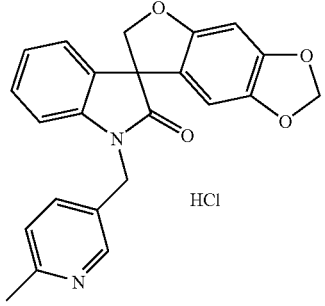

Following the procedure as described in EXAMPLE 10.21, and making non-critical variations using (6-methylpyridin-3-yl)methyl 4-methylbenzenesulfonate to replace 2-bromomethyl-5-(trifloromethyl)furan, and spiro[furo[2,3- f][1,3]benzodioxole-7,3'-indol]-2'(1H)-one to replace 5,5-dimethyl-5,6-dihydrospiro[benzo[1,2-b:5,4-b']difuran-3,3'-indol]-2'(1'H)-one, 1'-[(6-methylpyridin-3-yl)methyl]spiro[furo[2,3-f][1,3]benzodioxole-7,3'-indol]-2'(1'H)-one was obtained (56%), which was treated with 2.0 M HCl in diethyl ether to give the title compound: ¹H NMR (300 MHz, CD₃OD) δ 8.77 (s, 1H), 8.46 (dd, 1H), 7.91 (d, 1H), 7.33 (t, 1H), 7.24-7.09 (m, 3H), 6.52 (s, 1H), 6.14 (s, 1H), 5.86 (s, 2H), 5.18 (s, 2H), 4.93-4.85 (m, 1H), 4.71 (d, 1H), 2.77 (s, 3H); ¹³C NMR (75 MHz, CD₃OD) δ 180.0, 157.6, 155.1, 150.6, 146.6, 143.8, 142.7, 141.2, 135.7, 133.5, 130.3, 129.5, 125.3, 125.2, 120.5, 110.3, 103.8, 103.0, 94.3, 81.5, 59.7, 41.5, 19.5; MS (ES+) m/z 387.4 (M+1).

EXAMPLE 10.25

Synthesis of 1'-[(6-methoxypyridin-3-yl)methyl]spiro[furo[2,3-f][1,3]benzodioxole-7,3'-indol]-2'(1'H)-one

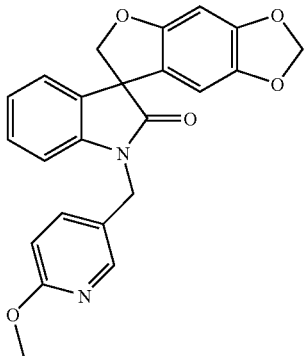

Following the procedure as described in EXAMPLE 10.21, and making non-critical variations using (6-methoxypyridin-3-yl)methyl 4-methylbenzenesulfonate to replace 2-bromomethyl-5-(trifloromethyl)furan, and spiro[furo[2,3-f][1,3]benzodioxole-7,3'-indol]-2'(1'H)-one to replace 5,5-dimethyl-5,6-dihydrospiro[benzo[1,2-b:5,4-b']difuran-3,3'-indol]-2'(1'H)-one, the title compound was obtained (45%): ¹H NMR (300 MHz, CDCl₃) δ 8.19 (d, 1H), 7.59 (dd, 1H), 7.26-7.12 (m, 2H), 7.02 (t, 1H), 6.83 (d, 1H), 6.74 (d, 1H), 6.50 (s, 1H), 6.07 (s, 1H), 5.89-5.82 (m, 2H), 5.00-4.90 (m, 2H), 4.76 (d, 1H), 4.65 (d, 1H), 3.93 (s, 3H); ¹³C NMR (75 MHz, CDCl₃) δ 177.6, 163.7, 155.9, 149.0, 145.3, 142.4, 141.6, 138.9, 132.2, 129.0, 124.4, 124.1, 123.7, 119.2, 111.7, 109.0, 102.9, 101.5, 93.7, 80.4, 58.2, 53.9, 41.1; MS (ES+) m/z 403.2 (M+1).

EXAMPLE 10.26

Synthesis of 1'-[(6-chloropyridin-3-yl)methyl]spiro[furo[2,3-f][1,3]benzodioxole-7,3'-indol]-2'(1'H)-one

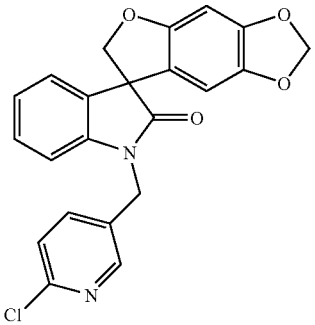

Following the procedure described in EXAMPLE 10.21, and making non-critical variations using 2-chloro-5-(chloromethyl)pyridine to replace 2-bromomethyl-5-(trifloromethyl)furan, and spiro[furo[2,3-f][1,3]benzodioxole-7,3'-indol]-2'(1'H)-one to replace 5,5-dimethyl-5,6-dihydrospiro[benzo[1,2-b:5,4-b']difuran-3,3'-indol]-2'(1'H)-one, the title compound was obtained (69%): ¹H NMR (300 MHz, CDCl₃) δ 8.42 (d, 1H), 7.63 (dd, 1H), 7.34-7.14 (m, 3H), 7.05 (t, 1H), 6.77 (d, 1H), 6.51 (s, 1H), 6.06 (s, 1H), 5.89-5.84 (m, 2H), 5.07-4.78 (m, 3H), 4.66 (d, 1H); MS (ES+) m/z 407.3 (M+1).

EXAMPLE 10.27

Synthesis of 1'-{[6-(dimethylamino)pyridin-3-yl]methyl}spiro[furo[2,3-t][1,3]benzodioxole-7,3'-indol]-2'(1'H)-one hydrochloride

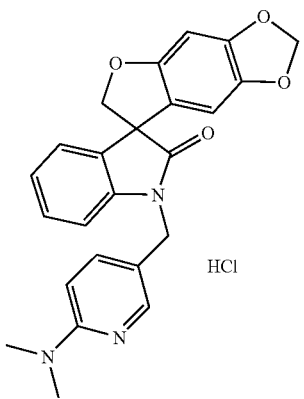

To a seal tube was added 1'-((6-chloropyridin-3-yl)methyl)-6H-spiro[benzofuro[6,5-d][1,3]dioxole-7,3'-indolin]-2'-one (0.10 g, 0.25 mmol) and dimethylamine (2.00 mL of 2 M THF solution, 4.00 mmol). The mixture was stirred at 130° C. overnight. After cooling down to ambient temperature, the mixture was concentrated in vacuo. The residue was subjected to column chromatography (ethyl acetate/hexane, 1/2) to give 1'-{[6-(dimethylamino)pyridin-3-yl]methyl}spiro[furo[2,3-f][1,3]benzodioxole-7,3'-indol]-2'(1'H)-one as a white solid (50 mg, 48%), which was treated with 2.0 M HCl in diethyl ether to give the title compound: mp 146-150° C.; ¹H NMR (300 MHz, CD₃OD) δ 8.03 (d, 1H), 7.95 (dd, 1H), 7.36 (td, 1H), 7.25-7.12 (m, 4H), 6.57 (s, 1H), 6.09 (s, 1H), 5.90 (s, 2H), 5.07-4.87 (m, 3H), 4.72 (d, 1H), 3.27 (s, 6H); $^{13}$C NMR (75 MHz, CD$_3$OD) δ 179.9, 157.6, 154.6, 150.5, 143.8, 143.4, 142.9, 137.7, 133.5, 130.2, 125.1, 121.8, 120.6, 113.2, 110.4, 103.7, 103.0, 94.3, 81.4, 59.7, 41.1, 39.5; MS (ES+) m/z 416.5 (M+1).

EXAMPLE 10.28

Synthesis of 1'-[(6-morpholin-4-ylpyridin-3-yl)methyl]spiro[furo[2,3-f][1,3]benzodioxole-7,3'-indol]-2'(1'H)-one hydrochloride

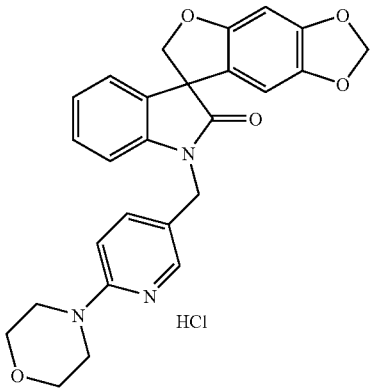

Following the procedure as described in EXAMPLE 10.27, and making non-critical variations using morpholine to replace dimethylamine solution, the title compound was obtained (52%): mp 185-200° C.; $^1$H NMR (300 MHz, CD$_3$OD) δ 8.13-8.04 (m, 2H), 7.45 (d, 1H), 7.37 (t, 1H), 7.26-7.14 (m, 3H), 6.56 (s, 1H), 6.10 (s, 1H), 5.89 (s, 2H), 5.10-4.87 (m, 3H), 4.72 (d, 1H), 3.91-3.84 (m, 4H), 3.73-3.67 (m, 4H); $^{13}$C NMR (75 MHz, CD$_3$OD) δ 180.0, 157.6, 153.7, 150.5, 145.1, 143.8, 142.8, 136.3, 133.5, 130.3, 125.2, 125.1, 123.6, 120.6, 114.6, 110.4, 103.7, 103.0, 94.3, 81.5, 66.7, 59.7, 47.2, 40.9; MS (ES+) m/z 458.5 (M+1).

EXAMPLE 10.29

Synthesis of 1'-[(6-pyrrolidin-1-ylpyridin-3-yl)methyl]spiro[furo[2,3-f][1,3]benzodioxole-7,3'-indol]-2'(1'H)-one hydrochloride

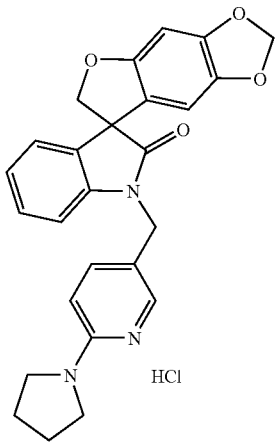

Following the procedure as described in EXAMPLE 10.27, and making non-critical variations using pyrrolidine to replace dimethylamine solution, the title compound was obtained (45%): mp 160-165° C.; $^1$H NMR (300 MHz, CD$_3$OD) δ 7.99-7.91 (m, 2H), 7.33 (td, 1H), 7.22-7.06 (m, 4H), 6.53 (s, 1H), 6.05 (s, 1H), 5.86 (s, 2H), 5.04-4.82 (m, 3H), 4.68 (d, 1H), 3.57 (t, 4H), 2.13 (t, 4H); $^{13}$C NMR (75 MHz, CD$_3$OD) δ 177.0, 154.6, 148.0, 147.6, 141.1, 140.8, 139.9, 132.5, 130.5, 127.3, 122.2, 118.8, 117.6, 112.0, 107.4, 100.7, 100.0, 91.3, 78.5, 56.7, 38.0, 23.2; MS (ES+) m/z 442.2 (M+1).

EXAMPLE 10.30

Synthesis of 1'-(2-chloro-4-fluorobenzyl)spiro[furo[2,3-f][1,3]benzodioxole-7,3'-indol]-2'(1'H)-one

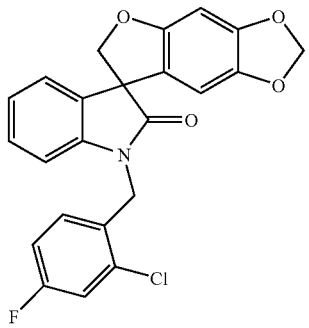

Following the procedure described in EXAMPLE 10.21, and making non-critical variations using spiro[furo[2,3-f][1,3]benzodioxole-7,3'-indol]-2'(1'H)-one to replace 5,5-dimethyl-5,6-dihydrospiro[benzo[1,2-b:5,4-b']difuran-3,3'-indol]-2'(1'H)-one, and 1-(bromomethyl)-2-chloro-4-fluorobenzene to replace 2-(bromomethyl)-5-(trifluoromethyl)furan, the title compound was obtained (54%) as a white solid: mp 174-175° C.; MS (ES+) m/z 424.2 (M+1).

EXAMPLE 10.31

Synthesis of 1'-[(2-methylcyclopropyl)methyl]spiro[furo[2,3-f][1,3]benzodioxole-7,3'-indol]-2'(1'H)-one

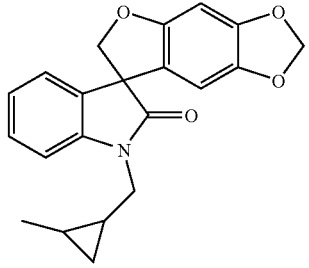

Following the procedure described in EXAMPLE 10.21, and making non-critical variations using spiro[furo[2,3-f][1,3]benzodioxole-7,3'-indol]-2'(1'H)one to replace 5,5-dimethyl-5,6-dihydrospiro[benzo[1,2-b:5,4-b']difuran-3,3'-indol]-2'(1'H)-one, and 1-(bromomethyl)-2-methylcyclopropane to replace 2-(bromonmethyl)-5-(trifluoromethyl)furan, the title compound was obtained (37%) as a white solid: MS (ES+) m/z 350.3 (M+1).

EXAMPLE 10.32

Synthesis of 1'-(3-cyclopropylpropyl)spiro[furo[2,3-f][1,3]benzodioxole-7,3'-indol]-2'(1'H)-one

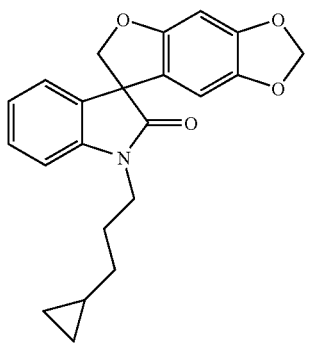

Following the procedure described in EXAMPLE 10.21, and making non-critical variations using spiro[furo[2,3-f][1,3]benzodioxole-7,3'-indol]-2'(1'H)-one to replace 5,5-dimethyl-5,6-dihydrospiro[benzo[1,2-b:5,4-b']difuran-3,3'-indol]-2'(1'H)-one, and (3-bromopropyl)cyclopropane to replace 2-(bromomethyl)-5-(trifluoromethyl)furan, the title compound was obtained (51%) as a white solid: mp 111-113° C.; MS (ES+) m/z 364.3 (M+1).

EXAMPLE 10.33

Synthesis of 1'-butylspiro[furo[2,3-f][1,3]benzodioxole-7,3'-indol]-2'(1'H)-one

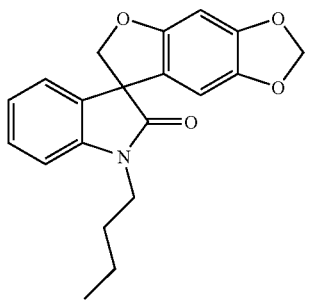

Following the procedure described in EXAMPLE 10.21, and making non-critical variations using spiro[furo[2,3-f][1,3]benzodioxole-7,3'-indol]-2'(1'H)-one to replace 5,5-dimethyl-5,6-dihydrospiro[benzo[1,2-b:5,4-b']difuran-3,3'-indol]-2'(1'H)-one, and 1-bromobutane to replace 2-(bromomethyl)-5-(trifluoromethyl)furan, the title compound was obtained (62%) as a white solid: mp 119-120° C.; MS (ES+) m/z 338.3 (M+1).

EXAMPLE 10.34

Synthesis of 1'-[(5-methylisoxazol-4-yl)methyl]spiro[furo[2,3-f][1,3]benzodioxole-7,3'indol]-2'(1H)-one

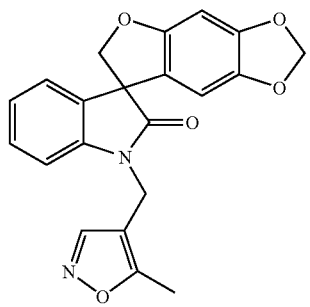

Following the procedure described in EXAMPLE 10.21, and making non-critical variations using spiro[furo[2,3-f][1,3]benzodioxole-7,3'-indol]-2'(1'H)-one to replace 5,5-dimethyl-5,6-dihydrospiro[benzo[1,2-b:5,4-b']difuran-3,3'-indol]-2'(1'H)-one, and 4-(bromomethyl)-5-methylisoxazole to replace 2-(bromomethyl)-5-(trifluoromethyl)furan, the title compound was obtained (25%) as a white solid: mp 159-161° C.; $^1$H NMR (300 MHz, DMSO-$d_6$) δ 7.39-6.91 (m, 4H), 6.50 (s, 1H), 6.11 (s, 1H), 5.94 (d, 1H), 5.85 (ABq, 2H), 4.95 (ABq, 2H), 4.78 (ABq, 2H), 2.37 (s, 3H); MS (ES+) m/z 377.3 (M+1).

EXAMPLE 10.35

Synthesis of 1-(tetrahydro-2H-pyran-4-ylmethyl)spiro[furo[2,3-f][1,3]benzodioxole-7,3'-indol]-2'(1H)-one

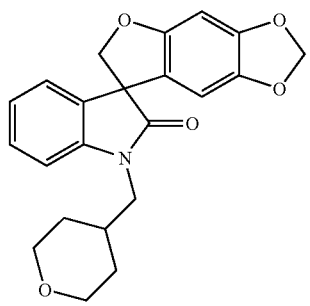

Following the procedure described in EXAMPLE 10.21, and making non-critical variations using spiro[furo[2,3-f][1,3]benzodioxole-7,3'-indol]-2'(1'H)-one to replace 5,5-dimethyl-5,6-dihydrospiro[benzo[1,2-b:5,4-b']difuran-3,3'-indol]-2'(1'H)-one, and 4-(bromomethyl)tetrahydro-2H-pyran to replace 2-(bromomethyl)-5-(trifluoromethyl)furan, the title compound was obtained (25%) as a white solid: mp 142-144° C.; $^1$H NMR (300 MHz, DMSO-$d_6$) δ 7.34-6.85 (m, 4H), 6.50 (s, 1H), 6.08 (s, 1H), 5.85 (ABq, 2H), 4.76 (ABq, 2H), 4.18-3.86 (m, 2H), 3.63 (ddd, 2H), 3.34 (t, 2H), 2.38-1.92 (m, 1H), 1.70-1.36 (m, 4H); MS (ES+) m/z 380.3 (M+1).

EXAMPLE 10.36

Synthesis of 1'[2-(trifluoromethoxy)benzyl]spiro[furo[2,3-f][1,3]benzodioxole-7,3'-indol]-2'(1'H)-one

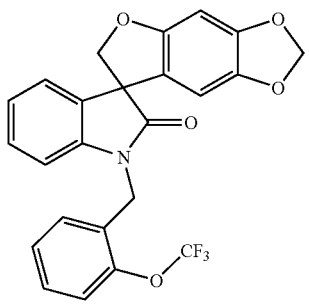

Following the procedure described in EXAMPLE 10.21, and making non-critical variations using spiro[furo[2,3-f][1,3]benzodioxole-7,3'-indol]-2'(1'H)-one to replace 5,5-dimethyl-5,6-dihydrospiro[benzo[1,2-b:5,4-b']difuran-3,3'-indol]-2'(1'H)-one, and 1-(bromomethyl)-2-(trifluoromethoxy)benzene to replace 2-(bromomethyl)-5-(trifluoromethyl)furan, the title compound was obtained (77%) as a white solid: mp 130-135° C.; MS (ES+) m/z 456.3 (M+1).

EXAMPLE 10.37

Synthesis of 1'[3-(trifluoromethoxy)benzyl]spiro[furo[2,3-f][1,3]benzodioxole-7,3'-indol]-2'(1'H)-one

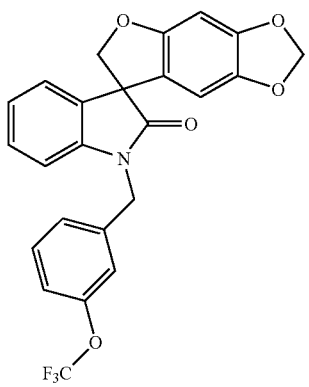

Following the procedure described in EXAMPLE 10.21, and making non-critical variations using spiro[furo[2,3-f][1,3]benzodioxole-7,3'-indol]-2'(1'H)-one to replace 5,5-dimethyl-5,6-dihydrospiro[benzo[1,2-b:5,4-b']difuran-3,3'-indol]-2'(1'H)-one, and 1-(bromomethyl)-3-(trifluoromethoxy)benzene to replace 2-(bromomethyl)-5-(trifluoromethyl)furan, the title compound was obtained (65%) as a white solid: mp 88-91° C.; MS (ES+) m/z 456.3 (M+1).

EXAMPLE 10.38

Synthesis of 1'[4-(trifluoromethoxy)benzyl]spiro[furo[2,3-f][1,3]benzodioxole-7,3'-indol]-2'(1'H)-one

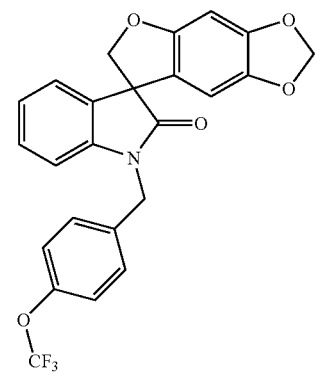

Following the procedure described in EXAMPLE 10.21, and making non-critical variations using spiro[furo[2,3-f][1,3]benzodioxole-7,3'-indol]-2'(1'H)-one to replace 5,5-dimethyl-5,6-dihydrospiro[benzo[1,2-b:5,4-b']difuran-3,3'-indol]-2'(1'H)-one, and 1-(bromomethyl)-4-(trifluoromethoxy)benzene to replace 2-(bromomethyl)-5-(trifluoromethyl)furan, the title compound was obtained (50%) as a white solid: mp 99-101° C.; MS (ES+) m/z 456.3 (M+1).

EXAMPLE 10.39

Synthesis of 1'-methylspiro[furo[2,3-f][1,3]benzodioxole-7,3'-indol]-2'(1'H)-one

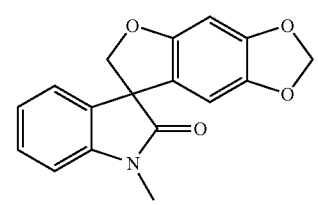

Following the procedure described in EXAMPLE 10.21, and making non-critical variations using spiro[furo[2,3-f][1,3]benzodioxole-7,3'-indol]-2'(1'H)-one to replace 5,5-dimethyl-5,6-dihydrospiro[benzo[1,2-b:5,4-b'] difuran-3,3'-indol]-2'(1'H)-one, and iodomethane to replace 2-(bromomethyl)-5-(trifluoromethyl)furan, the title compound was obtained (72%) as a white solid: mp 142-144° C.; MS (ES+) m/z 296.2 (M+1).

EXAMPLE 10.40

Synthesis of 1'-Propylspiro[furo[2,3-f][1,3]benzodioxole-7,3'-indol]-2'(1'H)-one

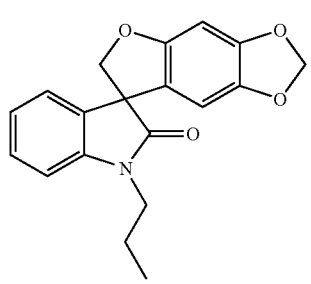

Following the procedure described in EXAMPLE 10.21, and making non-critical variations using spiro[furo[2,3-f][1,3]benzodioxole-7,3'-indol]-2'(1'H)-one to replace 5,5-dimethyl-5,6-dihydrospiro[benzo[1,2-b:5,4-b']difuran-3,3'-indol]-2'(1'H)-one, and 1-bromopropane to replace 2-(bromomethyl)-5-(trifluoromethyl)furan, the title compound was obtained (64%) as a white solid: mp 158-160° C.; MS (ES+) m/z 324.4 (M+1).

EXAMPLE 10.41

Synthesis of 1'-(2,1,3-benzoxadiazol-5-ylmethyl)spiro[furo[2,3-f][1,3]benzodioxole-7,3'-indon]-2'(1'H)-one

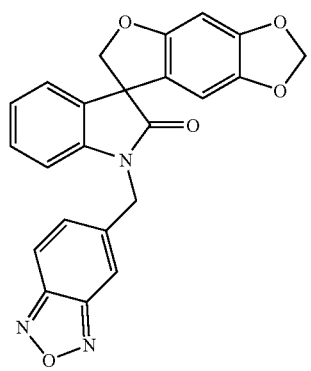

Following the procedure described in EXAMPLE 10.21, and making non-critical variations using spiro[furo[2,3-f][1,3]benzodioxole-7,3'-indol]-2'(1'H)-one to replace 5,5-dimethyl-5,6-dihydrospiro[benzo[1,2-b:5,4-b']difuran-3,3'-indol]-2'(1'H)-one, and 5-(bromomethyl)benzo[c][1,2,5]oxadiazole to replace 2-(bromomethyl)-5-(trifluoromethyl)furan, the title compound was obtained (17%) as a white solid: mp 163-165° C.; MS (ES+) m/z 414.4 (M+1).

EXAMPLE 10.42

Synthesis of 1'-[(1-methyl-1H-benzotriazol-6-yl)methyl]spiro[furo2,3-f][1,3]benzodioxole-7,3'-indol]-2'(1'H)-one

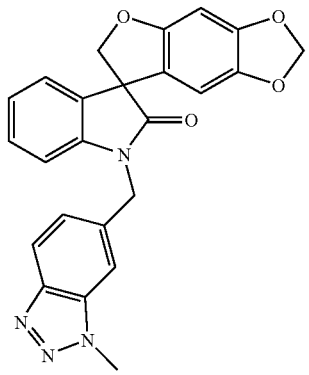

Following the procedure described in EXAMPLE 10.21, and making non-critical variations using spiro[furo[2,3-f][1,3]benzodioxole-7,3'-indol]-2'(1'H)-one to replace 5,5-dimethyl-5,6-dihydrospiro[benzo[1,2-b:5,4-b']difuran-3,3'-indol]-2'(1'H)-one, and 6-(bromomethyl)-1'-methyl-1H-benzotriazole to replace 2-(bromomethyl)-5-(trifluoromethyl)furan, the title compound was obtained (17%) as a white solid: mp 230-235° C.; MS (ES+) m/z 427.3 (M+1).

EXAMPLE 10.43

Synthesis of tert-butyl 4-[(2'-oxo-5,6-dihydrospiro[benzo[1,2-b:5,4-b']difuran-3,3'-indol]-1'(2'H)-yl)methyl]piperidine 1-carboxylate

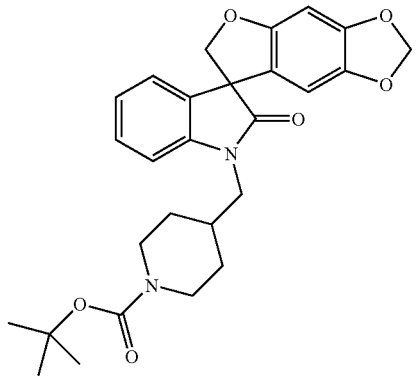

Following the procedure described in EXAMPLE 10.21, and making non-critical variations using 5,6-dihydrospiro[benzo[1,2-b:5,4-b']difuran-3,3'-indol]-2'(1'H)-one to replace 5,5-dimethyl-5,6-dihydrospiro[benzo[1,2-b:5,4-b']difuran-3,3'-indol]-2'(1'H)-one, and tert-butyl 4-(bromomethyl)peridine-1'-carboxylate to replace 2-(bromomethyl)-5-(trifluoromethyl)furan, the title compound was obtained (58%) as a white solid: mp 96-98° C.; $^1$H NMR (300 MHz, DMSO-$d_6$) δ 7.84-6.85 (m, 4H), 6.40 (s, 1H), 6.37 (s, 1H), 4.68 (ABq, 2H), 4.46 (t, 2H), 4.06-3.73 (m, 2H), 3.68-3.45 (m, 2H), 2.92 (t, 2H), 2.63 (s, 2H), 2.04-1.82 (m, 1H), 1.76-0.66 (m, 13H); MS (ES+) m/z 477.4 (M+1).

EXAMPLE 10.44

Synthesis of t-(2,3-difluorobenzyl)-5,6-dihydrospyro[benzo[1,2-b:5,4-b']difuran-3,3'-indol]-2'(1'H)-one

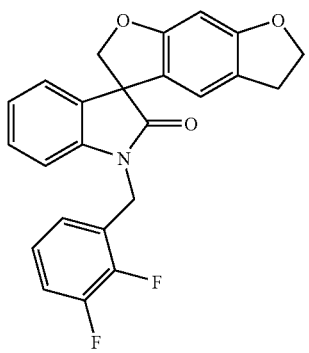

Following the procedure described in EXAMPLE 10.21, and making non-critical variations using 5,6-dihydrospiro[benzo[1,2-b:5,4-b']difuran-3,3'-indol]-2'(1'H)-one to replace 5,5-dimethyl-5,6-dihydrospiro[benzo[1,2-b:5,4-b']difuran-3,3'-indol]-2'(1'H)-one, and 1-(bromomethyl)-2,3-difluorobenzene to replace 2-(bromomethyl)-5-(trifluoromethyl)furan, the title compound was obtained (67%) as a white solid: mp 156-158° C.; $^1$H NMR (300 MHz, DMSO-d$_6$) δ 7.50-6.85 (m, 7H), 6.43 (s, 1H), 6.39 (s, 1H), 5.01 (q, 2H), 4.75 (dd, 2H), 4.46 (t, 2H), 2.92 (t, 2H); MS (ES+) m/z 406.2 (M+1).

EXAMPLE 10.45

Synthesis of 1-(pyridin-2-ylmethyl)-5,6-dihydrospiro[benzo[1,2-b:5,4-b']difuran-3,3'-indol]-2'(1'H)-one hydrochloride

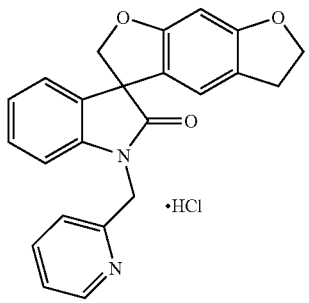

Following the procedure described in EXAMPLE 10.21, and making non-critical variations using 5,6-dihydrospiro[benzo[1,2-b:5,4-b']difuran-3,3'-indol]-2'(1'H)-one to replace 5,5-dimethyl-5,6-dihydrospiro[benzo[1,2-b:5,4-b']difuran-3,3'-indol]-2'(1'H)-one, and 2-(bromomethyl)pyridine hydrobromide to replace 2-(bromomethyl)-5-(trifluoromethyl)furan, 1'-(pyridin-2-ylmethyl)-5,6-dihydrospyro[benzo[1,2-b:5,4-b']difuran-3,3'-indol]2'(1'H)-one was obtained (27%) as a white solid, which was treated in CH$_2$Cl$_2$ with excess of HCl in ether to give the tilte compound: mp 208-210° C.; $^1$H NMR (300 MHz, DMSO-d$_6$) δ 8.78-8.53 (m, 1H), 8.05 (t, 1H), 7.64-7.47 (m, 2H), 7.30-6.92 (m, 4H), 6.59 (s, 1H), 6.38 (s, 1H), 5.24-5.06 (m, 2H), 4.78 (ABq, 2H), 4.46 (t, 2H), 2.94 (t, 2H); MS (ES+) m/z 371.4 (M+1).

EXAMPLE 10.46

Synthesis of 1-(4-methoxybenzyl)-5,6-dihydrospiro[benzo[1,2-b:5,4-b']difuran-3,3'-indol]-2'(1'H)-one

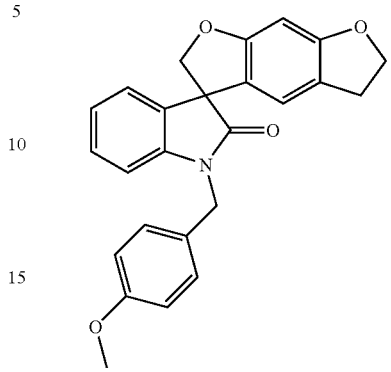

Following the procedure described in EXAMPLE 10.21, and making non-critical variations using 5,6-dihydrospiro[benzo[1,2-b:5,4-b']difuran-3,3'-indol]-2'(1'H)-one to replace 5,5-dimethyl-5,6-dihydrospiro[benzo[1,2-b:5,4-b']difuran-3,3'-indol]-2'(1'H)-one, and 1-(chloromethyl)-4-methoxybenzene to replace 2-(bromomethyl)-5-(trifluoromethyl)furan, the title compound was obtained (56%) as a white solid: mp 120-121° C.; MS (ES+) m/z 400.2 (M+1).

EXAMPLE 10.47

Synthesis of 4'-bromo-1'-{[5-(trifluoromethyl)-2-furyl]methyl}spiro[furo[2,3-f][1,3]benzodioxole-7,3'-indol]-2'(1'H)-one

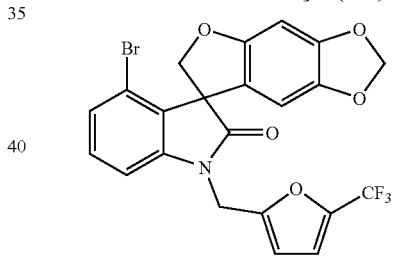

To a solution of 4'-bromospiro[furo[2,3-f][1,3]benzodioxole-7,3'-indol]-2'(1'H)-one (0.48 g, 1.33 mmol) in N,N-dimethylformamide (5.00 mL) was added sodium hydride (0.08 g, 1.98 mmol, 60% dispersion in mineral oil) in one portion at 0° C. The reaction mixture was stirred for 0.5 h followed by the addition of a solution of 2-(bromomethyl)-5-trifluoromethyl)furan in N,N-dimethylformamide (1.00 mL). The reaction mixture was stirred at ambient temperature for 16 h and quenched by slow addition of water (5.00 mL). The reaction mixture was extracted with ethyl acetate (3×20.0 mL), washed with brine, dried over anhydrous sodium sulfate and filtered. The filtrate was concentrated in vacuo to dryness. The residue was subjected to column chromatography eluting with ethyl acetate:hexane (35%) to afford the title compound (0.46 g, 69%) as a colorless solid: $^1$H NMR (300 MHz, CDCl$_3$) δ 7.22-7.14 (m, 2H), 6.94 (dd, 1H), 6.73 (d, 1H), 6.46 (s, 1H), 6.39 (d, 1H), 6.04 (s, 1H) 5.86 (dd, 2H), 4.94 (ABq, 2H), 4.92 (ABq, 2H); $^{13}$C NMR (75 MHz, CDCl$_3$) δ 177.0, 157.2, 151.6, 151.5, 149.3, 143.4, 142.2, 130.5, 127.8, 129.6, 120.1, 116.0, 112.7, 109.5, 107.9, 102.5, 101.6, 93.3, 77.1, 59.6, 37.1; MS (ES+) m/z 508.2 (M+2).

EXAMPLE 10.48

Synthesis of 4'-bromo-1'-{[5-(trifluoromethyl)-2-furyl]methyl}-5,6-dihydrospiro[benzo[1,2-b:5,4-b']difuran-3,3'-indol]-2'(1'H)-one

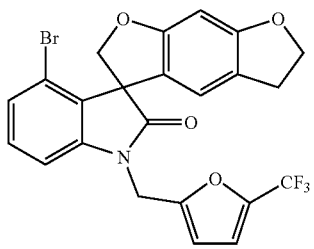

Following the procedure described in EXAMPLE 10.47, and making non-critical variations using 4'-bromo-5,6-dihydrospiro[benzo[1,2-b:5,4-b']difuran-3,3'-indol]-2'(1'H)-one to replace 4'-bromospiro[furo[2,3-f][1,3]benzodioxole-7,3'-indol]-2'(1'H)-one, the title compound was obtained (76%) as a colorless solid: mp 182-184° C.; $^1$H NMR (300 MHz, CDCl$_3$) δ 7.21-7.11 (m, 2H), 6.92 (dd, 1H), 6.74 (d1H), 6.41 (d, 1H), 6.38 (s, 1H), 6.37 (s, 1H), 5.10 (d, 1H), 5.02 (d, 1H), 4.87 (d, 1H), 4.81 (d, 1H), 4.53 (t, 2H), 2.98 (t, 2H); $^{13}$C NMR (75 MHz, CDCl$_3$) δ 177.3, 162.4, 162.2, 151.5, 143.4, 130.2, 127.7, 120.5, 120.0, 119.7, 118.4, 117.0, 112.7, 112.6, 109.5, 107.8, 92.9, 77.1, 72.4, 59.1, 37.0, 28.9; MS (ES+) m/z 506.3 (M+1).

EXAMPLE 10.49

Synthesis of 4'-bromo-1'-methylspiro[furo[2,3-f][1,3]benzodioxole-7,3'-indol]-2'(1'H)-one

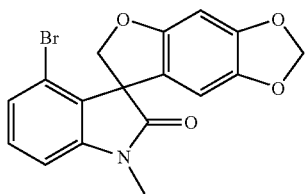

Following the procedure described in EXAMPLE 10.47, and making non-critical variations using iodomethane to replace 2-(bromomethyl)-5-(trifluoromethyl)furan, the title compound was obtained (79%) as a colorless solid: mp 155-157° C.; $^1$H NMR (300 MHz, CDCl$_3$) δ 7.19 (d, 1H), 7.17 (s, 1H), 6.84 (dd, 1H), 6.46 (s, 1H), 6.08 (s, 1H), 5.86 (dd, 2H), 4.90 (ABq, 2H), 3.25 (s, 3H); $^{13}$C NMR (75 MHz, CDCl$_3$) δ 177.3, 157.2, 149.2, 145.1, 142.0, 130.4, 129.9, 127.3, 119.9, 116.3, 107.3, 102.7, 101.5, 93.3, 77.3, 59.7, 26.9; MS (ES+) m/z 376.4 (M+2).

EXAMPLE 10.50

Synthesis of tert-butyl 4-[(4'-bromo-2'-oxospiro[furo[2,3-f][1,3]benzodioxole-7,3'-indol]-1'(2'H)-yl)methyl]piperidine-1'-carboxylate

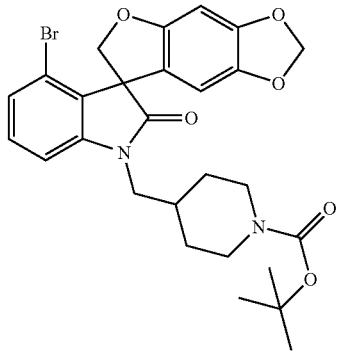

Following the procedure described in EXAMPLE 10.47, and making non-critical variations using tert-butyl 4-({[(4-methylphenyl)sulfonyl]oxy}methyl)piperidine-1-carboxylate to replace 2-(bromomethyl)-5-(trifluoromethyl)furan, the title compound was obtained (43%) as a colorless solid: $^1$H NMR (300 MHz, CDCl$_3$) δ 7.17 (d, 2H), 6.83 (t, 1H), 6.46 (s, 1H), 6.04 (s, 1H), 5.87 (d, 2H), 4.89 (ABq, 2H), 4.11 (d, 2H), 3.73-3.42 (m, 3H), 2.66 (t, 2H), 2.03-1.90 (m, 1H), 1.43 (s, 9H); $^{13}$C NMR (75 MHz, CDCl$_3$) δ 177.6, 157.3, 154.7, 149.2, 144.8, 142.1, 130.3, 129.8, 127.3, 120.2, 116.3, 107.6, 102.4, 101.6, 93.4, 79.6, 77.2, 59.6, 46.1, 43.4, 34.9, 28.4; MS (ES+) m/z 581.4 (M+23), 579.4 (M+23), 503.3 (M−57), 501.3 (M−57).

EXAMPLE 10.51

Synthesis of 1'-[(3,5-dimethylisoxazol-4-yl)methyl]spiro[furo[2,3-f][1,3]benzodioxole-7,3'-indol]-2'(1'H)-one

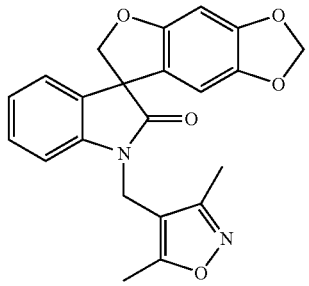

Following the procedure described in EXAMPLE 10.47, and making non-critical variations using spiro[furo[2,3-f][1,3]benzodioxole-7,3'-indol]-2'(1'H)-one to replace 4'-bromospiro[furo[2,3-f][1,3]benzodioxole-7,3'-indol]-2'(1'H)-one, and 4-(chloromethyl)-3,5-dimethylisoxazole to replace 2-(bromomethyl)-5-(trifluoromethyl)furan, the title compound was obtained (35%) as a colorless solid: mp 165-167° C.; $^1$H NMR (300 MHz, CDCl$_3$) δ 7.24 (t, 1H), 7.16 (d, 1H), 7.05 (t, 1H), 6.72 (d, 1H), 6.50 (s, 1H), 6.05 (s, 1H), 5.85 (d, 2H), 4.75 (ABq, 2H), 4.67 (ABq, 2H), 2.46 (s, 3H), 2.22 (s, 3H); $^{13}$C NMR (75 MHz, CDCl$_3$) δ 177.5, 167.1, 159.1, 156.1, 149.1, 142.4, 141.7, 131.8, 129.0, 124.3, 123.8, 118.9, 108.8, 108.6, 102.9, 101.6, 93.8, 80.6, 58.2, 33.3, 11.5, 10.7; MS (ES+) m/z 391.3 (M+1).

EXAMPLE 10.52

Synthesis of 1-(2-furylmethyl)spiro[furo[2,3-f][1,3]benzodioxole-7,3'-indol]-2'(1'H)-one

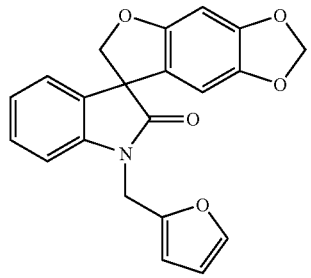

Following the procedure described in EXAMPLE 10.47, and making non-critical variations using spiro[furo[2,3-f][1,3]benzodioxole-7,3'-indol]-2'(1'H)-one to replace 4'-bromo-spiro[furo[2,3-f][1,3]benzodioxole-7,3'-indol]-2'(1'H)-one, and 2-chloromethylfuran to replace 2-(bromomethyl)-5-(trifluoromethyl)furan, the title compound (40%) as a colorless solid: mp 110-112° C.; $^1$H NMR (300 MHz, CDCl$_3$) δ 7.35-7.33 (m, 1H), 7.29-7.23 (m, 1H), 7.15 (d, 1H), 7.06-7.00 (m, 2H), 6.50 (s, 1H), 6.34-6.31 (m, 2H), 6.10 (s, 1H), 5.85 (dd, 2H), 4.92 (ABq, 2H), 4.79 (ABq, 2H); $^{13}$C NMR (75 MHz, CDCl$_3$) δ 177.1, 155.9, 149.0, 148.9, 142.6, 142.3, 141.8, 132.2, 128.9, 123.8, 123.5, 119.5, 110.6, 109.3, 108.7, 103.1, 101.5, 93.6, 80.4, 58.2, 37.1; MS (ES+) m/z 362.5 (M+1).

EXAMPLE 10.53

Synthesis of ethyl 5-(2'-oxospiro[furo[2,3-f][1,3]benzodioxole-7,3'-indol]-1'(2'H)-yl)pentanoate

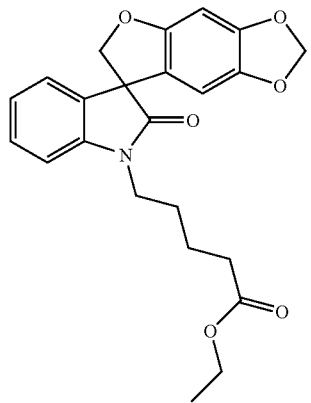

Following the procedure described in EXAMPLE 10.47, and making non-critical variations using spiro[furo[2,3-f][1,3]benzodioxole-7,3'-indol]-2'(1'H)-one to replace 4'-bromo-spiro[furo[2,3-f][1,3]benzodioxole-7,3'-indol]-2'(1'H)-one, and ethyl 5-bromovalerate to replace 2-(bromomethyl)-5-(trifluoromethyl)furan, the title compound was obtained (62%) as a gummy material: $^1$H NMR (300 MHz, CDCl$_3$) δ 7.28 (t, 1H), 7.14 (d, 1H), 7.03 (t, 1H), 6.88 (d, 1H), 6.48 (s, 1H), 6.13 (s, 1H), 5.84 (d, 2H), 4.76 (ABq, 2H), 4.07 (q, 2H), 3.87-3.65 (m, 2H), 2.35 (t, 2H), 1.80-1.64 (m, 4H), 1.20 (t, 3H); $^{13}$C NMR (75 MHz, CDCl$_3$) δ 177.4, 173.1, 155.9, 148.8, 142.3, 142.2, 132.5, 128.9, 124.04, 123.3, 119.5, 108.6, 103.0, 101.5, 93.6, 80.5, 60.4, 58.2, 39.9, 33.7, 26.8, 22.2, 14.2; MS (ES+) m/z 432.09 (M+23).

EXAMPLE 10.54

Synthesis of ethyl 4-(2'-oxospiro[furo[2,3-f][1,3]benzodioxole-7,3'-indol]-1'(2'H)-yl)butanoate

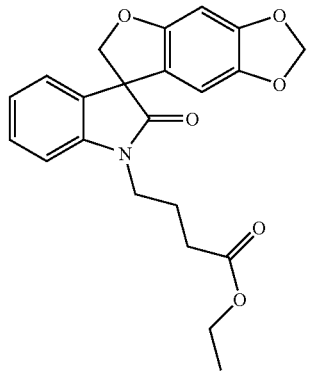

Following the procedure described in EXAMPLE 10.47, and making non-critical variations using spiro[furo[2,3-f][1,3]benzodioxole-7,3'-indol]-2'(1'H)-one to replace 4'-bromo-spiro[furo[2,3-f][1,3]benzodioxole-7,3'-indol]-2'(1'H)-one, and ethyl 4-bromobutyrate to replace 2-(bromomethyl)-5-(trifluoromethyl)furan, the title compound was obtained (80%) as a gummy material: $^1$H NMR (300 MHz, CDCl$_3$) δ 7.29 (t, 1H), 7.14 (d, 1H), 7.04 (d, 1H), 6.99 (d, 1H), 6.48 (s, 1H), 6.18 (s, 1H), 5.84 (d, 2H), 4.76 (ABq, 2H), 4.11 (q, 2H), 3.88-3.71 (m, 2H), 2.40 (t, 2H), 2.03 (t, 2H), 1.21(t, 3H); $^{13}$C NMR (75 MHz, CDCl$_3$) δ 177.4, 172.8, 156.0, 148.9, 142.4, 142.2, 132.4, 129.0, 124.0, 123.3, 119.4, 108.7, 103.0, 101.5, 93.6, 80.5, 60.7, 58.2, 39.6, 31.2, 22.6, 14.3; MS (ES+) m/z 418.08 (M+23), 396.1 (M+1).

EXAMPLE 10.55

Synthesis of 1'-(1,2,4-oxadiazol-3-ylmethyl)spiro[furo[2,3-f][1,3]benzodioxole-7,3'-indol]-2'(1'H)-one

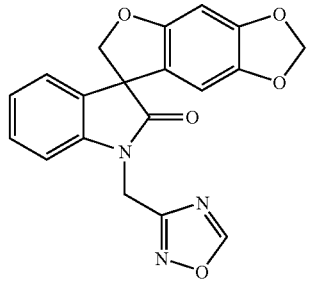

Following the procedure described in EXAMPLE 10.47, and making non-critical variations using spiro[furo[2,3-f][1,3]benzodioxole-7,3'-indol]-2'(1'H)-one to replace 4'-bromo-spiro[furo[2,3-f][1,3]benzodioxole-7,3'-indol]-2'(1'H)-one, and 3-(chloromethyl)-1,2,4-oxadiazole to replace 2-(bromomethyl)-5-(trifluoromethyl)furan, the title compound was obtained (36%)) as a colorless solid: mp 160-162° C.; $^1$H NMR (300 MHz, CDCl$_3$) δ 7.39 (dt, 1H), 7.20-7.13 (m, 3H), 7.05 (d, 1H), 6.50 (s, 1H), 6.12 (s, 1H), 5.86 (dd, 2H), 4.78 (ABq, 2H), 4.68 (s, 2H); $^{13}$C NMR (75 MHz, CDCl$_3$) δ 176.7, 156.0, 149.3, 142.5, 139.6, 131.6, 129.4, 124.8, 124.5, 118.4, 113.6, 108.7, 103.0, 101.7, 93.7, 80.3, 58.2, 29.7, 28.0; MS (ES+) m/z 365.2 (M+1).

EXAMPLE 10.56

Synthesis of 1'-{[5-(3-chlorophenyl)-2-furyl]methyl}spiro[furo[2,3-f][1,3]benzodioxole-7,3'-indol]-2'(1'H)-one

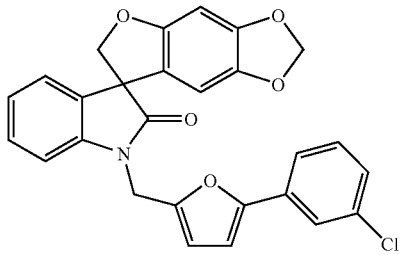

Following the procedure described in EXAMPLE 10.47, and making non-critical variations using spiro[furo[2,3-f][1,3]benzodioxole-7,3'-indol]-2'(1'H)-one to replace 4'-bromospiro[furo[2,3-f][1,3]benzodioxole-7,3'-indol]-2'(1'H)-one, and 2-(chloromethyl)-5-[3-chlorophenyl]furan to replace 2-(bromomethyl)-5-(trifluoromethyl)furan, the title compound was obtained (22%) as a colorless solid: mp 205-207° C.; $^1$H NMR (300 MHz, CDCl$_3$) δ 7.55 (t, 1H), 7.46 (dt, 1H), 7.28 (d, 2H), 7.21-7.14 (m, 2H), 7.09-7.04 (m, 2H), 6.59 (d, 1H), 6.50 (s, 1H), 6.40 (d, 1H), 6.10 (s, 1H), 5.84 (dd, 2H), 4.98 (ABq, 2H), 4.80 (ABq, 2H); $^{13}$C NMR (75 MHz, CDCl$_3$) δ 177.2, 155.9, 152.5, 149.2, 148.9, 142.4, 141.7, 134.8, 132.1, 132.0, 130.1, 128.9, 127.5, 124.0, 123.7, 123.6, 121.7, 119.4, 110.8, 109.2, 106.9, 103.0, 101.5, 93.6, 80.4, 58.2, 37.3; MS (ES+) m/z 472.2 (M+1).

EXAMPLE 10.57

Synthesis of 1'-(3-chloropropyl)spiro[furo[2,3-f][1,3]benzodioxole-7,3'-indol]-2'(1'H)-one

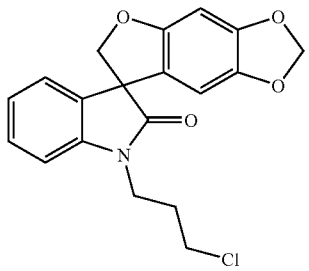

Following the procedure described in EXAMPLE 10.47, and making non-critical variations using spiro[furo[2,3-f][1,3]benzodioxole-7,3'-indol]-2'(1'H)-one to replace 4'-bromospiro[furo[2,3-f][1,3]benzodioxole-7,3'-indol]-2'(1'H)-one, and 1-bromo-3-chloropropane to replace 2-(bromomethyl)-5-(trifluoromethyl)furan, the title compound was obtained (22%) as a colorless solid: mp 144-146° C.; $^1$H NMR (300 MHz, CDCl$_3$) δ 7.31 (dt, 1H), 7.14-7.12 (m, 2H), 7.01(t, 1H), 6.65 (s, 1H), 6.23 (s, 1H), 5.89 (s, 2H), 4.68 (ABq, 2H), 3.85-3.79 (m, 2H), 3.67 (t, 2H), 2.06 (t, 1H); $^{13}$C NMR (75 MHz, DMSO-d$_6$) δ 177.2, 155.8, 148.7, 142.9, 142.2, 132.4, 129.3, 124.1, 123.3, 120.3, 109.3, 103.6, 101.7, 80.3, 57.8, 43.4, 30.6; MS(ES+) m/z 358.2 (M+1).

EXAMPLE 10.58

Synthesis of 1'-[(2-isopropyl-1,3-oxazol-4-yl)methyl]spiro[furo[2,3-f][1,3]benzodioxole-7,3'-indol]-2'(1'H)-one

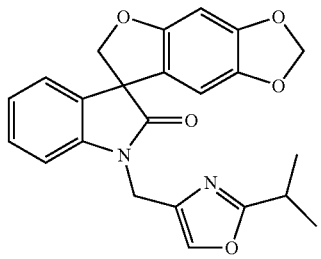

Following the procedure described in EXAMPLE 10.47, and making non-critical variations using spiro[furo[2,3-f][1,3]benzodioxole-7,3'-indol]-2'(1'H)-one to replace 4'-bromospiro[furo[2,3-f][1,3]benzodioxole-7,3'-indol]-2'(1'H)-one, and 4-chloromethyl-2-isopropyloxazole to replace 2-(bromomethyl)-5-(trifluoromethyl)furan, the title compound was obtained (22%) as a colorless solid: mp 118-120° C.; $^1$H NMR (300 MHz, DMSO-d$_6$) δ 7.97 (s, 1H), 7.24 (t, 1H), 7.13 (d, 1H), 7.05 (d, 1H), 6.98 (t, 1H), 6.65 (s, 1H), 6.26 (s, 1H), 5.88 (d, 2H), 4.85 (d, 1H), 4.77 (d, 1H), 4.71-4.66 (m, 2H), 3.04-2.95 (m, 1H), 1.18 (dd, 6H); $^{13}$C NMR (75 MHz, DMSO-d$_6$) δ 176.9, 169.1, 155.6, 148.7, 142.4, 142.2, 136.8, 135.2, 132.4, 129.2, 123.9, 123.4, 120.5, 109.9, 103.6, 101.9, 93.7, 79.9, 57.9, 36.2, 28.1, 20.7, 20.6; MS (ES+) m/z 405.2 (M+1).

EXAMPLE 10.59

Synthesis of 1'-[(1-methyl-1H-benzimidazol-2-yl)methyl]spiro[furo[2,3-f][1,3]benzodioxole-7,3'-indol]-2'(1'H)-one

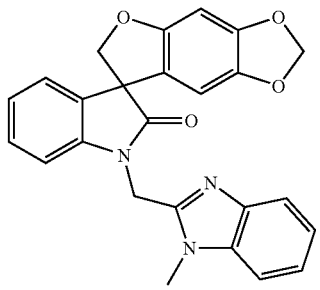

Following the procedure described in EXAMPLE 10.47, and making non-critical variations using spiro[furo[2,3-f][1,3]benzodioxole-7,3'-indol]-2'(1'H)-one to replace 4'-bromospiro[furo[2,3-f][1,3]benzodioxole-7,3'-indol]-2'(1'H)-one, and 2-(bromomethyl)-1-methyl-1H-benzimidozole to replace 2-(bromomethyl)-5-(trifluoromethyl)furan, the title compound was obtained (22%) as a colorless solid: mp>250° C.; $^1$H NMR (300 MHz, CDCl$_3$) δ 7.71 (d, 1H), 7.65 (d, 1H), 7.54 (t, 1H), 7.39 (t, 1H), 7.30-7.24 (m, 1H), 7.16 (d, 1H), 7.05 (d, 2H), 6.63 (s, 1H), 6.49 (s, 1H), 6.44 (d, 1H), 6.11 (s, 1H), 5.83 (d, 2H), 4.99 (ABq, 2H), 4.80 (ABq, 2H); $^{13}$C NMR (75 MHz, CDCl$_3$) δ 177.2, 155.9, 150.6, 149.6, 148.9, 142.3, 141.7, 132.1, 131.8, 129.8, 128.9, 127.9, 126.8, 126.7, 126.6, 123.9, 123.6, 119.4, 111.0, 110.9, 110.6, 109.3, 103.1, 101.5, 93.6, 80.4, 58.2, 37.3; MS (ES+) m/z 506.3 (M+1).

EXAMPLE 10.60

Synthesis of 1'-[(2-oxo-1,3-benzothiazol-3(2H)-yl)methyl]spiro[furo[2,3-f][1,3]benzodioxole-7,3'-indol]-2'(1'H)-one

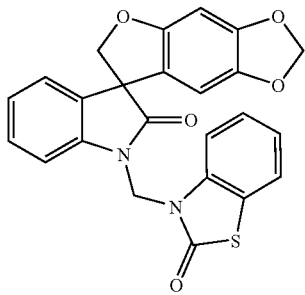

Following the procedure described in EXAMPLE 10.47, and making non-critical variations using spiro[furo[2,3-f][1,3]benzodioxole-7,3"-indol]-2"(1"H)-one to replace 4"-bromospiro[furo[2,3-f][1,3]benzodioxole-7,3"-indol]-2"(1"H)-one, and 3-(bromomethyl)-benzo[d]thiazol-2(3H)-one to replace 2-(bromomethyl)-5-(trifluoromethyl)furan, the title compound was obtained (31%) as a colorless solid: $^1$H NMR (300 MHz, DMSO-$d_6$) δ 7.67 (d, 1H), 7.41 (d, 1H), 7.35-7.29 (m, 3H), 7.23-7.14 (m, 2H), 7.05 (t, 1H), 6.68 (s, 1H), 5.94-5.85 (m, 5H), 4.69 (td, 1H); $^{13}$C NMR (75 MHz, DMSO-$d_6$) δ 178.1, 170.6, 155.9, 148.9, 142.2, 141.0, 136.1, 131.8, 129.6, 127.3, 124.5, 124.4, 124.3, 123.7, 121.5, 119.8, 112.1, 110.0, 103.4, 101.9, 93.8, 80.3, 58.3, 47.9; MS (ES+) m/z 467.2 (M+23).

EXAMPLE 10.61

Synthesis of 1'-[(5-chloro-2-thienyl)methyl]-5'-fluorospiro[furo[2,3-f][1,3]benzodioxole-7,3'-indol]-2'(1'H)-one

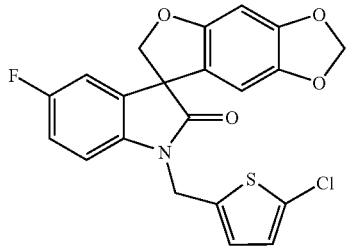

Following the procedure described in EXAMPLE 10.47, and making non-critical variations using 5'-fluorospiro[furo[2,3-f][1,3]benzodioxole-7,3'-indol]-2'(1'H)-one to replace 4'-bromospiro[furo[2,3-f][1,3]benzodioxole-7,3'-indol]-2'(1'H)-one, and 5-chloro-2-(chloromethyl)thiophene to replace 2-(bromomethyl)-5-(trifluoromethyl)furan, the title compound was obtained (76%) as a colorless solid: mp 142-144° C.; $^1$H NMR (300 MHz, DMSO-$d_6$) δ 7.22-7.17 (m, 1H), 7.14-7.13 (m, 1H), 7.12-7.10 (m, 2H), 6.96 (d, 1H), 6.68 (s, 1H), 6.13 (s, 1H), 5.91 (d, 2H), 5.02 (ABq, 2H), 4.73 (ABq, 2H); $^{13}$C NMR (75 MHz, DMSO-$d_6$) δ 176.9, 161.0, 157.8, 156.0, 149.0, 142.2, 138.3, 138.2 (d, $^4J_{cF}$=7.0 Hz) 133.6 (d, $^3J_{cF}$=33 Hz), 128.3, 127.8, 127.1, 119.5, 115.6 (d, $^1J_{cF}$=93 Hz), 112.5 (d, $^1J_{cF}$=100 Hz), 110.8 (d, $^3J_{cF}$=32 Hz), 103.2, 102.0, 93.9, 79.8, 58.2 (d, $^4J_{cF}$=7.0 Hz), 39.0; MS (ES+) m/z 430.1 (M+1).

EXAMPLE 10.62

Synthesis of 1'-[(5-chloro-2-furyl)methyl]spiro[furo[2,3-f][1,3]benzodioxole-7,3'-indol]-2'(1'H)-one

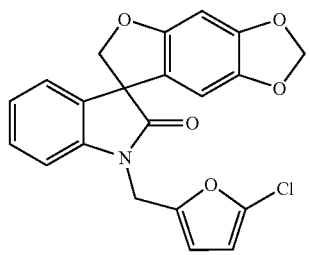

To an ice-cooled solution of (5-chloro-2-furyl)methanol (2.03 g, 15.3 mmol) in anhydrous dichloromethane (50.0 mL) was added triethylamine (4.64 g, 45.9 mmol) followed by thionyl chloride (3.64 g, 30.6 mmol). The reaction mixture was stirred at 0° C. for 30 min and quenched with saturated ammonium chloride (25.0 mL). After the aqueous layer was separated, the organic layer was washed with 10% aqueous HCl (20.0 mL), brine (20 mL), dried over anhydrous sodium sulfate and filtered. The filtrate was concentrated in vacuo to drynessto give 5-chloro-2-chloromethylfuran as a yellow oil. A solution of this oil in anhydrous N,N-dimethylformamide (3.00 mL) was added directly without any further purification to a mixture of spiro[furo[2,3-f][1,3]benzodioxole-7,3'-indol]-2'(1'H)-one (0.84 g, 3.00 mmol) and sodium hydroxide (0.48 g, 12.0 mmol) in anhydrous N,N-dimethylformamide (9.00 mL). The reaction mixture was heated at 70° C. for 16 h, cooled to ambient temperature followed by the addition of saturated ammonium chloride (5.0). N,N-Dimethylformamide was removed under high vacuum. The residue was diluted with ethyl acetate (100 mL), washed with 10% aqueous HCl (25.0 mL), brine (25.0 mL), dried over anhydrous sodium sulfate and filtered. The filtrate was concentrated in vacuo to dryness. The brown residue was subjected to column chromatography eluting with ethyl acetate/hexane (35%) to afford the title compound (0.74 g, 62%) as a colorless solid: mp 148-150° C.; $^1$H NMR (300 MHz, DMSO-$d_6$) δ 7.29 (t, 1H), 7.15-7.12 (m, 2H), 7.01 (d, 1H), 6.67 (s, 1H), 6.60 (d, 1H), 6.39 (d, 1H), 6.10 (s, 1H), 5.89 (d, 2H), 4.89 (ABq, 2H), 4.72 (ABq, 2H); $^{13}$C NMR (75 MHz, DMSO-$d_6$) δ 176.9 155.8 149.7, 148.8, 142.2, 142.1, 134.8, 132.1, 129.3 124.1, 123.7 120.2, 112.0, 109.9, 108.2 103.2, 101.9, 93.8, 80.0, 57.9 37.0; MS (ES+) m/z 396 (M+1).

EXAMPLE 10.63

Synthesis of 1'-[(4-hydroxy-1,2,2,6,6-pentamethylpiperidin-4-yl)methyl]spiro[furo[2,3-f][1,3]benzodioxole-7,3'-indol]-2'(1'H)-one

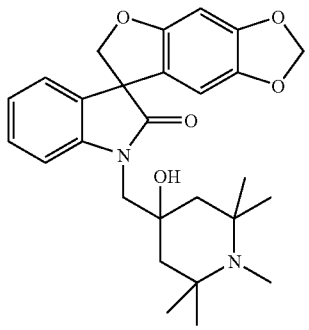

Following the procedure described in EXAMPLE 10.62, and making non-critical variations using 5,5,6,7,7-pentamethyl-1'-oxa-6-azaspiro[2.5]octane to replace (5-chloro-2-furyl)methanol, the title compound was obtained (70%) as a colorless solid: mp 210-214° C.; $^1$H NMR (300 MHz, DMSO-$d_6$) δ 7.29 (d, 1H), 7.24 (t, 1H), 7.10 (d, 1H), 7.01 (t, 1H), 6.66 (s, 1H), 6.45 (s, 1H), 5.90 (d, 2H), 5.20 (br, 1H), 4.70 (ABq, 2H), 3.57 (q, 2H), 3.30 (s, 3H), 2.01-1.83 (m, 4H), 1.45 (s, 6H), 1.34 (s, 6H); $^{13}$C NMR (75 MHz, DMSO-$d_6$) δ 178.5, 156.0, 148.7, 144.5, 142.2, 132.3, 128.9, 123.8, 123.2, 120.3, 110.9, 104.1, 101.9, 93.7, 80.9, 71.6, 65.3, 57.8, 52.6, 30.2, 28.7, 22.1; MS (ES+) m/z 465.4 (M+1).

EXAMPLE 10.64

Synthesis of 1'-{[5-(2-chlorophenyl)-2-furyl]methyl}spiro[furo[2,3-f][1,3]benzodioxole-7,3'-indol]-2'(1'H)-one

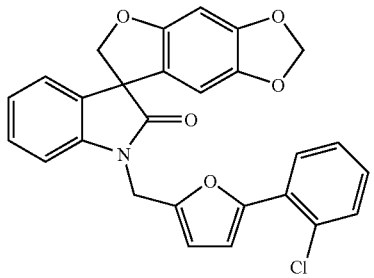

Following the procedure described in EXAMPLE 10.62, and making non-critical variations using [5-(2-chlorophenyl)-2-furyl]methanol to replace (5-chloro-2-furyl)methanol, the title compound was obtained (48%) as a colorless solid: mp 148-150° C.; $^1$H NMR (300 MHz, CDCl$_3$) δ 7.74 (d, 1H), 7.39 (d, 1H), 7.29 (d, 1H), 7.24 (d, 1H), 7.19-7.15 (m, 2H), 7.08-7.04 (m, 3H), 6.51 (s, 1H), 6.45 (d, 1H), 6.12 (s, 1H), 6.84 (s, 2H), 4.99 (ABq, 2H), 4.78 (ABq, 2H); $^{13}$C NMR (75 MHz, CDCl$_3$) δ 177.2, 155.9, 150.3, 149.0, 148.6, 142.4, 141.8, 132.1, 130.8, 130.0, 128.9, 128.7, 128.2, 127.7, 126.9, 123.9, 123.6, 119.4, 111.8, 110.7, 109.2, 103.1, 101.5, 93.6, 80.4, 58.2, 37.3; MS (ES+) m/z 472.2 (M+1).

EXAMPLE 10.65

Synthesis of 1'-[(5-methyl-2-furyl)methyl]spiro[furo[2,3-f][1,3]benzodioxole-7,3'-indol]-2'(1'H)-one

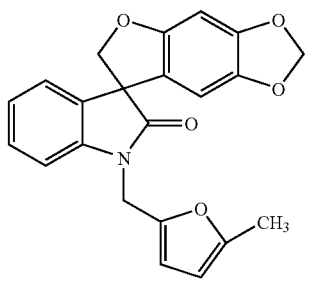

Following the procedure described in EXAMPLE 10.62, and making non-critical variations using (5-methyl-2-furyl)methanol to replace (5-chloro-2-furyl)methanol, the title compound was obtained (70%) as a colorless solid: mp 117-119° C.; $^1$H NMR (300 MHz, DMSO-$d_6$) δ 7.26 (t, 1H), 7.12 (t, 2H), 6.99 (t, 1H), 6.67 (s, 1H), 6.32 (d, 1H), 6.07 (s, 1H), 5.97 (d, 1H), 5.89 (d, 2H), 4.84 (ABq, 2H), 4.72 (ABq, 2H); $^{13}$C NMR (75 MHz, DMSO-$d_6$) δ 176.8, 155.7, 151.9, 148.8, 147.7, 142.3, 142.2, 132.1, 129.2, 124.0, 123.5, 120.4, 110.1, 110.0, 107.0, 103.2, 101.9, 93.8, 79.9, 57.9, 37.2, 13.7; MS (ES+) m/z 376 (M+1).

EXAMPLE 10.66

Synthesis of 1'-[(5-bromo-2-furyl)methyl]spiro[furo[2,3-f][1,3]benzodioxole-7,3'-indol]-2'(1'H)-one

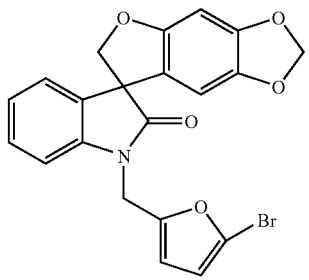

Following the procedure described in EXAMPLE 10.62, and making non-critical variations using (5-bromo-2-furyl)methanol to replace (5-chloro-2-furyl)methanol, the title compound was obtained (76%) as a colorless solid: $^1$H NMR (300 MHz, DMSO-$d_6$) δ 9.29 (s, 1H), 7.69 (dt, 1H), 7.32-7.26 (m, 2H), 7.04 (d, 1H), 6.99 (d, 1H), 6.71 (d, 1H), 6.02 (s, 1H), 4.91 (ABq, 2H), 4.47 (t, 2H), 3.08 (t, 2H); $^{13}$C NMR (75 MHz, DMSO-$d_6$) δ 176.9, 160.4, 156.3, 153.8, 149.7, 146.1, 137.5, 130.9, 130.8, 126.5, 125.8, 123.1, 121.5, 118.8, 116.4, 108.3, 96.7, 76.6, 71.9, 45.7, 29.1; MS (ES+) m/z 440.1 (M+1), 442.1 (M+1).

EXAMPLE 10.67

Synthesis of 1'-[(5-chloro-2-thienyl)methyl]spiro[furo[2,3-f][1,3]benzodioxole-7,3'-indol]-2'(1H)-one

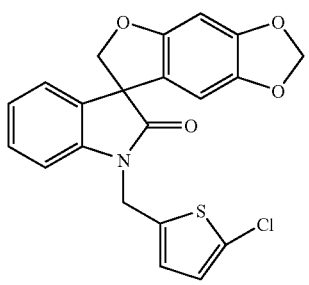

Following the procedure described in EXAMPLE 10.62, and making non-critical variations using (5-chloro-2-thienyl)methanol to replace (5-chloro-2-furyl)methanol, the title compound was obtained (77%) as a colorless solid: mp 145-146° C.; $^1$H NMR (300 MHz, DMSO-$d_6$) δ 7.28 (t, 1H), 7.20-7.14 (m, 2H), 7.10 (d, 1H), 7.01 (t, 1H), 6.95 (d, 1H), 6.67 (s, 1H), 6.09 (s, 1H), 5.89 (d, 2H), 5.02 (ABq, 2H), 4.71 (ABq, 2H); MS (ES+) m/z 411.9 (M+1).

EXAMPLE 10.68

Synthesis of 1'-{[3-hydroxy-5-(trifluoromethyl)-2-thienyl]methyl}spiro[furo[2,3-f][1,3]benzodioxole-7,3'-indol]-2'(1'H)-one

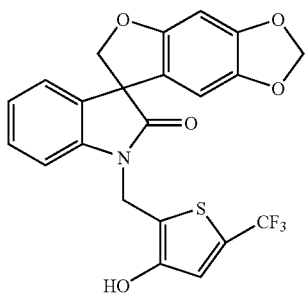

Following the procedure described in EXAMPLE 10.62, and making non-critical variations using 2-(hydroxymethyl)-5-(trifluoromethyl)thiophene-3-ol to replace (5-chloro-2-furyl)methanol, the title compound was obtained (48%) as a colorless solid: mp 225-227° C.; $^1$H NMR (300 MHz, DMSO-$d_6$) δ 10.4 (s, 1H), 7.29 (dt, 1H), 7.16-7.10 (m, 3H), 7.01 (dt, 1H), 6.68 (s, 1H), 6.09 (s, 1H), 5.89 (d, 2H), 4.94 (ABq, 2H), 4.70 (ABq, 2H); $^{13}$C NMR (75 MHz, DMSO-$d_6$) δ 176.9, 155.8, 152.3, 148.9, 142.2, 141.9, 132.1, 129.4, 125.9, 125.4, 124.5, 124.2, 123.8, 122.6, 120.9, 120.0, 116.5, 109.5, 103.3, 101.9, 93.8, 80.2, 57.9, 34.9; MS (ES+) m/z 460.38 (M−1).

EXAMPLE 10.69

Synthesis of 1'((5-(2-(trifluoromethyl)phenyl)furan-2-yl)methyl)-6H-spiro[benzofuro[6,5-d][1,3]dioxole-7,3'-indolin]-2'-one

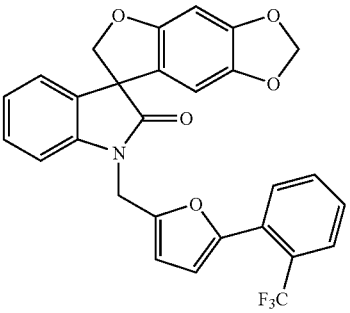

Following the procedure described in EXAMPLE 10.62, and making non-critical variations using {5-[2-(trifluoromethyl)phenyl]-2-furyl}methanol to replace (5-chloro-2-furyl)methanol, the title compound was obtained (28%) as a colorless solid: mp 124-126° C.; $^1$H NMR (300 MHz, CDCl$_3$) δ 7.71 (d, 1H), 7.65 (d, 1H), 7.54 (t, 1H), 7.39 (t, 1H), 7.30-7.24 (m, 1H), 7.16 (d, 1H), 7.05 (d, 2H), 6.63 (s, 1H), 6.49 (s, 1H), 6.44 (d, 1H), 6.11 (s, 1H), 5.83 (d, 2H), 4.99 (ABq, 2H), 4.80 (ABq, 2H); $^{13}$C NMR (75 MHz, CDCl$_3$) δ 177.2, 155.9, 150.6, 149.6, 148.9, 142.3, 141.7, 132.1, 131.8, 129.8, 128.9, 127.9, 126.8, 126.7, 126.6, 123.9, 123.6, 119.4, 111.0, 110.9, 110.6, 109.3, 103.1, 101.5, 93.6, 80.4, 58.2, 37.3; MS (ES+) m/z 506.27 (M+1).

EXAMPLE 10.70

Synthesis of 1'[(2-chloro-1,3-thiazol-5-yl)methyl]spiro[furo[2,3-f][1,3]benzodioxole-7,3'-indol]-2'(1'H)-one

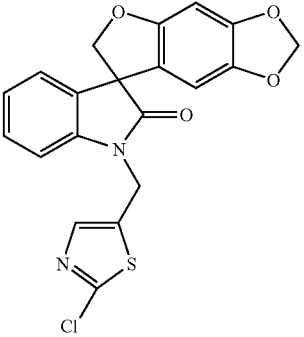

To a solution of (2-chloro-1,3-thiazol-5-yl)methanol (0.30 g, 2.00 mmol) in anhydrous CH$_2$Cl$_2$ (20.0 mL) was added thionyl chloride (0.50 g, 4.20 mmol) followed by triethylamine (0.40 g, 4.00 mmol) at 0° C. After stirring at 0° C. for one hour and ambient temperature for one hour, the reaction mixture was diluted with CH$_2$Cl$_2$ (50.0 mL) and extracted with water (2×20 mL). The organic phase was dried over Na$_2$SO$_4$ and filtered. The filtrate was concentrated in vacuo to dryness. The residue was dissolved in methyl-ethyl ketone (10.0 mL) followed by the additions of spiro[furo[2,3-f][1,3]benzodioxole-7,3'-indol]-2'(1'H)-one (0.36 g, 2.00 mmol) and cesium carbonate (1.95 g, 6.00 mmol). The reaction mixture was heated at 70° C. overnight, cooled, filtered and the filtrate was concentrated in vacuo to dryness. The residue was subjected to column chromatography to yield the title compound (0.032 g, 3.4%) as a colorless solid: mp 195-198° C.; ¹H NMR (300 MHz, DMSO-d₆) δ 7.81 (s, 1H), 7.39-6.93 (m, 5H), 6.66 (s, 1H), 6.15-6.12 (m, 1H), 5.89 (d, 2H), 5.10 (s, 2H), 4.70 (dd, 2H); MS (ES+) m/z 413.1 (M+1).

EXAMPLE 10.71

Synthesis of 1'-{[5-(trifluoromethyl)-2-furyl]methy}-6,7-dihydrospiro[benzo[1,2-b:4,5-b']difuran-3,3'-indol]-2'(1'H)-one

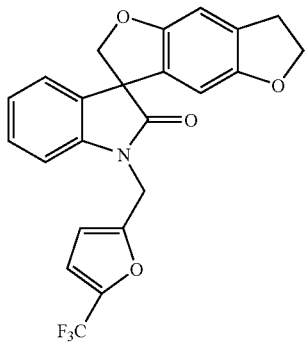

Following the procedure as described in EXAMPLE 10.21, and making non-critical variations using 6,7-dihydrospiro[benzo[1,2-b:4,5-b']difuran-3,3'-indol]-2'(1H)-one to replace 5,5-dimethyl-5,6-dihydrospiro[benzo[1,2-b:5,4-b']difuran-3,3'-indol]-2'(1H)-one, the title compound was obtained (19%) as a white solid: mp 174-177° C.; ¹H NMR (300 MHz, DMSO-d₆) δ 7.33-6.95 (m, 5H), 6.84 (s, 1H), 6.71 (d, 1H), 5.88 (s, 1H), 5.03 (ABq, 2H), 4.70 (ABq, 2H), 4.46-4.31 (m, 2H), 3.07 (t, 2H); MS (ES+) m/z 428.0 (M+1).

EXAMPLE 10.72

Synthesis of 1'{[5-(trifluoromethyl)-2-furyl]methyl}5,6-dihydrospyro[benzo[1,2-b:5,4-b']difuran-3,3'-indol]2'(1'H)-one

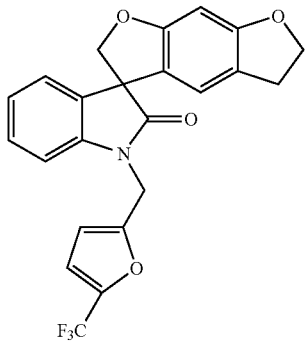

Following the procedure described in EXAMPLE 10.21, and making non-critical variations using 5,6-dihydrospyro[benzo[1,2-b:5,4-b']difuran-3,3'-indol]2'(1'H)-one to replace 5,5-dimethyl-5,6-dihydrospiro[benzo[1,2-b:5,4-b']difuran-3,3'-indol]-2'(1'H)-one, the title compound was obtained (71%) as a white solid: mp 173-176° C.; ¹H NMR (300 MHz, DMSO-d₆) δ 7.50-6.90 (m, 5H), 6.73 (d, 1H), 6.38 (s, 1H), 6.32 (s, 1H), 5.04 (ABq, 2H), 4.75 (ABq, 2H), 4.55-4.36 (m, 2H), 2.88 (t, 2H); ¹³C NMR (75 MHz, DMSO-d₆) δ 177.2, 161.7, 161.0, 153.5, 142.0, 140.3, 139.7, 139.2, 132.6, 129.1, 124.1, 123.8, 121.2, 121.0, 120.3, 119.1, 117.7, 114.6, 114.5, 110.4, 109.6, 93.0, 80.0, 72.5, 57.3, 36.8, 28.7; MS (ES+) m/z 428.2 (M+1).

EXAMPLE 10.73

Synthesis of 1'-{[5-(trifluoromethyl)-2-thienyl]methyl}spiro[furo[2,3-f][1,3]benzodioxole-7,3'-indol]-2'(1'H)-one

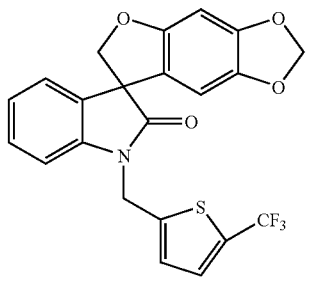

To a solution of 1-{[3-hydroxy-5-(trifluoromethyl)-2-thienyl]methyl}spiro[furo[2,3-f][1,3]benzodioxole-7,3'-indol]-2'(1'H)-one (0.75 g, 1.62 mmol) in anhydrous dichloromethane (12.0 mL) was added triethylamine (0.49 g, 0.70 mL, 4.85 mmol) and trifluoromethanesulfonic anhydride (0.91 g, 0.50 mL, 3.24 mmol) at 0° C. under nitrogen. The reaction mixture was stirred for 30 min and quenched with saturated ammonium chloride (15.0 mL). After the aqueous layer was separated, the organic layer was washed with 10% HCl (10.0 mL), brine (10.0 mL), dried over anhydrous sodium sulfate and filtered. The filtrate was concentrated in vacuo to dryness. The residue was subjected to column chromatography to provide brown gummy material as the triflate. A mixture of this triflate (15.3 mmol), tetrakis(triphenylphosphine)palladium(0) (0.19 g, 0.17 mmol), triethylamine (1.66 g, 2.30 mL, 16.5 mmol), and formic acid (0.76 mg, 0.60 mL, 16.5 mmol) in anhydrous dioxane (24 mL) was heated at reflux for 16 h. After the reaction mixture was cooled down to ambient temperature, the solvent was removed under reduced pressure. The black residue was diluted with ethyl acetate (50.0 mL), washed with 10% HCl (20.0 mL), saturated ammonium chloride (20.0 mL), brine (20.0 mL), dried over anhydrous sodium sulfate and filtered. The filtrate was concentrated in vacuo to dryness. The residue was subjected to column chromatography eluting with ethyl acetate:hexane (35%) to afford the title compound (0.65 g, 89%) as a colorless solid: mp 127-130° C.; ¹H NMR (300 MHz, DMSO-d₆) δ 7.58-7.56 (m, 1H), 7.32-7.27 (m, 2H), 7.22 (s, 1H), 7.18 (d, 1H), 7.16 (s, 1H), 7.09 (dt, 1H), 6.68 (s, 1H), 6.10 (s, 1H), 5.89 (d, 2H), 5.17 (ABq, 2H), 4.72 (ABq, 2H); ¹³C NMR (75 MHz, DMSO-d₆) δ 177.0, 155.9, 148.9, 144.7, 142.2, 141.8, 132.1, 130.6, 130.5, 129.3, 128.7, 128.0, 124.3, 123.9, 120.0, 109.8, 103.3, 102.0, 93.9, 80.2, 57.8, 38.7; MS (ES+) m/z 446.1 (M+1).

EXAMPLE 10.74

Synthesis of 1'-{[3-methoxy-5-(trifluoromethyl)-2-thienyl]methyl}spiro[furo[2,3-f][1,3]benzodioxole-7,3'-indol]-2'(1'H)-one

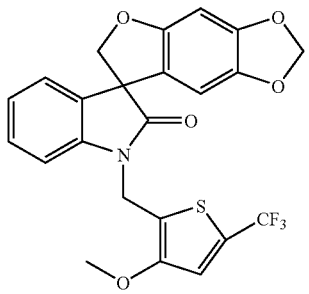

A mixture of 1'-{[3-hydroxy-5-(trifluoromethyl)-2-thienyl]methyl}spiro[furo[2,3-f][1,3]benzodioxole-7,3'-indol]-2'(1H)-one (0.18 g, 0.39 mmol), NaOH (0.08 g, 1.96 mmol) and iodomethane (0.17 g, 1.18 mmol) in anhydrous N,N-dimethylformamide (2.00 mL) was stirred at ambient temperature for 16 h. The reaction was quenched by addition of saturated ammonium chloride (10.0 mL) and extracted with ethyl acetate (3×50.0 mL). The combined organic layers was washed with water (3×20.0 mL), brine (20.0 mL), dried over anhydrous sodium sulfate and filtered. The filtrate was concentrated in vacuo to dryness. The colorless solid was triturated with ether to give the title compound (0.15 g, 81%): mp 178-180° C.; $^1$H NMR (300 MHz, DMSO-$d_6$) δ 7.71 (s, 1H), 7.30 (dt, 1H), 7.15 (d, 1H), 7.07-7.02 (m, 2H), 6.68 (s, 1H), 6.08 (s, 1H), 5.89 (d, 2H), 4.95 (ABq, 2H), 4.70 (ABq, 2H), 3.90 (s, 3H); $^{13}$C NMR (75 MHz, DMSO-$d_6$) δ 177.0, 155.8, 154.9, 148.9, 142.2, 141.8, 132.1, 129.4, 125.7, 124.3, 123.8, 120.4, 120.3, 120.0, 119.5, 109.4, 103.2, 102.0, 93.9, 80.1, 59.9, 57.9, 34.9; MS (ES+) m/z 476.3 (M+1).

EXAMPLE 10.75

Synthesis of 4'-methyl-1'-{[5-(trifluoromethyl)-2-furyl]methyl}spiro[furo[2,3-f][1,3]benzodioxole-7,3'-indol]-2'(1'H)-one

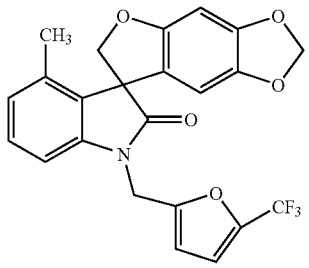

A mixture of 4'-bromo-1'-((5-(trifluoromethyl)furan-2-yl)methyl)-6H-spiro[benzofuro[6,5-d][1,3]dioxole-7,3'-indolin]-2'-one (0.51 g, 1.00 mmol), lithium chloride (0.09 mg, 2.00 mmol), Pd$_2$(dba)$_3$ (0.09 mg, 10 mole %) was flushed with nitrogen. To the above mixture was added anhydrous 1-methyl-2-pyrrolidinone (5.00 mL) and tetramethyltin (0.27 mg, 0.20 mL, 1.50 mmol). The reaction mixture was heated at 60° C. for 16 h and quenched with saturated ammonium chloride (10.0 mL). The reaction mixture was extracted with ethyl acetate (3×10.0 mL). The combined organic layers was dried over anhydrous sodium sulfate and filtered. The filtrate was concentrated in vacuo to dryness. The residue was subjected to column chromatography eluting with ethyl acetate:hexane (20%) to afford the title compound (0.07 g, 16%) as a colorless solid: mp 117-119° C.; $^1$H NMR (300 MHz, CDCl$_3$) δ 7.18 (t, 1H), 6.82 (t, 2H), 6.72 (d, 1H), 6.47 (s, 1H), 6.37 (d, 1H), 6.09 (s, 1H), 5.86 (d, 2H), 4.95 (ABq, 2H), 4.83 (ABq, 2H), 2.03 (s, 3H); $^{13}$C NMR (75 MHz, CDCl$_3$) δ 177.6, 156.2, 152.0, 149.1, 142.3, 141.3, 135.6, 129.4, 128.9, 126.0, 120.6, 117.2, 112.7, 112.6, 109.2, 106.5, 102.9, 101.6, 93.3, 78.4, 58.3, 37.0, 17.1; MS (ES+) m/z 444.1 (M+1).

EXAMPLE 10.76

Synthesis of 5'-methyl-1'-{[5-(trifluoromethyl)-2-furyl]methyl}spiro[furo[2,3-f][1,3]benzodioxole-7,3'-indol]-2'(1H)-one

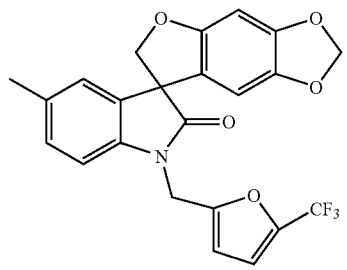

Following the procedure described in EXAMPLE 10.47, and making non-critical variations using 5'-methylspiro[furo[2,3-f][1,3]benzodioxole-7,3'-indol]-2'(1'H)-one to replace 4'-bromospiro[furo[2,3-f][1,3]benzodioxole-7,3'-indol]-2'(1'H)-one, the title compound was obtained (77%): mp 96-98° C.; $^1$H NMR (300 MHz, CDCl$_3$) δ 7.09 (d, 1H), 7.00 (s, 1H), 6.87 (d, 1H), 6.74 (d, 1H), 6.52 (s, 1H), 6.38 (d, 1H), 6.11 (s, 1H), 5.88 (d, 2H), 4.96 (ABq, 2H), 4.80 (ABq, 2H), 2.29 (s, 3H); MS (ES+) m/z 444.2 (M+1).

EXAMPLE 10.77

Synthesis of 1'-({5-[4-(trifluoromethyl)phenyl]-1,2,4-oxadiazol-3-yl}methyl)spiro[furo[2,3-f][1,3]benzodioxole-7,3'-indol]-2'(1'H)-one

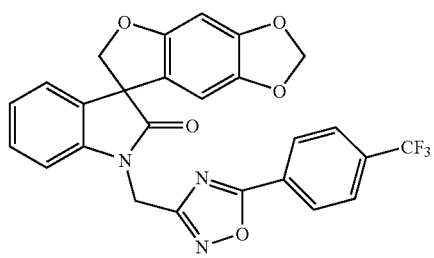

Following the procedure described in EXAMPLE 10.47, and making non-critical variations using spiro[furo[2,3-f][1,3]benzodioxole-7,3'-indol]-2'(1'H)-one to replace 4'-bromo-spiro[furo[2,3-f][1,3]benzodioxole-7,3'-indol]-2'(1'H)-one, and 3-chloromethyl-5-[4-(trifluoromethyl)phenyl]-1,2,4-oxadiazole to replace 2-(bromomethyl)-5-(trifluoromethyl)furan, the title compound was obtained (44%): $^1$H NMR (300 MHz, CDCl$_3$) δ 8.22 (d, 2H), 7.76 (d, 2H), 7.30-7.18 (m, 2H), 7.06 (t, 1H), 6.91 (d, 1H), 6.51 (s, 1H), 6.40 (s, 1H), 5.88 (s, 2H), 5.17 (ABq, 2H), 4.86 (ABq, 2H); MS (ES+) m/z 508.1 (M+1).

EXAMPLE 10.78

Synthesis of 1'-(2-thienylmethyl)spiro[furo[2,3-f][1,3]benzodioxole-7,3'-indol]-2'(1'H)-one

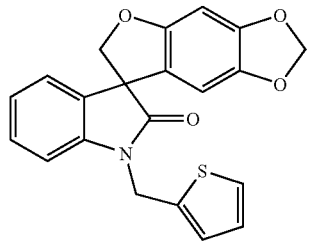

Following the procedure described in EXAMPLE 10.62, and making non-critical variations using 2-thiophenemethanol to replace (5-chloro-2-furyl)methanol, the title compound was obtained (37%) as a colorless solid: $^1$H NMR (300 MHz, CDCl$_3$) δ 7.26-7.20 (m, 2H), 7.18-7.13 (m, 1H), 7.10-6.98 (m, 2H), 6.97-6.90 (m, 2H), 6.50 (s, 1H), 6.12 (s, 1H), 5.85 (d, 2H), 5.10 (ABq, 2H), 4.79 (ABq, 2H); MS (ES+) m/z 378.19 (M+1).

EXAMPLE 10.79

Synthesis of 5-[(2'-oxospiro[furo[2,3-f][1,3]benzodioxole-7,3'-indol]-1(2'H)-yl)methyl]thiophene-2-carbonitrile

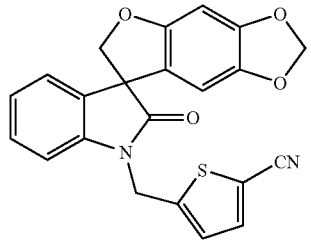

A mixture of 1'-[(5-bromo-2-thienyl)methyl]spiro[furo[2,3-f][1,3]benzodioxole-7,3'-indol]-2'(1'H)-one (0.23 g, 0.49 mmol), zinc cyanide (0.07 g, 0.59 mmol), tris(dibenzylideneacetone)dipalladium(0) (0.10 g, 0.11 mmol), 1,1'-bis(diphenylphosphino)ferrocene (0.06 g, 0.11 mmol), N,N-dimethylformamide (6.00 mL) and a catalytic amount of water (2 drops) was heated at 120° C. for 24 hours. After cooling down to ambient temperature, the organic solvent was evaporated in vacuo. The residue was extracted with ethyl acetate (5×15.0 mL) and the combined organic solution was passed through a bed of celite. The filtrate was successively washed with saturated aqueous ammonium chloride (25.0 mL), water (2×35.0 mL) and brine (40.0 mL). The organic layer was dried over sodium sulfate and filtered. The filtrate was concentrated in vacuo to dryness. The residue was subjected to column chromatography eluted with 20-35% ethyl acetate in hexanes to afford solid which was further purified by preparative thin layer chromatography, eluted with 20% ethyl acetate in hexanes to afford the title compound (0.09 g, 44%): $^1$H NMR (300 MHz, CDCl$_3$) δ 7.50 (d, 1H), 7.32-7.16 (m, 2H), 7.12-7.04 (m, 2H), 6.86 (d, 1H), 6.51 (s, 1H), 6.08 (s, 1H), 5.87 (d, 2H), 5.10 (ABq, 2H), 4.78 (ABq, 2H); MS (ES+) m/z 403.0 (M+1).

EXAMPLE 10.80

Synthesis of 5-[(2'-oxospiro[furo[2,3-f][1,3]benzodioxole-7,3'-indol]-1'(2'H)-yl)methyl]-2-furonitrile

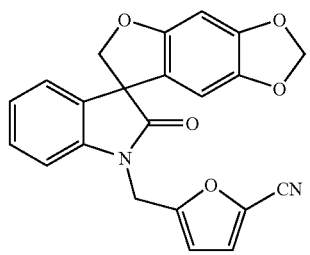

Following the procedure described in EXAMPLE 10.79, and making non-critical variations using 1'-[(5-bromo-2-furyl)methyl]spiro[furo[2,3-f][1,3]benzodioxole-7,3'-indol]-2'(1'H)-one to replace 1'-[(5-bromo-2-thienyl)methyl]spiro[furo[2,3-t][1,3]benzodioxole-7,3'-indol]-2'(1'H)-one, the title compound was obtained (44%) as a colorless solid: mp 167-169° C.; $^1$H NMR (300 MHz, CDCl$_3$) δ 7.34-7.27 (m, 1H), 7.21-7.17 (m, 1H), 7.12-7.08 (m, 1H), 7.07-7.03 (m, 1H), 6.95 (d, 1H), 6.51 (s, 1H), 6.44 (d, 1H), 6.08 (s, 1H), 5.86 (q, 2H), 4.96 (ABq, 2H), 4.78 (ABq, 2H); MS (ES+) m/z 387.2 (M+1).

EXAMPLE 10.81

Synthesis of 1'-{[5-(methylsulfonyl)-2-furyl]methyl}spiro[furo[2,3-f][1,3]benzodioxole-7,3'-indol]-2'(1'H)one

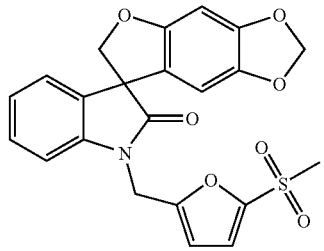

A mixture of 1'-[(5-bromo-2-furyl)methyl]spiro[furo[2,3-f][1,3]benzodioxole-7,3'-indol]-2'(1'H)-one (0.70 g, 1.59 mmol), sodium methanesulfinate (85%, 0.23 g, 1.91 mmol), copper (I) iodide (0.04 g, 0.22 mmol), L-proline (0.04 g, 0.35 mmol) and dimethyl sulfoxide (4.00 mL) was heated at 100° C. After 3 days, the reaction mixture was cooled down to ambient temperature, quenched with water (50.0 mL) and extracted with ethyl acetate (3×40.0 mL). The combined organic layers was washed with brine (2×50.0 mL), dried over sodium sulfate and filtered. The filtrate was concentrated in vacuo to dryness. The residue was subjected to column chromatography eluting with ethyl acetate:hexane (30-50%) to afford the title compound (0.50 g, 71%): mp 177-179° C.; $^1$H NMR (300 MHz, CDCl$_3$) δ 7.29 (t, 1H), 7.19 (d, 1H), 7.12-7.04 (m, 2H), 6.94 (d, 1H), 6.50 (s, 1H), 6.42 (d, 1H), 6.11 (s, 1H), 5.86 (s, 2H), 5.00 (ABq, 2H), 4.79 (ABq, 2H), 3.11 (s, 3H); $^{13}$C NMR (75 MHz, CDCl$_3$) δ 177.3, 155.9, 154.5, 149.1, 149.1, 142.4, 141.1, 131.9, 129.1, 124.2, 124.1, 119.0, 118.4, 109.9, 108.7, 102.9, 101.6, 93.7, 80.3, 58.2, 43.4, 37.2; MS (ES+) m/z 440.0 (M+1).

EXAMPLE 10.82

Synthesis of 1'-[(6-oxo-1,6-dihydropyridin-3-yl)methyl]spiro[furo[2,3-f][1,3]benzodioxole-7,3'-indol]-2'(1'H)-one

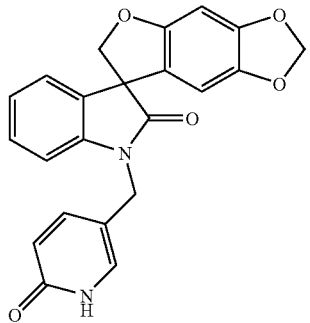

To a mixture of 1'-[(6-methoxypyridin-3-yl)methyl]spiro[furo[2,3-f][1,3]benzodioxole-7,3'-indol]-2'(1'H)-one (0.23 g, 0.57 mmol), sodium iodide (0.28 g, 1.87 mmol), water (2 drops) in anhydrous acetonitrile (5.00 mL) was added chlorotrimethylsilane (0.19 g, 1.78 mmol) at 0° C. The reaction mixture was stirred at ambient temperature for 16 h and quenched with sodium bisulfite (0.20 g). The reaction mixture was diluted with ethyl acetate (100 mL) and washed with brine (2×25.0 mL), dried over anhydrous sodium sulfate and filtered. The filtrate was concentrated in vacuo to dryness. The residue was triturated with ether (2×10.0 mL) to give the title compound (0.16 g, 72%) as la ight yellow solid: mp 247-250° C.; $^1$H NMR (300 MHz, DMSO-$d_6$,) δ 11.50 (br, 1H), 7.50 (bd, 1H), 7.36-7.24 (m, 2H), 7.17-7.12 (m, 2H), 7.01 (dt, 1H), 6.67 (s, 1H), 6.28 (d, 1H), 6.09 (s, 1H), 5.91-5.88 (m, 2H), 4.78 (d, 1H), 4.67-4.62 (m, 3H); MS (ES+) m/z 389.15 (M+1).

EXAMPLE 10.83

Synthesis of 1'-[(1-methyl-6-oxo-1,6-dihydropyridin-3-yl)methyl]spiro[furo[2,3-f][1,3]benzodioxole-7,3'-indol]-2'(1'H)-one

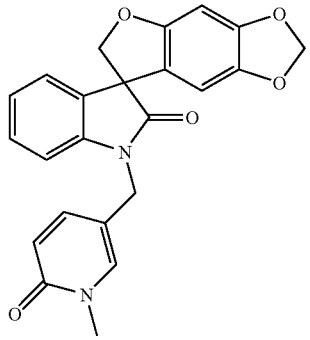

Following the procedure described in PREPARATION 1A, and making non-critical variations using 1'-[(6-oxo-1,6-dihydropyridin-3-yl)methyl]spiro[furo[2,3-f][1,3]benzodioxole-7,3'-indol]-2'(1'H)-one to replace 4-bromoindole, and methyl iodide to replace 1-bromopentane, the title compound was obtained (78%): mp 115-118° C.; $^1$H NMR (300 MHz, CDCl$_3$) δ 7.39-7.23 (m, 3H), 7.18 (d, 1H), 7.06 (t, 1H), 6.87 (d, 1H), 6.57-6.48 (m, 2H), 6.02 (s, 1H), 5.87-5.83 (m, 2H), 4.90 (d, 1H), 4.75-4.52 (m, 3H), 3.51 (s, 3H); $^{13}$C NMR (75 MHz, CDCl$_3$) δ 177.8, 162.5, 155.9, 149.1, 142.4, 141.6, 139.7, 137.6, 132.1, 129.1, 124.4, 123.9, 121.3, 119.1, 114.0, 108.6, 102.8, 101.6, 93.7, 80.3, 58.2, 40.8, 38.0; MS (ES+) m/z 403.3 (M+1).

EXAMPLE 10.84

Synthesis of 5-bromo-1'-[(5-chloro-2-thienyl)methyl]spiro[1-benzofuran-3,3'-indol]-2'(1'H)-one

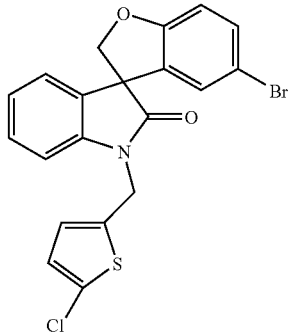

Following the procedure described in EXAMPLE 10, and making non-critical variations using 5-bromospiro[1-benzofuran-3,3'-indol]-2'(1'H)one to replace spiro[furo[2,3-f][1,3]benzodioxole-7,3'-indol]-2'(1'H)-one, and 2-chloro-5-(chloromethyl)thiophene to replace 4-fluorobenzyl bromide, the title compound was obtained (95%) as a white solid: mp 140-142° C.; $^1$H NMR (300 MHz, CDCl$_3$) δ 7.33-7.26 (m, 2H), 7.16-7.02 (m, 2H), 6.94 (d, 1H), 6.97-6.75 (m, 4H), 5.07-4.91 (m, 3H), 4.68 (d, 1H); MS (ES+) m/z 446.7 (M+1), 448.7 (M+1).

EXAMPLE 10.85

Synthesis of 1'-[(5-chloro-1,3,4-thiadiazol-2-yl)methyl]spiro[furo[2,3-f][1,3]benzodioxole-7,3'-indol]-2'(1'H)-one

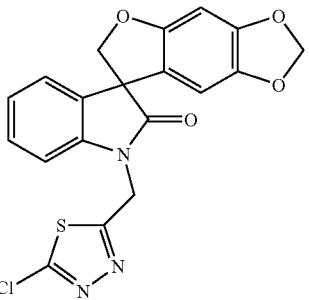

To a solution of spiro[furo[2,3-f][1,3]benzodioxole-7,3'-indol]-2'(1'H)-one (0.56 g, 1.99 mmol) and (5-chloro-1,3,4-thiadiazol-2-yl)methanol (0.30 g, 1.99 mmol) in anhydrous tetrahydrofuran (12.0 mL) was added tributylphosphine (0.60 g, 2.99 mmol) at 0° C. The reaction mixture was stirred for 15 min followed by the addition of N,N,N',N'-tetramethylazodicarboxamide (0.51 g, 2.99 mmol). The reaction mixture was stirred at ambient temperature overnight, quenched with aqueous ammonium chloride (10.0 mL) and diluted with ethyl acetate (350 mL). The organic layer was washed with aqueous saturated sodium chloride (2×25.0 mL), dried over anhydrous sodium sulfate and filtered. The filtrate was concentrated in vacuo to dryness. The residue was subjected to column chromatography (ethyl acetate/hexane, 1/2) to give the title compound (0.20 g, 24%) as a yellowish solid: mp 194-197° C.; $^1$H NMR (300 MHz, DMSO-$d_6$,) δ 7.30 (dt, 1H), 7.20-7.12 (m, 2H), 7.05 (dt, 1H), 6.67 (s, 1H), 6.28 (s, 1H), 5.90 (s, 2H), 5.43 (d, 1H), 5.34 (d, 1H), 4.78 (d, 1H), 4.67 (d, 1H); $^{13}$C NMR (75 MHz, DMSO-$d_6$) δ 177.2, 168.3, 155.8, 155.4, 148.9, 142.2, 141.9, 132.2, 129.4, 124.2, 124.0, 120.1, 109.8, 103.7, 101.9, 93.8, 80.1, 67.5, 57.9, 25.6; MS (ES+) m/z 414.2 (M +1), 416.2 (M+1).

EXAMPLE 10.86

Synthesis of 1'-[(1-pyridin-2-ylpiperidin-4-yl)methyl]spiro[furo[2,3-f][1,3]benzodioxole-7,3'-indol]-2'(1'H)-one

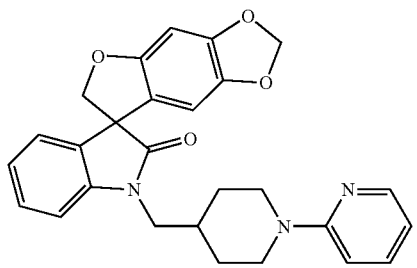

A mixture of 1'-(piperidin-4-ylmethyl)spiro[furo[2,3-f][1,3]benzodioxole-7,3'-indol]-2'(1'H)-one hydrobromide(0.20 g, 0.44 mmol), 2-bromopyridine (0.16 mL, 0.65 mmol), tetrabutyl ammonium iodide (0.05 g) and DBU (0.16 mL, 1.09 mmol) in DMF (5.00 mL) was heated at 120° C. for 15 hrs. After cooling down to ambient temperature, water (30.0 mL) was added. The above mixture was extracted twice with ethyl acetate (50.0 mL), the combined organic phase was dried over Na$_2$SO$_4$ and filtered. The filtrate was concentrated in vacuo to dryness. The residue was subjected to flash chromatography eluting with 30% ethyl acetate in hexane to give a white solid (0.05 g, 27%): mp 95-97° C.; $^1$H NMR (300 MHz, CDCl$_3$) δ 8.17 (d, 1H), 7.47 (td, 1H), 7.31 (t, 1H), 7.18 (d, 1H), 7.06 (t, 1H), 6.92 (d, 1H), 6.66 (d, 1H), 6.59 (dd, 1H), 6.52 (s, 1H), 6.12 (s, 1H), 5.91-5.84 (m, 2H), 4.91 (d, 1H), 4.66 (d, 1H), 4.42-4.27 (m, 2H), 3.82-3.53 (m, 2H), 2.85 (t, 2H), 2.22-2.05 (m, 1H), 1.85-1.70 (m, 2H), 1.53-1.35 (m, 2H); $^{13}$C NMR(75 MHz, CDCl$_3$) δ 177.9, 158.8, 156.1, 149.0, 147.4, 142.8, 142.5, 138.0, 132.4, 129.1, 124.2, 123.5, 119.5, 112.9, 108.8, 107.7, 103.1, 101.7, 93.8, 80.7, 58.3, 46.0, 45.5, 45.4, 35.2, 29.8, 29.7; MS (ES+) m/z 456 (M+1).

EXAMPLE 10.87

Synthesis of 1'-[(1-phenyl-2-ylpiperidin-4-yl)methyl]spiro[furo[2,3-f][1,3]benzodioxole-7,3'-indol]-2'(1'H)-one

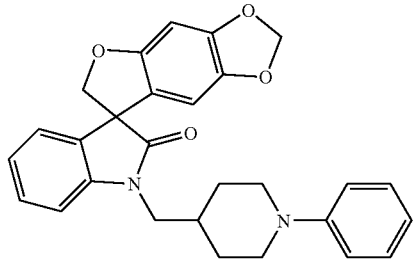

A mixture of 1-(piperidin-4-ylmethyl)spiro[furo[2,3-f][1,3]benzodioxole-7,3'-indol]-2'(1'H)one hydrobromide (0.20 g, 0.44 mmol), 2-bromobenzene(0.07 mL, 0.65 mmol), Pd$_2$(dba)$_3$ (0.03 g, 0.03 mmol), BINAP (0.06 g, 0.10 mmol) and NaOBu$^t$ (0.13 g, 1.30 mmol) in toluene was heated at 100° C. for 15 hrs under nitrogen. After cooling down to ambient temperature, water (30.0 mL) was added. The above mixture was extracted twice with ethyl acetate (50.0 mL), the combined organic phase was dried over Na$_2$SO$_4$ and filtered. The filtrate was concentrated in vacuo to dryness. The residue was subjected to flash chromatography eluting 30% ethyl acetate in hexane to give a white solid (0.10 g, 48%): mp 76-78° C.; $^1$H NMR (300 MHz, CDCl$_3$) δ 7.37-7.16 (m, 4H), 7.12-6.80 (m, 5H), 6.53 (s, 1H), 6.14 (s, 1H), 5.87 (dd, 2H), 4.92 (d, 1H), 4.66 (d, 1H), 3.87-3.55 (m, 4H), 2.72 (t, 2H), 2.12-1.94 (m, 1H), 1.89-1.73 (m, 2H), 1.71-1.45 (m, 2H); $^{13}$C NMR(75 MHz, CDCl$_3$) δ 177.9, 156.1, 149.0, 142.9, 142.5, 132.4, 129.2, 129.1, 124.2, 123.4, 119.9, 119.5, 116.9, 108.8, 103.1, 101.6, 93.8, 80.8, 60.5, 58.3, 49.8, 46.1, 34.8, 30.1, 30.0; MS (ES+) m/z 455 (M+1).

EXAMPLE 10.88

Synthesis of 1'-(pyridin-2-ylmethyl)-6-(trifluoromethoxy)spiro[1-benzofuran-3,3'-indol]-2'(1'H)-one hydrochloride

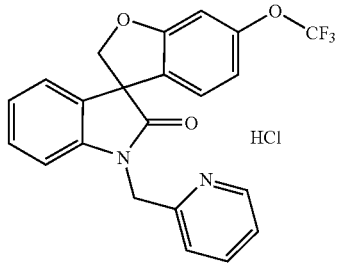

Following the procedure described in EXAMPLE 10.47, and making non-critical variations using 6-(trifluoromethoxy)spiro[1-benzofuran-3,3'-indol]-2'(1'H)-one to replace 4'-bromospiro[furo[2,3-f][1,3]benzodioxole-7,3'-indol]-2'(1'H)-one, and 2-(bromomethyl)pyridine hydrobromide to replace 2-(bromomethyl)-2-(trifluoromethyl)furan, 1'-(pyridin-2-ylmethyl)-6-(trifluoromethoxy)spiro[1-benzofuran-3,3'-indol]-2'(1'H)-one was obtained, which was treated with 4.0 M HCl in dioxane to give the title compound (39%): mp 150-152° C.; $^1$H NMR (300 MHz, CD$_3$OD) δ 8.89-8.78 (m, 1 H), 8.62-8.47 (m, 1H), 8.07-7.00 (m, 2H), 7.42-6.70 (m, 7H), 5.52-5.31 (m, 2H), 5.05 (d, 1H), 4.89 (d, 1H); $^{13}$C NMR(75 MHz, CD$_3$OD) δ 179.4, 163.5, 153.1, 152.7, 148.2, 143.8, 142.8, 133.1, 130.6, 129.3, 127.4, 126.8, 125.7, 125.6, 125.4, 114.9, 110.4, 104.9, 82.0, 58.9, 43.0; MS (ES+) m/z 413 (M+1).

EXAMPLE 10.89

Synthesis of 1'-(pyridin-3-ylmethyl)-6-(trifluoromethoxy)spiro[1-benzofuran-3,3'-indol]-2'(1'H)-one hydrochloride

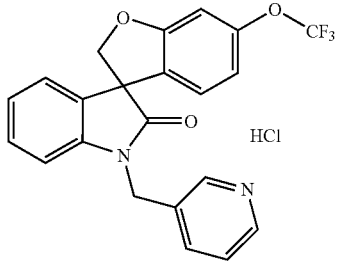

Following the procedure described in EXAMPLE 10.47, and making non-critical variations using 6-(trifluoromethoxy)spiro[1-benzofuran-3,3'-indol]-2'(1'H)-one to replace 4'-bromospiro[furo[2,3-f][1,3]benzodioxole-7,3'-indol]-2'(1'H)-one, and 3-(bromomethyl)pyridine hydrobromide to replace 2-(bromomethyl)-5-(trifluoromethyl)furan, 1'-(pyridin-3-ylmethyl)-6-(trifluoromethoxy)spiro[1-benzofuran-3,3'-indol]-2'(1'H)-one was obtained, which was treated with 4.0 M HCl in dioxane to give the title compound (70%) as a white solid: mp 151-153° C.; $^1$H NMR (300 MHz, CD$_3$OD) δ 9.07-8.61 (m, 3 H), 8.19-8.04 (m, 1H), 7.42-6.71 (m, 7H), 5.28 (s, 2H), 5.05 (d, 1H), 4.86 (d, 1H); $^{13}$C NMR (75 MHz, CD$_3$OD) δ 179.43, 163.5, 151.8, 147.0, 142.9, 142.4, 142.2, 133.0, 130.6, 129.3, 128.9, 125.5, 125.4, 125.3, 114.9, 110.5, 104.9, 82.0, 58.9, 42.0; MS (ES+) m/z 413 (M+1).

EXAMPLE 10.90

Synthesis of 6-(trifluoromethoxy)-1'-{[5-(trifluoromethyl)-2-furyl]methyl}spiro[1-benzofuran-3,3'-indol]-2'(1'H)-one

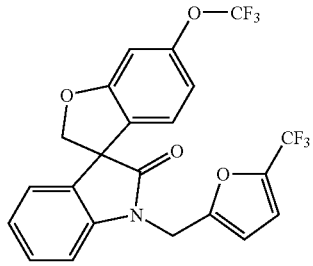

Following the procedure described in EXAMPLE 10.47, and making non-critical variations using 6-(trifluoromethoxy)spiro[1-benzofuran-3,3'-indol]-2'(1'H)-one to replace 4'-bromospiro[furo[2,3-f][1,3]benzodioxole-7,3'-indol]-2'(1'H)-one, the title compound was obtained (82%) as a white solid: mp 78-80° C.; $^1$H NMR (300 MHz, CDCl$_3$) δ 7.33 (td, 1H), 7.21-6.98 (m, 3H), 6.86-6.73 (m, 2H), 6.67 (s, 2H), 6.42 (d, 1H), 5.09 (d, 1H), 5.04 (d, 1H), 4.88 (d, 1H), 4.77 (d, 1H); $^{13}$C NMR (75 MHz, CDCl$_3$) δ 176.7, 161.7, 151.9, 150.6, 141.5, 131.7, 129.5, 127.5, 124.2, 124.2, 124.0, 114.1, 112.8, 112.8, 109.6, 109.2, 104.3, 80.7, 57.6, 37.1; MS (ES+) m/z 470 (M+1).

EXAMPLE 10.91

Synthesis of 1'-(4-methoxybenzyl)-6-(trifluoromethoxy)spiro[1-benzofuran-3,3'-indol]-2'(1'H)-one

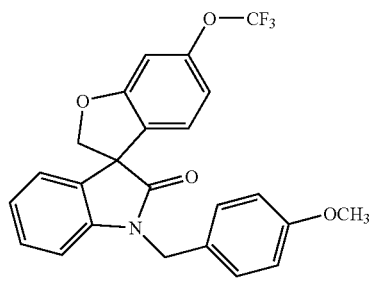

Following the procedure described in EXAMPLE 10.47, and making non-critical variations using 6-(trifluoromethoxy)spiro[1-benzofuran-3,3'-indol]-2'(1'H)-one to replace 4'-bromospiro[furo[2,3-f][1,3]benzodioxole-7,3'-indol]-2'(1'H)-one, and 4-methoxybenzyl chloride to replace 2-(bromomethyl)-5-(trifluoromethyl)furan, the title compound was obtained (91%) as a white solid: mp 82-84° C.; $^1$H NMR (300 MHz, CDCl$_3$) δ 7.32-6.80 (m, 9H), 6.68 (s, 2H), 5.06 (d, 1H), 5.03 (d, 1H), 4.80 (d, 1H), 4.77 (d, 1H), 3.80 (s, 3H); $^{13}$C NMR (75 MHz, CDCl$_3$) δ 171.1, 161.8, 159.4, 150.5, 142.3, 132.0, 129.2, 128.9, 127.7, 124.1, 124.0, 123.7, 122.2, 118.8, 114.4, 114.1, 109.7, 104.3, 80.9, 57.6, 55.4, 43.9; MS (ES+) m/z 442 (M+1).

EXAMPLE 10.92

Synthesis of 1'-(cyclohexylmethyl)spiro[furo[2,3-f][1,3]benzodioxole-7,3'-indol]-2'(1H)-one

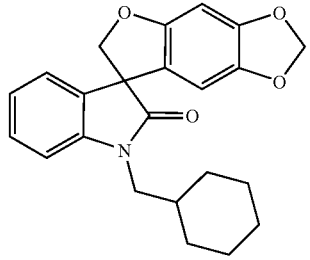

Following the procedure described in EXAMPLE 10.47, and making non-critical variations using spiro[furo[2,3-f][1,3]benzodioxole-7,3'-indol]-2'(1'H)-one to replace 4'-bromospiro[furo[2,3-f][1,3]benzodioxole-7,3'-indol]-2'(1'H)-one, and bromomethyl cyclohexane to replace 2-(bromomethyl)-5-(trifluoromethyl)furan, the title compound was obtained (74%) as a white solid: mp 153-154° C.; $^1$H NMR (300 MHz, CDCl$_3$) δ 7.30 (td, 1H), 7.16 (d, 1H), 7.04 (t, 1H), 6.90 (d, 1H), 6.51 (s, 1H), 6.14 (s, 1H), 5.90-5.84 (m, 2H), 4.91 (d, 1H), 4.65 (d, 1H), 3.72-3.44 (m, 2H), 1.94-1.60 (m, 6H), 1.32-0.99 (m, 5H); $^{13}$C NMR (75 MHz, CDCl$_3$) δ 177.8, 156.1, 148.9, 143.0, 142.4, 132.5, 128.9, 124.0, 123.2, 119.7, 109.0, 103.2, 101.6, 93.7, 80.8, 58.3, 46.8, 36.3, 31.1, 31.0, 26.4, 25.9, 25.8; MS (ES+) m/z 378 (M+1), 400 (M+23).

EXAMPLE 10.93

Synthesis of 1'-(methylsulfonyl)spiro[furo[2,3-f][1,3]benzodioxole-7,3'-indol]-2'(1'H)-one

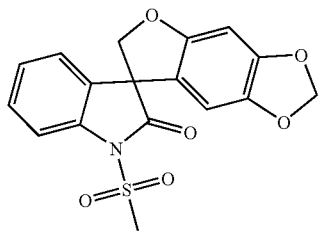

Following the procedure described in EXAMPLE 10.47, and making non-critical variations using spiro[furo[2,3-f][1,3]benzodioxole-7,3'-indol]-2'(1'H)-one to replace 4'-bromo-spiro[furo[2,3-f][1,3]benzodioxole-7,3'-indol]-2'(1'H)-one, and methanesulfonyl chloride to replace 2-(bromomethyl)-5-(trifluoromethyl)furan, the title compound was obtained (51%) as a white solid: mp 215-217° C.; $^1$H NMR (300 MHz, CDCl$_3$) δ 7.83 (d, 1H), 7.42-7.31 (m, 1H), 7.25-7.17 (m, 2H), 6.52 (s, 1H), 6.20 (s, 1H), 5.93-5.87 (m, 2H), 4.98 (d, 1H), 4.68 (d, 1H), 3.46 (s, 3H); $^{13}$C NMR (75 MHz, CDCl$_3$) δ 176.9, 155.8, 149.5, 142.7, 138.1, 130.5, 129.7, 125.9, 124.3, 118.5, 113.8, 102.9, 101.8, 93.8, 80.6, 58.8, 41.8; MS (ES+) m/z 360 (M+1), 382 (M+23).

EXAMPLE 10.94

Synthesis of 1'-(2-piperidin-1-ylethyl)spiro[furo[2,3-f][1,3]benzodioxole-7,3'-indol]-2'(1'H)-one hydrochloride

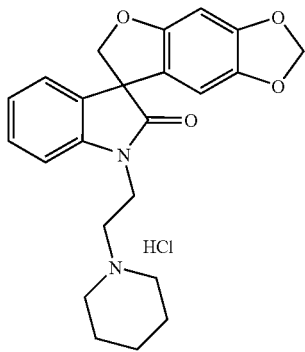

A mixture of 1'-(2-aminoethyl)spiro[furo[2,3-f][1,3]benzodioxole-7,3'-indol]-2'(1'H)-one (0.20 g, 0.62 mmol), 1,5-dibromopentane (0.08 mL, 0.62 mmol) and triethyl amine (0.17 mL, 1.23 mmol) in THF (10.0 mL) was refluxed for 15 hrs and concentrated in vacuo to dryness. The residue was subjected to flash chromatography eluting with 10% methanol in ethyl acetate to give 1'-(2-piperidin-1-ylethyl)spiro[furo[2,3-f][1,3]benzodioxole-7,3'-indol]-2'(1'H)-one, which was treated with 4.0 M HCl in dioxane to give the title compound (28%): mp>240° C.; $^1$HNMR (300 MHz, CD$_3$OD) δ 7.40 (t, 1H), 7.27-7.11 (m, 3H), 6.51 (s, 1H), 6.17 (s, 1H), 5.86 (s, 2H), 4.91 (d, 1H), 4.71 (d, 1H), 4.40-4.13 (m, 2H), 3.95-3.84 (m, 1H), 3.66-3.37 (m, 3H), 3.14-2.96 (m, 2H), 2.06-1.45 (m, 6H); $^{13}$C NMR (75 MHz, CD$_3$OD) δ 180.4, 157.5, 150.5, 143.8, 142.5, 133.9, 130.3, 125.3, 125.1, 120.6, 110.2, 103.9, 102.9, 94.2, 81.4, 59.7, 55.4, 54.9, 53.9, 36.4, 24.2, 22.6; MS (ES+) m/z 393 (M+1).

EXAMPLE 10.95

Synthesis of 1'-[2-(pyridin-2-ylamino)ethyl]spiro[furo[2,3-f][1,3]benzodioxole-7,3'-indol]-2'(1'H)-one and 1'-[2-(dipyridin-2-ylamino)ethyl]spiro[furo[2,3-f][1,3]benzodioxole-7,3'-indol]-2'(1'H)-one

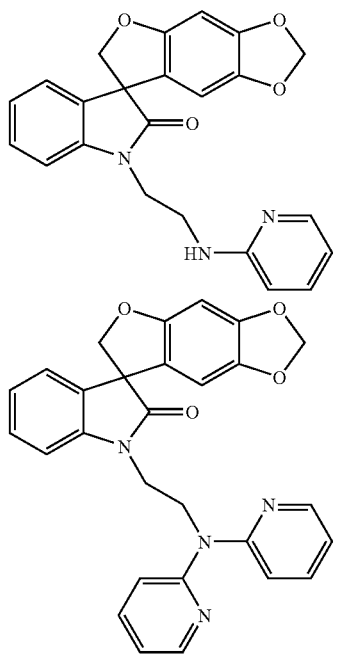

Following the procedure described in EXAMPLE 10.87, and making non-critical variations using 1'-(2-aminoethyl)spiro[furo[2,3-f][1,3]benzodioxole-7,3'-indol]-2'(1'H)-one to replace 1'-(piperidin-4-ylmethyl)spiro[furo[2,3-f][1,3]benzodioxole-7,3'-indol]-2'(1H)-one, and 2-bromopyridine to replace 2-bromobenzene, 1'-(2-(pyridin-2-ylamino)ethyl)-spiro[furo[2,3-f][1,3]benzodioxole-7,3'-indol]-2'(1'H)-one was obtained as the first fraction from the chromatography as a white solid (5%): mp 61-63° C.; $^1$H NMR (300 MHz, CDCl$_3$) δ 8.05 (d, 1H), 7.50-6.97 (m, 5H), 6.57 (dd, 1H), 6.50 (s, 1H), 6.38 (d, 1H), 6.03 (s, 1H), 5.85 (s, 1H), 5.84 (s, 1H), 4.84 (d, 1H), 4.79 (t, 1H), 4.60 (d, 1H), 4.15-3.94 (m, 2H), 3.81-3.64 (m, 2H); $^{13}$C NMR (75 MHz, CDCl$_3$) δ 178.4, 158.2, 156.0, 149.0, 148.0, 142.4, 142.38, 137.4, 132.3, 129.1, 124.0, 123.5, 119.5, 113.3, 109.0, 108.3, 103.2, 101.6, 93.7, 80.5, 58.3, 40.1, 39.9; MS (ES+) m/z 402 (M+1). 1'40 -(2-(dipyridin-2-ylamino)ethyl)-spiro[furo[2,3-f][1,3]benzodioxole-7,3'-indol]-2'(1'H)-one was obtained as the second fraction from the chromatography (31%): mp 165-167° C.; $^1$H NMR (300 MHz, CDCl$_3$) δ 8.31 (dd, 2H), 7.48 (d, 2H), 7.23 (t, 1H), 7.09-6.83 (m, 7H), 6.47 (s, 1H), 5.95 (s, 1H), 5.88-5.81(m, 2H), 4.73 (d, 1H), 4.67-4.49(m, 2H), 4.46 (d, 1H), 4.20 (t, 2H); $^{13}$C NMR(75 MHz, CDCl$_3$) δ 177.6, 157.0, 156.0, 148.8, 148.4, 143.1, 142.3, 137.4, 132.3, 128.9, 123.6, 123.1, 119.6, 117.5, 114.5, 109.3, 103.4, 101.6, 93.6, 80.7, 58.2, 45.9, 39.5; MS (ES+) m/z 479 (M+1).

EXAMPLE 10.96

Synthesis of tert-butyl 4-[2-(2'-oxospiro[furo[2,3-f][1,3]benzodioxole-7,3'-indol]-1'(2'H)-yl)ethyl]piperidine-1-carboxylate

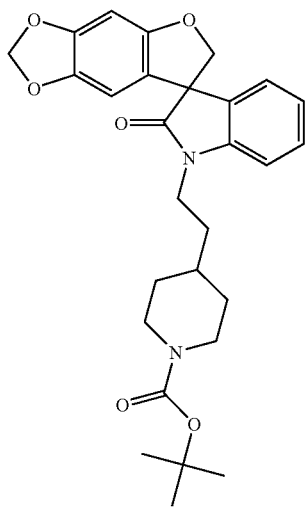

Following the procedure as described in EXAMPLE 10, and making non-critical variations using tert-butyl 4-(2-{[(4-methylphenyl)sulfonyl]oxy}ethyl)piperidine-1-carboxylate to replace 4-fluorobenzyl bromide, the title compound was obtained in 95% yield: mp 173-175° C.; $^1$H NMR (300 MHz, CDCl$_3$) δ 7.31 (t, 1H), 7.17 (d, 1H), 7.06 (t, 1H), 6.88 (d, 1H), 6.51 (s, 1H), 6.10 (s, 1H), 5.90-5.84 (m, 2H), 4.90 (d, 1H), 4.65 (d, 1H), 4.0-3.64 (m, 4H), 2.75-2.58 (m, 2H), 1.85-1.09 (m, 16H); $^{13}$C NMR (75 MHz, CDCl$_3$) δ 177.5, 156.0, 155.0, 149.0, 142.4, 142.2, 132.6, 129.0, 124.2, 123.4, 119.5, 108.6, 103.0, 101.6, 93.8, 80.5, 79.5, 58.3, 38.0, 34.0, 33.9, 32.1, 31.9, 28.6; MS (ES+) m/z 515 (M+23), 393 (M−100).

EXAMPLE 10.97

Synthesis of 1'-(2-piperidin-4-ylethyl)spiro[furo[2,3-f][1,3]benzodioxole-7,3'-indol]-2'(1'H)-one hydrochloride

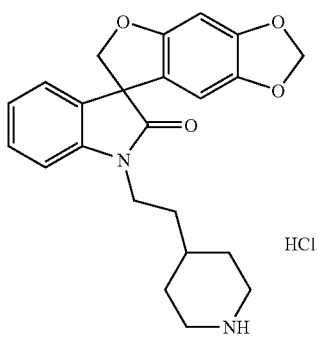

To a solution of tert-butyl 4-[2-(2'-oxospiro[furo[2,3-f][1,3]benzodioxole-7,3'-indol]-1'(2'H)-yl)ethyl]piperidine-1-carboxylate (0.94 g, 1.91 mmol) in dioxane (5.00 mL) was added 4.0 M HCl in dioxane (2.00 mL, 8.00 mmol). The mixture was stirred at ambient temperature for 30 min followed by the addition of anhydrous ether (40.0 mL). The precipitated white solid was filtered, washed with ether and dried to give the title compound (0.75 g, 91%): $^1$H NMR (300 MHz, CD$_3$OD) δ 7.37 (t, 1H), 7.20-7.07 (m, 3H), 6.52 (s, 1H), 6.10 (s, 1H), 5.86 (s, 2H), 4.83 (d, 1H), 4.67 (d, 1H), 3.97-3.75 (m, 2H), 3.45-3.33 (m, 2H), 3.01-2.85 (m, 2H), 2.15-2.01 (m, 2H), 1.82-1.37 (m, 5H); $^{13}$C NMR(75 MHz, CD$_3$OD) δ 179.8, 157.6, 150.4, 143.7, 143.4, 133.6, 130.3, 124.9, 124.8, 120.8, 110.3, 103.7, 102.9, 94.3, 81.4, 59.8, 45.2, 38.5, 34.4, 32.6, 29.8, 29.7; MS (ES+) m/z 393 (M+1).

EXAMPLE 10.98

Synthesis of 1'-[2-(1-cyclopentylpiperidin-4-yl)ethyl]spiro[furo[2,3-f][1,3]benzodioxole-7,3'-indol]-2'(1'H)-one hydrochloride

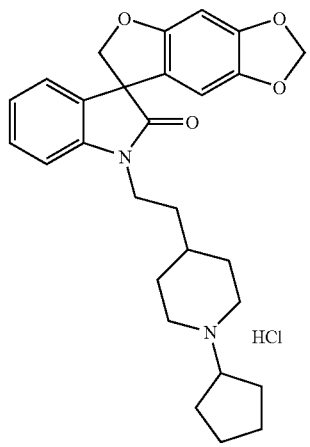

To a solution of cyclopentanone (0.04 mL, 0.45 mmol) and triethyl amine (0.12 mL, 0.84 mmol) in dichloroethane (5.00 mL) was added 1'-(2-piperidin-4-ylethyl)spiro[furo[2,3-f][1,3]benzodioxole-7,3'-indol]-2'(1'H)-one hydrochloride (0.12 g, 0.28 mmol) and sodium triacetoxyborohydride (0.10 g, 0.45 mmol). The reaction mixture was stirred for 16 hrs and concentrated in vacuo to dryness. The residue was subjected to flash chromatography eluting with ethyl acetate/methanol/ammonium hydroxide (15/1/0.1) to give 1'-[2-(1-cyclopentylpiperidin-4-yl)ethyl]spiro[furo[2,3-f][1,3]benzodioxole-7,3'-indol]-2'(1'H)-one as a white solid, which was treated with 4.0 M HCl in dioxane to give the title compound (0.05 g, 32% yield): mp 153-155° C.; $^1$H NMR (300 MHz, CD$_3$OD) δ 7.37 (td, 1H), 7.21-7.08 (m, 3H), 6.53 (s, 1H), 6.11 (s, 1H), 5.88 (s, 1H), 5.87 (s, 1H), 4.83 (d, 1H), 4.69 (d, 1H), 3.98-3.75 (m, 2H), 3.68-3.38 (m, 3H), 3.01-2.83 (m, 2H), 2.25-2.08 (m, 4H), 1.92-1.37 (m, 11H); $^{13}$C NMR (75 MHz, CD$_3$OD) δ 179.8, 157.6, 150.4, 143.8, 143.4, 133.6, 130.3, 124.9, 124.8, 120.8, 110.3, 103.7, 103.0, 94.3, 81.4, 69.1, 59.8, 53.2, 38.6, 34.3, 32.5, 30.6, 30.5, 29.4, 24.7; MS (ES+) m/z 461 (M+1).

EXAMPLE 10.99

Synthesis of 1'-[2-(1-isopropylpiperidin-4-yl)ethyl]spiro[furo[2,3-f][1,3]benzodioxole-7,3'-indol]-2'(1'H)-one hydrochloride

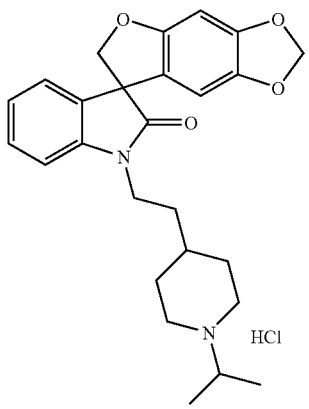

Following the procedure as described in EXAMPLE 10.98, and making non-critical variations using acetone to replace cyclopentanone, the title compound was obtained (42%) as a white solid: mp 155-156° C.; $^1$H NMR (300 MHz, CD$_3$OD) δ 7.37 (t, 1H), 7.21-7.08 (m, 3H), 6.53 (s, 1H), 6.11 (s, 1H), 5.87 (s, 2H), 4.84 (d, 1H), 4.69 (d, 1H), 3.98-3.75 (m, 2H), 3.58-3.38 (m, 3H), 3.05-2.85 (m, 2H), 2.23-2.09 (m, 2H), 1.82-.44 (m, 5H), 1.35 (d, 6H); $^{13}$C NMR (75 MHz, CD$_3$OD) δ 179.8, 157.6, 150.5, 143.8, 143.4, 133.6, 130.3, 125.0, 124.8, 120.8, 110.3, 103.7, 103.0, 94.3, 81.4, 59.8, 59.6, 38.6, 34.2, 32.7, 30.6, 30.5, 24.2, 16.9. 15.4; MS (ES+) m/z 435 (M+1).

EXAMPLE 10.100

Synthesis of 1'-[2-(1-cyclobutylpiperidin-4-yl)ethyl]spiro[furo[2,3 f][1,3]benzodioxole-7,3'-indol]-2'(1'H)-one hydrochloride

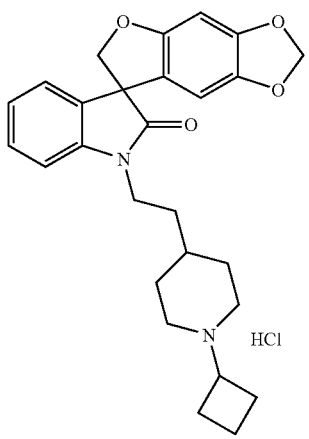

Following the procedure as described in EXAMPLE 10.98, and making non-critical variations using cyclobutanone to replace cyclopentanone, the title compound was obtained (81%) as a white solid: mp 158-160° C.; $^1$H NMR (300 MHz, CD$_3$OD) δ 7.37 (t, 1H), 7.21-7.05 (m, 3H), 6.52 (s, 1H), 6.10 (s, 1H), 5.86 (s, 2H), 4.83 (d, 1H), 4.67 (d, 1H), 3.98-3.39 (m, 5H), 2.85-2.59 (m, 2H), 2.43-1.42 (m, 13H); $^{13}$C NMR (75 MHz, CD$_3$OD) δ 179.8, 157.6, 150.4, 143.7, 143.4, 133.6, 130.3, 124.9, 124.8, 120.8, 110.4, 103.8, 103.0, 94.2, 81.5, 60.5, 59.8, 50.8, 38.6, 34.4, 32.5, 30.1, 26.8, 14.4; MS (ES+) m/z 447 (M+1).

EXAMPLE 10.101

Synthesis of 1'-{2-[1-(tetrahydro-2H-pyran-4-yl)piperidin-4-yl]ethyl}spiro[furo[2,3-f][1,3]benzodioxole-7,3'-indol]-2'(1'H)-one hydrochloride

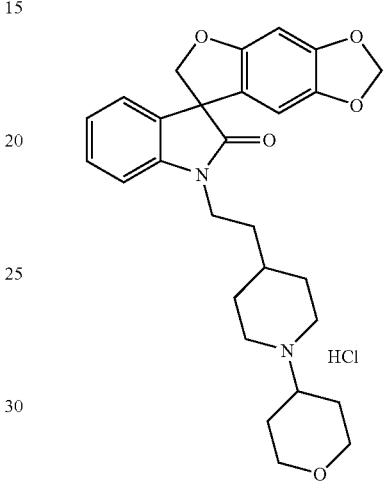

Following the procedure as described in EXAMPLE 10.98, and making non-critical variations using tetrahydro-4H-pyran-4-one to replace cyclopentanone, the title compound was obtained (45%) as a white solid: mp 168-170° C.; $^1$H NMR (300 MHz, CD$_3$OD) δ 7.37 (t, 1H), 7.21-7.06 (m, 3H), 6.52 (s, 1H), 6.11 (s, 1H), 5.86 (s, 2H), 4.83 (d, 1H), 4.67 (d, 1H), 4.12-3.31 (m, 9H), 3.05-2.85 (m, 2H), 2.25-1.45 (m, 11H); $^{13}$C NMR (75 MHz, CD$_3$OD) δ 179.8, 157.6, 150.4, 143.7, 143.4, 133.6, 130.3, 125.0, 124.8, 120.8, 110.3, 103.8, 102.9, 94.3, 81.4, 67.2, 64.1, 59.8, 50.7, 38.6, 34.2, 32,7, 30.6, 30.5, 28.7; MS (ES+) m/z 477 (M+1).

EXAMPLE 11

Synthesis of 4-[(2'-oxospiro[furo[2,3-f][1,3]benzodioxole-7,3'-indol]-1'(2'H)-yl)methyl]benzoic acid

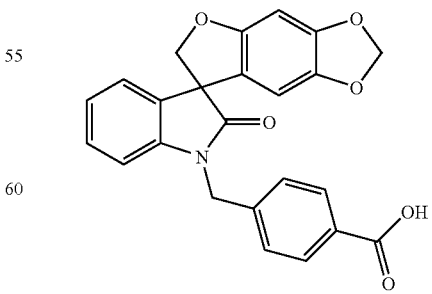

Following the procedure described in EXAMPLE 6, and making non-critical variations using methyl 4-[(2'-oxospiro

[furo[2,3-f][1,3]benzodioxole-7,3'-indol]-1'(2'H)-yl)methyl]benzoate to replace methyl 2-[(2'-oxospiro[furo[2,3-f][1,3]benzodioxole-7,3'-indol]-1'(2'H)-yl)methyl]benzoate, the title compound was obtained (100%): $^1$H NMR (300 MHz, CDCl$_3$) δ 12.96 (s, 1H), 7.90 (d, 2H), 7.43 (d, 2H), 7.22 (t, 1H), 7.17 (d, 1H), 7.00 (t, 1H), 6.94 (d, 1H), 6.68 (s, 1H), 6.21 (s, 1H), 5.90 (s, 2H), 4.98 (s, 2H), 4.76 (ABq, 2H); $^{13}$C NMR (75 MHz, CDCl$_3$) δ 177.4, 167.5, 156.0, 148.9, 142.6, 142.3, 141.8, 132.1, 130.5, 130.3, 129.3, 127.7, 124.2, 123.7, 120.1, 109.9, 103.5, 101.9, 93.8, 80.4, 58.0, 43.4.

EXAMPLE 12

Synthesis of N-(3-fluorophenyl)-4-[(2'-oxospiro[furo[2,3-f][1,3]benzodioxole-7,3'-indol]-1'(2'H)-yl)methyl]benzamide

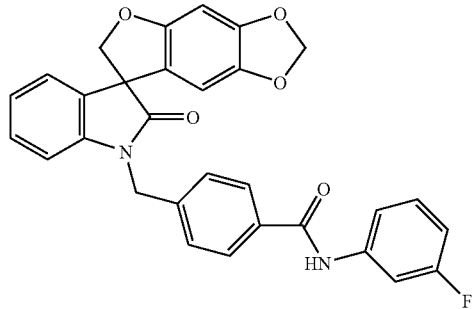

A. Preparation of stock solution of 4-[(2'-oxospiro[furo[2,3-f][1,3]benzodioxole-7,3'-indol]-1'(2'H)-yl)methyl]benzoyl chloride To a stirred slurry of 4-[(2'-oxospiro[furo[2,3-f][1,3]benzodioxole-7,3'-indol]-1'(2'H)-yl)methyl]benzoic acid (2.08 g, 5.00 mmol) in dry chloroform (50.0 mL) was added oxalyl chloride (0.95 g, 7.50 mmol) at ambient temperature followed by 1 drop of DMF. The mixture was stirred at ambient temperature for 2 h and evaporated to dryness in vacuo. The residue was dissolved in dry dichlormethane (60.0 mL) to form an acid chloride stock solution for use.

B. Synthesis of N-(3-fluorophenyl)-4-[2'-oxospiro[furo[2,3-f][1,3]benzodioxole-7,3'-indol]-1'(2'H)-yl) methyl]benzamide To a solution of 3-fluorophenylamine (0.02 mL, 0.24 mmol) in dry dichloromethane (2.00 mL) and triethylamine (0.05 mL, 0.32 mmol) was added the acid chloride stock solution (2.0 mL, 0.081 M in dichloromethane) obtained above at ambient temperature. The mixture was stirred for 2 h, washed with 15% HCl solution and water. The organic layer was separated, dried over Na$_2$SO$_4$ and filtered. The filtrate was concentrated in vacuo to dryness. The residue was dissolved in ethyl acetate, and the product was precipitated by the addition of hexane. The white solid was filtered and collected to yield the title compound (0.06 g) in 70% yield: $^1$H NMR (300 MHz, CDCl$_3$) δ 8.30 (s, 1H), 7.83 (d, 2H), 7.58 (ddd, 1H), 7.38 (d, 2H), 7.27-7.23 (m, 2H), 7.21-7.16 (m, 2H), 7.04 (dt, 1H), 6.85-6.78 (m, 1H), 6.74 (d, 1H), 6.46 (s, 1H), 6.10 (s, 1H), 5.77 (d, 1H), 5.68 (d, 1H), 4.97 (ABq, 2H), 4.76 (ABq, 2H); MS (ES+), m/z 509.1 (M+1).

EXAMPLE 12.1

The compounds listed in the following table were prepared using the similar procedure as described in EXAMPLE 12. As previously noted, the compound numbers listed below do not correspond to the compound numbers provided in the general Reaction Schemes above.

| Compound Number | Name | MS (m/z, M + 1) |
|---|---|---|
| 500 | N-butyl-4-[(2'-oxospiro[furo[2,3-f][1,3]benzodioxole-7,3'-indol]-1'(2'H)-yl)methyl]benzamide | 471.2 |
| 501 | N-(3-fluorobenzyl)-4-[(2'-oxospiro[furo[2,3-f][1,3]benzodioxole-7,3'-indol]-1'(2'H)-yl)methyl]benzamide | 523.1 |
| 502 | 1'-[4-(piperidin-1-ylcarbonyl)benzyl]spiro[furo[2,3-f][1,3]benzodioxole-7,3'-indol]-2'(1'H)-one | 483.2 |
| 503 | N,N-diisopropyl-4-[(2'-oxospiro[furo[2,3-f][1,3]benzodioxole-7,3'-indol]-1'(2'H)-yl)methyl]benzamide | 499.1 |
| 504 | N-(4-chlorobenzyl)-4-[(2'-oxospiro[furo[2,3-f][1,3]benzodioxole-7,3'-indol]-1'(2'H)-yl)methyl]benzamide | 540.1 |
| 505 | N-(3-chlorophenyl)-4-[(2'-oxospiro[furo[2,3-f][1,3]benzodioxole-7,3'-indol]-1'(2'H)-yl)methyl]benzamide | 526.1 |
| 506 | N-(2-fluorophenyl)-4-[(2'-oxospiro[furo[2,3-f][1,3]benzodioxole-7,3'-indol]-1'(2'H)-yl)methyl]benzamide | 509.2 |
| 507 | N-(2-ethylphenyl)-4-[(2'-oxospiro[furo[2,3-f][1,3]benzodioxole-7,3'-indol]-1'(2'H)-yl)methyl]benzamide | 519.2 |
| 508 | N-(4-ethylphenyl)-4-[(2'-oxospiro[furo[2,3-f][1,3]benzodioxole-7,3'-indol]-1'(2'H)-yl)methyl]benzamide | 519.2 |
| 509 | N-(4-methylphenyl)-4-[(2'-oxospiro[furo[2,3-f][1,3]benzodioxole-7,3'-indol]-1'(2'H)-yl)methyl]benzamide | 505.2 |

| Compound Number | Name | MS (m/z, M + 1) |
| --- | --- | --- |
| 510 | N-(3,5-dimethylphenyl)-4-[(2'-oxospiro[furo[2,3-f][1,3]benzodioxole-7,3'-indol]-1'(2'H)-yl)methyl]benzamide | 519.2 |
| 511 | N-(2,3-dimethylphenyl)-4-[(2'-oxospiro[furo[2,3-f][1,3]benzodioxole-7,3'-indol]-1'(2'H)-yl)methyl]benzamide | 519.2 |
| 512 | 4-[(2'-oxospiro[furo[2,3-f][1,3]benzodioxole-7,3'-indol]-1'(2'H)-yl)methyl]-N-pentylbenzamide | 485.1 |
| 513 | 4-[(2'-oxospiro[furo[2,3-f][1,3]benzodioxole-7,3'-indol]-1'(2'H)-yl)methyl]-N-propylbenzamide | 457.1 |
| 514 | N-isopropyl-4-[(2'-oxospiro[furo[2,3-f][1,3]benzodioxole-7,3'-indol]-1'(2'H)-yl)methyl]benzamide | 457.1 |
| 515 | N-isobutyl-4-[(2'-oxospiro[furo[2,3-f][1,3]benzodioxole-7,3'-indol]-1'(2'H)-yl)methyl]benzamide | 471.1 |
| 516 | N-hexyl-4-[(2'-oxospiro[furo[2,3-f][1,3]benzodioxole-7,3'-indol]-1'(2'H)-yl)methyl]benzamide | 499.2 |
| 517 | N-cyclohexyl-4-[(2'-oxospiro[furo[2,3-f][1,3]benzodioxole-7,3'-indol]-1'(2'H)-yl)methyl]benzamide | 497.2 |
| 518 | N-cyclopentyl-4-[(2'-oxospiro[furo[2,3-f][1,3]benzodioxole-7,3'-indol]-1'(2'H)-yl)methyl]benzamide | 483.2 |
| 519 | N-heptyl-4-[(2'-oxospiro[furo[2,3-f][1,3]benzodioxole-7,3'-indol]-1'(2'H)-yl)methyl]benzamide | 513.2 |
| 520 | N-(2-methoxybenzyl)-4-[(2'-oxospiro[furo[2,3-f][1,3]benzodioxole-7,3'-indol]-1'(2'H)-yl)methyl]benzamide | 535.2 |
| 521 | N-(2,6-dimethylphenyl)-4-[(2'-oxospiro[furo[2,3-f][1,3]benzodioxole-7,3'-indol]-1'(2'H)-yl)methyl]benzamide | 519.2 |
| 522 | N-(2-methoxyphenyl)-4-[(2'-oxospiro[furo[2,3-f][1,3]benzodioxole-7,3'-indol]-1'(2'H)-yl)methyl]benzamide | 521.2 |
| 523 | N-cyclopropyl-4-[(2'-oxospiro[furo[2,3-f][1,3]benzodioxole-7,3'-indol]-1'(2'H)-yl)methyl]benzamide | 455.1 |
| 524 | N-(3-methoxypropyl)-4-[(2'-oxospiro[furo[2,3-f][1,3]benzodioxole-7,3'-indol]-1'(2'H)-yl)methyl]benzamide | 487.2 |
| 525 | 4-[(2'-oxospiro[furo[2,3-f][1,3]benzodioxole-7,3'-indol]-1'(2'H)-yl)methyl]-N-phenylbenzamide | 491.2 |
| 526 | N-(2,4-dimethylphenyl)-4-[(2'-oxospiro[furo[2,3-f][1,3]benzodioxole-7,3'-indol]-1'(2'H)-yl)methyl]benzamide | 519.2 |
| 527 | 4-[(2'-oxospiro[furo[2,3-f][1,3]benzodioxole-7,3'-indol]-1'(2'H)-yl)methyl]-N-(tetrahydrofuran-2-ylmethyl)benzamide | 499.2 |
| 528 | N,N-dibenzyl-4-[(2'-oxospiro[furo[2,3-f][1,3]benzodioxole-7,3'-indol]-1'(2'H)-yl)methyl]benzamide | 595.2 |
| 529 | N-[2-(diethylamino)ethyl-4-[(2'-oxospiro[furo[2,3-f][1,3]benzodioxole-7,3'-indol]-1'(2'H)-yl)methyl]benzamide | 514.2 |
| 530 | N-methyl-4-[(2'-oxospiro[furo[2,3-f][1,3]benzodioxole-7,3'-indol]-1'(2'H)-yl)methyl]benzamide | 429.2 |
| 531 | 4-[(2'-oxospiro[furo[2,3-f][1,3]benzodioxole-7,3'-indol]-1'(2'H)-yl)methyl]-N-[3-(trifluoromethyl)phenyl]benzamide | 559.1 |
| 532 | N-ethyl-4-[(2'-oxospiro[furo[2,3-f][1,3]benzodioxole-7,3'-indol]-1'(2'H)-yl)methyl]benzamide | 443.1 |
| 533 | N-(3-ethoxypropyl)-4-[(2'-oxospiro[furo[2,3-f][1,3]benzodioxole-7,3'-indol]-1'(2'H)-yl)methyl]benzamide | 501.2 |
| 534 | N-(4-methoxybenzyl)-4-[(2'-oxospiro[furo[2,3-f][1,3]benzodioxole-7,3'-indol]-1'(2'H)-yl)methyl]benzamide | 535.2 |
| 535 | N-(3,5-dichlorophenyl)-4-[(2'-oxospiro[furo[2,3-f][1,3]benzodioxole-7,3'-indol]-1'(2'H)-yl)methyl]benzamide | 560.2 |
| 536 | 4-[(2'-oxospiro[furo[2,3-f][1,3]benzodioxole-7,3'-indol]-1'(2'H)-yl)methyl]-N-pyridin-3-ylbenzamide | 492.2 |
| 537 | N-(4-cyanophenyl)-4-[(2'-oxospiro[furo[2,3-f][1,3]benzodioxole-7,3'-indol]-1'(2'H)-yl)methyl]benzamide | 516.2 |

| Compound Number | Name | MS (m/z, M + 1) |
|---|---|---|
| 538 | N-(4-methylpentyl)-4-[(2'-oxospiro[furo[2,3-f][1,3]benzodioxole-7,3'-indol]-1'(2'H)-yl)methyl]benzamide | 499.2 |
| 539 | 4-[(2'-oxospiro[furo[2,3-f][1,3]benzodioxole-7,3'-indol]-1'(2'H)-yl)methyl]-N-(2,2,2-trifluoroethyl)benzamide | 497.2 |
| 540 | 4-[(2'-oxospiro[furo[2,3-f][1,3]benzodioxole-7,3'-indol]-1'(2'H)-yl)methyl]-N-(pyridin-4-ylmethyl)benzamide | 506.1 |
| 541 | N-[2-(3-chlorophenyl)ethyl]-4-[(2'-oxospiro[furo[2,3-f][1,3]benzodioxole-7,3'-indol]-1'(2'H)-yl)methyl]benzamide | 554 |
| 542 | N-(2-furylmethyl)-4-[(2'-oxospiro[furo[2,3-f][1,3]benzodioxole-7,3'-indol]-1'(2'H)-yl)methyl]benzamide | 495.1 |
| 543 | N-(3-fluoro-2-methylphenyl)-4-[(2'-oxospiro[furo[2,3-f][1,3]benzodioxole-7,3'-indol]-1'(2'H)-yl)methyl]benzamide | 523.1 |
| 544 | N-hexyl-N-methyl-4-[(2'-oxospiro[furo[2,3-f][1,3]benzodioxole-7,3'-indol]-1'(2'H)-yl)methyl]benzamide | 513.1 |
| 545 | N-(3-isopropoxypropyl)-4-[(2'-oxospiro[furo[2,3-f][1,3]benzodioxole-7,3'-indol]-1'(2'H)-yl)methyl]benzamide | 515.2 |
| 546 | N-(2-ethoxyethyl)-4-[(2'-oxospiro[furo[2,3-f][1,3]benzodioxole-7,3'-indol]-1'(2'H)-yl)methyl]benzamide | 487.2 |
| 547 | N-(cyclopropylmethyl)-4-[(2'-oxospiro[furo[2,3-f][1,3]benzodioxole-7,3'-indol]-1'(2'H)-yl)methyl]benzamide | 469.1 |
| 548 | N-(4-methoxyphenyl)-4-[(2'-oxospiro[furo[2,3-f][1,3]benzodioxole-7,3'-indol]-1'(2'H)-yl)methyl]benzamide | 521.1 |
| 549 | N-cyclobutyl-4-[(2'-oxospiro[furo[2,3-f][1,3]benzodioxole-7,3'-indol]-1'(2'H)-yl)methyl]benzamide | 469.1 |
| 550 | N-(2,2-diphenylethyl)-4-[(2'-oxospiro[furo[2,3-f][1,3]benzodioxole-7,3'-indol]-1'(2'H)-yl)methyl]benzamide | 595.2 |
| 551 | N-[2-(4-fluorophenyl)ethyl]-4-[(2'-oxospiro[furo[2,3-f][1,3]benzodioxole-7,3'-indol]-1'(2'H)-yl)methyl]benzamide | 537.2 |
| 552 | N-(cyclohexylmethyl)-4-[(2'-oxospiro[furo[2,3-f][1,3]benzodioxole-7,3'-indol]-1'(2'H)-yl)methyl]benzamide | 511.2 |
| 553 | N-(2-fluoro-4-methylphenyl)-4-[(2'-oxospiro[furo[2,3-f][1,3]benzodioxole-7,3'-indol]-1'(2'H)-yl)methyl]benzamide | 523.2 |
| 554 | N-[2-(4-methylphenyl)ethyl]-4-[(2'-oxospiro[furo[2,3-f][1,3]benzodioxole-7,3'-indol]-1'(2'H)-yl)methyl]benzamide | 533.2 |
| 555 | N-(2-ethylbutyl)-4-[(2'-oxospiro[furo[2,3-f][1,3]benzodioxole-7,3'-indol]-1'(2'H)-yl)methyl]benzamide | 499.2 |
| 556 | N-benzyl-4-[(2'-oxospiro[furo[2,3-f][1,3]benzodioxole-7,3'-indol]-1'(2'H)-yl)methyl]benzamide | 505.1 |
| 557 | N-(2-methoxyethyl)-4-[(2'-oxospiro[furo[2,3-f][1,3]benzodioxole-7,3'-indol]-1'(2'H)-yl)methyl]benzamide | 473.1 |
| 558 | 1'-[4-(morpholin-4-ylcarbonyl)benzyl]spiro[furo[2,3-f][1,3]benzodioxole-7,3'-indol]-2'(1'H)-one | 485.1 |
| 559 | N-(1-benzylpiperidin-4-yl)-4-[(2'-oxospiro[furo[2,3-f][1,3]benzodioxole-7,3'-indol]-1'(2'H)-yl)methyl]benzamide | 588.2 |
| 560 | N-[2-(4-methoxyphenyl)ethyl]-4-[(2'-oxospiro[furo[2,3-f][1,3]benzodioxole-7,3'-indol]-1'(2'H)-yl)methyl]benzamide | 549.2 |
| 561 | 4-[(2'-oxospiro[furo[2,3-f][1,3]benzodioxole-7,3'-indol]-1'(2'H)-yl)methyl]-N-[2-(trifluoromethyl)phenyl]benzamide | 559.1 |
| 562 | N-[4-chloro-2-(trifluoromethyl)phenyl]-4-[(2'-oxospiro[furo[2,3-f][1,3]benzodioxole-7,3'-indol]-1'(2'H)-yl)methyl]benzamide | 594.1 |
| 563 | N-[4-fluoro-2-(trifluoromethyl)phenyl]-4-[(2'-oxospiro[furo[2,3-f][1,3]benzodioxole-7,3'-indol]-1'(2'H)-yl)methyl]benzamide | 577.1 |

-continued

| Compound Number | Name | MS (m/z, M + 1) |
| --- | --- | --- |
| 564 | N-(2-cyanoethyl)-4-[(2'-oxospiro[furo[2,3-f][1,3]benzodioxole-7,3'-indol]-1'(2'H)-yl)methyl]benzamide | 468.1 |
| 565 | N-[(1S)-1-cyclohexylethyl]-4-[(2'-oxospiro[furo[2,3-f][1,3]benzodioxole-7,3'-indol]-1'(2'H)-yl)methyl]benzamide | 525.2 |
| 566 | N-[(1R)-1-cyclohexylethyl]-4-[(2'-oxospiro[furo[2,3-f][1,3]benzodioxole-7,3'-indol]-1'(2'H)-yl)methyl]benzamide | 525.2 |
| 567 | N-(2,4-difluorophenyl)-4-[(2'-oxospiro[furo[2,3-f][1,3]benzodioxole-7,3'-indol]-1'(2'H)-yl)methyl]benzamide | 527.1 |
| 568 | N-(2,3-dihydro-1H-inden-1-yl)-4-[(2'-oxospiro[furo[2,3-f][1,3]benzodioxole-7,3'-indol]-1'(2'H)-yl)methyl]benzamide | 531.2 |
| 569 | 4-[(2'-oxospiro[furo[2,3-f][1,3]benzodioxole-7,3'-indol]-1'(2'H)-yl)methyl]-N-(2-thienylmethyl)benzamide | 511.2 |
| 570 | N-[(1-ethylpyrrolidin-2-yl)methyl]-4-[(2'-oxospiro[furo[2,3-f][1,3]benzodioxole-7,3'-indol]-1'(2'H)-yl)methyl]benzamide | 526.2 |
| 571 | 4-[(2'-oxospiro[furo[2,3-f][1,3]benzodioxole-7,3'-indol]-1'(2'H)-yl)methyl]-N-(4-propylphenyl)benzamide | 533.2 |
| 572 | N-(2,5-difluorobenzyl)-4-[(2'-oxospiro[furo[2,3-f][1,3]benzodioxole-7,3'-indol]-1'(2'H)-yl)methyl]benzamide | 541.1 |
| 573 | N-(2,3-dihydro-1H-inden-5-yl)-4-[(2'-oxospiro[furo[2,3-f][1,3]benzodioxole-7,3'-indol]-1'(2'H)-yl)methyl]benzamide | 531.2 |
| 574 | N-(2,5-difluorophenyl)-4-[(2'-oxospiro[furo[2,3-f][1,3]benzodioxole-7,3'-indol]-1'(2'H)-yl)methyl]benzamide | 527.1 |
| 575 | 4-[(2'-oxospiro[furo[2,3-f][1,3]benzodioxole-7,3'-indol]-1'(2'H)-yl)methyl]-N-[4-(trifluoromethyl)benzyl]benzamide | 573.1 |
| 576 | 4-[(2'-oxospiro[furo[2,3-f][1,3]benzodioxole-7,3'-indol]-1'(2'H)-yl)methyl]-N-[2-(2-thienyl)ethyl]benzamide | 525.1 |
| 577 | 4-[(2'-oxospiro[furo[2,3-f][1,3]benzodioxole-7,3'-indol]-1'(2'H)-yl)methyl]-N-(pyridin-3-ylmethyl)benzamide | 506.2 |
| 578 | 4-[(2'-oxospiro[furo[2,3-f][1,3]benzodioxole-7,3'-indol]-1'(2'H)-yl)methyl]-N-[2-(trifluoromethyl)benzyl]benzamide | 573.1 |
| 579 | N-[2-(4-chlorophenyl)ethyl]-4-[(2'-oxospiro[furo[2,3-f][1,3]benzodioxole-7,3'-indol]-1'(2'H)-yl)methyl]benzamide | 554 |
| 580 | 4-[(2'-oxospiro[furo[2,3-f][1,3]benzodioxole-7,3'-indol]-1'(2'H)-yl)methyl]-N-(2-pyrrolidin-1-ylethyl)benzamide | 512.2 |
| 581 | N-(3-methylpyridin-2-yl)-4-[(2'-oxospiro[furo[2,3-f][1,3]benzodioxole-7,3'-indol]-1'(2'H)-yl)methyl]benzamide | 506.1 |
| 582 | N-[3-(dimethylamino)propyl]-N-methyl-4-[(2'-oxospiro[furo[2,3-f][1,3]benzodioxole-7,3'-indol]-1'(2'H)-yl)methyl]benzamide | 514.2 |
| 583 | N-1,3-benzodioxol-5-yl-4-[(2'-oxospiro[furo[2,3-f][1,3]benzodioxole-7,3'-indol]-1'(2'H)-yl)methyl]benzamide | 535.1 |
| 584 | N-(2-morpholin-4-ylethyl)-4-[(2'-oxospiro[furo[2,3-f][1,3]benzodioxole-7,3'-indol]-1'(2'H)-yl)methyl]benzamide | 528.2 |
| 585 | 1'-{4-[(4-pyrimidin-2-ylpiperazin-1-yl)carbonyl]benzyl}spiro[furo[2,3-f][1,3]benzodioxole-7,3'-indol]-2'(1'H)-one | 562.2 |
| 586 | 4-[(2'-oxospiro[furo[2,3-f][1,3]benzodioxole-7,3'-indol]-1'(2'H)-yl)methyl]-N-1,3-thiazol-2-ylbenzamide | 498.1 |
| 587 | N-(6-methoxypyridin-3-yl)-4-[(2'-oxospiro[furo[2,3-f][1,3]benzodioxole-7,3'-indol]-1'(2'H)-yl)methyl]benzamide | 522.1 |
| 588 | N-(3,5-dichlorobenzyl)-4-[(2'-oxospiro[furo[2,3-f][1,3]benzodioxole-7,3'-indol]-1'(2'H)-yl)methyl]benzamide | 574.1 |
| 589 | N-1-naphthyl-4-[(2'-oxospiro[furo[2,3-f][1,3]benzodioxole-7,3'-indol]-1'(2'H)-yl)methyl]benzamide | 541.2 |
| 590 | 1'-(4-{[4-(1,3-benzodioxol-5-ylmethyl)piperazin-1-yl]carbonyl}benzyl)spiro[furo[2,3-f][1,3]benzodioxole-7,3'-indol]-2'(1'H)-one | 618.2 |

-continued

| Compound Number | Name | MS (m/z, M + 1) |
|---|---|---|
| 591 | N-(4,6-dimethylpyridin-2-yl)-4-[(2'-oxospiro[furo[2,3-f][1,3]benzodioxole-7,3'-indol]-1'(2'H)-yl)methyl]benzamide | 520.2 |
| 592 | 4-[(2'-oxospiro[furo[2,3-f][1,3]benzodioxole-7,3'-indol]-1'(2'H)-yl)methyl]-N-pyrimidin-4-ylbenzamide | 493.1 |
| 593 | N-(5-methyl-1,3-thiazol-2-yl)-4-[(2'-oxospiro[furo[2,3-f][1,3]benzodioxole-7,3'-indol]-1'(2'H)-yl)methyl]benzamide | 512.2 |
| 594 | N-(2-cyano-6-fluorophenyl)-4-[(2'-oxospiro[furo[2,3-f][1,3]benzodioxole-7,3'-indol]-1'(2'H)-yl)methyl]benzamide | 534.1 |
| 595 | N-(4-methylbenzyl)-4-[(2'-oxospiro[furo[2,3-f][1,3]benzodioxole-7,3'-indol]-1'(2'H)-yl)methyl]benzamide | 519.1 |
| 596 | N-[3-(1H-imidazol-1-yl)propyl]-4-[(2'-oxospiro[furo[2,3-f][1,3]benzodioxole-7,3'-indol]-1'(2'H)-yl)methyl]benzamide | 523.1 |
| 597 | N-(4-morpholin-4-ylphenyl)-4-[(2'-oxospiro[furo[2,3-f][1,3]benzodioxole-7,3'-indol]-1'(2'H)-yl)methyl]benzamide | 576.2 |
| 598 | 1'-{4-[(4-methylpiperazin-1-yl)carbonyl]benzyl}spiro[furo[2,3-f][1,3]benzodioxole-7,3'-indol]-2'(1'H)-one | 498.2 |
| 599 | N-(5-cyclopropyl-1,3,4-thiadiazol-2-yl)-4-[(2'-oxospiro[furo[2,3-f][1,3]benzodioxole-7,3'-indol]-1'(2'H)-yl)methyl]benzamide | 539.2 |

EXAMPLE 13

Synthesis of 1'-(3-hydroxypropyl)spiro[furo[2,3-f][1,3]benzodioxole-7,3'-indol]-2'(1'H)-one

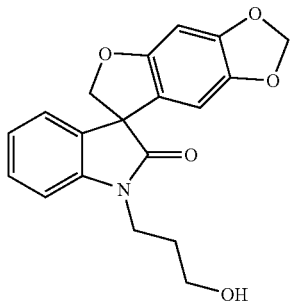

A suspension of 1'-[3-(benzyloxy)propyl]spiro[furo[2,3-f][1,3]benzodioxole-7,3'-indol]-2'(1'H)-one (6.27 g, 14.5 mmol) and 10% Pd/C (0.5 g) in MeOH (150 mL) was hydrogenated under the normal pressure of hydrogen overnight and filtered through a pad of celite. The filtrate was concentrated in vacuo to dryness. The residue was crystallized from ether to yield the title compound (4.82 g) as a white solid in 98% yield: $^1$H NMR (300 MHz, CDCl$_3$) δ 7.38-6.93 (m, 4H), 6.49 (s, 1H), 6.10 (s, 1H), 4.87 (m, 1H), 4.63 (m, 1H), 4.01-3.81 (m, 2H), 3.62 (t, 2H), 2.89 (br, 1H), 1.99-1.91(m, 2H); $^{13}$C NMR (75 MHz, CDCl$_3$) δ 178.8, 156.0, 148.9, 142.4, 142.1, 132.3, 129.0, 128.9, 124.1, 123.9, 119.0, 108.6, 103.0, 101.5, 93.6, 80.4, 58.3, 37.8, 29.8; MS (ES+) m/z 340.2 (M+1).

EXAMPLE 14

Synthesis of 3-(2'-oxospiro[furo[2,3-f][1,3]benzodioxole-7,3'-indol]-1'(2'H)-yl)propanal To a solution of 1'-(3-hydroxypropyl)spiro[furo[2,3-f][1,3]benzodioxole-7,3'-indol]-2'(1'H)-one (4.82 g, 14.2 mmol) in dichloromethane (150 mL) was added 1,1,1-triacetoxy-1,1-dihydro-1,2-benziodoxol-3(1H)-one (7.00 g, 16.7 mmol) at 0° C. The resulting mixture was stirred at 0° C. for 4 h, diluted with ethyl acetate, washed sequentially with 10% Na$_2$S$_2$O$_3$ solution, saturated NaHCO$_3$ and brine, dried over anhydrous Na$_2$SO$_4$ and filtered. The filtrate was concentrated in vacuo to dryness. The residue was subjected to flash chromatography and the product was recrystallized from ethyl acetate/hexanes to afford the title compound (3.86 g) in 80% yield: $^1$H NMR (300 MHz, CDCl$_3$) δ 9.83 (s, 1H), 7.33-6.92 (m, 4H), 6.48 (s, 1H), 6.08 (s, 1H), 4.86 (m, 1H), 4.61(m, 1H), 4.15-3.98 (m, 2H), 2.97-2.84 (m, 2H); MS (ES+, m/z) 338.1 (M+1).

EXAMPLE 15

Synthesis of 1-{3-[(cyclopropylmethyl)amino]propyl}spiro[furo[2,3-f][1,3]benzodioxole-7,3'-indol]-2'(1H)-one

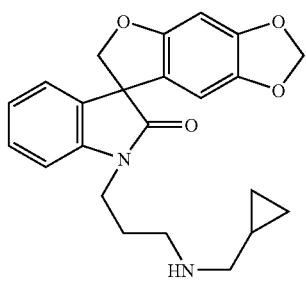

To a solution of 3-(2'-oxospiro[furo[2,3-f][1,3]benzodioxole-7,3'-indol]-1'(2'H)-yl)propanal (0.07 g, 0.20 mmol) in THF (5.00 mL) was added (aminomethyl)cyclopropane (0.30 mmol) and MP-triacetoxyborohydride (0.26 g, 0.60 mmol). After overnight shaking, the polymer-bound 4-phenyloxybenzaldehyde (0.25 g, 0.18 mmol) was added. After another overnight shaking, the mixture was diluted with ether (10.0 mL) and filtered. The filtrate was concentrated in vacuo to dryness. The residue was recrystallized to give the title compound (0.05 g) in 62% yield as a white solid: $^1$H NMR (300 MHz, CDCl$_3$) δ 7.32-6.92 (m, 4H), 6.49 (s, 1H), 6.12 (s, 1H), 5.83 (m, 2H), 4.86 (m, 1H), 4.64 (m, 1H), 3.97-3.77(m, 2H), 2.87-2.80 (m, 2H), 2.66-2.56 (m, 2H), 1.02-0.94 (m, 1H), 0.56-0.47 (m, 2H), 0.25-0.18 (m, 2H); MS (ES+) m/z 393.3 (M+1).

EXAMPLE 15.1

The compounds listed in the following table were prepared using the similar procedure as described in EXAMPLE 15. As previously noted, the compound numbers listed below do not correspond to the compound numbers provided in the general Reaction Schemes above.

| Compound Number | Name | MS (m/z, M + 1) |
| --- | --- | --- |
| 600 | 1'-{3-[(4-fluorobenzyl)amino]propyl}spiro[furo[2,3-f][1,3]benzodioxole-7,3'-indol]-2'(1'H)-one | 447.0 |
| 601 | 1'-{3-[(4-chlorophenyl)amino]propyl}spiro[furo[2,3-f][1,3]benzodioxole-7,3'-indol]-2'(1'H)-one | 449.2 |
| 602 | 1'-[3-(pentylamino)propyl]spiro[furo[2,3-f][1,3]benzodioxole-7,3'-indol]-2'(1'H)-one | 409.1 |
| 603 | 1'-{3-[(2-ethoxyethyl)amino]propyl}spiro[furo[2,3-f][1,3]benzodioxole-7,3'-indol]-2'(1'H)-one | 411.1 |
| 604 | 1'-{3-[(3-methoxypropyl)amino]propyl}spiro[furo[2,3-f][1,3]benzodioxole-7,3'-indol]-2'(1'H)-one | 411.1 |
| 605 | 1'-{3-[(3-methylbutyl)amino]propyl}spiro[furo[2,3-f][1,3]benzodioxole-7,3'-indol]-2'(1'H)-one | 409.6 |
| 606 | 1'-{3-[(3-ethoxypropyl)amino]propyl}spiro[furo[2,3-f][1,3]benzodioxole-7,3'-indol]-2'(1'H)-one | 425.6 |
| 607 | 1'-{3-[(2,2-dimethylpropyl)amino]propyl}spiro[furo[2,3-f][1,3]benzodioxole-7,3'-indol]-2'(1'H)-one | 409.1 |
| 608 | 3-{[3-(2'-oxospiro[furo[2,3-f][1,3]benzodioxole-7,3'-indol]-1'(2'H)-yl)propyl]amino}propanenitrile | 392.4 |
| 609 | 1'-{3-[(2,2,2-trifluoroethyl)amino]propyl}spiro[furo[2,3-f][1,3]benzodioxole-7,3'-indol]-2'(1'H)-one | 421.1 |
| 610 | 1'-[3-(cyclopropylamino)propyl]spiro[furo[2,3-f][1,3]benzodioxole-7,3'-indol]-2'(1'H)-one | 379.1 |
| 611 | 1'-[3-(cyclobutylamino)propyl]spiro[furo[2,3-f][1,3]benzodioxole-7,3'-indol]-2'(1'H)-one | 393.1 |
| 612 | 1'-{3-[(2-cyclopropylethyl)amino]propyl}spiro[furo[2,3-f][1,3]benzodioxole-7,3'-indol]-2'(1'H)-one | 407.1 |
| 613 | 1'-[3-(isobutylamino)propyl]spiro[furo[2,3-f][1,3]benzodioxole-7,3'-indol]-2'(1'H)-one | 395.1 |
| 614 | 1'-[3-(hexylamino)propyl]spiro[furo[2,3-f][1,3]benzodioxole-7,3'-indol]-2'(1'H)-one | 423.5 |
| 615 | 1'-[3-(heptylamino)propyl]spiro[furo[2,3-f][1,3]benzodioxole-7,3'-indol]-2'(1'H)-one | 437.1 |
| 616 | 1'-[3-(isopropylamino)propyl]spiro[furo[2,3-f][1,3]benzodioxole-7,3'-indol]-2'(1'H)-one | 381.7 |
| 617 | 1'-{3-[(tetrahydrofuran-2-ylmethyl)amino]propyl}spiro[furo[2,3-f][1,3]benzodioxole-7,3'-indol]-2'(1'H)-one | 423.1 |
| 618 | 1'-[3-(benzylamino)propyl]spiro[furo[2,3-f][1,3]benzodioxole-7,3'-indol]-2'(1'H)-one | 429.1 |
| 619 | 1'-{3-[(2-phenylethyl)amino]propyl}spiro[furo[2,3-f][1,3]benzodioxole-7,3'-indol]-2'(1'H)-one | 443.1 |
| 620 | 1'-[3-(dibenzylamino)propyl]spiro[furo[2,3-f][1,3]benzodioxole-7,3'-indol]-2'(1'H)-one | 519.4 |
| 621 | 1'-[3-(propylamino)propyl]spiro[furo[2,3-f][1,3]benzodioxole-7,3'-indol]-2'(1'H)-one | 381.1 |
| 622 | 1'-(3-{[2-(3-fluorophenyl)ethyl]amino}propyl)spiro[furo[2,3-f][1,3]benzodioxole-7,3'-indol]-2'(1'H)-one | 461.5 |
| 623 | 1'-{3-[(3-phenylpropyl)amino]propyl}spiro[furo[2,3-f][1,3]benzodioxole-7,3'-indol]-2'(1'H)-one | 457.5 |
| 624 | 1'-{3-[(2,2-diphenylethyl)amino]propyl}spiro[furo[2,3-f][1,3]benzodioxole-7,3'-indol]-2'(1'H)-one | 519.4 |
| 625 | 1'-(3-{[2-(4-methylphenyl)ethyl]amino}propyl)spiro[furo[2,3-f][1,3]benzodioxole-7,3'-indol]-2'(1'H)-one | 457.5 |
| 626 | 1'-(3-{[2-(3-chlorophenyl)ethyl]amino}propyl)spiro[furo[2,3-f][1,3]benzodioxole-7,3'-indol]-2'(1'H)-one | 477.3 |
| 627 | 1'-{3-[(2-pyridin-4-ylethyl)amino]propyl}spiro[furo[2,3-f][1,3]benzodioxole-7,3'-indol]-2'(1'H)-one | 444.2 |
| 628 | 1'-{3-[(pyridin-4-ylmethyl)amino]propyl}spiro[furo[2,3-f][1,3]benzodioxole-7,3'-indol]-2'(1'H)-one | 430.5 |
| 629 | 1'-(3-{[2-(4-fluorophenyl)ethyl]amino}propyl)spiro[furo[2,3-f][1,3]benzodioxole-7,3'-indol]-2'(1'H)-one | 461.0 |
| 630 | 1'-{3-[(pyridin-2-ylmethyl)amino]propyl}spiro[furo[2,3-f][1,3]benzodioxole-7,3'-indol]-2'(1'H)-one | 430.2 |
| 631 | 1'-(3-{[(1R)-1-cyclohexylethyl]amino}propyl)spiro[furo[2,3-f][1,3]benzodioxole-7,3'-indol]-2'(1'H)-one | 449.1 |
| 632 | 1'-{3-[(2-furylmethyl)amino]propyl}spiro[furo[2,3-f][1,3]benzodioxole-7,3'-indol]-2'(1'H)-one | 419.4 |

-continued

| Compound Number | Name | MS (m/z, M + 1) |
|---|---|---|
| 633 | 1'-{3-[(4-chlorobenzyl)amino]propyl}spiro[furo[2,3-f][1,3]benzodioxole-7,3'-indol]-2'(1'H)-one | 463.1 |
| 634 | 1'-{3-[(4-methoxybenzyl)amino]propyl}spiro[furo[2,3-f][1,3]benzodioxole-7,3'-indol]-2'(1'H)-one | 459.4 |
| 635 | 1'-{3-[(3-isopropoxypropyl)amino]propyl}spiro[furo[2,3-f][1,3]benzodioxole-7,3'-indol]-2'(1'H)-one | 439.1 |
| 636 | 1'-(3-{[2-(2-fluorophenyl)ethyl]amino}propyl)spiro[furo[2,3-f][1,3]benzodioxole-7,3'-indol]-2'(1'H)-one | 461.0 |
| 637 | 1'-{3-[(3,3-dimethylbutyl)amino]propyl}spiro[furo[2,3-f][1,3]benzodioxole-7,3'-indol]-2'(1'H)-one | 423.5 |
| 638 | 1'-{3-[(cyclohexylmethyl)amino]propyl}spiro[furo[2,3-f][1,3]benzodioxole-7,3'-indol]-2'(1'H)-one | 435.0 |
| 639 | 1'-{3-{[(1S)-1-cyclohexylethyl]amino}propyl)spiro[furo[2,3-f][1,3]benzodioxole-7,3'-indol]-2'(1'H)-one | 436.5 |
| 640 | 1'-{3-[(2-piperidin-1-ylethyl)amino]propyl}spiro[furo[2,3-f][1,3]benzodioxole-7,3'-indol]-2'(1'H)-one | 449.1 |
| 641 | 1'-{3-[(2-pyrrolidin-1-ylethyl)amino]propyl}spiro[furo[2,3-f][1,3]benzodioxole-7,3'-indol]-2'(1'H)-one | 450.5 |
| 642 | 1'-{3-[(2-morpholin-4-ylethyl)amino]propyl}spiro[furo[2,3-f][1,3]benzodioxole-7,3'-indol]-2'(1'H)-one | 452.4 |
| 643 | 1'-[3-(cyclohexylamino)propyl]spiro[furo[2,3-f][1,3]benzodioxole-7,3'-indol]-2'(1'H)-one | 421.5 |
| 644 | 1'-[3-(cyclopentylamino)propyl]spiro[furo[2,3-f][1,3]benzodioxole-7,3'-indol]-2'(1'H)-one | 407.3 |
| 645 | 1'-{3-[(2-chlorobenzyl)amino]propyl}spiro[furo[2,3-f][1,3]benzodioxole-7,3'-indol]-2'(1'H)-one | 463.2 |
| 646 | 1'-(3-pyrrolidin-1-ylpropyl)spiro[furo[2,3-f][1,3]benzodioxole-7,3'-indol]-2'(1'H)-one | 393.5 |
| 647 | 1'-[3-(dibutylamino)propyl]spiro[furo[2,3-f][1,3]benzodioxole-7,3'-indol]-2'(1'H)-one | 451.5 |
| 648 | 1'-(3-piperidin-1-ylpropyl)spiro[furo[2,3-f][1,3]benzodioxole-7,3'-indol]-2'(1'H)-one | 407.0 |
| 649 | 1'-[3-(dipropylamino)propyl]spiro[furo[2,3-f][1,3]benzodioxole-7,3'-indol]-2'(1'H)-one | 423.2 |
| 650 | 1'-{3-{[2-(dimethylamino)ethyl]amino}propyl)spiro[furo[2,3-f][1,3]benzodioxole-7,3'-indol]-2'(1'H)-one | 410.5 |
| 651 | 1'-(3-{[2-(diethylamino)ethyl](methyl)amino}propyl)spiro[furo[2,3-f][1,3]benzodioxole-7,3'-indol]-2'(1'H)-one | 452.1 |
| 652 | 1'-(3-{[2-(diisopropylamino)ethyl]amino}propyl)spiro[furo[2,3-f][1,3]benzodioxole-7,3'-indol]-2'(1'H)-one | 466.1 |
| 653 | 1'-[3-(diisopropylamino)propyl]spiro[furo[2,3-f][1,3]benzodioxole-7,3'-indol]-2'(1'H)-one | 423.0 |
| 654 | 1'-[3-(methylamino)propyl]spiro[furo[2,3-f][1,3]benzodioxole-7,3'-indol]-2'(1'H)-one | 353.0 |
| 655 | 1'-[3-(ethylamino)propyl]spiro[furo[2,3-f][1,3]benzodioxole-7,3'-indol]-2'(1'H)-one | 367.0 |
| 656 | 1'-{3-[bis(2-methoxyethyl)amino]propyl}spiro[furo[2,3-f][1,3]benzodioxole-7,3'-indol]-2'(1'H)-one | 455.0 |
| 657 | 1'-{3-[(2-fluorobenzyl)amino]propyl}spiro[furo[2,3-f][1,3]benzodioxole-7,3'-indol]-2'(1'H)-one | 446.9 |
| 658 | 1'-{3-[(3,5-difluorobenzyl)amino]propyl}spiro[furo[2,3-f][1,3]benzodioxole-7,3'-indol]-2'(1'H)-one | 464.9 |
| 659 | 1'-(3-{[3-(dimethylamino)propyl]amino}propyl)spiro[furo[2,3-f][1,3]benzodioxole-7,3'-indol]-2'(1'H)-one | 424.0 |
| 660 | 1'-[3-(diethylamino)propyl]spiro[furo[2,3-f][1,3]benzodioxole-7,3'-indol]-2'(1'H)-one | 394.9 |
| 661 | 1'-[3-(octylamino)propyl]spiro[furo[2,3-f][1,3]benzodioxole-7,3'-indol]-2'(1'H)-one | 451.5 |
| 662 | 1'-{3-[(1-methylbutyl)amino]propyl}spiro[furo[2,3-f][1,3]benzodioxole-7,3'-indol]-2'(1'H)-one | 409.0 |
| 663 | 1'-{3-[butyl(methyl)amino]propyl}spiro[furo[2,3-f][1,3]benzodioxole-7,3'-indol]-2'(1'H)-one | 409.0 |
| 664 | 1'-{3-[(2-isopropoxyethyl)amino]propyl}spiro[furo[2,3-f][1,3]benzodioxole-7,3'-indol]-2'(1'H)-one | 425.0 |
| 665 | 1'-{3-[(2,4-difluorobenzyl)amino]propyl}spiro[furo[2,3-f][1,3]benzodioxole-7,3'-indol]-2'(1'H)-one | 464.9 |
| 666 | 1'-{3-[(2-methylbenzyl)amino]propyl}spiro[furo[2,3-f][1,3]benzodioxole-7,3'-indol]-2'(1'H)-one | 443.0 |
| 667 | 1'-{3-[(3-fluorobenzyl)amino]propyl}spiro[furo[2,3-f][1,3]benzodioxole-7,3'-indol]-2'(1'H)-one | 446.9 |
| 668 | 1'-{3-[(2,6-difluorobenzyl)amino]propyl}spiro[furo[2,3-f][1,3]benzodioxole-7,3'-indol]-2'(1'H)-one | 464.9 |
| 669 | 1'-{3-[(1,2-dimethylpropyl)amino]propyl}spiro[furo[2,3-f][1,3]benzodioxole-7,3'-indol]-2'(1'H)-one | 409.0 |

-continued

| Compound Number | Name | MS (m/z, M + 1) |
|---|---|---|
| 670 | 1'-(3-{[2-(1-methylpyrrolidin-2-yl)ethyl]amino}propyl)spiro[furo[2,3-f][1,3]benzodioxole-7,3'-indol]-2'(1'H)-one | 450.4 |
| 671 | 1'-{3-[(2-pyridin-3-ylethyl)amino]propyl}spiro[furo[2,3-f][1,3]benzodioxole-7,3'-indol]-2'(1'H)-one | 444.5 |
| 672 | 1'-{3-[(1-methyl-2-phenylethyl)amino]propyl}spiro[furo[2,3-f][1,3]benzodioxole-7,3'-indol]-2'(1'H)-one | 457.0 |
| 673 | 1'-(3-{[2-(2-chlorophenyl)ethyl]amino}propyl)spiro[furo[2,3-f][1,3]benzodioxole-7,3'-indol]-2'(1'H)-one | 476.9 |
| 674 | 1'-{3-[(2-cyclohexylethyl)amino]propyl}spiro[furo[2,3-f][1,3]benzodioxole-7,3'-indol]-2'(1'H)-one | 448.1 |
| 675 | 1'-{3-[(2-pyridin-2-ylethyl)amino]propyl}spiro[furo[2,3-f][1,3]benzodioxole-7,3'-indol]-2'(1'H)-one | 444.2 |
| 676 | 1'-{3-[(2-biphenyl-4-ylethyl)amino]propyl}spiro[furo[2,3-f][1,3]benzodioxole-7,3'-indol]-2'(1'H)-one | 519.6 |
| 677 | 1'-{3-[(3-morpholin-4-ylpropyl)amino]propyl}spiro[furo[2,3-f][1,3]benzodioxole-7,3'-indol]-2'(1'H)-one | 466.2 |
| 678 | 1'-(3-{[(5-methyl-2-furyl)methyl]amino}propyl)spiro[furo[2,3-f][1,3]benzodioxole-7,3'-indol]-2'(1'H)-one | 433.3 |
| 679 | 1'-{3-[(3-methylbenzyl)amino]propyl}spiro[furo[2,3-f][1,3]benzodioxole-7,3'-indol]-2'(1'H)-one | 443.4 |

EXAMPLE 16

Synthesis of 1'-(3-aminopropyl)spiro[furo[2,3-f][1,3]benzodioxole-7,3'-indol]-2'(1'H)-one

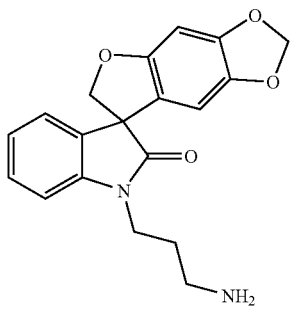

To a solution of 2-[3-(2'-oxospiro[furo[2,3-f][1,3]benzodioxole-7,3'-indol]-1'(2'H)-yl)propyl]-1H-isoindole-1,3(2H)-dione (3.20 g, 6.80 mmol) in ethanol (70.0 mL) was added hydrazine monohydrate (1.87 g, 37.0 mmol). The mixture was stirred at ambient temperature for 4 h. The solvent was removed under reduced pressure and the residue was re-dissolved in ethyl acetate. The solution was washed with sodium bicarbonate and brine solution, dried over $MgSO_4$ and filtered. The filtrate was concentrated in vacuo to dryness. The residue was crystallized from hexane to yield the title compound (2.50 g) in 75% yield: $^1$H NMR (300 MHz, $CDCl_3$) δ 7.31-7.24 (m, 1H), 7.16-7.14 (m, 1H), 7.06-7.01 (m, 1H), 6.94-6.91 (m, 1H), 6.48 (s, 1H), 6.10 (s, 1H), 5.82 (m, 2H), 4.90-4.87 (m, 1H), 4.61 (d, 1H), 3.98-3.71 (m, 2H), 2.77-2.73 (m, 2H), 1.97 (br, 2H), 1.84-1.81 (m, 2H); $^{13}$C NMR (75 MHz, $CDCl_3$) δ 177.8, 155.9, 148.9, 142.3, 142.2, 132.4, 129.0, 124.0, 123.4, 119.4, 108.7, 103.0, 101.5, 93.6, 80.5, 58.2, 38.8, 37.5, 30.6; MS (ES+) m/z 339.3 (M+1).

EXAMPLE 17

Synthesis of 3-chloro-N-[3-(2'-oxospiro[furo[2,3-f][1,3]benzodioxole-7,3'-indol]-1'(2'H)-yl)propyl]thiophene-2-carboxamide

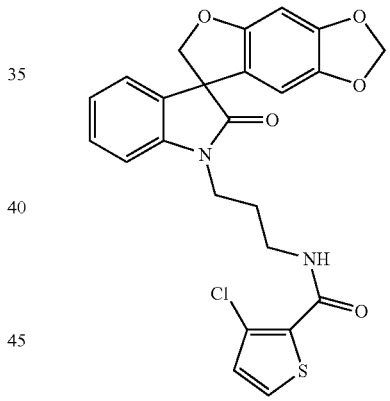

To a solution of 1'-(3-aminopropyl)spiro[furo[2,3-f][1,3]benzodioxole-7,3'-indol]-2'(1'H)-one (0.05 g, 0.13 mmol) in dichloromethane (4.00 mL) was added triethylamine (0.03 g, 0.26 mmol) and 3-chlorothiophene-2-carbonyl chloride (0.02 g, 0.12 mmol) at 0° C. The mixture was stirred for 2 h, washed with 15% HCl solution and water. The organic layer was dried over $MgSO_4$ and filtered. The filtrate was concentrated in vacuo to dryness. The residue was dissolved in ethyl acetate, and the product was precipitated with the addition of hexane. The white solid was collected by filtration and dried in vacuo to yield the title compound (0.04 g) in 67% yield: $^1$H NMR (300 MHz, $CDCl_3$) δ 7.60 (t, 1H), 7.41 (d, 1H), 7.33-7.27-(m, 1H), 7.17 (d, 1H), 7.08-7.03-(m, 1H), 6.93 (t, 1H), 6.49 (s, 1H), 6.11 (s, 1H), 5.95 (m, 2H), 4.90 (d, 1H), 4.65 (d, 1H), 3.96-3.79-(m, 2H), 3.53-3.36-(m, 2H), 2.04-1.93-(m, 2H); $^{13}$C NMR (75 MHz, $CDCl_3$) δ 178.3, 160.6, 156.0, 149.0, 142.4, 141.8, 132.5, 129.4, 129.2, 129.1, 124.2, 123.7, 123.6, 119.2, 108.5, 102.9, 101.6, 93.7, 80.5, 58.3, 37.4, 36.5, 27.3; MS (ES+) m/z 483 (M+1).

EXAMPLE 17.1

The compounds listed in the following table were synthesized using the similar procedure as described in EXAMPLE 17. As previously noted, the compound numbers listed below do not correspond to the compound numbers provided in the general Reaction Schemes above.

| Compound Number | Name | MS (m/z, M + 1) |
| --- | --- | --- |
| 680 | N-[3-(2'-oxospiro[furo[2,3-f][1,3]benzodioxole-7,3'-indol]-1'(2'H)-yl)propyl]cyclopropanecarboxamide | 407.3 |
| 681 | N-[3-(2'-oxospiro[furo[2,3-f][1,3]benzodioxole-7,3'-indol]-1'(2'H)-yl)propyl]cyclobutanecarboxamide | 421.3 |
| 682 | 2-chloro-N-[3-(2'-oxospiro[furo[2,3-f][1,3]benzodioxole-7,3'-indol]-1'(2'H)-yl)propyl]nicotinamide | 478.3 |
| 683 | N-[3-(2'-oxospiro[furo[2,3-f][1,3]benzodioxole-7,3'-indol]-1'(2'H)-yl)propyl]cyclopentanecarboxamide | 435.3 |
| 684 | 2,2-dimethyl-N-[3-(2'-oxospiro[furo[2,3-f][1,3]benzodioxole-7,3'-indol]-1'(2'H)-yl)propyl]propanamide | 423.3 |
| 685 | 2-(4-methoxyphenyl)-N-[3-(2'-oxospiro[furo[2,3-f][1,3]benzodioxole-7,3'-indol]-1'(2'H)-yl)propyl]acetamide | 487.3 |
| 686 | 4-tert-butyl-N-[3-(2'-oxospiro[furo[2,3-f][1,3]benzodioxole-7,3'-indol]-1'(2'H)-yl)propyl]benzamide | 499.2 |
| 687 | 3,3-dimethyl-N-[3-(2'-oxospiro[furo[2,3-f][1,3]benzodioxole-7,3'-indol]-1'(2'H)-yl)propyl]butanamide | 437.3 |
| 688 | N-[3-(2'-oxospiro[furo[2,3-f][1,3]benzodioxole-7,3'-indol]-1'(2'H)-yl)propyl]biphenyl-4-carboxamide | 519.3 |
| 689 | 3-methyl-N-[3-(2'-oxospiro[furo[2,3-f][1,3]benzodioxole-7,3'-indol]-1'(2'H)-yl)propyl]-1-benzofuran-2-carboxamide | 497.2 |
| 690 | 2-(benzyloxy)-N-[3-(2'-oxospiro[furo[2,3-f][1,3]benzodioxole-7,3'-indol]-1'(2'H)-yl)propyl]acetamide | 487.3 |
| 691 | N-[3-(2'-oxospiro[furo[2,3-f][1,3]benzodioxole-7,3'-indol]-1'(2'H)-yl)propyl]-2-furamide | 433.3 |
| 692 | N-[3-(2'-oxospiro[furo[2,3-f][1,3]benzodioxole-7,3'-indol]-1'(2'H)-yl)propyl]-1,3-benzodioxole-5-carboxamide | 487.3 |
| 693 | N-[3-(2'-oxospiro[furo[2,3-f][1,3]benzodioxole-7,3'-indol]-1'(2'H)-yl)propyl]quinoline-2-carboxamide | 494.3 |
| 694 | N-[3-(2'-oxospiro[furo[2,3-f][1,3]benzodioxole-7,3'-indol]-1'(2'H)-yl)propyl]-2-phenylacetamide | 457.4 |
| 695 | N-[3-(2'-oxospiro[furo[2,3-f][1,3]benzodioxole-7,3'-indol]-1'(2'H)-yl)propyl]piperidine-1-carboxamide | 450.3 |
| 696 | 2-methoxy-N-[3-(2'-oxospiro[furo[2,3-f][1,3]benzodioxole-7,3'-indol]-1'(2'H)-yl)propyl]acetamide | 411.2 |
| 697 | 4-(dimethylamino)-N-[3-(2'-oxospiro[furo[2,3-f][1,3]benzodioxole-7,3'-indol]-1'(2'H)-yl)propyl]benzamide | 486.3 |
| 698 | 4-ethoxy-N-[3-(2'-oxospiro[furo[2,3-f][1,3]benzodioxole-7,3'-indol]-1'(2'H)-yl)propyl]benzamide | 487.3 |
| 699 | 2-methyl-N-[3-(2'-oxospiro[furo[2,3-f][1,3]benzodioxole-7,3'-indol]-1'(2'H)-yl)propyl]butanamide | 423.3 |
| 700 | N-[3-(2'-oxospiro[furo[2,3-f][1,3]benzodioxole-7,3'-indol]-1'(2'H)-yl)propyl]-2-phenoxyacetamide | 473.2 |
| 701 | N-[3-(2'-oxospiro[furo[2,3-f][1,3]benzodioxole-7,3'-indol]-1'(2'H)-yl)propyl]quinoxaline-2-carboxamide | 495.0 |
| 702 | N-[3-(2'-oxospiro[furo[2,3-f][1,3]benzodioxole-7,3'-indol]-1'(2'H)-yl)propyl]cyclohexanecarboxamide | 449.3 |
| 703 | 4-fluoro-N-[3-(2'-oxospiro[furo[2,3-f][1,3]benzodioxole-7,3'-indol]-1'(2'H)-yl)propyl]benzamide | 461.3 |
| 704 | 2-ethyl-N-[3-(2'-oxospiro[furo[2,3-f][1,3]benzodioxole-7,3'-indol]-1'(2'H)-yl)propyl]butanamide | 437.3 |
| 705 | 2-(4-fluorophenyl)-N-[3-(2'-oxospiro[furo[2,3-f][1,3]benzodioxole-7,3'-indol]-1'(2'H)-yl)propyl]acetamide | 475.3 |
| 706 | 6-chloro-N-[3-(2'-oxospiro[furo[2,3-f][1,3]benzodioxole-7,3'-indol]-1'(2'H)-yl)propyl]nicotinamide | 478.0 |
| 707 | 2-fluoro-N-[3-(2'-oxospiro[furo[2,3-f][1,3]benzodioxole-7,3'-indol]-1'(2'H)-yl)propyl]benzamide | 461.4 |
| 708 | N-[3-(2'-oxospiro[furo[2,3-f][1,3]benzodioxole-7,3'-indol]-1'(2'H)-yl)propyl]-2-phenylcyclopropanecarboxamide | 482.8 |

| Compound Number | Name | MS (m/z, M + 1) |
|---|---|---|
| 709 | 4-methyl-N-[3-(2'-oxospiro[furo[2,3-f][1,3]benzodioxole-7,3'-indol]-1'(2'H)-yl)propyl]benzamide | 457.7 |
| 710 | 1-(4-fluorophenyl)-5-methyl-N-[3-(2'-oxospiro[furo[2,3-f][1,3]benzodioxole-7,3'-indol]-1'(2'H)-yl)propyl]-1H-pyrazole-4-carboxamide | 541.2 |
| 711 | N-[3-(2'-oxospiro[furo[2,3-f][1,3]benzodioxole-7,3'-indol]-1'(2'H)-yl)propyl]-1-benzofuran-5-carboxamide | 483.1 |
| 712 | N-[3-(2'-oxospiro[furo[2,3-f][1,3]benzodioxole-7,3'-indol]-1'(2'H)-yl)propyl]-2,1,3-benzoxadiazole-5-carboxamide | 485.4 |
| 713 | 2,4-dichloro-N-[3-(2'-oxospiro[furo[2,3-f][1,3]benzodioxole-7,3'-indol]-1'(2'H)-yl)propyl]benzamide | 513.1 |
| 714 | 1-methyl-N-[3-(2'-oxospiro[furo[2,3-f][1,3]benzodioxole-7,3'-indol]-1'(2'H)-yl)propyl]-1H-1,2,3-benzotriazole-5-carboxamide | 498.4 |
| 715 | 5-fluoro-2-methyl-N-[3-(2'-oxospiro[furo[2,3-f][1,3]benzodioxole-7,3'-indol]-1'(2'H)-yl)propyl]benzamide | 475.1 |
| 716 | 2-chloro-N-[3-(2'-oxospiro[furo[2,3-f][1,3]benzodioxole-7,3'-indol]-1'(2'H)-yl)propyl]isonicotinamide | 478.1 |
| 717 | N-[3-(2'-oxospiro[furo[2,3-f][1,3]benzodioxole-7,3'-indol]-1'(2'H)-yl)propyl]-2,3-dihydro-1,4-benzodioxine-6-carboxamide | 501.1 |
| 718 | 5-methyl-N-[3-(2'-oxospiro[furo[2,3-f][1,3]benzodioxole-7,3'-indol]-1'(2'H)-yl)propyl]isoxazole-3-carboxamide | 448.2 |
| 719 | N-[3-(2'-oxospiro[furo[2,3-f][1,3]benzodioxole-7,3'-indol]-1'(2'H)-yl)propyl]-1-benzofuran-2-carboxamide | 483.1 |
| 720 | N-[3-(2'-oxospiro[furo[2,3-f][1,3]benzodioxole-7,3'-indol]-1'(2'H)-yl)propyl]-1-benzothiophene-2-carboxamide | 499.1 |
| 721 | N-[3-(2'-oxospiro[furo[2,3-f][1,3]benzodioxole-7,3'-indol]-1'(2'H)-yl)propyl]-2,3-dihydro-1,4-benzodioxine-2-carboxamide | 501.1 |
| 722 | N-[3-(2'-oxospiro[furo[2,3-f][1,3]benzodioxole-7,3'-indol]-1'(2'H)-yl)propyl]-4-(1H-pyrazol-1-yl)benzamide | 509.1 |
| 723 | 1,3-dimethyl-N-[3-(2'-oxospiro[furo[2,3-f][1,3]benzodioxole-7,3'-indol]-1'(2'H)-yl)propyl]-1H-pyrazole-5-carboxamide | 461.2 |
| 724 | 4-methyl-N-[3-(2'-oxospiro[furo[2,3-f][1,3]benzodioxole-7,3'-indol]-1'(2'H)-yl)propyl]-3,4-dihydro-2H-1,4-benzoxazine-7-carboxamide | 514.2 |
| 725 | N-[3-(2'-oxospiro[furo[2,3-f][1,3]benzodioxole-7,3'-indol]-1'(2'H)-yl)propyl]quinoxaline-6-carboxamide | 495.2 |
| 726 | N-[3-(2'-oxospiro[furo[2,3-f][1,3]benzodioxole-7,3'-indol]-1'(2'H)-yl)propyl]-2,3-dihydro-1-benzofuran-2-carboxamide | 485.2 |
| 727 | N-[3-(2'-oxospiro[furo[2,3-f][1,3]benzodioxole-7,3'-indol]-1'(2'H)-yl)propyl]-2,3-dihydro-1-benzothiophene-5-carboxamide | 499.1 |
| 728 | N-[3-(2'-oxospiro[furo[2,3-f][1,3]benzodioxole-7,3'-indol]-1'(2'H)-yl)propyl]-2-(trifluoromethoxy)benzamide | 526.9 |
| 729 | N-[3-(2'-oxospiro[furo[2,3-f][1,3]benzodioxole-7,3'-indol]-1'(2'H)-yl)propyl]pentanamide | 445.2 |
| 730 | N-[3-(2'-oxospiro[furo[2,3-f][1,3]benzodioxole-7,3'-indol]-1'(2'H)-yl)propyl]heptanamide | 473.2 |
| 731 | 3-cyclopentyl-N-[3-(2'-oxospiro[furo[2,3-f][1,3]benzodioxole-7,3'-indol]-1'(2'H)-yl)propyl]propanamide | 463.0 |
| 732 | 9-oxo-N-[3-(2'-oxospiro[furo[2,3-f][1,3]benzodioxole-7,3'-indol]-1'(2'H)-yl)propyl]-9H-fluorene-4-carboxamide | 545.0 |
| 733 | N-[3-(2'-oxospiro[furo[2,3-f][1,3]benzodioxole-7,3'-indol]-1'(2'H)-yl)propyl]-4-(trifluoromethyl)benzamide | 511.4 |
| 734 | 2,5-difluoro-N-[3-(2'-oxospiro[furo[2,3-f][1,3]benzodioxole-7,3'-indol]-1'(2'H)-yl)propyl]benzamide | 479.3 |
| 735 | 2,5-dimethyl-N-[3-(2'-oxospiro[furo[2,3-f][1,3]benzodioxole-7,3'-indol]-1'(2'H)-yl)propyl]-3-furamide | 461.4 |
| 736 | N-[3-(2'-oxospiro[furo[2,3-f][1,3]benzodioxole-7,3'-indol]-1'(2'H)-yl)propyl]-4-phenoxybutanamide | 523.3 |
| 737 | 4-fluoro-N-[3-(2'-oxospiro[furo[2,3-f][1,3]benzodioxole-7,3'-indol]-1'(2'H)-yl)propyl]-2-(trifluoromethyl)benzamide | 529.0 |
| 738 | N-[3-(2'-oxospiro[furo[2,3-f][1,3]benzodioxole-7,3'-indol]-1'(2'H)-yl)propyl]-2-(2-thienyl)acetamide | 463.3 |

-continued

| Compound Number | Name | MS (m/z, M + 1) |
|---|---|---|
| 739 | 2-chloro-5-fluoro-N-[3-(2'-oxospiro[furo[2,3-f][1,3]benzodioxole-7,3'-indol]-1'(2'H)-yl)propyl]benzamide | 495.0 |
| 740 | N-[3-(2'-oxospiro[furo[2,3-f][1,3]benzodioxole-7,3'-indol]-1'(2'H)-yl)propyl]-2-naphthamide | 493.0 |
| 741 | 2-(4-chlorophenoxy)-N-[3-(2'-oxospiro[furo[2,3-f][1,3]benzodioxole-7,3'-indol]-1'(2'H)-yl)propyl]acetamide | 507.3 |
| 742 | 2,4-dimethoxy-N-[3-(2'-oxospiro[furo[2,3-f][1,3]benzodioxole-7,3'-indol]-1'(2'H)-yl)propyl]benzamide | 503.4 |
| 743 | 2-nitro-N-[3-(2'-oxospiro[furo[2,3-f][1,3]benzodioxole-7,3'-indol]-1'(2'H)-yl)propyl]benzamide | 488.4 |
| 744 | 2-(4-chlorophenyl)-3-methyl-N-[3-(2'-oxospiro[furo[2,3-f][1,3]benzodioxole-7,3'-indol]-1'(2'H)-yl)propyl]butanamide | 533.4 |
| 745 | 4-amino-N-[3-(2'-oxospiro[furo[2,3-f][1,3]benzodioxole-7,3'-indol]-1'(2'H)-yl)propyl]benzamide | 458.4 |
| 746 | 3,4-dimethoxy-N-[3-(2'-oxospiro[furo[2,3-f][1,3]benzodioxole-7,3'-indol]-1'(2'H)-yl)propyl]benzamide | 503.3 |
| 747 | N-[3-(2'-oxospiro[furo[2,3-f][1,3]benzodioxole-7,3'-indol]-1'(2'H)-yl)propyl]-5H-dibenzo[b,f]azepine-5-carboxamide | 558.4 |
| 748 | N-[3-(2'-oxospiro[furo[2,3-f][1,3]benzodioxole-7,3'-indol]-1'(2'H)-yl)propyl]adamantane-1-carboxamide | 501.5 |
| 749 | 2-[(2-isopropyl-5-methylcyclohexyl)oxy]-N-[3-(2'-oxospiro[furo[2,3-f][1,3]benzodioxole-7,3'-indol]-1'(2'H)-yl)propyl]acetamide | 535.5 |
| 750 | N-[3-(2'-oxospiro[furo[2,3-f][1,3]benzodioxole-7,3'-indol]-1'(2'H)-yl)propyl]-3,5-bis(trifluoromethyl)benzamide | 579.3 |
| 751 | 2-(2,5-dimethoxyphenyl)-N-[3-(2'-oxospiro[furo[2,3-f][1,3]benzodioxole-7,3'-indol]-1'(2'H)-yl)propyl]acetamide | 517.4 |
| 752 | 2-chloro-N-[3-(2'-oxospiro[furo[2,3-f][1,3]benzodioxole-7,3'-indol]-1'(2'H)-yl)propyl]benzamide | 477.3 |
| 753 | 3-chloro-N-[3-(2'-oxospiro[furo[2,3-f][1,3]benzodioxole-7,3'-indol]-1'(2'H)-yl)propyl]benzamide | 477.3 |
| 754 | 4-chloro-N-[3-(2'-oxospiro[furo[2,3-f][1,3]benzodioxole-7,3'-indol]-1'(2'H)-yl)propyl]benzamide | 477.3 |
| 755 | N-[3-(2'-oxospiro[furo[2,3-f][1,3]benzodioxole-7,3'-indol]-1'(2'H)-yl)propyl]hexanamide | 437.4 |
| 756 | 2,6-difluoro-N-[3-(2'-oxospiro[furo[2,3-f][1,3]benzodioxole-7,3'-indol]-1'(2'H)-yl)propyl]benzamide | 479.4 |
| 757 | 2-chloro-N-[3-(2'-oxospiro[furo[2,3-f][1,3]benzodioxole-7,3'-indol]-1'(2'H)-yl)propyl]acetamide | 415.3 |
| 758 | N-[3-(2'-oxospiro[furo[2,3-f][1,3]benzodioxole-7,3'-indol]-1'(2'H)-yl)propyl]-2,5-bis(trifluoromethyl)benzamide | 579.4 |
| 759 | N-[3-(2'-oxospiro[furo[2,3-f][1,3]benzodioxole-7,3'-indol]-1'(2'H)-yl)propyl]pyrrolidine-1-carboxamide | 436.4 |
| 760 | 2-bromo-2,2-difluoro-N-[3-(2'-oxospiro[furo[2,3-f][1,3]benzodioxole-7,3'-indol]-1'(2'H)-yl)propyl]acetamide | 497.3 |
| 761 | 2,3,5-trifluoro-N-[3-(2'-oxospiro[furo[2,3-f][1,3]benzodioxole-7,3'-indol]-1'(2'H)-yl)propyl]benzamide | 497.3 |
| 762 | 5-fluoro-N-[3-(2'-oxospiro[furo[2,3-f][1,3]benzodioxole-7,3'-indol]-1'(2'H)-yl)propyl]-2-(trifluoromethyl)benzamide | 529.4 |
| 763 | 5-chloro-N-[3-(2'-oxospiro[furo[2,3-f][1,3]benzodioxole-7,3'-indol]-1'(2'H)-yl)propyl]-2-(trifluoromethyl)benzamide | 545.3 |
| 764 | N-[3-(2'-oxospiro[furo[2,3-f][1,3]benzodioxole-7,3'-indol]-1'(2'H)-yl)propyl]thiophene-2-carboxamide | 449.3 |
| 765 | N-[3-(2'-oxospiro[furo[2,3-f][1,3]benzodioxole-7,3'-indol]-1'(2'H)-yl)propyl]morpholine-4-carboxamide | 452.4 |
| 766 | 2-(1-naphthyl)-N-[3-(2'-oxospiro[furo[2,3-f][1,3]benzodioxole-7,3'-indol]-1'(2'H)-yl)propyl]acetamide | 507.4 |
| 767 | 2-methyl-N-[3-(2'-oxospiro[furo[2,3-f][1,3]benzodioxole-7,3'-indol]-1'(2'H)-yl)propyl]propanamide | 409.4 |
| 768 | N-[3-(2'-oxospiro[furo[2,3-f][1,3]benzodioxole-7,3'-indol]-1'(2'H)-yl)propyl]-N-propionylpropanamide | 451.4 |
| 769 | N-[3-(2'-oxospiro[furo[2,3-f][1,3]benzodioxole-7,3'-indol]-1'(2'H)-yl)propyl]-4-pentylbenzamide | 513.3 |

-continued

| Compound Number | Name | MS (m/z, M + 1) |
|---|---|---|
| 770 | 4,7,7-trimethyl-3-oxo-N-[3-(2'-oxospiro[furo[2,3-f][1,3]benzodioxole-7,3'-indol]-1'(2'H)-yl)propyl]-2-oxabicyclo[2.2.1]heptane-1-carboxamide | 519.4 |
| 771 | 2-bromo-N-[3-(2'-oxospiro[furo[2,3-f][1,3]benzodioxole-7,3'-indol]-1'(2'H)-yl)propyl]benzamide | 523.2 |
| 772 | 3-cyano-N-[3-(2'-oxospiro[furo[2,3-f][1,3]benzodioxole-7,3'-indol]-1'(2'H)-yl)propyl]benzamide | 468.3 |
| 773 | 4-cyano-N-[3-(2'-oxospiro[furo[2,3-f][1,3]benzodioxole-7,3'-indol]-1'(2'H)-yl)propyl]benzamide | 468.3 |

EXAMPLE 18

Synthesis of 1'-(2-aminoethyl)spiro[furo[2,3-f][1,3]benzodioxole-7,3'-indol]-2'(1'H)-one

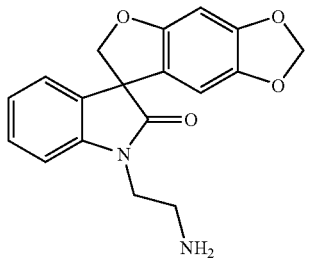

To a suspension of 2-[2-(2'-oxospiro[furo[2,3-f][1,3]benzodioxole-7,3'-indol]-1'(2'H)-yl)ethyl]-1H-isoindole-1,3(2H)-dione (20.0 g, 44.0 mmol) in methanol (400 mL) was added hydrazine (8.00 mL). The mixture was stirred at ambient temperature for 48 h and filtered. The filtrate was concentrated in vacuo to dryness. The residue was subjected to flash chromatography eluting with ethyl acetate/methanol/ammonia (10/1/0.2) to afford the crude product which was recrystalized from ethyl acetate to yield the title compound (8.0 g) in 56% yield as a white solid: $^1$H NMR (300 MHz, CDCl$_3$) δ 7.34 (m, 1H), 7.17 (dd, 1H), 7.06 (dd, 1H), 6.95 (d, 1H), 6.51 (s, 1H), 6.18 (s, 1H), 5.89-5.82-(ABq, 2H), 4.93 (d, 1H), 4.66 (d, 1H), 3.95-3.74-(m, 2H), 3.06 (t, 2H), 1.59-1.35-(br, 2H); $^{13}$C NMR (75 MHz, CDCl$_3$) δ 178.0, 155.9, 148.8, 142.3, 132.4, 128.9, 124.0, 123.4, 119.5, 108.6, 103.1, 101.5, 93.6, 80.5, 58.2, 43.4, 39.8; MS (ES+) m/z 325 (M+1), 308 (M−16).

EXAMPLE 19

Synthesis of 1-(4-fluorophenyl)-3-[2-(2'-oxospiro[furo[2,3-f][1,3]benzodioxole-7,3'-indol]-1'(2'H)-yl)ethyl]urea

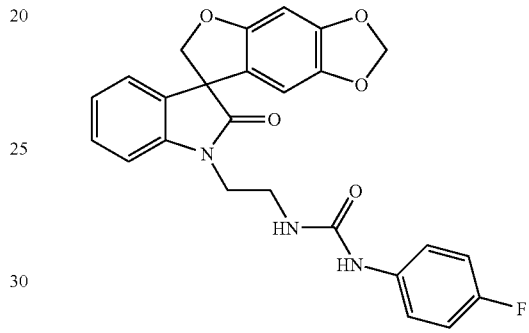

To a mixture of 1'-(2-aminoethyl)spiro[furo[2,3-f][1,3]benzodioxole-7,3'-indol]-2'(1'H)-one (0.15 mmol) and triethylamine (0.01 mmol) in anhydrous dichloromethane was added 1-fluoro-4-isocyanatobenzene (0.14 mmol) at ambient temperature. The mixture was stirred for 16 h, diluted with of dichloromethane (5.00 mL), washed with 10% HCl solution and brine, dried over Na$_2$SO$_4$ and filtered. The filtrate was concentrated in vacuo to dryness to give the title compound (0.05 g) in 82% yield: $^1$H NMR (300 MHz, DMSO-d$_6$) δ 8.54 (s, 1H), 7.35-7.25 (m, 3H), 7.19 (d, 1H), 7.11 (d, 1H), 7.06-6.91 (m, 3H), 6.67 (s, 1H), 6.52 (t, 1H), 5.94-5.84 (ABq, 2H), 4.74 (d, 1H), 4.61 (d, 1H), 3.91-3.69 (m, 2H), 3.49-3.34 (m, 2H); MS (ES+) m/z 462 (M+1), 484 (M+23).

EXAMPLE 19.1

The compounds listed in the following table were synthesized using the similar procedure as described in EXAMPLE 19. As previously noted, the compound numbers listed below do not correspond to the compound numbers provided in the general Reaction Schemes above.

| Compound Number | Name | MS (m/z, M + 1) |
|---|---|---|
| 774 | 1-benzyl-3-[2-(2'-oxospiro[furo[2,3-f][1,3]benzodioxole-7,3'-indol]-1'(2'H)-yl)ethyl]urea | 458 |
| 775 | 1-[2-(2'-oxospiro[furo[2,3-f][1,3]benzodioxole-7,3'-indol]-1'(2'H)-yl)ethyl]-3-(4-phenoxyphenyl)urea | 536 |
| 776 | 1-butyl-3-[2-(2'-oxospiro[furo[2,3-f][1,3]benzodioxole-7,3'-indol]-1'(2'H)-yl)ethyl]urea | 424 |
| 777 | 1-cyclohexyl-3-[2-(2'-oxospiro[furo[2,3-f][1,3]benzodioxole-7,3'-indol]-1'(2'H)-yl)ethyl]urea | 450 |
| 778 | 1-ethyl-3-[2-(2'-oxospiro[furo[2,3-f][1,3]benzodioxole-7,3'-indol]-1'(2'H)-yl)ethyl]urea | 396 |

-continued

| Compound Number | Name | MS (m/z, M + 1) |
|---|---|---|
| 779 | 1-isopropyl-3-[2-(2'-oxospiro[furo[2,3-f][1,3]benzodioxole-7,3'-indol]-1'(2'H)-yl)ethyl]urea | 410 |
| 780 | 1-[2-(2'-oxospiro[furo[2,3-f][1,3]benzodioxole-7,3'-indol]-1'(2'H)-yl)ethyl]-3-propylurea | 410 |
| 781 | 1-tert-butyl-3-[2-(2'-oxospiro[furo[2,3-f][1,3]benzodioxole-7,3'-indol]-1'(2'H)-yl)ethyl]urea | 424 |
| 782 | 1-cyclopentyl-3-[2-(2'-oxospiro[furo[2,3-f][1,3]benzodioxole-7,3'-indol]-1'(2'H)-yl)ethyl]urea | 436 |
| 783 | 1-[2-(2'-oxospiro[furo[2,3-f][1,3]benzodioxole-7,3'-indol]-1'(2'H)-yl)ethyl]-3-pentylurea | 438 |
| 784 | 1-[2-(2'-oxospiro[furo[2,3-f][1,3]benzodioxole-7,3'-indol]-1'(2'H)-yl)ethyl]-3-phenylurea | 444 |
| 785 | 1-(2-furylmethyl)-3-[2-(2'-oxospiro[furo[2,3-f][1,3]benzodioxole-7,3'-indol]-1'(2'H)-yl)ethyl]urea | 448 |
| 786 | 1-hexyl-3-[2-(2'-oxospiro[furo[2,3-f][1,3]benzodioxole-7,3'-indol]-1'(2'H)-yl)ethyl]urea | 452 |
| 787 | ethyl N-({[2-(2'-oxospiro[furo[2,3-f][1,3]benzodioxole-7,3'-indol]-1'(2'H)-yl)ethyl]amino}carbonyl)glycinate | 454 |
| 788 | 1-(3-methylphenyl)-3-[2-(2'-oxospiro[furo[2,3-f][1,3]benzodioxole-7,3'-indol]-1'(2H)-yl)ethyl]urea | 458 |
| 789 | 1-(4-methylphenyl)-3-[2-(2'-oxospiro[furo[2,3-f][1,3]benzodioxole-7,3'-indol]-1'(2'H)-yl)ethyl]urea | 458 |
| 790 | ethyl N-({[2-(2'-oxospiro[furo[2,3-f][1,3]benzodioxole-7,3'-indol]-1'(2'H)-yl)ethyl]amino}carbonyl)-beta-alaninate | 468 |
| 791 | 1-(4-cyanophenyl)-3-[2-(2'-oxospiro[furo[2,3-f][1,3]benzodioxole-7,3'-indol]-1'(2'H)-yl)ethyl]urea | 469 |
| 792 | N-({[2-(2'-oxospiro[furo[2,3-f][1,3]benzodioxole-7,3'-indol]-1'(2'H)-yl)ethyl]amino}carbonyl)benzamide | 472 |
| 793 | 1-[2-(2'-oxospiro[furo[2,3-f][1,3]benzodioxole-7,3'-indol]-1'(2'H)-yl)ethyl]-3-(2-phenylethyl)urea | 473 |
| 794 | 1-(4-methylbenzyl)-3-[2-(2'-oxospiro[furo[2,3-f][1,3]benzodioxole-7,3'-indol]-1'(2'H)-yl)ethyl]urea | 472 |
| 795 | 1-(2-methylbenzyl)-3-[2-(2'-oxospiro[furo[2,3-f][1,3]benzodioxole-7,3'-indol]-1'(2'H)-yl)ethyl]urea | 472 |
| 796 | 1-(4-ethylphenyl)-3-[2-(2'-oxospiro[furo[2,3-f][1,3]benzodioxole-7,3'-indol]-1'(2'H)-yl)ethyl]urea | 472 |
| 797 | 1-(3-methoxyphenyl)-3-[2-(2'-oxospiro[furo[2,3-f][1,3]benzodioxole-7,3'-indol]-1'(2'H)-yl)ethyl]urea | 474 |
| 798 | 1-(2-fluoro-5-methylphenyl)-3-[2-(2'-oxospiro[furo[2,3-f][1,3]benzodioxole-7,3'-indol]-1'(2'H)-yl)ethyl]urea | 476 |
| 799 | 1-(3-fluoro-4-methylphenyl)-3-[2-(2'-oxospiro[furo[2,3-f][1,3]benzodioxole-7,3'-indol]-1'(2'H)-yl)ethyl]urea | 476 |
| 800 | 1-(4-chlorophenyl)-3-[2-(2'-oxospiro[furo[2,3-f][1,3]benzodioxole-7,3'-indol]-1'(2'H)-yl)ethyl]urea | 479 |
| 801 | 2-[({[2-(2'-oxospiro[furo[2,3-f][1,3]benzodioxole-7,3'-indol]-1'(2'H)-yl)ethyl]amino}carbonyl)amino]ethyl 2-methylacrylate | 480 |
| 802 | 1-[2-(2'-oxospiro[furo[2,3-f][1,3]benzodioxole-7,3'-indol]-1'(2'H)-yl)ethyl]-3-(1,1,3,3-tetramethylbutyl)urea | 480 |
| 803 | ethyl 4-[({[2-(2'-oxospiro[furo[2,3-f][1,3]benzodioxole-7,3'-indol]-1'(2'H)-yl)ethyl]amino}carbonyl)amino]butanoate | 482 |
| 804 | 1-[4-(cyanomethyl)phenyl]-3-[2-(2'-oxospiro[furo[2,3-f][1,3]benzodioxole-7,3'-indol]-1'(2'H)-yl)ethyl]urea | 483 |
| 805 | 1-(2,3-dihydro-1H-inden-5-yl)-3-[2-(2'-oxospiro[furo[2,3-f][1,3]benzodioxole-7,3'-indol]-1'(2'H)-yl)ethyl]urea | 483 |
| 806 | 1-(3-acetylphenyl)-3-[2-(2'-oxospiro[furo[2,3-f][1,3]benzodioxole-7,3'-indol]-1'(2'H)-yl)ethyl]urea | 484 |
| 807 | 1-(4-acetylphenyl)-3-[2-(2'-oxospiro[furo[2,3-f][1,3]benzodioxole-7,3'-indol]-1'(2'H)-yl)ethyl]urea | 486 |
| 808 | 1-(4-isopropylphenyl)-3-[2-(2'-oxospiro[furo[2,3-f][1,3]benzodioxole-7,3'-indol]-1'(2'H)-yl)ethyl]urea | 486 |
| 809 | 1-(2-methoxybenzyl)-3-[2-(2'-oxospiro[furo[2,3-f][1,3]benzodioxole-7,3'-indol]-1'(2'H)-yl)ethyl]urea | 486 |
| 810 | 1-(4-methoxybenzyl)-3-[2-(2'-oxospiro[furo[2,3-f][1,3]benzodioxole-7,3'-indol]-1'(2'H)-yl)ethyl]urea | 488 |
| 811 | 1-(4-methoxy-2-methylphenyl)-3-[2-(2'-oxospiro[furo[2,3-f][1,3]benzodioxole-7,3'-indol]-1'(2'H)-yl)ethyl]urea | 4882 |
| 812 | 1-(4-chloro-2-methylphenyl)-3-[2-(2'-oxospiro[furo[2,3-f][1,3]benzodioxole-7,3'-indol]-1'(2'H)-yl)ethyl]urea | 488 |
| 813 | 1-(3-chloro-4-methylphenyl)-3-[2-(2'-oxospiro[furo[2,3-f][1,3]benzodioxole-7,3'-indol]-1'(2'H)-yl)ethyl]urea | 493 |
| 814 | 1-(3-chloro-2-methylphenyl)-3-[2-(2'-oxospiro[furo[2,3-f][1,3]benzodioxole-7,3'-indol]-1'(2'H)-yl)ethyl]urea | 493 |

-continued

| Compound Number | Name | MS (m/z, M + 1) |
|---|---|---|
| 815 | 1-(5-chloro-2-methylphenyl)-3-[2-(2'-oxospiro[furo[2,3-f][1,3]benzodioxole-7,3'-indol]-1'(2'H)-yl)ethyl]urea | 493 |
| 816 | 1-(2-chlorobenzyl)-3-[2-(2'-oxospiro[furo[2,3-f][1,3]benzodioxole-7,3'-indol]-1'(2'H)-yl)ethyl]urea | 493 |
| 817 | 1-(1-naphthyl)-3-[2-(2'-oxospiro[furo[2,3-f][1,3]benzodioxole-7,3'-indol]-1'(2'H)-yl)ethyl]urea | 493 |
| 818 | 1-(2-naphthyl)-3-[2-(2'-oxospiro[furo[2,3-f][1,3]benzodioxole-7,3'-indol]-1'(2'H)-yl)ethyl]urea | 494 |
| 819 | 1-(3-chloro-2-fluorophenyl)-3-[2-(2'-oxospiro[furo[2,3-f][1,3]benzodioxole-7,3'-indol]-1'(2'H)-yl)ethyl]urea | 494 |
| 820 | 1-[2-(2'-oxospiro[furo[2,3-f][1,3]benzodioxole-7,3'-indol]-1'(2'H)-yl)ethyl]-3-(5,6,7,8-tetrahydronaphthalen-1-yl)urea | 497 |
| 821 | 1-(4-tert-butylphenyl)-3-[2-(2'-oxospiro[furo[2,3-f][1,3]benzodioxole-7,3'-indol]-1'(2'H)-yl)ethyl]urea | 498 |
| 822 | 1-(4-butylphenyl)-3-[2-(2'-oxospiro[furo[2,3-f][1,3]benzodioxole-7,3'-indol]-1'(2'H)-yl)ethyl]urea | 500 |
| 823 | 1-[2-(4-ethylphenyl)ethyl]-3-[2-(2'-oxospiro[furo[2,3-f][1,3]benzodioxole-7,3'-indol]-1'(2'H)-yl)ethyl]urea | 500 |
| 824 | 1-(2,3-dihydro-1,4-benzodioxin-6-yl)-3-[2-(2'-oxospiro[furo[2,3-f][1,3]benzodioxole-7,3'-indol]-1'(2'H)-yl)ethyl]urea | 500 |
| 825 | methyl 4-[({[2-(2'-oxospiro[furo[2,3-f][1,3]benzodioxole-7,3'-indol]-1'(2'H)-yl)ethyl]amino}carbonyl)amino]benzoate | 502 |
| 826 | 1-(2-ethoxybenzyl)-3-[2-(2'-oxospiro[furo[2,3-f][1,3]benzodioxole-7,3'-indol]-1'(2'H)-yl)ethyl]urea | 502 |
| 827 | 1-(3,4-dimethoxyphenyl)-3-[2-(2'-oxospiro[furo[2,3-f][1,3]benzodioxole-7,3'-indol]-1'(2'H)-yl)ethyl]urea | 502 |
| 828 | 1-(3,5-dimethoxyphenyl)-3-[2-(2'-oxospiro[furo[2,3-f][1,3]benzodioxole-7,3'-indol]-1'(2'H)-yl)ethyl]urea | 504 |
| 829 | 1-(3-chloro-4-methoxyphenyl)-3-[2-(2'-oxospiro[furo[2,3-f][1,3]benzodioxole-7,3'-indol]-1'(2'H)-yl)ethyl]urea | 504 |
| 830 | 1-[4-(difluoromethoxy)phenyl]-3-[2-(2'-oxospiro[furo[2,3-f][1,3]benzodioxole-7,3'-indol]-1'(2'H)-yl)ethyl]urea | 509 |
| 831 | 1-[2-(difluoromethoxy)phenyl]-3-[2-(2'-oxospiro[furo[2,3-f][1,3]benzodioxole-7,3'-indol]-1'(2'H)-yl)ethyl]urea | 510 |
| 832 | 1-[2-(2'-oxospiro[furo[2,3-f][1,3]benzodioxole-7,3'-indol]-1'(2'H)-yl)ethyl]-3-[3-(trifluoromethyl)phenyl]urea | 510 |
| 833 | 1-[2-(2'-oxospiro[furo[2,3-f][1,3]benzodioxole-7,3'-indol]-1'(2'H)-yl)ethyl]-3-[2-(trifluoromethyl)phenyl]urea | 512 |
| 834 | 1-[2-(2'-oxospiro[furo[2,3-f][1,3]benzodioxole-7,3'-indol]-1'(2'H)-yl)ethyl]-3-[4-(trifluoromethyl)phenyl]urea | 512 |
| 835 | 1-(3,4-dichlorophenyl)-3-[2-(2'-oxospiro[furo[2,3-f][1,3]benzodioxole-7,3'-indol]-1'(2'H)-yl)ethyl]urea | 512 |
| 836 | 1-(2,3-dichlorophenyl)-3-[2-(2'-oxospiro[furo[2,3-f][1,3]benzodioxole-7,3'-indol]-1'(2'H)-yl)ethyl]urea | 513 |
| 837 | 1-(3,5-dichlorophenyl)-3-[2-(2'-oxospiro[furo[2,3-f][1,3]benzodioxole-7,3'-indol]-1'(2'H)-yl)ethyl]urea | 513 |
| 838 | ethyl 4-[({[2-(2'-oxospiro[furo[2,3-f][1,3]benzodioxole-7,3'-indol]-1'(2'H)-yl)ethyl]amino}carbonyl)amino]benzoate | 513 |
| 839 | ethyl 2-[({[2-(2'-oxospiro[furo[2,3-f][1,3]benzodioxole-7,3'-indol]-1'(2'H)-yl)ethyl]amino}carbonyl)amino]benzoate | 516 |
| 840 | 1-[2-(1,3-benzodioxol-5-yl)ethyl]-3-[2-(2'-oxospiro[furo[2,3-f][1,3]benzodioxole-7,3'-indol]-1'(2'H)-yl)ethyl]urea | 516 |
| 841 | methyl 2-methyl-3-[({[2-(2'-oxospiro[furo[2,3-f][1,3]benzodioxole-7,3'-indol]-1'(2'H)-yl)ethyl]amino}carbonyl)amino]benzoate | 516 |
| 842 | 1-(4-butoxyphenyl)-3-[2-(2'-oxospiro[furo[2,3-f][1,3]benzodioxole-7,3'-indol]-1'(2'H)-yl)ethyl]urea | 516 |
| 843 | 1-(2-methoxy-4-nitrophenyl)-3-[2-(2'-oxospiro[furo[2,3-f][1,3]benzodioxole-7,3'-indol]-1'(2'H)-yl)ethyl]urea | 516 |
| 844 | 1-biphenyl-2-yl-3-[2-(2'-oxospiro[furo[2,3-f][1,3]benzodioxole-7,3'-indol]-1'(2'H)-yl)ethyl]urea | 519 |
| 845 | 1-[4-methyl-3-(trifluoromethyl)phenyl]-3-[2-(2'-oxospiro[furo[2,3-f][1,3]benzodioxole-7,3'-indol]-1'(2'H)-yl)ethyl]urea | 520 |
| 846 | 1-(2,4-dichlorobenzyl)-3-[2-(2'-oxospiro[furo[2,3-f][1,3]benzodioxole-7,3'-indol]-1'(2'H)-yl)ethyl]urea | 526 |

-continued

| Compound Number | Name | MS (m/z, M + 1) |
|---|---|---|
| 847 | 1-[2-(2'-oxospiro[furo[2,3-f][1,3]benzodioxole-7,3'-indol]-1'(2'H)-yl)ethyl]-3-[2-(trifluoromethoxy)phenyl]urea | 527 |
| 848 | 1-[4-fluoro-2-(trifluoromethyl)phenyl]-3-[2-(2'-oxospiro[furo[2,3-f][1,3]benzodioxole-7,3'-indol]-1'(2'H)-yl)ethyl]urea | 528 |
| 849 | 1-(5-tert-butyl-2-methoxyphenyl)-3-[2-(2'-oxospiro[furo[2,3-f][1,3]benzodioxole-7,3'-indol]-1'(2'H)-yl)ethyl]urea | 530 |
| 850 | 1-[2-(3,5-dimethoxyphenyl)ethyl]-3-[2-(2'-oxospiro[furo[2,3-f][1,3]benzodioxole-7,3'-indol]-1'(2'H)-yl)ethyl]urea | 530 |
| 851 | 1-(9H-fluoren-2-yl)-3-[2-(2'-oxospiro[furo[2,3-f][1,3]benzodioxole-7,3'-indol]-1'(2'H)-yl)ethyl]urea | 532 |
| 852 | 1-(9H-fluoren-9-yl)-3-[2-(2'-oxospiro[furo[2,3-f][1,3]benzodioxole-7,3'-indol]-1'(2'H)-yl)ethyl]urea | 532 |
| 853 | 1-[2-(2'-oxospiro[furo[2,3-f][1,3]benzodioxole-7,3'-indol]-1'(2'H)-yl)ethyl]-3-(3,4,5-trimethoxyphenyl)urea | 532 |
| 854 | 1-(diphenylmethyl)-3-[2-(2'-oxospiro[furo[2,3-f][1,3]benzodioxole-7,3'-indol]-1'(2'H)-yl)ethyl]urea | 534 |
| 855 | 1-[2-(2'-oxospiro[furo[2,3-f][1,3]benzodioxole-7,3'-indol]-1'(2'H)-yl)ethyl]-3-(2-phenoxyphenyl)urea | 534 |
| 856 | 1-(2-biphenyl-4-ylethyl)-3-[2-(2'-oxospiro[furo[2,3-f][1,3]benzodioxole-7,3'-indol]-1'(2'H)-yl)ethyl]urea | 536 |
| 857 | 1-[2-(2'-oxospiro[furo[2,3-f][1,3]benzodioxole-7,3'-indol]-1'(2'H)-yl)ethyl]-3-(3,4,5-trimethoxybenzyl)urea | 548 |
| 858 | 1-(2-nitrophenyl)-3-[2-(2'-oxospiro[furo[2,3-f][1,3]benzodioxole-7,3'-indol]-1'(2'H)-yl)ethyl]urea | 548 |
| 859 | 1-(1,3-benzodioxol-5-yl)-3-[2-(2'-oxospiro[furo[2,3-f][1,3]benzodioxole-7,3'-indol]-1'(2'H)-yl)ethyl]urea | 489 |
| 860 | 1-[4-(dimethylamino)phenyl]-3-[2-(2'-oxospiro[furo[2,3-f][1,3]benzodioxole-7,3'-indol]-1'(2'H)-yl)ethyl]urea | 488 |
| 861 | 1-(2-fluorobenzyl)-3-[2-(2'-oxospiro[furo[2,3-f][1,3]benzodioxole-7,3'-indol]-1'(2'H)-yl)ethyl]urea | 487 |
| 862 | 1-(4-fluoro-3-methylphenyl)-3-[2-(2'-oxospiro[furo[2,3-f][1,3]benzodioxole-7,3'-indol]-1'(2'H)-yl)ethyl]urea | 476 |
| 863 | 1-(3-fluorobenzyl)-3-[2-(2'-oxospiro[furo[2,3-f][1,3]benzodioxole-7,3'-indol]-1'(2'H)-yl)ethyl]urea | 476 |
| 864 | 1-(cyclohexylmethyl)-3-[2-(2'-oxospiro[furo[2,3-f][1,3]benzodioxole-7,3'-indol]-1'(2'H)-yl)ethyl]urea | 476 |
| 865 | 1-(2-methylphenyl)-3-[2-(2'-oxospiro[furo[2,3-f][1,3]benzodioxole-7,3'-indol]-1'(2'H)-yl)ethyl]urea | 464 |
| 866 | 1-[4-(6-methyl-1,3-benzothiazol-2-yl)phenyl]-3-[2-(2'-oxospiro[furo[2,3-f][1,3]benzodioxole-7,3'-indol]-1'(2'H)-yl)ethyl]urea | 458 |

EXAMPLE 20

Synthesis of 1'-pentyl-7H-spiro[furo[3,4-f][1,3]benzodioxole-5,3'-indol]-2'(1'H)-one

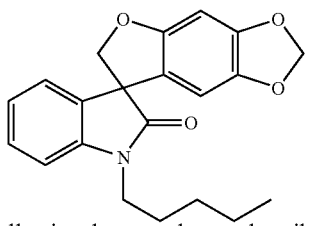

Following the procedure as described in EXAMPLE 1, and making non-critical variations using 3-hydroxy-3-[6-(hydroxymethyl)-1,3-benzodioxol-5-yl]-1-pentyl-1,3-dihydro-2H-indol-2-one to replace 1-(2-cyclopropylethyl)-3-(6-hydroxy-1,3-benzodioxol-5-yl)-3-(hydroxymethyl)-1,3-dihydro-2H-indol-2-one, the title compound was obtained (45%) as a colorless solid: mp 113-115° C.; $^1$H NMR (300 MHz, CDCl$_3$) δ7.24-7.33 (m, 1H), 7.12 (dd, 1H), 7.01 (t, 1H), 6.87 (d, 1H), 6.74 (s, 1H), 6.15 (s, 1H), 5.92 (dd, 2H), 5.48 (d, 1H), 5.27 (d, 1H), 3.76-3.56 (m, 2H), 1.71-1.64-(m, 2H), 1.37-1.27-(, 4H), 0.89-0.84 (m, 3H); $^{13}$C NMR (75 MHz, CDCl$_3$) δ 175.9, 148.7, 148.1, 143.6, 133.7, 132.1, 130.3, 129.8, 125.3, 125.0, 123.1, 113.5, 109.1, 108.7, 101.9, 101.7, 88.7, 74.4, 40.0, 29.7, 29.0, 25.3, 13.3; MS (ES+) m/z 352.1 (M+1).

EXAMPLE 21

Synthesis of 1'-pentylspiro[indeno[5,6-d][1,3]dioxole-5,3'-indole]-2',7(1'H,6H)-dione

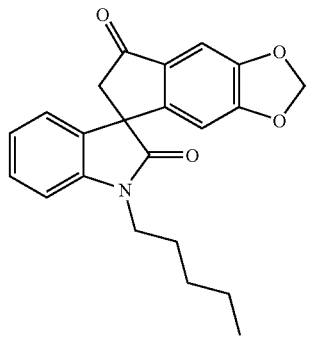

To a solution of [3-(1,3-benzodioxol-5-yl)-2-oxo-1-pentyl-2,3-dihydro-1H-indol-3-yl]acetic acid (0.28 g, 0.73 mmol) was added one drop of DMF and oxalyl chloride (0.32 mL, 3.7 mmol) in toluene (10 mL). The mixture was stirred at ambient temperature overnight and concentrated under vacuum to dryness to afford a brown oil. This substance was dissovled in dichloromethane (15.0 mL) followed by the addition of tin (IV) chloride (0.07 mL, 0.57 mmol) at 0° C. The mixture was stirred at ambient temperature overnight and quenched with ice water. The mixture was poured into water (100 mL), and the mixture was extracted with dichloromethane (150 mL). The organic layer was washed with water, dried over sodium sulfate and filtered. The filtrate was concentrated in vacuo to dryness. The residue was subjected to flash column chromatography to afford the title compound (0.09 g, 67%) as a white solid: $^1$H NMR (300 MHz, CDCl$_3$) δ 7.31 (td, 1H), 7.14 (s, 1H), 7.02 (td, 1H), 6.97-6.92 (m, 2H), 6.22 (s, 1H), 6.03-5.98 (m, 2H), 3.87-3.63 (m, 2H), 3.17 (d, 1H), 2.85 (d, 1H), 1.79-1.66 (m, 2H), 1.41-1.30 (m, 4H), 0.88 (t, 3H); $^{13}$C NMR (75 MHz, CDCl$_3$) δ 201.4, 177.5, 154.8, 151.8, 149.6, 143.1, 132.5, 131.6, 128.9, 123.4, 123.2, 108.9, 103.5, 102.6, 102.5, 53.8, 47.7, 40.5, 29.0, 27.1, 22.3, 14.0; MS (ES+), m/z 386.1 (M+23), 364.1 (M+1).

EXAMPLE 22

Synthesis of 1-pentyl-6'H-spiro[indole-3,5'-naphtho[2,3-d][1,3]dioxole]-2,8'(1H,7'H)-dione

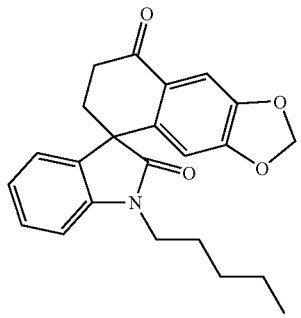

Following the procedure as described in EXAMPLE 21, and making non-critical variations using 3-[3-(1,3-benzodioxol-5-yl)-2-oxo-1-pentyl-2,3-dihydro-1H-indol-3-yl]propanoic acid to replace [3-(1,3-benzodioxol-5-yl)-2-oxo-1-pentyl-2,3-dihydro-1H-indol-3-yl]acetic acid, the title compound was obtained (32%) as a white solid: $^1$H NMR (300 MHz, CDCl$_3$) δ 7.57 (s, 1H), 7.37-7.28 (m, 1H), 7.08-7.03 (m, 2H), 6.95 (d, 1H), 6.02 (s, 1H), 5.95-5.91 (m, 2H), 3.73 (t, 2H), 3.37-3.24 (m, 1H), 2.79-2.67 (m, 1H), 2.41-2.32 (m, 2H), 1.76-1.64 (m, 2H), 1.38-1.28 (m, 4H), 0.87 (t, 3H); $^{13}$C NMR (75 MHz, CDCl$_3$) δ 195.4, 177.4, 152.3, 148.0, 142.7, 138.9, 133.6, 128.8, 128.4, 124.1, 122.9, 108.9, 106.9, 106.6, 101.9, 51.7, 40.2, 33.1, 32.8, 29.0, 27.1, 22.3, 14.0; MS (ES+) m/z 400.1 (M+23), 378.1 (M+1).

EXAMPLE 23

Synthesis of 1'-pentyl-6,7-dihydrospiro[indeno[5,6-d][1,3]dioxole-5,3'-indol]-2'(1'H)-one

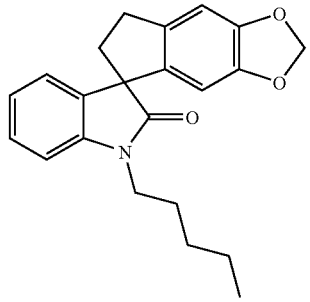

A mixture of 1'-pentylspiro[indeno[5,6-d][1,3]dioxole-5,3'-indole]-2',7(1'H,6H)-dione (0.04 g, 0.11 mmol), triethylsilane (1.50 mL) and trifluroacetic acid (2.00 mL, excess) was stirred at ambient temperature overnight. The mixture was concentrated in vacuo to dryness. The residue was subjected to flash column chromatography to afford the title compound (0.02 g, 47%) as an oil: $^1$H NMR (300 MHz, CDCl$_3$) δ 7.25 (td, 1H), 7.06-6.95 (m, 2H), 6.88 (d, 1H), 6.77 (s, 1H), 6.05 (s, 1H), 5.88-5.82 (m, 2H), 3.81-3.60 (m, 2H), 3.37-3.24 (m, 1H), 3.13-3.01 (m, 1H), 2.70-2.59 (m, 1H), 2.44-2.32 (m, 1H), 1.76-1.64 (m, 2H), 1.39-1.28 (m, 4H), 0.88 (t, 3H); $^{13}$C NMR (75 MHz, CDCl$_3$) δ 179.5, 147.9, 147.0, 142.9, 138.2, 136.7, 134.7, 128.1, 123.5, 122.6, 108.3, 105.3, 103.6, 101.2, 59.9, 40.0, 38.3, 31.6, 29.0, 27.1, 22.6, 14.0; MS (ES+) m/z 372.1 (M+23), 350.1 (M+1).

EXAMPLE 24

Synthesis of 1-pentyl-7',8'-dihydro-6'H-spiro[indole-3,5'-naphtho[2,3-][1,3]dioxol]-2(1H)-one

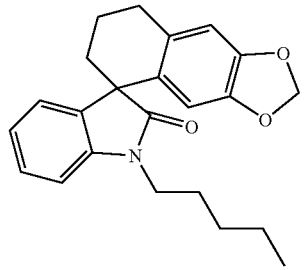

Following the procedure as described in EXAMPLE 23, and making non-critical variations using 1-pentyl-6'H-spiro[indole-3,5'-naphtho[2,3-d][1,3]dioxole]-2,8'(1H,7'H)-dione to replace 1'-pentylspiro[indeno[5,6-d][1,3]dioxole-5,3'-indole]-2',7(1'H,6H)-dione, the title compound was obtained (69%) as an oil: $^1$H NMR (300 MHz, CDCl$_3$) δ 7.25 (td, 1H), 7.08-6.94 (m, 2H), 6.90 (d, 1H), 6.60 (s, 1H), 5.89 (s, 1H), 5.81-5.76 (m, 2H), 3.81-3.66 (m, 2H), 2.96-2.77 (m, 2H), 2.38-2.24 (m, 1H), 2.17-2.06 (m, 1H), 2.02-1.83 (m, 2H), 1.78-1.65 (m, 2H), 1.42-1.29 (m, 4H), 0.89 (t, 3H); $^{13}$C NMR (75 MHz, CDCl$_3$) δ 180.3, 146.7, 146.1, 142.4, 137.3, 131.6, 127.8, 127.8, 124.1, 122.5, 109.0, 108.3, 107.3, 100.7, 52.0, 40.0, 34.0, 29.4, 29.1, 27.1, 22.4, 18.8, 14.0; MS (ES+) m/z 364.1 (M+1).

EXAMPLE 25

Synthesis of 8',8'-difluoro-1-pentyl-7',8'-dihydro-6'H-spiro[indole-3,5'-naphtho[2,3-d][1,3]dioxol]-2(1H)-one

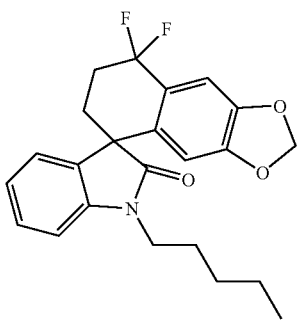

A mixture of 1-pentyl-6'H-spiro[indole-3,5'-naphtho[2,3-d][1,3]dioxole]-2,8'(1H,7'H)-dione (0.02 g, 0.05 mmol), bis(2-methoxyethyl)aminosulfur trifluoride (0.50 mL) and one drop of ethanol was stirred at 85° C. for 72 hours in a Teflon bottle and quenched by slowly addition of water. The mixture was poured into water (100 mL) and extracted with ethyl acetate (100 mL). The organic layer was washed with water, dried over sodium sulfate and filtered. The filtrate was concentrated in vacuo to dryness. The residue was subjected to flash column chromatography to afford the title compound (0.01 g, 47%) as an oil: $^1$H NMR (300 MHz, CDCl$_3$) δ 7.57 (s, 1H), 7.38-7.28 (m, 1H), 7.09-7.01 (m, 2H), 6.95 (d, 1H), 6.03 (s, 1H), 5.96-5.90 (m, 2H), 3.73 (t, 2H), 3.38-3.24 (m, 1H), 2.79-2.67 (m, 1H), 2.41-2.32 (m, 2H), 1.77-1.63 (m, 2H), 1.39-1.28 (m, 4H), 0.90 (t, 3H); $^{13}$C NMR (75 MHz, CDCl$_3$) δ 195.4, 177.4, 152.3, 148.0, 142.7, 138.9, 133.6, 128.8, 128.4, 124.1, 122.9, 108.9, 106.9, 106.6, 101.9, 51.7, 40.2, 33.1, 32.8, 29.0, 27.1, 22.3, 14.0; MS (ES+) m/z 422.2 (M+23), 380.2 (M+1).

EXAMPLE 26

Synthesis of 7-hydroxy-1'-pentyl-6,7-dihydrospiro[indeno[5,6-d][1,3]dioxole-5,3'-indol]-2'(1'H)-one

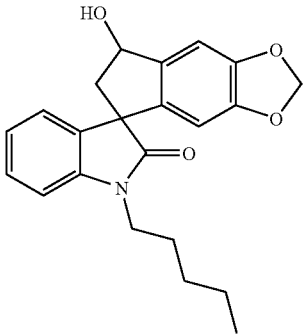

To a solution of 1-pentyl-6'H-spiro[indole-3,5'-naphtho[2,3-d][1,3]dioxole]-2,8'(1H,7'H)-dione (0.20 g, 0.55 mmol) in methanol (10.0 mL) was added sodium borohydride (0.03 g, 0.83 mmol). The reaction mixture was stirred at ambient temperature for 2 h and poured into of water (100 mL) and extracted with ethyl acetate (100 mL). The organic layer was washed with water, dried over sodium sulfate and filtered. The filtrate was concentrated in vacuo to dryness. The residue was subjected to flash column chromatography to afford the title compound (0.18 g, 90%) as an oil: $^1$H NMR (300 MHz, CDCl$_3$) δ 7.36-7.29 (m, 1H), 7.11-6.99 (m, 3H), 6.93 (d, 1H), 5.98 (s, 1H), 5.94-5.87 (m, 2H), 5.16 (d, 1H), 3.80-3.61 (m, 2H), 2.69 (br, 1H), 2.39 (d, 1H), 1.75-1.62 (m, 2H), 1.38-1.22 (m, 4H), 0.87 (t, 3H); $^{13}$C NMR (75 MHz, CDCl$_3$) δ 180.5, 148.9, 148.5, 143.7, 140.5, 136.9, 132.1, 128.7, 123.7, 123.3, 108.8, 105.7, 103.2, 101.5, 74.8, 59.6, 40.4, 28.9, 27.0, 22.3, 14.0; MS (ES+) m/z 388.4 (M+23).

EXAMPLE 27

Synthesis of 7-methoxy-1'-pentyl-6,7-dihydrospiro[indeno[5,6-d][1,3]dioxole-5,3'-indol]-2'(1H)-one

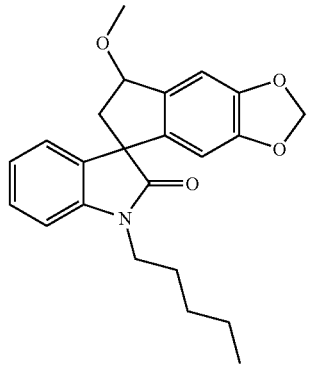

To a solution of 7-hydroxy-1'-pentyl-6,7-dihydrospiro[indeno[5,6-d][1,3]dioxole-5,3'-indol]-2'(1'H)-one (0.05 g, 0.14 mmol) in THF (10.0 mL) was added sodium hydride (0.01 mg, 0.21 mmol) at 0° C. The reaction mixture was stirred for half an hour followed by the addition of iodomethane (0.50 mL). The mixture was stirred at ambient temperature for two hours, then poured into water (100 mL), and extracted with ethyl acetate (100 mL). The organic layer was washed with water, dried over sodium sulfate and filtered. The filtrate was concentrated in vacuo to dryness. The residue was subjected to flash column chromatography to afford the title compound (0.03 g, 57%) as an oil: $^1$H NMR (300 MHz, CDCl$_3$) δ 7.26-7.18 (m, 1H), 6.98-6.82 (m, 4H), 6.10 (s, 1H), 5.88 (s, 2H), 5.26 t, 1H), 3.88-3.63 (m, 2H), 3.45 (s, 3H), 2.71-2.54 (m, 2H), 1.80-1.65 (m, 2H), 1.45-1.29 (m, 4H), 0.90 (t, 3H); $^{13}$C NMR (75 MHz, CDCl$_3$) δ 178.3, 148.9, 148.4, 142.4, 136.8, 136.6, 135.1, 128.1, 123.1, 122.6, 108.5, 105.0, 103.2, 101.5, 82.7, 57.9, 55.6, 43.4, 40.3, 29.1, 27.2, 22.4, 14.0: MS (ES+) m/z 402.4 (M+23).

EXAMPLE 28

Synthesis of 1'-pentyl-6,7-dihydro-5H-spiro[1,3-dioxolo[4,5-g]isoquinoline-8,3'-indole]-2',5(1'H)-dione

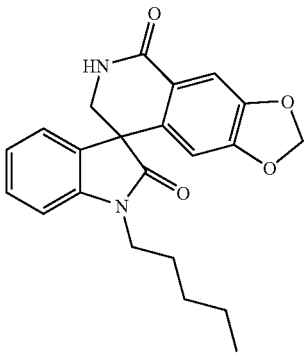

A mixture of 1'-pentylspiro[indeno[5,6-d][1,3]dioxole-5,3'-indole]-2',7(1'H,6H)-dione (0.10 g, 0.28 mmol), sodium azide (0.09 g, 1.40 mmol) and trifluoroacetic acid (2.00 mL) was stirred at 50° C. overnight. The mixture was poured into water (100 mL) and extracted with ethyl acetate (100 mL). The organic layer was washed with water, dried over sodium sulfate and filtered. The filtrate was concentrated in vacuo to dryness. The residue was subjected to flash column chromatography to afford the title compound (0.08 g, 74%) as a white solid: $^1$H NMR (300 MHz, CDCl$_3$) δ 7.60 (s, 1H), 7.30 (td, 1H), 7.20 (dd, 1H), 6.98 (td, 1H), 6.93 (d, 1H), 6.32 (br, 1H), 6.21 (s, 1H), 5.97-5.92 (m, 2H), 4.02 (dd, 1H), 3.87-3.70 (m, 2H), 3.47 (dd, 1H), 1.80-1.66 (m, 2H), 1.42-4.30 (m, 4H), 0.90 (t, 3H); $^{13}$C NMR (75 MHz, CDCl$_3$) δ 175.8, 165.2, 151.6, 147.9, 141.7, 134.3, 130.9, 129.0, 124.5, 123.2, 122.9, 109.0, 108.5, 105.4, 101.9, 51.9, 48.2, 40.4, 29.1, 27.1, 22.3, 14.0; MS (ES+) m/z 379.3 (M+1).

EXAMPLE 29

Synthesis of 2'-oxo-1'-pentyl-N-pyridin-2-yl-1',2'-dihydrospiro[furo[2,3-f][1,3]benzodioxole-7,3'-indole]-4'-carboxamide

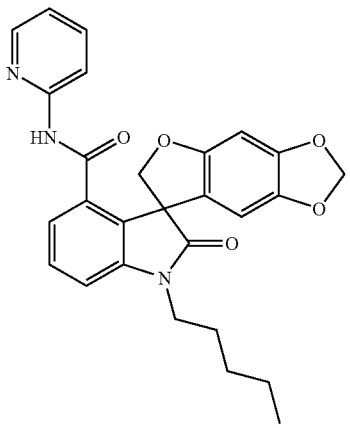

A mixture of 4'-bromo-1'-pentylspiro[furo[2,3-f][1,3]benzodioxole-7,3'-indol]-2'(1'H)-one (0.28 g, 0.65 mmol), tetrakis(triphenylphosphine)palladium(0) (0.08 g, 10 mole %), triethylamine (0.33 g, 0.50 mL, 3.25 mmol) and 2-aminopyridine (0.12 g, 1.30 mmol) in N,N-dimethylformamide (5.00 mL) was subjected to carbon monoxide (40 Psi). The reaction mixture was heated at 80° C. for 16 h. After cooling down to ambient temperature, the reaction mixture was diluted with ethyl acetate (20.0 mL), washed with water (3×20.0 mL), brine (2×20.0 mL), dried over anhydrous sodium sulfate and filtered. The filtrate was concentrated in vacuo to dryness. The residue was subjected to column chromatography to give the title compound (0.04 g, 14%) as a solid: $^1$H NMR (300 MHz, CDCl$_3$) δ 8.52 (d, 1H), 7.87 (br, 1H), 7.69-7.62 (m, 3H), 7.53-7.51 (m, 1H), 7.47-7.38 (m, 3H), 7.04-6.98 (m, 1H), 5.79 (d, 2H), 4.97 (ABq, 2H), 3.84-3.66 (m, 2H), 1.77-1.67 (m, 2H), 1.38-1.33 (m, 4H), 0.90 (t, 3H); $^{13}$C NMR (75 MHz, CDCl$_3$) δ 177.5, 158.2, 156.7, 149.2, 143.5, 142.1, 132.2, 132.0, 131.9, 131.8, 129.6, 128.6, 128.4, 121.8, 118.2, 110.7, 102.0, 101.4, 93.9, 79.5, 77.2, 58.5, 40.6, 29.0, 27.0, 22.3, 14.0; MS (ES+) m/z 473.2 (M+2).

EXAMPLE 29.1

Synthesis of N-(3-methoxyphenyl)-2'-oxo-1'-pentyl-1',2'-dihydrospiro[furo[2,3-f][1,3]benzodioxole-7,3'-indole]-4'-carboxamide

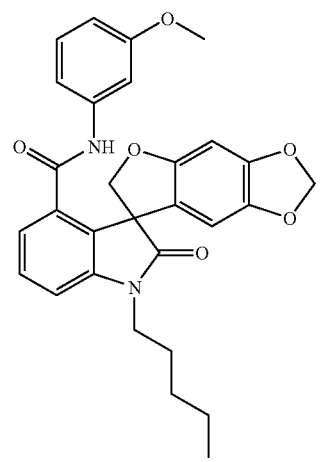

Following the procedure described in EXAMPLE 29, and making non-critical variations using 3-methoxyaniline to replace 2-aminopyridine, the title compound was obtained (20%) as a colorless solid: mp 173-175° C.; $^1$H NMR (300 MHz, CDCl$_3$) δ 7.42 (t, 1H), 7.30-7.27 (m, 1H), 7.14 (t, 1H), 7.04-6.97 (m, 2H), 7.23 (s, 1H), 7.64-6.62 (m, 2H), 6.31 (s, 1H), 6.16 (s, 1H), 5.83 (dd, 2H), 4.87-5.01 (m, 2H), 3.91-3.63 (m, 5H), 1.73-1.78 (m, 2H), 1.37-1.32 (m, 4H), 0.93-0.86 (m, 3H); $^{13}$C NMR (75 MHz, CDCl$_3$) δ 177.8, 165.1, 159.9, 149.3, 143.6, 143.5, 142.1, 138.1, 134.5, 129.7, 129.5, 127.9, 122.4, 118.3, 112.2, 110.7, 110.5, 105.6, 101.9, 101.6, 94.3, 79.2, 58.3, 55.3, 40.5, 28.9, 26.9, 22.3, 13.9; MS (ES+) m/z 501.5 (M+1).

EXAMPLE 30

Synthesis of 2'-oxo-1'-pentyl-1',2'-dihydrospiro[furo [2,3-f][1,3]benzodioxole-7,3'-indole]-4'-carbonitrile

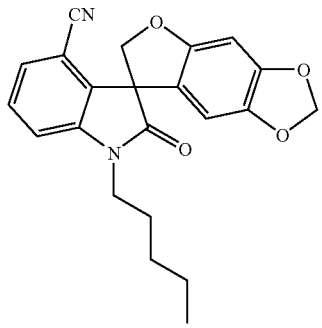

A mixture of 4'-bromo-1'-pentylspiro[furo[2,3-f][1,3]benzodioxole-7,3'-indol]-2'(1'H)-one (0.10 g, 0.23 mmol), tris(dibenzylideneacetone)dipalladium(0) (0.21 g, 0.23 mmol) and 2-(di-tert-butylphosphino)biphenyl (0.07, 0.23 mmol), tributyltin cyanide (0.07 g, 0.23 mmol) and potassium cyanide (0.02 g, 0.23 mmol) was purged with nitrogen and anhydrous acetonitrile (10.0 mL) was added. The reaction mixture was refluxed for 16 h. After cooling down to ambient temperature, the reaction mixture was diluted with ethyl acetate (20.0 mL), washed with water (20.0 mL), brine (20.0 mL), dried over anhydrous sodium sulfate and filtered. The filtrate was concentrated in vacuo to dryness. The brown residue was subjected to column chromatography eluting with ethyl acetate/hexane (65%) to give the title compound (0.03 g, 33%) which was recrystallized from ether to get a colorless solid: mp 128-129° C.; $^1$H NMR (300 MHz, CDCl$_3$) δ 9.10 (s, 1H), 7.42-7.37 (m, 1H), 7.29-7.27 (m, 1H), 7.09 (d, 1H), 6.53 (s, 1H), 6.03 (s, 1H), 5.87 (dd, 2H), 4.91 (q, 2H), 3.86-3.63 (m, 2H), 1.74-1.62 (m, 2H), 1.43-1.26 (m, 4H), 0.89 (t, 3H); $^{13}$C NMR (75 MHz, CDCl$_3$) δ 176.5, 157.1, 149.5, 143.5, 142.4, 135.4, 129.7, 128.3, 126.4, 116.3, 114.8, 112.3, 108.8, 102.2, 93.7, 78.7, 58.3, 40.6, 28.9, 26.7, 22.2, 13.9; MS (ES+) m/z 377.5 (M+1).

EXAMPLE 31

Synthesis of 1'-hexylspiro[1,3-dioxolo[4,5-g]chromene-8,3'-indole]-2',6(1'H,7H)-dione

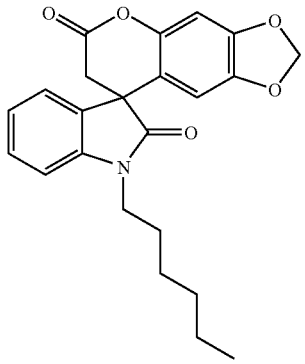

To a solution of 2-(1-hexyl-3-(6-hydroxybenzo[d][1,3]dioxol-5-yl)-2-oxoindolin-3-yl)acetate (0.19 g, 0.43 mmol) in THF:H$_2$O (2:1) was added lithium hydroxide (0.04 g, 0.86 mmol). The mixture was stirred at ambient temperature for 4 hrs. The organic solvent was removed in vacuo and the pH of the aqueous residue was adjusted to 2 followed by extraction with ethyl acetate. The organic layer was dried over anhydrous sodium sulfate and filtered. The filtrate was concentrated in vacuo to dryness and the residue was subjected to column chromatography eluting with 25% ethyl acetate/hexane to yield the title compound (0.09 g, 53%) as a white solid: $^1$H NMR (300 MHz, CDCl$_3$) δ 7.33 (dt, 1H), 7.14-7.03 (m, 2H), 6.93 (d, 1H), 6.66 (s, 1H), 6.06 (s, 1H), 5.88 (dd, 2H), 3.76-3.63 (m, 2H), 2.94 (q, 2H), 1.69-1.62 (m, 2H) 1.34-1.22 (m, 6H), 0.83 (t, 3H); $^{13}$C NMR (75 MHz, CDCl$_3$) δ 175.9, 165.8, 148.3, 147.2, 144.6, 142.6, 129.9, 129.6, 123.8, 123.4, 114.7, 109.2, 105.1, 101.9, 99.8, 49.6, 40.3, 37.2, 31.2, 27.2, 26.4, 22.4, 13.9; MS (ES+) m/z 394.5 (M+1).

EXAMPLE 32

Synthesis of 1-pentylspiro[1-benzofuran-3,3'-indol]-2'(1'H)-one

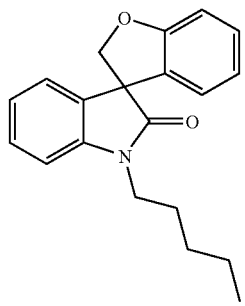

A mixture of 6-bromo-1'-pentylspiro[1-benzofuran-3,3'-indol]-2'(1'H)-one (0.10 g, 0.27 mmol) and palladium/carbon (0.09 g, 0.01 mmol) in methanol/ethyl acetate (1/1, 4.00 mL) was stirred under hydrogen at atmospheric pressure for 16 h. The solvent was evaporated and the black residue was subjected to column chromatography (ethyl acetate/hexane, 1/6) to give the title compound (0.08 g, 97%) as a white solid: $^1$H NMR (300 MHz, CDCl$_3$) δ 7.30 (dd, 1H), 7.18 (dd, 1H), 7.20 (d, 1H), 7.02 (dd, 1H), 6.96-6.90 (m, 2H), 6.79 (dd, 1H), 6.69 (d, 1H), 4.93 (d, 1H), 4.67 (d, 1H), 3.89-3.64 (m, 2H), 1.81-1.66 (m, 2H), 1.44-1.31 (m, 4H), 0.92 (t, 3H); $^{13}$C NMR (75 MHz, CDCl$_3$) δ 177.2, 160.7, 142.5, 132.8, 129.7, 129.0, 128.8, 123.9, 123.3, 123.1, 121.3, 110.4, 108.6, 58.1, 40.4, 29.0, 27.2, 22.3, 14.0; MS (ES+) m/z 308.5 (M+1).

EXAMPLE 33

Synthesis of 6-anilino-1'-pentylspiro[1-benzofuran-3,3'-indol]-2'(1H)-one

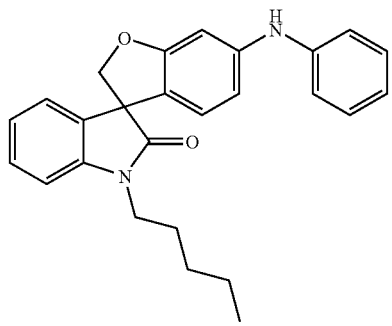

To a solution of 6-bromo-1'-pentylspiro[1-benzofuran-3,3'-indol]-2'(1'H)-one (0.08 g, 0.19 mmol) in anhydrous toluene (4.00 mL) was added aniline (0.03 g, 0.29 mmol), xanthphos (0.02 g, 0.03 mmol) and tris(dibenzylideneacetone) dipalladium(0) (0.02 g, 0.02 mmol). The reaction mixture was refluxed for 16 h, cooled down to ambient temperature and concentrated in vacuo to dryness. The black residue was subjected to column chromatography (ethyl acetate/hexane, 1/7) to give the title compound (0.05 g, 62%) as a yellow oil: $^1$H NMR (300 MHz, CDCl$_3$) δ 7.40-7.25 (m, 6H), 7.18 (d, 1H), 7.12-7.05 (m, 3H), 6.98-6.90 (m, 2H), 6.71 (d, 1H), 6.57 (d, 1H), 6.48 (dd, 1H), 4.93 (d, 1H), 4.67 (d, 1H), 3.88-3.64 (m, 2H), 1.80-1.65 (m, 2H), 1.45-1.30 (m, 4H), 0.92 (t, 3H); MS (ES+) m/z 399.5 (M+1).

EXAMPLE 34

Synthesis of 6-morpholin-4-yl-1'-pentylspiro[1-benzofuran-3,3'-indol]-2'(1'H)-one (1:1)

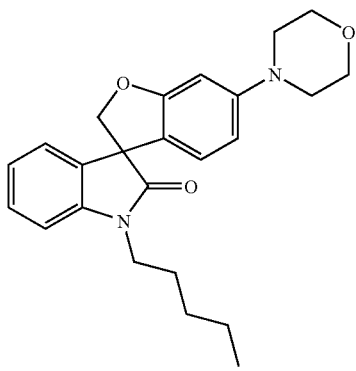

Following the procedure as described in EXAMPLE 33, and making non-critical variations using morphine to replace aniline, the title compound was obtained (42%) as a brown oil: $^1$H NMR (300 MHz, CDCl$_3$) δ 7.32 (d, 1H), 7.15 (d, 1H), 7.05 (dd, 1H), 6.91 (d, 1H), 6.59 (d, 1H), 6.50 (d, 1H), 6.35 (dd, 1H), 4.95 (d, 1H), 4.65 (d, 1H), 3.89-3.60 (m, 6H), 3.15-3.05 (m, 4H), 1.80-1.68 (m, 2H), 1.43-1.34 (m, 4H), 0.92 (t, 3H); $^{13}$C NMR (75 MHz, CDCl$_3$) δ 177.5, 162.2, 153.4, 142.6, 132.9, 128.7, 123.9, 123.4, 123.0, 120.1, 108.9, 108.5, 97.9, 80.3, 66.9, 57.7, 49.4, 40.3, 29.0, 27.1, 22.4, 14.0; MS (ES+) m/z 393.5 (M+1).

EXAMPLE 35

Synthesis of 6-amino-1'-pentylspiro[1-benzofuran-3,3'-indol]-2'(1'H)-one

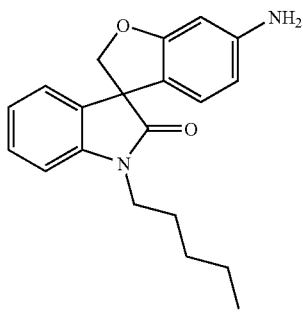

A. Synthesis of 6-[(diphenylmethylene)amino]-1'-pentylspiro[1-benzofuran-3,3'-indol]-2'(1'H)-one To a solution of 6-bromo-1'-pentylspiro[1-benzofuran-3,3'-indol]-2'(1'H)-one (0.10 g, 0.26 mmol) in anhydrous toluene (5.00 mL) was added benzophenone imine (0.09 g, 0.52 mmol), sodium t-butoxide (0.03 g, 0.36 mmol), tris(dibenzylideneacetone) dipalladium(0) (0.01 g, 0.07 mmol) and (±)-2,2'-bis(diphenylphosphino)-1,1'-binaphthalene (0.12 g, 0.19 mmol). The reaction mixture was refluxed for 16 h, cooled down to ambient temperature, diluted with dichloromethane (50.0 mL) and filtered through a celite bed. The filtrate was concentrated in vacuo to dryness to give the title compound which was used in next step without purification.

B. Synthesis of 6-amino-1'-pentylspiro[1-benzofuran-3,3'-indol]-2'(1'H)-one

To a solution of 6-[(diphenylmethylene)amino]-1'-pentylspiro[1-benzofuran-3,3'-indol]-2'(1H)-one in anhydrous tetrahydrofuran (4.00 mL) was added aqueous 10% hydrochloric acid (2.00 mL). The reaction mixture was stirred for 15 min, diluted with aqueous sodium bicarbonate (5.00 mL) and extracted with ethyl acetate (3×25.0 mL). The combined organic solution was dried over sodium sulfate and filtered. The filtrate was concentrated in vacuo to dryness. The residue was subjected to column chromatography (ethyl acetate/hexane, 1/1) to give the title compound (0.02 g, 24% yield) as a yellow oil: $^1$H NMR (300 MHz, CDCl$_3$) δ 7.26 (td, 1H), 7.12 (d, 1H), 6.99 (dd, 1H), 6.89 (d, 1H), 6.43 (d, 1H), 6.23 (d, 1H), 6.08 (dd, 1H), 4.86 (d, 1H), 4.60 (d, 1H), 3.86-3.60 (m, 2H), 1.77-1.65 (m, 2H), 1.41-1.30 (m, 4H), 0.89 (t, 3H); $^{13}$C NMR (75 MHz, CDCl$_3$) δ 177.8, 171.2, 162.1, 148.7, 142.5, 133.1, 128.6, 127.8, 123.9, 123.7, 123.0, 118.5, 108.5, 108.4, 97.2, 80.2, 77.6, 77.4, 77.2, 76.8, 64.0, 60.4, 57.6, 40.3, 29.7, 29.0, 27.1, 22.6, 22.4, 22.1, 19.1, 14.2, 14.0, 13.7; MS (ES+) m/z 323.5 (M+1).

EXAMPLE 36

Synthesis of 1'-pentyl-6-phenoxyspiro[1-benzofuran-3,3'-indol]-2'(1'H)-one

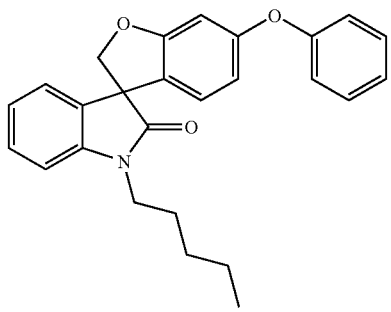

To a solution of 6-bromo-1'-pentylspiro[1-benzofuran-3,3'-indol]-2'(1'H)-one (0.08 g, 0.19 mmol) in anhydrous dioxane (4.00 mL) was added copper iodide (0.01 g, 0.01 mmol), N,N-dimethyl glycine hydrochloride (0.01 g, 0.01 mmol), cesium carbonate (0.17 g, 0.52 mmol) and phenol (0.03 g, 0.32 mmol). The resulted mixture was refluxed for 16 h under nitrogen, diluted with dichloromethane (50.0 mL) and filtered through a celite bed. The filtrate was concentrated in vacuo to dryness. The residue was subjected to column chromatography (ethyl acetate/hexane, ⅛) to give the title compound (0.07 g, 87%) as a colorless oil: $^1$H NMR (300 MHz, CDCl$_3$) δ 7.36-7.28 (m, 3H), 7.20-7.00 (m, 4H), 6.92 (d, 1H), 6.62 (dd, 1H), 6.58 (br, 1H), 6.44 (dd, 1H), 4.95 (d, 1H), 4.71 (d, 1H), 3.92-3.64 (m, 2H), 1.70-1.68 (m, 2H), 1.43-1.34 (m, 4H), 0.92 (t, 3H); MS (ES+) m/z 400.5 (M+1).

EXAMPLE 37

Synthesis of 1-pentyl-6-pyridin-3-ylspiro[1-benzofuran-3,3'-indol]-2'(1'H)-one

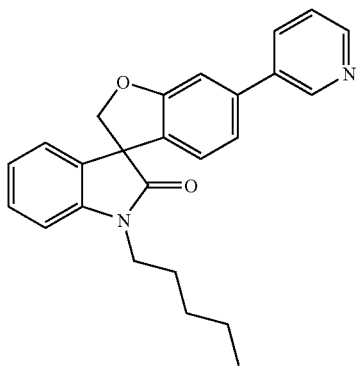

A mixture of 6-bromo-1'-pentylspiro[1-benzofuran-3,3'-indol]-2'(1'H)-one (0.08 g, 0.19 mmol), pyridine-3-boronic acid (0.05 g, 0.41 mmol), palladium acetate (0.002 g, 0.07 mmol), tri-O-tolylphosphine (0.0015 g, 0.005 mmol), 2 M sodium carbonate (1.00 mL) and 1,2-dimethoxyethane (9.00 mL) was heated at reflux for 16 hours under $N_2$. The solvent was evaporated and the black residue was extracted with ethyl acetate (4×15.0 mL). The combined organics was dried over sodium sulfate and filtered. The filtrate was concentrated in vacuo to dryness. The residue was subjected to column chromatography (ethyl acetate/hexane, 4/1) to give the title compound (0.07 g, 67% yield) as a white solid: $^1$H NMR (300 MHz, CDCl$_3$) δ 8.60 (br, 1H), 7.85 (d, 1H), 7.45-7.24 (m, 3H), 7.20-7.10 (m, 2H), 7.12-6.98 (m, 2H), 6.95 (d, 1H), 6.81 (d, 1H), 5.05 (d, 1H), 4.78 (d, 1H), 3.89-3.64 (m, 2H), 1.80-1.68 (m, 2H), 1.43-1.34 (m, 4H), 0.92 (t, 3H); $^{13}$C NMR (75 MHz, CDCl$_3$) δ 176.9, 161.6, 149.5, 147.3, 142.6, 139.9, 136.4, 135.6, 133.4, 130.1, 129.2, 124.9, 121.7, 119.5, 110.3, 109.7, 107.7, 80.1, 57.8, 42.3, 28.8, 27.1, 22.3, 14.85; MS (ES+) m/z 385.5 (M+1).

EXAMPLE 38

Synthesis of 1'-pentyl-6-pyridin-4-ylspiro[1-benzofuran-3,3'-indol]-2'(1'H)-one

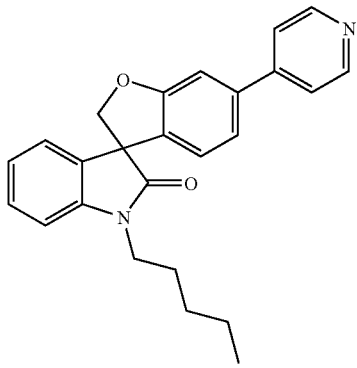

Following the procedure as described in EXAMPLE 37, and making non-critical variations using 4-pyridine boronic acid to replace 3-pyridine boronic acid, the title compound was obtained (38%) as white solid: mp 107-110° C.; $^1$H NMR (300 MHz, CDCl$_3$) δ 8.64-8.58 (m, 2H), 7.45-7.40 (m, 2H), 7.31 (dt, 1H), 7.19-7.13 (m, 2H), 6.93 (d, 1H), 6.79 (d, 1H), 4.95 (d, 1H), 4.75 (d, 1H), 3.88-3.64 (m, 2H), 1.80-1.68 (m, 2H), 1.43-1.34 (m, 4H), 0.90 (t, 3H); MS (ES+) m/z 385.5 (M+1).

EXAMPLE 39

Synthesis of 6-(methylsulfonyl)-1'-pentylspiro[1-benzofuran-3,3'-indol]-2'(1'H)-one

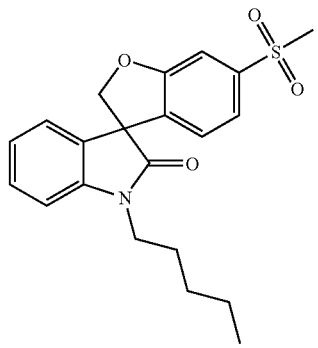

A mixture of 6-bromo-1'-pentylspiro[1-benzofuran-3,3'-indol]-2'(1'H)-one (0.60 g, 1.55 mmol), sodium methanesulfinate (0.19 g, 1.86 mmol), copper iodide (0.03 g, 0.16 mmol), and L-proline (0.04 g, 0.31 mmol) in dimethyl sulfoxide (3.00 mL) was heated at 100° C. for 2 days under $N_2$. The reaction mixture was diluted with water (50.0 mL) and extracted with ethyl acetate (4×15.0 mL). The combined organics was dried over sodium sulfate and filtered. The filtrate was concentrated in vacuo to dryness. The residue was subjected to column chromatography (ethyl acetate/hexane, ⅔) to give the title compound (0.03 g, 46%) as a light yellow oil: $^1$H NMR (300 MHz, CDCl$_3$) δ 7.46-7.48 (m, 1H), 7.38 (dt, 1H), 7.34 (dt, 1H), 7.13-7.02 (m, 2H), 6.94 (d, 1H), 6.86 (d, 1H), 5.03 (d, 1H), 4.78 (d, 1H), 3.87-3.64 (m, 2H), 3.02 (s, 3H), 1.79-1.68 (m, 2H), 1.41-1.32 (m, 4H), 0.90 (t, 3H); $^{13}$C NMR (75 MHz, CDCl$_3$) δ 176.1, 161.2, 142.6, 142.1, 135.4, 131.5, 129.5, 124.3, 124.0, 123.5, 120.7, 109.5, 109.0, 80.5, 57.7, 44.5, 40.6, 29.0, 27.1, 22.3, 14.0; MS (ES+) m/z 386.5 (M+1).

EXAMPLE 40

Synthesis of 1'-pentyl-6-(phenylsulfonyl)spiro[1-benzofuran-3,3'-indol]-2'(1'H)-one

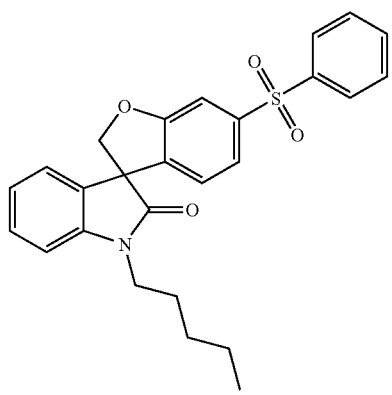

Following the procedure as described in EXAMPLE 39, and making non-critical variations using sodium phenyl sulfinate to replace sodium methanesulfinate, the title compound was obtained (50%) as a yellowish oil: $^1$H NMR (300 MHz, CDCl$_3$,) δ 7.94-7.88 (m, 2H), 7.60-7.44 (m, 4H), 7.40 (dd, 1H), 7.31 (dt, 1H), 7.10-6.99 (m, 2H), 6.92 (d, 1H), 6.78 (d, 1H), 4.98 (d, 1H), 4.72 (d, 1H), 3.84-3.61 (m, 2H), 1.75-1.65 (m, 2H), 1.39-1.30 (m, 4H), 0.88 (t, 3H); $^{13}$C NMR (75 MHz, CDCl$_3$) δ 176.1, 161.2, 143.2, 142.5, 141.2, 134.9, 133.3, 129.4, 129.3, 127.8, 124.1, 124.0, 123.5, 121.1, 109.8, 108.9, 80.5, 57.7, 40.5, 29.0, 27.1, 22.3, 14.0; MS (ES+) m/z 448.5 (M+1).

EXAMPLE 41

Synthesis of 1'-pentyl-5-phenoxyspiro[1-benzofuran-3,3'-indol]-2'(1'H)-one

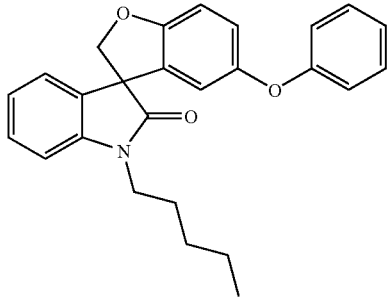

Following the procedure as described in EXAMPLE 36, and making non-critical variations using 5-bromo-1'-pentyl-spiro[1-benzofuran-3,3'-indol]-2'(1'H)-one to replace 6-bromo-1'-pentylspiro[1-benzofuran-3,3'-indol]-2'(1'H)-one, the title compound was obtained (10% yield) as a colorless oil: $^1$H NMR (300 MHz, CDCl$_3$) δ 7.32-7.10 (m, 5H), 7.06-6.82 (m, 6H), 6.42 (d, 1H), 4.95 (d, 1H), 4.71 (d, 1H), 3.82-3.62 (m, 2H), 1.75-1.63 (m, 2H), 1.43-1.34 (m, 4H), 0.85 (t, 3H); MS (ES+) m/z 400.4 (M+1).

EXAMPLE 42

Synthesis of 1'-(diphenylmethyl)-5-(4,4,5,5-tetramethyl-1,3,2-dioxaborolan-2-yl)spiro[1-benzofuran-3,3'-indol]-2'(1'H)-one

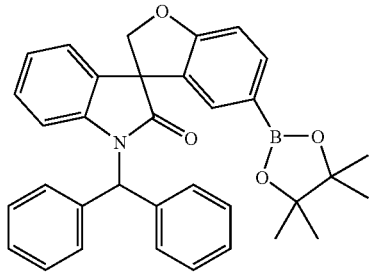

A mixture of 5-bromo-1'-(diphenylmethyl)spiro[1-benzofuran-3,3'-indol]-2'(1'H)-one (3.00 g, 6.22 mmol), bis(pinacolato)diboron (1.80 g, 7.09 mmol), (1,1'-bis(diphenylphosphino)ferrocene)dichloropalladium(II) (0.45 g, 9 mole %), and potassium acetate (5.49 g, 56.0 mmol) in anhydrous dimethyl sulfoxide (40.0 mL) was stirred at 100° C. under N$_2$ for 16 h. The reaction mixture was diluted with water (600 mL). The aqueous mixture was extracted with ethyl acetate (3×200 mL). The combined organic layers was dried over anhydrous sodium sulfate and filtered. The filtrate was concentrated in vacuo. The residue was subjected to column chromatography (ethyl acetate/hexane, 1/6) to give the title compound (1.00 g, 30%) as a white solid: $^1$H NMR (300 MHz, CDCl$_3$) δ 7.68 (dd, 1H), 7.40-7.25 (m, 10H), 7.18 (br, 1H), 7.11 (dd, 1H), 7.06-6.91 (m, 4H), 6.50 (d, 1H), 4.99 (d, 1H), 4.74 (d, 1H), 1.27 (d, 12H); MS (ES+) m/z 530.32 (M+1).

EXAMPLE 43

Synthesis of 1'-(diphenylmethyl)-5-hydroxyspiro[1-benzofuran-3,3'-indol]-2'(1'H)-one

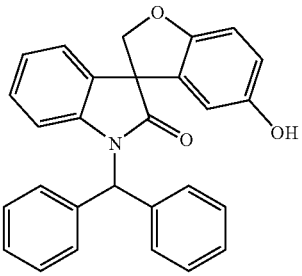

A mixture of 1'-(diphenylmethyl)-5-(4,4,5,5-tetramethyl-1,3,2-dioxaborolan-2-yl)spiro[1-benzofuran-3,3'-indol]-2'(1'H)-one (4.50 g, 8.50 mmol), hydrogen peroxide (4.86 mL, 30% solution, 42.5 mmol), sodium hydroxide (16.38 mL, 10% solution, 40.82 mmol) in methanol was stirred at 0° C. for 30 min and ambient temperature for 16 h. The reaction mixture was quenched with sodium bisulfite. The pH of the reaction mixture was adjusted to 4 using 14% hydrochloric acid. The mixture was extracted with ethyl acetate (3×250 mL). The combined organic layers was dried over anhydrous sodium sulfate and filtered. The filtrate was concentrated in vacuo. The residue was triturated with hexane (20.0 mL), followed by ether (15.0 mL) to give the title compound (3.20 g, 90%) as a white solid: $^1$H NMR (300 MHz, CDCl$_3$) δ 7.45-7.38 (m, 10H), 7.13 (dd, 1H), 7.07-6.91 (m, 3H), 6.79 (d, 1H), 6.63 (dd, 1H), 6.50 (d, 1H), 6.12 (d, 1H), 4.96 (d, 1H), 4.69 (d, 1H); MS (ES+) m/z 420.23 (M+1).

EXAMPLE 44

Synthesis of 5-hydroxyspiro[1-benzofuran-3,3'-indol]-2'(1'H)-one

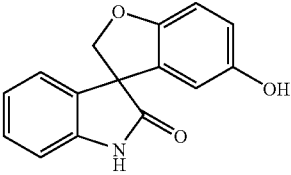

Following the procedure as described in EXAMPLE 1.28, and making non-critical variations using 1'-(diphenylmethyl)-5-hydroxyspiro[1-benzofuran-3,3'-indol]-2'(1'H)-one to replace 1'-(diphenylmethyl)-5'-methylspiro[furo[2,3-f][1,3]benzodioxole-7,3'-indol]-2'(1'H)-one, the title compound was obtained (48%) as a white solid: $^1$H NMR (300 MHz, DMSO-d$_6$) δ 10.58 (s, 1H), 8.85 (s, 1H), 7.21 (dt, 1H), 7.06 (d, 1H), 6.94 (dd, 1H), 6.89 (d, 1H), 6.72 (d, 1H), 6.54 (dd, 1H), 6.02 (d, 1H), 4.70 (d, 1H), 4.57 (d, 1H); MS (ES+) m/z 254.2 (M+1).

EXAMPLE 45

Synthesis of 2'-oxo-1',2'-dihydrospiro[1-benzofuran-3,3'-indol]-5-yl trifluoromethanesulfonate

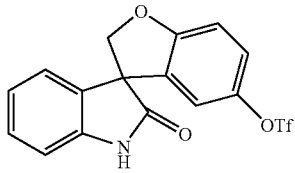

To a mixture of 5-hydroxyspiro[1-benzofuran-3,3'-indol]-2'(1'H)-one (0.18 g, 0.70 mmol) and trifluoromethane sulfonic anhydride (0.26 g, 0.91 mmol) in dichloromethane (5.00 mL) was added triethylamine (0.14 g, 1.93 mmol) at 0° C. The reaction mixture was stirred at ambient temperature for 16 h and diluted with dichloromethane (100 mL). After washing with aqueous saturated sodium chloride (2×20.0 mL), the organic layer was dried over anhydrous sodium sulfate and filtered. The filtrate was concentrated in vacuo. The residue was subjected to column chromatography (ethyl acetate/hexane, ½) to give the title compound (0.07 g, 25%) as a light yellow solid: $^1$H NMR (300 MHz, CDCl$_3$) δ 7.92 (br, 1H), 7.29 (dt, 1H), 7.15-7.03 (m, 3H), 7.99-6.94 (m, 2H), 6.69 (d, 1H), 5.03 (d, 1H), 4.76 (d, 1H); MS (ES+) m/z 386.5 (M+1).

EXAMPLE 46

Synthesis of 2'-oxo-1'-{[5-(trifluoromethyl)-2-furyl]methyl}-1',2'-dihydrospiro[1-benzofuran-3,3'-indol]-5-yl trifluoromethanesulfonate

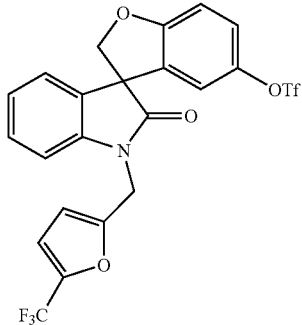

To a mixture of 2'-oxo-1',2'-dihydrospiro[1-benzofuran-3,3'-indol]-5-yl trifluoromethanesulfonate (0.42 g, 1.10 mmol) and sodium hydroxide (0.07 g, 1.65 mmol) in N,N-dimethylformamide (5.00 mL) was added 2-(bromomethyl)-5-(trifluoromethyl)furan (0.50 g, 2.20 mmol) at 0° C. The reaction mixture was stirred at ambient temperature for 16 h and diluted with ethyl acetate (200 mL). After washing with aqueous saturated sodium chloride (2×20.0 mL), the organic layer was dried over anhydrous sodium sulfate and filtered. The filtrate was concentrated in vacuo. The residue was subjected to column chromatography (ethyl acetate/hexane, ⅓) to give the title compound (0.47 g, 80%) as a clear oil: $^1$H NMR (300 MHz, CDCl$_3$) δ 7.34 (t, 1H), 7.18-6.94 (m, 5H), 6.74 (dd, 1H), 6.55 (dd, 1H), 6.40 (d, 1H), 5.09-4.72 (m, 4H); MS (ES+) m/z 534.4 (M+1).

EXAMPLE 47

Synthesis of 5-pyridin-3-yl-1'-{[5-(trifluoromethyl)-2-furyl]methyl}spiro[1-benzofuran-3,3'-indol]-2'(1'H)-one hydrochloride

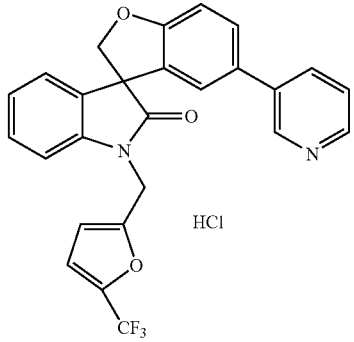

Following the procedure as described in EXAMPLE 4.2, and making non-critical variations using 2'-oxo-1'-{[5-(trifluoromethyl)-2-furyl]methyl}-1',2'-dihydrospiro[1-benzofuran-3,3'-indol]-5-yl trifluoromethanesulfonate to replace 2-(4'-bromo-5,6-difluoro-2'-oxospiro[1-benzofuran-3,3'-indol]-1'(2'H)-yl)-N-(2-fluorophenyl)acetamide, and pyridin-3-ylboronic acid to replace pyrimidine-5-boronic acid, 5-pyridin-3-yl-1'-{[5-(trifluoromethyl)-2-furyl]methyl}spiro[1-benzofuran-3,3'-indol]-2'(1'H)-one was obtained (74%) as a white solid, which was treated with HCl in ether to give the title compound: mp 98-100° C.; $^1$H NMR (300 MHz, CD$_3$OD) δ 8.96 (br, 1H), 8.74-8.65 (m, 2H), 8.04 (dd, 1H), 7.73 (dd, 1H), 7.37 (dt, 1H), 7.25-7.09 (m, 5H), 6.95 (dd, 1H), 6.67 (d, 1H), 5.20-4.83 (m, 4H); $^{13}$C NMR (75 MHz, CD$_3$OD) δ 175.7, 161.3, 151.1, 142.1, 140.2, 138.6, 137.5, 137.4, 130.0, 129.4, 128.1, 127.5, 125.6, 125.5, 122.3, 122.1, 120.8, 111.4, 111.3, 109.7, 108.1, 107.7, 78.7, 58.3, 34.9; MS (ES+) m/z 463.1 (M+1).

EXAMPLE 48

Synthesis of 1'-pentyl-5-pyridin-3-ylspiro[1-benzofuran-3,3'-indol]-2'(1'H)-one

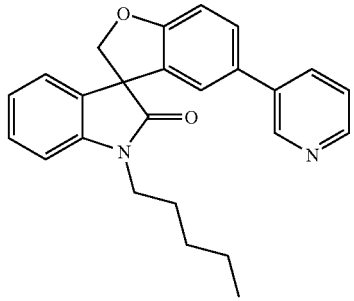

Following the procedure as described in EXAMPLE 4.2, and making non-critical variations using 5-bromo-1'-pentylspiro[1-benzofuran-3,3'-indol]-2'(1'H)-one to replace 2-(4'-bromo-5,6-difluoro-2'-oxospiro[1-benzofuran-3,3'-indol]-1'(2'H)-yl)-N-(2-fluorophenyl)acetamide, and pyridin-3-ylboronic acid to replace pyrimidine-5-boronic acid, the title compound was obtained (70%) was obtained as a white solid: $^1$H NMR (300 MHz, CDCl$_3$) δ 8.55 (br, 1H), 7.65 (d, 1H), 7.45-6.98 (m, 7H), 6.92 (d, 1H), 6.85 (d, 1H), 4.98 (d, 1H), 4.72 (d, 1H), 3.89-3.64 (m, 2H), 1.80-1.68 (m, 2H), 1.43-1.34 (m, 4H), 0.86 (t, 3H); MS (ES+) m/z 385.5 (M+1).

EXAMPLE 49

Synthesis of 1'-pentyl-5-pyrimidin-5-ylspiro[1-benzofuran-3,3'-indol]-2'(1H)-one

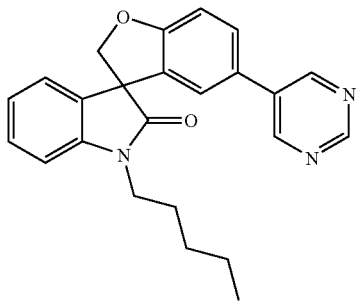

Following the procedure as described in EXAMPLE 4.2, and making non-critical variations using 5-bromo-1'-pentylspiro[1-benzofuran-3,3'-indol]-2'(1'H)-one to replace 2-(4'-bromo-5,6-difluoro-2'-oxospiro[1-benzofuran-3,3'-indol]-1'(2'H)-yl)-N-(2-fluorophenyl)acetamide, the title compound was obtained (40%) was obtained as a white solid: mp 115-117° C.; $^1$H NMR (300 MHz, CDCl$_3$) δ 9.08 (s, 1H), 8.74 (s, 1H), 7.41 (dd, 1H), 7.33 (dt, 1H), 7.16 (dd, 1H), 7.11-7.01 (m, 2H), 6.95 (d, 1H), 6.86 (d, 1H), 5.01 (d, 1H), 4.75 (d, 1H), 3.89-3.64 (m, 2H), 1.80-1.68 (m, 2H), 1.43-1.34 (m, 4H), 0.88 (t, 3H); MS (ES+) m/z 386.4 (M+1).

EXAMPLE 50

Synthesis of 1-pentyl-5-pyridin-4-ylspiro[1-benzofuran-3,3'-indol]-2'(1'H)-one

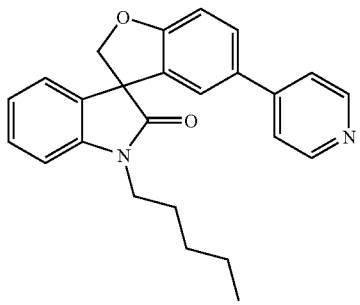

Following the procedure as described in EXAMPLE 4.2, and making non-critical variations using 5-bromo-1'-pentylspiro[1-benzofuran-3,3'-indol]-2'(1'H)-one to replace 2-(4'-bromo-5,6-difluoro-2'-oxospiro[1-benzofuran-3,3'-indol]-1'(2'H)-yl)-N-(2-fluorophenyl)acetamide, and pyridin-4-ylboronic acid to replace pyrimidine-5-boronic acid, the title compound was obtained (95%) as a white solid: $^1$H NMR (300 MHz, CDCl$_3$) δ 8.55-8.47 (m, 2H), 7.52-7.46 (dd, 1H), 7.35-7.26 (m, 3H), 7.15 (dd, 1H), 7.07-7.00 (m, 2H), 6.97-6.92 (m, 2H), 4.99 (d, 1H), 4.73 (d, 1H), 3.89-3.67 (m, 2H), 1.80-1.68 (m, 2H), 1.43-1.34 (m, 4H), 0.92 (t, 3H); MS (ES+) m/z 385.5 (M+1).

EXAMPLE 51

Synthesis of 2'-oxo-1'-pentyl-1',2'-dihydrospiro[1-benzofuran-3,3'-indole]-5-carbonitrile

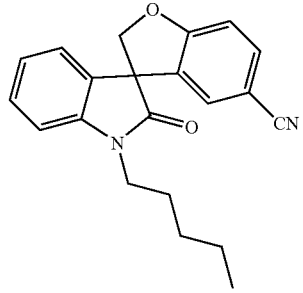

Following the procedure as described in EXAMPLE 30, and making non-critical variations using 5-bromo-1'-pentylspiro[1-benzofuran-3,3'-indol]-2'(1'H)-one to replace 4'-bromo-1'-pentylspiro[furo[2,3-f][1,3]benzodioxole-7,3'-indol]-2'(1'H)-one, the title compound was obtained (78%) as a white solid: $^1$H NMR (300 MHz, CDCl$_3$) δ 7.51 (dt, 1H), 7.34 (dt, 1H), 7.12-6.91 (m, 5H), 5.01 (d, 1H), 4.76 (d, 1H), 3.86-3.63 (m, 2H), 1.80-1.68 (m, 2H), 1.43-1.32 (m, 4H), 0.92 (t, 3H); $^{13}$C NMR (75 MHz, CDCl$_3$) δ 176.2, 164.1, 142.6, 134.8, 131.4, 130.8, 129.6, 127.8, 123.9, 123.5, 118.8, 111.5, 109.1, 104.7, 80.6, 57.3, 40.6, 29.0, 27.1, 22.3, 14.0; MS (ES+) m/z 333.5 (M+1).

EXAMPLE 52

Synthesis of N-(2-fluorophenyl)-2-(2'-oxo-5-pyridin-3-ylspiro[1-benzofuran-3,3'-indol]-1'(2'H)-yl)acetamide

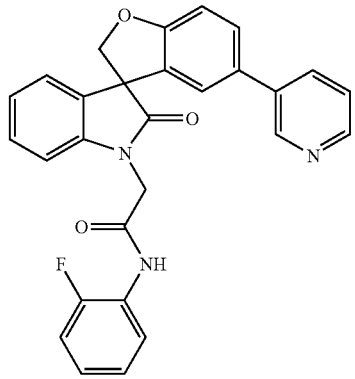

Following the procedure as described in EXAMPLE 37, and making non-critical variations using 2-(5-bromo-2'-oxospiro[1-benzofuran-3,3'-indol]-1'(2'H)-yl)-N-(2-fluorophenyl)acetamide to replace 6-bromo-1'-pentylspiro[1-benzofuran-3,3'-indol]-2'(1'H)-one, the title compound was obtained (55% yield) was obtained as a white solid: mp 98-100° C.; $^1$H NMR (300 MHz, CDCl$_3$) δ 8.60-8.53 (m, 2H), 8.14 (dd, 1H), 7.65 (dd, 1H), 7.41 (dd, 1H), 7.32-6.90 (m, 11H), 5.02 (d, 1H), 4.76 (d, 1H), 4.72 (d, 1H), 4.56 (d, 1H); $^{13}$C NMR (75 MHz, CDCl$_3$) δ 177.9, 164.8, 160.9, 154.2, 151.0, 147.1, 141.7, 134.2, 131.7, 131.5, 129.9, 129.4, 129.1, 125.1, 124.6, 124.5, 124.2, 124.0, 122.5, 122.2, 115.1, 114.8, 111.0, 109.1, 80.0, 58.1, 44.6; MS (ES+) m/z 466.4 (M+1).

EXAMPLE 53

Synthesis of 1'-[(5-fluoro-1H-benzimidazol-2-yl)methyl]spiro[furo[2,3-f][1,3]benzodioxole-7,3'-indol]-2'(1'H)-one

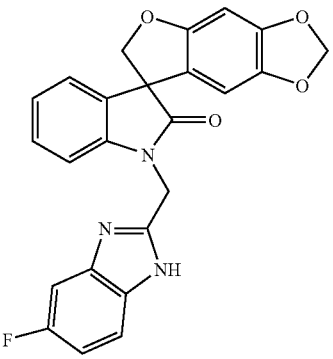

A mixture of (2'-oxospiro[furo[2,3-f][1,3]benzodioxole-7,3'-indol]-1'(2'H)-yl)acetic acid (0.50 g, 1.47 mmol) and 4-fluorobenzene-1,2-diamine (0.15 g, 1.18 mmol) in anhydrous toluene (20.0 mL) was refluxed overnight under $N_2$. The reaction mixture was diluted with water (250 mL) and extracted with ethyl acetate (2×200 mL). The combined organic extracts was dried over anhydrous sodium sulfate and filtered. The filtrate was concentrated in vacuo to dryness. The residue was subjected to column chromatography (ethyl acetate/hexane, 2/1) to give the title compound (0.13 g, 22%): mp 138-142° C.; $^1$H NMR (300 MHz, CDCl$_3$) δ 7.47-7.39 (m, 1H), 7.32-7.22 (m, 2H), 7.16-6.93 (m, 3H), 6.18 (s, 1H), 6.07 (s, 1H), 5.84-5.78 (m, 2H), 5.20-5.14 (m, 2H), 4.98 (d, 1H), 4.60 (d, 1H); $^{13}$C NMR (75 MHz, CDCl$_3$) δ 179.2, 161.3, 158.1, 156.2, 149.2, 149.1, 142.5, 141.2, 131.5, 129.5, 124.4, 124.0, 118.0, 111.6, 111.2, 109.9, 103.1, 101.7, 93.5, 80.5, 58.5, 38.9; MS (ES+) m/z 430.2 (M+1).

EXAMPLE 54

Synthesis of 1-(diphenylmethyl)-5-pyridin-3-ylspiro[1-benzofuran-3,3'-indol]-2'(1'H)-one

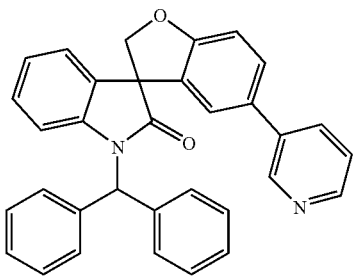

Following the procedure as described in EXAMPLE 4.2, and making non-critical variations using 5-bromo-1'-(diphenylmethyl)spiro[1-benzofuran-3,3'-indol]-2'(1'H)-one to replace 2-(4'-bromo-5,6-difluoro-2'-oxospiro[1-benzofuran-3,3'-indol]-1'(2'H)-yl)-N-(2-fluorophenyl)acetamide, and pyridin-3-ylboronic acid to replace pyrimidine-5-boronic acid, the title compound was obtained (74%) as a white solid: mp 204-207° C.; $^1$H NMR (300 MHz, CDCl$_3$) δ 8.62-8.46 (m, 2H), 7.62 (d, 1H), 7.43-7.26 (m, 11H), 7.16 (dd, 1H), 7.03-6.94 (m, 4H), 6.76 ((d, 1H), 6.54 (d, 1H), 5.09 (d, 1H), 4.82 (d, 1H); MS (ES+) m/z 481.5 (M+1).

EXAMPLE 55

Synthesis of tert-butyl 3-(2'-oxo-1',2'-dihydrospiro[1-benzofuran-3,3'-indol]-5-yl)piperidine-1-carboxylate

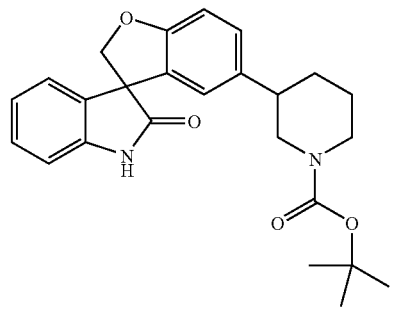

A. Synthesis of 5-piperidin-3-ylspiro[1-benzofuran-3,3'-indol]-2'(1'H)-one

Following the procedure as described in EXAMPLE 1.28, and making non-critical variations using 1-(diphenylmethyl)-5-pyridin-3-ylspiro[1-benzofuran-3,3'-indol]-2'(1'H)-one to replace 1'-(diphenylmethyl)-5'-methylspiro[furo[2,3-f][1,3]benzodioxole-7,3'-indol]-2'(1'H)-one, the title compound was obtained that was used in the next step.

B. Synthesis of tert-butyl 3-(2'-oxo-1',2'-dihydrospiro[1-benzofuran-3,3'-indol]-5-yl)piperidine-1-carboxylate To a mixture of 5-piperidin-3-ylspiro[1-benzofuran-3,3'-indol]-2'(1H)-one, triethylamine (0.95 g, 9.36 mmol) in anhydrous dichloromethane (15.0 mL) was added di-tert-butyl dicarbonate (1.02 g, 4.68 mmol) at 0° C. The reaction mixture was stirred at ambient temperature and stirred over night under $N_2$, diluted with dichloromethane (100 mL) and filtered through celite. The filtrate was concentrated in vacuo to dryness. The brown residue was subjected to column chromatography (ethyl acetate/hexane, 1/1) to give the title compound (0.50 g, 40%) as a white solid: mp 120-123° C.; $^1$H NMR (300 MHz, CDCl$_3$) δ 7.82 (br, 1H), 7.23-7.21 (m, 2H), 7.14-6.86 (m, 5H), 6.63 (br, 1H), 4.95 (d, 1H), 4.69 (d, 1H), 4.10-4.00 (m, 2H), 2.70-2.45 (m, 2H), 1.95-1.80 (m, 2H), 1.48-1.38 (m, 11H); MS (ES+) m/z 443.4 (M+1).

EXAMPLE 56

Synthesis of tert-butyl 3-(2'-oxo-1'-{[5-(trifluoromethyl)-2-furyl]methyl}-1',2'-dihydrospiro[1-benzofuran-3,3'-indol]-5-yl)piperidine-1-carboxylate

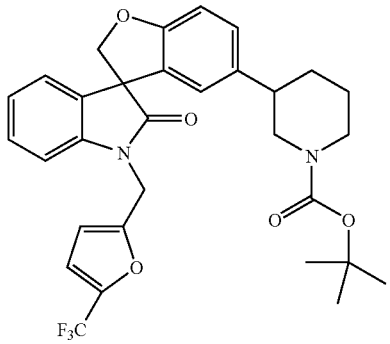

Following the procedure as described in PREPARATION 1A, and making non-critical variations using tert-butyl 3-(2'-oxo-1',2'-dihydrospiro[1-benzofuran-3,3'-indol]-5-yl)piperidine-1-carboxylate to replace 4-bromoindole, and 2-(bromomethyl)-5-(trifluoromethyl)furan to replace 1-bromopentane, the title compound was obtained (10%) as a white solid: mp 59-61° C.; $^1$H NMR (300 MHz, CDCl$_3$) δ 7.34-7.23 (m, 2H), 7.12 (d, 1H), 7.04-6.96 (m, 2H), 6.89 (d, 1H), 6.75 (s, 1H), 6.50 (s, 1H), 6.41 (s, 1H), 5.10-4.86 (m, 3H), 4.66 (d, 1H), 4.16-3.94 (m, 2H), 2.68-2.38 (m, 2H), 1.90-1.60 (m, 3H), 1.40 (s, 10H), 1.27-1.21 (m, 1H); MS (ES+) m/z 591.2 (M+23).

EXAMPLE 57

Synthesis of 5-pyridin-4-yl-1'-{[5-(trifluoromethyl)-2-furyl]methyl}spiro[1-benzofuran-3,3'-indol]-2'(1'H)-one hydrochloride

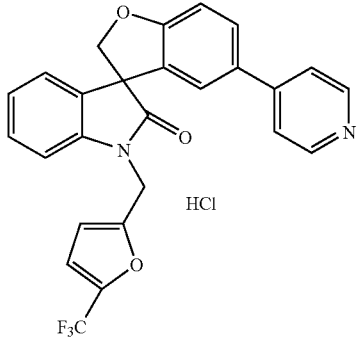

Following the procedure as described in EXAMPLE 4.2, and making non-critical variations using 2'-oxo-1'-{[5-(trifluoromethyl)-2-furyl]methyl}-1',2'-dihydrospiro[1-benzofuran-3,3'-indol]-5-yl trifluoromethanesulfonate to replace 2-(4'-bromo-5,6-difluoro-2'-oxospiro[1-benzofuran-3,3'-indol]-1'(2'H)-yl)-N-(2-fluorophenyl)acetamide, and pyridin-4-ylboronic acid to replace pyrimidine-5-boronic acid, 5-pyridin-4-yl-1'-{[5-(trifluoromethyl)-2-furyl]methyl}spiro[1-benzofuran-3,3'-indol]-2'(1'H)-one was obtained as a white solid, which was treated with HCl in ether to give the title compound (54%): mp 108-110° C.; $^1$H NMR (300 MHz, CDCl$_3$) δ 8.57-8.47 (m, 2H), 7.52 (dd, 1H), 7.37-7.29 (m, 3H), 7.18 (dd, 1H), 7.12-7.00 (m, 3H), 6.92 (d, 1H), 6.75 (dd, 1H), 6.43 (d, 1H), 5.11 4.83 (m, 3H), 4.75 (d, 1H); $^{13}$C NMR (75 MHz, CDCl$_3$) δ 176.2, 164.3, 156.7, 151.5, 141.5, 140.8, 131.5, 131.1, 130.7, 129.8, 127.7, 124.3, 124.1, 123.4, 123.1, 112.9, 112.2, 110.0, 109.4, 80.9, 57.5, 37.3; MS (ES+) m/z 466.4 (M+1).

EXAMPLE 58

Synthesis of 5-methoxy-1'-methylspiro[1-benzofuran-3,3'-indol]-2'(1'H)-one

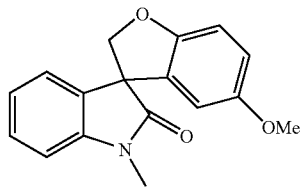

To a mixture of 5-hydroxyspiro[1-benzofuran-3,3'-indol]-2'(1'H)-one (0.10 g, 0.39 mmol), triphenylphosphine (0.20 g, 0.76 mmol) and methanol (0.05 g, 1.6 mmol) in anhydrous tetrahydrofuran was added diethyl azodicarboxylate (0.14 g, 0.80 mmol) at 0° C. The reaction mixture was stirred at ambient temperature under N$_2$ for 16 h and concentrated in vacuo to dryness. The brown residue was subjected to column chromatography (ethyl acetate/hexane, 1/1) to give the title compound (0.02 g, 14% yield) as a yellowish solid: mp 159-161° C.; $^1$H NMR (300 MHz, CDCl$_3$) δ 7.32 (dt, 1H), 7.14 (d, 1H), 7.05 (t, 1H), 6.93-6.83 (m, 2H), 6.74 (dd, 1H), 6.25 (d, 1H), 4.89 (d, 1H), 4.63 (d, 1H), 3.63 (s, 3H), 3.28 (s, 3H); MS (ES+) 282.3 (M+1).

EXAMPLE 59

Synthesis of N-[2-(2'-oxospiro[furo[2,3-f][1,3]benzodioxole-7,3'-indol]-1'(2'H)-yl)ethyl]-2-(trifluoromethoxy)benzamide

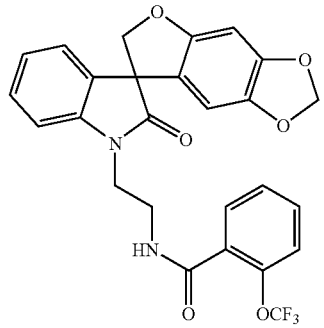

Following the procedure as described in EXAMPLE 17, and making non-critical variations using 1'-(2-aminoethyl)spiro[furo[2,3-f][1,3]benzodioxole-7,3'-indol]-2'(1'H)-one to replace 1'-(3-aminopropyl)spiro[furo[2,3-f][1,3]benzodioxole-7,3'-indol]-2'(1'H)-one, and 2-(trifluoromethoxy)benzoyl chloride to replace 3-chlorothiophene-2-carbonyl chloride, the title compound was obtained (91%) as a colorless solid: mp 183-184° C.; $^1$H NMR (300 MHz, CDCl$_3$) δ 7.86-7.83 (m, 1H), 7.50-7.45 (m, 1H), 7.37-7.27 (m, 3H), 7.16-7.11 (m, 2H), 7.07-7.02 (m, 1H), 6.84 (t, 1H), 6.47 (s, 1H), 6.10 (s, 1H), 5.82 (dd, 2H), 4.87 (d, 1H), 4.64 (d, 1H), 4.10-3.94 (m, 2H), 3.90-3.68 (m, 2H); $^{13}$C NMR (75 MHz, CDCl$_3$) δ 178.2, 165.0, 155.9, 148.8, 145.9, 142.3, 141.9, 132.4, 132.1, 131.3, 129.2, 127.6, 127.3, 124.0, 123.6, 121.2, 121.1, 119.2, 108.7, 103.0, 101.4, 93.6, 80.4, 58.2, 39.5, 38.2; MS (ES+) m/z 513.4 (M+1).

BIOLOGICAL ASSAYS

Various techniques are known in the art for testing the activity of compounds of the invention. In order that the invention described herein may be more fully understood, the following biological assays are set forth. It should be understood that these examples are for illustrative purposes only and are not to be construed as limiting this invention in any manner.

BIOLOGICAL EXAMPLE 1

Guanidine Influx Assay (In Vitro Assay)

This example describes an in vitro assay for testing and profiling test agents against human or rat sodium channels stably expressed in cells of either an endogenous or recombinant origin. The assay is also useful for determining the IC-50 of a sodium channel blocking compound. The assay is based on the guanidine flux assay described by Reddy, N. L., et al., *J Med Chem* (1998), 41(17):3298-302.

The guanidine influx assay is a radiotracer flux assay used to determine ion flux activity of sodium channels in a high-throughput microplate-based format. The assay uses $^{14}$C-guanidine hydrochloride in combination with various known sodium channel modulators, to assay the potency of test agents. Potency is determined by an IC-50 calculation. Selectivity is determined by comparing potency of the compound for the channel of interest to its potency against other sodium channels (also called 'selectivity profiling').

Each of the test agents is assayed against cells that express the channels of interest. Voltage gated sodium channels are either TTX sensitive or insensitive. This property is useful when evaluating the activities of a channel of interest when it resides in a mixed population with other sodium channels. The following Table 1 summarizes cell lines useful in screening for a certain channel activity in the presence or absence of TTX.

binant cells are known to those skilled in the art (see, for example, Klugbauer, N, et al., *EMBO J.* (1995), 14(6):1084-90; and Lossin, C., et al., *Neuron* (2002), 34, pp. 877-884)

Cells expressing the channel of interest are grown according to the supplier or in the case of a recombinant cell in the presence of selective growth media such as G418 (Gibco/Invitrogen). The cells are disassociated from the culture dishes with an enzymatic solution (1×) Trypsin/EDTA (Gibco/Invitrogen) and analyzed for density and viability using haemocytometer (Neubauer). Disassociated cells are washed and resuspended in their culture media then plated into Scintiplates (Beckman Coulter Inc.) (approximately 100,000 cells/ well) and incubated at 37° C./5% $CO_2$. for 20-24 hours. After an extensive wash with Low sodium HEPES-buffered saline solution (LNHBSS) (150 mM Choline Chloride, 20 nM HEPES (Sigma), 1 mM Calcium Chloride, 5 mM Potassium Chloride, 1 mM Magnesium Chloride, 10 mM Glucose) agents diluted with LNHBSS are added to each well. (Varying concentrations of test agent may be used). The activation/radiolabel mixture contains aconitine (Sigma), and $^{14}$C-guanidine hydrochloride (ARC).

After loading the cells with test agent and activation/radio-label mixture, the

Scintiplates are incubated at ambient temperature. Following the incubation, the Scintplates are extensively washed with LNHBSS supplemented with guanidine (Sigma). The Scintiplates are dried and then counted using a Wallac Micro-Beta TriLux (Perkin-Elmer Life Sciences). The ability of the test agent to block sodium channel activity is determined by comparing the amount of $^{14}$C-guanidine present inside the cells expressing the different sodium channels. Based on this data, a variety of calculations, as set out elsewhere in this specification, may be used to determine whether a test agent is selective for a particular sodium channel.

IC-50 value of a test agent for a specific sodium channel may be determined using the above general method. IC-50 may be determined using a 3, 8, 10, 12 or 16 point curve in

TABLE 1

| CELL LINE | mRNA Expression | Functional Characterization |
|---|---|---|
| CHO-K1 (Chinese Hamster Ovary; recommended host cell line) ATTC accession number CCL-61 | $Na_v1.4$ expression has been shown by RT-PCR. No other $Na_v$ expression has been detected | The 18-20-fold increase in [$^{14}$C] Guanidine influx was completely blocked using TTX. ($Na_v1.4$ is a TTX sensitive channel) |
| L6 (rat myoblast cell) ATTC Number CRL-1458 | Expression of Nav1.4 and 1.5 | The 10-15 fold increase in [$^{14}$C] Guanidine influx was only partially blocked by TTX ($Na_v1.5$ is TTX resistant |
| SH-SY5Y (Human neuroblastoma) ATTC Number CRL-2266 | Published Expression of $Na_v1.9$ and $Na_v1.7$ (Blum et al) | The 10-16-fold increase in [$^{14}$C] Guanidine influx above background. was partially blocked by TTX ($Na_v1.9$ is TTX resistant |
| SK-N-BE2C (a human neuroblastoma cell line ATCC Number CRL-2268) | Expression of NaV1.8 | Stimulation of BE2C cells with pyrethroids results in a 6 fold increase in [$^{14}$C] Guanidine influx above background. TTX partially blocked influx (NaV1.8 is TTX resistant) |
| PC12 (rat pheochromocytoma) ATTC Number CRL-1721 | Expression of $Na_v1.2$ expression | The 8-12-fold increase in [$^{14}$C] Guanidine influx was completely blocked using TTX. ($Na_v1.2$ is a TTX sensitive channel) |

It is also possible to employ recombinant cells expressing these sodium channels. Cloning and propagation of recomduplicate or triplicate with a starting concentration of 1, 5 or 10 μM diluted serially with a final concentration reaching the sub-nanomolar, nanomolar and low micromolar ranges. Typically the mid-point concentration of test agent is set at 1 µM, and sequential concentrations of half dilutions greater or smaller are applied (e.g. 0.5 µM; 5 µM and 0.25 µM; 10 µM and 0.125 µM; 20 µM etc.). The IC-50 curve is calculated using the 4 Parameter Logistic Model or Sigmoidal Dose-Response Model formula (fit=(A+((B−A)/(1+((C/x)^D)))).

The fold selectivity, factor of selectivity or multiple of selectivity, is calculated by dividing the IC-50 value of the test sodium channel by the reference sodium channel, for example, $Na_v1.5$.

BIOLOGICAL EXAMPLE 2

Electrophysiological Assay (In Vitro Assay)

Cells expressing the channel of interest were cultured in DMEM growth media (Gibco) with 0.5 mg/mL G418, ±1% PSG, and 10% heat-inactivated fetal bovine serum at 37° C. and 5% $CO_2$. For electrophysiological recordings, cells were plated on 10 mm dishes.

Whole cell recordings were examined by established methods of whole cell voltage clamp (Bean et al., op. cit.) using an Axopatch 200B amplifier and Clampex software (Axon Instruments, Union City, Calif.). All experiments were performed at ambient temperature. Electrodes were fire-polished to resistances of 2-4 Mohms Voltage errors and capacitance artifacts were minimized by series resistance compensation and capacitance compensation, respectively. Data were acquired at 40 kHz and filtered at 5 kHz. The external (bath) solution consisted of: NaCl (140 mM), KCl (5 mM), $CaCl_2$ (2 mM), $MgCl_2$ (1 mM), HEPES (10 mM) at pH 7.4. The internal (pipette) solution consisted of (in mM): NaCl (5), $CaCl_2$ (0.1) $MgCl_2$ (2), CsCl (10), CsF (120), HEPES (10), EGTA (10), at pH 7.2.

To estimate the steady-state affinity of compounds for the resting and inactivated state of the channel ($K_r$ and $K_i$, respectively), 12.5 ms test pulses to depolarizing voltages from −60 to +90 mV from a holding potential of −110 mV was used to construct current-voltage relationships (I-V curves). A voltage near the peak of the IV-curve (−30 to 0 mV) was used as the test pulse throughout the remainder of the experiment. Steady-state inactivation (availability) curves were then constructed by measuring the current activated during a 8.75 ms test pulse following 1 second conditioning pulses to potentials ranging from −110 to −10 mV. To monitor channels at steady-state, a single "diary" protocol with a holding potential of −110 mV was created to record the resting state current (10 ms test pulse), the current after fast inactivation (5 ms pre-pulse of −80 to −50 mV followed by a 10 ms test pulse), and the current during various holding potentials (35 ms ramp to test pulse levels). Compounds were applied during the "diary" protocol and the block was monitored at 15 s intervals.

After the compounds equilibrated, the voltage-dependence of the steady-state inactivation in the presence of the compound was determined. Compounds that block the resting state of the channel decreased the current elicited during test pulses from all holding potentials, whereas compounds that primarily blocked the inactivated state decreased the current elicited during test pulses at more depolarized potentials. The currents at the resting state ($I_{rest}$) and the currents during the inactivated state ($I_{inactivated}$) were used to calculate steady-state affinity of compounds. Based on the Michaelis-Menton model of inhibition, the $K_r$ and $K_i$ was calculated as the concentration of compound needed to cause 50% inhibition of the $I_{rest}$ or the $I_{inactivated}$, respectively.

$$\% \text{ inhibition} = \frac{V_{max}^*[\text{Drug}]^h}{[\text{Drug}]^h + K_m^h}$$

$V_{max}$ is the rate of inhibition, h is the Hill coefficient (for interacting sites), $K_m$ is Michaelis-Menten constant, and [Drug] is the concentration of the test compound. At 50% inhibition ($\frac{1}{2}V_{max}$) of the $I_{rest}$ or $I_{inactivated}$, the drug concentration is numerically equal to $K_m$ and approximates the $K_r$ and $K_i$, respectively.

BIOLOGICAL EXAMPLE 3

Analgesia Induced by Sodium Channel Blockers

Heat Induced Tail Flick Latency Test

In this test, the analgesia effect produced by administering a compound of the invention was observed through heat-induced tail-flick in mice. The test includes a heat source consisting of a projector lamp with a light beam focused and directed to a point on the tail of a mouse being tested. The tail-flick latencies, which were assessed prior to drug treatment, and in response to a noxious heat stimulus, i.e., the response time from applying radiant heat on the dorsal surface of the tail to the occurrence of tail flick, were measured and recorded at 40, 80, 120, and 160 minutes.

For the first part of this study, 65 animals underwent assessment of baseline tail flick latency once a day over two consecutive days. These animals were then randomly assigned to one of the 11 different treatment groups including a vehicle control, a morphine control, and 9 compounds at 30 mg/kg were administered intramuscularly. Following dose administration, the animals were closely monitored for signs of toxicity including tremor or seizure, hyperactivity, shallow, rapid or depressed breathing and failure to groom. The optimal incubation time for each compound was determined via regression analysis. The analgesic activity of the test compounds was expressed as a percentage of the maximum possible effect (% MPE) and was calculated using the following formula:

$$\% \text{ MPE} \frac{\text{Postdrug latency} - \text{Predrug latency}}{\text{Cut-off time (10 s)} - \text{Predrug latency}} \times 100\%$$

where:

Postdrug latency=the latency time for each individual animal taken before the tail is removed (flicked) from the heat source after receiving drug.

Predrug latency=the latency time for each individual animal taken before the tail is flicked from the heat source prior to receiving drug.

Cut-off time (10 s)=is the maximum exposure to the heat source.

Acute Pain (Formalin Test)

The formalin test is used as an animal model of acute pain. In the formalin test, animals were briefly habituated to the plexiglass test chamber on the day prior to experimental day for 20 minutes. On the test day, animals were randomly injected with the test articles. At 30 minutes after drug administration, 50 µL of 10% formalin was injected subcutaneously into the plantar surface of the left hind paw of the rats. Video data acquisition began immediately after formalin administration, for duration of 90 minutes.

The images were captured using the Actimetrix Limelight software which stores files under the *.Ilii extension, and then converts it into the MPEG-4 coding. The videos are then analyzed using behaviour analysis software "The Observer 5.1", (Version 5.0, Noldus Information Technology, Wageningen, The Netherlands). The video analysis was done by watching the animal behaviour and scoring each according to type, and defining the length of the behaviour (Dubuisson and Dennis, 1977). Scored behaviours include: (1) normal behaviour, (2) putting no weight on the paw, (3) raising the paw, (4) licking/biting or scratching the paw. Elevation, favoring, or excessive licking, biting and scratching of the injected paw indicate a pain response. Analgesic response or protection from compounds is indicated if both paws are resting on the floor with no obvious favoring, excessive licking, biting or scratching of the injected paw.

Analysis of the formalin test data is done according to two factors: (1) Percent Maximal Potential Inhibitory Effect (% MPIE) and (2) pain score. The % MPIEs was calculated by a series of steps, where the first is to sum the length of non-normal behaviours (behaviours 1,2,3) of each animal. A single value for the vehicle group was obtained by averaging all scores within the vehicle treatment group. The following calculation yields the MPIE value for each animal:

$$\text{MPIE (\%)}=100-[(\text{treatment sum/average vehicle value})\times 100\%]$$

The pain score is calculated from a weighted scale as described above. The duration of the behaviour is multiplied by the weight (rating of the severity of the response), and divided by the total length of observation to determine a pain rating for each animal. The calculation is represented by the following formula:

$$\text{Pain rating}=[0(T_0)+1(T_1)+2(T_2)+3(T_3)]/(T_0+T_1+T_2+T_3)$$

Compounds of the present invention were shown to be efficacious within a range of 30 mg/kg and 0.1 mg/kg.

CFA Induced Chronic Inflammatory Pain

In this test, tactile allodynia was assessed with calibrated von Frey filaments. Following a full week of acclimatization to the vivarium facility, 150 µL of the "Complete Freund's Adjuvant" (CFA) emulsion (CFA suspended in an oil/saline (1:1) emulsion at a concentration of 0.5 mg/mL) was injected subcutaneously into the plantar surface of the left hind paw of rats under light isoflurane anaesthesia. Animals were allowed to recover from the anaesthesia and the baseline thermal and mechanical nociceptive thresholds of all animals are assessed one week after the administration of CFA. All animals were habituated to the experimental equipment for 20 minutes on the day prior to the start of the experiment. The test and control articles were administered to the animals, and the nociceptive thresholds measured at defined time points after drug administration to determine the analgesic responses to each of the six available treatments. The time points used were previously determined to show the highest analgesic effect for each test compound.

Thermal nociceptive thresholds of the animals were assessed using the Hargreaves test. Animals were placed in a Plexiglas enclosure set on top of an elevated glass platform with heating units. The glass platform is thermostatically controlled at a temperature of approximately 30° C. for all test trials. Animals were allowed to accommodate for 20 minutes following placement into the enclosure until all exploration behaviour ceases. The Model 226 Plantar/Tail Stimulator Analgesia Meter (IITC, Woodland Hills, Calif.) was used to apply a radiant heat beam from underneath the glass platform to the plantar surface of the hind paws. During all test trials, the idle intensity and active intensity of the heat source were set at 1 and 45 respectively, and a cut off time of 20 seconds was employed to prevent tissue damage.

The response thresholds of animals to tactile stimuli were measured using the Model 2290 Electrovonfrey anesthesiometer (IITC Life Science, Woodland Hills, Calif.) following the Hargreaves test. Animals were placed in an elevated Plexiglas enclosure set on a mire mesh surface. After 10 minutes of accommodation, pre-calibrated Von Frey hairs were applied perpendicularly to the plantar surface of both paws of the animals in an ascending order starting from the 0.1 g hair, with sufficient force to cause slight buckling of the hair against the paw. Testing continues until the hair with the lowest force to induce a rapid flicking of the paw is determined or when the cut off force of approximately 20 g is reached. This cut off force was used because it represent approximately 10% of the animals' body weight and it serves to prevent raising of the entire limb due to the use of stiffer hairs, which would change the nature of the stimulus. The compounds of the present invention were shown to be efficacious within a range of 30 mg/Kg and 0.1 mg/Kg.

Postoperative Models of Nociception

In this model, the hypealgesia caused by an intra-planar incision in the paw is measured by applying increased tactile stimuli to the paw until the animal withdraws its paw from the applied stimuli. While animals were anaesthetized under 3.5% isofluorane, which was delivered via a nose cone, a 1 cm longitudinal incision was made using a number 10 scalpel blade in the plantar aspect of the left hind paw through the skin and fascia, starting 0.5 cm from the proximal edge of the heel and extending towards the toes. Following the incision, the skin was apposed using 2, 3-0 sterilized silk sutures. The injured site was covered with Polysporin and Betadine. Animals were returned to their home cage for overnight recovery.

The withdrawal thresholds of animals to tactile stimuli for both operated (ipsilateral) and unoperated (contralateral) paws can be measured using the Model 2290 Electrovonfrey anesthesiometer (IITC Life Science, Woodland Hills, Calif.). Animals were placed in an elevated Plexiglas enclosure set on a mire mesh surface. After at least 10 minutes of acclimatization, pre-calibrated Von Frey hairs were applied perpendicularly to the plantar surface of both paws of the animals in an ascending order starting from the 10 g hair, with sufficient force to cause slight buckling of the hair against the paw. Testing continued until the hair with the lowest force to induce a rapid flicking of the paw is determined or when the cut off force of approximately 20 g is reached. This cut off force is used because it represent approximately 10% of the animals' body weight and it serves to prevent raising of the entire limb due to the use of stiffer hairs, which would change the nature of the stimulus.

Compounds of the present invention were shown to be efficacious within a range of 30 mg/Kg and 0.1 mg/Kg.

Neuropathic Pain Model; Chronic Constriction Injury

Briefly, an approximately 3 cm incision was made through the skin and the fascia at the mid thigh level of the animals' left hind leg using a no. 10 scalpel blade. The left sciatic nerve was exposed via blunt dissection through the biceps femoris with care to minimize haemorrhagia. Four loose ligatures were tied along the sciatic nerve using 4-0 non-degradable sterilized silk sutures at intervals of 1 to 2 mm apart. The tension of the loose ligatures was tight enough to induce slight constriction of the sciatic nerve when viewed under a dissection microscope at a magnification of 4 fold. In the sham-operated animal, the left sciatic nerve was exposed without further manipulation. Antibacterial ointment was applied directly into the wound, and the muscle was closed using sterilized sutures. Betadine was applied onto the muscle and its surroundings, followed by skin closure with surgical clips.

The response thresholds of animals to tactile stimuli were measured using the Model 2290 Electrovonfrey anesthesiometer (IITC Life Science, Woodland Hills, Calif.). Animals were placed in an elevated Plexiglas enclosure set on a mire mesh surface. After 10 minutes of accommodation, pre-calibrated Von Frey hairs were applied perpendicularly to the plantar surface of both paws of the animals in an ascending order starting from the 0.1 g hair, with sufficient force to cause slight buckling of the hair against the paw. Testing continues until the hair with the lowest force to induce a rapid flicking of the paw is determined or when the cut off force of approximately 20 g is reached. This cut off force is used because it represents approximately 10% of the animals' body weight and it serves to prevent raising of the entire limb due to the use of stiffer hairs, which would change the nature of the stimulus. Compounds of the present invention were shown to be efficacious within a range of 30 mg/kg and 0.1 mg/Kg.

Thermal nociceptive thresholds of the animals were assessed using the Hargreaves test. Following the measurement of tactile thresholds, animals were placed in a Plexiglass enclosure set on top of an elevated glass platform with heating units. The glass platform is thermostatically controlled at a temperature of approximately 24 to 26° C. for all test trials. Animals were allowed to accommodate for 10 minutes following placement into the enclosure until all exploration behaviour ceases. The Model 226 Plantar/Tail Stimulator Analgesia Meter (IITC, Woodland Hills, Calif.) was used to apply a radiant heat beam from underneath the glass platform to the plantar surface of the hind paws. During all test trials, the idle intensity and active intensity of the heat source were set at 1 and 55 respectively, and a cut off time of 20 seconds was used to prevent tissue damage.

BIOLOGICAL EXAMPLE 4

Aconitine Induced Arrhythmia Test

The antiarrhythmic activity of compounds of the invention is demonstrated by the following test. Arrhythmia was provoked by intravenous administration of aconitine(2.0 μg/Kg) dissolved in physiological saline solution. Test compounds of the invention were intravenously administered 5 minutes after the administration of aconitine. Evaluation of the antiarrhythmic activity was conducted by measuring the time from the aconitine administration to the occurrence of extrasystole (ES) and the time from the aconitine administration to the occurrence of ventricular tachycardia (VT).

In rates under isoflurane anaesthesia (¼ to ⅓ of 2%), a tracheotomy was performed by first creating an incision in the neck area, then isolating the trachea and making a 2 mm incision to insert tracheal tube 2 cm into the trachea such that the opening of the tube was positioned just on top of the mouth. The tubing was secured with sutures and attached to a ventilator for the duration of the experiment.

Incisions (2.5 cm) were then made into the femoral areas and using a blunt dissection probe, the femoral vessels were isolated. Both femoral veins were cannulated, one for pentobarbital anaesthetic maintenance (0.02-0.05 mL) and one for the infusion and injection of drug and vehicle. The femoral artery was cannulated with the blood pressure gel catheter of the transmitter.

The ECG leads were attached to the thoracic muscle in the Lead II position (upper right/above heart—white lead and lower left/below heart—red lead). The leads were secured with sutures.

All surgical areas were covered with gauze moistened with 0.9% saline. Saline (1-1.5 mL of a 0.9% solution) was supplied to moisten the areas post-surgery. The animals' ECG and ventilation were allowed to equilibrate for at least 30 minutes.

The arrhythmia was induced with a 2 μg/Kg/min aconitine infusion for 5 minutes. During this time the ECG was recorded and continuously monitoired. An intravenous bolus injection of a test compound of the invention (10, 30 or 100 μg/kg) resulted in a complete return to normal baseline ECG.

Accordingly, compounds of the invention, when tested in this model, demonstrated anti-arrhythmia activity.

BIOLOGICAL EXAMPLE 5

Ischemia Induced Arrhythmia Test

Rodent models of ventricular arrhythmias, in both acute cardioversion and prevention paradigms have been employed in testing potential therapeutics for both atrial and ventricular arrhythmias in humans. Cardiac ischemia leading to myocardial infarction is a common cause of morbidity and mortality. The ability of a compound to prevent ischemia-induced ventricular tachycardia and fibrillation is an accepted model for determining the efficacy of a compound in a clinical setting for both atrial and ventricular tachycardia and fibrillation.

Anaesthesia is first induced by pentobarbital (i.p.), and maintained by an i.v. bolus infusion. Male SD rats have their trachea cannulated for artificial ventilation with room air at a stroke volume of 10 ml/Kg, 60 strokes/minute. The right femoral artery and vein are cannulated with PE50 tubing for mean arterial blood pressure (MAP) recording and intravenous administration of compounds, respectively.

The chest was opened between the $4^{th}$ and $5^{th}$ ribs to create a 1.5 cm opening such that the heart was visible. Each rat was placed on a notched platform and metal restraints were hooked onto the rib cage opening the chest cavity. A suture needle was used to penetrate the ventricle just under the lifted atrium and exited the ventricle in a downward diagonal direction so that a >30% to <50% occlusion zone (OZ) would be obtained. The exit position was ~0.5 cm below where the aorta connects to the left ventricle. The suture was tightened such that a loose loop (occluder) was formed around a branch of the artery. The chest was then closed with the end of the occluder accessible outside of the chest.

Electrodes were placed in the Lead II position (right atrium to apex) for ECG measurement as follows: one electrode inserted into the right forepaw and the other electrode inserted into the left hind paw.

The body temperature, MAP, ECG, and heart rate were constantly recorded throughout the experiment. Once the critical parameters had stabilized, a 1-2 minute recording was taken to establish the baseline values. Infusion of a compound of the invention or control substance was initiated once baseline values were established. After a 5-minute infusion of compound or control, the suture was pulled tight to ligate the LCA and create ischemia in the left ventricle. The critical parameters were recorded continuously for 20 minutes after ligation, unless the MAP reached the critical level of 20-30 mmHg for at least 3 minutes, in which case the recording was stopped because the animal would be declared deceased and was then sacrificed. The ability of compounds of the invention to prevent arrhythmias and sustain near-normal MAP and HR was scored and compared to control.

Compound of the invention, when tested in this model, demonstatrated the ability to prevent ischemia-induced ventricular tachycardia and fibrillation.

All of the U.S. patents, U.S. patent application publications, U.S. patent applications, foreign patents, foreign patent applications and non-patent publications referred to in this specification and/or listed in the Application Data Sheet are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of treating or ameliorating, but not preventing, pain in a mammal, wherein the method comprises administering to the mammal in need thereof a therapeutically effective amount of a compound of formula (I):

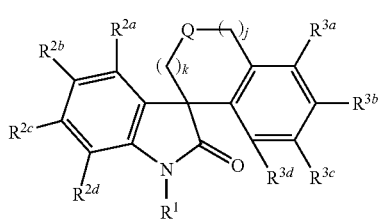

wherein:
j and k are each independently 0, 1, 2 or 3;
Q is —O—;
$R^1$ is hydrogen, alkyl, alkenyl, alkynyl, haloalkyl, aryl, cycloalkyl, cycloalkylalkyl, heteroaryl, heterocyclyl, —$R^8$—C(O)$R^5$, —$R^8$—C(O)O$R^5$, —$R^8$—C(O)N($R^4$)$R^5$, —S(O)$_2$—$R^5$, —$R^9$—S(O)$_m$—$R^5$ (where m is 0, 1 or 2), —$R^8$—O$R^5$, —$R^8$—CN, —$R^9$—P(O)(O$R^5$)$_2$, or —$R^9$—O—$R^9$—O$R^5$;
or $R^1$ is aralkyl substituted by —C(O)N($R^6$)$R^7$ where:
$R^6$ is hydrogen, alkyl, aryl or aralkyl; and
$R^7$ is hydrogen, alkyl, haloalkyl, —$R^9$—CN, —$R^9$—O$R^5$, —$R^9$—N($R^4$)$R^5$, aryl, aralkyl, cycloalkyl, cycloalkylalkyl, heterocyclyl, heterocyclylalkyl, heteroaryl or heteroarylalkyl;
or $R^6$ and $R^7$, together with the nitrogen to which they are attached, may form a heterocyclyl or heteroaryl;
and wherein each aryl, aralkyl, cycloalkyl, cycloalkylalkyl, heterocyclyl, heterocyclylalkyl, heteroaryl and heteroarylalkyl group for $R^6$ and $R^7$ may be optionally substituted by one or more substituents selected from the group consisting of alkyl, cycloalkyl, aryl, aralkyl, halo, haloalkyl, —$R^8$—CN, —$R^8$—O$R^5$, heterocyclyl and heteroaryl;
or $R^1$ is aralkyl optionally substituted by one or more substituents selected from the group consisting of —$R^8$—O$R^5$, —C(O)O$R^5$, halo, haloalkyl, alkyl, nitro, cyano, aryl, aralkyl, heterocyclyl and heteroaryl;
or $R^1$ is —$R^9$—N($R^{10}$)$R^{11}$, —$R^9$—N($R^{12}$)C(O)$R^{11}$ or —$R^9$—N($R^{10}$)C(O)N($R^{10}$)$R^{11}$ (where:
each $R^{10}$ is hydrogen, alkyl, aryl, aralkyl or heteroaryl;
each $R^{11}$ is hydrogen, alkyl, haloalkyl, cycloalkyl, cycloalkylalkyl, aryl, aralkyl, heterocyclyl, heterocyclylalkyl, heteroaryl, heteroarylalkyl, —$R^9$—OC(O)$R^5$, —$R^9$—C(O)O$R^5$, —$R^9$—C(O)N($R^4$)$R^5$, —$R^9$—C(O)$R^5$, —$R^9$—N($R^4$)$R^5$, —$R^9$—O$R^5$, or —$R^9$—CN; and
$R^{12}$ is hydrogen, alkyl, aryl, aralkyl or —C(O)$R^5$;
and wherein each aryl, aralkyl, cycloalkyl, cycloalkylalkyl, heterocyclyl, heterocyclylalkyl, heteroaryl and heteroarylalkyl group for $R^{10}$ and $R^{11}$ may be optionally substituted by one or more substituents selected from the group consisting of alkyl, cycloalkyl, aryl, aralkyl, halo, haloalkyl, nitro, —$R^8$—CN, —$R^8$—O$R^5$, —$R^8$—C(O)$R^5$, heterocyclyl and heteroaryl;
or $R^1$ is heterocyclylalkyl or heteroarylalkyl where the heterocyclylalkyl or the heteroarylalkyl group is optionally substituted by one or more substituents selected from the group consisting of oxo, alkyl, halo, haloalkyl, cycloalkyl, cycloalkylalkyl, aryl, aralkyl, heterocyclyl, heterocyclylalkyl, heteroaryl, heteroarylalkyl, —$R^8$—O$R^5$, —$R^8$—C(O)O$R^5$, —$R^8$—N($R^4$)$R^5$, —$R^8$—C(O)N($R^4$)$R^5$, —$R^8$—N($R^5$)C(O)$R^4$, —$R^8$—S(O)$_m$$R^4$ (where m is 0, 1 or 2), —$R^8$—CN, and —$R^8$—NO$_2$;
$R^{2a}$, $R^{2b}$, $R^{2c}$ and $R^{2d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—NO$_2$, —$R^8$—O$R^5$, —$R^8$—N($R^4$)$R^5$, —N=C($R^4$)$R^5$, —S(O)$_m$$R^4$, —OS(O)$_2$CF$_3$, —$R^8$—C(O)$R^4$, —C(S)$R^4$, —C($R^4$)$_2$C(O)O$R^5$, —$R^8$—C(O)O$R^4$, —C(S)O$R^4$, —$R^8$—C(O)N($R^4$)$R^5$, —C(S)N($R^4$)$R^5$, —N($R^5$)C(O)$R^4$, —N($R^5$)C(S)$R^4$, —N($R^5$)C(O)O$R^4$, —N($R^5$)C(S)O$R^4$, —N($R^5$)C(O)N($R^4$)$R^5$, —N($R^5$)C(S)N($R^4$)$R^5$, —N($R^5$)S(O)$_n$$R^4$, —N($R^5$)S(O)$_n$N($R^4$)$R^5$, —$R^8$—S(O)$_n$N($R^4$)$R^5$, —N($R^5$)C(=N$R^5$)N($R^4$)$R^5$, and —N($R^5$)C(=N—CN)N($R^4$)$R^5$, wherein each m is independently 0, 1, or 2 and each n is independently 1 or 2;
and wherein each of the cycloalkyl, cycloalkylalkyl, aryl, aralkyl, aralkenyl, heterocyclyl, heterocyclylalkyl, heteroaryl and heteroarylalkyl groups for $R^{2a}$, $R^{2b}$, $R^{2c}$ and $R^{2d}$ may be optionally substituted by one or more substituents selected from the group consisting of alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—CN, —$R^8$—NO$_2$, —$R^8$—O$R^5$, —$R^8$—N($R^4$)$R^5$, —S(O)$_m$$R^4$, —$R^8$—S(O)$_n$N($R^4$)$R^5$, —$R^8$—C(O)$R^4$, —$R^8$—C(O)O$R^4$, —$R^8$—C(O)N($R^4$)$R^5$, —N($R^5$)C(O)$R^4$, and —N($R^5$)S(O)$_n$$R^4$, wherein each m is independently 0, 1, or 2 and each n is independently 1 or 2;
or $R^{2a}$ and $R^{2b}$, together with the carbon ring atoms to which they are directly attached, may form a fused ring selected from cycloalkyl, aryl, heterocyclyl and heteroaryl, and $R^{2c}$ and $R^{2d}$ are as defined above;
or $R^{2b}$ and $R^2$, together with the carbon ring atoms to which they are directly attached, may form a fused ring selected from cycloalkyl, aryl, heterocyclyl and heteroaryl, and $R^{2a}$ and $R^{2d}$ are as defined above;
or $R^{2c}$ and $R^{2d}$, together with the carbon ring atoms to which they are directly attached, may form a fused ring selected from cycloalkyl, aryl, heterocyclyl and heteroaryl, and $R^{2a}$ and $R^{2b}$ are as defined above;
$R^{3a}$, $R^{3b}$, $R^3$ and $R^{3d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —R⁸—NO₂, —R⁸—OR⁵, —R⁸—N(R⁴)R⁵, —N=C(R⁴)R⁵, —S(O)ₘR⁴, —OS(O)₂CF₃, —R⁸—C(O)R⁴, —C(S)R⁴, —C(R⁴)₂C(O)R⁵, —R⁸—C(O)OR⁴, —C(S)OR⁴, —R⁸—C(O)N(R⁴)R⁵, —C(S)N(R⁴)R⁵, —N(R⁵)C(O)R⁴, —N(R⁵)C(S)R⁴, —N(R⁵)C(O)OR⁴, —N(R⁵)C(S)OR⁴, —N(R⁵)C(O)N(R⁴)R⁵, —N(R⁵)C(S)N(R⁴)R⁵, —N(R⁵)S(O)ₙR⁴, —N(R⁵)S(O)ₙN(R⁴)R⁵, —R⁸—S(O)ₙN(R⁴)R⁵, —N(R⁵)C(=NR⁵)N(R⁴)R⁵, and —N(R⁵)C(N=C(R⁴)R⁵)N(R⁴)R⁵, wherein each m is independently 0, 1, or 2 and each n is independently 1 or 2;

or R³ᵃ and R³ᵇ, together with the carbon ring atoms to which they are directly attached, may form a fused ring selected from cycloalkyl, heterocyclyl, aryl or heteroaryl, and R³ᶜ and R³ᵈ are as defined above;

or R³ᵇ and R³ᶜ, together with the carbon ring atoms to which they are directly attached, may form a fused ring selected from cycloalkyl, heterocyclyl, aryl or heteroaryl, and R³ᵃ and R³ᵈ are as defined above;

or R³ᶜ and R³ᵈ, together with the carbon ring atoms to which they are directly attached, may form a fused ring selected from cycloalkyl, heterocyclyl, aryl or heteroaryl, and R³ᵃ and R³ᵇ are as defined above;

each R⁴ and R⁵ is independently selected from the group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when R⁴ and R⁵ are each attached to the same nitrogen atom, then R⁴ and R⁵, together with the nitrogen atom to which they are attached, may form a heterocyclyl or heteroaryl;

each R⁸ is a direct bond or a straight or branched alkylene chain, a straight or branched alkenylene chain or a straight or branched alkynylene chain; and each R⁹ is a straight or branched alkylene chain, a straight or branched alkenylene chain or a straight or branched alkynylene chain;

as a stereoisomer, enantiomer, tautomer thereof or mixtures thereof;

or a pharmaceutically acceptable salt thereof.

2. The method of claim 1, wherein the pain is selected from the group consisting of neuropathic pain, inflammatory pain, visceral pain, cancer pain, chemotherapy pain, trauma pain, surgical pain, post-surgical pain, childbirth pain, labor pain, dental pain, chronic pain, persistent pain, peripherally mediated pain, centrally mediated pain, chronic headache, migraine headache, sinus headache, tension headache, phantom limb pain and peripheral nerve injury, and combinations thereof.

3. The method of claim 1, wherein the pain is associated with a disease or condition selected from HIV, HIV treatment induced neuropathy, heat sensitivity, tosarcoidosis, irritable bowel syndrome, Crohns disease, multiple sclerosis, amyotrophic lateral sclerosis diabetic neuropathy, peripheral neuropathy, rheumatoid arthritis, osteoarthritis, atherosclerosis, paroxysmal dystonia, myasthenia syndromes, myotonia, malignant hyperthermia, cystic fibrosis, pseudoaldosteronism, rhabdomyolysis, hypothyroidism, bipolar depression, anxiety, schizophrenia, sodium channel toxin related illnesses, neurogenic bladder, ulcerative colitis, cancer, epilepsy, partial and general tonic seizures, restless leg syndrome, arrhythmias, ischaemic conditions caused by stroke or neural trauma, tachy-arrhythmias, atrial fibrillation and ventricular fibrillation.

4. A method of treating or ameliorating, but not preventing, pain through inhibition of ion flux through a voltage-dependent sodium channel in a mammal, wherein the method comprises administering to the mammal in need thereof a therapeutically effective amount of a compound of formula (I):

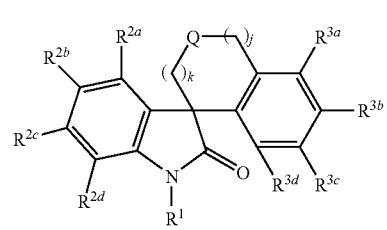

wherein:
j and k are each independently 0, 1, 2 or 3;
Q is —O—;
R¹ is hydrogen, alkyl, alkenyl, alkynyl, haloalkyl, aryl, cycloalkyl, cycloalkylalkyl, heteroaryl, heterocyclyl, —R⁸—C(O)R⁵, —R⁸—C(O)OR⁵, —R⁸—C(O)N(R⁴)R⁵, —S(O)₂—R⁵, —R⁹—S(O)ₘ—R⁵ (where m is 0, 1 or 2), —R⁸—OR⁵, —R⁸—CN, —R⁹—P(O)(OR⁵)₂, or —R⁹—O—R⁵;

or R¹ is aralkyl substituted by —C(O)N(R⁶)R⁷ where:
R⁶ is hydrogen, alkyl, aryl or aralkyl; and
R⁷ is hydrogen, alkyl, haloalkyl, —R⁹—CN, —R⁹—OR⁵, —R⁹—N(R⁴)R⁵, aryl, aralkyl, cycloalkyl, cycloalkylalkyl, heterocyclyl, heterocyclylalkyl, heteroaryl or heteroarylalkyl;

or R⁶ and R⁷, together with the nitrogen to which they are attached, may form a heterocyclyl or heteroaryl;

and wherein each aryl, aralkyl, cycloalkyl, cycloalkylalkyl, heterocyclyl, heterocyclylalkyl, heteroaryl and heteroarylalkyl group for R⁶ and R⁷ may be optionally substituted by one or more substituents selected from the group consisting of alkyl, cycloalkyl, aryl, aralkyl, halo, haloalkyl, —R⁸—CN, —R⁸—OR⁵, heterocyclyl and heteroaryl;

or R¹ is aralkyl optionally substituted by one or more substituents selected from the group consisting of —R⁸—OR⁵, —C(O)OR⁵, halo, haloalkyl, alkyl, nitro, cyano, aryl, aralkyl, heterocyclyl and heteroaryl;

or R¹ is —R⁹—N(R¹⁰)R¹¹, —R⁹—N(R¹²)C(O)R¹¹ or —R⁹—N(R¹⁰)C(O)N(R¹⁰)R¹¹ where:
each R¹⁰ is hydrogen, alkyl, aryl, aralkyl or heteroaryl;
each R¹¹ is hydrogen, alkyl, haloalkyl, cycloalkyl, cycloalkylalkyl, aryl, aralkyl, heterocyclyl, heterocyclylalkyl, heteroaryl, heteroarylalkyl, —R⁹—OC(O)R⁵, —R⁹—C(O)OR⁵, —R⁹—C(O)N(R⁴)R⁵, —R⁹—C(O)R⁵, —R⁹—N(R⁴)R⁵, —R⁹—OR⁵, or —R⁹—CN; and
R¹² is hydrogen, alkyl, aryl, aralkyl or —C(O)R⁵;

and wherein each aryl, aralkyl, cycloalkyl, cycloalkylalkyl, heterocyclyl, heterocyclylalkyl, heteroaryl and heteroarylalkyl group for R¹⁰ and R¹¹ may be optionally substituted by one or more substituents selected from the group consisting of alkyl, cycloalkyl, aryl, aralkyl, halo, haloalkyl, nitro, —R⁸—CN, —R⁸—OR⁵, —R⁸—C(O)R⁵, heterocyclyl and heteroaryl;

or R¹ is heterocyclylalkyl or heteroarylalkyl where the heterocyclylalkyl or the heteroarylalkyl group is optionally substituted by one or more substituents selected from the group consisting of oxo, alkyl, halo, haloalkyl, cycloalkyl, cycloalkylalkyl, aryl, aralkyl, heterocyclyl, heterocyclylalkyl, heteroaryl, heteroarylalkyl, —R⁸—OR⁵, —R⁸—C(O)OR⁵, —R⁸—N(R⁴)R⁵, —R⁸—C(O)

N(R⁴)R⁵, —R⁸—N(R⁵)C(O)R⁴, —R⁸—S(O)$_m$R⁴ (where m is 0, 1 or 2), —R⁸—CN, and —R⁸—NO₂;

R$^{2a}$, R$^{2b}$, R$^{2c}$ and R$^{2d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —R⁸—CN, —R⁸—NO₂, —R⁸—OR⁵, —R⁸—N(R⁴)R⁵, —N=C(R⁴)R⁵, —S(O)$_m$R⁴, —OS(O)₂CF₃, —R⁸—C(O)R⁴, —C(S)R⁴, —C(R⁴)₂C(O)R⁵, —R⁸—C(O)OR⁴, —C(S)OR⁴, —R⁸—C(O)N(R⁴)R⁵, —C(S)N(R⁴)R⁵, —N(R⁵)C(O)R⁴, —N(R⁵)C(S)R⁴, —N(R⁵)C(O)OR⁴, —N(R⁵)C(S)OR⁴, —N(R⁵)C(O)N(R⁴)R⁵, —N(R⁵)C(S)N(R⁴)R⁵, —N(R⁵)S(O)$_n$R⁴, —N(R⁵)S(O)$_n$(R⁴)R⁵, —R⁸—S(O)$_n$N(R⁴)R⁵, —N(R⁵)C(=NR⁵)N(R⁴)R⁵, and —N(R⁵)C(=N—CN)N(R⁴)R⁵, wherein each m is independently 0, 1, or 2 and each n is independently 1 or 2;

and wherein each of the cycloalkyl, cycloalkylalkyl, aryl, aralkyl, aralkenyl, heterocyclyl, heterocyclylalkyl, heteroaryl and heteroarylalkyl groups for R$^{2a}$, R$^{2b}$, R$^{2c}$ and R$^{2d}$ may be optionally substituted by one or more substituents selected from the group consisting of alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —R⁸—CN, —R⁸—NO₂, —R⁸—OR⁵, —R⁸—N(R⁴)R⁵, —S(O)$_m$R⁴,—R⁸—S(O)$_n$N(R⁴)R⁵,—R⁸—C(O)R⁴, —R⁸—C(O)OR⁴—R⁸—C(O)N(R⁴)R⁵, —N(R⁵)C(O)R⁴, and —N(R⁵)S(O)$_n$R⁴, wherein each m is independently 0, 1, or 2 and each n is independently 1 or 2;

or R$^{2a}$ and R$^{2b}$, together with the carbon ring atoms to which they are directly attached, may form a fused ring selected from cycloalkyl, aryl, heterocyclyl and heteroaryl, and R$^{2c}$ and R$^{2d}$ are as defined above;

or R$^{2b}$ and R$^{2c}$, together with the carbon ring atoms to which they are directly attached, may form a fused ring selected from cycloalkyl, aryl, heterocyclyl and heteroaryl, and R$^{2a}$ and R$^{2d}$ are as defined above;

or R$^{2d}$ and R$^{2d}$, together with the carbon ring atoms to which they are directly attached, may form a fused ring selected from cycloalkyl, aryl, heterocyclyl and heteroaryl, and R$^{2a}$ and R$^{2b}$ are as defined above;

R$^{3a}$, R$^{3b}$, R$^{3c}$ and R$^{3d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —R⁸—CN, —R⁸—NO₂, —R⁸—OR⁵, —R⁸—N(R⁴)R⁵, —N=C(R⁴)R⁵, —S(O)$_m$R⁴, —OS(O)₂CF₃, —R⁸—C(O)R⁴, —C(S)R⁴, —C(R⁴)₂C(O)R⁵, —R⁸—C(O)OR⁴, —C(S)OR⁴, —R⁸—C(O)N(R⁴)R⁵, —C(S)N(R⁴)R⁵, —N(R⁵)C(O)R⁴, —N(R⁵)C(S)R⁴, —N(R⁵)C(O)OR⁴, —N(R⁵)C(S)OR⁴, —N(R⁵)C(O)N(R⁴)R⁵, —N(R⁵)C(S)N(R⁴)R⁵, —N(R⁵)S(O)$_n$R⁴, —N(R⁵)S(O)$_n$N(R⁴)R⁵, —R⁸—S(O)$_n$N(R⁴)R⁵, —N(R⁵)C(=NR⁵)N(R⁴)R⁵, and —N(R⁵)C(N=C(R⁴)R⁵)N(R⁴)R⁵, wherein each m is independently 0, 1, or 2 and each n is independently 1 or 2;

or R$^{3a}$ and R$^{3b}$, together with the carbon ring atoms to which they are directly attached, may form a fused ring selected from cycloalkyl, heterocyclyl, aryl or heteroaryl, and R$^{3c}$ and R$^{3d}$ are as defined above;

or R$^{3b}$ and R$^{3c}$, together with the carbon ring atoms to which they are directly attached, may form a fused ring selected from cycloalkyl, heterocyclyl, aryl or heteroaryl, and R$^{3a}$ and R$^{3d}$ are as defined above;

or R$^{3c}$ and R$^{3d}$, together with the carbon ring atoms to which they are directly attached, may form a fused ring selected from cycloalkyl, heterocyclyl, aryl or heteroaryl, and R$^{3a}$ and R$^{3b}$ are as defined above;

each R⁴ and R⁵ is independently selected from the group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when R⁴ and R⁵ are each attached to the same nitrogen atom, then R⁴ and R⁵, together with the nitrogen atom to which they are attached, may form a heterocyclyl or heteroaryl;

each R⁸ is a direct bond or a straight or branched alkylene chain, a straight or branched alkenylene chain or a straight or branched alkynylene chain; and each R⁹ is a straight or branched alkylene chain, a straight or branched alkenylene chain or a straight or branched alkynylene chain;

as a stereoisomer, enantiomer, tautomer thereof or mixtures thereof;

or a pharmaceutically acceptable salt thereof.

5. A method of decreasing ion flux through a voltage-dependent sodium channel in a cell in a mammal, wherein the method comprises contacting the cell with a compound of formula (I):

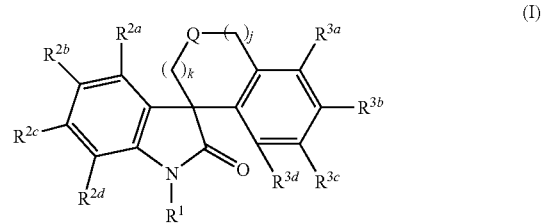

wherein:
j and k are each independently 0, 1, 2 or 3;
Q is —O—;
R¹ is hydrogen, alkyl, alkenyl, alkynyl, haloalkyl, aryl, cycloalkyl, cycloalkylalkyl, heteroaryl, heterocyclyl, —R⁸—C(O)R⁵, —R⁸—C(O)OR⁵, —R⁸—C(O)N(R⁴)R⁵, —S(O)₂—R⁵, —R⁹—S(O)$_m$—R⁵ (where m is 0, 1 or 2), —R⁸—OR⁵, —R⁸—CN, —R⁹—P(O)(OR⁵)₂, or —R⁹—O—R⁹—OR⁵;

or R¹ is aralkyl substituted by —C(O)N(R⁶)R⁷ where:
R⁶ is hydrogen, alkyl, aryl or aralkyl; and
R⁷ is hydrogen, alkyl, haloalkyl, —R⁹—CN, —R⁹—OR⁵, —R⁹—N(R⁴)R⁵, aryl, aralkyl, cycloalkyl, cycloalkylalkyl, heterocyclyl, heterocyclylalkyl, heteroaryl or heteroarylalkyl;
or R⁶ and R⁷, together with the nitrogen to which they are attached, may form a heterocyclyl or heteroaryl;
and wherein each aryl, aralkyl, cycloalkyl, cycloalkylalkyl, heterocyclyl, heterocyclylalkyl, heteroaryl and heteroarylalkyl group for R⁶ and R⁷ may be optionally substituted by one or more substituents selected from the group consisting of alkyl, cycloalkyl, aryl, aralkyl, halo, haloalkyl, —R⁸—CN, —R⁸—OR⁵, heterocyclyl and heteroaryl;

or R¹ is aralkyl optionally substituted by one or more substituents selected from the group consisting of —R⁸—

$OR^5$, —$C(O)OR^5$, halo, haloalkyl, alkyl, nitro, cyano, aryl, aralkyl, heterocyclyl and heteroaryl;

or $R^1$ is —$R^9$—$N(R^{10})R^{11}$, —$R^9$—$N(R^{12})C(O)R^{11}$ or —$R^9$—$N(R^{10})C(O)N(R^{10})R^{11}$ where:

each $R^{10}$ is hydrogen, alkyl, aryl, aralkyl or heteroaryl;

each $R^{11}$ is hydrogen, alkyl, haloalkyl, cycloalkyl, cycloalkylalkyl, aryl, aralkyl, heterocyclyl, heterocyclylalkyl, heteroaryl, heteroarylalkyl, —$R^9$—$OC(O)R^5$, —$R^9$—$C(O)OR^5$, —$R^9$—$C(O)N(R^4)R^5$, —$R^9$—$C(O)R^5$, —$R^9$—$N(R^4)R^5$, —$R^9$—$OR^5$, or —$R^9$—$CN$; and $R^{12}$ is hydrogen, alkyl, aryl, aralkyl or —$C(O)R^5$;

and wherein each aryl, aralkyl, cycloalkyl, cycloalkylalkyl, heterocyclyl, heterocyclylalkyl, heteroaryl and heteroarylalkyl group for $R^{10}$ and $R^{11}$ may be optionally substituted by one or more substituents selected from the group consisting of alkyl, cycloalkyl, aryl, aralkyl, halo, haloalkyl, nitro, —$R^8$—$CN$, —$R^8$—$OR^5$, —$R^8$—$C(O)R^5$, heterocyclyl and heteroaryl;

or $R^1$ is heterocyclylalkyl or heteroarylalkyl where the heterocyclylalkyl or the heteroarylalkyl group is optionally substituted by one or more substituents selected from the group consisting of oxo, alkyl, halo, haloalkyl, cycloalkyl, cycloalkylalkyl, aryl, aralkyl, heterocyclyl, heterocyclylalkyl, heteroaryl, heteroarylalkyl, —$R^8$—$OR^5$, —$R^8$—$C(O)OR^5$, —$R^8$—$N(R^4)R^5$, —$R^8$—$C(O)N(R^4)R^5$, —$R^8$—$N(R^5)C(O)R^4$, —$R^8$—$S(O)_mR^4$ (where m is 0, 1 or 2), —$R^8$—$CN$, and —$R^8$—$NO_2$;

$R^{2a}$, $R^{2b}$, $R^{2c}$ and $R^{2d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—$CN$, —$R^8$—$NO_2$, —$R^8$—$OR^5$, —$R^8$—$N(R^4)R^5$, —$N{=}C(R^4)R^5$, —$S(O)_mR^4$, —$OS(O)_2CF_3$, —$R^8$—$C(O)R^4$, —$C(S)R^4$, —$C(R^4)_2C(O)R^5$, —$R^8$—$C(O)OR^4$, —$C(S)OR^4$, —$R^8$—$C(O)N(R^4)R^5$, —$C(S)N(R^4)R^5$, —$N(R^5)C(O)R^4$, —$N(R^5)C(S)R^4$, —$N(R^5)C(O)OR^4$, —$N(R^5)C(S)OR^4$, —$N(R^5)C(O)N(R^4)R^5$, —$N(R^5)C(S)N(R^4)R^5$, —$N(R^5)S(O)_nR^4$, —$N(R^5)S(O)_nN(R^4)R^5$, —$R^8$—$S(O)_nN(R^4)R^5$, —$N(R^5)C({=}NR^5)N(R^4)R^5$, and —$N(R^5)C({=}N{-}CN)N(R^4)R^5$, wherein each m is independently 0, 1, or 2 and each n is independently 1 or 2;

and wherein each of the cycloalkyl, cycloalkylalkyl, aryl, aralkyl, aralkenyl, heterocyclyl, heterocyclylalkyl, heteroaryl and heteroarylalkyl groups for $R^{2a}$, $R^{2b}$, $R^{2c}$ and $R^{2d}$ may be optionally substituted by one or more substituents selected from the group consisting of alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—$CN$, —$R^8$—$NO_2$, —$R^8$—$OR^5$, —$R^8$—$N(R^4)R^5$, —$S(O)_mR^4$, —$R^8$—$S(O)_nN(R^4)R^5$, —$R^8$—$C(O)R^5$, —$R^8$—$C(O)R^4$, —$R^8$—$C(O)OR^4$—$R^8$—$C(O)N(R^4)R^5$, —$N(R^5)C(O)R^4$, and —$N(R^5)C(O)R^4$, and —$N(R^5)S(O)_nR^4$, wherein each m is independently 0, 1, or 2 and each n is independently 1 or 2;

or $R^{2a}$ and $R^{2b}$, together with the carbon ring atoms to which they are directly attached, may form a fused ring selected from cycloalkyl, aryl, heterocyclyl and heteroaryl, and $R^{2c}$ and $R^{2d}$ are as defined above;

or $R^{2b}$ and $R^{2c}$, together with the carbon ring atoms to which they are directly attached, may form a fused ring selected from cycloalkyl, aryl, heterocyclyl and heteroaryl, and $R^{2a}$ and $R^{2d}$ are as defined above;

or $R^{2c}$ and $R^{2d}$, together with the carbon ring atoms to which they are directly attached, may form a fused ring selected from cycloalkyl, aryl, heterocyclyl and heteroaryl, and $R^{2a}$ and $R^{2b}$ are as defined above;

$R^{3a}$, $R^{3b}$, $R^{3c}$ and $R^{3d}$ are each independently selected from the group consisting of hydrogen, alkyl, alkenyl, alkynyl, alkoxy, halo, haloalkyl, haloalkenyl, haloalkoxy, cycloalkyl, cycloalkylalkyl, aryl, aralkyl, aralkenyl, heterocyclyl, heterocyclylalkyl, heteroaryl, heteroarylalkyl, —$R^8$—$CN$, —$R^8$—$NO_2$, —$R^8$—$OR^5$, —$R^8$—$N(R^4)R^5$, —$N{=}C(R^4)R^5$, —$S(O)_mR^4$, —$OS(O)_2CF_3$, —$R^8$—$C(O)R^4$, —$C(S)R^4$, —$C(R^4)_2C(O)R^5$, —$R^8$—$C(O)OR^4$, —$C(S)OR^4$, —$R^8$—$C(O)N(R^4)R^5$, —$C(S)N(R^4)R^5$, —$N(R^5)C(O)R^4$, —$N(R^5)C(S)R^4$, —$N(R^5)C(O)OR^4$, —$N(R^5)C(S)OR^4$, —$N(R^5)C(O)N(R^4)R^5$, —$N(R^5)C(S)N(R^4)R^5$, —$N(R^5)S(O)_nR^4$, —$N(R^5)S(O)_nN(R^4)R^5$, —$R^8$—$S(O)_nN(R^4)R^5$, —$N(R^5)C({=}NR^5)N(R^4)R^5$, and —$N(R^5)C(N{=}C(R^4)R^5)N(R^4)R^5$, wherein each m is independently 0, 1, or 2 and each n is independently 1 or 2;

or $R^{3a}$ and $R^{3b}$, together with the carbon ring atoms to which they are directly attached, may form a fused ring selected from cycloalkyl, heterocyclyl, aryl or heteroaryl, and $R^{3c}$ and $R^{3d}$ are as defined above;

or $R^{3b}$ and $R^{3c}$, together with the carbon ring atoms to which they are directly attached, may form a fused ring selected from cycloalkyl, heterocyclyl, aryl or heteroaryl, and $R^{3a}$ and $R^{3d}$ are as defined above;

or $R^{3c}$ and $R^{3d}$, together with the carbon ring atoms to which they are directly attached, may form a fused ring selected from cycloalkyl, heterocyclyl, aryl or heteroaryl, and $R^{3a}$ and $R^{3b}$ are as defined above;

each $R^4$ and $R^5$ is independently selected from the group consisting of hydrogen, alkyl, alkenyl, alkynyl, haloalkyl, alkoxyalkyl, cycloalkyl, cycloalkylalkyl, aryl, aralkyl, heterocyclyl, heterocyclylalkyl, heteroaryl, and heteroarylalkyl;

or when $R^4$ and $R^5$ are each attached to the same nitrogen atom, then $R^4$ and $R^5$, together with the nitrogen atom to which they are attached, may form a heterocyclyl or heteroaryl;

each $R^8$ is a direct bond or a straight or branched alkylene chain, a straight or branched alkenylene chain or a straight or branched alkynylene chain; and each $R^9$ is a straight or branched alkylene chain, a straight or branched alkenylene chain or a straight or branched alkynylene chain;

as a stereoisomer, enantiomer, tautomer thereof or mixtures thereof;

or a pharmaceutically acceptable salt thereof.

6. The method of claim 1 wherein the pain is selected from trigeminal neuralgia, post-herpetic neuralgia, eudynia, familial erythromelalgia, primary erythromelalgia, familial rectal pain or fibromyalgia.

* * * * *

UNITED STATES PATENT AND TRADEMARK OFFICE
CERTIFICATE OF CORRECTION

PATENT NO. : 8,106,087 B2
APPLICATION NO. : 12/650196
DATED : January 31, 2012
INVENTOR(S) : Mikhail Chafeev et al.

It is certified that error appears in the above-identified patent and that said Letters Patent is hereby corrected as shown below:

Item 56:
"ADAMS et al., "Bicyclic N-Hydroxyurea Inhibitors of 5-Lipoxygenase: Pharmacodynamic, Pharmacokinetic, and *in Vitro* Metabolic Studies Characterizing *N*-Hydroxy-*N*-(2,3-dihydro-6-(phenylmethoxy)-3-benzofuranyl)urea," *J. Med. Chem. 39*(26): 5035-5046, 1996. AKAI, "Development of Novel Asymmetric Reactions Oriented to Next-Generation Enzymatic Organic Syntheses," *Yakugaku Zasshi 123*(11): 919-931, 2003." should read,
--ADAMS et al., "Bicyclic N-Hydroxyurea Inhibitors of 5-Lipoxygenase: Pharmacodynamic, Pharmacokinetic, and *in Vitro* Metabolic Studies Characterizing *N*-Hydroxy-*N*-(2,3-dihydro-6-(phenylmethoxy)-3-benzofuranyl)urea," *J. Med. Chem. 39*(26): 5035-5046, 1996.

AKAI, "Development of Novel Asymmetric Reactions Oriented to Next-Generation Enzymatic Organic Syntheses," *Yakugaku Zasshi 123*(11): 919-931, 2003.--.

Column 324, Line 63, Claim 1:
"$R^{3a}$, $R^{3b}$, $R^3$ and $R^{3d}$ are each independently selected from" should read, --$R^{3a}$, $R^{3b}$, $R^{3c}$ and $R^{3d}$ are each independently selected from--.

Column 325, Line 1, Claim 1:
"heteroarylalkyl, -$R^8$-$NO_2$," should read, --heteroarylalkyl, -$R^8$-CN, -$R^8$-$NO_2$,--.

Column 327, Lines 14-15, Claim 4:
"-$N(R^5)S(O)_n(R^4)R^5$," should read, -- -$N(R^5)S(O)_nN(R^4)R^5$,--.

Column 327, Line 42, Claim 4:
"or $R^{2d}$ and $R^{2d}$, together with the carbon ring atoms to" should read, --or $R^{2c}$ and $R^{2d}$, together with the carbon ring atoms to--.

Signed and Sealed this
Twenty-ninth Day of January, 2013

David J. Kappos
*Director of the United States Patent and Trademark Office*

CERTIFICATE OF CORRECTION (continued)
U.S. Pat. No. 8,106,087 B2

Column 329, Lines 54-58, Claim 5:

"-$R^8$-CN, -$R^8$-$NO_2$, -$R^8$-$OR^5$, -$R^8$-$N(R^4)R^5$, -$S(O)_m R^4$, -$R^8$-$S(O)_n N(R^4)R^5$, -$R^8$-$C(O)R^5$, -$R^8$-$C(O)R^4$, -$R^8$-$C(O)OR^4$-$R^8$ -$C(O)N(R^4)R^5$, -$N(R^5)C(O)R^4$, and –$N(R^5)C(O)R^4$, and -$N(R^5)S(O)_n R^4$," should read, -- -$R^8$-CN, -$R^8$-$NO_2$, -$R^8$-$OR^5$, -$R^8$-$N(R^4)R^5$, -$S(O)_m R^4$, -$R^8$-$S(O)_n N(R^4)R^5$, -$R^8$-$C(O)R^4$, -$R^8$-$C(O)OR^4$, -$R^8$-$C(O)N(R^4)R^5$, -$N(R^5)C(O)R^4$, and -$N(R^5)S(O)_n R^4$,--.